(12) United States Patent
Bravo-Altamirano et al.

(10) Patent No.: US 10,433,555 B2
(45) Date of Patent: *Oct. 8, 2019

(54) PICOLINAMIDE COMPOUNDS WITH FUNGICIDAL ACTIVITY

(71) Applicant: DOW AGROSCIENCES LLC, Indianapolis, IN (US)

(72) Inventors: Karla Bravo-Altamirano, Indianapolis, IN (US); Kyle A. Dekorver, Indianapolis, IN (US); David M. Jones, Indianapolis, IN (US); John F. Daeuble, Sr., Indianapolis, IN (US); Jessica Herrick, Indianapolis, IN (US); Jeffrey B. Epp, Indianapolis, IN (US); Johnathan E. Delorbe, Indianapolis, IN (US); Kevin G. Meyer, Indianapolis, IN (US); Chenglin Yao, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/540,799

(22) PCT Filed: Dec. 21, 2015

(86) PCT No.: PCT/US2015/067113
§ 371 (c)(1),
(2) Date: Jun. 29, 2017

(87) PCT Pub. No.: WO2016/109289
PCT Pub. Date: Jul. 7, 2016

(65) Prior Publication Data
US 2018/0000075 A1 Jan. 4, 2018

Related U.S. Application Data

(60) Provisional application No. 62/098,089, filed on Dec. 30, 2014, provisional application No. 62/098,097, filed on Dec. 30, 2014, provisional application No. 62/255,144, filed on Nov. 13, 2015, provisional application No. 62/255,152, filed on Nov. 13, 2015, provisional application No. 62/255,163, filed on Nov. 13, 2015, provisional application No. 62/255,168, filed on Nov. 13, 2015, provisional application No. 62/255,125, filed on Nov. 13, 2015, provisional application No. 62/255,131, filed on Nov. 13, 2015.

(51) Int. Cl.
| A01N 47/18 | (2006.01) |
| A01N 43/40 | (2006.01) |
| C07D 213/81 | (2006.01) |
| A01N 37/44 | (2006.01) |
| A01N 25/00 | (2006.01) |

(52) U.S. Cl.
CPC ............. *A01N 47/18* (2013.01); *A01N 25/00* (2013.01); *A01N 37/44* (2013.01); *A01N 43/40* (2013.01); *C07D 213/81* (2013.01)

(58) Field of Classification Search
CPC ........ A01N 37/44; A01N 43/40; A01N 25/00; A01N 47/18; C07D 213/81
See application file for complete search history.

(56) References Cited

U.S. PATENT DOCUMENTS

| 4,051,173 | A | 9/1977 | Schact et al. |
| 4,588,735 | A | 5/1986 | Spatz |
| 5,342,835 | A | 8/1994 | Pepin et al. |
| 5,401,871 | A | 3/1995 | Feldmann-Krane et al. |
| 5,475,132 | A | 12/1995 | Pepin et al. |
| 5,563,165 | A | 10/1996 | Talley |
| 5,760,068 | A | 6/1998 | Talley |
| 5,852,042 | A | 12/1998 | Jakobi et al. |
| 6,355,660 | B1 | 3/2002 | Ricks et al. |
| 6,410,572 | B1 | 6/2002 | Schelberger et al. |
| 6,436,421 | B1 | 8/2002 | Schindler et al. |
| 6,521,622 | B1 | 2/2003 | Ricks et al. |
| 6,706,740 | B2 | 3/2004 | Ricks et al. |
| 6,861,390 | B2 | 3/2005 | Meyer et al. |
| 6,903,219 | B2 | 6/2005 | Niyaz et al. |
| 6,916,932 | B2 | 7/2005 | Meyer et al. |
| 6,927,225 | B2 | 8/2005 | Ricks et al. |
| 6,953,807 | B2 | 10/2005 | Hutin |

(Continued)

FOREIGN PATENT DOCUMENTS

| CL | 2015001862 | 10/2015 |
| CN | 101530104 | 9/2009 |

(Continued)

OTHER PUBLICATIONS

Cantacuzene, D., "Optimization of the papain catalyzed esterification of animo acids by alcohols and diols." Tetrahedron 45.3 (1989): 741-748.*
Washburn, W. N.,"Identification of a nonbasic melanin hormone receptor 1 antagonist as an antiobesity clinical candidate." Journal of medicinal chemistry 57.18 (2014): 7509-7522.*
CAS Registry Entries No. 1354261-15-6 and 1348619-55-5 (Chemical Abstracts Service 2018).*
Zhang, Z., Nanjing Daxue Xuebao, Ziran Kexue (1992), 28(3) 404-10 (Abstract).*

(Continued)

*Primary Examiner* — John M Mauro

(57) ABSTRACT

This disclosure relates to picolinamides of Formula I and their use as fungicides.

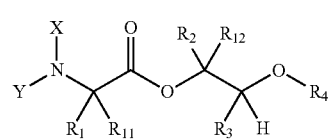

12 Claims, No Drawings

(56) References Cited

U.S. PATENT DOCUMENTS

| | | | |
|---|---|---|---|
| 7,034,035 B2 | 4/2006 | Ricks et al. |
| 7,183,278 B1 | 2/2007 | Imamura et al. |
| 7,241,804 B1 | 7/2007 | Hockenberry et al. |
| 7,250,389 B1 | 7/2007 | Sakanaka et al. |
| RE39,991 E | 1/2008 | Ricks et al. |
| 7,442,672 B2 | 12/2008 | Muller et al. |
| 7,459,581 B2 | 12/2008 | Derrer et al. |
| 7,560,565 B2 | 7/2009 | Bacque et al. |
| 7,927,617 B2 | 4/2011 | Koltzenburg |
| 8,008,231 B2 | 8/2011 | Leatherman |
| 8,153,819 B2 | 4/2012 | Dietz |
| 8,236,962 B2 | 8/2012 | Hoekstra et al. |
| 8,349,877 B2 | 1/2013 | Brix et al. |
| 8,415,274 B2 | 4/2013 | Wachendorff-Neumann et al. |
| 8,465,562 B2 | 6/2013 | Chen |
| 8,470,840 B2 | 6/2013 | Klittich et al. |
| 8,476,193 B2 | 7/2013 | Keeney et al. |
| 8,586,550 B2 | 11/2013 | Lee et al. |
| 8,604,215 B2 | 12/2013 | Phiasivongsa et al. |
| 8,785,479 B2 | 7/2014 | Meyer et al. |
| 8,835,462 B2 | 9/2014 | Meyer et al. |
| 8,883,811 B2 | 11/2014 | Owen et al. |
| 8,916,579 B2 | 12/2014 | Boebel et al. |
| 9,006,259 B2 | 4/2015 | Boebel et al. |
| 9,084,418 B2 | 7/2015 | Ehr et al. |
| 9,131,690 B2 | 9/2015 | Meyer et al. |
| 9,144,239 B2 | 9/2015 | Meyer et al. |
| 9,155,305 B2 | 10/2015 | Gary |
| 9,156,816 B2 | 10/2015 | Ito et al. |
| 9,179,674 B2 | 11/2015 | Martin et al. |
| 9,185,911 B2 | 11/2015 | Inami et al. |
| 9,198,419 B2 | 12/2015 | Owen et al. |
| 9,247,741 B2 | 2/2016 | DeLorbe et al. |
| 9,265,253 B2 | 2/2016 | Li et al. |
| 9,265,255 B2 | 2/2016 | Funke |
| 9,271,496 B2 | 3/2016 | Kemmitt |
| 9,271,497 B2 | 3/2016 | Lorsbach |
| 9,414,596 B2 | 8/2016 | Hoekstra et al. |
| 9,439,422 B2 | 9/2016 | Martin et al. |
| 9,482,661 B2 | 11/2016 | Ross |
| 9,549,555 B2 | 1/2017 | DeLorbe et al. |
| 9,549,556 B2 | 1/2017 | DeKorver et al. |
| 9,629,365 B2 | 4/2017 | Li et al. |
| 9,681,664 B2 | 6/2017 | LaLonde et al. |
| 9,686,984 B2 | 6/2017 | DeKorver et al. |
| 9,700,047 B2 | 7/2017 | Lu |
| 9,750,248 B2 | 9/2017 | Ouimette et al. |
| 9,840,475 B2 | 12/2017 | Lorsbach |
| 9,936,697 B2 | 4/2018 | Hopkins |
| 9,955,690 B2 | 5/2018 | Owen |
| 9,955,691 B2 | 5/2018 | Boebel |
| 9,974,304 B2 | 5/2018 | DeKorver |
| 2002/0119979 A1 | 8/2002 | Degenhardt et al. |
| 2002/0177578 A1 | 11/2002 | Ricks et al. |
| 2003/0018052 A1 | 1/2003 | Ricks et al. |
| 2003/0022902 A1 | 1/2003 | Ricks et al. |
| 2003/0022903 A1 | 1/2003 | Ricks et al. |
| 2005/0239873 A1 | 10/2005 | Hockenbery et al. |
| 2006/0167281 A1 | 7/2006 | Meijer |
| 2007/0010401 A1 | 1/2007 | Noon |
| 2007/0066629 A1 | 3/2007 | Tormo i Blasco et al. |
| 2009/0203770 A1 | 8/2009 | Hockenberry et al. |
| 2009/0306142 A1 | 12/2009 | Carson et al. |
| 2010/0016163 A1 | 1/2010 | Keiper et al. |
| 2011/0070278 A1 | 3/2011 | Lopez |
| 2011/0082162 A1 | 4/2011 | Lorsbach et al. |
| 2012/0245031 A1 | 9/2012 | Gewehr et al. |
| 2013/0296372 A1 | 11/2013 | Owen et al. |
| 2014/0051678 A1 | 2/2014 | Clement-Schatlo et al. |
| 2014/0128411 A1 | 5/2014 | Ogawa et al. |
| 2014/0187587 A1 | 7/2014 | Ouimette et al. |
| 2014/0357713 A1 | 12/2014 | Damaj et al. |
| 2015/0018374 A1 | 1/2015 | Taggi et al. |
| 2015/0065529 A1 | 3/2015 | Owen et al. |
| 2015/0181868 A1 | 7/2015 | DeKorver et al. |
| 2015/0289508 A1 | 10/2015 | Meyer et al. |
| 2015/0322051 A1 | 11/2015 | Lu et al. |
| 2016/0007601 A1 | 1/2016 | Boebel et al. |
| 2016/0037774 A1 | 2/2016 | Schulz |
| 2016/0183526 A1 | 6/2016 | Hopkins et al. |
| 2016/0183527 A1 | 6/2016 | Hopkins et al. |
| 2016/0183528 A1 | 6/2016 | Hopkins et al. |
| 2017/0107244 A1* | 4/2017 | Kalayanov ............ C07H 19/06 |
| 2017/0183324 A1 | 6/2017 | Li et al. |
| 2017/0360038 A1 | 6/2017 | Yao |
| 2017/0273303 A1 | 9/2017 | DeKorver et al. |
| 2017/0273306 A1 | 9/2017 | LaLonde et al. |
| 2017/0290333 A1 | 10/2017 | Bravo-Altamirano et al. |
| 2017/0295792 A1 | 10/2017 | Bravo-Altamirano et al. |
| 2017/0369421 A1 | 12/2017 | Yao |
| 2018/0000080 A1 | 1/2018 | Buchan et al. |
| 2018/0000084 A1 | 1/2018 | Yao |
| 2018/0000085 A1 | 1/2018 | Bravo-Altamirano et al. |
| 2018/0002288 A1 | 1/2018 | Buchan |
| 2018/0002319 A1 | 1/2018 | Wilmot |
| 2018/0002320 A1 | 1/2018 | Wilmot |
| 2018/0037541 A1 | 2/2018 | Yao |

FOREIGN PATENT DOCUMENTS

| | | | |
|---|---|---|---|
| FR | 2649699 | 1/1991 |
| JP | 199400026884 | 9/1995 |
| JP | 1998053583 | 2/1998 |
| JP | H10-045747 | 2/1998 |
| WO | 1996010016 | 4/1996 |
| WO | 199637472 | 11/1996 |
| WO | 1997019908 | 6/1997 |
| WO | 199741103 | 11/1997 |
| WO | 1998018751 | 5/1998 |
| WO | 1999011127 | 11/1999 |
| WO | 2000076979 | 12/2000 |
| WO | 200114339 | 3/2001 |
| WO | 2005121069 | 12/2005 |
| WO | 2008079387 | 7/2008 |
| WO | WO-2010042682 A1 * | 4/2010 | ............ C07D 487/04 |
| WO | 2012016989 | 2/2012 |
| WO | 2012020777 | 2/2012 |
| WO | 2014105844 | 7/2014 |
| WO | 2016007525 | 1/2016 |
| WO | 2016109288 | 7/2016 |
| WO | 2016109290 | 7/2016 |
| WO | 2016109291 | 7/2016 |
| WO | 2016109300 | 7/2016 |
| WO | 2016109301 | 7/2016 |
| WO | 2016109302 | 7/2016 |
| WO | 2016109303 | 7/2016 |
| WO | 2016109304 | 7/2016 |
| WO | 2016109305 | 7/2016 |
| WO | 2015005355 | 3/2017 |

OTHER PUBLICATIONS

Anonymous, Synergistic Fungicidal Composition of Heterocyclic Aromatic Amides and Triazoles, ip.com Journal, ip.com, Electronic Publication, West Henrietta, NY, US, Jul. 2004, 11 pages.

Backman, P., Fungicide Formulation: Relationship to Biological Activity, Ann. Rev. Phytopathol, 1978, 16, pp. 211-237.

BASF New Fungicide Xemium Got Full Approval in EU, Agronews, Jul. 18, 2012 [retrieved on Apr. 2, 2014]. Retrieved from the Internet: ,URL:http://news.agropages.com/News/NewsDetail---7386.htm, 1 page.

Bolton, M. et al., "Wheat leaf rust caused by Puccinia triticina," Molecular Plant Pathology, vol. 9, No. 5, 2008, pp. 563-575 [online] [retrieved on Feb. 3, 2016]. Retrieved from the Internet URL: https://www.researchgate.net/profile/Melvin_Bolton/publication/23483068_Wheat_leaf_rust_caused_by_Puccinia_triticina/links/0046352d94b8d5f209000000.pdf.

Davari, M. et al. "Quantum Chemical Investigation of Intramolecular Thione-Thiol Tautomerism of 1, 2, 4-triazole-3-thione and its disubstituted derivatives," Journal of Molecular Modeling, Sep. 2009, 16(5), pp. 841-55.

(56) References Cited

OTHER PUBLICATIONS

FRAC Code List: Fungicides Sorted by Mode of Action (including FRAC Code numbering), Fungicide Resistance Action Committee, Dec. 2008, 10 pages.
Fungicidal Mixtures, IP.com Prior Art Database Technical Disclosure, (Jul. 5, 2005), XP055073888, DOI: http://ip.com/pdf/ipcompad/IPCOM000126160D.pdf, 12 pages.
Gisi, U., "Synergistic Interaction of Fungicides in Mixtures," The American Phytopathological Society, vol. 86, No. 11, 1996, pp. 1273-1279.
Hu, Z. et al., "Synthesis of Novel Analogues of Antimycin A3," Tetrahedron Letters 49 (2008), pp. 5192-5195.
Huang, C. et al., "Synergistic Interactions between Chitinase ChiCW and Fungicides Against Plant Fungal Pathogens," J. Microbiol. Biotechnol., 2008, 18(4), pp. 784-787.
Kissling, E., "Crop Protection Pipeline Value Jumps to Euro 2.4 Billion," BASF SE, Mar. 10, 2011 [retrieved on Apr. 2, 2014], Retrieved from the internet: ,URL:http://agro.basf.com/agri/AP-Internet/en/content/news_room/news/basf-crop-protection-pipeline-value, 4 pages.
Koyanagi, T. et al., "Bioisoterism in Agrochemicals," Synthesis and Chemistry of Agrochemicals IV; Baker, D. et al., ACS Symposium Series; American Chemical Society: Washington, D.C., 1995, pp. 15-24.
Latin, R., et al, "Re-Examining Fungicide Synergism for Dollar Spot Control;" GCM, Jul. 2008, pp. 84-87.
Ueki, M., et al., "Uk-2A, B, C, and D, Novel Antifungal Antibiotics from *Streptomyces* sp. 517-02 I. Fermentation, Isolation, and Biological Properties," The Journal of Antibiotics, vol. 49, No. 7, Jul. 1996, pp. 639-634.
O'Sullivan, E., et al., "Fungicide Resistance—an Increasing Problem," Proceedings of National Tillage Conference 2007, Published by Crop Research Centre, Oak Park, Carlow, Jan. 31, 2007, pp. 43-56.
Parker, J.E., et al., "Mechanism of Binding of Prothioconazole to Mycosphaerella graminicola CYP51 Differs from That of Other Azole Antifungals," Applied and Environmental Microbiology, vol. 77, No. 4, Feb. 2011, pp. 1460-1465.
PubChem: Open Chemistry Database, Substance Record for SID 74383515. Deposit Date Jun. 11, 2009 [retrieved on May 25, 2016] Retrieved from internet. <URL:https://pubchem.ncbi.nlm.nih.gov/substance/74383515#section=Top>, 5 pages.
Science for a Better Life, Bayer CropScience "Positioned for Growth", Jun. 2008, 22 pages.
Calcium Dodecyl Benzene Sulfonate, CAS 26264-06-2, (http://www.hichem.com/product/showproduct.php?id=334639) Mar. 28, 2013, 4 pages.
Tani, K. et al., The Journal of Antibiotics, vol. 55, No. 3, Mar. 2002, pp. 315-321.
The Merck Index, Twelfth Edition, S. Budavari, Ed., Merck and Co., Inc., Whitehouse Station, NJ, 1996, pp. 2220, 3666, 7937 and 7946.
Usuki, Y., et al., "Semi-synthesis and biological evaluation of analogues of UK-2A, a novel antifungal antibiotic from *Streptomyces* sp. 517-02," Bioorganic & Medicinal Chemistry Letters, vol. 15, No. 8, 2005, pp. 2011-2014.
Usuki, Y. et al., Journal of Antibiotics, vol. 55, No. 6, Jun. 2002, pp. 607-610.
Webster's New World Dictionary, Second College Edition, Guralnik, D, Ed., The World Publishing Co., New York, p. 1127 (1972).
Wilson, C.L. et al. "Fruit Volatiles Inhibitory to Monilinia Fruiticola and Botrytis cinerea," 1987, Plant Disease, vol. 71, No. 4, pp. 316-319.
Written Opinion and Search Report for PCT Patent Application No. PCT/US2015/067113 dated Mar. 11, 2016, 10 pages.
Guseynov et al: "Study of the reaction of aminoacetic acid with dihydric alcohols and production of epoxy esters" Chemical Problems, 2009 (1), pp. 188-190. English Machine Translation attached.
Amiri et al. "Sensitivity of Botrytis cinerea field isolates to the novel succinate dehydrogenase inhibitors fluopyram, penthiopyrad, and fluxapuroxad". Annual Meeting of the American Phytopathological Society, Phytopathology, vol. 102 (2012). (Uploaded in three parts due to size restrictions).
Cooke et al. "The effect of fungicide programmes based on epoxiconazole on the control and DMI sensitivity of Rhynchosporium secalis in winter barley." Crop Protection, vol. 23, No. 5, pp. 393-406 (2004).
Fujita T, Ed. "Quantitative structure-activity analysis and database-aided bioisosteric structural transformation procedure as methodologies of agrochemical design"; Classical and Three Dimensional QSAR in Agrochemistry, American Chemical Society Symposium Series, Washington, D.C. vol. 606, pp. 13-34 (1995).
Goellner et al. "Phakopsora pachyrhizi, the causal agent of Asian soybean rust." Molecular Plant Pathology, vol. 11, No. 2, pp. 169-177 (2010).
Kendall, S. et al. "Changes in sensitivity to DMI fungicides in Rhynchosporium secalis". Crop Protection, vol. 12, No. 5, pp. 357-362 (1993).
Lippard, S. "The Art of Chemistry". Nature, vol. 416, p. 587 (2002).
Patani et al. "Biosterism: A rational approach in drug design". Chemical Reviews, vol. 96, No. 8, pp. 3147-3176 (1996).
Shimano et al. "Total synthesis of the antifungal dilactones UK-2A and UK-3A: The determination of their relative and absolute configurations, analog synthesis and antifungal activities". Tetrahedron, vol. 54, pp. 12745-12774 (1998).
Chitwood, D. "Nematicides". Encyclopedia of Agrochemicals (3), pp. 1104-1115, John Wiley & Sons, New York, NY, http://naldc.nal.usda.gov/download/43874/PDF (2003).
Hanafi et al. "UK2A, B, C, and D, Novel Antifungal Antibiotics from *Streptomyces* sp 517-02 II. Structural Elucidation." The Journal of Antibiotics, vol. 49, Issue 12, pp. 1226-1231 (1996).
Shibata et al. "UK1, A Novel Cytotoxic Metabolite from *Streptomyces* sp. 517-02 II. Structural Elucidation." The Journal of Antibiotics, vol. 46, Issue 7, pp. 1095-1100 (1993).
Shimano et al. "Enantioselective Total Synthesis of the Antifungal Dilactone, UK-2A: The Determination of the Relative and Absolute Configurations". Tetrahedron Letters, vol. 39, pp. 4363-4366 (1998).
Stephenson, G., et al. "Glossary of terms relating to pesticides". Pure and Applied Chemistry, vol. 78, No. 11, pp .2075-2154, International Union of Pure and Applied Chemistry (2006).
Ueki, M., et al., "UK-1, A Novel Cytotoxic Metabolite from *Streptomyces* sp. 517-02 I. Taxonomy, Fermentation, Isolation, Physico-chemical and Biological Properties." The Journal of Antibiotics, vol. 46, No. 7, pp. 1089-1094 (1993).
Ueki et al. "UK-3A, A Novel Antifungal Antibiotic from *Streptomyces* sp. 517-02: Fermentation, Isolation, Structural Elucidation and Biological Properties". The Journal of Antibiotics, vol. 50, Issue 7, pp. 551-555 (1997).
Ueki et al. "The mode of action of UK-2A and UK-3A, Novel antifungal antibiotics from *Streptomyces* sp. 517-02". The Journal of Antibiotics, vol. 50, Issue 12, pp. 1052-1057 (1997).
International Searching Authority, International Search Report for PCT/US14/058070, dated Dec. 15, 2014, 4 pages.
International Searching Authority, Written Opinion for PCT/US14/058070, dated Dec. 15, 2014, 5 pages.
International Searching Authority, International Search Report and Written Opinion for PCT/US14/58061 dated Dec. 15, 2014, 9 pages.
International Searching Authority, International Search Report and Written Opinion for PCT/US1458065 dated Dec. 22, 2014, 9 pages.
International Searching Authority, International Search Report and Written Opinion for PCT/US1528407 dated Aug. 5, 2015, 8 pages.
International Searching Authority, International Search Report and Written Opinion for PCT/US1539407 dated Sep. 30, 2015, 9 pages.
International Searching Authority, International Search Report and Written Opinion for PCT/US1539409 dated Oct. 5, 2015, 10 pages.
International Searching Authority, International Search Report and Written Opinion for PCT/US1544383 dated Mar. 16, 2016, 11 pages.
International Searching Authority, International Search Report and Written Opinion for PCT/US1567206 dated Mar. 7, 2016, 8 pages.
International Searching Authority, International Search Report and Written Opinion for PCT/US1567111 dated Mar. 11, 2016, 11 pages.

(56) References Cited

OTHER PUBLICATIONS

International Searching Authority, International Search Report and Written Opinion for PCT/US1567116 dated Mar. 1, 2016, 8 pages.
International Searching Authority, International Search Report and Written Opinion for PCT/US1567199 dated Mar. 11, 2016, 9 pages.
International Searching Authority, International Search Report and Written Opinion for PCT/US1567200 dated Mar. 10, 2016, 10 pages.
International Searching Authority, International Search Report and Written Opinion for PCT/US1567201 dated Mar. 11, 2016, 8 pages.
International Searching Authority, International Search Report and Written Opinion for PCT/US1567204 dated Mar. 1, 2016, 10 pages.
International Searching Authority, International Search Report and Written Opinion for PCT/US1567207 dated Mar. 11, 2016, 12 pages.
International Searching Authority, International Search Report and Written Opinion for PCT/US2013039726 dated Sep. 17, 2013, 9 pages.
International Searching Authority, International Search Report and Written Opinion for PCT/US2013039735 dated Oct. 18, 2013, 8 pages.
International Searching Authority, International Search Report and Written Opinion for PCT/US2013077472 dated Apr. 16, 2014, 9 pages.
International Searching Authority, International Search Report and Written Opinion for PCT/US2013077537 dated Apr. 16, 2014, 11 pages.
International Searching Authority, International Search Report and Written Opinion for PCT/US2014071692 dated Apr. 20, 2015, 6 pages.
International Searching Authority, International Search Report and Written Opinion for PCT/US2014071695 dated Apr. 17, 2015, 6 pages.
International Searching Authority, International Search Report and Written Opinion for PCT/US2014071699 dated Apr. 20, 2015, 6 pages.
International Searching Authority, International Search Report and Written Opinion for PCT/US2014071700 dated Apr. 17, 2015, 9 pages.
International Searching Authority, International Search Report and Written Opinion for PCT/US2015066760 dated Apr. 14, 2016, 11 pages.
International Searching Authority, International Search Report and Written Opinion for PCT/US2015066764 dated Apr. 28, 2016, 11 pages.
International Searching Authority, International Search Report and Written Opinion for PCT/US20150051598 dated Dec. 6, 2010, 5 pages.
International Searching Authority, International Search Report for PCT/US14/058067, dated Dec. 22, 2014, 4 pages.
International Searching Authority, Written Opinion for PCT/US14/058067, dated Dec. 22, 2014, 5 pages.
International Searching Authority, International Search Report and Written Opinion for PCT/US2015/067115, dated Mar. 11, 2016, 6 pages.
International Searching Authority, International Search Report PCT/US2000/021523 dated Jul. 7, 2001, 7 pages.
Database Chemabs Online, Chemical Abstracts Service, Columbus Ohio, US: accession No. CA63:16300d XP002164206 (Cited in International Search Report for PCT/US2000/021523).

\* cited by examiner

PICOLINAMIDE COMPOUNDS WITH FUNGICIDAL ACTIVITY

CROSS REFERENCE TO RELATED APPLICATIONS

This application is a U.S. National Phase filing of International Application No. PCT/US2015/067113, filed Dec. 21, 2015, which claims the benefit of U.S. Provisional Patent Application Serial Nos. 62/098,089 filed Dec. 30, 2014, 62/098,097 filed Dec. 30, 2014, 62/255,144 filed Nov. 13, 2015, 62/255,152 filed Nov. 13, 2015, 62/255,163 filed Nov. 13, 2015, 62/255,168 filed Nov. 13, 2015, 62/255,125 filed Nov. 13, 2015 and 62/255,131 filed Nov. 13, 2015 the disclosures of which are hereby expressly incorporated by reference herein in their entirety.

BACKGROUND & SUMMARY

The present disclosure relates to picolinamides and their use as fungicides. The compounds of the present disclosure may offer protection against ascomycetes, basidiomycetes, deuteromycetes and oomycetes.

One embodiment of the present disclosure may include compounds of Formula I:

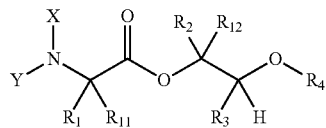

X is hydrogen or $C(O)R_5$;
Y is hydrogen, $C(O)R_5$, or Q;
Q is

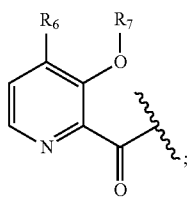

$R_1$ and $R_{11}$ are independently chosen from hydrogen or alkyl, optionally substituted with 0, 1 or multiple $R_8$; Alternatively, $R_1$ and $R_{11}$ may be taken together to form a 3-6 membered saturated or partially saturated carbocycle or heterocycle, optionally substituted with 0, 1 or multiple $R_8$;

$R_2$ and $R_{12}$ are independently chosen from hydrogen, alkyl, aryl, or alkenyl, each optionally substituted with 0, 1 or multiple $R_8$;

$R_3$ is chosen from hydrogen, $C_2$-$C_6$ alkyl, aryl, or alkenyl, each optionally substituted with 0, 1 or multiple $R_8$;

$R_4$ is chosen from alkyl, aryl, or acyl, each optionally substituted with 0, 1 or multiple $R_8$;

$R_5$ is chosen from alkoxy or benzyloxy, each optionally substituted with 0, 1, or multiple $R_8$;

$R_6$ is chosen from hydrogen, alkoxy, or halo, each optionally substituted with 0, 1, or multiple $R_8$;

$R_7$ is chosen from hydrogen, $-C(O)R_9$, or $-CH_2OC(O)R_9$;

$R_8$ is chosen from hydrogen, alkyl, aryl, acyl, halo, alkenyl, alkoxy, or heterocyclyl, each optionally substituted with 0, 1, or multiple $R_{10}$;

$R_9$ is chosen from alkyl, alkoxy, or aryl, each optionally substituted with 0, 1, or multiple $R_8$;

$R_{10}$ is chosen from hydrogen, alkyl, aryl, acyl, halo, alkenyl, alkoxy, or heterocyclyl.

Another embodiment of the present disclosure may include a fungicidal composition for the control or prevention of fungal attack comprising the compounds described above and a phytologically acceptable carrier material.

Yet another embodiment of the present disclosure may include a method for the control or prevention of fungal attack on a plant, the method including the steps of applying a fungicidally effective amount of one or more of the compounds described above to at least one of the fungus, the plant, and an area adjacent to the plant.

It will be understood by those skilled in the art that the following terms may include generic "R"-groups within their definitions, e.g., "the term alkoxy refers to an —OR substituent". It is also understood that within the definitions for the following terms, these "R" groups are included for illustration purposes and should not be construed as limiting or being limited by substitutions about Formula I.

The term "alkyl" refers to a branched, unbranched, or saturated cyclic carbon chain, including, but not limited to, methyl, ethyl, propyl, butyl, isopropyl, isobutyl, tertiary butyl, pentyl, hexyl, cyclopropyl, cyclobutyl, cyclopentyl, cyclohexyl, and the like.

The term "alkenyl" refers to a branched, unbranched or cyclic carbon chain containing one or more double bonds including, but not limited to, ethenyl, propenyl, butenyl, isopropenyl, isobutenyl, cyclobutenyl, cyclopentenyl, cyclohexenyl, and the like.

The term "alkynyl" refers to a branched or unbranched carbon chain containing one or more triple bonds including, but not limited to, propynyl, butynyl, and the like.

The terms "aryl" and "Ar" refer to any aromatic ring, mono- or bi-cyclic, containing 0 heteroatoms.

The term "heterocyclyl" refers to any aromatic or non-aromatic ring, mono- or bicyclic, containing one or more heteroatoms The term "alkoxy" refers to an —OR substituent.
The term "acyloxy" refers to an —OC(O)R substituent.
The term "cyano" refers to a —C≡N substituent.
The term "hydroxyl" refers to an —OH substituent.
The term "amino" refers to a —$N(R)_2$ substituent.
The term "arylalkoxy" refers to —$O(CH_2)_n$Ar where n is an integer selected from the list 1, 2, 3, 4, 5, or 6.
The term "haloalkoxy" refers to an —OR—X substituent, wherein X is Cl, F, Br, or I, or any combination thereof.
The term "haloalkyl" refers to an alkyl, which is substituted with Cl, F, I, or Br or any combination thereof.
The term "halogen" or "halo" refers to one or more halogen atoms, defined as F, Cl, Br, and I.
The term "nitro" refers to a —$NO_2$ substituent.
The term thioalkyl refers to an —SR substituent.

Throughout the disclosure, reference to the compounds of Formula I is read as also including all stereoisomers, for example diastereomers, enantiomers, and mixtures thereof. In another embodiment, Formula (I) is read as also including salts or hydrates thereof. Exemplary salts include, but are not limited to: hydrochloride, hydrobromide, hydroiodide, trifluoroacetate, and trifluoromethane sulfonate.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or roots.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

DETAILED DESCRIPTION

The compounds of the present disclosure may be applied by any of a variety of known techniques, either as the compounds or as formulations comprising the compounds. For example, the compounds may be applied to the roots or foliage of plants for the control of various fungi, without damaging the commercial value of the plants. The materials may be applied in the form of any of the generally used formulation types, for example, as solutions, dusts, wettable powders, flowable concentrate, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water-suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water-dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 1 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil-soluble salts or sulfated polyglycol ethers and appropriate salts of phosphated polyglycol ether.

Representative organic liquids which may be employed in preparing the emulsifiable concentrates of the compounds of the present disclosure are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soy bean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 1 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting, and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present disclosure in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank-mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis, Bacillus subtilis* strain QST713, benalaxyl, benomyl, benthiavalicarb-isopropyl, benzovindiflupyr benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofosmethyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

Additionally, the compounds described herein may be combined with other pesticides, including insecticides, nematocides, miticides, arthropodicides, bactericides or combinations thereof that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank-mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and any combinations thereof.

Additionally, the compounds described herein may be combined with herbicides that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank-mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-P, glyphosate, halauxifen, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac, tritosulfuron, vernolate, and xylachlor.

Another embodiment of the present disclosure is a method for the control or prevention of fungal attack. This method comprises applying to the soil, plant, roots, foliage, or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those skilled in the art that the efficacy of the compound for the foregoing fungi establishes the general utility of the compounds as fungicides.

The compounds have broad ranges of activity against fungal pathogens. Exemplary pathogens may include, but are not limited to, causing agent of wheat leaf blotch (*Zymoseptoria tritici*), wheat brown rust (*Puccinia triticina*), wheat stripe rust (*Puccinia striiformis*), scab of apple (*Venturia inaequalis*), powdery mildew of grapevine (*Uncinula necator*), barley scald (*Rhynchosporium secalis*), blast of rice (*Pyricularia oryzae*), rust of soybean (*Phakopsora pachyrhizi*), glume blotch of wheat (*Leptosphaeria nodorum*), powdery mildew of wheat (*Blumeria graminis I* sp. *tritici*), powdery mildew of barley (*Blumeria graminis f.* sp. *hordei*), powdery mildew of cucurbits (*Erysiphe cichoracearum*), anthracnose of cucurbits (*Colletotrichum lagenarium*), leaf spot of beet (*Cercospora beticola*), early blight of tomato (*Alternaria solani*), and spot blotch of barley (*Cochliobolus sativus*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, $g/m^2$).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

General Schemes

The following schemes illustrate approaches to generating picolinamide compounds of Formula (I). The following descriptions and examples are provided for illustrative purposes and should not be construed as limiting in terms of substituents or substitution patterns.

Compounds of Formulae 1.1, 1.2, 1.3, 1.5, 1.6, and 1.8, wherein P.G. is benzyl (Bn) or para-methoxy benzyl (PMB) and $R_3$ is as originally defined, and compounds of Formula 1.10, wherein P.G. is triisopropylsilyl (TIPS) and $R_3$ is as originally defined, can be prepared by the methods shown in Scheme 1, steps a-h. Compounds of Formula 1.0, wherein Z is ethoxy (—$OCH_2CH_3$, OEt) or pyrrolidine and P.G. is Bn or PMB, can be treated with a mixture of an organometallic nucleophile, such as cyclopentylmagnesium bromide, and a reducing agent, such as lithium borohydride ($LiBH_4$), in a polar, aprotic solvent such as tetrahydrofuran (THF) at a reduced temperature of about −20° C. to about 0° C. to afford compounds of Formulae 1.1 and 1.2, wherein $R_3$ is as previously defined, as shown in a. The alcohol of Formula 1.3, wherein P.G. is Bn, can be prepared from the compound of Formula 1.0, wherein Z is OEt and P.G. is Bn, by treating with lithium aluminum hydride (LAH) in an ethereal solvent, such as diethyl ether ($Et_2O$), at a temperature of about 0° C., as shown in b. Additionally, the compound of Formula 1.0, wherein Z is OEt and P.G. is Bn or PMB, can be converted to the aldehyde of Formula 1.4 by treating with a catalyst, such as chlorobis(cyclooctene)iridium(I) dimer ($Ir_2(coe)_4Cl_2$), and a reducing agent, such as diethylsilane ($Et_2SiH_2$), in a halogenated solvent like dichloromethane ($CH_2Cl_2$), as described by Cheng, C.; Brookhart, M. *Angew. Chem. Int. Ed.* 2012, 51, 9422-9424 and shown in c. The compounds of Formulae 1.5 and 1.6, wherein $R_3$ is as previously defined, can be obtained by treating the aldehyde of Formula 1.4 with a carbon nucleophile, for example phenyl magnesium bromide or (E)-prop-1-en-1-ylmagnesium bromide, in a polar, aprotic solvent like THF at a reduced temperature of about −78° C. to about 23° C., as depicted in d. A mixture of compounds of Formulae 1.5 and 1.6, wherein $R_3$ is as previously defined, can be oxidized to give a compound of Formula 1.7, wherein $R_3$ is as originally defined, by treating with an oxidant, such as Dess-Martin Periodinane (DMP), in a solvent like $CH_2Cl_2$ at a temperature of about 0° C. to about 23° C., as shown in e. Compounds of Formula 1.8, wherein $R_3$ is as previously defined, can be prepared by treating compounds of Formula 1.7, wherein $R_3$ is as previously defined, with a reducing agent, such as zinc borohydride, prepared in situ from zinc(II) chloride ($ZnCl_2$) and sodium borohydride ($NaBH_4$), in an ethereal solvent like $Et_2O$ at a temperature of about 0° C. to about 23° C., as depicted in f. The compound of Formula 1.0, wherein P.G. is TIPS, can be treated with a reducing agent, such as diisobutylaluminum hydride (DIBAL), in a halogenated solvent like $CH_2Cl_2$ at a temperature of about −78° C. to about 0° C. to afford the aldehyde of Formula 1.9, as depicted in g. The compound of Formula 1.10 can be prepared from the aldehyde of Formula 1.9 by treating with a nucleophile, such as (+)-$Ipc_2$-allylborane, in an ethereal solvent like $Et_2O$ at a temperature of about −78° C. to about 0° C., as shown in h.

$R_8$ is as previously defined, can be prepared from compounds of Formula 2.1, wherein $R_8$ is as previously defined, by treating with a benzyl (Bn) or p-methoxybenzyl (PMB) protected, lactate-derived aldehyde, such as a compound of Formula 2.2, as shown in b.

Scheme 2

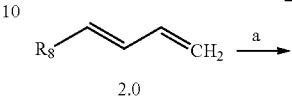

2.0

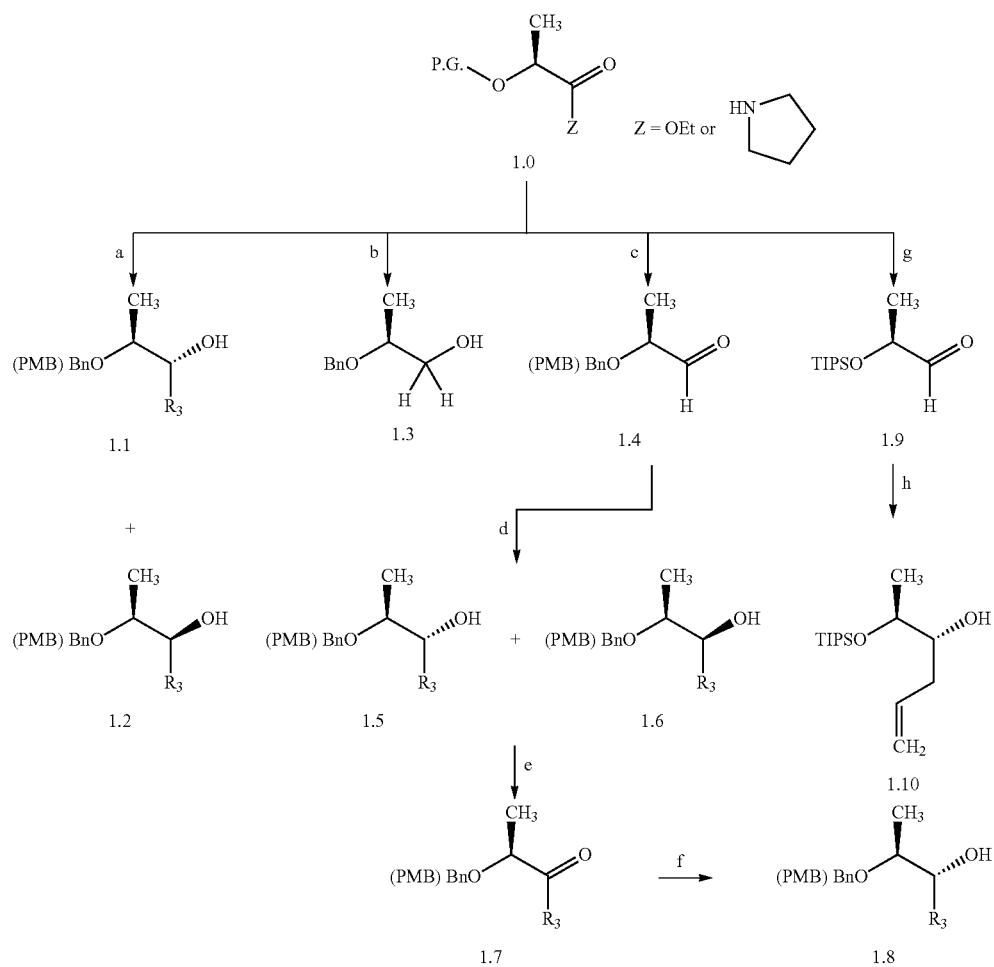

Scheme 1

Compounds of Formula 2.3, wherein $R_8$ is as originally defined, can be prepared by the method shown in Scheme 2, steps a-b. As depicted in a, compounds of Formula 2.1, wherein $R_8$ is as originally defined, can be prepared from compounds of Formula 2.0, wherein $R_8$ is as originally defined, by treating with an alkoxy borane, such as pinacol borane, in the presence of a nickel catalyst, such as bis (cyclooctadiene)nickel(0) ($Ni(cod)_2$), at a temperature of about 0° C. to about 23° C. in an aprotic solvent like toluene, as described by Ely, R. J.; Morken, J. P. *J. Am. Chem. Soc.* 2010, 132, 2534-2535. Compounds of Formula 2.3, wherein -continued

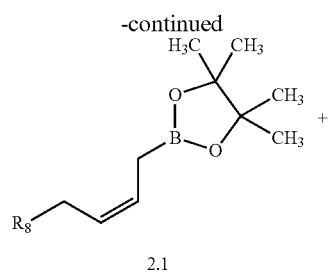

2.1

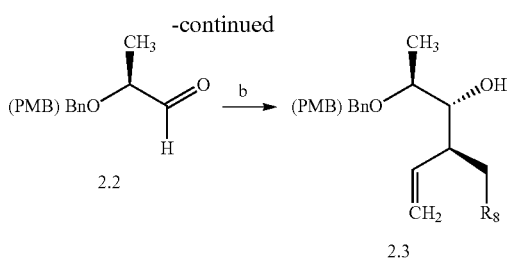

Compounds of Formula 3.2, wherein $R_8$ is as originally defined, can be prepared by the method shown in Scheme 3, steps a-b. Compounds of Formula 3.1, wherein $R_8$ is as originally defined, can be prepared by treating compounds of Formula 3.0, wherein $R_8$ is as originally defined, with an alkyllithium reagent, such as sec-butyllithium, followed by an alkoxyborane, such as B-methoxydiisopinocampheylborane, in a polar, aprotic solvent like THF at a temperature of about −78° C. to about 23° C., as described by Brown, H. C.; Jadhav, P. K.; Bhat, K. S. *J. Am. Chem. Soc.* 1988, 110, 1535-1538, and shown in a. Compounds of Formula 3.2, wherein $R_8$ is as previously defined, can be prepared from compounds of Formula 3.1, wherein $R_8$ is as previously defined, by treating with a Lewis acid, such as borontrifluoride diethyl etherate, followed by a Bn or PMB protected lactate-derived aldehyde, such as a compound of Formula 2.2, at a temperature of about −78° C. to about 23° C., as shown in b.

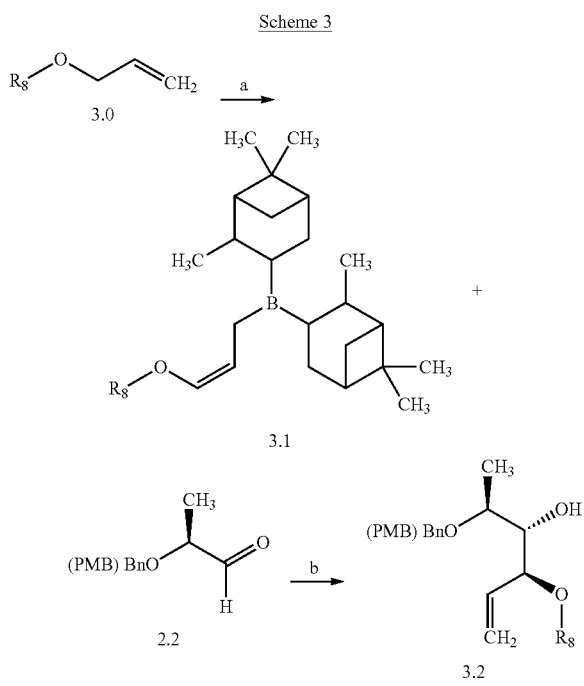

Compounds of Formulae 4.1, 4.2, 4.3, and 4.4, wherein $R_3$ is as originally defined, can be obtained using the methods outlined in Scheme 4, steps a-f Compounds of Formula 4.1, wherein $R_3$ is as previously defined and $R_4$ is acyl, can be prepared from compounds of Formula 4.0, wherein $R_3$ is as previously defined, by treating with an acyl halide, such as isobutyryl chloride, in the presence of a base, such as triethylamine (TEA), and an amine catalyst, such as N,N-dimethylaminopyridine (DMAP), in a halogenated solvent like $CH_2Cl_2$, as shown in a. Compounds of Formula 4.2, wherein $R_3$ is as previously defined and $R_4$ is aryl, can be prepared by treating solutions of compounds of Formula 4.0, wherein $R_3$ is as previously defined, in a solvent like toluene, with an organometallic species, such as bis(acetate-O)triphenyl-bismuth(V) ($Ph_3Bi(OAc)_2$), in the presence of a catalyst, such as copper(II) acetate ($Cu(OAc)_2$), at an elevated temperature of about 50° C., as shown in b. Alternatively, arylated products of Formula 4.2, wherein $R_3$ is as previously defined, can be prepared by treating compounds of Formula 4.0, wherein $R_3$ is as previously defined, with an aryl fluoride, such as 1,3-difluorobenzene, and an alkoxide base, such as potassium tert-butoxide (KOt-Bu), in a polar, aprotic solvent like N,N-dimethyl formamide (DMF) at an elevated temperature of about 50° C. to about 70° C., as shown in c. Compounds of Formula 4.3, wherein $R_3$ is as previously defined and $R_4$ is alkyl, can be prepared from compounds of Formula 4.0, wherein $R_3$ is as previously defined, by treating with a base such as KOt-Bu or sodium hydride (NaH) and an electrophile, for example an alkyl halide like (bromomethyl)cyclopropane, in a polar, aprotic solvent like DMF at an elevated temperature of about 50° C., as shown in d. Compounds of Formula 4.4, wherein $R_3$ is as previously defined and $R_4$ is alkenyl, can be prepared from compounds of Formula 4.0, wherein $R_3$ is as previously defined, by treatment with a base, such as KOt-Bu or NaH, and an allylic electrophile, such as 3-bromo-2-methylprop-1-ene, in a polar, aprotic solvent like DMF at an elevated temperature of about 50° C., as shown in e. Alternatively, compounds of Formula 4.4, wherein $R_3$ is as previously defined and $R_4$ is alkenyl, can be prepared from compounds of Formula 4.0, by treating with a a symmetric or mixed allyl-carbonate, such as tert-butyl cyclopent-2-en-1-yl carbonate, in the presence of a palladium catalyst, for example tris(dibenzylideneacetone)-dipalladium(0) ($Pd_2(dba)_3$), and ligand, such as 1,1′-bis(diphenylphosphino)ferrocene (dppf), in a polar, aprotic solvent like THF at an elevated temperature of about 65° C., as depicted in f.

Scheme 4

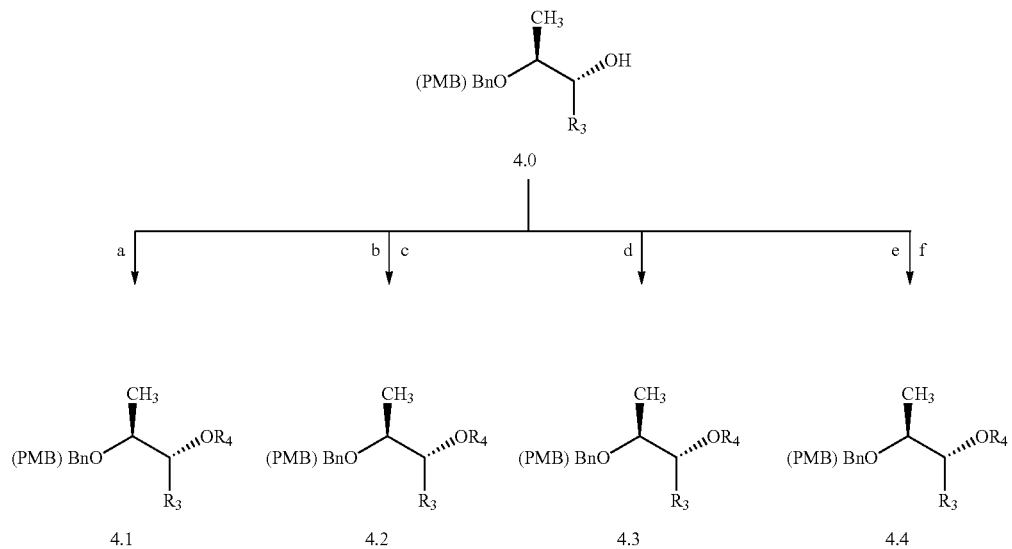

Compounds of Formula 5.1, wherein $R_3$ is as originally defined, but not alkenyl, can be prepared according to the method outlined in Scheme 5. Compounds of Formula 5.0, wherein $R_3$ is as originally defined, but not alkenyl, can be treated with a palladium catalyst like tetrakis(triphenylphosphine)palladium(0) ($Pd(PPh_3)_4$) and a boronate ester or boronic acid, such as phenylboronic acid, in the presence of an alkali carbonate base, such as sodium carbonate ($Na_2CO_3$), in a mixed solvent system, such as aqueous dioxane, at an elevated temperature of about 80° C. to afford compounds of Formula 5.1, wherein $R_3$ is as previously defined, as shown in a.

Scheme 5

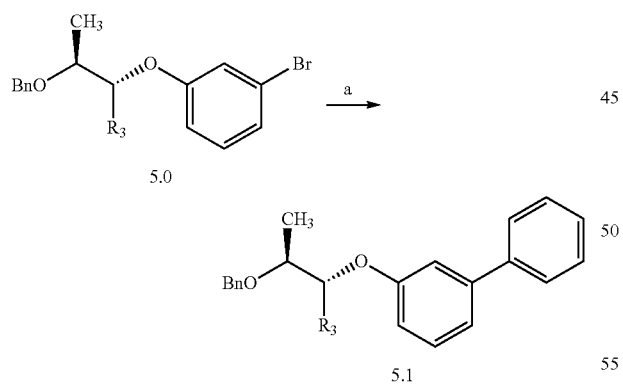

Compounds of Formulae 6.2, 6.4, and 6.5, wherein Z is methylene ($CH_2$) or Oxygen (O), $R_4$ and $R_8$ are as originally defined, but not alkenyl, and $R_{10}$ is alkyl, can be obtained via the methods outlined in Scheme 6, steps a-f Compounds of Formula 6.1, wherein Z is $CH_2$ or O and $R_4$ and $R_8$ are as originally defined, but not alkenyl, can be prepared from compounds of Formula 6.0, wherein Z is $CH_2$ or O and $R_4$ and $R_8$ are as originally defined, but not alkenyl, through standard hydroboration conditions, namely by treating with a borane reagent, such as 9-borabicyclo[3.3.1]nonane (9-BBN), in a polar, aprotic solvent like THF at about 23° C., and oxidation of the resultant boron intermediate by treating with sodium hydroxide (NaOH) and hydrogen peroxide ($H_2O_2$), as shown in a. Compounds of Formula 6.2, wherein Z, $R_4$, $R_8$ and $R_{10}$ are as previously defined, can be prepared by treating compounds of Formula 6.1, wherein Z, $R_4$, and $R_8$ are as previously defined, with an electrophile, such as trimethyloxonium tetrafluoroborate, in the presence of a base, such as N,N,N',N'-tetramethylnaphthalene-1,8-diamine (Proton Sponge®), in a polar, aprotic solvent like $CH_2Cl_2$ at a temperature of about 0° C. to about 23° C., as shown in b. Alternatively, alcohols of Formula 6.1, wherein Z, $R_4$, and $R_8$ are as previously defined, can be further functionalized by treating with a protected aziridine, for example (R)-2-benzyl 1-tert-butyl aziridine-1,2-dicarboxylate, in the presence of a lewis acid, such as scandium(III) triflate ($Sc(OTf)_3$), in an aprotic solvent like $CH_2Cl_2$ at a temperature of about 0° C. to about 23° C., as shown in c. Compounds of Formula 6.3, wherein Z is $CH_2$ or O and $R_4$ and $R_8$ are as originally defined, but not alkenyl, can be prepared by subjecting compounds of Formula 6.0, wherein Z, $R_4$, and $R_8$ are as previously defined, to standard ozonolysis/reduction conditions, namely treatment with ozone ($O_3$) in a solvent mixture such as $CH_2Cl_2$ and methanol (MeOH) at a temperature of about −78° C., followed by the addition of sodium borohydride ($NaBH_4$) and MeOH, as shown in d. Compounds of Formula 6.4, wherein Z, $R_4$, $R_8$, and $R_{10}$ are as previously defined, can be prepared from compounds of Formula 6.3, wherein Z, $R_4$, and $R_8$ are as previously defined, by treatment with an electrophile, such as trimethyloxonium tetrafluoroborate, and a base, such as Proton Sponge®, in an aprotic solvent like $CH_2Cl_2$ at a temperature of about 0° C. to about 23° C., as shown in e. Cyclopropyl compounds of Formula 6.5, wherein Z, $R_4$, and $R_8$ are as previously defined, can be prepared by treating etherial solutions of compounds of Formula 6.0, wherein Z, $R_4$, and $R_8$ are as previously defined, with a dihalomethane reagent, such as diiodomethane, in the presence of diethyl zinc ($Et_2Zn$) at a temperature of about 0° C. to about 23° C., as shown in f.

Scheme 6

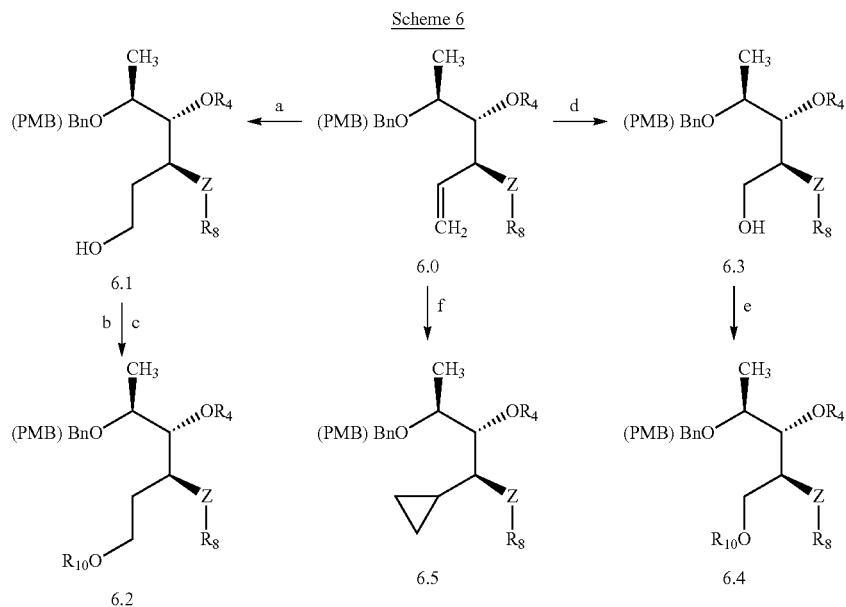

Compounds of Formula 7.2, wherein $R_4$ and $R_{10}$ are as originally defined, can be prepared according to the methods outlined in Scheme 7, steps a-b. Compounds of Formula 7.0, wherein $R_4$ is as originally defined, can be subjected to the ozonolysis conditions described in Scheme 6, step d, to afford compounds of Formula 7.1, wherein $R_4$ is as originally defined, as shown in a. Compounds of Formula 7.2, wherein $R_4$ is as originally defined and $R_{10}$ is alkyl, can be prepared from compounds of Formula 7.1, wherein $R_4$ is as previously defined, by treating with a base, such as NaH, in a polar, aprotic solvent like DMF at a temperature of about 0° C. to about 23° C. and quenching the resultant alkoxide with an electrophile, such as propyl 4-methylbenzenesulfonate, as shown in b. Additionally, compounds of Formula 7.2, wherein $R_4$ is as originally defined and $R_{10}$ is aryl, can be prepared from alcohols of Formula 7.1, wherein $R_4$ is as previously defined, using the arylation conditions described in Scheme 4, step b, as shown in c.

Scheme 7

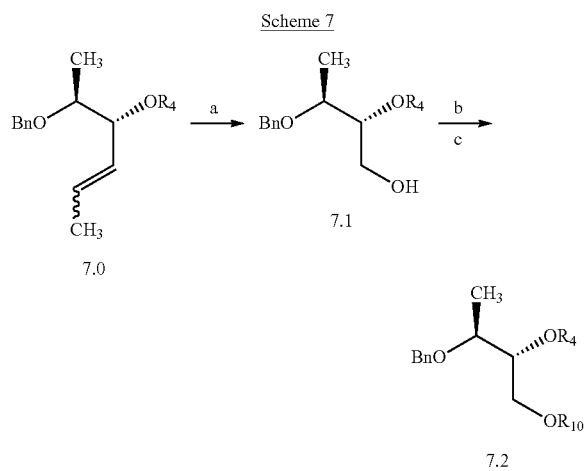

Compounds of Formula 8.3, wherein $R_3$ and $R_4$ are as originally defined, can be prepared according to the methods outlined in Scheme 8, steps a-d. Compounds of Formula 8.3, wherein $R_3$ and $R_4$ are as previously defined, but not alkenyl, can be prepared by treating compounds of Formula 8.0, wherein $R_3$ and $R_4$ are originally defined, with a catalyst, such as palladium on carbon (Pd/C), in the presence of hydrogen gas ($H_2$) in a polar solvent like ethyl acetate (EtOAc) or MeOH or with an alternate source of hydrogen, such as cyclohexene, in a polar solvent like EtOH, as shown in a. Additionally, compounds of Formula 8.0, wherein $R_3$ is as previously defined and $R_4$ is an aryl chloride, can be subjected to modified hydrogenolysis conditions, namely exposing an EtOH solution of the aryl chloride to $H_2$ in the presence of Pd/C and $NEt_3$ to afford compounds of Formula 8.3, wherein $R_3$ and $R_4$ are as originally defined, but $R_3$ is not alkenyl, as shown in b. Compounds of Formula 8.3, wherein $R_3$ and $R_4$ are as originally defined, can be obtained by treating compounds of Formula 8.1, wherein $R_3$ and $R_4$ are as originally defined, with an oxidant, such as 2,3-dichloro-5,6-dicyano-1,4-benzoquinone (DDQ), in a solvent mixture like aqueous $CH_2Cl_2$, as indicated in c. Compounds of Formula 8.3, wherein $R_3$ and $R_4$ are as originally defined, may also be prepared by treating compounds of Formula 8.2, wherein $R_3$ and $R_4$ are as originally defined, with a fluoride source, such as tetra-N-butyl ammonium fluoride (TBAF), in a solvent like THF at a temperature of about 0° C. to about 23° C., as depicted in d.

Scheme 8

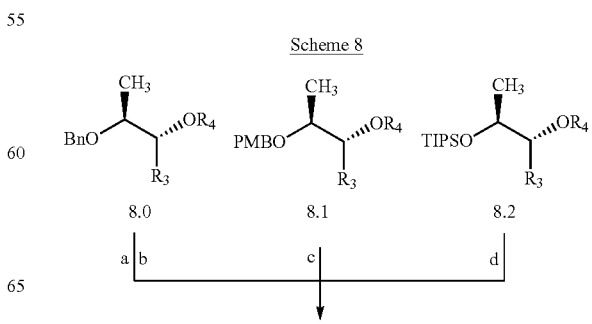

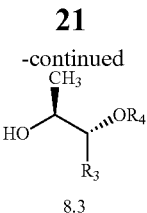

8.3

Compounds of Formula 9.3, wherein $R_3$ is as originally defined, but not alkenyl, can be prepared according to the methods outlined in Scheme 9, steps a-c. As depicted in a, the compound of Formula 9.0 can be treated with a reducing agent, such as $LiBH_4$, and a carbon nucleophile, for example a Grignard reagent like i-propyl magnesium chloride, in a polar, aprotic solvent like THF at a temperature of about $-10°$ C. to about $0°$ C. to afford compounds of Formula 9.1, wherein $R_3$ is as originally defined. Compounds of Formula 9.2, wherein $R_3$ is as originally defined, can be prepared from compounds of Formula 9.1, wherein $R_3$ is as previously defined, by treating with a base, such as KOt-Bu, and quenching the resultant alkoxide anion with an electrophile, such as 1-chloro-3-fluorobenzene, in a polar, aprotic solvent like DMF, as shown in b. Compounds of Formula 9.3, wherein $R_3$ is as previously defined, can be prepared from compounds of Formula 9.2, wherein $R_3$ is as previously defined, using the methodology described in Scheme 8, step b, as shown in c.

Scheme 9

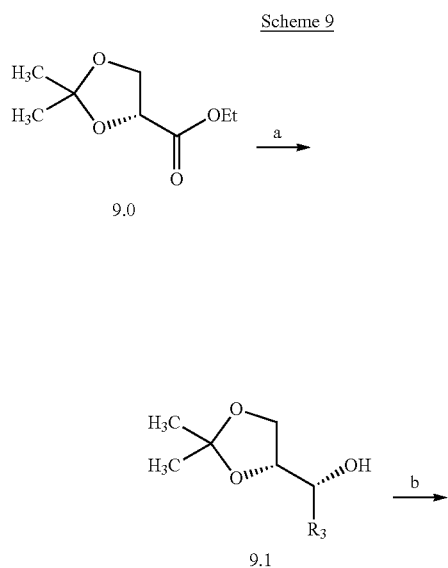

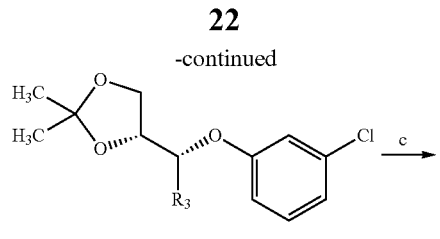

9.2

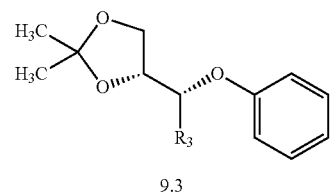

9.3

Compounds of Formula 10.2 and 10.3, wherein $R_2$ and $R_3$ are as originally defined, can be prepared using the methods described in Scheme 10, steps a-d. Compounds of Formula 9.3, wherein $R_3$ is as originally defined, can be treated with an aqueous acid solution, such as 1 normal (N) hydrogen chloride (HCl), to afford diols of Formula 10.0, wherein $R_3$ is as originally defined, as depicted in a. Compounds of Formula 10.1, wherein $R_3$ is as originally defined, can be prepared from compounds of Formula 10.0, wherein $R_3$ is as previously defined, by treating with an oxidant, such as sodium periodate ($NaIO_4$), in a halogenated solvent like $CH_2Cl_2$ at a temperature of about $23°$ C., as shown in b. Aldehydes of Formula 10.1, wherein $R_3$ is as previously defined, can be treated with a reducing agent, such as $NaBH_4$, in a solvent like MeOH at a temperature of about $23°$ C. to afford alcohols of Formula 10.2, wherein $R_2$ and $R_{12}$ are hydrogen and $R_3$ is as previously defined, as shown in c. Additionally, aldehydes of Formula 10.1, wherein $R_3$ is as previously defined, can be treated with a carbon nucleophile, for example a Grignard reagent like ethyl magnesium bromide (EtMgBr), in a polar, aprotic solvent like THF at a temperature of about $-78°$ C. to afford compounds of Formula 10.3, wherein $R_2$ and $R_3$ are as originally defined and $R_{12}$ is hydrogen, as depicted in d.

Scheme 10

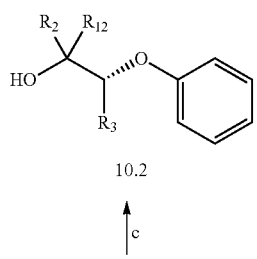

10.2

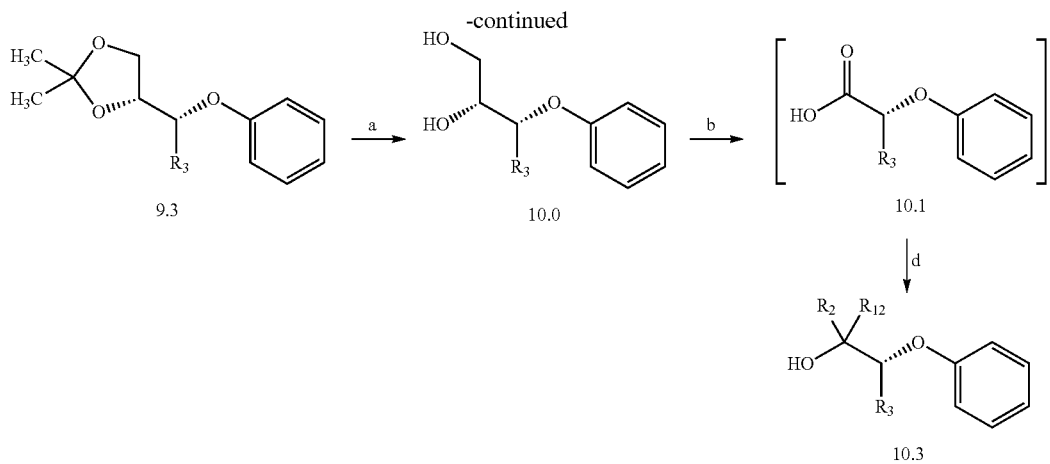

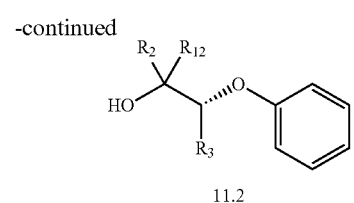

Compounds of Formula 11.2, wherein $R_2$, $R_3$, and $R_{12}$ are as originally defined, can be prepared according to the methods outlined in Scheme 11, steps a-c. As shown in a, acetals of Formula 9.3, wherein $R_3$ is as originally defined, can be treated with an oxidant, such as orthoperiodic acid, in a mixed solvent system, such as acetonitrile ($CH_3CN$), carbon tetrachloride ($CCl_4$), and water ($H_2O$), followed by a second oxidant, such as ruthenium trichloride ($RuCl_3$), to afford carboxylic acids of Formula 11.0, wherein $R_3$ is as originally defined. Compounds of Formula 11.0, wherein $R_3$ is as previously defined, can be treated with trimethylsilyl diazomethane in a solvent mixture like THF, benzene, and MeOH to afford esters of Formula 11.1, wherein $R_3$ is as originally defined, as shown in b. Compounds of Formula 11.2, wherein $R_2$, $R_3$, and $R_{12}$ are as previously defined, can be prepared from esters of Formula 11.1, wherein $R_3$ is as previously defined, by treating with a carbon nucleophile, for example a Grignard reagent like methyl magnesium bromide (MeMgBr) in a mixture of ethereal solvents, such as THF and $Et_2O$, at a temperature of about 0° C. to about 23° C., as shown in c.

Compounds of Formula 12.2, wherein $R_1$, $R_2$, $R_3$, $R_4$, $R_{11}$, and $R_{12}$, are as originally defined, can be prepared according to the method outlined in Scheme 12. Alcohols of Formula 12.0, wherein $R_2$, $R_3$, $R_4$, and $R_{12}$, are as originally defined, can be treated with compounds of Formula 12.1, wherein $R_1$ and $R_{11}$ are as originally defined, a coupling reagent, such as 3-(ethyliminomethyleneamino)-N,N-dimethylpropan-1-amine hydrochloride (EDC) or a polymer-supported carbodiimide (PS-CDI), and a catalyst, such as DMAP, in a halogenated solvent like $CH_2Cl_2$ to afford compounds of Formula 12.2, wherein $R_1$, $R_2$, $R_3$, $R_4$, $R_{11}$, and $R_{12}$ are as previously defined, as shown in a.

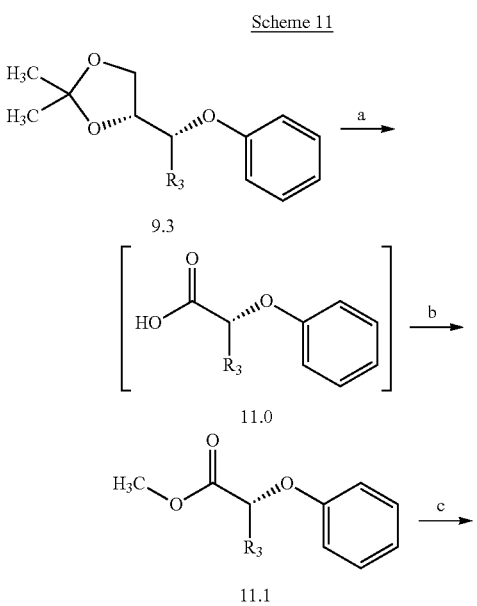

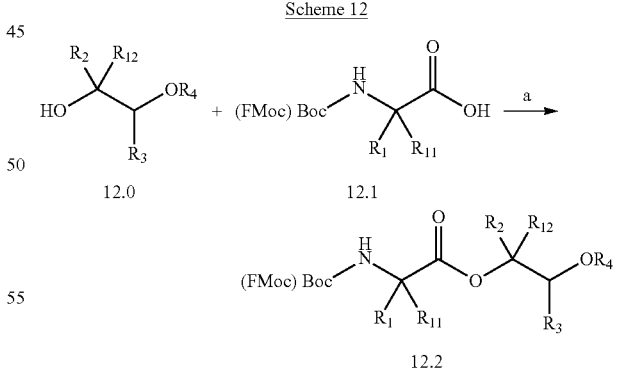

Compounds of Formula 13.3, wherein $R_1$, $R_4$, and $R_{11}$ are as originally defined and $R_8$ is alkyl, can be prepared according to the methods outlined in Scheme 13, steps a-c. As depicted in a, compounds of Formula 13.1, wherein $R_1$, $R_4$, and $R_{11}$ are as originally defined, can be prepared by treating compounds of Formula 13.0, wherein $R_1$, $R_4$, and $R_{11}$ are as originally defined, with di-tert-butyl dicarbonate ($BOC_2O$) and DMAP in an aprotic solvent like $CH_3CN$ at about 23° C. Compounds of Formula 13.2, wherein $R_1$, $R_4$, and $R_{11}$ are as originally defined, can be prepared from compounds of Formula 13.1, wherein $R_1$, $R_4$, and $R_{11}$ are as previously defined, using the ozonolysis conditions described in Scheme 6, step d, as shown in b. Compounds of Formula 13.3, wherein $R_1$, $R_4$, $R_8$, and $R_{11}$ are as previously defined, can be prepared from compounds of Formula 13.2, wherein $R_1$, $R_4$, and $R_{11}$ are as previously defined, using the methodology described in Scheme 6, step b, as shown in c.

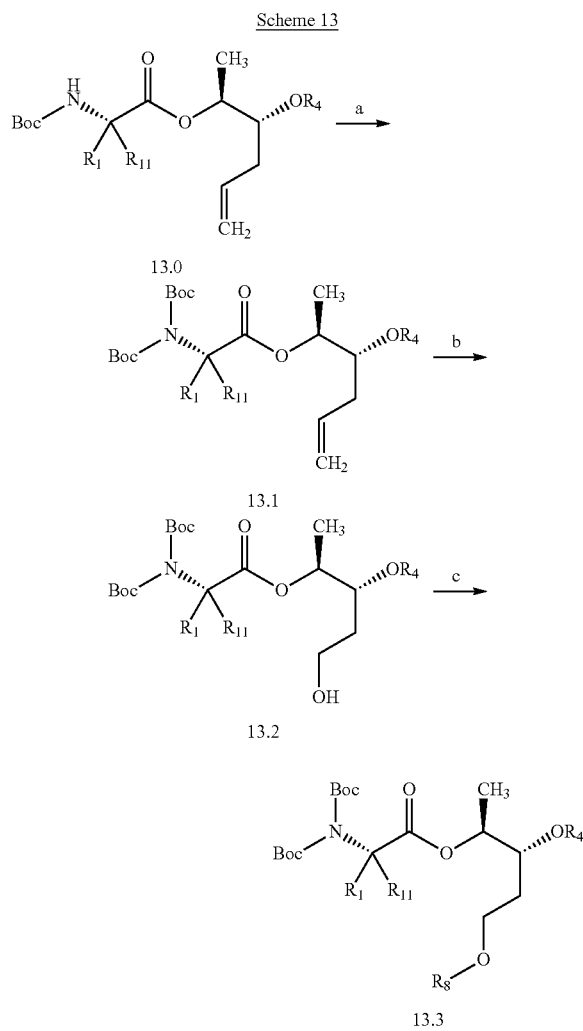

Compounds of Formula 14.7, wherein $R_1$, $R_2$, $R_3$, $R_4$, $R_6$, $R_{11}$, and $R_{12}$ are as originally defined, can be prepared according to the methods outlined in Scheme 14, steps a-e. Compounds of Formula 14.0, wherein $R_1$, $R_2$, $R_3$, $R_4$, $R_{11}$, and $R_{12}$ are as originally defined, but not alkenyl, can be treated with an acid, such as a 4 N solution of HCl in dioxane, in a halogenated solvent like $CH_2Cl_2$ to afford compounds of Formula 14.2, wherein $R_1$, $R_2$, $R_3$, $R_4$, $R_{11}$, and $R_{12}$, are as originally defined, but not alkenyl, as shown in a. Compounds of Formula 14.3, wherein $R_1$, $R_2$, $R_3$, $R_4$, $R_{11}$, and $R_{12}$ are as originally defined, can be prepared by treating compounds of Formula 14.0, wherein $R_1$, $R_2$, $R_3$, $R_4$, $R_{11}$, and $R_{12}$ are as originally defined, with an acid, such as 2,2,2-trifluoroacetic acid, in a halogenated solvent like $CH_2Cl_2$, as shown in b. Compounds of Formula 14.4, wherein $R_1$, $R_2$, $R_3$, $R_4$, $R_{11}$, and $R_{12}$ are as originally defined, can be prepared by treating compounds of Formula 14.0, wherein $R_1$, $R_2$, $R_3$, $R_4$, $R_{11}$, and $R_{12}$ are as originally defined, with a reagent such as trimethylsilyl trifluoromethansulfonate (TMSOTf) and an amine base, such as 2,6-lutidine, in a halogenated solvent like $CH_2Cl_2$, as shown in c. Compounds of Formula 14.5, wherein $R_1$, $R_2$, $R_3$, $R_4$, $R_{11}$, and $R_{12}$ are as previously defined, can be prepared by treating compounds of Formula 14.1, wherein $R_1$, $R_2$, $R_3$, $R_4$, $R_{11}$, and $R_{12}$ are as originally defined, with an amine base, such as morpholine, in a polar, aprotic solvent like THF, as shown in d. Compounds of Formulae 14.2, 14.3, 14.4, and 14.5, wherein $R_1$, $R_2$, $R_3$, $R_4$, $R_{11}$, and $R_{12}$ are as originally defined, can be treated with compounds of Formula 14.6, wherein $R_6$ is as originally defined, in the presence of a base, such as diisopropylethylamine, and a peptide coupling reagent, such as benzotriazol-1-yl-oxytripyrrolidinophosphonium hexafluorophosphate (PyBOP) or O-(7-azabenzo-triazol-1-yl)-N,N,N',N'-tetramethyluronium hexafluorophosphate (HATU), in an halogenated solvent like $CH_2Cl_2$, to afford compounds of Formula 14.7, wherein $R_1$, $R_2$, $R_3$, $R_4$, $R_6$, $R_{11}$, and $R_{12}$ are as previously defined, as shown in e.

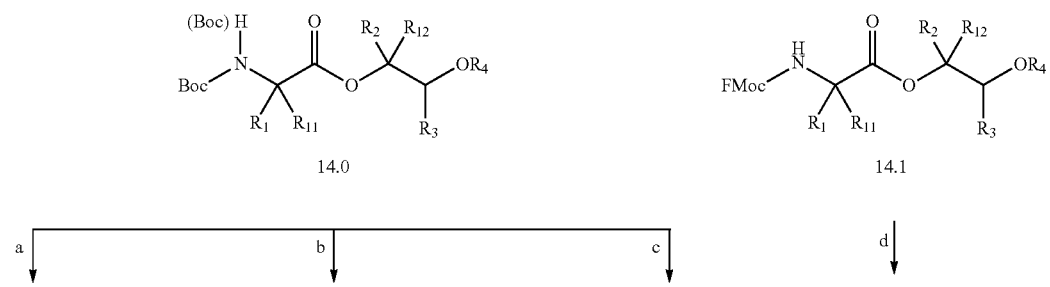

-continued

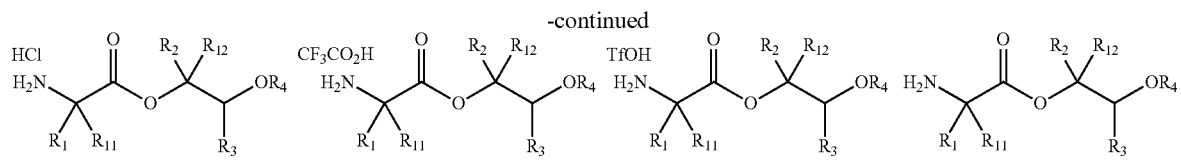

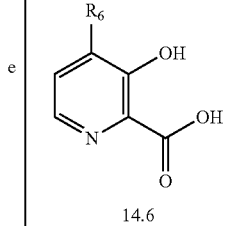

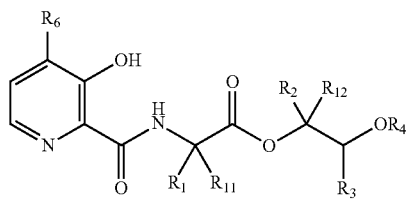

Compounds of Formula 15.1, wherein $R_1$, $R_2$, $R_3$, $R_6$, $R_{11}$, and $R_{12}$ are as originally defined, but not alkenyl, and $R_8$ is as originally defined, but not alkenyl or chloro, can be prepared according to the method outlined in Scheme 15. Compounds of Formula 15.0, wherein $R_1$, $R_2$, $R_3$, $R_6$, $R_8$, $R_{11}$, and $R_{12}$ are as originally defined, can be subjected to the hydrogenation conditions described in Scheme 8, step b to afford compounds of Formula 15.1, wherein $R_1$, $R_2$, $R_3$, $R_6$, $R_8$, $R_{11}$, and $R_{12}$ are as defined above, as depicted in a.

according to the method outlined in Scheme 16. Compounds of Formula 16.0, wherein $R_1$, $R_2$, $R_3$, $R_4$, $R_6$, $R_{11}$, and $R_{12}$ are as previously defined, can be treated with an appropriate alkyl halide with or without a reagent such as sodium iodide (NaI) and an alkali carbonate base, such as $Na_2CO_3$ or potassium carbonate ($K_2CO_3$), in a solvent like acetone or by treatment with an acyl halide in the presence of an amine base, such as pyridine, $NEt_3$, DMAP, or mixtures thereof, in an aprotic solvent such as $CH_2Cl_2$, to afford compounds of Formula 16.1, wherein $R_1$, $R_2$, $R_3$, $R_4$, $R_6$, $R_7$, $R_{11}$, and $R_{12}$ are as previously defined, as shown in a.

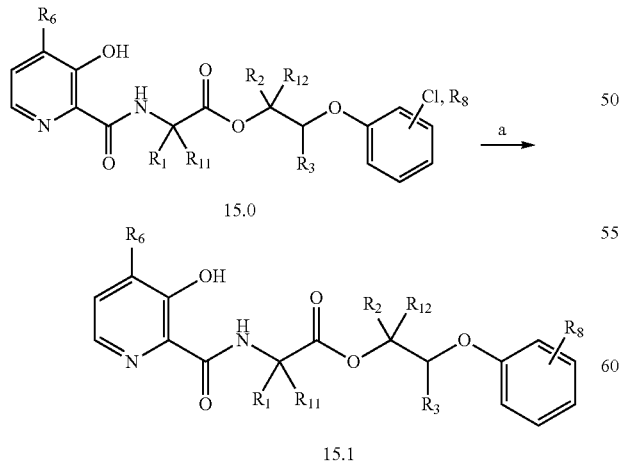

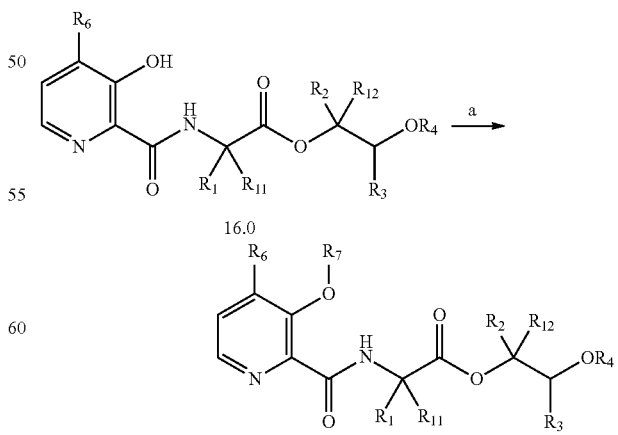

Compounds of Formula 16.1, wherein $R_1$, $R_2$, $R_3$, $R_4$, $R_6$, $R_7$, $R_{11}$, and $R_{12}$ are as originally defined, can be prepared

EXAMPLES

Example 1A: Preparation of (2S,3R)-2-(benzyloxy)-4-ethylhexan-3-ol and (2S,3S)-2-(benzyloxy)-4-ethylhexan-3-ol

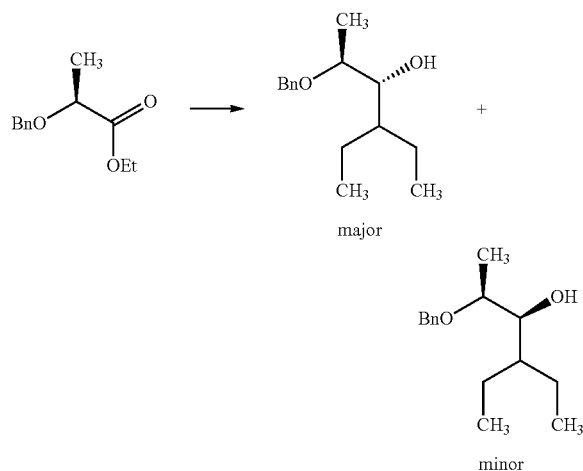

To a solution of pentan-3-ylmagnesium bromide (77.0 milliliters (mL), 154 millimoles (mmol)) and lithium borohydride (LiBH$_4$; 49.9 mL, 100 mmol, 2 molar (M) in THF) in THF (400 mL) at −5° C. was added neat (S)-ethyl 2-(benzyloxy)propanoate (16.0 grams (g), 77.0 mmol) dropwise via syringe pump addition over approximately a 1 hour (h) period, at a rate which maintained the internal temperature below −3° C. The reaction vessel was allowed to slowly warm to room temperature overnight, and the reaction mixture was quenched by slowly adding the mixture to water (H$_2$O, 300 mL) over a 30 minute (min) period. The mixture was diluted with diethyl ether (Et$_2$O; 300 mL), the phases were separated, and the aqueous (aq.) phase was extracted with Et$_2$O (2×100 mL). The combined organic phases were washed with saturated (sat.) aq. sodium chloride (NaCl, brine; 300 mL), dried over magnesium sulfate (MgSO$_4$), filtered, and concentrated. The resulting oil was purified by flash column chromatography (silica gel (SiO$_2$), 0→15% ethyl acetate (EtOAc) in hexanes) to afford the title compounds (9.61 g, 53% and 3.46 g, 19%, respectively) as colorless oils:

major: IR (Thin film) 3471, 3031, 2962, 2932, 2874, 1454, 1382 cm$^{-1}$; $^1$H NMR (400 MHz, CDCl$_3$) δ 7.38-7.26 (m, 5H), 4.60 (d, J=11.8 Hz, 1H), 4.51 (d, J=11.8 Hz, 1H), 3.68 (ddd, J=7.4, 3.6, 2.7 Hz, 1H), 3.63 (qd, J=6.2, 3.7 Hz, 1H), 2.05 (d, J=2.8 Hz, 1H), 1.65 (dq, J=9.9, 7.4 Hz, 1H), 1.44-1.34 (m, 2H), 1.36-1.18 (m, 2H), 1.18 (d, J=6.2 Hz, 3H), 0.88 (t, J=7.3 Hz, 3H), 0.84 (t, J=7.4 Hz, 3H); $^{13}$C NMR (101 MHz, CDCl$_3$) δ 138.53, 128.41, 127.63, 127.60, 75.65, 73.56, 70.50, 41.34, 20.59, 20.51, 13.13, 10.44, 10.29;

minor: IR (Thin film) 3472, 3031, 2961, 2932, 2874, 1497, 1454, 1376 cm$^{-1}$; $^1$H NMR (400 MHz, CDCl$_3$) δ 7.39-7.32 (m, 4H), 7.32-7.26 (m, 1H), 4.68 (d, J=11.3 Hz, 1H), 4.44 (d, J=11.4 Hz, 1H), 3.66-3.54 (m, 1H), 3.43 (dt, J=6.8, 3.8 Hz, 1H), 2.43 (dd, J=4.0, 0.8 Hz, 1H), 1.54-1.36 (m, 3H), 1.36-1.23 (m, 2H), 1.19 (d, J=6.1 Hz, 3H), 0.90 (t, J=7.4 Hz, 3H), 0.89 (t, J=7.3 Hz, 3H); $^{13}$C NMR (101 MHz, CDCl$_3$) δ 138.40, 128.46, 127.79, 127.73, 76.67, 76.07, 70.99, 42.65, 22.73, 20.79, 15.78, 11.98, 11.65.

Example 1B, Step 1: Preparation of (S)-2-((4-methoxybenzyl)oxy)propanal

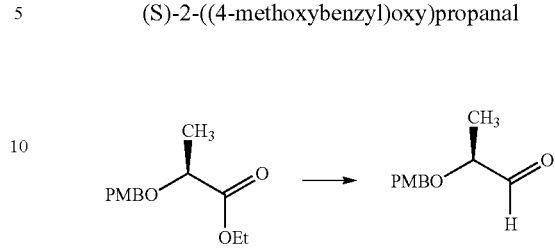

To a solution of (S)-ethyl 2-((4-methoxybenzyl)oxy)propanoate (5.00 g, 21.0 mmol) in CH$_2$Cl$_2$ (30 mL) at 0° C. was added chlorobis(cyclooctene)iridium(I) dimer (Ir$_2$Cl$_2$(coe)$_4$; 94.0 milligrams (mg), 0.105 mmol) followed by diethylsilane (Et$_2$SiH$_2$; 4.08 mL, 31.5 mmol) over a 10 min period. The mixture was stirred at 0° C. for 30 min, warmed to room temperature and stirred for 3 h, cooled to 0° C., and quenched by adding 1 normal (N) aq. hydrogen chloride (HCl; 12 mL). The resulting solution was warmed to room temperature and stirred for 15 min. The phases were separated and the aq. phase was extracted with CH$_2$Cl$_2$ (3×30 mL). The combined organic phases were washed with brine, dried over sodium sulfate (Na$_2$SO$_4$), filtered, evaporated, and purified by flash column chromatography (SiO$_2$, 2→50% acetone in hexanes) to afford the title compound (4.27 g, 100%) as a yellow oil: IR (Thin film) 2934, 2837, 2865, 1731, 1512 cm$^{-1}$; $^1$H NMR (300 MHz, CDCl$_3$) δ 9.64 (d, J=1.9 Hz, 1H), 7.35-7.21 (m, 2H), 6.95-6.79 (m, 2H), 4.63-4.40 (m, 2H), 3.94-3.76 (m, 1H), 3.81 (s, 3H), 1.31 (d, J=6.9 Hz, 3H); $^{13}$C NMR (101 MHz, CDCl$_3$) δ203.58, 159.54, 129.65, 129.37, 113.98, 79.14, 71.75, 55.30, 15.34.

Example 1B, Step 2: Preparation of (1S,2S)-2-((4-methoxybenzyl)oxy)-1-phenylpropan-1-ol

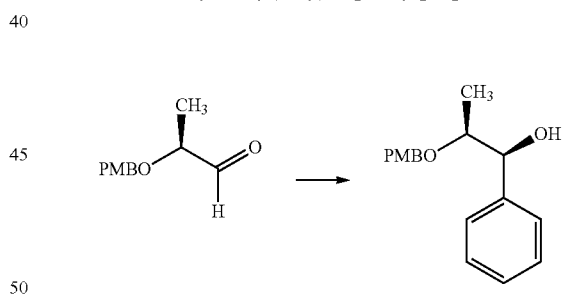

To a solution of (S)-2((4-methoxybenzyl)oxy)propanal (3.38 g, 17.4 mmol) in Et$_2$O (58 mL) at −78° C. was added phenylmagnesium bromide (34.8 mL, 34.8 mmol, 1 M in THF) dropwise, and the reaction mixture was allowed to warm to room temperature, stirred overnight, and quenched by the addition of sat. aq. ammonium chloride (NH$_4$Cl). The mixture was partitioned between H$_2$O and EtOAc, the phases were separated, and the aq. phase was extracted with EtOAc (2×). The combined organic phases were washed with brine, dried over Na$_2$SO$_4$, filtered, evaporated, and purified by flash column chromatography (SiO$_2$, 2→50% acetone in hexanes) to afford an inseparable mixture of diastereomers (d.r. 3:1 SS:RS) of the title compound (3.29 g, 66%) as a yellow oil: $^1$H NMR (400 MHz, CDCl$_3$; major) δ 7.37-7.25 (m, 7H), 6.89 (d, J=8.6 Hz, 2H), 4.62 (d, J=11.0 Hz, 1H), 4.44 (dd, J=7.8, 2.1 Hz, 1H), 4.41 (d, J=11.0 Hz, 1H), 3.82 (s, 3H), 3.60 (dq, J=7.8, 6.2 Hz, 1H), 3.21 (d, J=2.1 Hz, 1H), 1.05 (d, J=6.2 Hz, 3H); $^{13}$C NMR (101 MHz, CDCl$_3$) δ 159.34, 140.56, 130.21, 129.46, 128.31, 127.25, 126.31, 113.93, 79.66, 78.32, 70.92, 55.30, 15.56; ESIMS m/z 295 (([M+Na]$^+$)).

Example 1B, Step 3: Preparation of (S,E)-2-(benzyloxy)hex-4-en-3-one

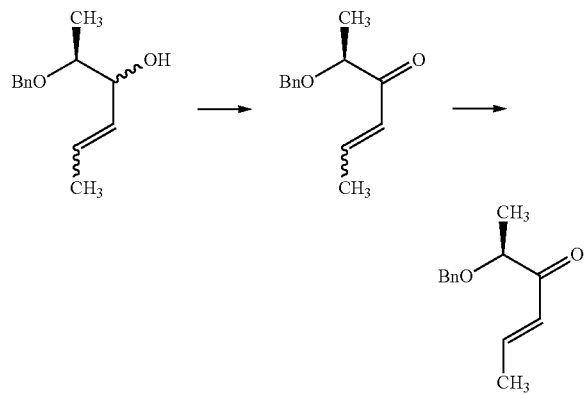

To a solution of (2S)-2-(benzyloxy)hex-4-en-3-ol (1.3 g, 6.30 mmol) and sodium bicarbonate (NaHCO$_3$; 0.582 g, 6.93 mmol) in CH$_2$Cl$_2$ (25.2 mL) at 0° C. was added Dess-Martin Periodinane (DMP; 2.94 g, 6.93 mmol), and the reaction mixture was removed from the cold bath, stirred at room temperature for 6 h, and quenched by the addition of sat. aq. sodium thiosulfate (Na$_2$S$_2$O$_3$; 10 mL). The mixture was diluted with CH$_2$Cl$_2$ (10 mL) and the biphasic solution was stirred vigorously for 15 min, diluted with H$_2$O (10 mL), and the phases were separated. The aq. phase was extracted with CH$_2$Cl$_2$ (2×15 mL) and the combined organic phases were washed successively with sat. aq. NaHCO$_3$ (10 mL), H$_2$O (20 mL), and brine (20 mL), dried over Na$_2$SO$_4$, filtered, and concentrated. The crude residue was purified by flash column chromatography (SiO$_2$, 0→50% EtOAc in hexanes) to afford the title compound (480 mg, 37%) and (S,Z)-2-((4-methoxybenzyl)oxy)hex-4-en-3-one, the latter of which was dissolved in CH$_2$Cl$_2$ (5 mL) and stirred in the presence of DABCO (10 mg) for 18 h to afford additional title compound (400 mg, 31%): $^1$H NMR (400 MHz, CDCl$_3$) δ 7.40-7.26 (m, 5H), 7.08 (dq, J=15.6, 6.9 Hz, 1H), 6.55 (dq, J=15.6, 1.7 Hz, 1H), 4.57 (d, J=11.7 Hz, 1H), 4.43 (d, J=11.7 Hz, 1H), 4.05 (q, J=6.9 Hz, 1H), 1.93 (dd, J=6.9, 1.7 Hz, 3H), 1.36 (d, J=6.9 Hz, 3H); $^{13}$C NMR (101 MHz, CDCl$_3$) δ 201.11, 144.70, 137.66, 128.45, 127.84, 126.07, 80.00, 71.76, 18.56, 18.00; ESIMS m/z 205 (([M+H]$^+$)).

Example 1B, Step 4: Preparation of (2S,3R,E)-2-(benzyloxy)hex-4-en-3-ol

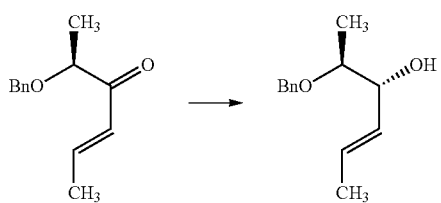

To a solution of NaBH$_4$ (445 mg, 11.8 mmol) in Et$_2$O (15.7 mL) at 0° C. was added zinc(II) chloride (ZnCl$_2$; 5.90 mL, 5.87 mmol, 1 M in Et$_2$O), and the mixture was removed from the cold bath and stirred at room temperature for 18 h. The reaction mixture was cooled to 0° C., treated dropwise with a solution of (S,E)-2-(benzyloxy)hex-4-en-3-one (800 mg, 3.92 mmol) in Et$_2$O (2 mL) and stirred for 2 h. The reaction mixture was warmed to room temperature, stirred at room temperature for 3 h, diluted with THF (5 mL) and stirring continued for an additional 1 h, and then quenched by the careful addition of sat. aq. NH$_4$Cl (25 mL). The phases were separated and the aq. phase was extracted with Et$_2$O (3×20 mL). The combined organic phases were washed with brine (10 mL), dried over Na$_2$SO$_4$, filtered, evaporated, and the crude residue was purified by flash column chromatography (SiO$_2$, 0→35% EtOAc in hexanes) to afford the title compound (620 mg, 77%) as a colorless oil: $^1$H NMR (400 MHz, CDCl$_3$) δ 7.38-7.24 (m, 5H), 5.80-5.66 (m, 1H), 5.55-5.43 (m, 1H), 4.63 (d, J=11.8 Hz, 1H), 4.53 (d, J=11.8 Hz, 1H), 4.20-4.12 (m, 1H), 3.57 (qd, J=6.4, 3.4 Hz, 1H), 2.28-2.22 (m, 1H), 1.75-1.68 (m, 3H), 1.14 (d, J=6.3 Hz, 3H); $^{13}$C NMR (101 MHz, CDCl$_3$) δ 138.54, 129.43, 128.68, 128.42, 127.64, 77.76, 74.62, 70.86, 17.91, 14.20; ESIMS m/z 229 (([M+Na]$^+$)).

Example 1C, Step 1: Preparation of (S)-2-((triisopropylsilyl)oxy)propanal

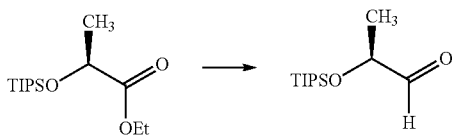

To a solution of (S)-ethyl 2-((triisopropylsilyl)oxy)propanoate (20.5 g, 74.7 mmol) in CH$_2$Cl$_2$ (373 mL) at −78° C. was added a solution of diisopropylaluminum hydride (DIBAL; 149 mL, 149 mmol, 1 M in CH$_2$Cl$_2$) over 4 h, and the reaction mixture was stirred at −78° C. for an additional 30 min, quenched with EtOAc (75 mL), and warmed to 0° C. The heterogeneous mixture was treated with aq. sodium tartrate (~200 mL) and the mixture was warmed to room temperature and stirred vigorously overnight. The phases were separated and the aq. phase was extracted with CH$_2$Cl$_2$ (2×150 mL). The combined organic phases were dried over Na$_2$SO$_4$, filtered, and concentrated to an oil, which was purified by flash column chromatography (SiO$_2$, 0→10% EtOAc in hexanes) to afford the title compound (12.64 g, 70%) as a clear, colorless oil: $^1$H NMR (400 MHz, CDCl$_3$) δ 9.66 (d, J=1.7 Hz, 1H), 4.18 (qd, J=6.8, 1.7 Hz, 1H), 1.31 (d, J=6.8 Hz, 3H), 1.07 (td, J=5.6, 5.0, 3.2 Hz, 21H); $^{13}$C NMR (101 MHz, CDCl$_3$) δ 204.58, 73.82, 18.95, 17.89, 12.14; EIMS m/z 187 [M-i-Pr]$^+$.

Example 1C, Step 2: Preparation of (2S,3R)-2-((triisopropylsilyl)oxy)hex-5-en-3-ol

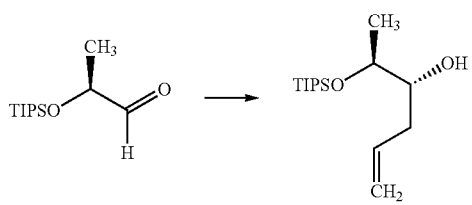

To a solution of (+)-Ipc$_2$-allylborane (25.0 mL, 25.0 mmol, 1 M in pentane) in Et$_2$O (100 mL) at −78° C. was added a solution of (S)-2-((triisopropylsilyl)oxy)propanal (4.61 g, 20.0 mmol) in Et$_2$O (60 mL) over 1.5 h, and the reaction mixture was stirred at −78° C. for an additional 1.5 h, treated with MeOH (50 mL), and stirred for 5 min. The mixture was treated with pH 7 buffer (70 mL), warmed to 0° C., and treated with 30% aq. H$_2$O$_2$ (60 mL). The reaction mixture was stirred at at 0° C. for 2.5 h, allowed to slowly warm to room temperature, and stirred for 30 h. The phases were separated and the aq. phase was extracted with Et$_2$O (3×100 mL). The combined organic phases were dried over MgSO$_4$, filtered, and concentrated to a clear oil, which was purified by flash column chromatography (SiO$_2$, 0→15% EtOAc in hexanes) to afford the title compound (5.00 g, 87%) as a clear, slightly rose-colored oil: IR (neat) 3480, 2943, 2866, 1463, 1067, 881 cm$^{-1}$; $^1$H NMR (400 MHz, CDCl$_3$) δ 5.85 (ddt, J=17.2, 10.2, 7.0 Hz, 1H), 5.22-4.97 (m, 2H), 3.93 (qd, J=6.2, 3.3 Hz, 1H), 3.70 (ddt, J=8.3, 5.7, 2.9 Hz, 1H), 2.34 (d, J=2.6 Hz, 1H), 2.30-2.09 (m, 2H), 1.14 (d, J=6.3 Hz, 3H), 1.12-1.03 (m, 21H); HRMS-ESI (m/z) ([M+H]$^+$) calcd for C$_{15}$H$_{33}$O$_2$Si, 274.2270; found, 274.2274.

Example 1D: Preparation of (S)-2-(benzyloxy)propan-1-ol

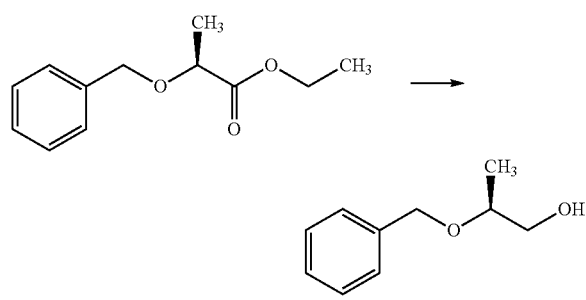

To a solution of LAH (48.0 ml, 24.0 mmol, 0.5M in Et$_2$O) at 0° C. was added (9-ethyl 2-(benzyloxy)propanoate (5.00 g, 24.0 mmol) dropwise over a 10 min period, and the reaction mixture was stirred at 0° C. for 3 h, quenched slowly by the successive addition of H$_2$O (900 μL), 1N NaOH (900 μL), and water (2.7 mL). The resulting slurry was stirred for 10 min at room temperature, treated with Na$_2$SO$_4$, and the mixture was filtered through Celite®. The filtrate was concentrated to provide the title compound (4.00 g, 24.1 mmol, 100%) as a colorless oil: $^1$H NMR (400 MHz, CDCl$_3$) δ 7.41-7.26 (m, 5H), 4.65 (d, J=11.6 Hz, 1H), 4.48 (d, J=11.6 Hz, 1H), 3.74-3.56 (m, 2H), 3.49 (ddd, J=11.5, 7.0, 4.6 Hz, 1H), 2.21 (dd, J=7.9, 4.6 Hz, 1H), 1.17 (d, J=6.2 Hz, 3H); $^{13}$C NMR (101 MHz, CDCl$_3$) δ 138.46, 128.48, 127.75, 127.73, 75.57, 70.82, 66.36, 15.89; EIMS m/z 166.

Example 1E: Preparation of (1S,2S)-2-((4-methoxybenzyl)oxy)-1-(thiophen-2-yl)propan-1-ol and (1R,2S)-2((4-methoxybenzyl)oxy)-1-(thiophen-2-yl)propan-1-ol

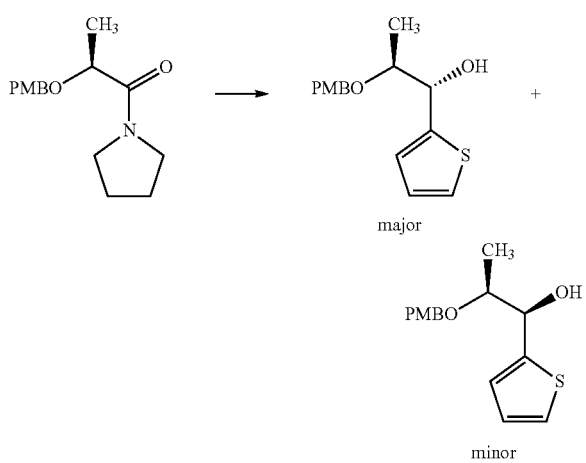

To a solution of thiophen-2-yllithium (4.00 mL, 4.00 mmol, 1 M in THF) and lithium borohydride (LiBH$_4$; 1.30 mL, 2.60 mmol, 2 M in THF) in THF (10 mL) at −10° C. was added neat (9-2((4-methoxybenzyl)oxy)-1-(pyrrolidin-1-yl)propan-1-one (0.527 g, 2.00 mmol) (for preparation see: Pellicena, M.; Solsona, J. G.; Romea, P.; Urpi, F. *Tetrahedron* 2012, 68, 10338.) dropwise via syringe pump addition over approximately a 1 h period, at a rate which maintained the internal temperature below −5° C. The reaction vessel was allowed to slowly warm to room temperature overnight, and the reaction mixture was quenched by the addition of sat. aq. NH$_4$Cl. The aq. phase was extracted with Et$_2$O (3×). The combined organic phases were washed with brine, dried over Na$_2$SO$_4$, filtered, evaporated, and purified by flash column chromatography (SiO$_2$, 2→10% acetone in hexanes) to afford the title compounds (0.231 g, 41% and 0.175 g, 31%, respectively) as colorless oils:

major: $^1$H NMR (300 MHz, CDCl$_3$) δ 7.32-7.21 (m, 3H), 7.05-6.93 (m, 2H), 6.94-6.83 (m, 2H), 5.03 (t, J=4.2 Hz, 1H), 4.61 (d, J=11.4 Hz, 1H), 4.48 (d, J=11.3 Hz, 1H), 3.81 (s, 3H), 3.88-3.73 (m, 1H), 2.59 (d, J=4.4 Hz, 1H), 1.13 (d, J=6.3 Hz, 3H); ESIMS m/z 579 ([2M+Na]$^+$).

minor: $^1$H NMR (300 MHz, CDCl$_3$) δ 7.34-7.22 (m, 3H), 7.06-6.92 (m, 2H), 6.95-6.84 (m, 2H), 4.73 (dd, J=7.3, 2.7 Hz, 1H), 4.63 (d, J=10.9 Hz, 1H), 4.44 (d, J=11.0 Hz, 1H), 3.82 (s, 3H), 3.67 (dq, J=7.3, 6.2 Hz, 1H), 3.29 (d, J=2.8 Hz, 1H), 1.14 (d, J=6.1 Hz, 3H); ESIMS m/z 579 ([2M+Na]$^+$).

Example 2: Preparation of (2S,3R,4S)-4-benzyl-2-(benzyloxy)hex-5-en-3-ol

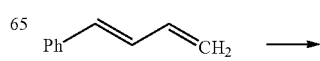

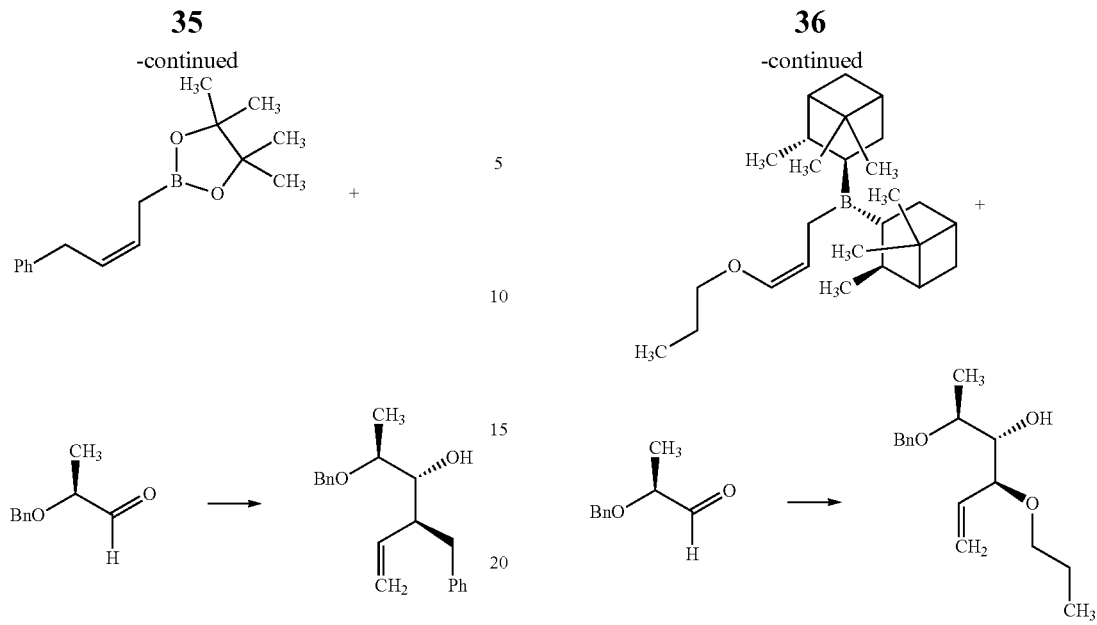

To a round-bottom flask were added bis(cyclooctadiene) nickel(0) (Ni(cod)$_2$; 0.168 g, 0.609 mmol) and tricyclohexylphosphine (P(C$_6$H$_{11}$)$_3$; 0.213 g, 0.761 mmol) under an inert atmosphere (nitrogen gas (N$_2$) glove bag), and the flask was capped and removed from the bag. The mixture was diluted with toluene (22 mL) and 4,4,5,5-tetramethyl-1,3,2-dioxaborolane (6.63 mL, 45.7 mmol) was added at room temperature. The reaction mixture was cooled to 0° C. in an ice bath and treated with neat (E)-buta-1,3-dien-1-ylbenzene (4.76 g, 36.5 mmol) dropwise over a 10 min period. The mixture was removed from the ice bath and stirred at room temperature for 2 h, cooled to −78° C. in a dry ice/acetone bath, and treated with (S)-2-(benzyloxy)propanal (5.00 g, 30.5 mmol) followed by BF$_3$.OEt$_2$(0.376 mL, 3.05 mmol). The reaction mixture was allowed to slowly warm to room temperature overnight and quenched by treating with MeOH (5 mL). After stirring for 30 min, the reaction mixture was concentrated and purified by flash column chromatography (SiO$_2$, 0→50% EtOAc in hexanes) to afford the title compound (8.95 g, 99%) as a colorless oil: $^1$H NMR (400 MHz, CDCl$_3$) δ 7.39-7.30 (m, 3H), 7.32-7.25 (m, 1H), 7.25-7.21 (m, 2H), 7.20-7.11 (m, 4H), 5.45 (ddd, J=17.2, 10.3, 9.5 Hz, 1H), 4.93 (dd, J=10.3, 1.8 Hz, 1H), 4.79 (ddd, J=17.2, 1.9, 0.7 Hz, 1H), 4.55 (d, J=11.7 Hz, 1H), 4.46 (d, J=11.7 Hz, 1H), 3.76 (ddd, J=9.2, 3.2, 2.2 Hz, 1H), 3.56 (qd, J=6.3, 3.1 Hz, 1H), 3.19 (dd, J=13.3, 3.5 Hz, 1H), 2.58 (dd, J=13.4, 9.3 Hz, 1H), 2.39 (dt, J=9.2, 3.4 Hz, 1H), 2.37 (d, J=2.3 Hz, 1H), 1.17 (d, J=6.3 Hz, 3H); $^{13}$C NMR (101 MHz, CDCl$_3$) δ 139.92, 138.48, 137.37, 129.81, 128.46, 127.94, 127.70, 127.66, 125.76, 117.21, 76.22, 73.78, 70.56, 48.44, 37.63, 12.21; ESIMS m/z 319 q[M+Na]$^+$)).

Example 3: Preparation of (2S,3S,4S)-2-(benzyloxy)-4-phenoxyhex-5-en-3-ol

To a solution of 3-propoxyprop-1-ene (5.77 g, 57.6 mmol) in THF (87 mL) at −78° C. was slowly added a solution of sec-butyllithium (s-BuLi; 37.4 mL, 52.4 mmol, 1.4 M in cyclohexane), and the resulting solution was stirred for 40 min at −78° C., treated with methoxybis((2S,3R)-2,6,6-trimethylbicyclo[3.1.1]heptan-3-yl)borane (16.57 g, 52.4 mmol), and stirred at −78° C. for an additional 2.5 h. The reaction mixture was warmed to 0° C. and quenched at 0° C. by the slow addition of aq. 1 N sodium hydroxide (NaOH; 63 mL) followed by 30% aq. hydrogen peroxide (H$_2$O$_2$; 21 mL). The resulting mixture was warmed to room temperature and stirred overnight. The phases were separated and the aq. phase was extracted with Et$_2$O (3×), and the combined organic extracts were washed with H$_2$O and brine, dried over Na$_2$SO$_4$, filtered, and evaporated. The resulting crude oil was purified by Kugelrhor distillation (Temperature (T)=60° C., 0.4-0.6 millimeters (mm) Hg) to afford the title compound (10.6 g, 77%) as a slightly yellow oil: $^1$H NMR (400 MHz, CDCl$_3$) δ 7.37-7.33 (m, 4H), 7.32-7.26 (m, 1H), 5.76 (ddd, J=17.2, 10.4, 7.5 Hz, 1H), 5.28 (ddd, J=8.9, 1.8, 0.9 Hz, 1H), 5.28-5.22 (m, 1H), 4.61 (d, J=11.6 Hz, 1H), 4.48 (d, J=11.7 Hz, 1H), 3.83 (ddt, J=7.5, 4.5, 0.9 Hz, 1H), 3.58 (p, J=6.1 Hz, 1H), 3.53-3.43 (m, 2H), 3.18 (dt, J=9.1, 6.6 Hz, 1H), 2.42 (d, J=5.8 Hz, 1H), 1.62-1.45 (m, 2H), 1.27 (d, J=6.2 Hz, 3H), 0.90 (t, J=7.4 Hz, 3H); $^{13}$C NMR (101 MHz, CDCl$_3$) δ 138.59, 135.88, 128.34, 127.77, 127.54, 118.33, 80.16, 76.18, 74.70, 70.69, 70.47, 23.01, 15.25, 10.70; HRMS-ESI (m/z) ([M+H]$^+$) calcd for C$_{16}$H$_{25}$O$_3$, 265.1798; found, 265.1793.

Example 4A: Preparation of (S)-2-(benzyloxy)propyl isobutyrate

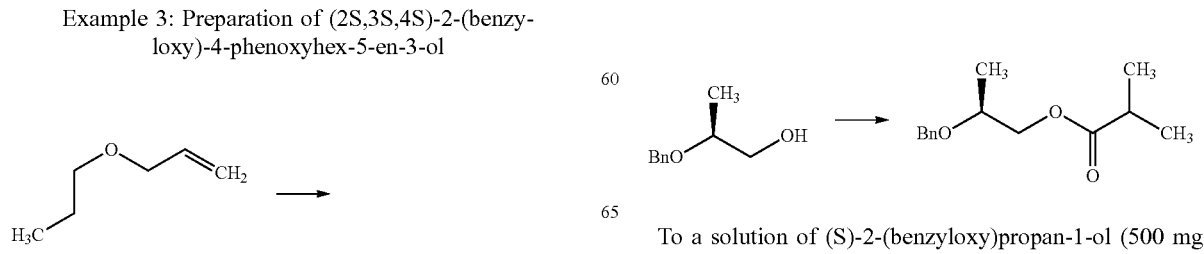

To a solution of (S)-2-(benzyloxy)propan-1-ol (500 mg, 3.01 mmol) in anhydrous CH$_2$Cl$_2$ (10 mL) were added triethylamine (NEt₃; 839 microliters (µL), 6.02 mmol), DMAP (36.7 mg, 0.301 mmol), and isobutyryl chloride (473 µL, 4.51 mmol), and the resulting solution was stirred overnight at room temperature. The reaction mixture was poured into aq. 1 N HCl (20 mL), the phases were separated, and the aq. phase was extracted with CH₂Cl₂ (2×20 mL). The organic extracts were combined, dried over Na₂SO₄, filtered, and evaporated to give a yellow oil which was purified by flash column chromatography (SiO₂, 0→20% acetone in hexanes) to afford the title compound (687 mg, 97%) as a clear, colorless oil: $^1$H NMR (400 MHz, CDCl₃) δ 7.37-7.26 (m, 5H), 4.61 (d, J=11.9 Hz, 1H), 4.58 (d, J=11.9 Hz, 1H), 4.18-4.04 (m, 2H), 3.76 (pd, J=6.3, 4.6 Hz, 1H), 2.58 (p, J=7.0 Hz, 1H), 1.22 (d, J=6.3 Hz, 3H), 1.19 (d, J=2.3 Hz, 3H), 1.17 (d, J=2.3 Hz, 3H); $^{13}$C NMR (101 MHz, CDCl₃) δ 176.98, 138.51, 128.37, 127.60, 127.58, 72.71, 71.04, 67.16, 34.00, 19.01, 18.99, 16.99; ESIMS m/z 237 (([M+H]⁺)).

Example 4B: Preparation of 1-((2S,3R,4S)-4-(benzyloxy)-3-phenoxy-2-vinylpentyl)-4-fluorobenzene

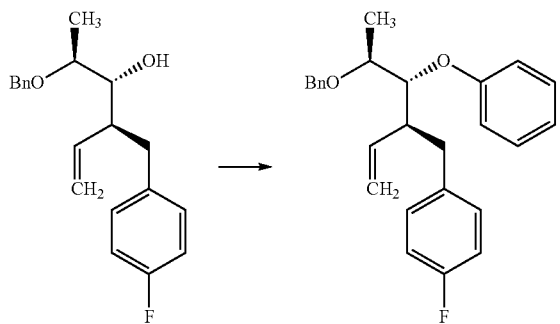 [SMILES: C=C[C@H](Cc1ccc(F)cc1)[C@@H](O)[C@H](C)OCc1ccccc1 ; C=C[C@H](Cc1ccc(F)cc1)[C@@H](Oc1ccccc1)[C@H](C)OCc1ccccc1]

To a solution of (2S,3R,4S)-2-(benzyloxy)-4-(4-fluorobenzyl)hex-5-en-3-ol (3 g, 9.54 mmol) in anhydrous toluene (48 mL) were added N-cyclohexyl-N-methylcyclohexanamine (3.04 mL, 14.3 mmol), Ph₃Bi(OAc)₂ (7.73 g, 14.3 mmol), and diacetoxycopper (Cu(OAc)₂; 0.347 g, 1.91 mmol). The resulting blue suspension was heated to and stirred at 50° C. for 15 h, cooled to room temperature, filtered through a plug of Celite®, and evaporated. The resulting crude material was purified by flash column chromatography (SiO₂, 1→5% EtOAc in hexanes) to give the title compound (2.77 g, 74%) as a clear, colorless oil: $^1$H NMR (400 MHz, CDCl₃) δ 7.38-7.18 (m, 7H), 7.09-6.99 (m, 2H), 6.99 6.84 (m, 5H), 5.62 (dt, J=17.2, 9.7 Hz, 1H), 4.96 (dd, J=10.3, 1.7 Hz, 1H), 4.83 (d, J=17.2 Hz, 1H), 4.61 (d, J=11.6 Hz, 1H), 4.44 (d, J=11.6 Hz, 1H), 4.32 (t, J=5.5 Hz, 1H), 3.82 (p, J=6.1 Hz, 1H), 3.09 (dd, J=13.5, 4.1 Hz, 1H), 2.71 (dt, J=9.7, 5.0 Hz, 1H), 2.57 (dd, J=13.3, 9.8 Hz, 1H), 1.27 (d, J=6.2 Hz, 3H); $^{13}$C NMR (151 MHz, CDCl₃) δ 162.06, 160.45, 159.51, 138.48, 138.05, 135.87, 135.85, 130.84, 130.79, 129.44, 128.35, 127.67, 127.55, 120.92, 117.28, 116.31, 114.82, 114.68, 82.38, 75.70, 70.67, 48.55, 35.96, 15.11; ESIMS m/z 413 (([M+Na]⁺)).

Example 4C: Preparation of 1-(1R,2S)-2-(benzyloxy)-1-cyclopentylpropoxy)-3-chlorobenzene

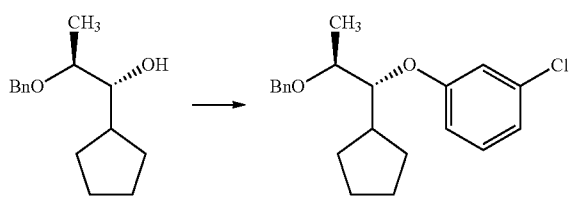 [SMILES: C[C@H](OCc1ccccc1)[C@H](O)C1CCCC1 ; C[C@H](OCc1ccccc1)[C@H](Oc1cccc(Cl)c1)C1CCCC1]

To a suspension of potassium tert-butoxide (KOt-Bu; 314 mg, 2.80 mmol) in anhydrous N,N-dimethylformamide (DMF; 2 mL) was added (1R,2S)-2-(benzyloxy)-1-cyclopentylpropan-1-ol (469 mg, 2.00 mmol) at room temperature, and the resulting orange solution was stirred for 5 min, treated with 1-chloro-3-fluorobenzene (643 µL, 6.00 mmol), and heated to and stirred at 60° C. overnight. The cooled reaction mixture was quenched with glacial acetic acid (HOAc; 300 µL), diluted with hexanes (2 mL), and the resulting suspension was purified by flash column chromatography (SiO₂, 2→8% acetone in hexanes) to afford the title compound (637 mg, 92%) as a colorless oil: IR (Thin film) 3065, 2949, 2866, 1590, 1474, 1452 cm⁻¹; $^1$H NMR (500 MHz, CDCl₃) δ 7.35-7.30 (m, 2H), 7.29-7.26 (m, 3H), 7.14 (t, J=8.1 Hz, 1H), 7.05 (t, J=2.2 Hz, 1H), 6.88 (dd, J=8.2, 2.1 Hz, 2H), 4.61 (d, J=11.7 Hz, 1H), 4.49 (d, J=11.8 Hz, 1H), 4.23 (dd, J=7.4, 3.7 Hz, 1H), 3.70 (qd, J=6.3, 3.7 Hz, 1H), 2.30-2.12 (m, 1H), 1.85 1.74 (m, 1H), 1.71-1.64 (m, 1H), 1.66-1.46 (m, 4H), 1.45-1.35 (m, 1H), 1.25 (d, J=6.3 Hz, 3H), 1.23-1.15 (m, 1H); $^{13}$C NMR (126 MHz, CDCl₃) δ 160.99, 138.48, 134.62, 130.03, 128.33, 127.51, 127.48, 120.72, 116.88, 114.73, 85.07, 76.56, 70.85, 42.16, 29.40, 28.98, 25.46, 25.12, 14.78.

Example 4D: Preparation of 4-((1R,2S)-2-(benzyloxy)-1-(cyclopropylmethoxy)-propyl)-1,1'-biphenyl

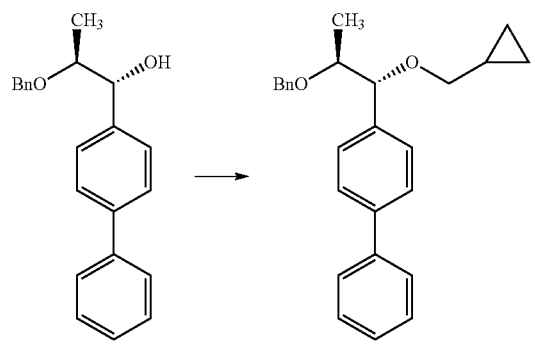 [SMILES: C[C@H](OCc1ccccc1)[C@H](O)c1ccc(-c2ccccc2)cc1 ; C[C@H](OCc1ccccc1)[C@H](OCC1CC1)c1ccc(-c2ccccc2)cc1]

To a solution of (1R,2S)-1-([1,1'-biphenyl]-4-yl)-2-(benzyloxy)propan-1-ol (272 mg, 0.854 mmol) in anhydrous DIVIF (2.8 mL) at 0° C. was added sodium hydride (NaH; 59.8 mg, 1.50 mmol, 60 wt % in mineral oil) and the reaction mixture was stirred at 0° C. for 15 min. The mixture was removed from the ice bath, stirred for an additional 15 min, cooled back to 0° C., and treated with (bromomethyl) cyclopropane (84 µL, 0.854 mmol). After 10 min, the reaction vessel was removed from the ice bath and the mixture was warmed to and stirred at room temperature overnight. The reaction mixture was carefully quenched by the addition of H$_2$O followed by stirring for 10 min and the phases were separated. The aq. phase was extracted with Et$_2$O (3×), and the combined organic phases were dried over Na$_2$SO$_4$, filtered, and concentrated. The resulting oil was purified by flash column chromatography (SiO$_2$, 0→10% acetone in hexanes) to afford the title compound (251 mg, 79%) as a colorless oil: $^1$H NMR (400 MHz, CDCl$_3$) δ 7.64-7.60 (m, 2H), 7.57 (d, J=8.2 Hz, 2H), 7.48-7.32 (m, 5H), 7.24-7.19 (m, 3H), 7.10-7.06 (m, 2H), 4.46 (d, J=11.9 Hz, 1H), 4.30 (d, J=11.9 Hz, 1H), 4.27 (d, J=6.4 Hz, 1H), 3.64 (p, J=6.2 Hz, 1H), 3.28-3.20 (m, 2H), 1.32 (d, J=6.2 Hz, 3H), 1.12-1.01 (m, 1H), 0.56-0.45 (m, 2H), 0.22-0.10 (m, 2H); $^{13}$C NMR (101 MHz, CDCl$_3$) δ 141.03, 140.33, 139.54, 138.60, 128.75, 128.18, 128.14, 127.67, 127.30, 127.18, 127.06, 126.73, 84.36, 78.56, 73.75, 71.47, 16.71, 10.74, 3.18, 2.83; ESIMS m/z 395 (([M+Na]$^+$)).

Example 4E: Preparation of (S)-(((1-(tert-butoxy)propan-2-yl)oxy)methyl)benzene

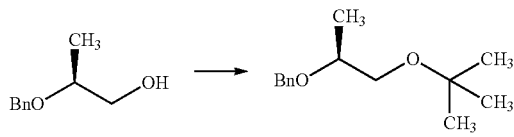

To a solution of (S)-2-(benzyloxy)propan-1-ol (300 mg, 1.80 mmol) in anhydrous CH$_2$Cl$_2$ (9.0 mL) were added di-tert-butyl dicarbonate (Boc$_2$O; 985 mg, 4.51 mmol) and scandium trifluoromethanesulfonate (Sc(OTf)$_3$; 89 mg, 0.180 mmol) at room temperature, and the resulting solution was stirred at room temperature for 20 h. The mixture was treated with additional Boc$_2$O (400 mg) and the mixture was heated to and stirred at 40° C. for 4 h. The reaction mixture was cooled to room temperature, concentrated, and the residue purified by flash column chromatography (SiO$_2$, 2→12% acetone in hexanes) to provide the title compound (223 mg, 56%) as a colorless oil: $^1$H NMR (400 MHz, CDCl$_3$) δ 7.40-7.29 (m, 4H), 7.29-7.23 (m, 1H), 4.63 (s, 2H), 3.64 (h, J=6.2 Hz, 1H), 3.48 (dd, J=9.2, 5.7 Hz, 1H), 3.27 (dd, J=9.2, 5.6 Hz, 1H), 1.23-1.16 (m, 12H); $^{13}$C NMR (126 MHz, CDCl$_3$) δ 139.13, 128.26, 127.61, 127.33, 74.56, 72.84, 71.21, 66.08, 27.52, 17.70; ESIMS m/z 245 (([M+Na]$^+$)).

Example 4F: Preparation of (((((1R,2S)-1-cyclopentyl-1-((2-methylallyl)oxy)propan-2-yl)oxy)methyl)benzene

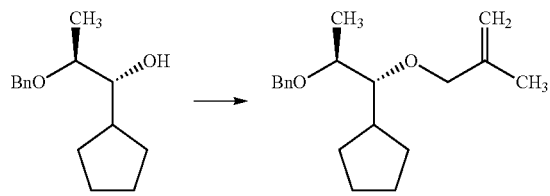 [SMILES: C[C@H](OCc1ccccc1)[C@H](O)C1CCCC1 ; C=C(C)CO[C@H](C1CCCC1)[C@H](C)OCc1ccccc1]

To a suspension of KOt-Bu (314 mg, 2.80 mmol) in anhydrous DMF (2 mL) was added (1R,2S)-2-(benzyloxy)-1-cyclopentylpropan-1-ol (469 mg, 2.00 mmol). The resulting orange solution was stirred at room temperature for 5 min, treated with 3-bromo-2-methylprop-1-ene (605 μL, 6.00 mmol), and warmed to and stirred at 60° C. overnight. The cooled reaction mixture was quenched with glacial HOAc (300 μL), diluted with hexanes (2 mL), and the resulting suspension purified by flash column chromatography (SiO$_2$, 2→8% acetone in hexanes) to afford the title compound (476 mg, 83%) as a colorless oil: IR (Thin film) 3066, 2947, 2865, 1726, 1656, 1452 cm$^{-1}$; $^1$H NMR (500 MHz, CDCl$_3$) δ 7.34 (d, J=4.3 Hz, 4H), 7.31-7.23 (m, 1H), 4.98 (dt, J=2.3, 1.2 Hz, 1H), 4.85-4.78 (m, 1H), 4.58 (d, J=11.9 Hz, 1H), 4.52 (d, J=12.0 Hz, 1H), 4.23 (d, J=12.0 Hz, 1H), 3.96 (d, J=12.0 Hz, 1H), 3.58 (qd, J=6.4, 2.7 Hz, 1H), 3.32 (dd, J=8.1, 2.6 Hz, 1H), 2.01-1.88 (m, 1H), 1.88-1.79 (m, 1H), 1.76 (d, J=1.3 Hz, 3H), 1.66-1.57 (m, 3H), 1.54-1.45 (m, 2H), 1.44-1.35 (m, 1H), 1.22 (d, J=6.3 Hz, 3H), 1.20-1.12 (m, 1H); $^{13}$C NMR (126 MHz, CDCl$_3$) δ 143.21, 139.04, 128.29, 127.38, 127.33, 111.68, 85.41, 77.83, 76.21, 70.61, 42.49, 29.89, 29.64, 25.44, 25.21, 19.90, 14.25.

Example 4G: Preparation of ((1R,2S)-2-(benzyloxy)-1-methoxypropyl)adamantane

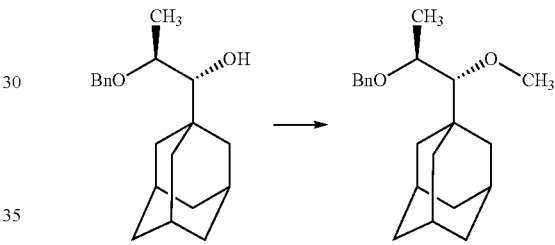

To a solution of (1R,2S)-1-(adamantan-1-yl)-2-(benzyloxy)propan-1-ol (0.550 g, 1.831 mmol) in CH$_2$Cl$_2$ (7.32 ml) at 0° C. was added Proton Sponge® (0.785 g, 3.66 mmol) and trimethyloxonium tetrafluoroborate (0.406 g, 2.75 mmol), and the reaction mixture was warmed to room temperature and stirred for 6 h. An additional equivalent of both Proton Sponge® and trimethyloxonium tetrafluoroborate were added, and the mixture was stirred at room temperature overnight. The reaction mixture was quenched with sat. NaHCO$_3$, the phases were separated, and the products were extracted from the aqueous phase with CH$_2$Cl$_2$ (2×). The combined organic phases were washed with 1N NaHSO$_4$ (2×), dried over Na$_2$SO$_4$, filtered and concentrated. The crude material was purified by flash column chromatography (SiO$_2$, 0→20% acetone in hexanes) to afford the title compound (501 mg, 87%) as a colorless oil: IR (Thin film) 2899.51, 1451.42, 1105.09, 1091.88 cm-1; $^1$H NMR (400 MHz, CDCl$_3$) δ 7.39-7.31 (m, 5H), 4.53 (d, J=11.9 Hz, 1H), 4.47 (d, J=11.9 Hz, 1H), 3.73 (qd, J=6.2, 2.2 Hz, 1H), 3.50 (s, 3H), 2.84 (d, J=2.3 Hz, 1H), 2.03-1.85 (d, J=3.4 Hz, 3H), 1.81-1.47 (m, 12H), 1.24 (d, J=6.3 Hz, 3H); $^{13}$C NMR (101 MHz, CDCl$_3$) δ 138.99, 128.30, 127.48, 127.35, 91.85, 75.25, 70.22, 61.34, 38.89, 37.27, 37.18, 28.40, 15.91; HRMS-ESI m/z (([M+Na]$^+$)) calcd for C$_{21}$H$_{30}$NaO$_2$, 337.2138; found, 337.2143.

Example 4H: Preparation of ((((2S)-1-(cyclopent-2-en-1-yloxy)propan-2-yl)oxy)-methyl)benzene

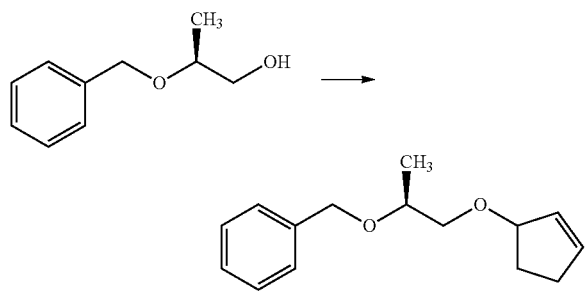

To a solution of (S)-2-(benzyloxy)propan-1-ol (300 mg, 1.81 mmol), DPPF (100 mg, 0.180 mmol), and Pd$_2$(dba)$_3$ (83 mg, 0.090 mmol) in anhydrous THF (9 mL) at 65° C. was added tert-butyl cyclopent-2-en-1-yl carbonate (665 mg, 3.61 mmol), and the reaction mixture was stirred at 65° C. for 7 h, cooled to room temperature, concentrated, and purified by flash column chromatography (SiO$_2$, 1→16% acetone in hexanes) to provide the title compound (192 mg, 0.826 mmol, 45.7%) as a light yellow oil. $^1$H NMR and $^{13}$C NMR show the product to be a 1:1 mixture of diastereomers, as reflected in the extra carbons present in the $^{13}$C spectrum: $^1$H NMR (400 MHz, CDCl$_3$) δ 7.42-7.30 (m, 4H), 7.30-7.19 (m, 1H), 6.01 (dtd, J=5.6, 2.2, 1.1 Hz, 1H), 5.91-5.81 (m, 1H), 4.70-4.53 (m, 3H), 3.78-3.64 (m, 1H), 3.54 (ddd, J=11.3, 9.9, 5.8 Hz, 1H), 3.41 (ddd, J=9.8, 7.4, 5.1 Hz, 1H), 2.56-2.42 (m, 1H), 2.32-2.20 (m, 1H), 2.20-2.07 (m, 1H), 1.86-1.72 (m, 1H), 1.20 (d, J=6.3 Hz, 3H); $^{13}$C NMR (126 MHz, CDCl$_3$) δ 139.02, 135.64, 135.60, 130.86, 130.78, 128.28, 127.61, 127.60, 127.37, 85.27, 74.24, 74.22, 72.52, 72.46, 71.17, 31.10, 31.09, 29.66, 29.60, 17.56, 17.54; ESIMS m/z 255.3 (([M+Na]$^+$)).

Example 5: Preparation of 3-(((2S,3R)-2-(benzyloxy)-4-ethylhexan-3-yl)oxy)-1,1'-biphenyl

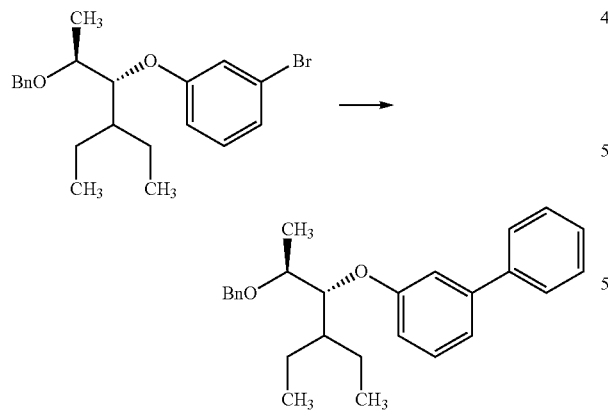

A mixture of 1-(((2S,3R)-2-(benzyloxy)-4-ethylhexan-3-yl)oxy)-3-bromobenzene (555 mg, 1.418 mmol), sodium carbonate (Na$_2$CO$_3$; 451 mg, 4.25 mmol), and phenylboronic acid (501 mg, 4.11 mmol) in dioxane (5.3 mL) and H$_2$O (1.8 mL) was deoxygenated by evacuating under gentle vacuum and back-filling with N$_2$ (3×), and the degassed mixture was treated with tetrakis(triphenylphosphine)palladium(0) (Pd(PPh$_3$)$_4$; 164 mg, 0.142 mmol). The degassing procedure was repeated and the mixture was heated to and stirred at 80° C. for 4 h, cooled to room temperature, and diluted with H$_2$O (20 mL). The phases were separated and the aq. phase was extracted with CH$_2$Cl$_2$ (20 mL). The organic phase was dried by passing through a phase separator cartridge and then evaporated. The resulting oil was purified by flash column chromatography (SiO$_2$, 1→5% EtOAc in hexanes) to afford the title compound (540 mg, 98%) as a colorless oil: IR (Thin film) 2961, 2931, 2873, 1595, 1569, 1476 cm$^{-1}$; $^1$H NMR (500 MHz, CDCl$_3$) δ 7.58-7.51 (m, 2H), 7.42-7.37 (m, 2H), 7.36-7.27 (m, 7H), 7.23 (dd, J=2.5, 1.7 Hz, 1H), 7.14 (ddd, J=7.6, 1.7, 1.0 Hz, 1H), 6.97 (ddd, J=8.2, 2.6, 0.9 Hz, 1H), 4.63 (d, J=11.6 Hz, 1H), 4.48 (d, J=11.7 Hz, 1H), 4.42 (t, J=5.1 Hz, 1H), 3.82 (qd, J=6.2, 5.2 Hz, 1H), 1.75-1.56 (m, 2H), 1.46-1.35 (m, 3H), 1.30 (d, J=6.2 Hz, 3H), 0.91 (t, J=7.4 Hz, 3H), 0.89 (t, J=7.4 Hz, 3H); $^{13}$C NMR (126 MHz, CDCl$_3$) δ 160.44, 142.57, 141.18, 138.56, 129.60, 128.66, 128.30, 127.62, 127.46, 127.24, 127.13, 119.38, 114.98, 114.77, 81.99, 75.43, 70.76, 43.00, 22.36, 21.44, 15.70, 11.85, 11.44.

Example 6A, Step 1: Preparation of (3S,4R,5S)-5-(benzyloxy)-3-(4-fluorobenzyl)-4-phenoxyhexan-1-ol

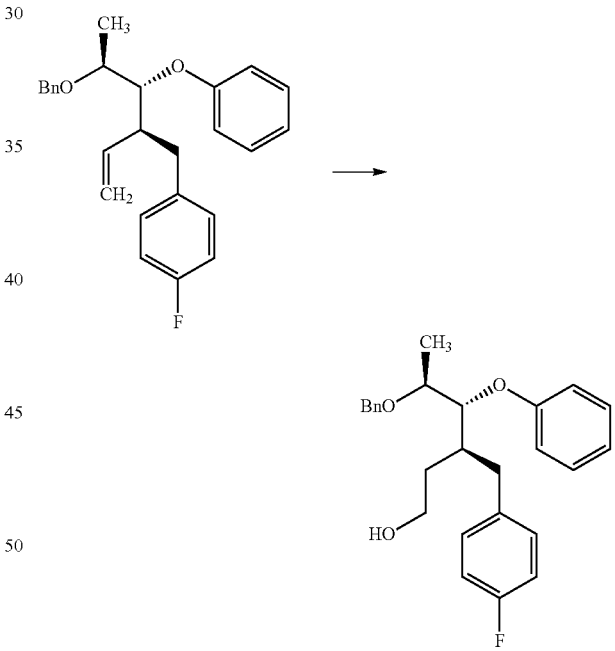

To a solution of 9-borabicyclo[3.3.1]nonane (9-BBN; 17.90 mL, 8.95 mmol, 0.5 M in THF) was added 1-((2S, 3R,4S)-4-(benzyloxy)-3-phenoxy-2-vinylpentyl)-4-fluorobenzene (2.33 g, 5.97 mmol) and the reaction mixture was stirred at room temperature for 2 h, cooled to 0° C., and treated dropwise with aq. 2 N NaOH (11.9 mL, 23.9 mmol) followed by aq. 30% H$_2$O$_2$ (2.44 mL, 23.9 mmol). The mixture was removed from the cold bath and stirred for 45 min, cooled back to 0° C., and quenched by the addition of sat. aq. sodium bisulfite (NaHSO$_3$). The phases were separated and the aq. phase was extracted with EtOAc (3×20 mL). The combined organic phases were dried over MgSO$_4$, filtered, and evaporated to give an oil which was purified by flash column chromatography (SiO₂, 4→20% acetone in hexanes) to afford the title compound (2.32 g, 95%) as a clear, colorless oil: ¹H NMR (400 MHz, CDCl₃) δ 7.36 (d, J=4.5 Hz, 4H), 7.34-7.27 (m, 1H), 7.27-7.18 (m, 2H), 7.11-7.03 (m, 2H), 6.97-6.87 (m, 3H), 6.85-6.76 (m, 2H), 4.67 (d, J=11.4 Hz, 1H), 4.41 (d, J=11.4 Hz, 1H), 4.31 (dd, J=7.5, 2.4 Hz, 1H), 3.97-3.80 (m, 1H), 3.56 (p, J=6.0 Hz, 2H), 3.00 (dd, J=13.8, 6.2 Hz, 1H), 2.55 (dd, J=13.8, 8.7 Hz, 1H), 2.29 (pd, J=8.3, 2.4 Hz, 1H), 1.76-1.61 (m, 1H), 1.58-1.48 (m, 2H), 1.28 (d, J=6.1 Hz, 3H); ¹³C NMR (101 MHz, CDCl₃) δ 162.54, 160.11, 158.77, 138.25, 136.81, 136.78, 130.72, 130.64, 129.60, 128.47, 127.96, 127.76, 120.95, 115.63, 115.13, 114.92, 81.00, 75.19, 70.83, 61.34, 39.38, 35.90, 33.50, 16.82; ESIMS m/z 431 (([M+Na]⁺)).

Example 6A, Step 2a: Preparation of 1-((2S,3R,4S)-4-(benzyloxy)-2-(2-methoxyethyl)-3-phenoxypentyl)-4-fluorobenzene

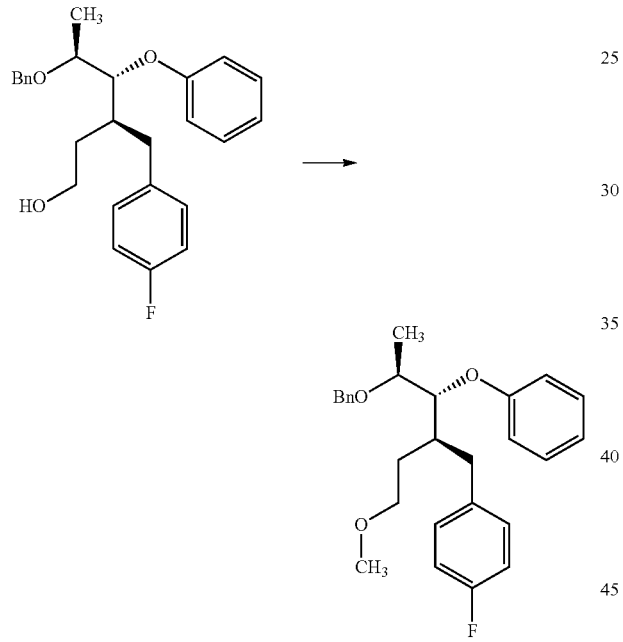

To a solution of (3S,4R,5S)-5-(benzyloxy)-3-(4-fluorobenzyl)-4-phenoxyhexan-1-ol (390 mg, 0.955 mmol) in anhydrous CH₂Cl₂ (10 mL) at 0° C. were added N¹,N¹,N⁸,N⁸-tetramethylnaphthalene-1,8-diamine (614 mg, 2.86 mmol) followed by trimethyloxonium tetrafluoroborate (282 mg, 1.91 mmol), and the mixture was stirred at 0° C. for 4 h and quenched with by the addition of aq. 1 N HCl (10 mL). The phases were separated and the aq. phase was extracted with CH₂Cl₂ (2×10 mL). The organic phases were combined, dried over Na₂SO₄, filtered, and evaporated to an oily white solid which was suspended in hexanes, filtered through Celite®, and concentrated to give an oil. The residual oil was purified by flash column chromatography (SiO₂, 1→20% acetone in hexanes) to afford the title compound (239 mg, 59%) as a clear, colorless oil: ¹H NMR (400 MHz, CDCl₃) δ 7.35 (d, J=4.1 Hz, 4H), 7.30 (dt, J=9.1, 4.5 Hz, 1H), 7.22 (t, J=8.0 Hz, 2H), 7.08 (dd, J=8.2, 5.7 Hz, 2H), 6.98-6.87 (m, 3H), 6.83 (d, J=8.4 Hz, 2H), 4.65 (d, J=11.5 Hz, 1H), 4.41 (d, J=11.5 Hz, 1H), 4.32 (dd, J=7.0, 2.5 Hz, 1H), 3.85 (p, J=6.2 Hz, 1H), 3.29 (t, J=6.8 Hz, 2H), 3.19 (d, J=1.3 Hz, 3H), 3.01 (dd, J=13.8, 5.9 Hz, 1H), 2.56 (dd, J=13.9, 8.8 Hz, 1H), 2.37-2.22 (m, 1H), 1.78-1.64 (m, 1H), 1.59-1.47 (m, 1H), 1.27 (d, J=6.1 Hz, 3H); ¹³C NMR (126 MHz, CDCl₃) δ 161.27 (d, J=243.4 Hz), 159.11, 138.44, 136.89 (d, J=3.2 Hz), 130.65 (d, J=7.7 Hz), 129.46, 128.38, 127.76, 127.59, 120.70, 115.73, 114.93 (d, J=21.0 Hz), 81.11, 75.18, 71.07, 70.74, 58.39, 39.20, 35.38, 30.20, 16.67; ESIMS m/z 423 (([M+H]⁺)).

Example 6A, Step 2b: Preparation of 1-((2S,3R,4S)-4-(benzyloxy)-2-(2-(tert-butoxy)ethyl)-3-phenoxypentyl)-4-methoxybenzene

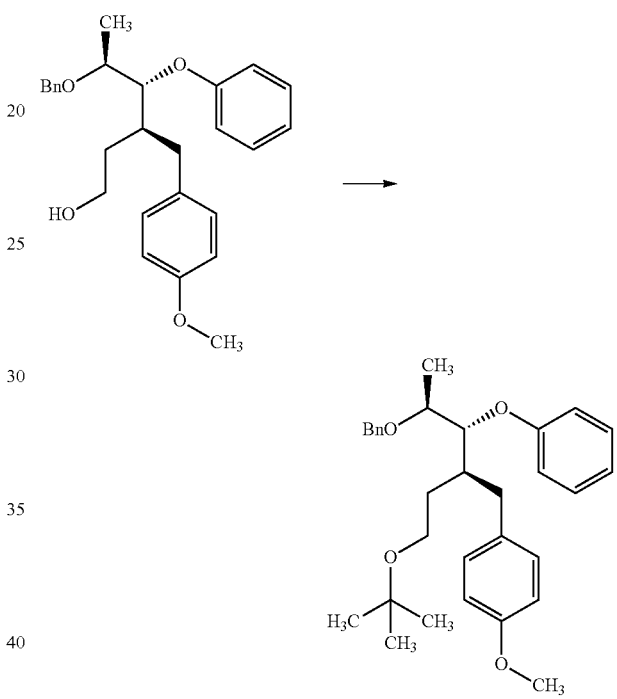

To a solution of (3S,4R,5S)-5-(benzyloxy)-3-(4-methoxybenzyl)-4-phenoxyhexan-1-ol (1.99 g, 4.73 mmol) and (R)-2-benzyl 1-tert-butyl aziridine-1,2-dicarboxylate (1.44 g, 5.21 mmol) in anhydrous CH₂Cl₂ (20 mL) at 0° C. was added Sc(OTf)₃ (0.233 g, 0.473 mmol), and the reaction mixture was stirred at 0° C. for 40 min and then allowed to warm room temperature overnight as the ice melted. The mixture was quenched with sat. aq. NaHCO₃ (25 mL), partitioned between H₂O (25 mL) and CH₂Cl₂ (50 mL), and the phases were separated. The aq. phase was extracted with CH₂Cl₂ (2×25 mL) and the combined organic phases were dried over Na₂SO₄, filtered, and evaporated to a colorless oil, which was purified by flash column chromatography (SiO₂, 2→25% acetone in hexanes) to afford the title compound (320 mg, 14%) as a colorless oil: ¹H NMR (400 MHz, CDCl₃) δ 7.34 (d, J=4.4 Hz, 4H), 7.33-7.26 (m, 1H), 7.21 (t, J=8.0 Hz, 2H), 7.07 (d, J=8.6 Hz, 2H), 6.88 (t, J=8.6 Hz, 3H), 6.79 (d, J=8.6 Hz, 2H), 4.63 (d, J=11.5 Hz, 1H), 4.45-4.36 (m, 2H), 3.86 (p, J=6.2 Hz, 1H), 3.78 (s, 3H), 3.32-3.18 (m, 2H), 2.99 (dd, J=13.9, 5.8 Hz, 1H), 2.54 (dd, J=13.9, 8.8 Hz, 1H), 2.37-2.22 (m, 1H), 1.66 (dq, J=14.0, 7.0 Hz, 1H), 1.60-1.46 (m, 1H), 1.27 (d, J=6.1 Hz, 3H), 1.08 (s, 9H); $^{13}$C NMR (151 MHz, CDCl$_3$) δ 159.44, 157.75, 138.64, 133.45, 130.26, 129.37, 128.32, 127.68, 127.47, 120.52, 115.94, 113.63, 81.62, 75.33, 72.50, 70.73, 60.26, 55.29, 39.62, 35.32, 31.25, 27.51, 16.62; ESIMS m/z 499 (([M+Na]$^+$)).

Example 6B, Step 1: Preparation of (2S,3S,4S)-4-(benzyloxy)-3-phenoxy-2-propoxypentan-1-ol

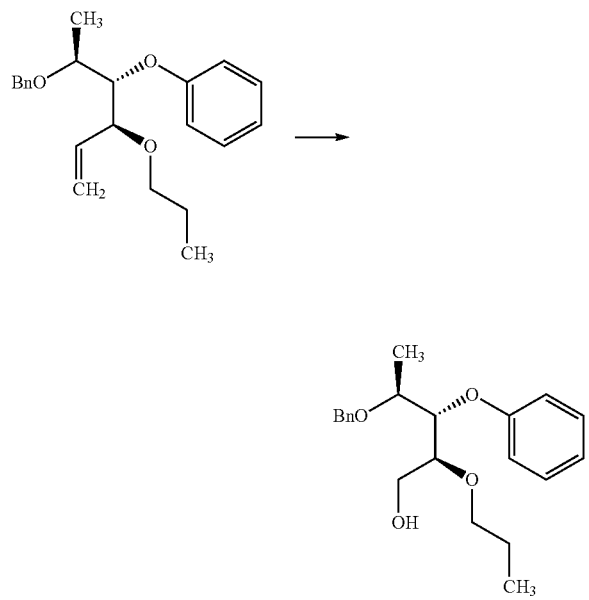

A solution of (((2S,3S,4S)-2-(benzyloxy)-4-propoxyhex-5-en-3-yl)oxy)benzene (500 mg, 1.47 mmol) and NaHCO$_3$ (12.3 mg, 0.147 mmol) in anhydrous MeOH (0.44 mL) and CH$_2$Cl$_2$ (14 mL) was treated with ozone (O$_3$) at −78° C. until the solution turned from colorless to blue. The reaction mixture was purged with oxygen (O$_2$) until colorless, treated with additional MeOH (4 mL) followed by NaBH$_4$ (167 mg, 4.41 mmol), and then warmed to room temperature and stirred for 4 h. The mixture was quenched with H$_2$O, diluted with CH$_2$Cl$_2$, and the phases were separated. The aq. phase was extracted with CH$_2$Cl$_2$ (2×) and the combined organic phases were washed with brine, dried over MgSO$_4$, filtered, and evaporated. The resulting crude residue was purified by flash column chromatography (SiO$_2$, 0→100% EtOAc in hexanes) to afford the title compound (458 mg, 91%) as a colorless oil: IR (Thin film) 3453, 2934, 2875, 1597, 1493, 1237 cm$^{-1}$; $^1$H NMR (400 MHz, CDCl$_3$) δ 7.36-7.22 (m, 7H), 7.06-7.02 (m, 2H), 6.97-6.91 (m, 1H), 4.63 (d, J=11.5 Hz, 1H), 4.51-4.44 (m, 2H), 3.95-3.87 (m, 1H), 3.79-3.66 (m, 3H), 3.60-3.49 (m, 2H), 2.08-2.04 (m, 1H), 1.60-1.51 (m, 2H), 1.29 (d, J=6.3 Hz, 3H), 0.86 (t, J=7.4 Hz, 3H); ESIMS m/z 345 (([M+H]$^+$)).

Example 6B, Step 2: Preparation of (((2S,3S,4S)-4-(benzyloxy)-1-methoxy-2-propoxypentan-3-yl)oxy)benzene

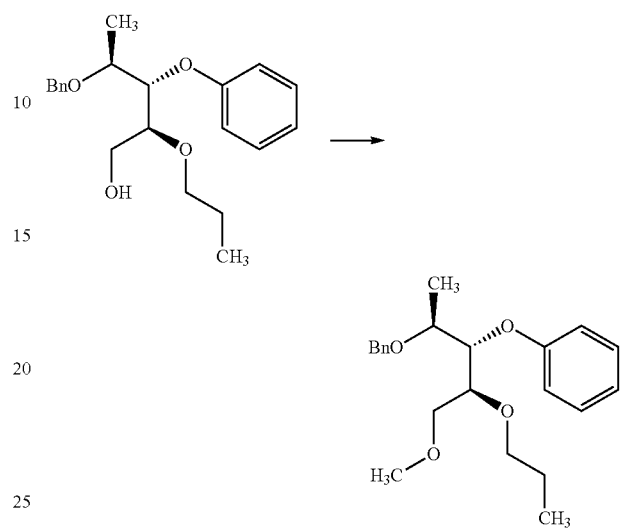

A solution of (2S,3S,4S)-4-(benzyloxy)-3-phenoxy-2-propoxypentan-1-ol (452 mg, 1.31 mmol), Proton Sponge® (1687 mg, 7.87 mmol), and trimethyloxonium tetrafluoroborate (485 mg, 3.28 mmol) in anhydrous CH$_2$Cl$_2$ (10 mL) was stirred at room temperature for 8 h, and the reaction mixture was quenched by the addition of sat. aq. NaHCO$_3$, diluted with CH$_2$Cl$_2$, and the phases were separated. The aq. phase was extracted with CH$_2$Cl$_2$ and the combined organic phases were washed with 1 M aq. HCl (3×), washed with brine, dried over MgSO$_4$, filtered, and evaporated. The residue waspurified by flash column chromatography (SiO$_2$, 0→100% EtOAc in hexanes) to afford the title compound (370 mg, 79%) as a colorless oil: IR (Thin film) 2930, 2875, 1597, 1493, 1237 cm$^{-1}$; $^1$H NMR (400 MHz, CDCl$_3$) δ 7.35-7.21 (m, 7H), 7.08-7.03 (m, 2H), 6.95-6.89 (m, 1H), 4.64 (d, J=11.5 Hz, 1H), 4.50-4.44 (m, 2H), 4.02-3.93 (m, 1H), 3.89-3.83 (m, 1H), 3.64-3.56 (m, 1H), 3.54-3.48 (m, 1H), 3.47-3.39 (m, 2H), 3.24 (s, 3H), 1.63-1.53 (m, 2H), 1.26 (d, J=6.3 Hz, 3H), 0.87 (t, J=7.4 Hz, 3H); ESIMS m/z 359 (([M+H]$^+$)).

Example 6C: Preparation of (((1S,2S,3S)-3-(benzyloxy)-1-cyclopropyl-1-propoxybutan-2-yl)oxy)benzene

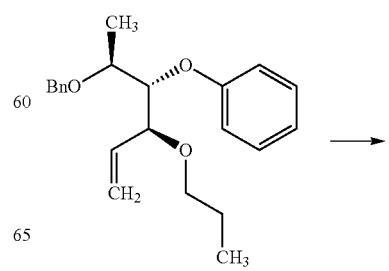

-continued

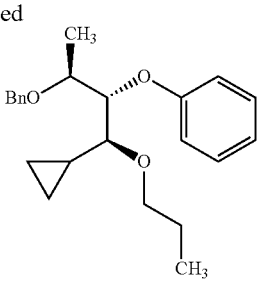

To a solution of (((2S,3S,4S)-2-(benzyloxy)-4-propoxyhex-5-en-3-yl)oxy)benzene (500 mg, 1.47 mmol) and diethylzinc (Et$_2$Zn; 1 M in hexanes, 14.7 mL, 14.7 mmol) in Et$_2$O (10 mL) was added diiodomethane (CH$_2$I$_2$; 2.37 mL, 29.4 mmol) at 0° C. dropwise, and the reaction mixture was warmed to room temperature over a 15 min period and stirred for 2 d. Excess Et$_2$Zn (5.0 mL, 5.0 mmol) and CH$_2$I$_2$ (0.83 mL, 10.3 mmol) were added at 0° C. and the reaction was warmed to and stirred at 45° C. 20 h. The reaction mixture was quenched by the addition of sat. aq. NH$_4$Cl and extracted with Et$_2$O. The combined organic extracts were washed with brine, dried over MgSO$_4$, filtered, concentrated, and purified by column chromatography (SiO$_2$, hexanes/EtOAc gradient) to furnish the title compound (113 mg, 22%) as a colorless oil: IR (neat) 2932, 2874, 1597, 1493, 1239, 1084 cm$^{-1}$; $^1$H NMR (400 MHz, CDCl$_3$) δ 7.39-7.20 (m, 7H), 7.09-7.04 (m, 2H), 6.94-6.88 (m, 1H), 4.62 (d, J=11.4 Hz, 1H), 4.47 (d, J=11.4 Hz, 1H), 4.35 (dd, J=7.3, 2.9 Hz, 1H), 4.08-4.00 (m, 1H), 3.82-3.74 (m, 1H), 3.35-3.28 (m, 1H), 2.98 (dd, J=9.0, 2.9 Hz, 1H), 1.66-1.55 (m, 2H), 1.26 (d, J=6.2 Hz, 3H), 0.98-0.85 (m, 4H), 0.70-0.62 (m, 1H), 0.49-0.41 (m, 1H), 0.38-0.30 (m, 1H), 0.21-0.13 (m, 1H); HRMS-ESI (m/z) [M]$^+$ calcd for C$_{23}$H$_{30}$O$_3$, 354.2195; found, 354.2195.

Example 7, Step 1: Preparation of (2R,3S)-3-(benzyloxy)-2-phenoxybutan-1-ol

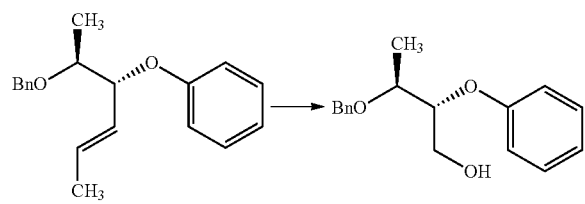 [SMILES: C/C=C/[C@@H](Oc1ccccc1)[C@H](C)OCc1ccccc1 ; C[C@H](OCc1ccccc1)[C@@H](CO)Oc1ccccc1]

To a solution of (((2S,3R,E)-2-(benzyloxy)hex-4-en-3-yl)oxy)benzene (740 mg, 2.62 mmol) in a mixture of CH$_2$Cl$_2$ (11 mL) and MeOH (1.2 mL) were added 2 drops of a 1% solution of Sudan III in CH$_2$Cl$_2$. The resulting pink solution was cooled to −78° C. and O$_3$ was bubbled through the reaction mixture until the pink color faded. The solution was purged with O$_2$ for 5 min, placed under an N$_2$ atmosphere, and treated with NaBH$_4$ (297 mg, 7.86 mmol). The reaction mixture was slowly warmed to room temperature, stirred overnight, diluted with CH$_2$Cl$_2$ (10 mL), and quenched with sat. aq. NH$_4$Cl (10 mL). The phases were separated, the aq. phase was extracted with CH$_2$Cl$_2$ (2×10 mL), and the combined organic phases were dried by passing through a phase separator cartridge and evaporated. The resulting crude material was purified by flash column chromatography (SiO$_2$, 0→60% EtOAc in hexanes) to afford the title compound (610 mg, 85%) as a colorless oil: $^1$H NMR (400 MHz, CDCl$_3$) δ 7.37-7.25 (m, 7H), 7.01-6.92 (m, 3H), 4.67 (d, J=11.6 Hz, 1H), 4.55 (d, J=11.5 Hz, 1H), 4.23 (app dt, J=6.0, 4.5 Hz, 1H), 3.97-3.84 (m, 3H), 2.30 (app t, J=6.4 Hz, 1H), 1.31 (d, J=6.3 Hz, 3H); $^{13}$C NMR (101 MHz, CDCl$_3$) δ 158.01, 138.07, 129.66, 128.49, 127.82, 127.81, 121.49, 116.16, 81.18, 75.24, 71.51, 62.02, 16.82; ESIMS m/z 273 ((([M+H]$^+$)).

Example 7, Step 2a: Preparation of (((2R,3S)-3-(benzyloxy)-1-propoxybutan-2-yl)oxy)benzene

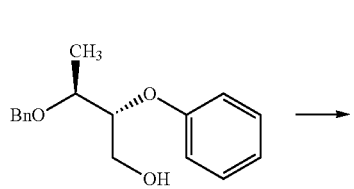

To a solution of (2R,3S)-3-(benzyloxy)-2-phenoxybutan-1-ol (150 mg, 0.551 mmol) in DMF (2.7 mL) at 0° C. was added NaH (44.1 mg, 1.10 mmol, 60 wt % in mineral oil), and the reaction mixture was stirred at 0° C. for 10 min, removed from the cold bath and stirred at room temperature for 15 min. treated with propyl 4-methylbenzenesulfonate (237 µL, 1.24 mmol), and stirred at room temperature for 16 h. The mixture was quenched by the addition of sat. aq. NH$_4$Cl (7 mL), diluted with Et$_2$O (10 mL), and the phases were separated. The aq. phase was extracted with Et$_2$O (2×10 mL) and the combined organic phases were washed with brine (5 mL), dried over Na$_2$SO$_4$, filtered and evaporated. The crude residue was purified by flash column chromatography (SiO$_2$, 0→30% EtOAc in hexanes) to afford the title compound (125 mg, 72%) as a colorless oil: $^1$H NMR (400 MHz, CDCl$_3$) δ 7.35-7.22 (m, 7H), 7.03-6.90 (m, 3H), 4.67-4.54 (m, 2H), 4.36 (app td, J=5.1, 3.9 Hz, 1H), 3.89 (qd, J=6.4, 5.0 Hz, 1H), 3.80-3.67 (m, 2H), 3.41 (app td, J=6.7, 2.6 Hz, 2H), 1.64-1.50 (m, 2H), 1.29 (d, J=6.4 Hz, 3H), 0.89 (app t, J=7.4 Hz, 3H); $^{13}$C NMR (101 MHz, CDCl$_3$) δ 158.67, 138.64, 129.41, 128.32, 127.69, 127.51, 121.09, 116.52, 80.85, 74.38, 73.30, 71.46, 69.48, 22.87, 16.26, 10.58; ESIMS m/z 315 ((([M+H]$^+$)).

Example 7, Step 2b: Preparation of (((2R,3S)-3-(benzyloxy)-1-phenoxybutan-2-yl)oxy)benzene

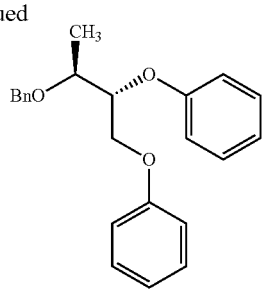

To a solution of (2R,3S)-3-(benzyloxy)-2-phenoxybutan-1-ol (290 mg, 1.06 mmol) in CH$_2$Cl$_2$ (5.3 mL) were added diacetoxycopper (19.3 mg, 0.106 mmol) and Ph$_3$Bi(OAc)$_2$ (654 mg, 1.17 mmol), and the mixture was stirred overnight at room temperature, filtered through a pad of Celite® rinsing with CH$_2$Cl$_2$ (2×10 mL), and concentrated. The crude residue was purified by flash column chromatography (SiO$_2$, 0→35% EtOAc in hexanes) to afford the title compound (290 mg, 76%) as a colorless oil: $^1$H NMR (400 MHz, CDCl$_3$) δ 7.31-7.24 (m, 9H), 7.04-6.83 (m, 6H), 4.66 (d, J=11.7 Hz, 1H), 4.61-4.50 (m, 2H), 4.34-4.21 (m, 2H), 4.01 (qd, J=6.3, 5.3 Hz, 1H), 1.36 (d, J=6.3 Hz, 3H); $^{13}$C NMR (101 MHz, CDCl$_3$) δ 158.72, 158.40, 138.34, 129.53, 129.43, 128.37, 127.80, 127.62, 121.44, 120.93, 116.56, 114.70, 80.25, 74.09, 71.58, 66.73, 16.46; ESIMS m/z 371 (([M+Na]$^+$)).

Example 8A: Preparation of (1R,2S)-1-(3-chlorophenoxy)-1-cyclopentylpropan-2-ol

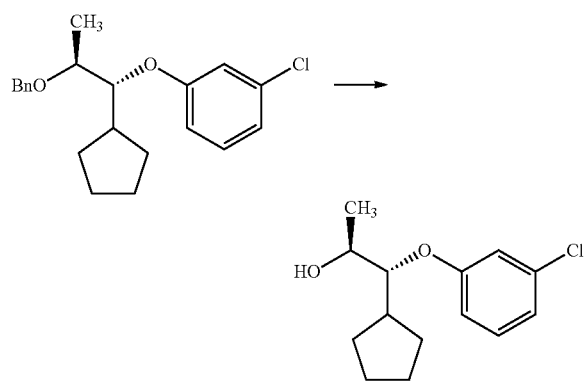

To a solution of 1-((1R,2S)-2-(benzyloxy)-1-cyclopentylpropoxy)-3-chlorobenzene (630 mg, 1.83 mmol) in a mixture of ethanol (EtOH; 6.1 mL) and cyclohexene (3.0 mL) was added 10% palladium on carbon (Pd/C; 97 mg, 0.091 mmol) and the resulting suspension was heated to and stirred at 65° C. for 2 h. The reaction mixture was filtered through a plug of Celite® and the filtrate was evaporated to give the title compound (476 mg, 97%) as a colorless oil: IR (Thin film) 3351, 2951, 2867, 1590, 1473, 1427, 1228 cm$^{-1}$; $^1$H NMR (500 MHz, CDCl$_3$) δ 7.17 (t, J=8.1 Hz, 1H), 7.03 (t, J=2.3 Hz, 1H), 6.94-6.87 (m, 2H), 4.21 (dd, J=8.0, 3.4 Hz, 1H), 3.99 (qd, J=6.4, 3.3 Hz, 1H), 2.21-2.07 (m, 1H), 1.87-1.77 (m, 1H), 1.70 (dtd, J=11.7, 7.6, 3.8 Hz, 1H), 1.66-1.44 (m, 5H), 1.38-1.30 (m, 1H), 1.27 (d, J=6.4 Hz, 3H), 1.31-1.19 (m, 1H); $^{13}$C NMR (126 MHz, CDCl$_3$) δ 160.86, 134.83, 130.23, 121.13, 116.87, 114.59, 86.65, 69.41, 42.15, 29.68, 29.22, 25.23, 25.03, 17.85.

Example 8B: Preparation of (2S,3R,4R)-4-benzyl-3-isobutoxyhexan-2-ol

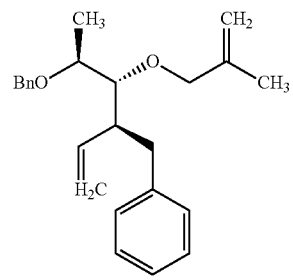

A Parr bottle was charged with a suspension of ((((2S,3R,4S)-4-benzyl-3-((2-methylallyl)oxy)hex-5-en-2-yl)oxy)methyl)benzene (1.85 g, 5.28 mmol) and 10% Pd/C (0.056 g, 0.53 mmol) in EtOH (10 mL) and the bottle was evacuated under gentle vacuum and back-filled with hydrogen gas (H$_2$; 3×). The bottle was loaded into the Paar shaker and the system was pressurized to 50 pounds per square inch (psi) with H$_2$ and agitated overnight at room temperature. The reaction mixture was filtered through Celite® and the filtrate was evaporated to afford the title compound (1.36 g, 97%) as a colorless oil: $^1$H NMR (400 MHz, CDCl$_3$) δ 7.30-7.24 (m, 2H), 7.22-7.14 (m, 3H), 3.96 (h, J=6.3 Hz, 1H), 3.39 (dd, J=8.6, 6.3 Hz, 1H), 3.30 (dd, J=8.6, 6.6 Hz, 1H), 3.21-3.17 (m, 1H), 3.05 (dd, J=13.8, 4.6 Hz, 1H), 2.44 (dd, J=13.8, 9.8 Hz, 1H), 1.86 (m, 2H), 1.76 (d, J=5.6 Hz, 1H), 1.45-1.24 (m, 2H), 1.25 (d, J=6.3 Hz, 3H), 0.95 (dd, J=6.7, 4.3 Hz, 6H), 0.85 (t, J=7.5 Hz, 3H); $^{13}$C NMR (100 MHz, CDCl$_3$) δ 142.04, 129.13, 128.19, 125.59, 83.76, 79.27, 68.23, 42.93, 35.69, 29.24, 22.76, 19.54, 19.50, 19.02, 11.30; [α]=3.048 (2.1 g/100 mL, CHCl$_3$).

Example 8C: Preparation of (2S,3R)-4-(cyclopentylmethyl)-3-(cyclopropylmethoxy)hexan-2-ol

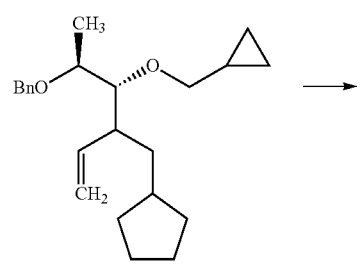

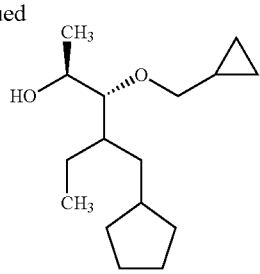

To a solution of 1-((2S,3R,4S)-4-(benzyloxy)-2-(2-methoxyethyl)-3-phenoxypentyl)-4-fluorobenzene (215 mg, 0.509 mmol) in EtOAc (5 mL) was added 5% Pd/C (54.2 mg, 0.025 mmol), and the reaction vessel was evacuated under gentle vacuum and back-filled with $H_2$ (3×). The mixture was placed under approximately 1 Atm of $H_2$ (balloon) and stirred overnight at room temperature. The reaction mixture was filtered through a plug of Celite® and concentrated to provide the title compound (176 mg, 99%) as a clear, colorless oil: $^1$H NMR (400 MHz, CDCl$_3$) δ 7.30-7.21 (m, 2H), 7.21-7.14 (m, 2H), 7.02-6.85 (m, 5H), 4.26 (dd, J=6.2, 3.9 Hz, 1H), 4.11 (h, J=6.2 Hz, 1H), 3.40-3.24 (m, 2H), 3.21 (s, 3H), 3.11 (dd, J=13.9, 5.5 Hz, 1H), 2.55 (dd, J=14.0, 9.0 Hz, 1H), 2.37-2.23 (m, 1H), 1.80-1.66 (m, 2H), 1.66-1.54 (m, 1H), 1.29 (d, J=6.3 Hz, 3H); $^{13}$C NMR (126 MHz, CDCl$_3$) δ 161.31 (d, J=243.7 Hz), 159.11, 136.75 (d, J=3.2 Hz), 130.55 (d, J=7.7 Hz), 129.57, 120.97, 115.83, 115.07 (d, J=21.0 Hz), 82.44, 70.82, 68.31, 58.46, 39.14, 35.48, 30.06, 20.18; ESIMS m/z 333 (([M+H]$^+$)).

Example 8D: Preparation of (1S,2S)-1-phenoxy-1-(thiophen-2-yl)propan-2-ol

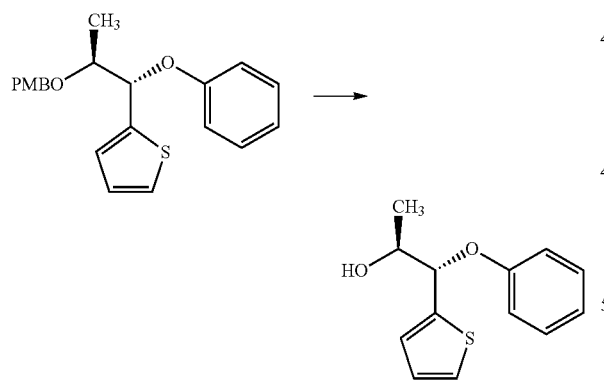

To a solution of 2-((1S,2S)-2-((4-methoxybenzyl)oxy)-1-phenoxypropyl)thiophene (0.223 g, 0.630 mmol) in a mixture of CH$_2$Cl$_2$ (3 mL) and H$_2$O (0.3 mL) at 0° C. was added 4,5-dichloro-3,6-dioxocyclohexa-1,4-diene-1,2-dicarbonitrile (0.150 g, 0.661 mmol), and the reaction mixture was stirred for 30 min quenched by the addition of aq. 1 N NaOH (0.66 mL), and diluted with CH$_2$Cl$_2$ (10 mL). The phases were separated and the aq. phase was extracted with CH$_2$Cl$_2$ (2×10 mL). The combined organic phases were dried over Na$_2$SO$_4$, filtered, evaporated, and purified by flash column chromatography (SiO$_2$, 2→20% acetone in hexanes) to afford the title compound (116 mg, 75%) as a colorless oil: IR (Thin film) 3390, 2923, 2851, 2865, 1597 cm$^{-1}$; $^1$H NMR (300 MHz, CDCl$_3$) δ 7.33-7.16 (m, 3H), 7.07 (ddd, J=3.5, 1.2, 0.7 Hz, 1H), 7.03-6.88 (m, 4H), 5.26 (d, J=4.9 Hz, 1H), 4.28-4.09 (m, 1H), 2.08 (d, J=4.9 Hz, 1H), 1.29 (d, J=6.3 Hz, 3H); $^{13}$C NMR (101 MHz, CDCl$_3$) δ 157.60, 140.58, 129.43, 126.59, 126.50, 125.94, 121.60, 116.21, 80.60, 70.73, 18.33.

Example 8E: Preparation of (2S,3R)-3-(benzyloxy)hex-5-en-2-ol

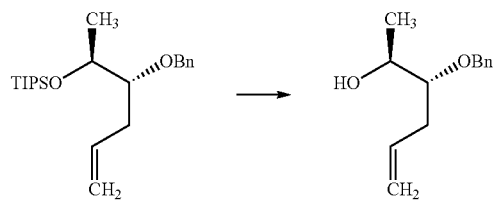

To a solution of (((2S,3R)-3-(benzyloxy)hex-5-en-2-yl)oxy)triisopropylsilane (4.04 g, 11.1 mmol) in THF (56 mL) at 0° C. was added tetra-N-butyl ammonium fluoride (TBAF; 14.7 mL, 14.7 mmol, 1 M in THF) over a 5 min period, and the reaction mixture was warmed to room tempearature and stirred for 4 h, poured into sat. aq. NH$_4$Cl (100 mL), and diluted with EtOAc (100 mL). The phases were separated and the aq. phase was extracted with EtOAc (2×100 mL). The combined organic phases were dried over MgSO$_4$, filtered, and concentrated to a yellow oil, which was purified by flash column chromatography (SiO$_2$, 0→25% EtOAc in hexanes) to afford the title compound (1.91 g, 83%) as a clear, colorless oil: IR (neat) 3419, 2977, 2872, 1454, 1069, 696 cm$^{-1}$; $^1$H NMR (400 MHz, CDCl$_3$) δ 7.39-7.20 (m, 5H), 5.87 (ddt, J=17.2, 10.2, 7.1 Hz, 1H), 5.18-5.09 (m, 1H), 5.06 (ddt, J=10.1, 2.2, 1.2 Hz, 1H), 4.62 (d, J=11.5 Hz, 1H), 4.55 (d, J=11.5 Hz, 1H), 4.00-3.82 (m, 1H), 3.40 (ddd, J=7.3, 5.2, 3.8 Hz, 1H), 2.41 (dtt, J=14.3, 7.1, 1.4 Hz, 1H), 2.33-2.23 (m, 1H), 2.21 (s, 1H), 1.17 (d, J=6.5 Hz, 3H); HRMS-ESI (m/z) ([M+H]$^+$) calcd for C$_{13}$H$_{19}$O$_2$, 207.1380; found, 207.1372.

Example 8F: Preparation of (2S,3R)-3-(p-tolyloxy)butan-2-ol

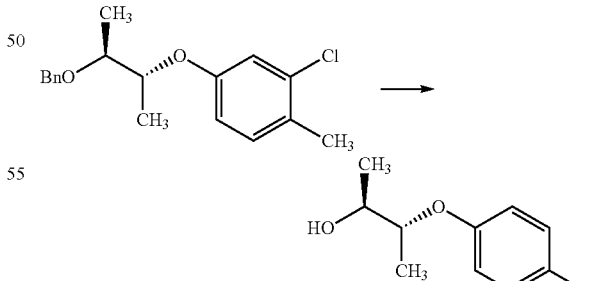

To a solution of 4-(((2R,3S)-3-(benzyloxy)butan-2-yl)oxy)-2-chloro-1-methylbenzene (330 mg, 1.08 mmol) in EtOH (11 mL) were added NEt$_3$ (0.30 mL, 2.17 mmol), 10% Pd/C (58 mg, 0.054 mmol), and the reaction vessel was evacuated and back-filled with $H_2$ (3×). The mixture was stirred under $H_2$ for 24 h at room temperature, filtered through a plug of Celite®, and concentrated to provide an oily solid. The residue was suspended in CH₂Cl₂ (20 mL), washed with 1N HCl (20 mL), dried over Na₂SO₄, filtered, and concentrated to provide 312 mg of a colorless oil, which was dissolved in a 2:1 mixture of EtOH:cyclohexene (10 mL), treated with 10% Pd/C (58 mg, 0.054 mmol), and warmed to and stirred at 65° C. for 20 h. The mixture was cooled to room temperature, filtered through a plug of Celite®, and concentrated to provide the title compound (188 mg, 96%) as a colorless oil: IR (Thin film) 3391, 2977, 2923, 1613, 1585, 1508, 1450, 1373, 1287, 1232, 1167, 1082, 1050, 1008, 993, 935, 901, 813, 746 cm⁻¹; ¹H NMR (300 MHz, CDCl₃) δ 7.08 (d, J=8.2 Hz, 2H), 6.91-6.68 (m, 2H), 4.27 (qd, J=6.3, 3.3 Hz, 1H), 4.02 (dd, J=6.2, 3.3 Hz, 1H), 2.29 (s, 3H), 2.07 (s, 1H), 1.25 (d, J=5.6 Hz, 3H), 1.23 (d, J=5.8 Hz, 3H); ¹³C NMR (126 MHz, CDCl₃) δ 155.35, 130.51, 130.00, 116.18, 77.60, 69.37, 20.48, 17.83, 13.45.

Example 8G: Preparation of (2S,3S,4S)-4-cyclopropyl-3-phenoxy-4-propoxybutan-2-ol

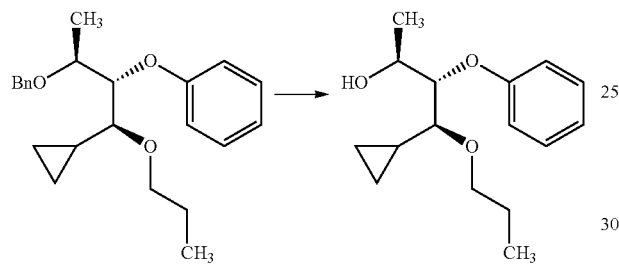

A high pressure steel reactor was charged with a solution of (((1S,2S,3S)-3-(benzyloxy)-1-cyclopropyl-1-propoxybutan-2-yl)oxy)benzene (112 mg, 0.316 mmol) in EtOH (10 mL), 10% Pd/C, Degussa type (17 mg, 0.016 mmol), and 3 drops of AcOH, and the reactor was charged with 600 psi of H₂ and heated to and vigorously stirred at 50° C. for 14 h. The reaction mixture was filtered through a plug of Celite®, concentrated, and the residue was diluted with EtOAc and washed with sat. aq. NaHCO₃. The aqueous phase was further extracted with EtOAc and the combined organic phases were washed with brine, dried over Na₂SO₄, filtered, and concentrated to yield the title compound (66.0 mg, 79%) as a colorless oil: IR (neat) 3448, 2963, 2932, 1597, 1492, 1238, 1079 cm⁻¹; ¹H NMR (400 MHz, CDCl₃) δ 7.31-7.25 (m, 2H), 7.01-6.98 (m, 2H), 6.98-6.93 (m, 1H), 4.34-4.25 (m, 1H), 4.20 (dd, J=7.0, 3.3 Hz, 1H), 3.80-3.72 (m, 1H), 3.47-3.40 (m, 1H), 3.33 (d, J=4.2 Hz, 1H), 3.11 (dd, J=8.2, 3.3 Hz, 1H), 1.66-1.57 (m, 2H), 1.27 (d, J=6.2 Hz, 3H), 1.14-1.04 (m, 1H), 0.93 (t, J=7.4 Hz, 3H), 0.71-0.63 (m, 1H), 0.53-0.45 (m, 1H), 0.45-0.38 (m, 1H), 0.26-0.14 (m, 1H); HRMS-ESI (m/z) [M]⁺ calcd for C₁₆H₂₄O₃, 264.1725; found, 264.1723.

Example 9, Step 1: Preparation of (R)-1-((R)-2,2-dimethyl-1,3-dioxolan-4-yl)-2-methylpropan-1-ol

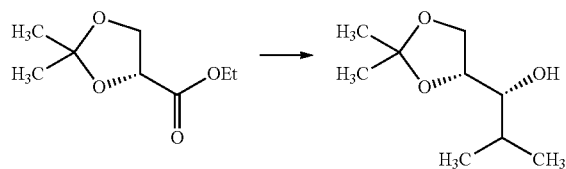

To a solution of isopropylmagnesium chloride (62 mL, 125 mmol, 2 M in THF) and lithiumborohydride (LiBH₄; 41 mL, 81 mmol, 2 M in THF) in anhydrous THF (350 mL) at −5° C. was added (R)-methyl 2,2-dimethyl-1,3-dioxolane-4-carboxylate (10 g, 62 mmol) dropwise at a rate that kept the temperature below 5° C. The reaction mixture was allowed to warm slowly to room temperature overnight, cooled to 0° C., and carefully quenched by the addition of H₂O. The phases were separated and the aq. phase was extracted with Et₂O. The organic phases were combined, dried over Na₂SO₄, filtered, and concentrated to a colorless oil, which was purified by flash column chromatography (SiO₂, 0→10% acetone in hexanes) to provide the title compound (5.07 g, 47%) as a colorless oil: ¹H NMR (400 MHz, CDCl₃) δ 4.21-4.10 (m, 1H), 4.02 (dd, J=8.0, 6.5 Hz, 1H), 3.76 (dd, J=8.0, 7.2 Hz, 1H), 3.23 (dt, J=6.2, 5.3 Hz, 1H), 2.13 (d, J=6.3 Hz, 1H), 1.76-1.62 (m, 1H), 1.44 (s, 3H), 1.38 (s, 3H), 0.98 (d, J=6.8 Hz, 6H); ¹³C NMR (101 MHz, CDCl₃) δ 109.17, 76.86, 76.30, 66.55, 31.56, 26.60, 25.44, 19.41, 17.49; ESIMS m/z 174 (([M+H]⁺)).

Example 9, Step 2: Preparation of (R)-4-((R)-1-(3-chlorophenoxy)-2-methylpropyl)-2,2-dimethyl-1,3-dioxolane

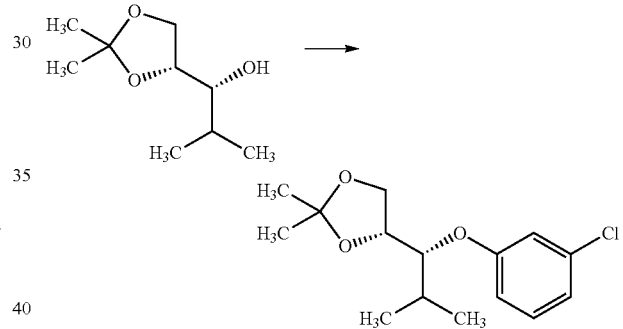

To a solution of (R)-1-((R)-2,2-dimethyl-1,3-dioxolan-4-yl)-2-methylpropan-1-ol (5.62 g, 32.3 mmol) in anhydrous DMF (32 mL) was added KOt-Bu (4.34 g, 38.7 mmol) in one portion, and the reaction mixture was stirred for 5 min at room temperature, treated with 1-chloro-3-fluorobenzene (10.3 mL, 97 mmol), and heated to and stirred at 55° C. for about 3 h. To the mixture were added additional KOt-Bu (1.8 g, 16.1 mmol) and 1-chloro-3-fluorobenzene (3.45 mL, 32.3 mmol) and stirring at 55° C. was continued until thin layer chromatography (TLC) indicated full consumption of the starting material. The reaction mixture was partitioned between Et₂O and H₂O and the phases were separated. The organic phase was washed with H₂O (2×), dried over Na₂SO₄, filtered, and evaporated. The crude material was purified by flash column chromatography (SiO₂, 0→5% acetone in hexanes) to provide the title compound (8.97 g, 98%) as a colorless oil: ¹H NMR (400 MHz, CDCl₃) δ 7.16 (t, J=8.2 Hz, 1H), 7.03 (t, J=2.2 Hz, 1H), 6.93-6.86 (m, 2H), 4.37 (dt, J=7.6, 6.4 Hz, 1H), 4.07-4.00 (m, 2H), 3.68 (t, J=7.9 Hz, 1H), 1.98-1.85 (m, 1H), 1.45 (s, 3H), 1.37 (s, 3H), 1.01 (d, J=6.8 Hz, 3H), 0.99 (d, J=6.8 Hz, 3H); ¹³C NMR (101 MHz, CDCl₃) δ 160.96, 134.64, 130.08, 121.03, 116.81, 114.66, 109.40, 83.92, 65.99, 30.69, 26.41, 25.58, 19.84, 17.35; EIMS m/z 284.

Example 9, Step 3: Preparation of (R)-2,2-dimethyl-4-((R)-2-methyl-1-phenoxypropyl)-1,3-dioxolane

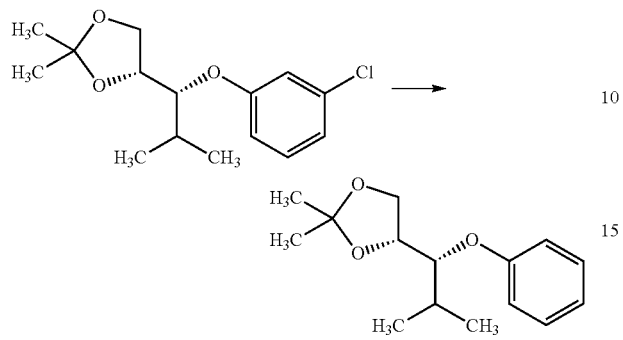

To a solution of (R)-4-((R)-1-(3-chlorophenoxy)-2-methylpropyl)-2,2-dimethyl-1,3-dioxolane (9.44 g, 33.1 mmol) in absolute ethanol (95 mL) were added 5% Pd/C (3.53 g, 1.66 mmol) and NEt$_3$ (13.1 mL, 99 mmol) and H$_2$ was bubbled through the solution for several minutes. The reaction mixture was placed under approximately 1 atmosphere (Atm) of H$_2$ (balloon) and stirred at room temperature overnight. The mixture was filtered through Celite®, rinsing with Et$_2$O and the filtrate was washed with aq. 0.1 N HCl (3×), dried over Na$_2$SO$_4$, filtered, and evaporated to provide the title compound (7.12 g, 86%) as a colorless oil. $^1$H NMR (400 MHz, CDCl$_3$) δ 7.28-7.22 (m, 2H), 7.00 (dt, J=7.9, 1.1 Hz, 2H), 6.92 (tt, J=7.3, 1.1 Hz, 1H), 4.39 (dt, J=7.8, 6.1 Hz, 1H), 4.09-3.98 (m, 2H), 3.71 (t, J=8.0 Hz, 1H), 2.01-1.91 (m, 1H), 1.45 (s, 3H), 1.37 (s, 3H), 1.03 (d, J=6.9 Hz, 3H), 1.00 (d, J=6.9 Hz, 3H); $^{13}$C NMR (101 MHz, CDCl$_3$) δ 160.19, 129.35, 120.85, 116.27, 109.23, 83.12, 65.99, 30.74, 26.43, 25.67, 19.83, 17.76; EIMS m/z 250.

Example 10, Step 1: Preparation of (2R,3R)-4-methyl-3-phenoxypentane-1,2-diol

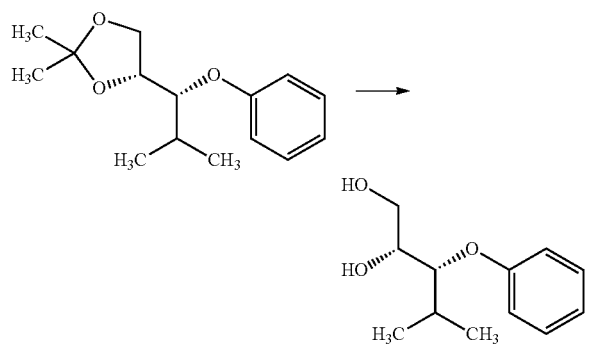

To a solution of (R)-2,2-dimethyl-4-((R)-2-methyl-1-phenoxypropyl)-1,3-dioxolane (7.1 g, 28.4 mmol) in THF (50 mL) was added aq. 1 N HCl (50 mL) and the reaction mixture was stirred vigorously overnight and diluted with Et$_2$O. The phases were separated and the aq. phase was extracted with Et$_2$O. The combined organic phases were then washed sequentially with sat. aq. NaHCO$_3$ and brine, dried over Na$_2$SO$_4$, filtered, and evaporated. The crude residue was purified by flash column chromatography (SiO$_2$, 0→50% acetone in hexanes) to provide the title compound (5.44 g, 91%) as a white solid: $^1$H NMR (400 MHz, CDCl$_3$) δ 7.30-7.20 (m, 2H), 6.99-6.90 (m, 3H), 4.14 (dd, J=5.8, 4.3 Hz, 1H), 3.97-3.88 (m, 1H), 3.68-3.55 (m, 2H), 2.71 (d, J=6.4 Hz, 1H), 2.51 (t, J=5.8 Hz, 1H), 2.15-2.04 (m, 1H), 0.99 (d, J=6.8, 1.6 Hz, 6H); $^{13}$C NMR (101 MHz, CDCl$_3$) δ 159.62, 129.63, 121.25, 115.99, 82.58, 72.12, 64.12, 30.01, 19.44, 18.03; EIMS m/z 210.

Example 10, Steps 2, 3a and 3b: Preparation of (R)-3-methyl-2-phenoxybutan-1-ol and (3S,4R)-5-methyl-4-phenoxyhexan-3-ol

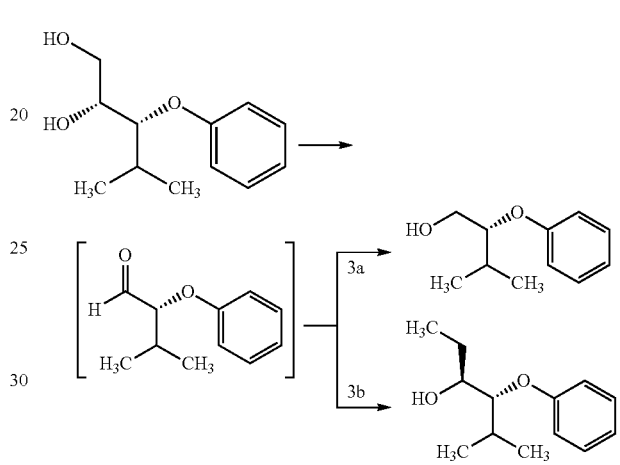

Step 2

To a solution of (2R,3R)-4-methyl-3-phenoxypentane-1,2-diol (0.5 g, 2.38 mmol) in CH$_2$Cl$_2$ (4 mL) and sat. aq. NaHCO$_3$ (1 mL) was added sodium periodate (2.034 g, 9.51 mmol) and the mixture was stirred vigously until TLC showed full consumption of the diol. The reaction mixture was filtered and the filtrate was washed with H$_2$O, dried over Na$_2$SO$_4$, filtered, and concentrated to give the intermediate aldehyde, (R)-3-methyl-2-phenoxybutanal, which was used without further purification.

Step 3a

To a solution of crude (R)-3-methyl-2-phenoxybutanal (~1 mmol) in MeOH (3.3 mL) was added NaBH$_4$ (76 mg, 2.0 mmol) in one portion and the mixture was stirred until TLC showed full consumption of the aldehyde. The reaction mixture was cautiously quenched with sat. aq. NH$_4$Cl (10 mL), diluted with CH$_2$Cl$_2$, and the phases were separated. The aq. phase was extracted with CH$_2$Cl$_2$ (2×) and the combined organic phases were dried by passing through a phase separator cartridge. The solvent was evaporated and the resulting crude material was purified by flash column chromatography (SiO$_2$, 0→15% acetone in hexanes) to provide the title compound (170 mg, 94%) as a colorless oil: $^1$H NMR (400 MHz, CDCl$_3$) δ 7.32-7.24 (m, 2H), 7.00-6.91 (m, 3H), 4.15 (td, J=6.1, 3.6 Hz, 1H), 3.88-3.73 (m, 2H), 2.14-2.01 (m, 1H), 1.80 (dd, J=7.3, 5.6 Hz, 1H), 1.01 (d, J=6.9 Hz, 3H), 0.97 (d, J=6.9 Hz, 3H); $^{13}$C NMR (101 MHz, CDCl$_3$) δ 158.86, 129.57, 121.18, 116.35, 83.94, 62.27, 29.25, 18.62, 18.09; ESIMS m/z 181 (([M+H]$^+$)).

Step 3b

To a solution of ethylmagnesium bromide (EtMgBr; 3.99 mL, 4 mmol, 1 M in THF) in THF at −78° C. was added a solution of crude (R)-3-methyl-2-phenoxybutanal (~2 mmol) in THF (6 mL), and the mixture was stirred until TLC showed full consumption of the aldehyde. The reaction mixture was cautiously quenched with sat. aq. $NH_4Cl$, diluted with $Et_2O$, and the phases were separated. The aq. phase was extracted with $Et_2O$, and the combined organic phases were dried over $Na_2SO_4$, filtered, and concentrated. The crude residue was purified by flash column chromatography ($SiO_2$, 0→10% acetone in hexanes) to provide the title compound (187 mg, 45%) as a colorless oil: $^1H$ NMR (400 MHz, $CDCl_3$) δ 7.29-7.22 (m, 2H), 7.00-6.96 (m, 2H), 6.95-6.89 (m, 1H), 4.11 (t, J=5.3 Hz, 1H), 3.80-3.71 (m, 1H), 2.15-2.03 (m, 1H), 1.76-1.64 (m, 1H), 1.57 (d, J=4.5 Hz, 1H), 1.49 (ddd, J=14.3, 9.6, 7.2 Hz, 1H), 1.02 (d, J=6.8 Hz, 3H), 1.01 (t, J=7.5 Hz, 3H), 0.97 (d, J=6.9 Hz, 3H); $^{13}C$ NMR (101 MHz, $CDCl_3$) δ 160.03, 129.50, 120.80, 116.01, 85.65, 73.83, 29.86, 25.33, 19.88, 18.19, 10.36; EIMS m/z 208.

Example 11, Step 1: Preparation of (R)-methyl 3-methyl-2-phenoxybutanoate

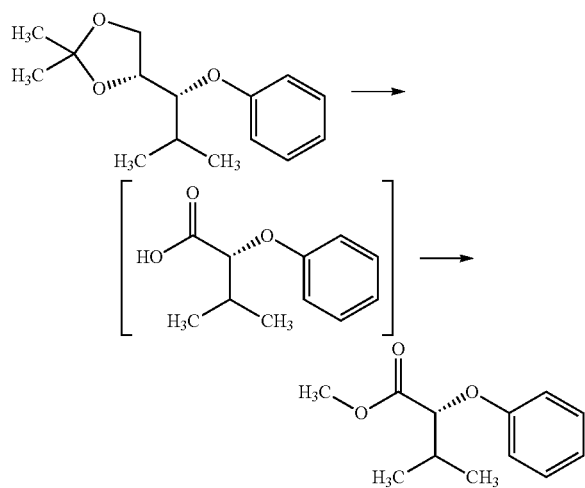

To a solution of (S)-2,2-dimethyl-4-((R)-2-methyl-1-phenoxypropyl)-1,3-dioxolane (1.45 g, 5.79 mmol) in a mixture of $CH_3CN$ (17 mL), carbon tetrachloride ($CCl_4$; 17 mL) and $H_2O$ (25 mL) was added orthoperiodic acid ($H_5IO_6$; 6.60 g, 29.0 mmol), and the resulting colorless mixture was stirred vigorously for 26 h, treated with ruthenium(III) chloride ($RuCl_3$; 0.024 g, 0.12 mmol), and stirred vigorously for 80 min. The reaction mixture was cooled to 0° C., quenched by the addition of sat. aq. $NaHSO_3$ (100 mL), and diluted with EtOAc (150 mL). The phases were separated and the organic phase was washed with brine (100 mL), dried over $MgSO_4$, filtered, and concentrated to a yellow oil, which was dissolved in a mixture of MeOH (8 mL) and benzene (22 mL). The resulting solution was treated with trimethylsilyldiazomethane (5.79 mL, 11.6 mmol, 2 M in $Et_2O$) and the reaction mixture was stirred at room temperature for 30 min. The solvent and volatile components were evaporated to give a yellow oil which was purified by flash column chromatography ($SiO_2$, 1→4% ethyl acetate in hexanes) to provide the title compound (671 mg, 56%) as a colorless oil: $^1H$ NMR (400 MHz, $CDCl_3$) δ 7.33-7.19 (m, 2H), 7.03-6.93 (m, 1H), 6.93-6.81 (m, 2H), 4.38 (d, J=5.6 Hz, 1H), 3.74 (s, 3H), 2.41-2.19 (m, 1H), 1.09 (d, J=6.8 Hz, 3H), 1.06 (d, J=6.9 Hz, 3H); $^{13}C$ NMR (101 MHz, $CDCl_3$) δ 171.91, 158.23, 129.54, 121.49, 115.07, 81.63, 51.99, 31.71, 18.62, 17.85; ESIMS m/z 209 (([M+H]$^+$)).

Example 11, Step 2: Preparation of (R)-2,4-dimethyl-3-phenoxypentan-2-ol

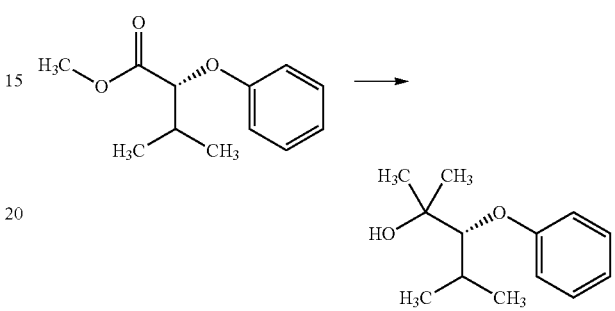

To a solution of (R)-methyl 3-methyl-2-phenoxybutanoate (671 mg, 3.22 mmol) in anhydrous $Et_2O$ (16 mL) was added methylmagnesium bromide (3.22 mL, 9.67 mmol, 3 M in $Et_2O$) at 0° C., and the flask was removed from the cooling bath and warmed to room temperature. After 2 h, the reaction mixture was quenched by adding $H_2O$ (20 mL), diluted with EtOAc (20 mL), and the mixture treated with 2 M HCl until the mixture became clear and biphasic. The phases were separated and the aq. phase was extracted with EtOAc (2×20 mL). The organic phases were combined, dried over $MgSO_4$, filtered, and evaporated to give an oil, which was purified by flash column chromatography ($SiO_2$, 2→10% acetone in hexanes) to afford the title compound (526 mg, 78%) as a clear, colorless oil: $^1H$ NMR (400 MHz, $CDCl_3$) δ 7.32-7.22 (m, 2H), 7.03-6.95 (m, 2H), 6.95-6.88 (m, 1H), 4.05 (d, J=3.4 Hz, 1H), 2.17 (s, 1H), 2.13 (ddp, J=10.3, 6.9, 3.4 Hz, 1H), 1.29 (s, 3H), 1.26 (s, 3H), 1.05 (d, J=6.8 Hz, 3H), 1.01 (d, J=6.9 Hz, 3H); $^{13}C$ NMR (101 MHz, $CDCl_3$) δ 160.53, 129.52, 120.78, 115.80, 87.85, 73.82, 29.86, 27.90, 25.53, 22.79, 17.62; ESIMS m/z 209 (([M+H]$^+$)).

Example 12A: Preparation of (S)-(1R,2S)-1-cyclopentyl-1-(cyclopropylmethoxy)-propan-2-yl-2-((tert-butoxycarbonyl)amino)propanoate (Cmpd 737)

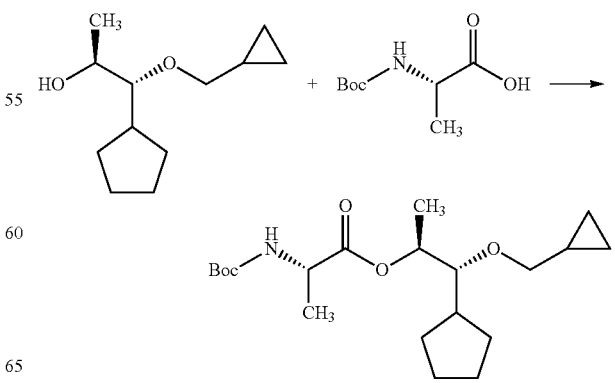

To a solution of (1R,2S)-1-cyclopentyl-1-(cyclopropylmethoxy)propan-2-ol (160 mg, 0.807 mmol) in CH$_2$Cl$_2$ (4.0 mL) were added (S)-2-((tert-butoxycarbonyl)amino)propanoic acid (Boc-Ala-OH; 168 mg, 0.888 mmol) and DMAP (9.86 mg, 0.081 mmol), followed by N$^1$-((ethylimino)methylene)-N$^3$,N$^3$-dimethylpropane-1,3-diamine hydrochloride (EDC; 309 mg, 1.61 mmol), and the reaction mixture was stirred at room temperature overnight and then concentrated to give a yellow oil. The crude material was purified by flash column chromatography (SiO$_2$, 1→12% acetone in hexanes) to afford the title compound (189 mg, 63%) as a colorless oil: IR (Thin film) 3362, 2951, 2869, 1714, 1500, 1451 cm$^{-1}$; $^1$H NMR (500 MHz, CDCl$_3$) δ 5.10-4.96 (m, 2H), 4.34-4.22 (m, 1H), 3.54 (dd, J=9.8, 7.0 Hz, 1H), 3.30 (dd, J=9.8, 6.8 Hz, 1H), 3.16 (dd, J=8.4, 2.5 Hz, 1H), 1.95-1.81 (m, 3H), 1.71-1.59 (m, 3H), 1.57-1.49 (m, 3H), 1.45 (s, 9H), 1.38 (d, J=7.2 Hz, 3H), 1.26 (d, J=6.6 Hz, 3H), 1.12-1.01 (m, 1H), 0.56-0.46 (m, 2H), 0.24-0.17 (m, 2H); ESIMS m/z 370 (([M+H]$^+$)).

Example 12B: Preparation of (R)-2,4-dimethyl-3-phenoxypentan-2-yl-2-((tert-butoxycarbonyl)amino)propanoate (Cmpd 728)

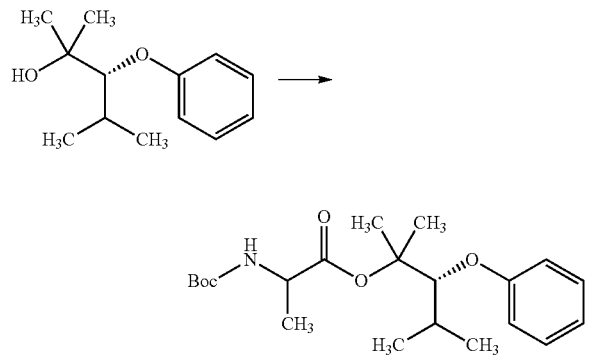

To a solution of (R)-2,4-dimethyl-3-phenoxypentan-2-ol (480 mg, 2.30 mmol), DMAP (845 mg, 6.91 mmol), Sc(OTf)$_3$ (680 mg, 1.38 mmol), and Boc-Ala-OH (1.31 g, 6.91 mmol) in CH$_2$Cl$_2$ (23 mL) at 0° C. was added N,N-methanediylidenebis(propan-2-amine) (DIC; 1.12 mL, 7.26 mmol), and the reaction mixture was heated to and stirred at reflux for 8 h, cooled to room temperature, and stirred for an additional 24 h. The mixture was filtered through a plug of Celite® and the filtrate was washed with 0.1 N HCl (30 mL), dried over Na$_2$SO$_4$, filtered, and evaporated to provide a 1:1 mixture of diastereomers of the title compound (219 mg, 24%) as a colorless oil: $^1$H NMR (400 MHz, CDCl$_3$) for one diastereomer δ 7.33-7.17 (m, 2H), 7.03-6.82 (m, 3H), 4.86 (s, 1H), 4.64 (dd, J=16.5, 4.4 Hz, 1H), 4.20-3.90 (m, 1H), 2.18-2.03 (m, 1H), 1.59-1.51 (m, 6H), 1.44 (s, 9H), 1.17 (t, J=6.9 Hz, 3H), 1.06 (dd, J=6.9, 1.5 Hz, 3H), 1.01 (dd, J=6.8, 1.6 Hz, 3H); $^{13}$C NMR (101 MHz, CDCl$_3$) for both diastereomers δ 172.48, 172.34, 160.23, 160.18, 155.11, 155.04, 129.47, 129.46, 120.69, 120.63, 115.70, 115.64, 86.67, 86.45, 84.13, 83.93, 79.61, 79.57, 49.94, 49.85, 29.60, 29.54, 28.34, 28.33, 23.56, 23.42, 22.59, 22.56, 22.45, 22.38, 18.37, 18.31, 18.30, 18.25; ESIMS m/z 380 (([M+H]$^+$)).

Example 13, Step 1: Preparation of (S)-(2S,3R)-3-(benzyloxy)hex-5-en-2-yl-2-((di-tert-butoxycarbonyl)amino)propanoate (Cmpd 34 and Cmpd 131)

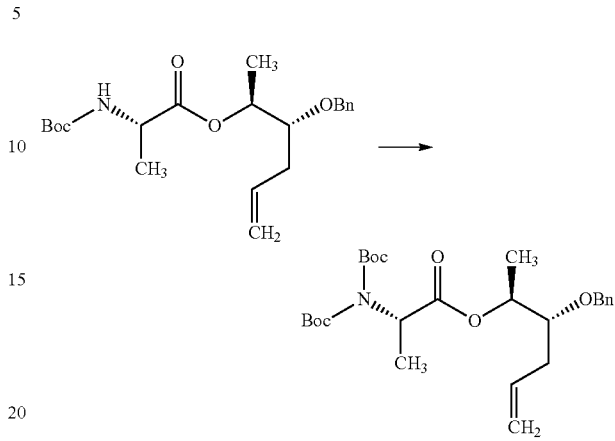

To a solution of (S)-(2S,3R)-3-(benzyloxy)hex-5-en-2-yl-2-((tert-butoxycarbonyl)amino)-propanoate (129.6 mg, 0.343 mmol) in CH$_3$CN (3.4 mL), were added DMAP (62.9 mg, 0.515 mmol) and Boc$_2$O (225 mg, 1.030 mmol), and the resulting pale orange reaction mixture was stirred at room temperature overnight. The mixture was treated with additional DMAP (62.9 mg, 0.515 mmol) and Boc$_2$O (225 mg, 1.030 mmol) and stirred at room temperature for an additional 2 h. The reaction mixture was concentrated to a brown/red oil which was purified by flash column chromatography (SiO$_2$, 0→20% EtOAc in hexanes) to afford the title compound (176.6 mg, 97%) as a clear, colorless oil: IR (Thin film) 2981, 2940, 1739, 1696, 1642, 1455 cm$^{-1}$; $^1$H NMR (400 MHz, CDCl$_3$) δ 7.39-7.22 (m, 10H), 5.90-5.75 (m, 1H), 5.17-4.90 (m, 4H), 4.68 (d, J=11.5 Hz, 1H), 4.53 (d, J=11.4 Hz, 1H), 3.58 (ddd, J=7.5, 5.3, 3.3 Hz, 1H), 2.39-2.18 (m, 2H), 1.51 (d, J=6.9 Hz, 3H), 1.48 (s, 18H), 1.27 (d, J=6.5 Hz, 3H); ESIMS m/z 500 (([M+Na]$^+$)).

Example 13, Step 2: Preparation of (S)-(2S,3R)-3-(benzyloxy)-5-hydroxypentan-2-yl-2-((di-tert-butoxycarbonyl)amino)propanoate (SM: Cmpd 131)

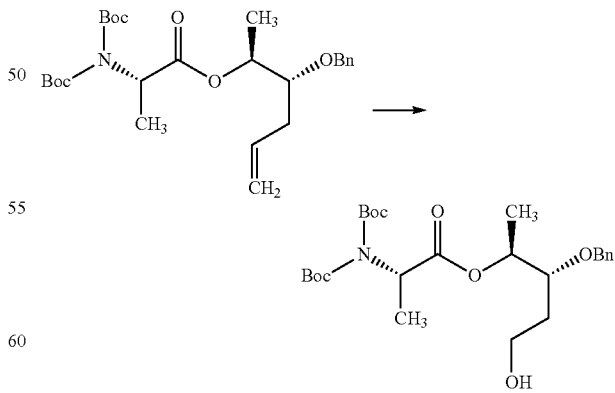

To a solution of (S)-(2S,3R)-3-(benzyloxy)hex-5-en-2-yl-2-((di-tert-butoxycarbonyl)-amino)propanoate (154.6 mg, 0.324 mmol) and NaHCO$_3$ (2.72 mg, 0.032 mmol) in a mixture of anhydrous CH$_2$Cl$_2$ (3.1 mL) and anhydrous MeOH (99 μL) were added 5 drops of a 1% solution of Sudan III in CH$_2$Cl$_2$. The reaction mixture was cooled to −78° C. and O$_3$ was bubbled through the solution until it became clear and colorless. The mixture was purged with O$_2$ for several min, purged with N$_2$ for several min, diluted with additional MeOH (1.2 mL), treated with a single portion of NaBH$_4$ (36.7 mg, 0.971 mmol), and the resulting solution was allowed to warm to room temperature with stirring overnight. The reaction mixture was quenched by the addition of H$_2$O (20 mL) and the phases were separated. The aq. phase was extracted with CH$_2$Cl$_2$ (3×20 mL) and the combined organic phases were dried by passing through a phase separator cartridge and evaporated to an oil, which was purified by flash column chromatography (SiO$_2$, 0→100% EtOAc in hexanes) to afford the title compound (132.6 mg, 81%) as a clear, colorless oil: IR (Thin film) 2981, 1734, 1694, 1455 cm$^{-1}$; $^1$H NMR (400 MHz, CDCl$_3$) δ 7.39-7.27 (m, 5H), 5.10 (qd, J=6.5, 2.5 Hz, 1H), 4.98 (q, J=6.9 Hz, 1H), 4.77 (d, J=11.3 Hz, 1H), 4.50 (d, J=11.3 Hz, 1H), 3.81-3.63 (m, 3H), 2.09 (t, J=5.4 Hz, 1H), 1.82-1.62 (m, 2H), 1.52 (d, J=7.0 Hz, 3H), 1.48 (s, 18H), 1.27 (d, J=6.5 Hz, 3H); HRMS-ESI (m/z) (([M+Na]$^+$)) calcd for C$_{25}$H$_{39}$NNaO$_8$, 504.2568; found, 504.2567.

Example 13, Step 3: Preparation of (S)-(2S,3R)-3-(benzyloxy)-5-methoxypentan-2-yl-2-((di-tert-butoxycarbonyl)amino)propanoate (Product: Cmpd 132)

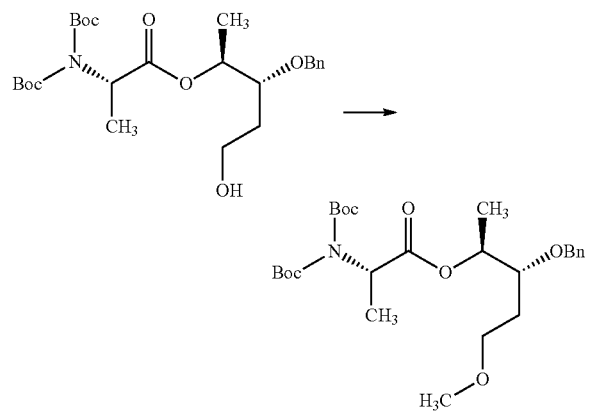

To a solution of (S)-(2S,3R)-3-(benzyloxy)-5-hydroxypentan-2-yl-2-((di-tert-butoxycarbonyl)-amino)propanoate (133 mg, 0.275 mmol) in CH$_2$Cl$_2$ (2.76 mL) were added Proton Sponge® (118 mg, 0.551 mmol) and trimethyloxonium tetrafluoroborate (52.9 mg, 0.358 mmol), and the resulting colorless reaction mixture was stirred at room temperature overnight. The resulting cloudy, orange mixture was carefully quenched by adding sat. aq. NaHCO$_3$ (20 mL) and the phases were separated. The aq. phase was extracted with CH$_2$Cl$_2$ (3×20 mL), and the combined organic phases were washed sequentially with aq. 1 N HCl (2×20 mL) and brine, dried by passing through a phase separator cartridge, and evaporated to give an oil, which was purified by flash column chromatography (SiO$_2$, 0→50% EtOAc in hexanes) to afford the title compound (113 mg, 79%) as a clear, colorless oil: IR (Thin film) 2980, 2936, 1739, 1696, 1455 cm$^{-1}$; $^1$H NMR (400 MHz, CDCl$_3$) δ 7.41-7.20 (m, 5H), 5.07 (qd, J=6.5, 2.6 Hz, 1H), 4.97 (q, J=6.9 Hz, 1H), 4.73 (d, J=11.3 Hz, 1H), 4.46 (d, J=11.3 Hz, 1H), 3.69 (ddd, J=8.7, 4.3, 2.6 Hz, 1H), 3.52-3.39 (m, 2H), 3.28 (s, 3H), 1.80-1.65 (m, 2H), 1.52 (d, J=6.9 Hz, 3H), 1.48 (s, 18H), 1.25 (d, J=6.5 Hz, 3H); HRMS-ESI (m/z) ([M+Na]$^+$) calcd for C$_{26}$H$_{41}$NNaO$_8$, 518.2724; found, 518.2718.

Example 14A, Steps 1 and 2: Preparation of (S)-(1R,2S)-1-cyclopentyl-1-(cyclopropyl-methoxy)propan-2-yl-2-(3-hydroxy-4-methoxypicolinamido)propanoate (Cmpd 737, Cmpd 786, and Cmpd 845)

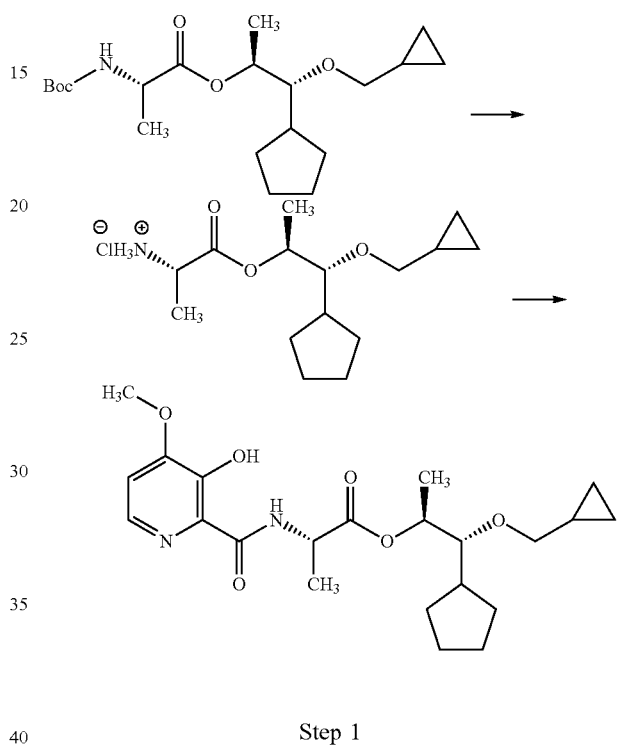

Step 1

To a solution of (S)-(1R,2S)-1-cyclopentyl-1-(cyclopropylmethoxy)propan-2-yl-2-((tert-butoxycarbonyl)amino)propanoate (189 mg, 0.512 mmol) in CH$_2$Cl$_2$ (3.4 mL) was added a 4 N solution of HCl in dioxane (2.6 mL, 10.2 mmol), and the mixture was stirred for 3 h at room temperature. The solvent was evaporated under a stream of N$_2$ to provide the intermediate amine hydrochloride, (S)-1-(((1R,2S)-1-cyclopentyl-1-(cyclopropylmethoxy)propan-2-yl)oxy)-1-oxopropan-2-aminium chloride, as a white solid: ESIMS m/z 340 ([M+H]$^+$).

Step 2

To a solution of (S)-1-(((1R,2S)-1-cyclopentyl-1-(cyclopropylmethoxy)propan-2-yl)oxy)-1-oxopropan-2-aminium chloride and 3-hydroxy-4-methoxypicolinic acid (95.0 mg, 0.563 mmol) in CH$_2$Cl$_2$ (3.4 mL) were added N-ethyl-N-isopropylpropan-2-amine (294 μL, 1.69 mmol) and PyBOP (293 mg, 0.563 mmol), and the reaction mixture was stirred for 4 h at room temperature. The solvent was evaporated and the crude oil was purified by flash column chromatography (SiO$_2$, 1→50% acetone in hexanes) to afford the title compound (118 mg, 55%) as a white solid: $^1$H NMR (300 MHz, CDCl$_3$) δ 12.13 (d, J=0.6 Hz, 1H), 8.47 (d, J=7.9 Hz, 1H), 7.99 (d, J=5.2 Hz, 1H), 6.88 (dd, J=5.3, 0.6 Hz, 1H), 5.09 (qd, J=6.5, 2.3 Hz, 1H), 4.78-4.66 (m, 1H), 3.95 (s, 3H), 3.51

(dd, J=9.8, 6.9 Hz, 1H), 3.23 (dd, J=9.9, 6.8 Hz, 1H), 3.17 (dd, J=8.5, 2.3 Hz, 1H), 2.01-1.72 (m, 2H), 1.75-1.45 (m, 6H), 1.56 (d, J=7.2 Hz, 3H), 1.46-1.29 (m, 1H), 1.28 (d, J=6.6 Hz, 3H), 1.11-0.96 (m, 1H), 0.55-0.41 (m, 2H), 0.15-0.06 (m, 2H); $^{13}$C NMR (101 MHz, CDCl$_3$) δ 171.45, 168.69, 155.40, 148.77, 140.50, 130.42, 109.46, 85.27, 77.27, 75.19, 56.09, 48.12, 42.50, 30.03, 29.15, 25.44, 25.11, 18.21, 13.72, 11.11, 2.87, 2.84; HRMS-ESI (m/z) ([M+H]$^+$) calcd for $C_{22}H_{33}N_2O_6$, 421.2333; found, 421.2331.

Example 14B, Steps 1 and 2: Preparation of (S)-(2S,3R)-3-(benzyloxy)hex-5-en-2-yl-2-(3-hydroxy-4-methoxypicolinamido)propanoate (Cmpd 34, Cmpd 180, and Cmpd 333)

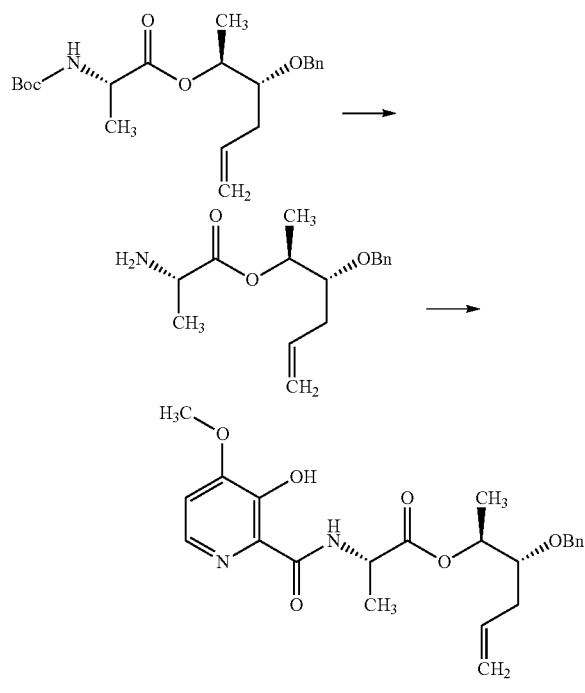

Step 1

To a solution of (S)-(2S,3R)-3-(benzyloxy)hex-5-en-2-yl-2-((tert-butoxycarbonyl)-amino)propanoate (182 mg, 0.483 mmol) in CH$_2$Cl$_2$ (1.6 mL) at 0° C. was added 2,2,2-trifluoroacetic acid (TFA; 400 μL, 5.19 mmol) dropwise over 30 seconds, and the resulting orange mixture was warmed to and stirred at room temperature for 2 h. The reaction mixture was diluted with CH$_2$Cl$_2$ (5 mL), washed with sat. aq. NaHCO$_3$ (5 mL), and the phases were separated. The aq. phase was extracted with CH$_2$Cl$_2$ (3×5 mL), and the combined organic layers were dried by passing through a phase separator cartridge and concentrated to afford the intermediate amine, (S)-(2S,3R)-3-(benzyloxy)hex-5-en-2-yl-2-aminopropanoate (135 mg, 100%), as a clear, colorless oil, which was used directly in the next step: HRMS-ESI (m/z) ([M+H]$^+$) calcd for $C_{16}H_{24}NO_3$, 278.1751; found, 278.1752.

Step 2

To a solution of (S)-(2S,3R)-3-(benzyloxy)hex-5-en-2-yl-2-aminopropanoate (135 mg, 0.487 mmol), 3-hydroxy-4-methoxypicolinic acid (99 mg, 0.584 mmol), and PYBOP (304 mg, 0.584 mmol) in CH$_2$Cl$_2$ (4.87 mL) was added N-ethyl-N-isopropylpropan-2-amine (305 μL, 1.75 mmol) dropwise over a 45 second (sec) period, and the reaction mixture was stirred at room temperature overnight. The mixture was concentrated and the resulting orange/brown oil was purified by flash column chromatography (SiO$_2$, 0→50% acetone in hexanes) to afford the title compound (212 mg, 86%) as a clear, colorless oil: IR (Thin film) 3369, 3063, 2981, 2940, 2877, 1737, 1648, 1576, 1528, 1481, 1452, 1438 cm$^{-1}$; $^1$H NMR (400 MHz, CDCl$_3$) δ 12.12 (d, J=0.6 Hz, 1H), 8.49 (d, J=7.9 Hz, 1H), 7.94 (d, J=5.2 Hz, 1H), 7.38-7.19 (m, 5H), 6.83 (dd, J=5.2, 2.6 Hz, 1H), 5.84 (ddt, J=17.2, 10.2, 7.0 Hz, 1H), 5.20-5.00 (m, 3H), 4.79-4.66 (m, 1H), 4.62 (d, J=11.5 Hz, 1H), 4.52 (d, J=11.5 Hz, 1H), 3.92 (s, 3H), 3.57 (ddd, J=7.2, 5.3, 3.5 Hz, 1H), 2.42-2.24 (m, 2H), 1.54 (d, J=7.2 Hz, 3H), 1.31 (d, J=6.5 Hz, 3H); HRMS-ESI (m/z) ([M+H]$^+$) calcd for $C_{23}H_{29}N_2O_6$, 429.2020; found, 429.2025.

Example 14C, Steps 1 and 2: Preparation of (S)-(2S,3R,4R)-4-benzyl-3-isobutoxyhexan-2-yl-2-(3-hydroxy-4-methoxypicolinamido)propanoate (Cmpd 4, Cmpd 146, and Cmpd 293)

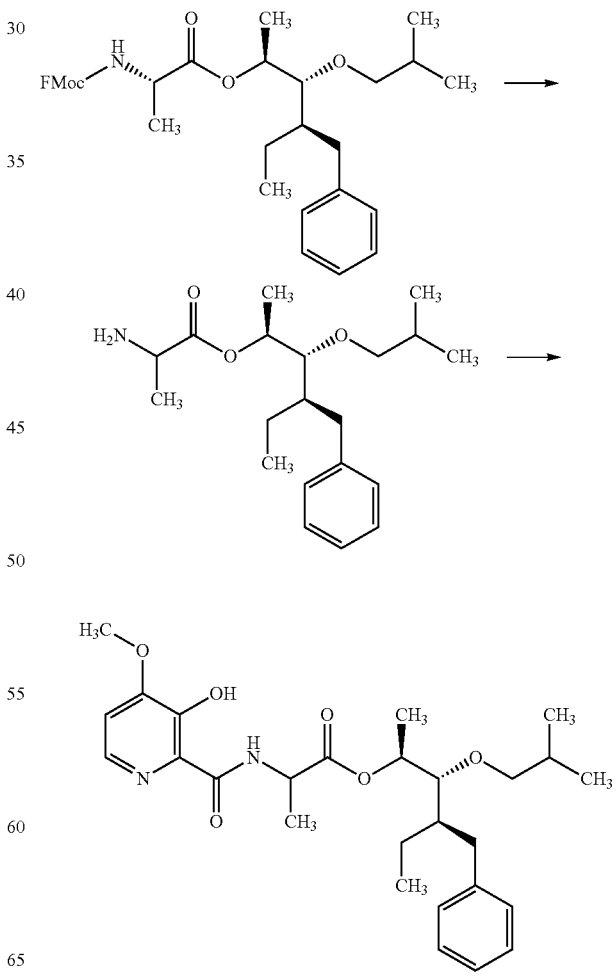

Step 1

To a solution of (S)-(2S,3R,4R)-4-benzyl-3-isobutoxy-hexan-2-yl-2-((((9H-fluoren-9-yl)methoxy)-carbonyl)amino)propanoate (350 mg, 0.63 mmol) in THF (6 mL) was added morpholine (0.63 mL, 7.2 mmol) and the resulting solution was stirred at room temperature for 4 d. The mixture was filtered and the filtrate was evaporated to give a sticky, white solid, which was purified by reverse phase column chromatography ($C_{18}$, $CH_3CN$ in $H_2O$, NaOAc buffer) to afford the intermediate aminium acetate,1-(((2S,3R,4R)-4-benzyl-3-isobutoxyhexan-2-yl)oxy)-1-oxopropan-2-aminium acetate. The aminium acetate was dissolved in EtOAc (10 mL), washed with sat. aq. $NaHCO_3$, and the phases were separated. The organic phase was dried over $Na_2SO_4$, filtered, and concentrated to give the intermediate amine, (2S,3R,4R)-4-benzyl-3-isobutoxyhexan-2-yl-2-ami- nopropanoate (90 mg, 43%, 1.5:1 mixture of diastereomers at the amine bearing carbon), as a colorless oil: $^1H$ NMR (400 MHz, $CDCl_3$) for both diastereomers δ 7.31-7.22 (m, 2H), 7.21-7.12 (m, 3H), 5.22-5.09 (m, 1H), 3.52 (adq, J=8.9, 7.0 Hz, 1H), 3.42 (atd, J=8.5, 6.4 Hz, 1H), 3.30 (at, J=4.9 Hz, 1H), 3.24 (addd, J=8.4, 6.4, 4.3 Hz, 1H), 2.98 (adt, J=13.8, 3.8 Hz, 1H), 2.43 (addd, J=13.6, 9.9, 2.6 Hz, 1H), 1.92-1.81 (m, 1H), 1.72 (adp, J=15.7, 5.1 Hz, 1H), 1.58 (b s, 2H), 1.40-1.24 (m, 2H), 1.34 (ad, J=7.0 Hz, 3H), 1.31-1.27 (m, 3H), 0.94 (ad, J=6.7 Hz, 6H), 0.87 (atd, J=7.5, 3.1 Hz, 3H).

Step 2

To a suspension of (2S,3R,4R)-4-benzyl-3-isobutoxyhexan-2-yl-2-aminopropanoate (0.09 g, 0.268 mmol), 3-hydroxy-4-methoxypicolinic acid (0.05 g, 0.295 mmol), and PYBOP (0.209 g, 0.402 mmol) in $CH_2Cl_2$ (1.5 mL) was added N-ethyl-N-isopropylpropan-2-amine (0.141 mL, 0.805 mmol), and the resulting dark brown solution was stirred at room temperature for 48 h The reaction mixture was partitioned between EtOAc and aq. 1 N HCl, and the phases were separated. The organic phase was washed with sat. aq. $NaHCO_3$, dried over $Na_2SO_4$, filtered, and concentrated. The resulting crude residue was purified by flash column chromatography ($SiO_2$, 30% EtOAc in hexanes) to afford a 1.5:1 mixture of disatereomers (at the amine bearing carbon) of the title compound (125 mg, 96%) as a colorless oil: $^1H$ NMR (400 MHz, $CDCl_3$) for both diastereomers δ 12.15 (add, J=11.4, 0.5 Hz, 1H), 8.49 (at, J=8.0 Hz, 1H), 7.97 (add, J=5.2, 3.5 Hz, 1H), 7.31-7.19 (m, 2H), 7.15 (m, 3H), 6.86 (ad, J=5.1 Hz, 1H), 5.25-5.16 (m, 1H), 4.76-4.66 (m, 1H), 3.94 (s, 3H), 3.42 (add, J=8.5, 6.4 Hz, 1H), 3.33 (aq, J=5.0 Hz, 1H), 3.22 (addd, J=17.7, 8.5, 6.4 Hz, 1H), 2.97 (add, J=13.8, 4.3 Hz, 1H), 2.42 (addd, J=13.6, 10.0, 3.2 Hz, 1H), 1.89-1.77 (m, 1H), 1.73 (apptt, J=10.2, 4.8 Hz, 1H), 1.56 (d, J=7.2 Hz, 3H), 1.39-1.25 (m, 2H), 1.37-1.22 (m, 3H), 0.96-0.81 (m, 9H); $^{13}C$ NMR (101 MHz, $CDCl_3$) for both diastereomers δ 171.51, 171.44, 168.76, 168.70, 155.38, 155.37, 148.77, 141.54, 141.53, 140.50, 130.43, 129.14, 128.19, 128.17, 125.66, 125.64, 109.46, 81.72, 79.54, 79.50, 73.20, 73.19, 56.08, 48.10, 48.01, 43.62, 43.55, 35.39, 29.20, 22.18, 22.00, 19.51, 19.46, 18.32, 18.23, 15.54, 15.30, 10.82, 10.63; ESIMS m/z 487 (([M+H]$^+$)).

Example 14D, Steps 1 and 2: Preparation of (R)-2, 4-dimethyl-3-phenoxypentan-2-yl 2-(3-hydroxy-4-methoxypicolinamido)propanoate (Cmpd 728, Cmpd 779, and Cmpd 835)

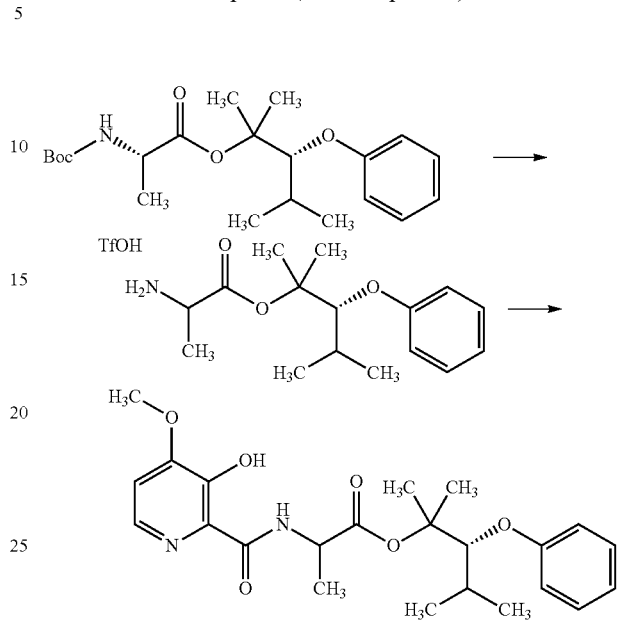

Step 1

To a solution of (R)-2,4-dimethyl-3-phenoxypentan-2-yl 2-((tert-butoxycarbonyl)amino)propanoate (197 mg, 0.519 mmol) in anhydrous $CH_2Cl_2$ (5 mL) was added 2,6-lutidine (302 μL, 2.60 mmol) followed by trimethylsilyl trifluoromethanesulfonate (281 μL, 1.56 mmol), and the resulting solution was stirred at room temperature for 4 h. The reaction mixture was diluted with MeOH (2.5 mL) and the resulting solution was stirred at room temperature for 30 min and concentrated to give the intermediate amine salt, (R)-2,4-dimethyl-3-phenoxypentan-2-yl 2-aminopropanoate trifluoromethanesulfonate (223 mg, 100%) as a yellow oil: ESIMS m/z 280.4 (([M+H]$^+$)).

Step 2

To a solution of (R)-2,4-dimethyl-3-phenoxypentan-2-yl 2-aminopropanoate trifluoromethanesulfonate (223 mg, 0.519 mmol) in anhydrous $CH_2Cl_2$ (5 mL) were added 3-hydroxy-4-methoxypicolinic acid (97 mg, 0.57 mmol), PyBOP (297 mg, 0.571 mmol), and Hunig's base (299 μL, 1.71 mmol), and the resulting mixture was stirred at room temperature for 2 h, concentrated, and the residue purified by column chromatography ($SiO_2$; 4→40% acetone in hexanes) to provide the title compound (24 mg, 11%) as an oil: $^1H$ NMR (400 MHz, $CDCl_3$) δ 12.18 (d, J=3.7 Hz, 1H), 8.40 (d, J=7.6 Hz, 1H), 7.99 (d, J=5.0 Hz, 1H), 7.26-7.17 (m, 2H), 6.96 (dd, J=7.8, 4.9 Hz, 2H), 6.92-6.80 (m, 2H), 4.67 (dd, J=19.2, 4.4 Hz, 1H), 4.47 (dp, J=29.2, 7.2 Hz, 1H), 3.94 (s, 3H), 2.12 (ddt, J=13.8, 6.9, 3.3 Hz, 1H), 1.62-1.54 (m, 6H), 1.38-1.31 (m, 3H), 1.06 (dd, J=6.9, 2.2 Hz, 3H), 1.01 (d, J=6.8 Hz, 3H); $^{13}C$ NMR (101 MHz, $CDCl_3$) δ 171.32, 171.28, 168.62, 168.55, 160.11, 155.36, 148.73, 148.71, 140.47, 130.55, 129.48, 120.75, 120.66, 115.72, 115.58, 109.41, 87.27, 86.97, 84.10, 83.64, 56.07, 48.53, 48.44, 29.71, 29.60, 23.77, 23.46, 22.65, 22.43, 22.29, 18.33, Example 15: Preparation of (S)-(1R,2S)-1-cyclopentyl-1-(p-tolyloxy)propan-2-yl-2-(3-hydroxy-4-methoxypicolinamido)propanoate (Cmpd 843 and Cmpd 846)

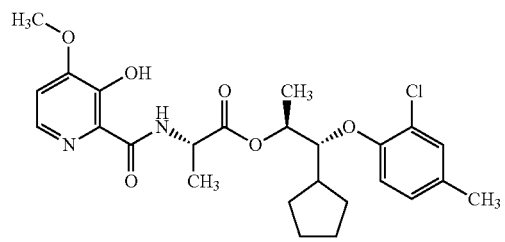

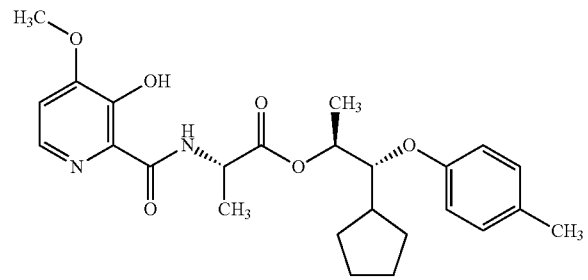

A suspension of (S)-(1R,2S)-1-(2-chloro-4-methylphenoxy)-1-cyclopentylpropan-2-yl-2-(3-hydroxy-4-methoxypicolinamido)propanoate (202 mg, 0.411 mmol), 5% Pd/C (88 mg, 0.041 mmol), and NEt$_3$ (172 µL, 1.234 mmol) in EtOH (8.2 mL) was stirred under approximately 1 Atm (balloon) of H$_2$ at room temperature for 72 h. The reaction mixture was filtered through a pad of Celite® and the filtrate was concentrated to give an oil, which was purified by flash column chromatography (SiO$_2$, 1→30% acetone in hexanes) to afford the title compound (166 mg, 88%) as a white foam: $^1$H NMR (400 MHz, CDCl$_3$) δ 12.11 (d, J=0.6 Hz, 1H), 8.38 (d, J=8.1 Hz, 1H), 7.96 (d, J=5.2 Hz, 1H), 7.01-6.96 (m, 2H), 6.86 (d, J=5.4 Hz, 1H), 6.81 (d, J=8.5 Hz, 2H), 5.15 (qd, J=6.5, 3.0 Hz, 1H), 4.64-4.49 (m, 1H), 4.28 (dd, J=8.2, 3.0 Hz, 1H), 3.94 (s, 3H), 2.24 (s, 3H), 2.18-2.04 (m, 1H), 1.91-1.78 (m, 1H), 1.78-1.64 (m, 2H), 1.62-1.40 (m, 5H), 1.37 (d, J=6.5 Hz, 3H), 1.24 (d, J=7.3 Hz, 3H); $^{13}$C NMR (101 MHz, CDCl$_3$) δ 171.62, 168.64, 157.82, 155.35, 148.73, 140.43, 130.46, 130.34, 129.84, 116.30, 109.40, 83.42, 74.16, 56.07, 47.99, 42.21, 29.65, 29.01, 25.43, 25.10, 20.44, 17.67, 14.26; HRMS-ESI (m/z) ([M+H]$^+$) calcd for C$_{25}$H$_{33}$N$_2$O$_6$, 457.2333; found, 457.2335.

18.26, 18.01, 17.92; HRMS-ESI (m/z) ([M+H]$^+$) calcd for C$_{23}$H$_{31}$N$_2$O$_6$, 431.2177; found, 431.2187.

Example 16A: Preparation of (S)-(1R,2S)-1-(3-chlorophenoxy)-1-cyclopentylpropan-2-yl-2-(3-acetoxy-4-methoxypicolinamido)propanoate (Cmpd 841 and Cmpd 920)

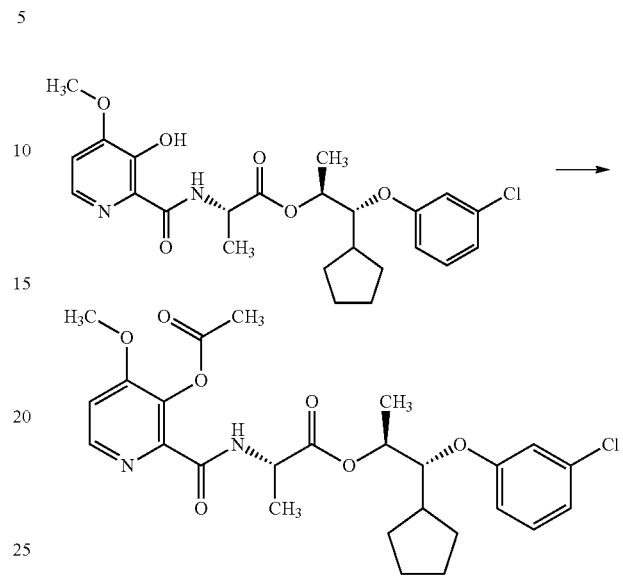

To a solution of (S)-(1R,2S)-1-(3-chlorophenoxy)-1-cyclopentylpropan-2-yl-2-(3-hydroxy-4-methoxypicolinamido)propanoate (100 mg, 0.210 mmol), NEt$_3$ (58.1 µL, 0.419 mmol), and DMAP (5.12 mg, 0.042 mmol) in CH$_2$Cl$_2$ (2.1 mL) was added acetyl chloride (22.4 µL, 0.314 mmol) at room temperature, and the reaction mixture was stirred overnight. The solvent was evaporated, and the resulting crude oil was purified by flash column chromatography (SiO$_2$, 1→40% acetone in hexanes) to afford the title compound (76 mg, 70%) as a colorless oil: $^1$H NMR (500 MHz, CDCl$_3$) δ 8.42 (d, J=8.0 Hz, 1H), 8.30 (d, J=5.4 Hz, 1H), 7.10 (t, J=8.2 Hz, 1H), 7.01-6.96 (m, 1H), 6.93 (t, J=2.2 Hz, 1H), 6.85 (ddd, J=7.9, 1.9, 0.9 Hz, 1H), 6.80 (ddd, J=8.4, 2.5, 0.9 Hz, 1H), 5.13 (qd, J=6.5, 2.9 Hz, 1H), 4.63-4.54 (m, 1H), 4.31 (dd, J=8.4, 3.0 Hz, 1H), 3.91 (s, 3H), 2.39 (s, 3H), 2.16-2.09 (m, 1H), 1.82 (td, J=10.1, 7.6, 4.9 Hz, 1H), 1.73 (qd, J=7.5, 3.4 Hz, 1H), 1.69-1.46 (m, 5H), 1.43-1.36 (m, 1H), 1.34 (d, J=6.5 Hz, 3H), 1.25 (d, J=7.2 Hz, 3H); $^{13}$C NMR (126 MHz, CDl$_3$) δ 172.16, 168.91, 162.37, 160.58, 159.44, 146.65, 141.43, 137.49, 134.72, 130.20, 121.15, 116.75, 114.47, 109.73, 83.60, 73.66, 56.29, 47.97, 42.12, 29.70, 28.93, 25.40, 25.07, 20.75, 18.01, 14.10; HRMS-ESI (m/z) ([M+H]$^+$) calcd for C$_{26}$H$_{32}$ClN$_2$O$_7$, 519.1893; found, 519.1888.

Example 16B: Preparation of (S)-(1R,2S)-1-(3-chlorophenoxy)-1-cyclopentylpropan-2-yl-2-(3-(acetoxymethoxy)-4-methoxypicolinamido)propanoate (Cmpd 841 and Cmpd 911)

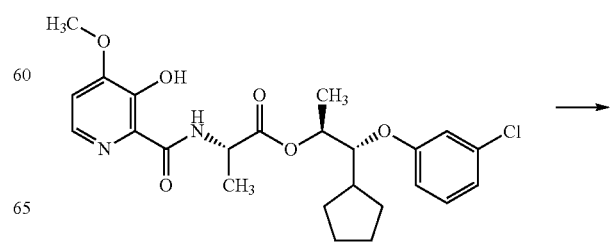

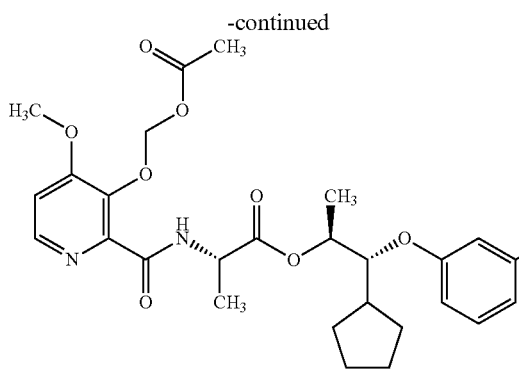

To a suspension of (S)-(1R,2S)-1-(3-chlorophenoxy)-1-cyclopentylpropan-2-yl-2-(3-hydroxy-4-methoxypicolinamido)propanoate (100 mg, 0.210 mmol) and K₂CO₃ (58.0 mg, 0.419 mmol) in acetone (2.1 mL) was added bromomethyl acetate (28.8 μL, 0.294 mmol) at room temperature, and the mixture was heated to and stirred at 55° C. for 3 h, cooled to room temperature, and stirred overnight. The solvent was evaporated and the resulting crude material was purified by flash column chromatography (SiO₂, 1→40% acetone in hexanes) to afford the title compound (53.9 mg, 47%) as a colorless oil: ¹H NMR (500 MHz, CDCl₃) δ 8.29-8.20 (m, 2H), 7.11 (t, J=8.1 Hz, 1H), 6.95-6.91 (m, 2H), 6.86 (ddd, J=8.0, 2.0, 0.9 Hz, 1H), 6.81 (ddd, J=8.4, 2.5, 0.9 Hz, 1H), 5.73 (s, 2H), 5.17-5.10 (m, 1H), 4.64-4.55 (m, 1H), 4.32 (dd, J=8.4, 3.0 Hz, 1H), 3.91 (s, 3H), 2.17-2.09 (m, 1H), 2.07 (s, 3H), 1.87-1.79 (m, 1H), 1.78-1.70 (m, 1H), 1.70-1.64 (m, 1H), 1.57 (s, 4H), 1.42-1.36 (m, 1H), 1.36 (d, J=6.6 Hz, 3H), 1.26 (d, J=7.1 Hz, 3H); ¹³C NMR (126 MHz, CDCl₃) δ 172.25, 170.29, 162.95, 160.59, 160.27, 145.68, 144.04, 142.35, 134.72, 130.19, 121.15, 116.73, 114.53, 109.53, 89.58, 83.63, 73.63, 56.17, 48.18, 42.12, 29.71, 28.91, 25.39, 25.05, 20.87, 17.84, 14.10; HRMS-ESI (m/z) ([M+H]⁺) calcd for C₂₇H₃₄ClN₂O₈, 549.1998; found, 549.1997.

Example 16C: Preparation of (S)-(2S,3S,4S)-4-phenoxy-3-propoxyhexan-2-yl-2-(3-((2-ethoxyacetoxy)methoxy)-4-methoxypicolinamido)propanoate (Cmpd 326 and Cmpd 512)

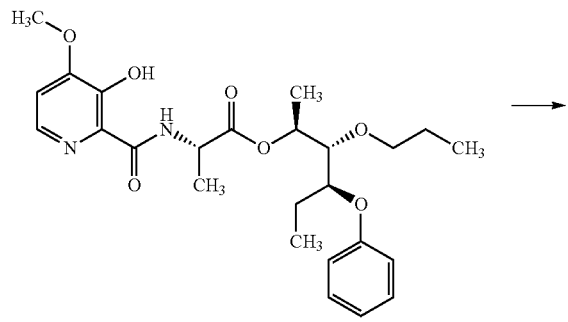

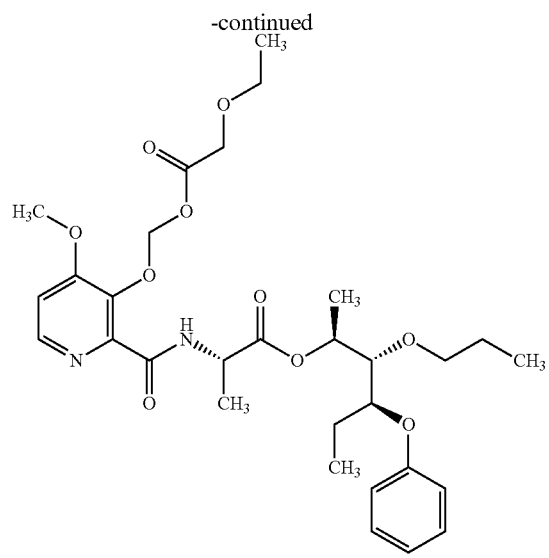

To a solution of (S)-(2S,3S,4S)-4-phenoxy-3-propoxyhexan-2-yl-2-(3-hydroxy-4-methoxypicolinamido)propanoate (103 mg, 0.217 mmol) in acetone (2 mL) were added Na₂CO₃ (46.0 mg, 0.434 mmol), sodium iodide (Ng; 6.5 mg, 0.043 mmol) and chloromethyl 2-ethoxyacetate (49.7 mg, 0.326 mmol), and the mixture was warmed to and stirred at 40° C. for 6 h, cooled to room temperature, and concentrated. The resulting residue was purified by flash column chromatography (SiO₂, 2→30% acetone in hexanes) to afford the title compound (41.4 mg, 32%) as a colorless oil: IR (Thin film) 3383, 2973, 2936, 2878, 1774, 1737, 1677 cm⁻¹; ¹H NMR (400 MHz, CDCl₃) δ 8.33 (d, J=7.8 Hz, 1H), 8.26 (d, J=5.4 Hz, 1H), 7.29-7.19 (m, 2H), 6.98-6.89 (m, 4H), 5.82 (d, J=1.0 Hz, 2H), 5.16 (qd, J=6.4, 4.2 Hz, 1H), 4.72-4.63 (m, 1H), 4.27-4.17 (m, 1H), 4.10 (s, 2H), 3.90 (s, 3H), 3.65-3.47 (m, 5H), 1.88-1.76 (m, 1H), 1.75-1.65 (m, 1H), 1.59-1.49 (m, 2H), 1.42 (d, J=7.2 Hz, 3H), 1.36 (d, J=6.4 Hz, 3H), 1.23 (t, J=7.0 Hz, 3H), 1.00 (t, J=7.4 Hz, 3H), 0.87 (t, J=7.4 Hz, 3H); HRMS-ESI (m/z) ([M+H]⁺) calcd for C₃₀H₄₃N₂O₁₀, 591.2912; found, 591.2913.

Example A: Evaluation of Fungicidal Activity: Leaf Blotch of Wheat (*Zymoseptoria tritici*; Bayer Code SEPTTR)

Technical grades of materials were dissolved in acetone, which were then mixed with nine volumes of water containing 110 ppm Triton X-100. The fungicide solutions were applied onto wheat seedlings using an automated booth sprayer to run-off. All sprayed plants were allowed to air dry prior to further handling. All fungicides were evaluated using the aforementioned method for their activity vs. all target diseases, unless stated otherwise. Wheat leaf blotch and brown rust activity were also evaluated using track spray applications, in which case the fungicides were formulated as EC formulations, containing 0.1% Trycol 5941 in the spray solutions.

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Zymoseptoria tritici* either prior to or after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a greenhouse set at 20° C. for disease to develop. When disease symptoms were fully expressed on the 1$^{st}$ leaves of untreated plants, infection levels were assessed on a scale of 0 to 100 percent disease severity. Percent disease control was calculated using the ratio of disease severity on treated plants relative to untreated plants.

Example B: Evaluation of Fungicidal Activity: Wheat Brown Rust (*Puccinia triticina*; Synonym: *Puccinia recondita f.* sp. *tritici*; Bayer Code PUCCRT)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Puccinia triticina* either prior to or after fungicide treatments. After inoculation the plants were kept in a dark dew room at 22° C. with 100% relative humidity overnight to permit spores to germinate and infect the leaf. The plants were then transferred to a greenhouse set at 24° C. for disease to develop. Fungicide formulation, application and disease assessment followed the procedures as described in the Example A.

Example C: Evaluation of Fungicidal Activity: Wheat Glume Blotch (*Leptosphaeria nodorum*; Bayer Code LEPTNO)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Leptosphaeria nodorum* 24 hr after fungicide treatments. After inoculation the plants were kept in 100% relative humidity (one day in a dark dew chamber followed by two days in a lighted dew chamber at 20° C.) to permit spores to germinate and infect the leaf. The plants were then transferred to a greenhouse set at 20° C. for disease to develop. Fungicide formulation, application and disease assessment followed the procedures as described in the Example A.

Example D: Evaluation of Fungicidal Activity: Apple Scab (*Venturia inaequalis*; Bayer Code VENTIN)

Apple seedlings (variety McIntosh) were grown in soil-less Metro mix, with one plant per pot. Seedlings with two expanding young leaves at the top (older leaves at bottom of the plants were trimmed) were used in the test. Plants were inoculated with a spore suspension of *Venturia inaequalis* 24 hr after fungicide treatment and kept in a 22° C. dew chamber with 100% relative humidity for 48 hr, and then moved to a greenhouse set at 20° C. for disease to develop. Fungicide formulation, application and disease assessment on the sprayed leaves followed the procedures as described in the Example A.

Example E: Evaluation of Fungicidal Activity: Powdery Mildew of Cucumber (*Erysiphe cichoracearum*; Bayer Code ERYSCI)

Cucumber seedlings (variety Bush Pickle) were grown in soil-less Metro mix, with one plant per pot, and used in the test when 12 to 14 days old. Plants were inoculated with a spore suspension 24 hr following fungicide treatments. After inoculation the plants remained in the greenhouse set at 20° C. until disease was fully expressed. Fungicide formulation, application and disease assessment on the sprayed leaves followed the procedures as described in the Example A.

Example F: Evaluation of Fungicidal Activity: Leaf Spot of Sugar Beets (*Cercospora beticola*; Bayer Code CERCBE)

Sugar beet plants (variety HH88) were grown in soil-less Metro mix and trimmed regularly to maintain a uniform plant size prior to test. Plants were inoculated with a spore suspension 24 hr after fungicide treatments. Inoculated plants were kept in a dew chamber at 22° C. for 48 hr then incubated in a greenhouse set at 24° C. under a clear plastic hood with bottom ventilation until disease symptoms were fully expressed. Fungicide formulation, application and disease assessment on the sprayed leaves followed the procedures as described in the Example A.

Example G: Evaluation of Fungicidal Activity: Asian Soybean Rust (*Phakopsora pachyrhizi*; Bayer Code PHAKPA)

Technical grades of materials were dissolved in acetone, which were then mixed with nine volumes of water containing 0.011% Tween 20. The fungicide solutions were applied onto soybean seedlings using an automated booth sprayer to run-off. All sprayed plants were allowed to air dry prior to further handling.

Soybean plants (variety Williams 82) were grown in soil-less Metro mix, with one plant per pot. Two weeks old seedlings were used for testing. Plants were inoculated either 3 days prior to or 1 day after fungicide treatments. Plants were incubated for 24 h in a dark dew room at 22° C. and 100% relative humidity then transferred to a growth room at 23° C. for disease to develop. Disease severity was assessed on the sprayed leaves.

Example H: Evaluation of Fungicidal Activity: Barley Scald (*Rhyncosporium secalis*, Bayer Code RHYNSE)

Barley seedlings (variety Harrington) were propagated in soil-less Metro mix, with each pot having 8 to 12 plants, and used in the test when first leaf was fully emerged. Test plants were inoculated by an aqueous spore suspension of *Rhyncosporium secalis* 24 hr after fungicide treatments. After inoculation the plants were kept in a dew room at 22° C. with 100% relative humidity for 48 hr. The plants were then transferred to a greenhouse set at 20° C. for disease to develop. Fungicide formulation, application and disease assessment on the sprayed leaves followed the procedures as described in the Example A.

Example I: Evaluation of Fungicidal Activity: Rice Blast (*Pyricularia oryzae*; Bayer Code PYRIOR)

Rice seedlings (variety Japonica) were propagated in soil-less Metro mix, with each pot having 8 to 14 plants, and used in the test when 12 to 14 days old. Test plants were inoculated with an aqueous spore suspension of *Pyricularia oryzae* 24 hr after fungicide treatments. After inoculation the plants were kept in a dew room at 22° C. with 100% relative humidity for 48 hr to permit spores to germinate and infect the leaf. The plants were then transferred to a greenhouse set at 24° C. for disease to develop. Fungicide formulation, application and disease assessment on the sprayed leaves followed the procedures as described in the Example A.

Example J: Evaluation of Fungicidal Activity: Tomato Early Blight (*Alternaria solani*; Bayer Code ALTESO)

Tomato plants (variety Outdoor Girl) were propagated in soil-less Metro mix, with each pot having one plant, and used when 12 to 14 days old. Test plants were inoculated with an aqueous spore suspension of *Alternaria solani* 24 hr after fungicide treatments. After inoculation the plants were kept in a dew room at 22° C. with 100% relative humidity for 48 h to permit spores to germinate and infect the leaf. The plants were then transferred to a growth room at 22° C. for disease to develop. Fungicide formulation, application and disease assessment on the sprayed leaves followed the procedures as described in the Example A.

Example K: Evaluation of Fungicidal Activity: Cucumber Anthracnose (*Colletotrichum lagenarium*; Bayer code COLLLA)

Cucumber seedlings (variety Bush Pickle) were propagated in soil-less Metro mix, with each pot having one plant, and used in the test when 12 to 14 days old. Test plants were inoculated with an aqueous spore suspension of *Colletotrichum lagenarium* 24 hr after fungicide treatments. After inoculation the plants were kept in a dew room at 22° C. with 100% relative humidity for 48 hr to permit spores to germinate and infect the leaf. The plants were then transferred to a growth room set at 22° C. for disease to develop. Fungicide formulation, application and disease assessment on the sprayed leaves followed the procedures as described in the Example A.

TABLE 1

Compound Structure, Appearance, and Preparation Method

| *Cmpd. No. | Structure | Prepared According to Example: | Appearance |
|---|---|---|---|
| 1 | 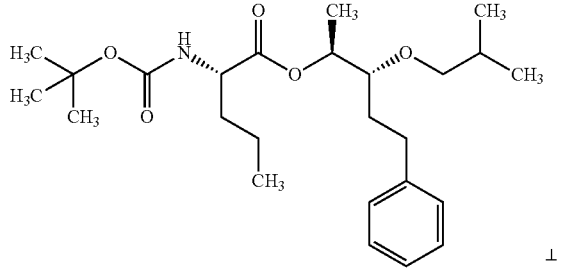 [SMILES: CCC[C@H](NC(=O)OC(C)(C)C)C(=O)O[C@@H](C)[C@@H](CCc1ccccc1)OCC(C)C] | Example 1A; Example 4F; Example 8B; Example 12A | Colorless Oil |
| 2 | 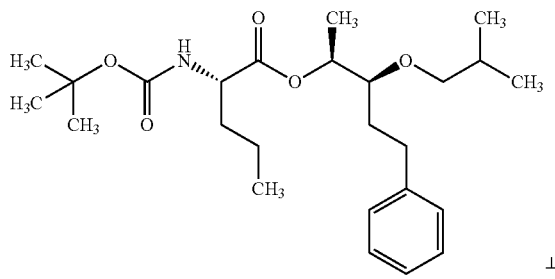 [SMILES: CCC[C@H](NC(=O)OC(C)(C)C)C(=O)O[C@@H](C)[C@H](CCc1ccccc1)OCC(C)C] | Example 1A; Example 4F; Example 8B; Example 12A | Colorless Oil |
| 3 | 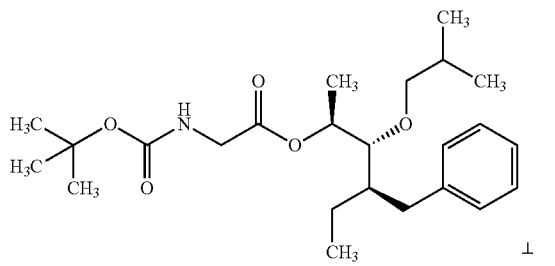 [SMILES: CC[C@H](Cc1ccccc1)[C@@H](OCC(C)C)[C@H](C)OC(=O)CNC(=O)OC(C)(C)C] | Example 2; Example 4F; Example 8B; Example 12A | Colorless Oil |

TABLE 1-continued

Compound Structure, Appearance, and Preparation Method

| *Cmpd. No. | Structure | Prepared According to Example: | Appearance |
|---|---|---|---|
| 4 | 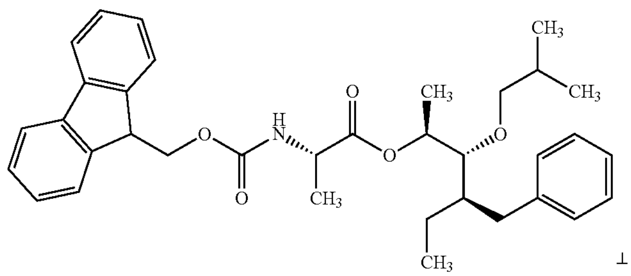 [SMILES: CC[C@H](Cc1ccccc1)[C@@H](OCC(C)C)[C@H](C)OC(=O)[C@H](C)NC(=O)OCC1c2ccccc2-c2ccccc21] | Example 2; Example 4F; Example 8B; Example 12A | Colorless Oil |
| 5 | 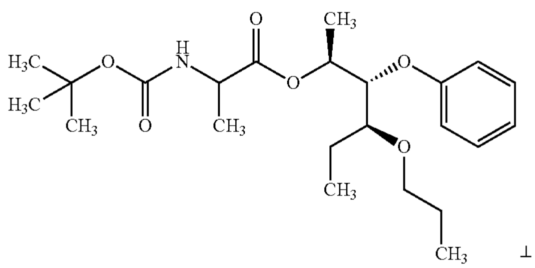 | Example 3; Example 4B; Example 8C; Example 12A | Colorless Oil |
| 6 | 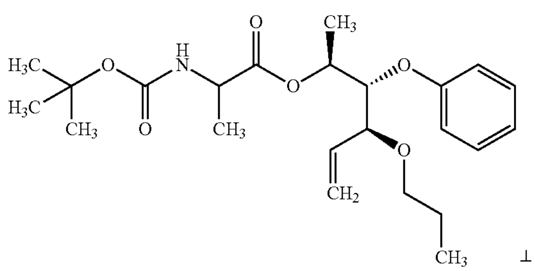 | Example 1B, Step 1; Example 3; Example 4B; Example 8D; Example 12A | Colorless Solid |
| 7 | 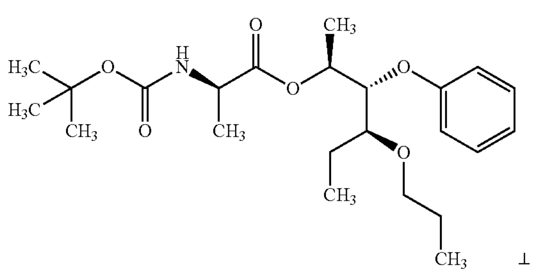 [SMILES: CCCO[C@@H](CC)[C@@H](Oc1ccccc1)[C@H](C)OC(=O)[C@@H](C)NC(=O)OC(C)(C)C] | Example 3; Example 4B; Example 8C; Example 12A | Colorless Oil |
| 8 | 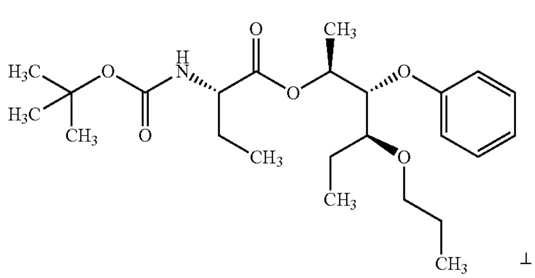 [SMILES: CCCO[C@@H](CC)[C@@H](Oc1ccccc1)[C@H](C)OC(=O)[C@H](CC)NC(=O)OC(C)(C)C] | Example 3; Example 4B; Example 8C; Example 12A | Colorless Oil |

TABLE 1-continued

Compound Structure, Appearance, and Preparation Method

| *Cmpd. No. | Structure | Prepared According to Example: | Appearance |
|---|---|---|---|
| 9 | 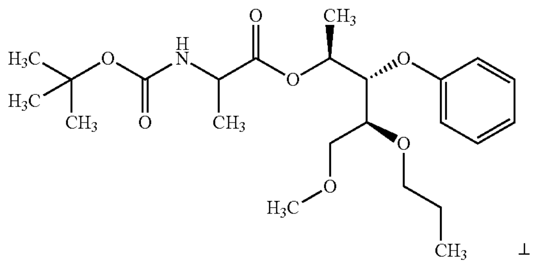 [SMILES: CCCO[C@@H](COC)[C@@H](Oc1ccccc1)[C@H](C)OC(=O)C(C)NC(=O)OC(C)(C)C] | Example 3; Example 4B; Example 6B, Steps 1-2; Example 8C; Example 12A | Colorless Sticky Oil |
| 10 | 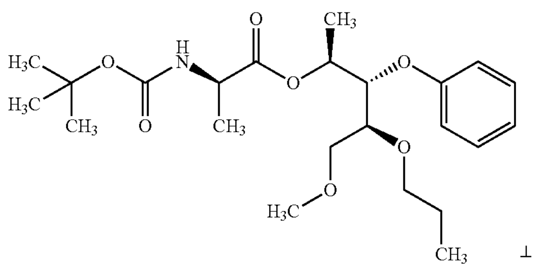 [SMILES: CCCO[C@@H](COC)[C@@H](Oc1ccccc1)[C@H](C)OC(=O)[C@@H](C)NC(=O)OC(C)(C)C] | Example 3; Example 4B; Example 6B, Steps 1, 2; Example 8C; Example 12A | Colorless Sticky Oil |
| 11 | 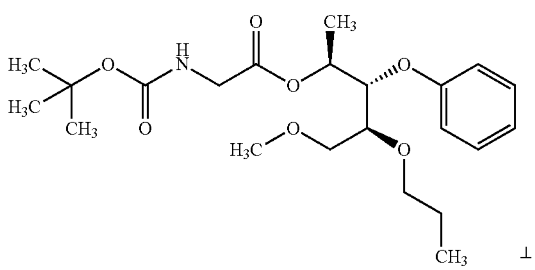 [SMILES: CCCO[C@@H](COC)[C@@H](Oc1ccccc1)[C@H](C)OC(=O)CNC(=O)OC(C)(C)C] | Example 3; Example 4B; Example 6B, Steps 1, 2; Example 8C; Example 12A | Colorless Sticky Oil |
| 12 | 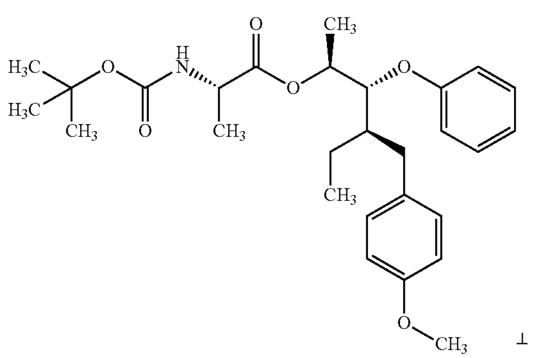 [SMILES: CC[C@H](Cc1ccc(OC)cc1)[C@@H](Oc1ccccc1)[C@H](C)OC(=O)[C@H](C)NC(=O)OC(C)(C)C] | Example 1B, Step 1; Example 2; Example 4B; Example 8C; Example 12A | Sticky Oil |
| 13 | 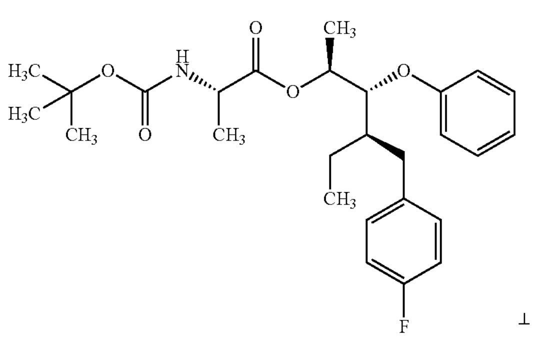 [SMILES: CC[C@H](Cc1ccc(F)cc1)[C@@H](Oc1ccccc1)[C@H](C)OC(=O)[C@H](C)NC(=O)OC(C)(C)C] | Example 1B, Step 1; Example 2; Example 4B; Example 8C; Example 12A | Sticky Oil |

TABLE 1-continued

Compound Structure, Appearance, and Preparation Method

| *Cmpd. No. | Structure | Prepared According to Example: | Appearance |
|---|---|---|---|
| 14 | 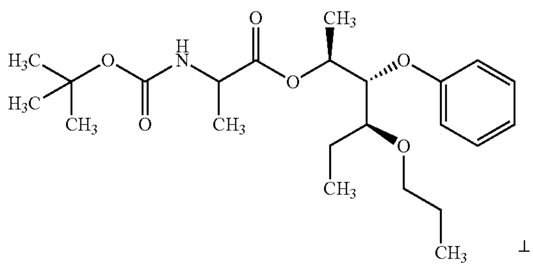 [SMILES: CCCO[C@@H](CC)[C@@H](Oc1ccccc1)[C@H](C)OC(=O)C(C)NC(=O)OC(C)(C)C] | Example 3; Example 4B; Example 8C; Example 12A | Colorless Oil |
| 15 | 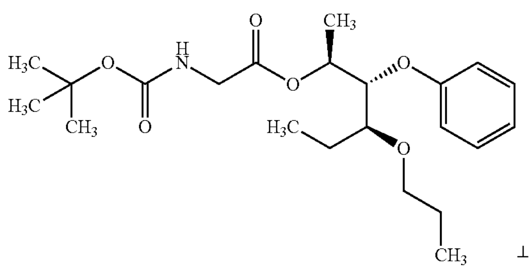 [SMILES: CCCO[C@@H](CC)[C@@H](Oc1ccccc1)[C@H](C)OC(=O)CNC(=O)OC(C)(C)C] | Example 3; Example 4B; Example 8C; Example 12A | Colorless Oil |
| 16 | 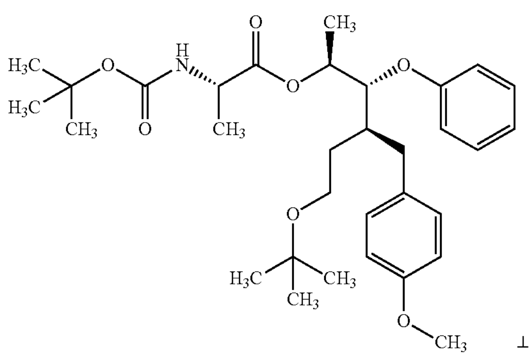 [SMILES: COc1ccc(C[C@@H](CCOC(C)(C)C)[C@@H](Oc2ccccc2)[C@H](C)OC(=O)[C@H](C)NC(=O)OC(C)(C)C)cc1] | Example 1B, Step 1; Example 2; Example 4B; Example 6A, Steps 1, 2b; Example 8C; Example 12A | Colorless Oil |
| 17 | 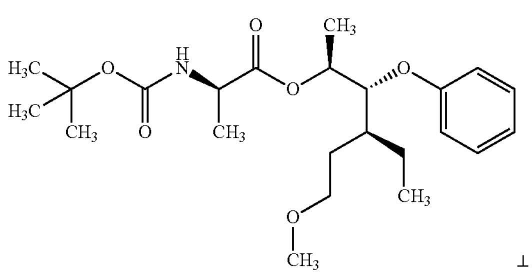 [SMILES: CC[C@@H](CCOC)[C@@H](Oc1ccccc1)[C@H](C)OC(=O)[C@@H](C)NC(=O)OC(C)(C)C] | Example 2; Example 4B; Example 6A, Step 1; Example 7, Step 2a; Example 8C; Example 12A | Colorless Oil |
| 18 | 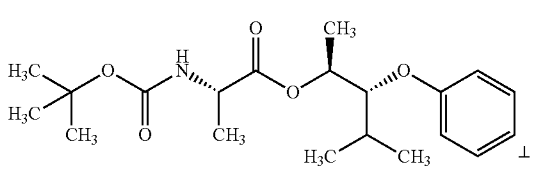 [SMILES: CC(C)[C@@H](Oc1ccccc1)[C@H](C)OC(=O)[C@H](C)NC(=O)OC(C)(C)C] | Example 1A; Example 4B; Example 8C; Example 12A | Colorless Oil |

TABLE 1-continued

Compound Structure, Appearance, and Preparation Method

| *Cmpd. No. | Structure | Prepared According to Example: | Appearance |
|---|---|---|---|
| 19 | 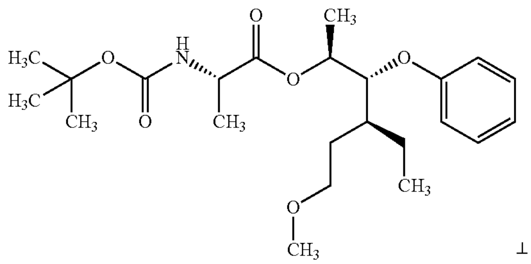 [SMILES: CC[C@@H](CCOC)[C@@H](Oc1ccccc1)[C@H](C)OC(=O)[C@H](C)NC(=O)OC(C)(C)C] | Example 2; Example 4B; Example 6A, Step 1; Example 7, Step 2a; Example 8C; Example 12A | Colorless Oil |
| 20 | 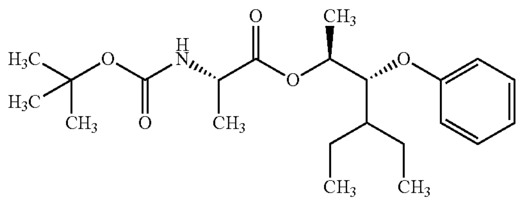 | Example 2; Example 4B; Example 8C; Example 12A | Colorless Oil |
| 21 | 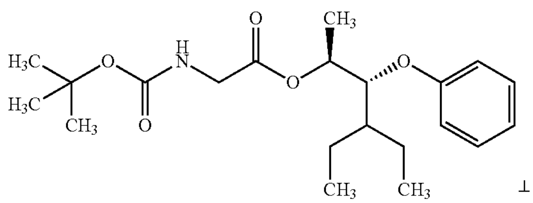 [SMILES: CCC(CC)[C@@H](Oc1ccccc1)[C@H](C)OC(=O)CNC(=O)OC(C)(C)C] | Example 2; Example 4B; Example 8C; Example 12A | Colorless Oil |
| 22 | 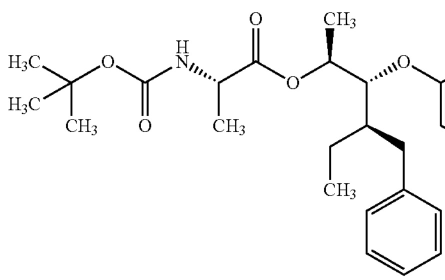 | Example 2; Example 4B; Example 8B; Example 12A | Colorless Oil |
| 23 | 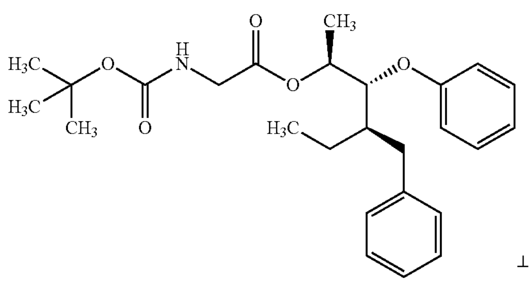 [SMILES: CC[C@H](Cc1ccccc1)[C@@H](Oc1ccccc1)[C@H](C)OC(=O)CNC(=O)OC(C)(C)C] | Example 2; Example 4B; Example 8B; Example 12A | Colorless Oil |
| 24 | 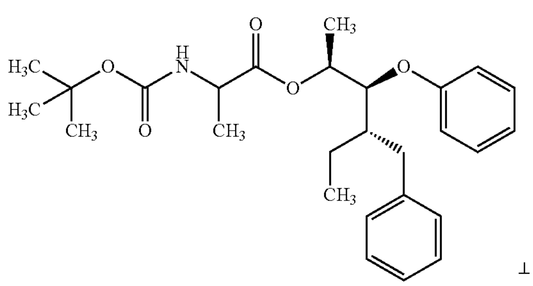 [SMILES: CC[C@@H](Cc1ccccc1)[C@H](Oc1ccccc1)[C@H](C)OC(=O)C(C)NC(=O)OC(C)(C)C] | Example 2; Example 4B; Example 8B; Example 12A | Colorless Oil |

TABLE 1-continued

Compound Structure, Appearance, and Preparation Method

| *Cmpd. No. | Structure | Prepared According to Example: | Appearance |
|---|---|---|---|
| 25 | 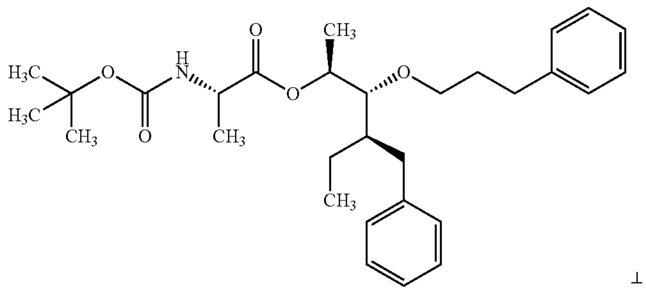 [SMILES: CC[C@H](Cc1ccccc1)[C@@H](OCCCc1ccccc1)[C@H](C)OC(=O)[C@H](C)NC(=O)OC(C)(C)C] | Example 2; Example 4F; Example 8B; Example 12A | Colorless Oil |
| 26 | 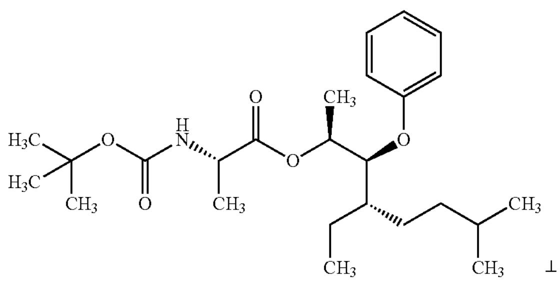 [SMILES: CC[C@@H](CCC(C)C)[C@H](Oc1ccccc1)[C@H](C)OC(=O)[C@H](C)NC(=O)OC(C)(C)C] | Example 1B, Step 1; Example 2; Example 4B; Example 8C; Example 8D; Example 12A | Colorless Oil |
| 27 | 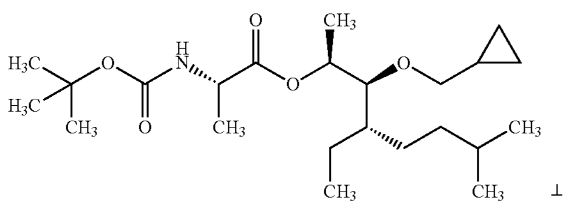 [SMILES: CC[C@@H](CCC(C)C)[C@H](OCC1CC1)[C@H](C)OC(=O)[C@H](C)NC(=O)OC(C)(C)C] | Example 1B, Step 1; Example 2; Example 4D; Example 8C; Example 8D; Example 12A | Colorless Oil |
| 28 | 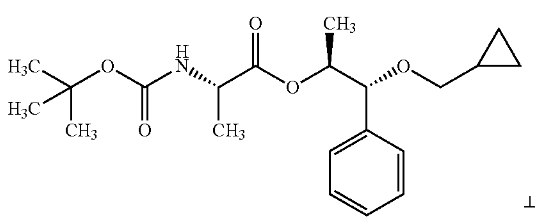 [SMILES: C[C@H](NC(=O)OC(C)(C)C)C(=O)O[C@@H](C)[C@H](OCC1CC1)c1ccccc1] | Example 1A; Example 4F; Example 8C; Example 12A | Colorless Semi Solid |
| 29 | 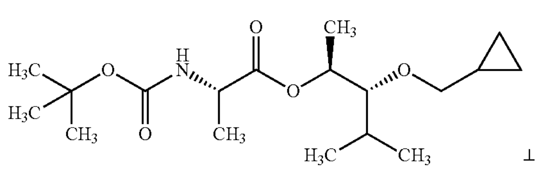 [SMILES: CC(C)[C@@H](OCC1CC1)[C@H](C)OC(=O)[C@H](C)NC(=O)OC(C)(C)C] | Example 1A; Example 4F; Example 8C; Example 12A | Colorless Oil |

TABLE 1-continued

Compound Structure, Appearance, and Preparation Method

| *Cmpd. No. | Structure | Prepared According to Example: | Appearance |
|---|---|---|---|
| 30 | 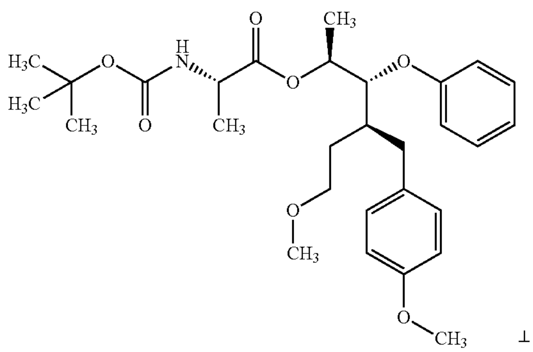 [SMILES: COCC[C@H](Cc1ccc(OC)cc1)[C@@H](Oc1ccccc1)[C@H](C)OC(=O)[C@H](C)NC(=O)OC(C)(C)C] | Example 1B, Step 1; Example 2; Example 4B; Example 6A; Steps 1, 2a; Example 8C; Example 12A | Colorless Oil |
| 31 | 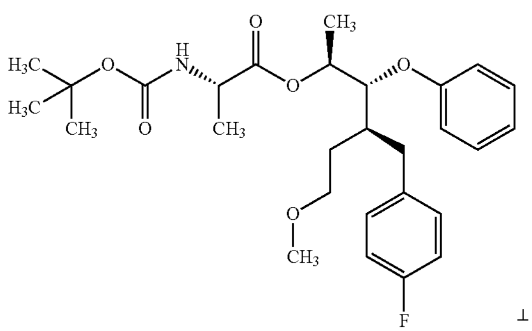 [SMILES: COCC[C@H](Cc1ccc(F)cc1)[C@@H](Oc1ccccc1)[C@H](C)OC(=O)[C@H](C)NC(=O)OC(C)(C)C] | Example 1B, Step 1; Example 2; Example 4B; Example 6A, Steps 1, 2a; Example 8C; Example 12A | Colorless Oil |
| 32 | 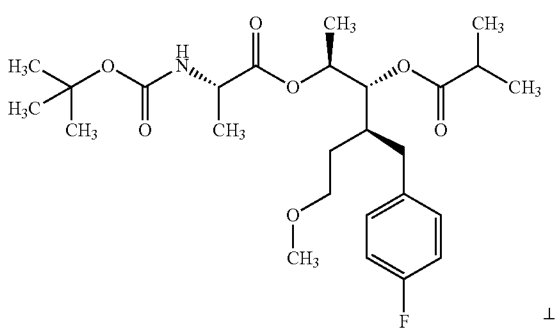 [SMILES: COCC[C@H](Cc1ccc(F)cc1)[C@@H](OC(=O)C(C)C)[C@H](C)OC(=O)[C@H](C)NC(=O)OC(C)(C)C] | Example 1B, Step 1; Example 2; Example 4A; Example 6A, Steps 1, 2a; Example 8C; Example 12A | Colorless Oil |
| 33 | 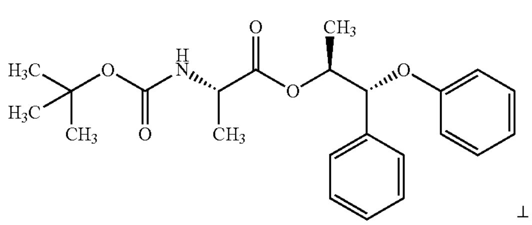 [SMILES: C[C@H](NC(=O)OC(C)(C)C)C(=O)O[C@@H](C)[C@H](Oc1ccccc1)c1ccccc1] | Example 1A; Example 4B; Example 8C; Example 12A | White Solid |
| 34 | 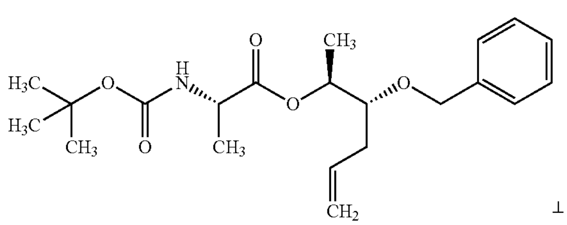 [SMILES: C=CC[C@@H](OCc1ccccc1)[C@H](C)OC(=O)[C@H](C)NC(=O)OC(C)(C)C] | Example 1C, Steps 1, 2; Example 4D; Example 8E; Example 12A | Clear, Colorless Oil |

TABLE 1-continued

Compound Structure, Appearance, and Preparation Method

| *Cmpd. No. | Structure | Prepared According to Example: | Appearance |
|---|---|---|---|
| 35 | 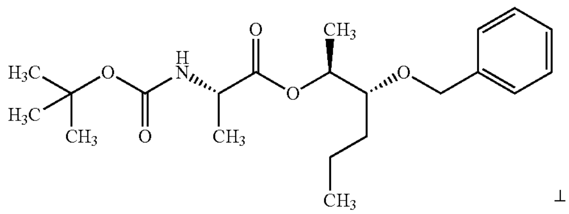 [SMILES: CCC[C@@H](OCc1ccccc1)[C@H](C)OC(=O)[C@H](C)NC(=O)OC(C)(C)C] | Example 1C, Steps 1, 2; Example 8C; Example 4D; Example 8E; Example 12A | Clear, Colorless Oil |
| 36 | 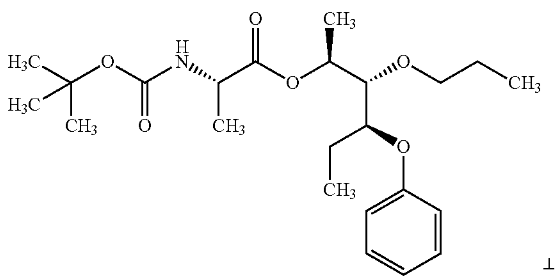 [SMILES: CCCO[C@@H]([C@H](C)OC(=O)[C@H](C)NC(=O)OC(C)(C)C)[C@H](CC)Oc1ccccc1] | Example 3; Example 4F; Example 8B; Example 12A | Yellow Oil |
| 37 | 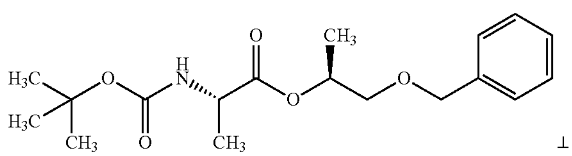 [SMILES: C[C@H](NC(=O)OC(C)(C)C)C(=O)O[C@@H](C)COCc1ccccc1] | Example 12A (From (S)-1-(benzyloxy)propan-2-ol) | Light Yellow Oil |
| 38 | 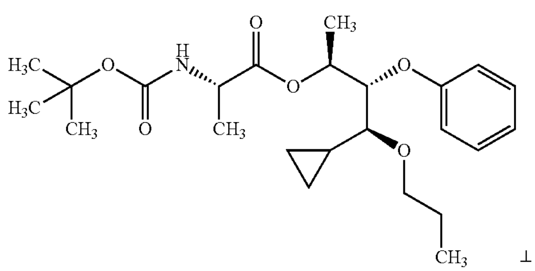 [SMILES: CCCO[C@@H](C1CC1)[C@@H](Oc1ccccc1)[C@H](C)OC(=O)[C@H](C)NC(=O)OC(C)(C)C] | Example 3; Example 4B; Example 6C; Example 8G; Example 12A | Pale Yellow Oil |
| 39 | 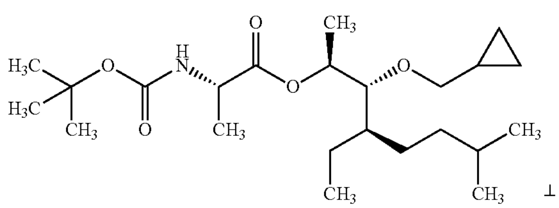 [SMILES: CC[C@H](CCC(C)C)[C@@H](OCC1CC1)[C@H](C)OC(=O)[C@H](C)NC(=O)OC(C)(C)C] | Example 1B, Step 1; Example 2; Example 4D; Example 8C; Example 8D; Example 12A | Pale Yellow Oil |
| 40 | 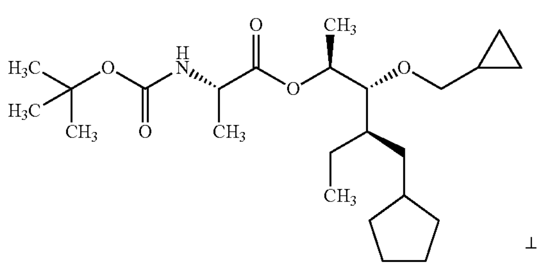 [SMILES: CC[C@H](CC1CCCC1)[C@@H](OCC1CC1)[C@H](C)OC(=O)[C@H](C)NC(=O)OC(C)(C)C] | Example 2; Example 4D; Example 8B; Example 12A | Pale Yellow Oil |

TABLE 1-continued

Compound Structure, Appearance, and Preparation Method

| *Cmpd. No. | Structure | Prepared According to Example: | Appearance |
|---|---|---|---|
| 41 | 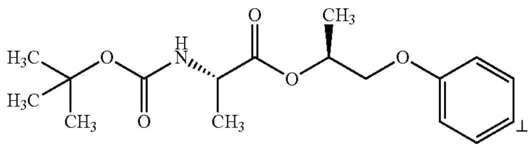 [SMILES: C[C@H](NC(=O)OC(C)(C)C)C(=O)O[C@@H](C)COc1ccccc1] | Example 1D; Example 4B; Example 8C; Example 12A | Colorless Oil |
| 42 | 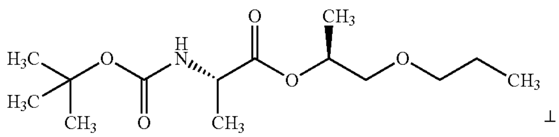 [SMILES: CCCOC[C@H](C)OC(=O)[C@H](C)NC(=O)OC(C)(C)C] | Example 1D; Example 4F; Example 8C; Example 12A | Colorless Oil |
| 43 | 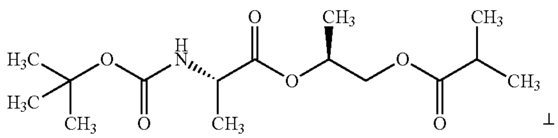 [SMILES: CC(C)C(=O)OC[C@H](C)OC(=O)[C@H](C)NC(=O)OC(C)(C)C] | Example 1D; Example 4A; Example 8C; Example 12A | Colorless Oil |
| 44 | 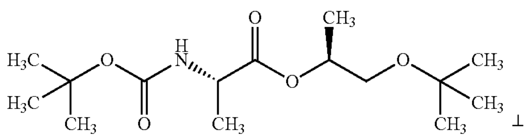 [SMILES: C[C@H](NC(=O)OC(C)(C)C)C(=O)O[C@@H](C)COC(C)(C)C] | Example 1D; Example 4E; Example 8C; Example 12A | Colorless Oil |
| 45 | 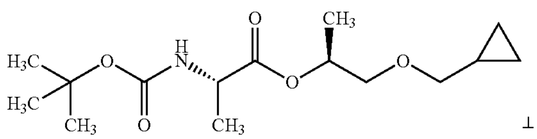 [SMILES: C[C@H](NC(=O)OC(C)(C)C)C(=O)O[C@@H](C)COCC1CC1] | Example 1D; Example 4D; Example 8C; Example 12A | Colorless Oil |
| 46 | 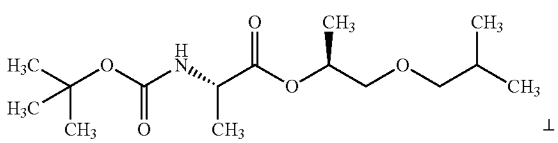 [SMILES: CC(C)COC[C@H](C)OC(=O)[C@H](C)NC(=O)OC(C)(C)C] | Example 1D; Example 4F; Example 8C; Example 12A | Colorless Oil |
| 47 | 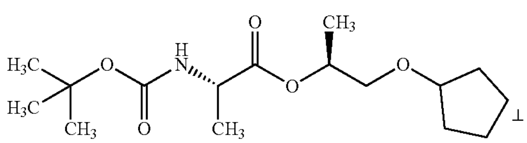 [SMILES: C[C@H](NC(=O)OC(C)(C)C)C(=O)O[C@@H](C)COC1CCCC1] | Example 1D; Example 4H; Example 8C; Example 12A | Colorless Oil |
| 48 | 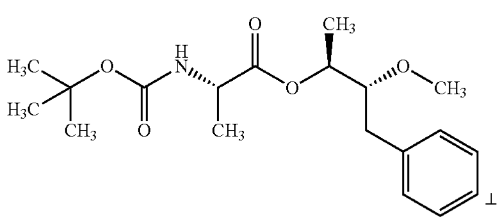 [SMILES: CO[C@H](Cc1ccccc1)[C@H](C)OC(=O)[C@H](C)NC(=O)OC(C)(C)C] | Example 1B, Steps 1, 2; Example 4D; Example 8C; Example 12A | Colorless Oil |
| 49 | 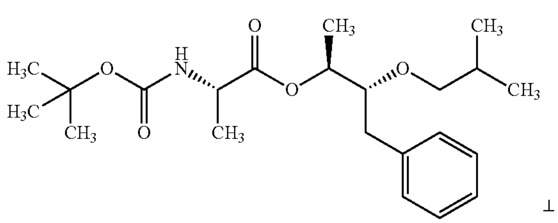 [SMILES: CC(C)CO[C@H](Cc1ccccc1)[C@H](C)OC(=O)[C@H](C)NC(=O)OC(C)(C)C] | Example 1B, Steps 1, 2; Example 4D; Example 8C; Example 12A | Colorless Oil |

TABLE 1-continued

Compound Structure, Appearance, and Preparation Method

| *Cmpd. No. | Structure | Prepared According to Example: | Appearance |
|---|---|---|---|
| 50 | 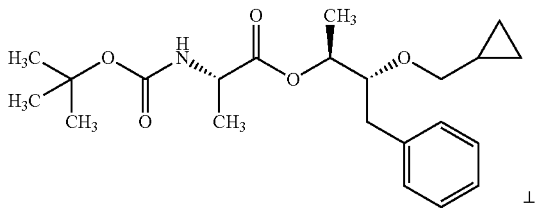 [SMILES: C[C@H](NC(=O)OC(C)(C)C)C(=O)O[C@@H](C)[C@@H](Cc1ccccc1)OCC1CC1] | Example 1B, Steps 1, 2; Example 4D; Example 8C; Example 12A | Colorless Oil |
| 51 | 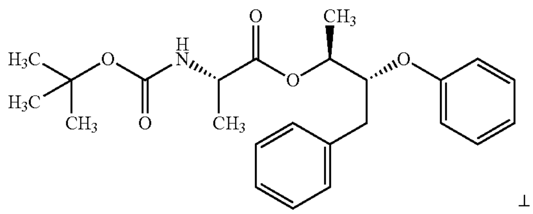 [SMILES: C[C@H](NC(=O)OC(C)(C)C)C(=O)O[C@@H](C)[C@@H](Cc1ccccc1)Oc1ccccc1] | Example 1B, Steps 1, 2; Example 4B; Example 8C; Example 12A | Colorless Oil |
| 52 | 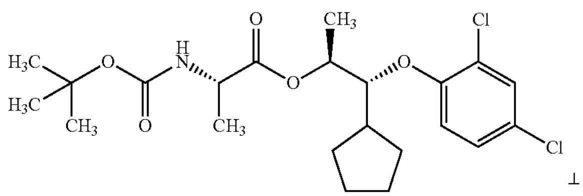 [SMILES: C[C@H](NC(=O)OC(C)(C)C)C(=O)O[C@@H](C)[C@H](Oc1ccc(Cl)cc1Cl)C1CCCC1] | Example 1B, Steps 1, 2; Example 4C; Example 8C; Example 12A | Colorless Oil |
| 53 | 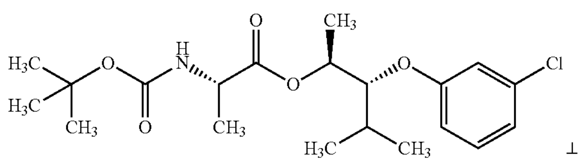 [SMILES: CC(C)[C@@H](Oc1cccc(Cl)c1)[C@H](C)OC(=O)[C@H](C)NC(=O)OC(C)(C)C] | Example 1A; Example 4C; Example 8A; Example 12A | Colorless Oil |
| 54 | 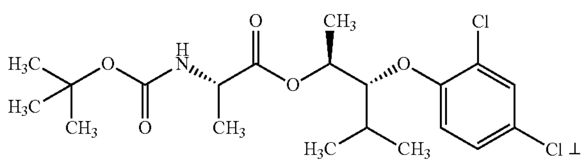 [SMILES: CC(C)[C@@H](Oc1ccc(Cl)cc1Cl)[C@H](C)OC(=O)[C@H](C)NC(=O)OC(C)(C)C] | Example 1A; Example 4C; Example 8A; Example 12A | Colorless Oil |
| 55 | 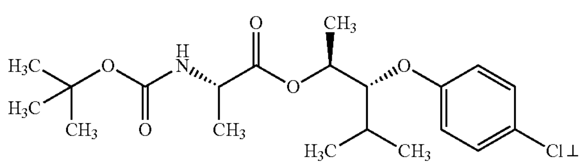 | Example 1A; Example 4C; Example 8A; Example 12A | Colorless Oil |
| 56 | 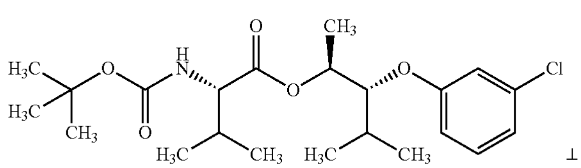 [SMILES: CC(C)[C@H](NC(=O)OC(C)(C)C)C(=O)O[C@@H](C)[C@H](Oc1cccc(Cl)c1)C(C)C] | Example 1A; Example 4C; Example 8A; Example 12A | Colorless Oil |
| 57 | 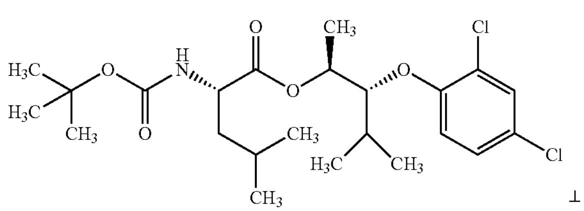 [SMILES: CC(C)C[C@H](NC(=O)OC(C)(C)C)C(=O)O[C@@H](C)[C@H](Oc1ccc(Cl)cc1Cl)C(C)C] | Example 1A; Example 4C; Example 8A; Example 12A | Colorless Oil |

TABLE 1-continued

Compound Structure, Appearance, and Preparation Method

| *Cmpd. No. | Structure | Prepared According to Example: | Appearance |
|---|---|---|---|
| 58 | 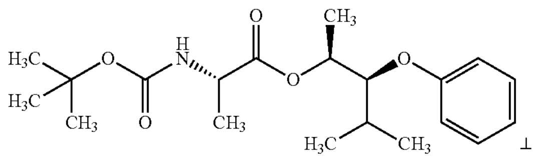 [SMILES: CC(C)[C@H](Oc1ccccc1)[C@H](C)OC(=O)[C@H](C)NC(=O)OC(C)(C)C] | Example 1A; Example 4B; Example 8C; Example 12A | White Solid |
| 59 | 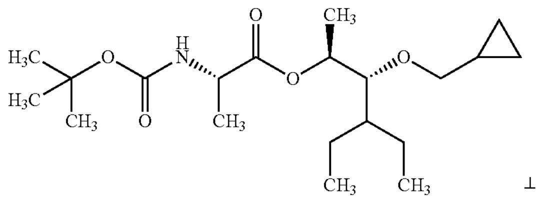 [SMILES: CCC(CC)[C@@H](OCC1CC1)[C@H](C)OC(=O)[C@H](C)NC(=O)OC(C)(C)C] | Example 1A; Example 4D; Example 8A; Example 12A | Colorless Oil |
| 60 | 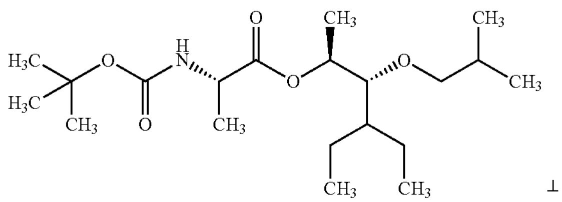 [SMILES: CCC(CC)[C@@H](OCC(C)C)[C@H](C)OC(=O)[C@H](C)NC(=O)OC(C)(C)C] | Example 1A; Example 4F; Example 8C; Example 12A | Colorless Oil |
| 61 | 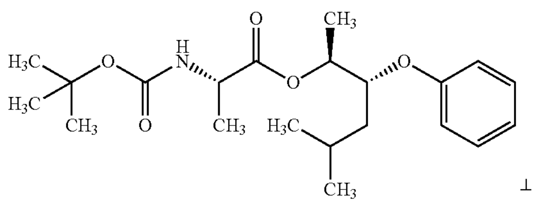 [SMILES: CC(C)C[C@@H](Oc1ccccc1)[C@H](C)OC(=O)[C@H](C)NC(=O)OC(C)(C)C] | Example 1B, Steps 1, 2; Example 4C; Example 8B; Example 12A | Colorless Oil |
| 62 | 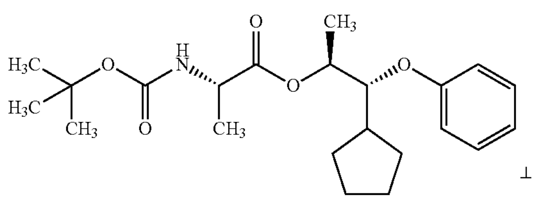 [SMILES: C[C@H](NC(=O)OC(C)(C)C)C(=O)O[C@@H](C)[C@H](Oc1ccccc1)C1CCCC1] | Example 1B, Steps 1, 2; Example 4B; Example 8C; Example 12A | Sticky Oil |
| 63 | 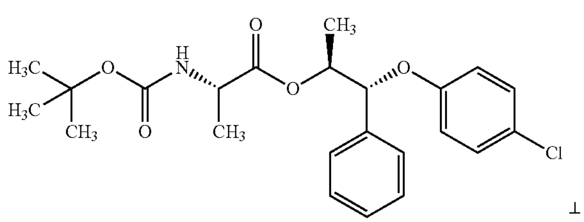 [SMILES: C[C@H](NC(=O)OC(C)(C)C)C(=O)O[C@@H](C)[C@H](Oc1ccc(Cl)cc1)c1ccccc1] | Example 1B, Steps 1, 2; Example 4C; Example 8C; Example 12A | Sticky Oil |
| 64 | 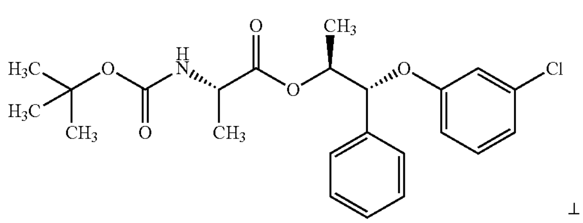 [SMILES: C[C@H](NC(=O)OC(C)(C)C)C(=O)O[C@@H](C)[C@H](Oc1cccc(Cl)c1)c1ccccc1] | Example 1B, Steps 1, 2; Example 4C; Example 8C; Example 12A | Sticky Oil |

TABLE 1-continued

Compound Structure, Appearance, and Preparation Method

| *Cmpd. No. | Structure | Prepared According to Example: | Appearance |
|---|---|---|---|
| 65 | 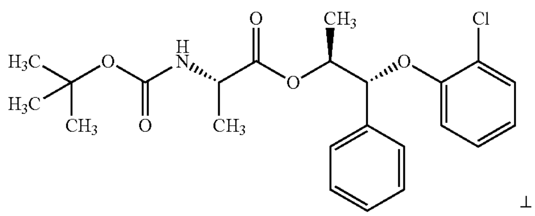 [SMILES: C[C@H](NC(=O)OC(C)(C)C)C(=O)O[C@@H](C)[C@H](Oc1ccccc1Cl)c1ccccc1] | Example 1B, Steps 1, 2; Example 4C; Example 8C; Example 12A | Sticky Oil |
| 66 | 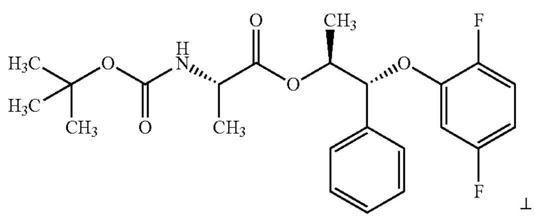 [SMILES: C[C@H](NC(=O)OC(C)(C)C)C(=O)O[C@@H](C)[C@H](Oc1cc(F)ccc1F)c1ccccc1] | Example 1B, Steps 1, 2; Example 4C; Example 8C; Example 12A | Sticky Oil |
| 67 | 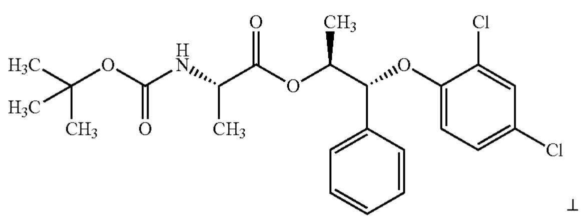 [SMILES: C[C@H](NC(=O)OC(C)(C)C)C(=O)O[C@@H](C)[C@H](Oc1ccc(Cl)cc1Cl)c1ccccc1] | Example 1B, Steps 1, 2; Example 4C; Example 8C; Example 12A | Sticky Oil |
| 68 | 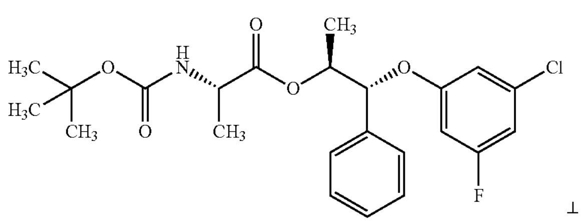 | Example 1B, Steps 1, 2; Example 4C; Example 8C; Example 12A | Sticky Oil |
| 69 | 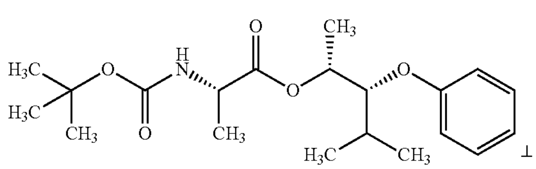 | Example 1A; Example 4B; Example 8A; Example 12A | Clear Oil |
| 70 | 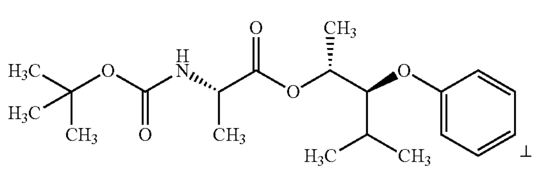 [SMILES: CC(C)[C@H](Oc1ccccc1)[C@@H](C)OC(=O)[C@H](C)NC(=O)OC(C)(C)C] | Example 1A; Example 4B; Example 8A; Example 12A | Sticky Wax |
| 71 | 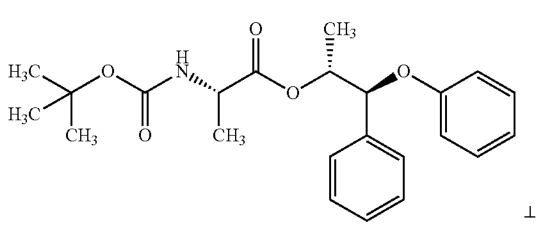 [SMILES: C[C@H](NC(=O)OC(C)(C)C)C(=O)O[C@H](C)[C@@H](Oc1ccccc1)c1ccccc1] | Example 1A; Example 4B; Example 8A; Example 12A | Sticky Wax |

TABLE 1-continued

Compound Structure, Appearance, and Preparation Method

| *Cmpd. No. | Structure | Prepared According to Example: | Appearance |
|---|---|---|---|
| 72 | 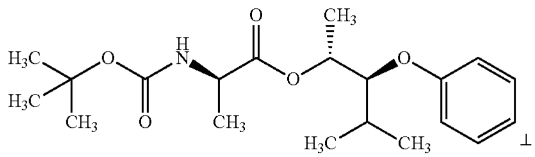 [SMILES: CC(C)[C@H](Oc1ccccc1)[C@@H](C)OC(=O)[C@@H](C)NC(=O)OC(C)(C)C] | Example 1A; Example 4B; Example 8A; Example 12A | Sticky Wax |
| 73 | 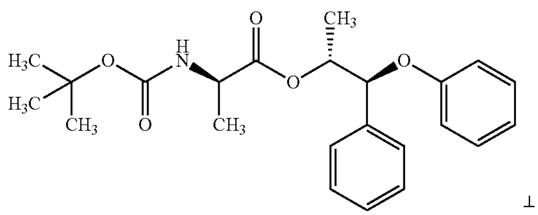 [SMILES: C[C@@H](NC(=O)OC(C)(C)C)C(=O)O[C@H](C)[C@@H](Oc1ccccc1)c1ccccc1] | Example 1A; Example 4B; Example 8A; Example 12A | Sticky Wax |
| 74 | 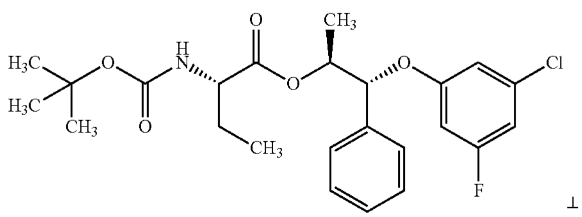 [SMILES: CC[C@H](NC(=O)OC(C)(C)C)C(=O)O[C@@H](C)[C@H](Oc1cc(F)cc(Cl)c1)c1ccccc1] | Example 1B, Steps 1, 2; Example 4C; Example 8C; Example 12A | Sticky Oil |
| 75 | 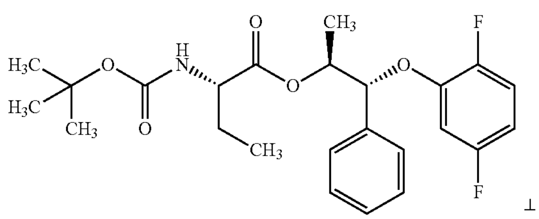 [SMILES: CC[C@H](NC(=O)OC(C)(C)C)C(=O)O[C@@H](C)[C@H](Oc1cc(F)ccc1F)c1ccccc1] | Example 1B, Steps 1, 2; Example 4C; Example 8C; Example 12A | White Solid |
| 76 | 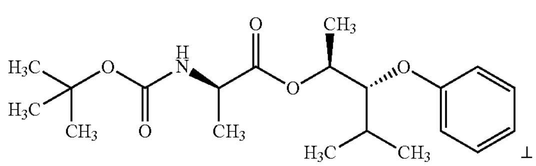 [SMILES: CC(C)[C@@H](Oc1ccccc1)[C@H](C)OC(=O)[C@@H](C)NC(=O)OC(C)(C)C] | Example 1A; Example 4B; Example 8A; Example 12A | Clear Oil |
| 77 | 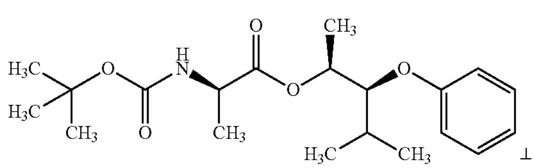 [SMILES: CC(C)[C@H](Oc1ccccc1)[C@H](C)OC(=O)[C@@H](C)NC(=O)OC(C)(C)C] | Example 1A; Example 4B; Example 8A; Example 12A | Clear Oil |
| 78 | 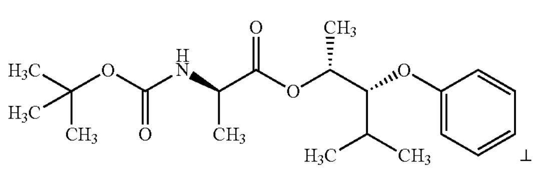 [SMILES: CC(C)[C@@H](Oc1ccccc1)[C@@H](C)OC(=O)[C@@H](C)NC(=O)OC(C)(C)C] | Example 1A; Example 4B; Example 8A; Example 12A | Clear Oil |

TABLE 1-continued

Compound Structure, Appearance, and Preparation Method

| *Cmpd. No. | Structure | Prepared According to Example: | Appearance |
|---|---|---|---|
| 79 | 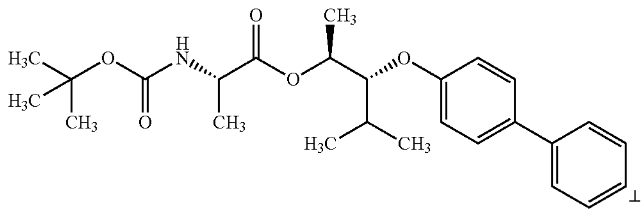 [SMILES: CC(C)[C@@H](Oc1ccc(-c2ccccc2)cc1)[C@H](C)OC(=O)[C@H](C)NC(=O)OC(C)(C)C] | Example 1A; Example 4C; Example 5; Example 8A; Example 12A | Colorless Oil |
| 80 | 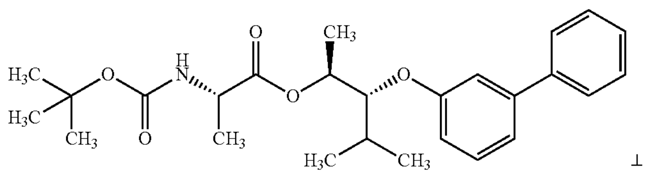 [SMILES: CC(C)[C@@H](Oc1cccc(-c2ccccc2)c1)[C@H](C)OC(=O)[C@H](C)NC(=O)OC(C)(C)C] | Example 1A; Example 4C; Example 5; Example 8A; Example 12A | Colorless Oil |
| 81 | 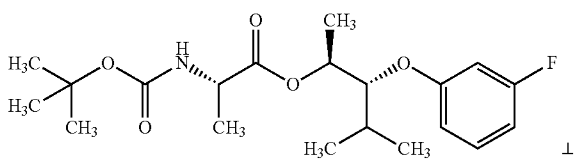 [SMILES: CC(C)[C@@H](Oc1cccc(F)c1)[C@H](C)OC(=O)[C@H](C)NC(=O)OC(C)(C)C] | Example 1A; Example 4C; Example 8A; Example 12A | Colorless Oil |
| 82 | 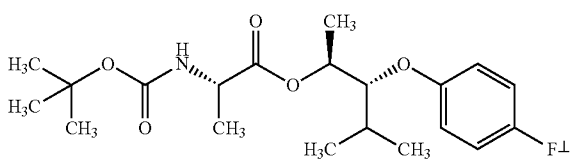 [SMILES: CC(C)[C@@H](Oc1ccc(F)cc1)[C@H](C)OC(=O)[C@H](C)NC(=O)OC(C)(C)C] | Example 1A; Example 4C; Example 8A; Example 12A | Colorless Oil |
| 83 | 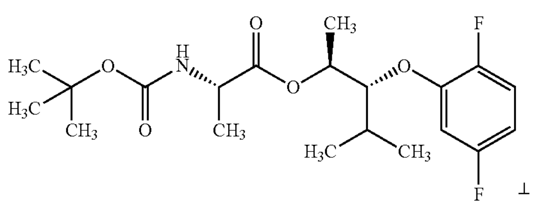 [SMILES: CC(C)[C@@H](Oc1cc(F)ccc1F)[C@H](C)OC(=O)[C@H](C)NC(=O)OC(C)(C)C] | Example 1A; Example 4C; Example 8A; Example 12A | White Solid |
| 84 | 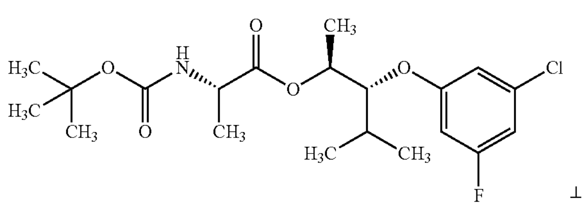 [SMILES: CC(C)[C@@H](Oc1cc(F)cc(Cl)c1)[C@H](C)OC(=O)[C@H](C)NC(=O)OC(C)(C)C] | Example 1A; Example 4C; Example 8A; Example 12A | White Solid |
| 85 | 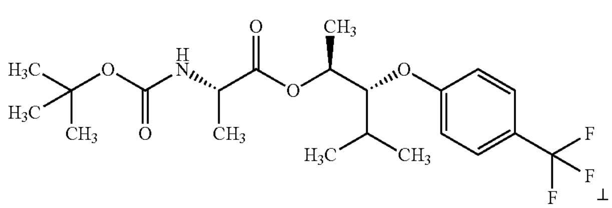 [SMILES: CC(C)[C@@H](Oc1ccc(C(F)(F)F)cc1)[C@H](C)OC(=O)[C@H](C)NC(=O)OC(C)(C)C] | Example 1A; Example 4C; Example 8A; Example 12A | Colorless Oil |

TABLE 1-continued

Compound Structure, Appearance, and Preparation Method

| *Cmpd. No. | Structure | Prepared According to Example: | Appearance |
|---|---|---|---|
| 86 | 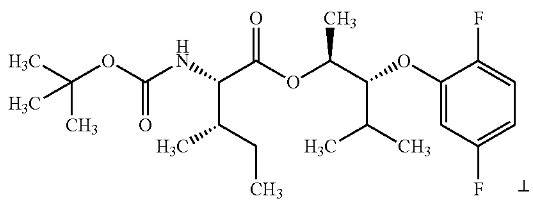 [SMILES: CC[C@H](C)[C@H](NC(=O)OC(C)(C)C)C(=O)O[C@@H](C)[C@H](Oc1cc(F)ccc1F)C(C)C] | Example 1A; Example 4C; Example 8A; Example 12A | Colorless Oil |
| 87 | 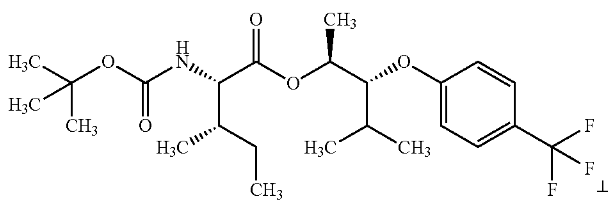 [SMILES: CC[C@H](C)[C@H](NC(=O)OC(C)(C)C)C(=O)O[C@@H](C)[C@H](Oc1ccc(C(F)(F)F)cc1)C(C)C] | Example 1A; Example 4C; Example 8A; Example 12A | Colorless Oil |
| 88 | 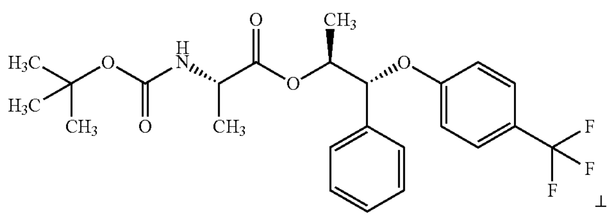 [SMILES: C[C@H](NC(=O)OC(C)(C)C)C(=O)O[C@@H](C)[C@H](Oc1ccc(C(F)(F)F)cc1)c1ccccc1] | Example 1B, Steps 1, 2; Example 4C; Example 8C; Example 12A | Sticky Glass |
| 89 | 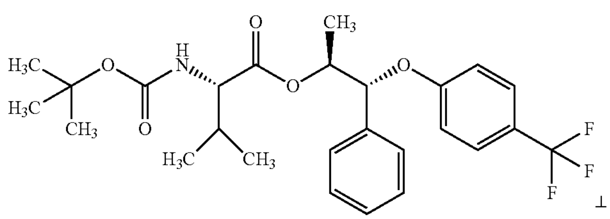 [SMILES: CC(C)[C@H](NC(=O)OC(C)(C)C)C(=O)O[C@@H](C)[C@H](Oc1ccc(C(F)(F)F)cc1)c1ccccc1] | Example 1B, Steps 1, 2; Example 4C; Example 8C; Example 12A | Sticky Glass |
| 90 | 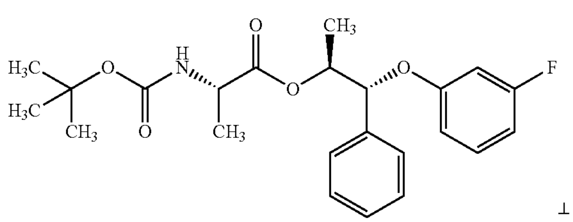 [SMILES: C[C@H](NC(=O)OC(C)(C)C)C(=O)O[C@@H](C)[C@H](Oc1cccc(F)c1)c1ccccc1] | Example 1B, Steps 1, 2; Example 4C; Example 8C; Example 12A | Sticky Oil |
| 91 | 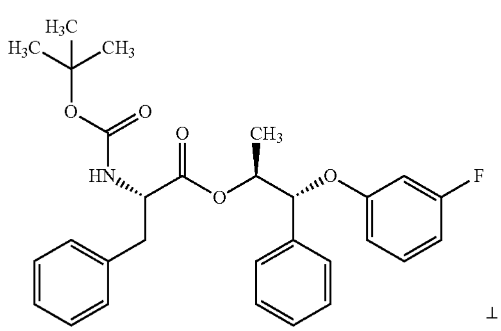 [SMILES: C[C@H](OC(=O)[C@H](Cc1ccccc1)NC(=O)OC(C)(C)C)[C@H](Oc1cccc(F)c1)c1ccccc1] | Example 1B, Steps 1, 2; Example 4C; Example 8C; Example 12A | Semi-Solid |

TABLE 1-continued

Compound Structure, Appearance, and Preparation Method

| *Cmpd. No. | Structure | Prepared According to Example: | Appearance |
|---|---|---|---|
| 92 | 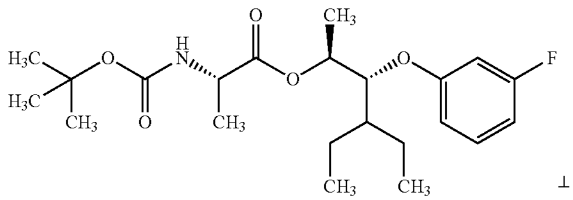 [SMILES: CCC(CC)[C@@H](Oc1cccc(F)c1)[C@H](C)OC(=O)[C@H](C)NC(=O)OC(C)(C)C] | Example 1A; Example 4C; Example 8A; Example 12A | Colorless Oil |
| 93 | 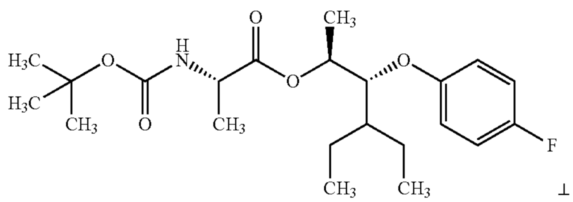 [SMILES: CCC(CC)[C@@H](Oc1ccc(F)cc1)[C@H](C)OC(=O)[C@H](C)NC(=O)OC(C)(C)C] | Example 1A; Example 4C; Example 8A; Example 12A | Colorless Oil |
| 94 | 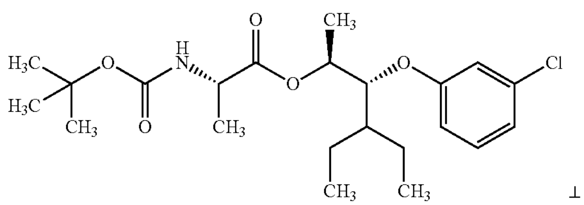 [SMILES: CCC(CC)[C@@H](Oc1cccc(Cl)c1)[C@H](C)OC(=O)[C@H](C)NC(=O)OC(C)(C)C] | Example 1A; Example 4C; Example 8A; Example 12A | Colorless Oil |
| 95 | 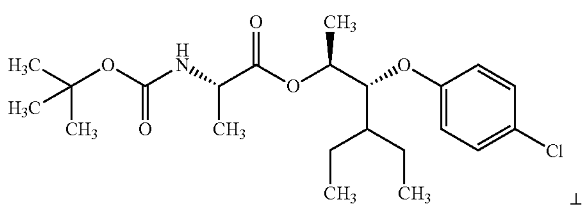 [SMILES: CCC(CC)[C@@H](Oc1ccc(Cl)cc1)[C@H](C)OC(=O)[C@H](C)NC(=O)OC(C)(C)C] | Example 1A; Example 4C; Example 8A; Example 12A | Colorless Oil |
| 96 | 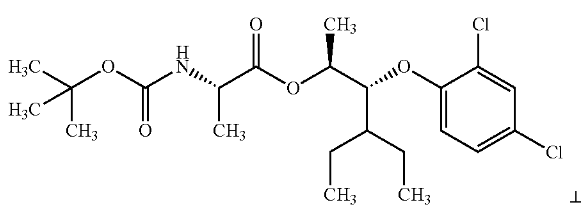 [SMILES: CCC(CC)[C@@H](Oc1ccc(Cl)cc1Cl)[C@H](C)OC(=O)[C@H](C)NC(=O)OC(C)(C)C] | Example 1A; Example 4C; Example 8A; Example 12A | Colorless Oil |
| 97 | 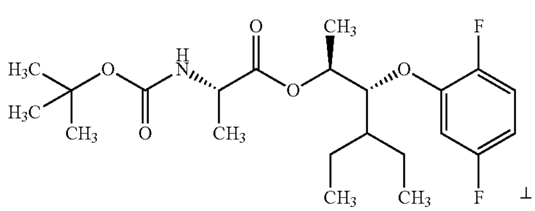 [SMILES: CCC(CC)[C@@H](Oc1cc(F)ccc1F)[C@H](C)OC(=O)[C@H](C)NC(=O)OC(C)(C)C] | Example 1A; Example 4C; Example 8A; Example 12A | Colorless Oil |
| 98 | 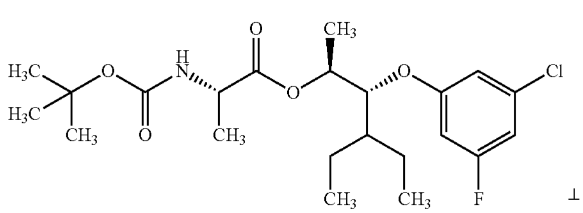 | Example 1A; Example 4C; Example 8A; Example 12A | Colorless Oil |

TABLE 1-continued

Compound Structure, Appearance, and Preparation Method

| *Cmpd. No. | Structure | Prepared According to Example: | Appearance |
|---|---|---|---|
| 99 | 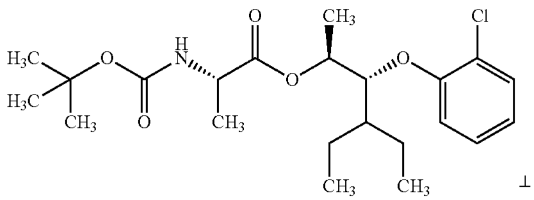 [SMILES: CCC(CC)[C@@H](Oc1ccccc1Cl)[C@H](C)OC(=O)[C@H](C)NC(=O)OC(C)(C)C] | Example 1A; Example 4C; Example 8A; Example 12A | Colorless Oil |
| 100 | 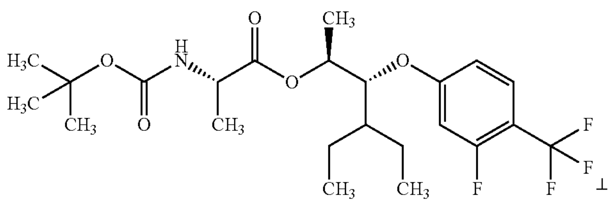 [SMILES: CCC(CC)[C@@H](Oc1ccc(C(F)(F)F)c(F)c1)[C@H](C)OC(=O)[C@H](C)NC(=O)OC(C)(C)C] | Example 1A; Example 4C; Example 8A; Example 12A | Colorless Oil |
| 101 | 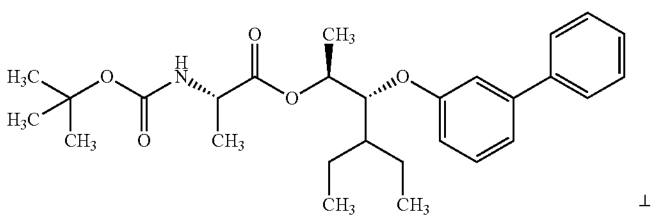 [SMILES: CCC(CC)[C@@H](Oc1cccc(-c2ccccc2)c1)[C@H](C)OC(=O)[C@H](C)NC(=O)OC(C)(C)C] | Example 1A; Example 4C; Example 5; Example 8A; Example 12A | Colorless Oil |
| 102 | 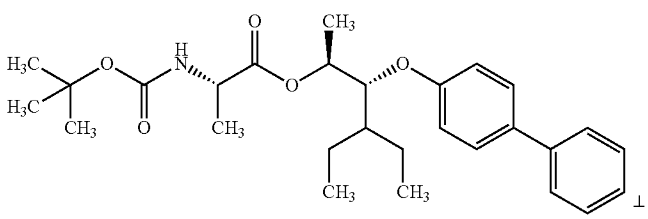 [SMILES: CCC(CC)[C@@H](Oc1ccc(-c2ccccc2)cc1)[C@H](C)OC(=O)[C@H](C)NC(=O)OC(C)(C)C] | Example 1A; Example 4C; Example 5; Example 8A; Example 12A | Colorless Oil |
| 103 | 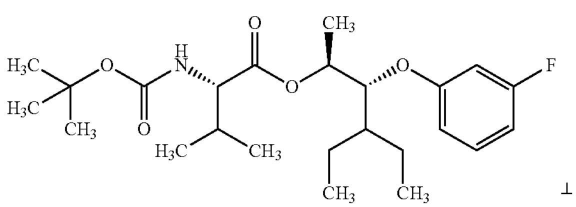 [SMILES: CCC(CC)[C@@H](Oc1cccc(F)c1)[C@H](C)OC(=O)[C@@H](NC(=O)OC(C)(C)C)C(C)C] | Example 1A; Example 4C; Example 8A; Example 12A | Colorless Oil |
| 104 | 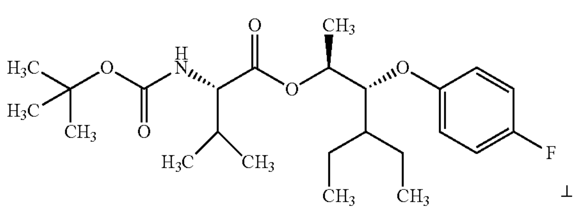 [SMILES: CCC(CC)[C@@H](Oc1ccc(F)cc1)[C@H](C)OC(=O)[C@@H](NC(=O)OC(C)(C)C)C(C)C] | Example 1A; Example 4C; Example 8A; Example 12 | Colorless Oil |
| 105 | 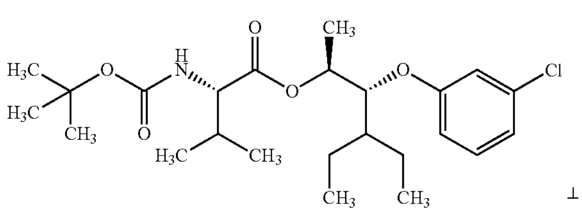 [SMILES: CCC(CC)[C@@H](Oc1cccc(Cl)c1)[C@H](C)OC(=O)[C@@H](NC(=O)OC(C)(C)C)C(C)C] | Example 1A; Example 4C; Example 8A; Example 12A | Colorless Oil |

TABLE 1-continued

Compound Structure, Appearance, and Preparation Method

| *Cmpd. No. | Structure | Prepared According to Example: | Appearance |
|---|---|---|---|
| 106 | [Structure: Boc-Val-O-CH(CH3)-CH(Et)-CH(OAr)-CH3 where Ar = 4-chlorophenyl] | Example 1A; Example 4C; Example 8A; Example 12A | Colorless Oil |
| 107 | [Structure: Boc-Val ester with 2,4-dichlorophenoxy group] | Example 1A; Example 4C; Example 8A; Example 12A | Colorless Oil |
| 108 | [Structure: Boc-Val ester with 2,5-difluorophenoxy group] | Example 1A; Example 4C; Example 8A; Example 12A | Colorless Oil |
| 109 | [Structure: Boc-Val ester with 3-chloro-5-fluorophenoxy group] | Example 1A; Example 4C; Example 8A; Example 12A | Colorless Oil |
| 110 | [Structure: Boc-Val ester with 2-chlorophenoxy group] | Example 1A; Example 4C; Example 8A; Example 12A | Colorless Oil |
| 111 | [Structure: Boc-Val ester with 4-(trifluoromethyl)phenoxy group] | Example 1A; Example 4C; Example 8A; Example 12A | Colorless Oil |
| 112 | [Structure: Boc-Val ester with 3-biphenyloxy group] | Example 1A; Example 4C; Example 5; Example 8A; Example 12A | Colorless Oil |

TABLE 1-continued

Compound Structure, Appearance, and Preparation Method

| *Cmpd. No. | Structure | Prepared According to Example: | Appearance |
|---|---|---|---|
| 113 | 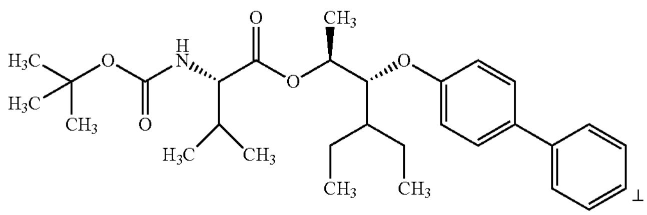 [SMILES: CCC(CC)[C@@H](Oc1ccc(-c2ccccc2)cc1)[C@H](C)OC(=O)[C@@H](NC(=O)OC(C)(C)C)C(C)C] | Example 1A; Example 4C; Example 5; Example 8A; Example 12A | Colorless Oil |
| 114 | 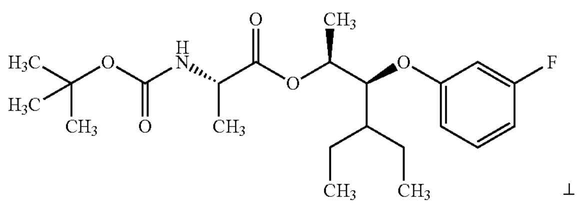 [SMILES: CCC(CC)[C@H](Oc1cccc(F)c1)[C@H](C)OC(=O)[C@H](C)NC(=O)OC(C)(C)C] | Example 1A; Example 4C; Example 8A; Example 12A | Colorless Oil |
| 115 | 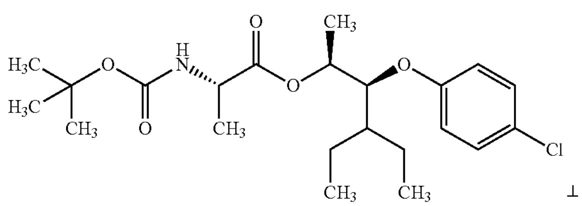 [SMILES: CCC(CC)[C@H](Oc1ccc(Cl)cc1)[C@H](C)OC(=O)[C@H](C)NC(=O)OC(C)(C)C] | Example 1A; Example 4C; Example 8A; Example 12A | Colorless Oil |
| 116 | 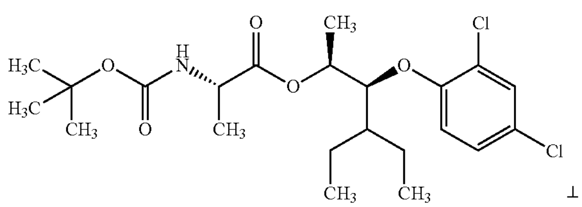 [SMILES: CCC(CC)[C@H](Oc1ccc(Cl)cc1Cl)[C@H](C)OC(=O)[C@H](C)NC(=O)OC(C)(C)C] | Example 1A; Example 4C; Example 8A; Example 12A | Colorless Oil |
| 117 | 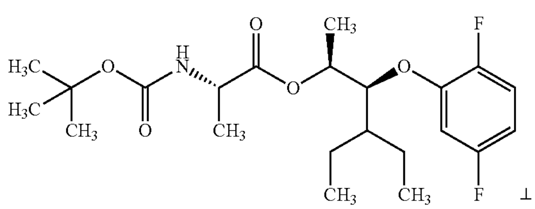 [SMILES: CCC(CC)[C@H](Oc1cc(F)ccc1F)[C@H](C)OC(=O)[C@H](C)NC(=O)OC(C)(C)C] | Example 1A; Example 4C; Example 8A; Example 12A | Colorless Oil |
| 118 | 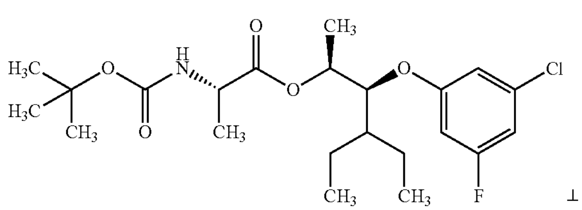 [SMILES: CCC(CC)[C@H](Oc1cc(F)cc(Cl)c1)[C@H](C)OC(=O)[C@H](C)NC(=O)OC(C)(C)C] | Example 1A; Example 4C; Example 8A; Example 12A | Colorless Oil |
| 119 | 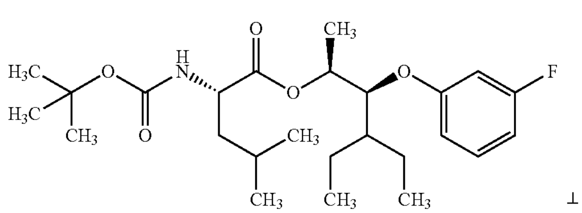 [SMILES: CCC(CC)[C@H](Oc1cccc(F)c1)[C@H](C)OC(=O)[C@H](CC(C)C)NC(=O)OC(C)(C)C] | Example 1A; Example 4C; Example 8A; Example 12A | Colorless Oil |

TABLE 1-continued

Compound Structure, Appearance, and Preparation Method

| *Cmpd. No. | Structure | Prepared According to Example: | Appearance |
|---|---|---|---|
| 120 | 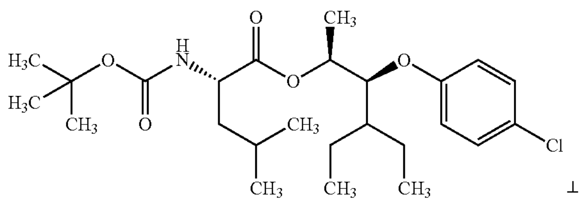 [SMILES: CCC(CC)[C@H](Oc1ccc(Cl)cc1)[C@H](C)OC(=O)[C@H](CC(C)C)NC(=O)OC(C)(C)C] | Example 1A; Example 4C; Example 8A; Example 12A | Colorless Oil |
| 121 | 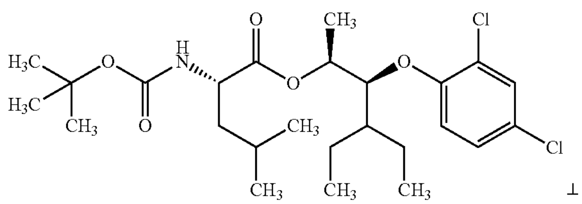 [SMILES: CCC(CC)[C@H](Oc1ccc(Cl)cc1Cl)[C@H](C)OC(=O)[C@H](CC(C)C)NC(=O)OC(C)(C)C] | Example 1A; Example 4C; Example 8A; Example 12A | Colorless Oil |
| 122 | 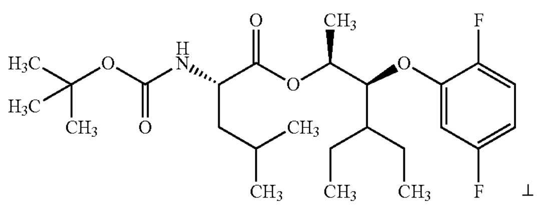 [SMILES: CCC(CC)[C@H](Oc1cc(F)ccc1F)[C@H](C)OC(=O)[C@H](CC(C)C)NC(=O)OC(C)(C)C] | Example 1A; Example 4C; Example 8A; Example 12A | Colorless Oil |
| 123 | 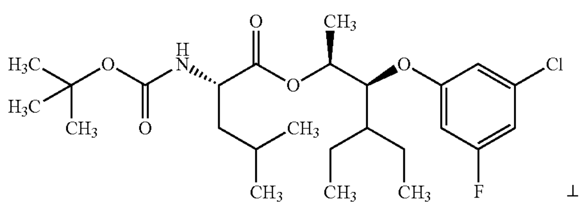 [SMILES: CCC(CC)[C@H](Oc1cc(F)cc(Cl)c1)[C@H](C)OC(=O)[C@H](CC(C)C)NC(=O)OC(C)(C)C] | Example 1A; Example 4C; Example 8A; Example 12A | Colorless Oil |
| 124 | 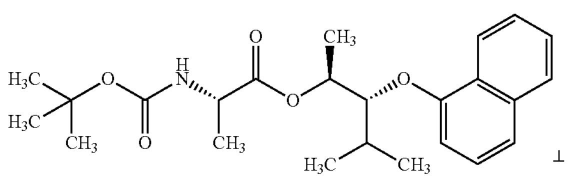 [SMILES: CC(C)[C@@H](Oc1cccc2ccccc12)[C@H](C)OC(=O)[C@H](C)NC(=O)OC(C)(C)C] | Example 1A; Example 4C; Example 8A; Example 12A | Oil |
| 125 | 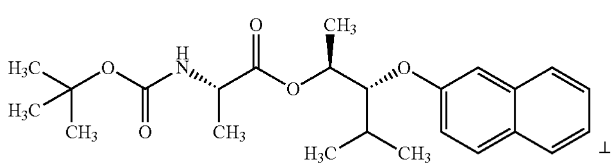 [SMILES: CC(C)[C@@H](Oc1ccc2ccccc2c1)[C@H](C)OC(=O)[C@H](C)NC(=O)OC(C)(C)C] | Example 1A; Example 4C; Example 8A; Example 12A | Colorless Oil |
| 126 | 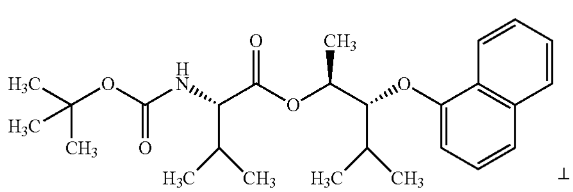 [SMILES: CC(C)[C@H](NC(=O)OC(C)(C)C)C(=O)O[C@@H](C)[C@H](Oc1cccc2ccccc12)C(C)C] | Example 1A; Example 4C; Example 8A; Example 12A | Colorless Oil |

TABLE 1-continued

Compound Structure, Appearance, and Preparation Method

| *Cmpd. No. | Structure | Prepared According to Example: | Appearance |
|---|---|---|---|
| 127 | 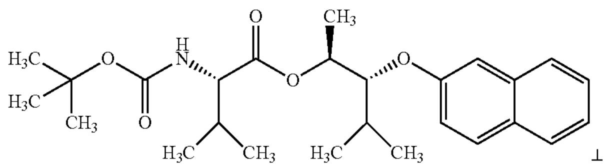 [SMILES: CC(C)[C@H](NC(=O)OC(C)(C)C)C(=O)O[C@@H](C)[C@H](Oc1ccc2ccccc2c1)C(C)C] | Example 1A; Example 4C; Example 8A; Example 12A | White Solid |
| 128 | 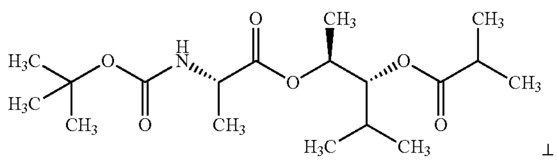 [SMILES: CC(C)C(=O)O[C@H](C(C)C)[C@H](C)OC(=O)[C@H](C)NC(=O)OC(C)(C)C] | Example 1A; Example 4A; Example 8C; Example 12A | Colorless Oil |
| 129 | 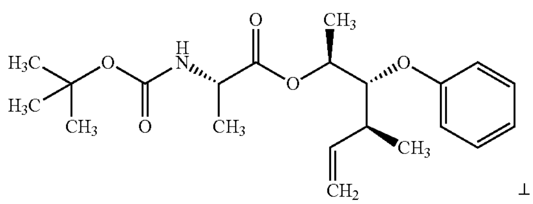 [SMILES: C=C[C@H](C)[C@@H](Oc1ccccc1)[C@H](C)OC(=O)[C@H](C)NC(=O)OC(C)(C)C] | Example 1B, Step 1; Example 3; Example 4B; Example 8D; Example 12A | White Solid |
| 130 | 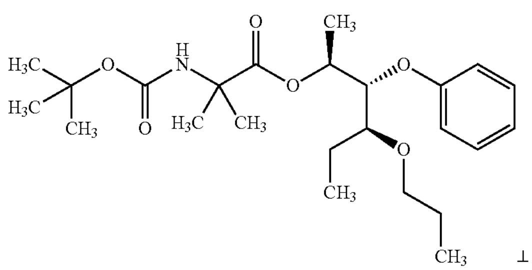 [SMILES: CCCO[C@@H](CC)[C@@H](Oc1ccccc1)[C@H](C)OC(=O)C(C)(C)NC(=O)OC(C)(C)C] | Example 3; Example 48; Example 8B; Example 12A | Colorless Oil |
| 131 | 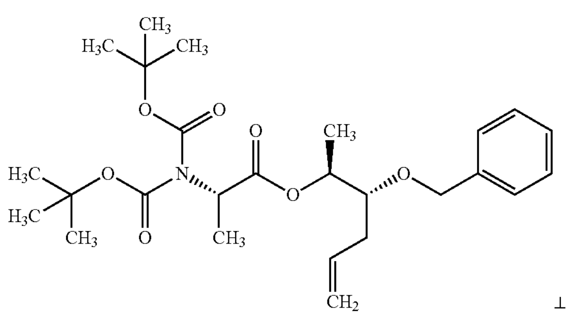 [SMILES: C=CC[C@@H](OCc1ccccc1)[C@H](C)OC(=O)[C@H](C)N(C(=O)OC(C)(C)C)C(=O)OC(C)(C)C] | Example 1C, Steps 1, 2; Example 4D; Example 8E; Example 12A; Example 13, Step 1 | Clear, Colorless Oil |
| 132 | 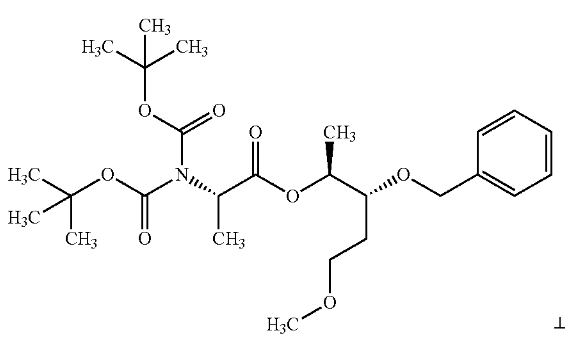 [SMILES: COCC[C@@H](OCc1ccccc1)[C@H](C)OC(=O)[C@H](C)N(C(=O)OC(C)(C)C)C(=O)OC(C)(C)C] | Example 1C, Steps 1, 2; Example 4D; Example 8E; Example 12A; Example 13, Steps 1-3 | Clear, Colorless Oil |

TABLE 1-continued

Compound Structure, Appearance, and Preparation Method

| *Cmpd. No. | Structure | Prepared According to Example: | Appearance |
|---|---|---|---|
| 133 | 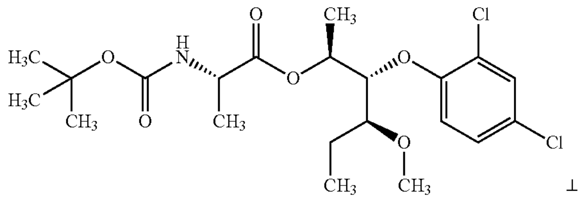 [SMILES: CC[C@H](OC)[C@@H](Oc1ccc(Cl)cc1Cl)[C@H](C)OC(=O)[C@H](C)NC(=O)OC(C)(C)C] | Example 2A; Example 3; Example 4C; Example 8C; | Colorless Oil |
| 134 | 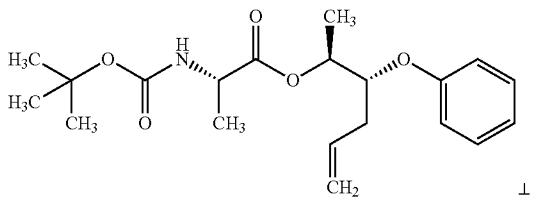 [SMILES: C=CC[C@@H](Oc1ccccc1)[C@H](C)OC(=O)[C@H](C)NC(=O)OC(C)(C)C] | Example 1C, Steps 1, 2; Example 4B; Example 8E; Example 12A | Clear, Colorless Oil |
| 135 | 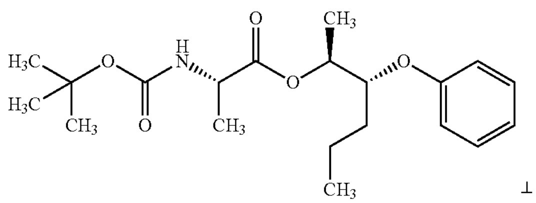 [SMILES: CCC[C@@H](Oc1ccccc1)[C@H](C)OC(=O)[C@H](C)NC(=O)OC(C)(C)C] | Example 1C, Steps 1, 2; Example 8C; Example 4B; Example 8E; Example 12A | Clear, Colorless Oil |
| 136 | 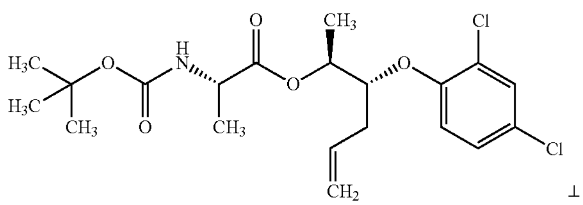 [SMILES: C=CC[C@@H](Oc1ccc(Cl)cc1Cl)[C@H](C)OC(=O)[C@H](C)NC(=O)OC(C)(C)C] | Example 1C, Steps 1, 2; Example 4C; Example 8E; Example 12A | White Semi-Crystalline Solid |
| 137 | 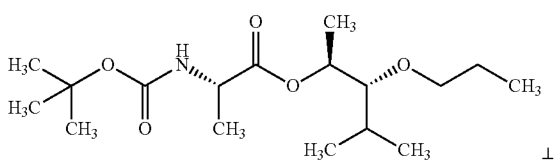 [SMILES: CCCO[C@H](C(C)C)[C@H](C)OC(=O)[C@H](C)NC(=O)OC(C)(C)C] | Example 1A; Example 4F; Example 8C; Example 12A | Colorless Oil |
| 138 | 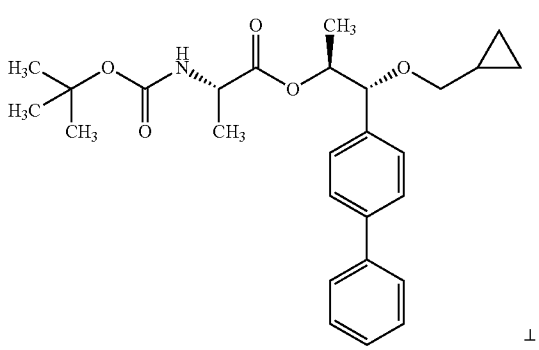 [SMILES: C[C@H](NC(=O)OC(C)(C)C)C(=O)O[C@@H](C)[C@H](OCC1CC1)c1ccc(-c2ccccc2)cc1] | Example 1A; Example 4D; Example 8A; Example 12A | Colorless Oil |

TABLE 1-continued

Compound Structure, Appearance, and Preparation Method

| *Cmpd. No. | Structure | Prepared According to Example: | Appearance |
|---|---|---|---|
| 139 | 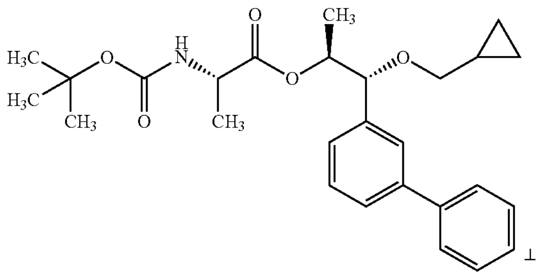 [SMILES: C[C@H](NC(=O)OC(C)(C)C)C(=O)O[C@@H](C)[C@H](OCC1CC1)c1cccc(-c2ccccc2)c1] | Example 1A; Example 4D; Example 8A; Example 12A | Colorless Oil |
| 140 | 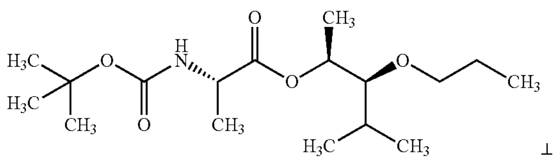 [SMILES: CCCO[C@@H](C(C)C)[C@H](C)OC(=O)[C@H](C)NC(=O)OC(C)(C)C] | Example 1A; Example 4F; Example 8C; Example 12A | Colorless Oil |
| 141 | 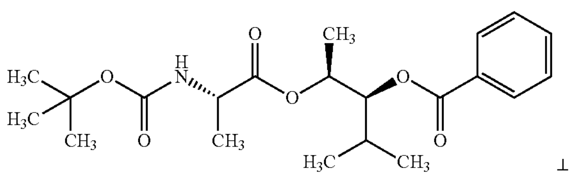 [SMILES: CC(C)[C@H](OC(=O)c1ccccc1)[C@H](C)OC(=O)[C@H](C)NC(=O)OC(C)(C)C] | Example 1A; Example 4A; Example 8C; Example 12A | Colorless Oil |
| 142 | 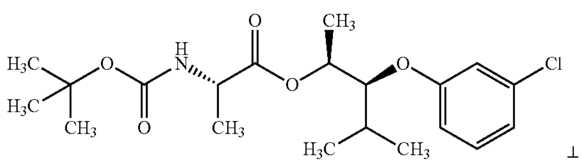 [SMILES: CC(C)[C@H](Oc1cccc(Cl)c1)[C@H](C)OC(=O)[C@H](C)NC(=O)OC(C)(C)C] | Example 1A; Example 4C; Example 8A; Example 12A | Yellow Oil |
| 143 | 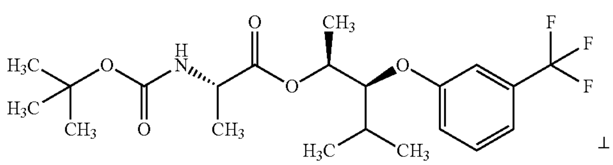 [SMILES: CC(C)[C@H](Oc1cccc(C(F)(F)F)c1)[C@H](C)OC(=O)[C@H](C)NC(=O)OC(C)(C)C] | Example 1A; Example 4C; Example 8A; Example 12A | Oil |
| 144 | 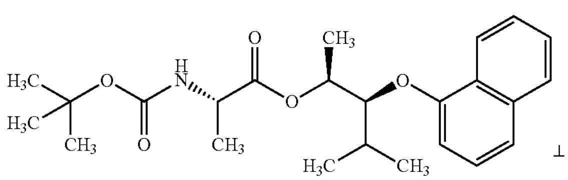 [SMILES: CC(C)[C@H](Oc1cccc2ccccc12)[C@H](C)OC(=O)[C@H](C)NC(=O)OC(C)(C)C] | Example 1A; Example 4C; Example 8A; Example 12A | Colorless Oil |
| 145 | 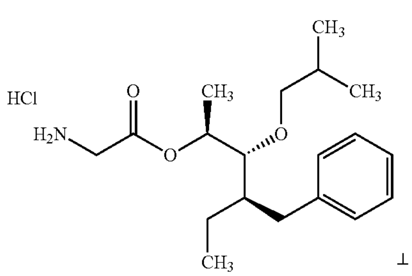 [SMILES: Cl ; CC[C@H](Cc1ccccc1)[C@@H](OCC(C)C)[C@H](C)OC(=O)CN] | Example 14A, Step 1 | Yellow Oil |

TABLE 1-continued
Compound Structure, Appearance, and Preparation Method
| *Cmpd. No. | Structure | Prepared According to Example: | Appearance |
|---|---|---|---|
| 146 | 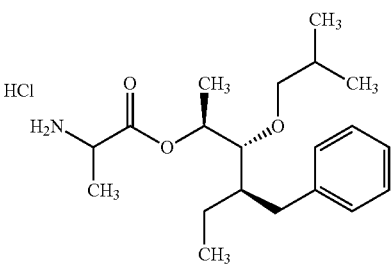 | Example 14C, Step 1 | Colorless Oil |
| 147 | 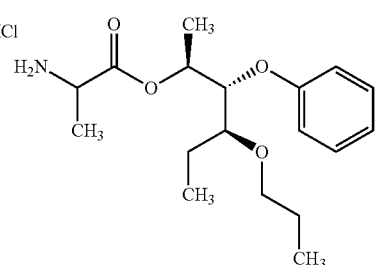 | Example 14A, Step 1 | Thick Colorless Oil |
| 148 | 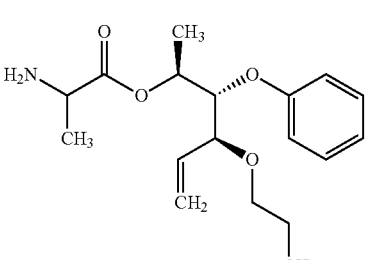 | Example 14B, Step 1 | Thick Colorless Oil |
| 149 | 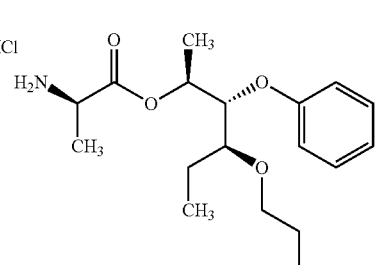 | Example 14A, Step 1 | Thick Colorless Oil |
| 150 | 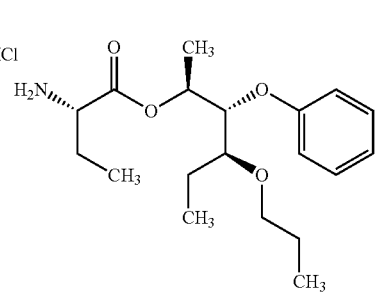 | Example 14A, Step 1 | Thick Colorless Oil |

TABLE 1-continued
Compound Structure, Appearance, and Preparation Method
| *Cmpd. No. | Structure | Prepared According to Example: | Appearance |
|---|---|---|---|
| 151 | 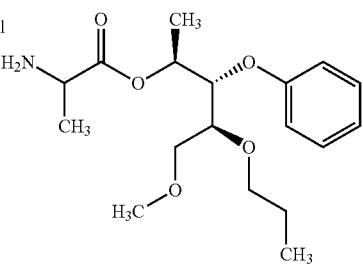 | Example 14A, Step 1 | Thick Colorless Oil |
| 152 | 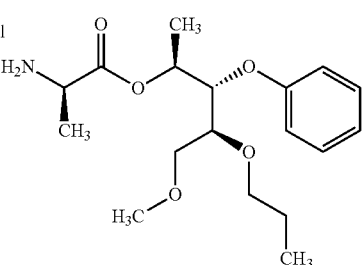 | Example 14A, Step 1 | Thick Colorless Oil |
| 153 | 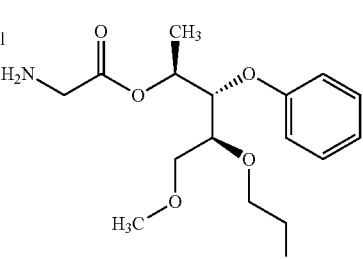 | Example 14A, Step 1 | Thick Colorless Oil |
| 154 | 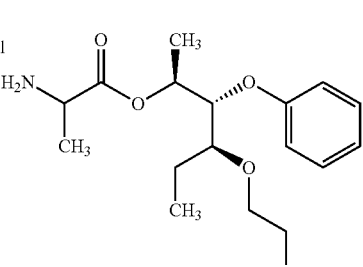 | Example 14A, Step 1 | Pale Yellow Oil |
| 155 | 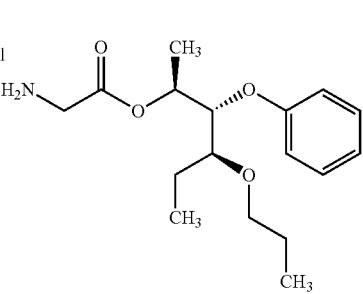 | Example 14A, Step 1 | Pale Yellow Oil |

TABLE 1-continued
Compound Structure, Appearance, and Preparation Method
| *Cmpd. No. | Structure | Prepared According to Example: | Appearance |
|---|---|---|---|
| 156 | 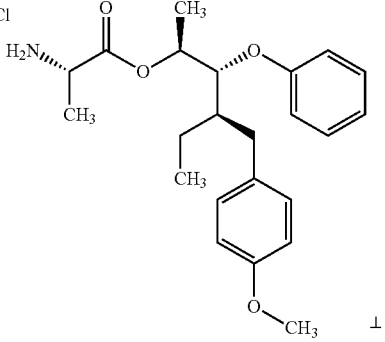 | Example 14A, Step 1 | Sticky Oil |
| 157 | 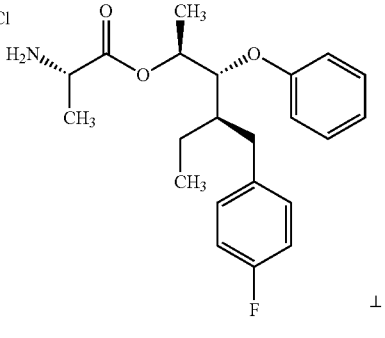 | Example 14A, Step 1 | Sticky Oil |
| 158 | 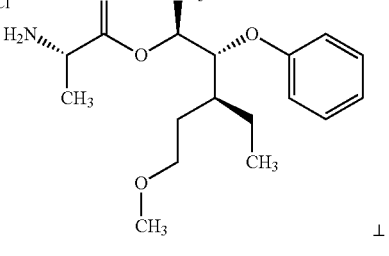 | Example 14A, Step 1 | White Solid |
| 159 | 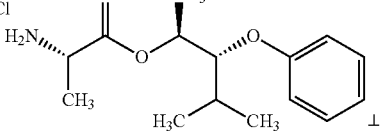 | Example 14A, Step 1 | Colorless Glass |
| 160 | 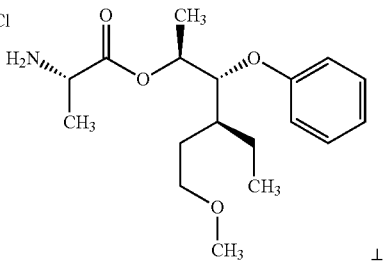 | Example 14A, Step 1 | White Solid |

TABLE 1-continued

Compound Structure, Appearance, and Preparation Method

| *Cmpd. No. | Structure | Prepared According to Example: | Appearance |
|---|---|---|---|
| 161 | (structure) | Example 14A, Step 1 | White Solid |
| 162 | (structure) | Example 14A, Step 1 | |
| 163 | (structure) | Example 1B, Steps 1-4; Example 4B; Example 7, Steps 1, 2a; Example 8C; Example 12A; Example 14A, Step 1 | Colorless Oil |
| 164 | (structure) | Example 1B, Steps 1-4; Example 4B; Example 7, Step 1, 2a; Example 8C; Example 12A; Example 14A, Step 1 | Colorless Oil |
| 165 | (structure) | Example 14B, Step 1 | Light Yellow Oil |
| 166 | (structure) | Example 14B, Step 1 | Light Yellow Oil |

TABLE 1-continued

Compound Structure, Appearance, and Preparation Method

| *Cmpd. No. | Structure | Prepared According to Example: | Appearance |
|---|---|---|---|
| 167 | (structure with CF$_3$CO$_2$H, H$_2$N-alanine ester, CH$_3$, O-phenyl, CH$_2$-phenyl branch) | Example 14B, Step 1 | Light Yellow Oil |
| 168 | (structure with HCl, H$_2$N-alanine ester, CH$_3$, O-phenyl, OCH$_2$-O-phenyl) | Example 1B, Steps 1-4; Example 4B; Example 7, Step 1, 2B; Example 8C; Example 12A; Example 14A, Step 1 | Colorless Oil |
| 169 | (structure with HCl, H$_2$N-aminobutyrate ester, CH$_3$, O-phenyl, OCH$_2$-O-phenyl) | Example 1B, Steps 1-4; Example 4B; Example 7, Step 1, 2B; Example 8C; Example 12A; Example 14A, Step 1 | Colorless Oil |
| 170 | (structure with HCl, H$_2$N-alanine ester, CH$_3$, O-CH$_2$-cyclopropyl, phenyl) | Example 14A, Step 1 | White Solid |
| 171 | (structure with HCl, H$_2$N-alanine ester, CH$_3$, O-CH$_2$-cyclopropyl, isopropyl) | Example 14A, Step 1 | White Solid |

TABLE 1-continued

Compound Structure, Appearance, and Preparation Method

| *Cmpd. No. | Structure | Prepared According to Example: | Appearance |
|---|---|---|---|
| 172 | (structure) | Example 14A, Step 1 | White Solid |
| 173 | (structure) | Example 14A, Step 1 | White Solid |
| 174 | (structure) | Example 14B, Step 1 | Light Orange Oil |
| 175 | (structure) | Example 14A, Step 1 | Sticky Oil |
| 176 | (structure) | Example 14A, Step 1 | Sticky Oil |

TABLE 1-continued

Compound Structure, Appearance, and Preparation Method

| *Cmpd. No. | Structure | Prepared According to Example: | Appearance |
|---|---|---|---|
| 177 | (structure) | Example 14A, Step 1 | Sticky Oil |
| 178 | (structure) | Example 14A, Step 1 | White Solid |
| 179 | (structure) | Example 14A, Step 1 | Clear, Colorless Oil |
| 180 | (structure) | Example 14B, Step 1 | Clear, Colorless Oil |
| 181 | (structure) | Example 14A, Step 1 | Sticky Solid |

TABLE 1-continued

Compound Structure, Appearance, and Preparation Method

| *Cmpd. No. | Structure | Prepared According to Example: | Appearance |
|---|---|---|---|
| 182 | 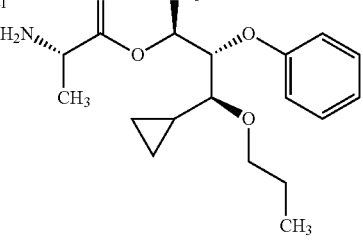 | Example 14A, Step 1 | Pale Yellow Thick Oil |
| 183 | 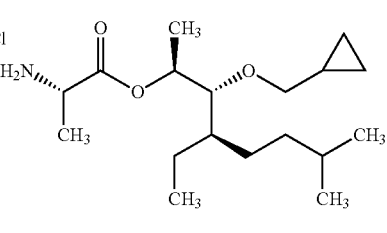 | Example 14A, Step 1 | Off-White Sticky Solid |
| 184 | 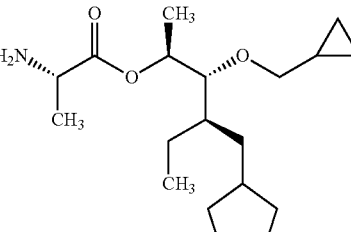 | Example 14A, Step 1 | Pale Yellow Thick Oil |
| 185 | 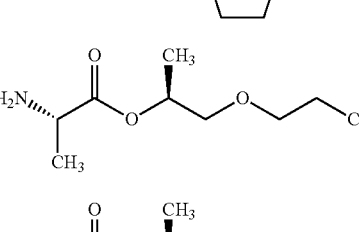 | Example 14A, Step 1 | Light Yellow Oil |
| 186 | 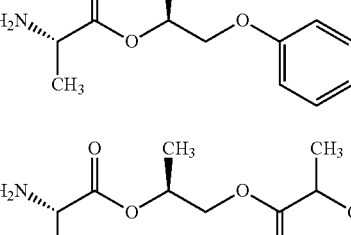 | Example 14A, Step 1 | — |
| 187 | 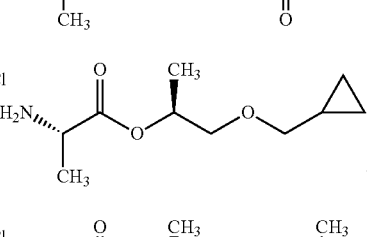 | Example 14A, Step 1 | White Solid |
| 188 | 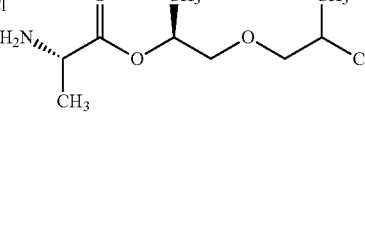 | Example 14A, Step 1 | White Solid |
| 189 | 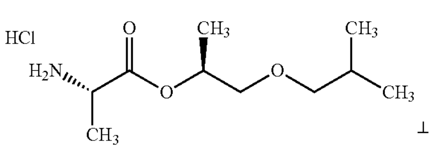 | Example 14A, Step 1 | White Solid |

TABLE 1-continued

Compound Structure, Appearance, and Preparation Method

| *Cmpd. No. | Structure | Prepared According to Example: | Appearance |
|---|---|---|---|
| 190 | 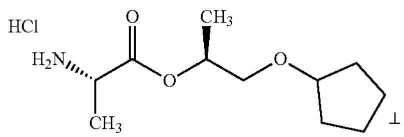 | Example 14A, Step 1 | Colorless Oil |
| 191 | 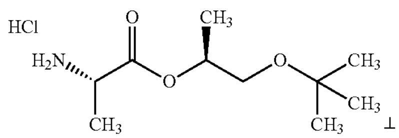 | Example 14A, Step 1 | Oil |
| 192 | 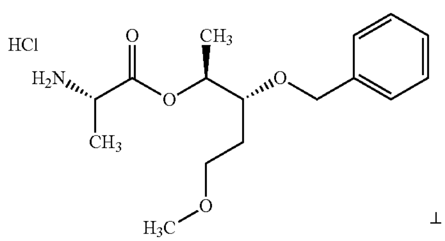 [SMILES: Cl ; COCC[C@@H](OCc1ccccc1)[C@H](C)OC(=O)[C@H](C)N] | Example 14A, Step 1 | Clear, Colorless Oil |
| 193 | 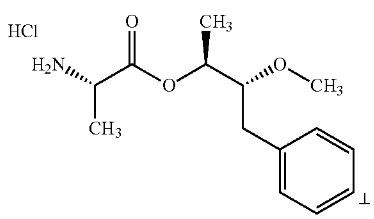 [SMILES: Cl ; CO[C@H](Cc1ccccc1)[C@H](C)OC(=O)[C@H](C)N] | Example 14A, Step 1 | White Foam |
| 194 | 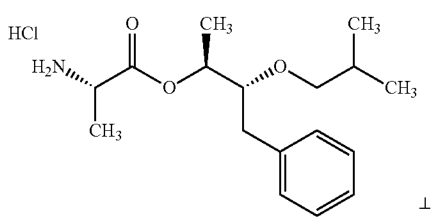 [SMILES: Cl ; CC(C)CO[C@H](Cc1ccccc1)[C@H](C)OC(=O)[C@H](C)N] | Example 14A, Step 1 | White Foam |
| 195 | 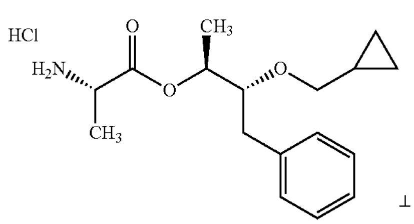 [SMILES: Cl ; C[C@H](N)C(=O)O[C@@H](C)[C@@H](Cc1ccccc1)OCC1CC1] | Example 14A, Step 1 | White Foam |
| 196 | 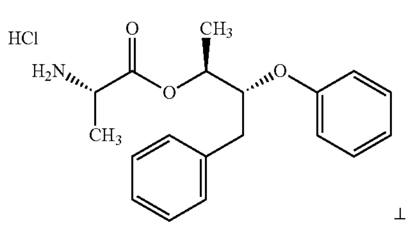 [SMILES: Cl ; C[C@H](N)C(=O)O[C@@H](C)[C@@H](Cc1ccccc1)Oc1ccccc1] | Example 14A, Step 1 | Sticky Oil |

TABLE 1-continued
Compound Structure, Appearance, and Preparation Method
| *Cmpd. No. | Structure | Prepared According to Example: | Appearance |
|---|---|---|---|
| 197 | 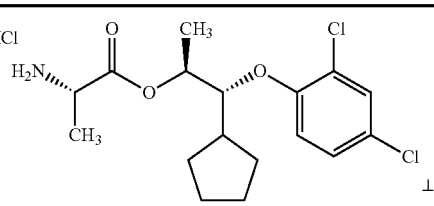 | Example 14A, Step 1 | White Solid |
| 198 | 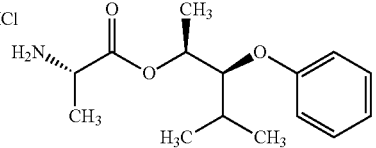 | Example 14A, Step 1 | Tan Solid |
| 199 | 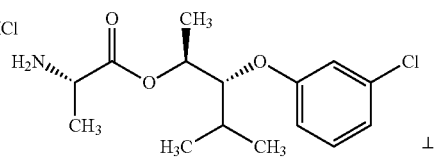 | Example 14A, Step 1 | Oil |
| 200 | 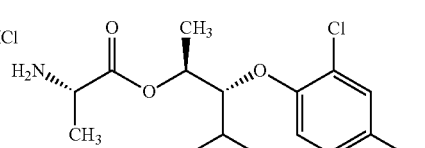 | Example 14A, Step 1 | Oil |
| 201 | 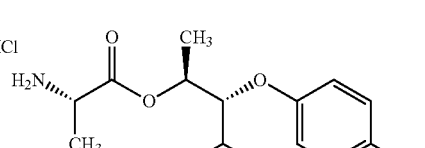 | Example 14A, Step 1 | White Solid |
| 202 | 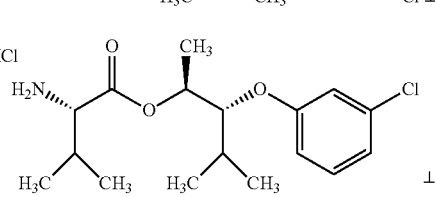 | Example 14A, Step 1 | Colorless Oil |
| 203 | 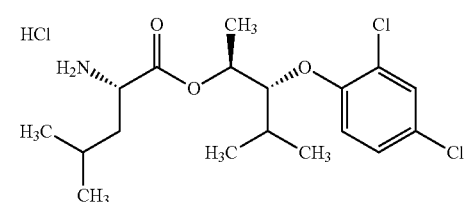 | Example 14A, Step 1 | Colorless Oil |
| 204 | 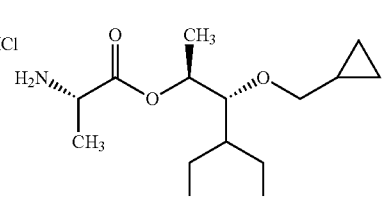 | Example 14A, Step 1 | Foam |

TABLE 1-continued

Compound Structure, Appearance, and Preparation Method

| *Cmpd. No. | Structure | Prepared According to Example: | Appearance |
|---|---|---|---|
| 205 | 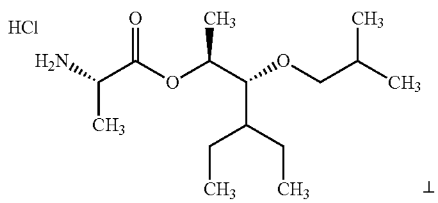 [SMILES: Cl ; CCC(CC)[C@@H](OCC(C)C)[C@H](C)OC(=O)[C@H](C)N] | Example 14A, Step 1 | Foam |
| 206 | 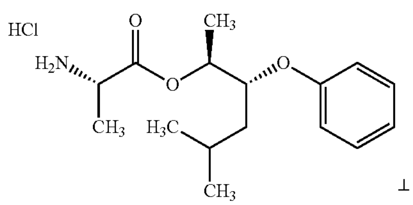 [SMILES: Cl ; CC(C)C[C@@H](Oc1ccccc1)[C@H](C)OC(=O)[C@H](C)N] | Example 14A, Step 1 | Sticky Solid |
| 207 | 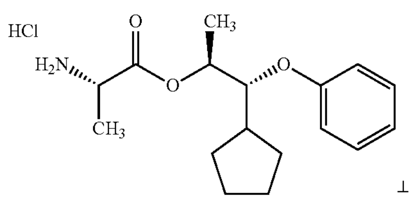 [SMILES: Cl ; C[C@H](N)C(=O)O[C@@H](C)[C@H](Oc1ccccc1)C1CCCC1] | Example 14A, Step 1 | White Powder |
| 208 | 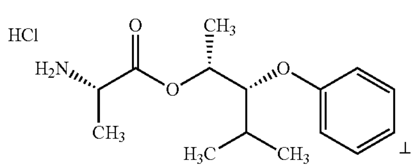 [SMILES: Cl ; CC(C)[C@@H](Oc1ccccc1)[C@@H](C)OC(=O)[C@H](C)N] | Example 14A, Step 1 | White Solid |
| 209 | 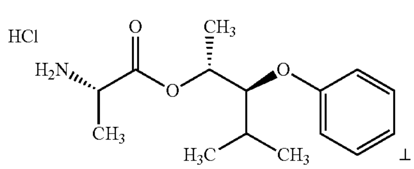 | Example 14A, Step 1 | Clear Glass |
| 210 | 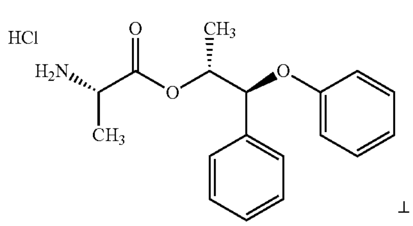 [SMILES: Cl ; C[C@H](N)C(=O)O[C@H](C)[C@@H](Oc1ccccc1)c1ccccc1] | Example 14A, Steps 1 | Clear Glass |
| 211 | 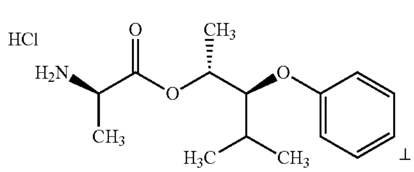 | Example 14A, Steps 1 | Clear Glass |

TABLE 1-continued

Compound Structure, Appearance, and Preparation Method

| *Cmpd. No. | Structure | Prepared According to Example: | Appearance |
|---|---|---|---|
| 212 | 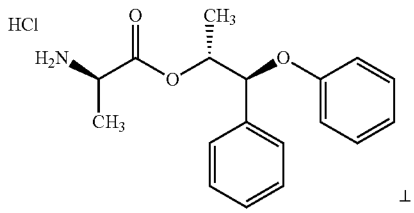 [SMILES: Cl ; C[C@@H](N)C(=O)O[C@H](C)[C@@H](Oc1ccccc1)c1ccccc1] | Example 14A, Steps 1 | Clear Glass |
| 213 | 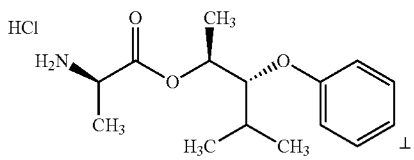 | Example 14A, Steps 1 | White Solid |
| 214 | 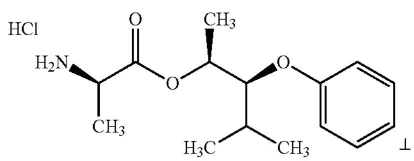 | Example 14A, Steps 1 | White Solid |
| 215 | 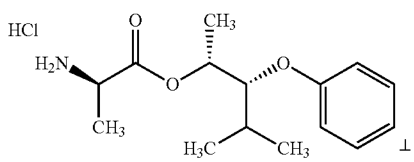 | Example 14A, Steps 1 | White Solid |
| 216 | 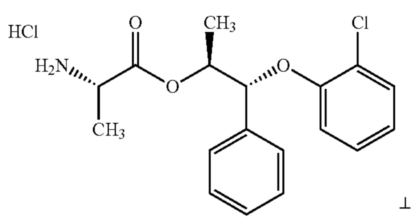 [SMILES: Cl ; C[C@H](N)C(=O)O[C@@H](C)[C@H](Oc1ccccc1Cl)c1ccccc1] | Example 14A, Step 1 | White Powder |
| 217 | 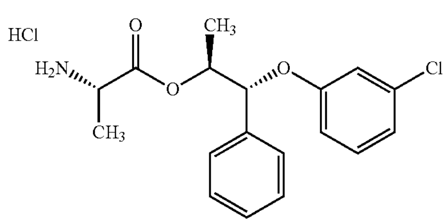 | Example 14A, Step 1 | White Powder |
| 218 | 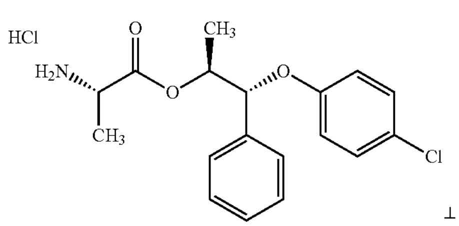 [SMILES: Cl ; C[C@H](N)C(=O)O[C@@H](C)[C@H](Oc1ccc(Cl)cc1)c1ccccc1] | Example 14A, Step 1 | White Powder |

TABLE 1-continued
Compound Structure, Appearance, and Preparation Method
| *Cmpd. No. | Structure | Prepared According to Example: | Appearance |
|---|---|---|---|
| 219 | 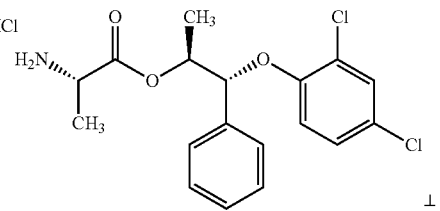 | Example 14A, Step 1 | White Powder |
| 220 | 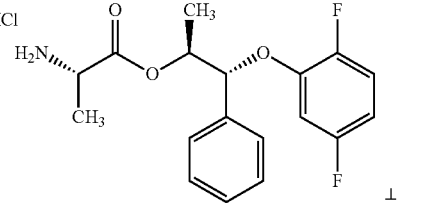 | Example 14A, Step 1 | White Powder |
| 221 | 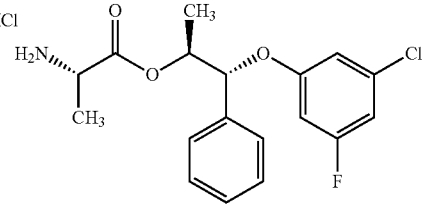 | Example 14A, Step 1 | White Powder |
| 222 | 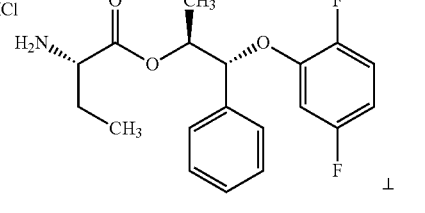 | Example 14A, Step 1 | White Powder |
| 223 | 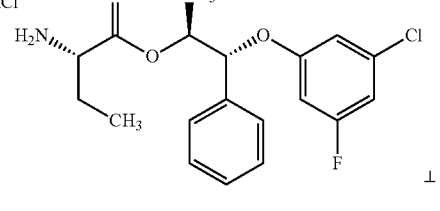 | Example 14A, Step 1 | White Powder |
| 224 | 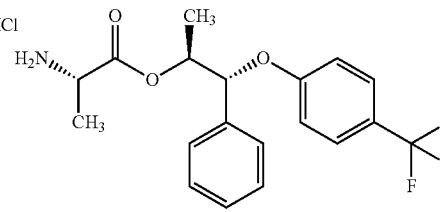 | Example 14A, Step 1 | White Powder |

TABLE 1-continued
Compound Structure, Appearance, and Preparation Method
| *Cmpd. No. | Structure | Prepared According to Example: | Appearance |
|---|---|---|---|
| 225 | 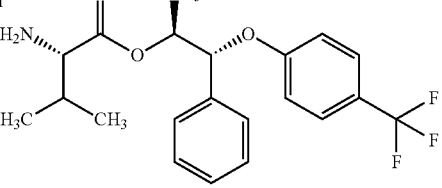 | Example 14A, Step 1 | White Powder |
| 226 | 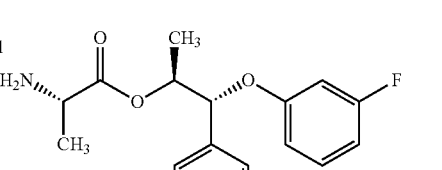 | Example 14A, Step 1 | White Powder |
| 227 | 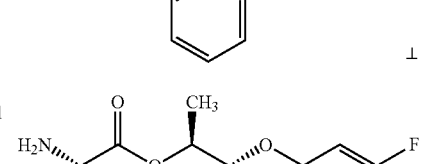 | Example 14A, Step 1 | White Powder |
| 228 | 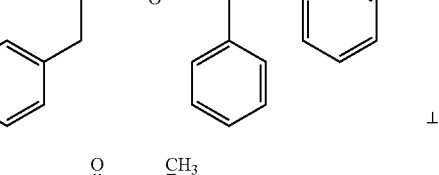 | Example 14A, Step 1 | Tacky Oil |
| 229 | 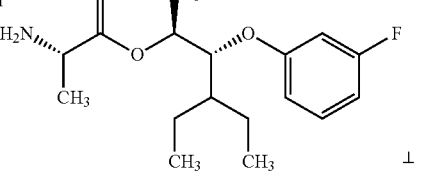 | Example 14A, Step 1 | Tacky Oil |
| 230 | 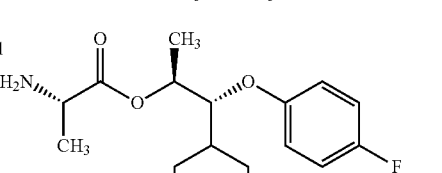 | Example 14A, Step 1 | Tacky Oil |
| 231 | 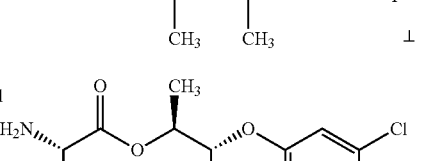 | Example 14A, Step 1 | Tacky Oil |

TABLE 1-continued
Compound Structure, Appearance, and Preparation Method
| *Cmpd. No. | Structure | Prepared According to Example: | Appearance |
|---|---|---|---|
| 232 | 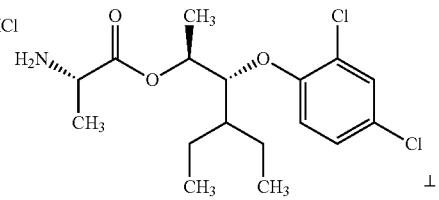 | Example 14A, Step 1 | Tacky Oil |
| 233 | 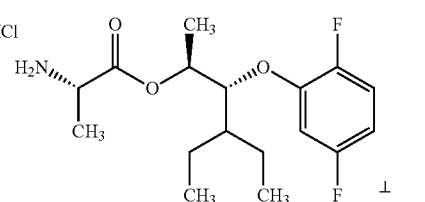 | Example 14A, Step 1 | Tacky Oil |
| 234 | 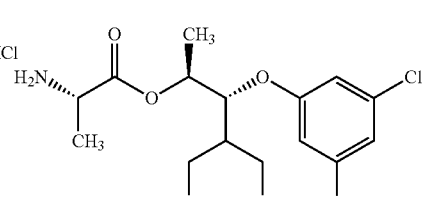 | Example 14A, Step 1 | Tacky Oil |
| 235 | 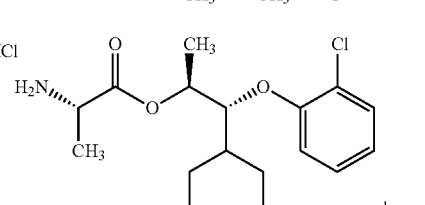 | Example 14A, Step 1 | Tacky Oil |
| 236 | 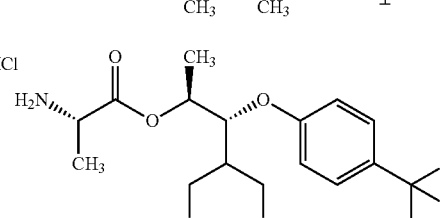 | Example 14A, Step 1 | Tacky Oil |
| 237 | 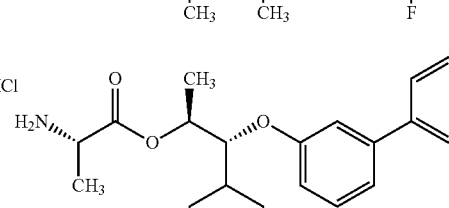 | Example 14A, Step 1 | Tacky Oil |
| 238 | 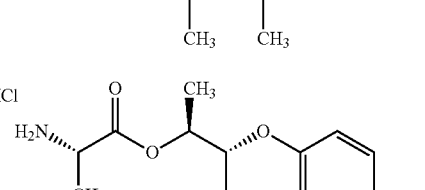 | Example 14A, Step 1 | Tacky Oil |

TABLE 1-continued

Compound Structure, Appearance, and Preparation Method

| *Cmpd. No. | Structure | Prepared According to Example: | Appearance |
|---|---|---|---|
| 239 | 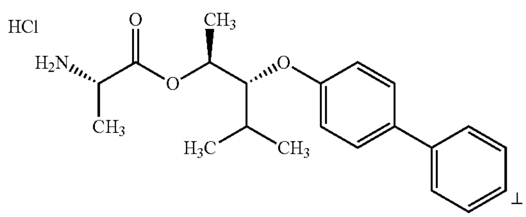 [SMILES: Cl ; CC(C)[C@@H](Oc1ccc(-c2ccccc2)cc1)[C@H](C)OC(=O)[C@H](C)N] | Example 14A, Step 1 | White Solid |
| 240 | 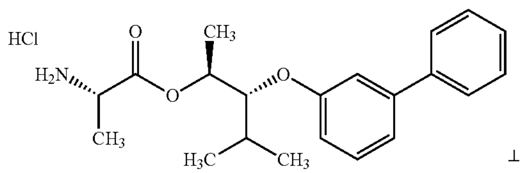 [SMILES: Cl ; CC(C)[C@@H](Oc1cccc(-c2ccccc2)c1)[C@H](C)OC(=O)[C@H](C)N] | Example 14A, Step 1 | Colorless Oil |
| 241 | 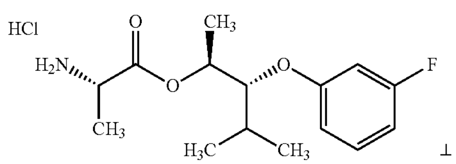 [SMILES: Cl ; CC(C)[C@@H](Oc1cccc(F)c1)[C@H](C)OC(=O)[C@H](C)N] | Example 14A, Step 1 | Colorless Oil |
| 242 | 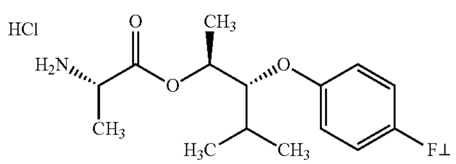 [SMILES: Cl ; CC(C)[C@@H](Oc1ccc(F)cc1)[C@H](C)OC(=O)[C@H](C)N] | Example 14A, Step 1 | White Solid |
| 243 | 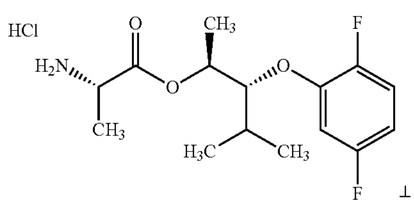 [SMILES: Cl ; CC(C)[C@@H](Oc1cc(F)ccc1F)[C@H](C)OC(=O)[C@H](C)N] | Example 14A, Step 1 | White Solid |
| 244 | 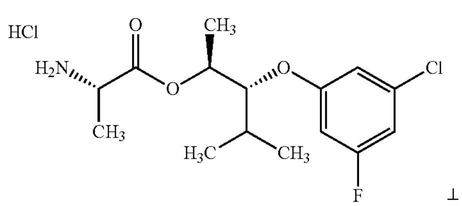 [SMILES: Cl ; CC(C)[C@@H](Oc1cc(F)cc(Cl)c1)[C@H](C)OC(=O)[C@H](C)N] | Example 14A, Step 1 | Sticky Solid |
| 245 | 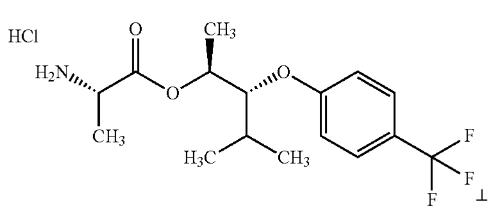 [SMILES: Cl ; CC(C)[C@@H](Oc1ccc(C(F)(F)F)cc1)[C@H](C)OC(=O)[C@H](C)N] | Example 14A, Step 1 | Colorless Oil |

TABLE 1-continued
Compound Structure, Appearance, and Preparation Method
| *Cmpd. No. | Structure | Prepared According to Example: | Appearance |
|---|---|---|---|
| 246 | 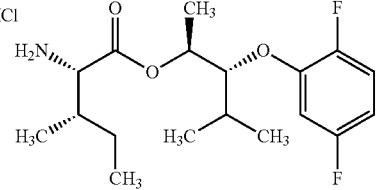 | Example 14A, Step 1 | White Solid |
| 247 | 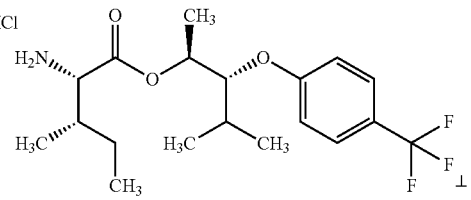 | Example 14A, Step 1 | White Solid |
| 248 | 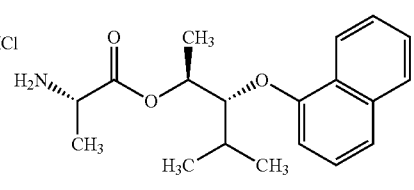 | Example 14A, Step 1 | Yellow Oil |
| 249 | 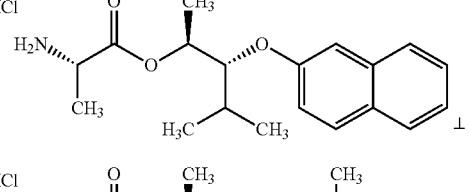 | Example 14A, Step 1 | Yellow Oil |
| 250 | 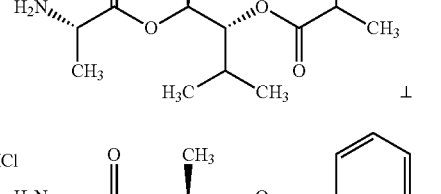 | Example 14A, Step 1 | White Solid |
| 251 | 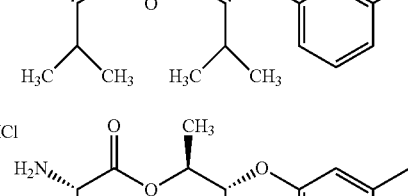 | Example 14A, Step 1 | Oil |
| 252 | 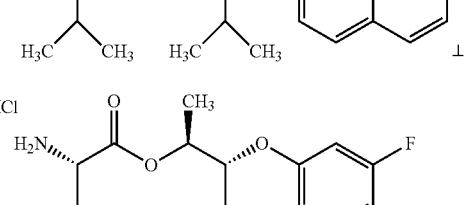 | Example 14A, Step 1 | White Solid |
| 253 | 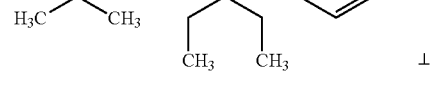 | Example 14A, Step 1 | Colorless Oil |

TABLE 1-continued

Compound Structure, Appearance, and Preparation Method

| *Cmpd. No. | Structure | Prepared According to Example: | Appearance |
|---|---|---|---|
| 254 | HCl salt of (S)-valine ester with 4-fluorophenoxy substituted alcohol | Example 14A, Step 1 | Colorless Oil |
| 255 | HCl salt of (S)-valine ester with 3-chlorophenoxy substituted alcohol | Example 14A, Step 1 | Waxy Solid |
| 256 | HCl salt of (S)-valine ester with 4-chlorophenoxy substituted alcohol | Example 14A, Step 1 | Waxy Solid |
| 257 | HCl salt of (S)-valine ester with 2,4-dichlorophenoxy substituted alcohol | Example 14A, Step 1 | Waxy Solid |
| 258 | HCl salt of (S)-valine ester with 2,5-difluorophenoxy substituted alcohol | Example 14A, Step 1 | Waxy Solid |
| 259 | HCl salt of (S)-valine ester with 3-chloro-5-fluorophenoxy substituted alcohol | Example 14A, Step 1 | Colorless Oil |
| 260 | HCl salt of (S)-valine ester with 2-chlorophenoxy substituted alcohol | Example 14A, Step 1 | Colorless Oil |

TABLE 1-continued

Compound Structure, Appearance, and Preparation Method

| *Cmpd. No. | Structure | Prepared According to Example: | Appearance |
|---|---|---|---|
| 261 | 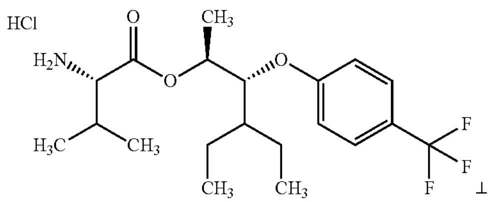 [SMILES: Cl ; CCC(CC)[C@@H](Oc1ccc(C(F)(F)F)cc1)[C@H](C)OC(=O)[C@@H](N)C(C)C] | Example 14A, Step 1 | Waxy Solid |
| 262 | 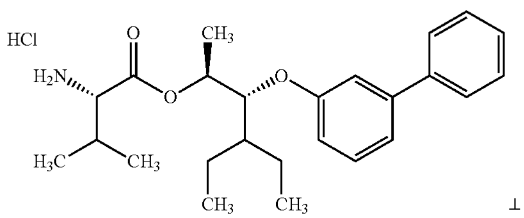 [SMILES: Cl ; CCC(CC)[C@@H](Oc1cccc(-c2ccccc2)c1)[C@H](C)OC(=O)[C@@H](N)C(C)C] | Example 14A, Step 1 | Colorless Oil |
| 263 | 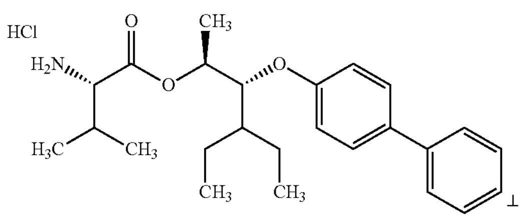 [SMILES: Cl ; CCC(CC)[C@@H](Oc1ccc(-c2ccccc2)cc1)[C@H](C)OC(=O)[C@@H](N)C(C)C] | Example 14A, Step 1 | Waxy Solid |
| 264 | 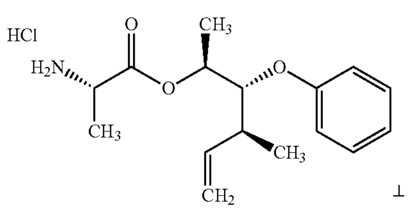 [SMILES: Cl ; C=C[C@H](C)[C@@H](Oc1ccccc1)[C@H](C)OC(=O)[C@H](C)N] | Example 14A, Step 1 | Clear Oil |
| 265 | 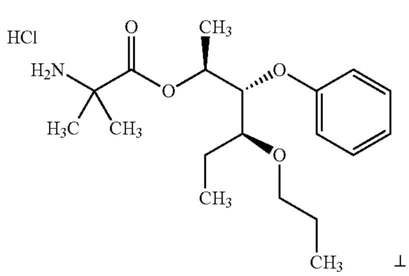 [SMILES: Cl ; CCCO[C@@H](CC)[C@@H](Oc1ccccc1)[C@H](C)OC(=O)C(C)(C)N] | Example 14A, Step 1 | Thick Colorless Oil |
| 266 | 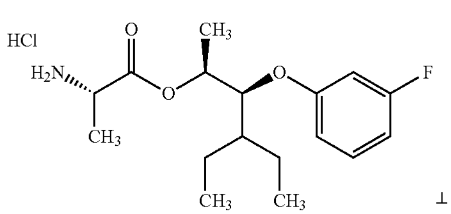 [SMILES: Cl ; CCC(CC)[C@H](Oc1cccc(F)c1)[C@H](C)OC(=O)[C@H](C)N] | Example 14A, Step 1 | Colorless Oil |

TABLE 1-continued

Compound Structure, Appearance, and Preparation Method

| *Cmpd. No. | Structure | Prepared According to Example: | Appearance |
|---|---|---|---|
| 267 | [Structure] | Example 14A, Step 1 | Colorless Oil |
| 268 | [Structure] | Example 14A, Step 1 | Colorless Oil |
| 269 | [Structure] | Example 14A, Step 1 | Colorless Oil |
| 270 | [Structure] | Example 14A, Step 1 | Colorless Oil |
| 271 | [Structure] | Example 14A, Step 1 | Colorless Oil |
| 272 | [Structure] | Example 14A, Step 1 | Colorless Oil |
| 273 | [Structure] | Example 14A, Step 1 | Coloress Oil |

TABLE 1-continued
Compound Structure, Appearance, and Preparation Method
| *Cmpd. No. | Structure | Prepared According to Example: | Appearance |
|---|---|---|---|
| 274 | 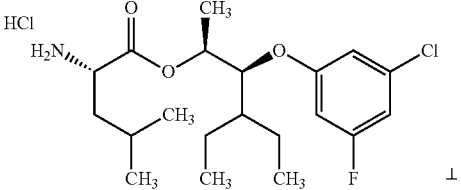 [SMILES: Cl ; CCC(CC)[C@H](Oc1cc(F)cc(Cl)c1)[C@H](C)OC(=O)[C@@H](N)CC(C)C] | Example 14A, Step 1 | Colorless Oil |
| 275 | 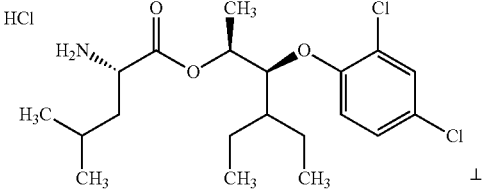 [SMILES: Cl ; CCC(CC)[C@H](Oc1ccc(Cl)cc1Cl)[C@H](C)OC(=O)[C@@H](N)CC(C)C] | Example 14A, Step 1 | Colorless Oil |
| 276 | 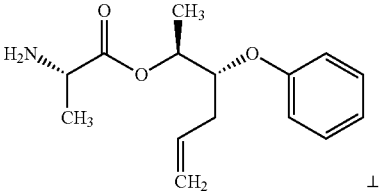 [SMILES: C=CC[C@@H](Oc1ccccc1)[C@H](C)OC(=O)[C@H](C)N] | Example 14B, Step 1 | Yellow Oil |
| 277 | 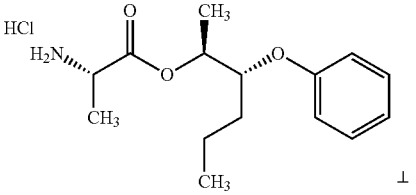 [SMILES: Cl ; CCC[C@@H](Oc1ccccc1)[C@H](C)OC(=O)[C@H](C)N] | Example 14A, Step 1 | Yellow Oil |
| 278 | 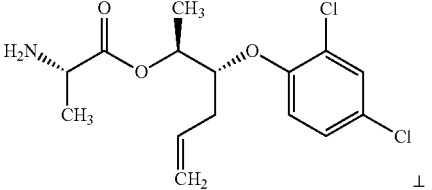 [SMILES: C=CC[C@@H](Oc1ccc(Cl)cc1Cl)[C@H](C)OC(=O)[C@H](C)N] | Example 14B, Step 1 | Pale Yellow Oil |
| 279 | 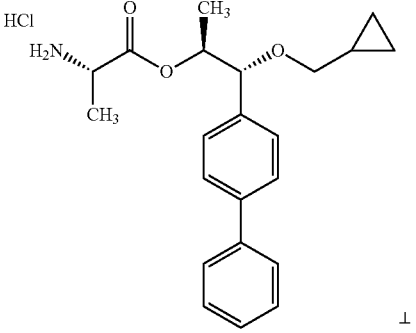 [SMILES: Cl ; C[C@H](N)C(=O)O[C@@H](C)[C@H](OCC1CC1)c1ccc(-c2ccccc2)cc1] | Example 14A, Step 1 | Colorless Oil |

TABLE 1-continued
Compound Structure, Appearance, and Preparation Method
| *Cmpd. No. | Structure | Prepared According to Example: | Appearance |
|---|---|---|---|
| 280 | 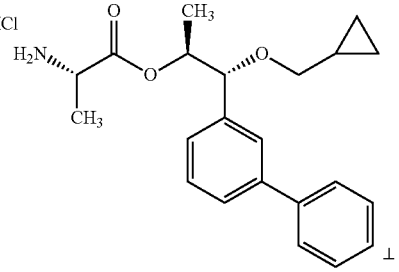 | Example 14A, Step 1 | Colorless Oil |
| 281 | 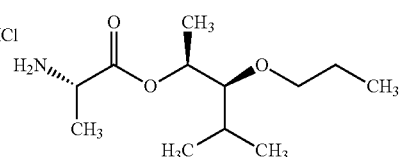 | Example 14A, Step 1 | White Solid |
| 282 | 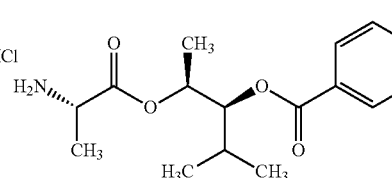 | Example 14A, Step 1 | White Foam |
| 283 | 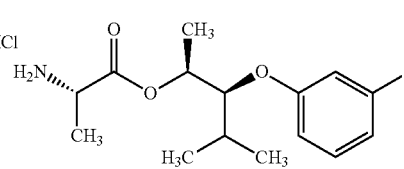 | Example 14A, Step 1 | White Foam |
| 284 | 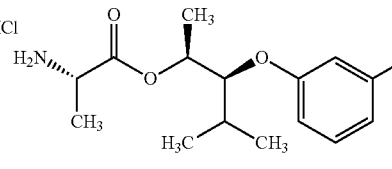 | Example 14A, Step 1 | White Foam |
| 285 | 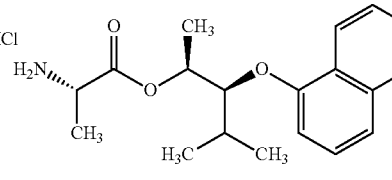 | Example 14A, Step 1 | White Foam |
| 286 | 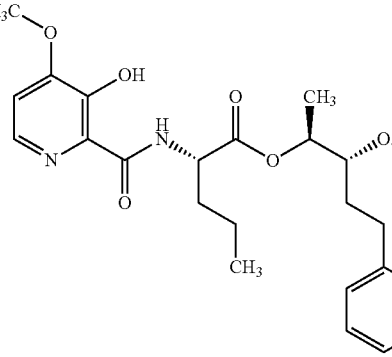 | Example 14A, Steps 1, 2 | Colorless Oil |

TABLE 1-continued
Compound Structure, Appearance, and Preparation Method
| *Cmpd. No. | Structure | Prepared According to Example: | Appearance |
|---|---|---|---|
| 287 | 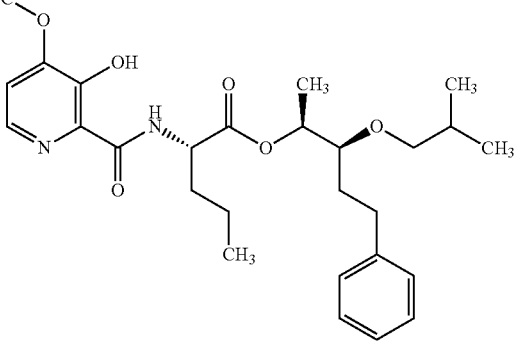 | Example 14A, Steps 1, 2 | Colorless Oil |
| 288 | 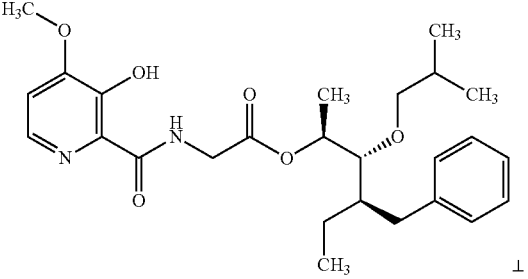 [SMILES: CC[C@H](Cc1ccccc1)[C@@H](OCC(C)C)[C@H](C)OC(=O)CNC(=O)c1nccc(OC)c1O] | Example 14A, Step 2 | Colorless Oil |
| 289 | 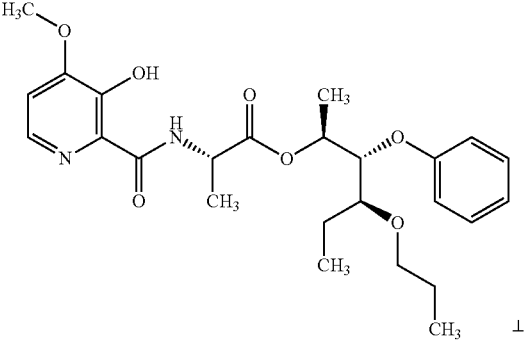 | Example 14A, Step 2 | Colorless Oil |
| 290 | 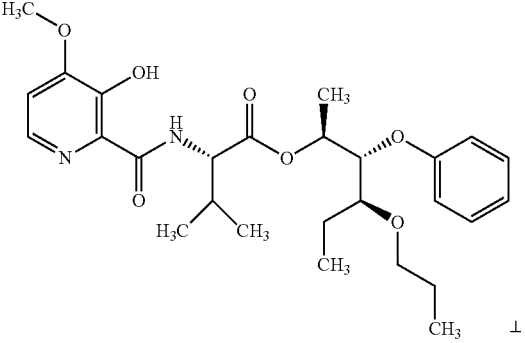 [SMILES: CCCO[C@@H](CC)[C@@H](Oc1ccccc1)[C@H](C)OC(=O)[C@@H](NC(=O)c1nccc(OC)c1O)C(C)C] | Example 3; Example 4B; Example 8C; Example 12A Example 14A, Steps 1, 2 | Colorless Oil |

TABLE 1-continued

Compound Structure, Appearance, and Preparation Method

| *Cmpd. No. | Structure | Prepared According to Example: | Appearance |
|---|---|---|---|
| 291 | 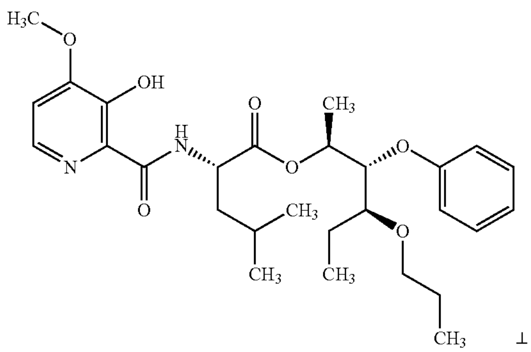 [SMILES: CCCO[C@@H](CC)[C@@H](Oc1ccccc1)[C@H](C)OC(=O)[C@H](CC(C)C)NC(=O)c1nccc(OC)c1O] | Example 3; Example 4B; Example 8C; Example 12A Example 14A, Steps 1, 2 | Colorless Oil |
| 292 | 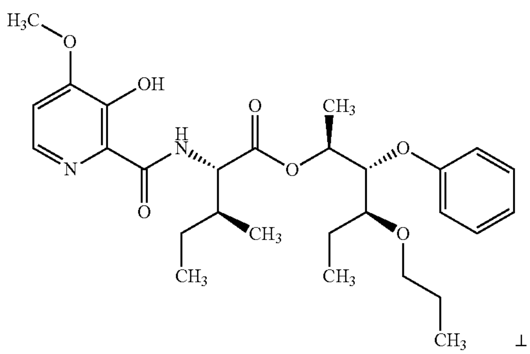 [SMILES: CCCO[C@@H](CC)[C@@H](Oc1ccccc1)[C@H](C)OC(=O)[C@@H](NC(=O)c1nccc(OC)c1O)[C@@H](C)CC] | Example 3; Example 4B; Example 8C; Example 12A Example 14A, Steps 1, 2 | Colorless Oil |
| 293 | 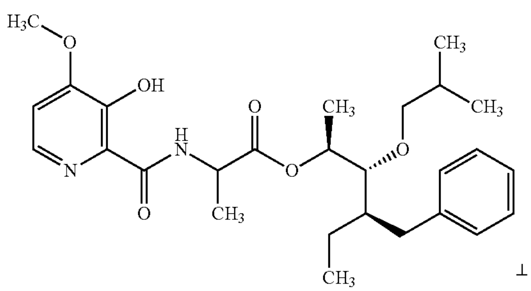 | Example 14C, Step 2 | Colorless Oil |
| 294 | 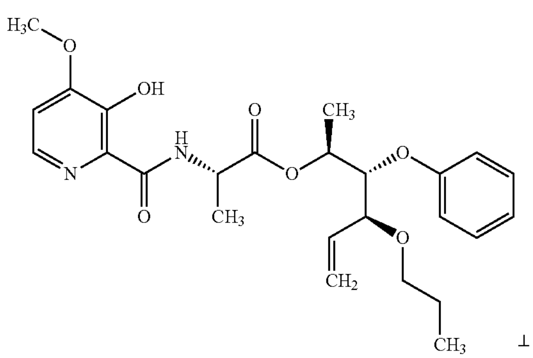 [SMILES: C=C[C@H](OCCC)[C@@H](Oc1ccccc1)[C@H](C)OC(=O)[C@H](C)NC(=O)c1nccc(OC)c1O] | Example 14B, Step 2 | Colorless Oil |

TABLE 1-continued

Compound Structure, Appearance, and Preparation Method

| *Cmpd. No. | Structure | Prepared According to Example: | Appearance |
|---|---|---|---|
| 295 | 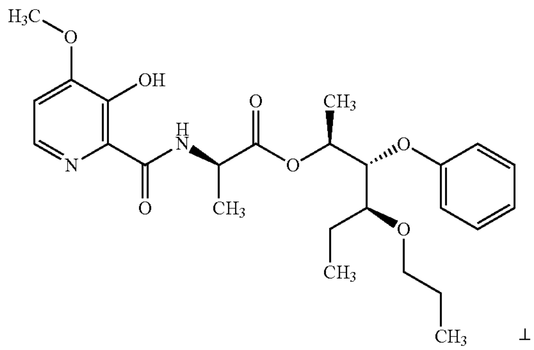 [SMILES: CCCO[C@@H](CC)[C@@H](Oc1ccccc1)[C@H](C)OC(=O)[C@@H](C)NC(=O)c1nccc(OC)c1O] | Example 14A, Step 2 | Colorless Oil |
| 296 | 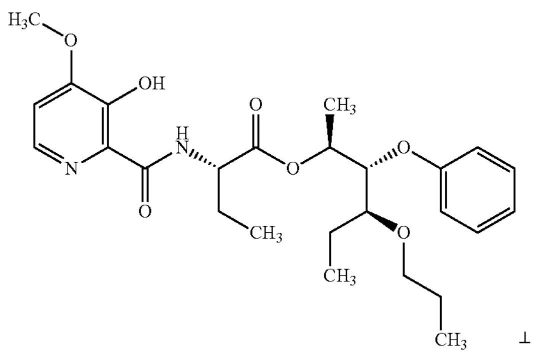 [SMILES: CCCO[C@@H](CC)[C@@H](Oc1ccccc1)[C@H](C)OC(=O)[C@H](CC)NC(=O)c1nccc(OC)c1O] | Example 14A, Step 2 | Colorless Oil |
| 297 | 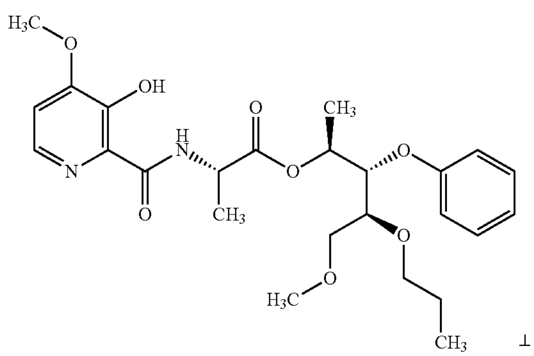 [SMILES: CCCO[C@@H](COC)[C@@H](Oc1ccccc1)[C@H](C)OC(=O)[C@H](C)NC(=O)c1nccc(OC)c1O] | Example 14A, Step 2 | Colorless Oil |
| 298 | 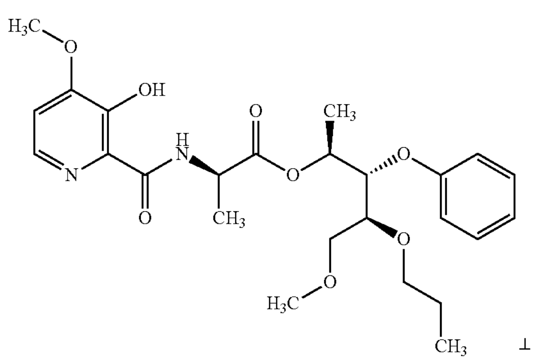 [SMILES: CCCO[C@@H](COC)[C@@H](Oc1ccccc1)[C@H](C)OC(=O)[C@@H](C)NC(=O)c1nccc(OC)c1O] | Example 14A, Step 2 | Colorless Oil |

TABLE 1-continued

Compound Structure, Appearance, and Preparation Method

| *Cmpd. No. | Structure | Prepared According to Example: | Appearance |
|---|---|---|---|
| 299 | 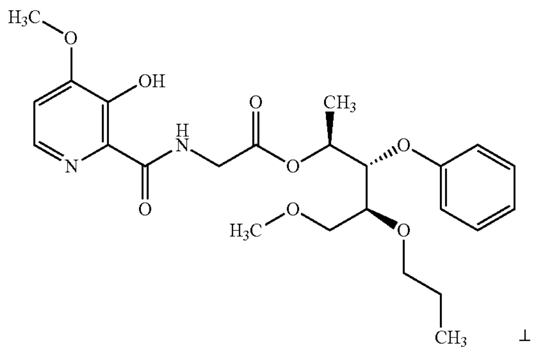 [SMILES: CCCO[C@@H](COC)[C@@H](Oc1ccccc1)[C@H](C)OC(=O)CNC(=O)c1nccc(OC)c1O] | Example 14A, Step 2 | Colorless Oil |
| 300 | 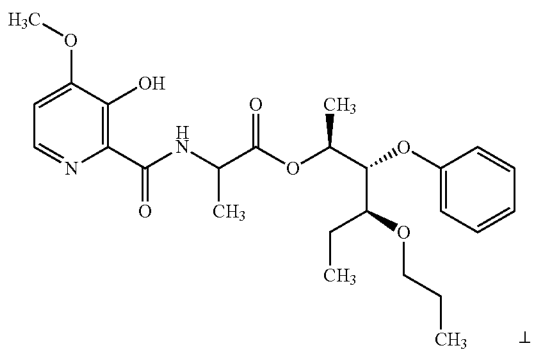 [SMILES: CCCO[C@@H](CC)[C@@H](Oc1ccccc1)[C@H](C)OC(=O)C(C)NC(=O)c1nccc(OC)c1O] | Example 14A, Step 2 | Colorless Oil |
| 301 | 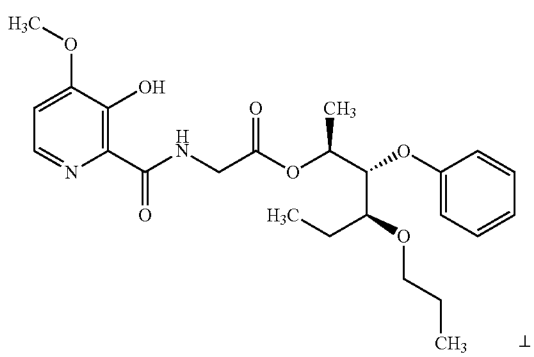 [SMILES: CCCO[C@@H](CC)[C@@H](Oc1ccccc1)[C@H](C)OC(=O)CNC(=O)c1nccc(OC)c1O] | Example 14A, Step 2 | Pale Yellow Oil |
| 302 | 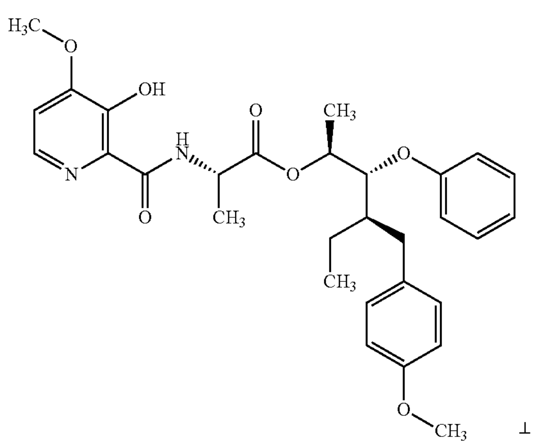 [SMILES: CC[C@H](Cc1ccc(OC)cc1)[C@@H](Oc1ccccc1)[C@H](C)OC(=O)[C@H](C)NC(=O)c1nccc(OC)c1O] | Example 14A, Step 2 | White Solid |

TABLE 1-continued

Compound Structure, Appearance, and Preparation Method

| *Cmpd. No. | Structure | Prepared According to Example: | Appearance |
|---|---|---|---|
| 303 | 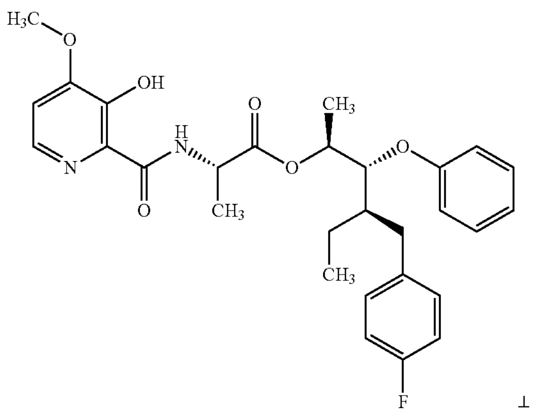 [SMILES: CC[C@H](Cc1ccc(F)cc1)[C@@H](Oc1ccccc1)[C@H](C)OC(=O)[C@H](C)NC(=O)c1nccc(OC)c1O] | Example 14A, Step 2 | White Solid |
| 304 | 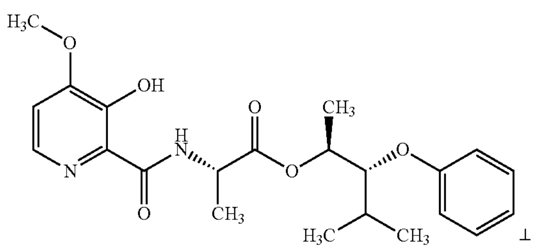 [SMILES: COc1ccnc(C(=O)N[C@@H](C)C(=O)O[C@@H](C)[C@H](Oc2ccccc2)C(C)C)c1O] | Example 14A, Step 2 | Colorless Oil |
| 305 | 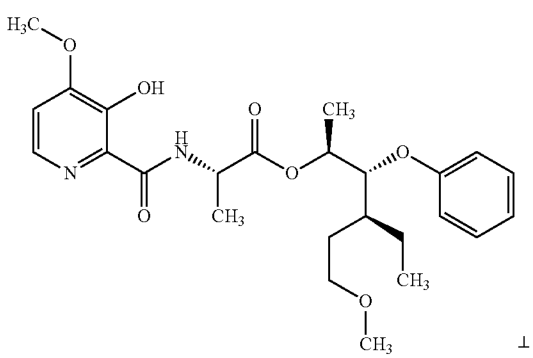 [SMILES: CC[C@@H](CCOC)[C@@H](Oc1ccccc1)[C@H](C)OC(=O)[C@H](C)NC(=O)c1nccc(OC)c1O] | Example 14A, Step 2 | Colorless Oil |
| 306 | 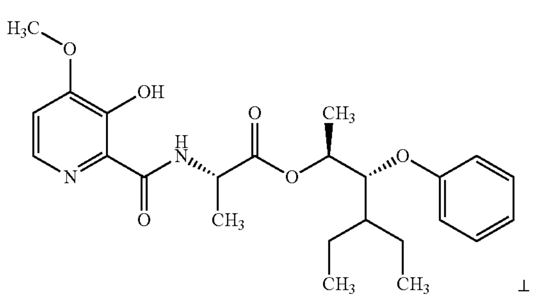 [SMILES: CCC(CC)[C@@H](Oc1ccccc1)[C@H](C)OC(=O)[C@H](C)NC(=O)c1nccc(OC)c1O] | Example 14A, Step 2 | Colorless Oil |

TABLE 1-continued

Compound Structure, Appearance, and Preparation Method

| *Cmpd. No. | Structure | Prepared According to Example: | Appearance |
|---|---|---|---|
| 307 | 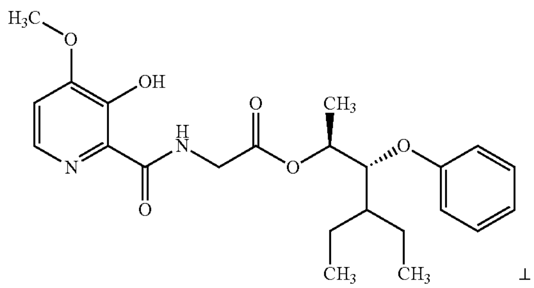 [SMILES: CCC(CC)[C@@H](Oc1ccccc1)[C@H](C)OC(=O)CNC(=O)c1nccc(OC)c1O] | Example 14A, Step 2 | White Solid |
| 308 | 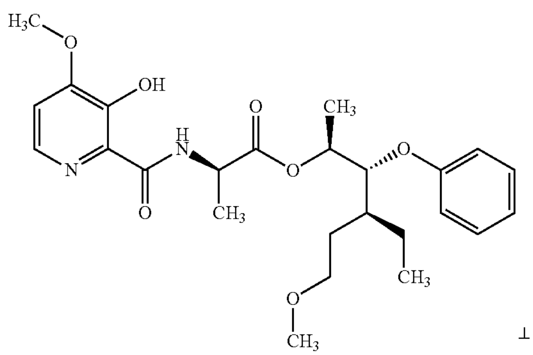 [SMILES: CC[C@@H](CCOC)[C@@H](Oc1ccccc1)[C@H](C)OC(=O)[C@@H](C)NC(=O)c1nccc(OC)c1O] | Example 14A, Step 2 | Colorless Semi Solid |
| 309 | 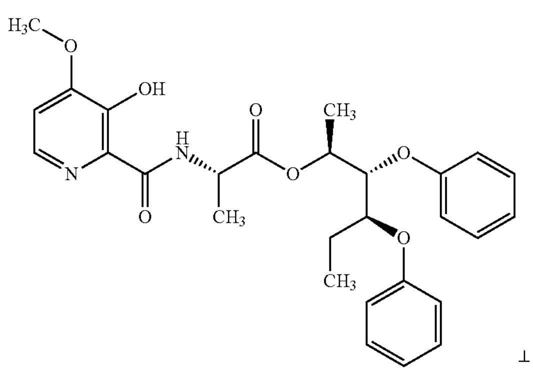 [SMILES: CC[C@H](Oc1ccccc1)[C@@H](Oc1ccccc1)[C@H](C)OC(=O)[C@H](C)NC(=O)c1nccc(OC)c1O] | Example 3; Example 4B; Example 8B; Example 12A; Example 14A, Steps 1, 2 | White Foam |
| 310 | 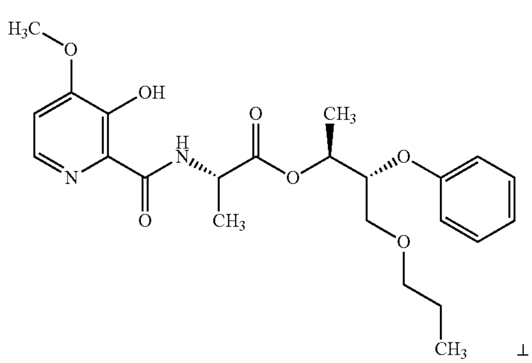 | Example 14A, Step 2 | Colorless Oil |

TABLE 1-continued

Compound Structure, Appearance, and Preparation Method

| *Cmpd. No. | Structure | Prepared According to Example: | Appearance |
|---|---|---|---|
| 311 | 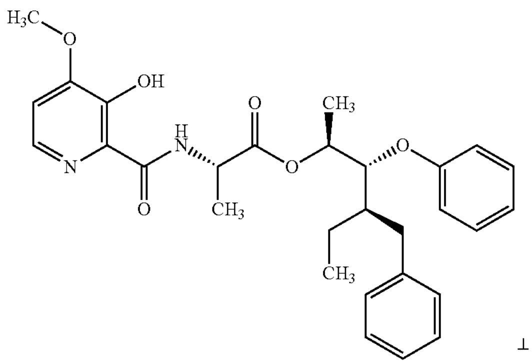 [SMILES: CC[C@H](Cc1ccccc1)[C@@H](Oc1ccccc1)[C@H](C)OC(=O)[C@H](C)NC(=O)c1nccc(OC)c1O] | Example 14B, Step 2 | Clear Oil |
| 312 | 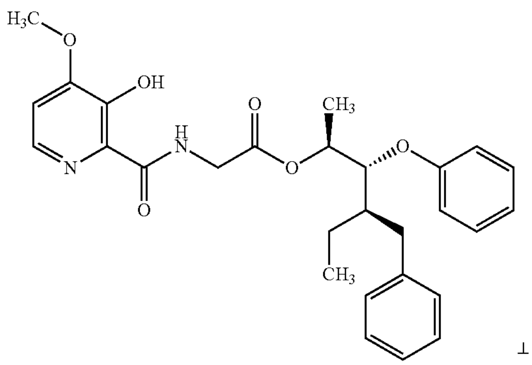 [SMILES: CC[C@H](Cc1ccccc1)[C@@H](Oc1ccccc1)[C@H](C)OC(=O)CNC(=O)c1nccc(OC)c1O] | Example 14B, Step 2 | Oily White Foam |
| 313 | 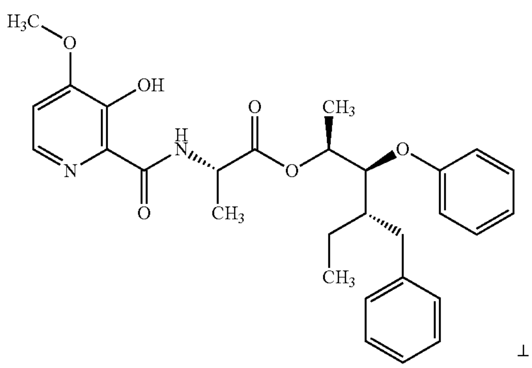 [SMILES: CC[C@@H](Cc1ccccc1)[C@H](Oc1ccccc1)[C@H](C)OC(=O)[C@H](C)NC(=O)c1nccc(OC)c1O] | Example 14B, Step 2 | Sticky White Foam |
| 314 | 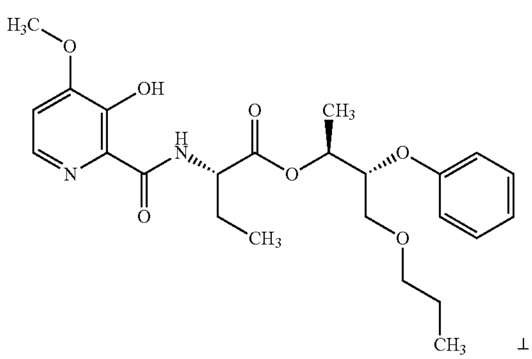 [SMILES: CCCOC[C@@H](Oc1ccccc1)[C@H](C)OC(=O)[C@H](CC)NC(=O)c1nccc(OC)c1O] | Example 14A, Step 2 | Colorless Oil |

TABLE 1-continued
Compound Structure, Appearance, and Preparation Method
| *Cmpd. No. | Structure | Prepared According to Example: | Appearance |
|---|---|---|---|
| 315 | 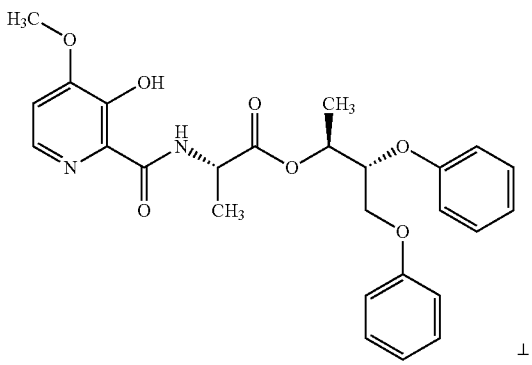 [SMILES: COc1ccnc(C(=O)N[C@@H](C)C(=O)O[C@@H](C)[C@@H](COc2ccccc2)Oc2ccccc2)c1O] | Example 14A, Step 2 | Colorless Oil |
| 316 | 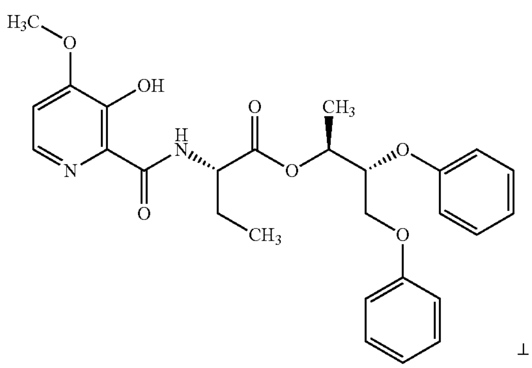 [SMILES: CC[C@H](NC(=O)c1nccc(OC)c1O)C(=O)O[C@@H](C)[C@@H](COc1ccccc1)Oc1ccccc1] | Example 14A, Step 2 | Colorless Oil |
| 317 | 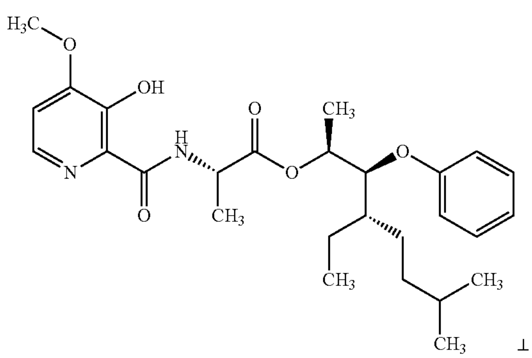 [SMILES: CC[C@@H](CCC(C)C)[C@H](Oc1ccccc1)[C@H](C)OC(=O)[C@H](C)NC(=O)c1nccc(OC)c1O] | Example 14A, Step 2 | Colorless Oil |
| 318 | 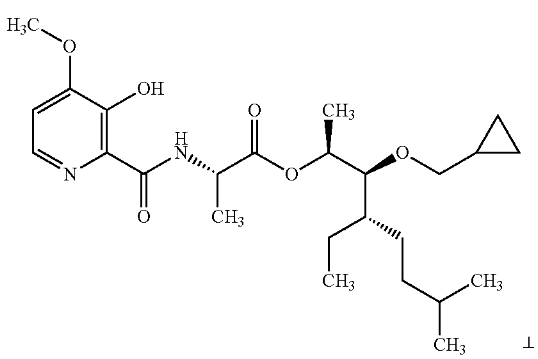 [SMILES: CC[C@@H](CCC(C)C)[C@H](OCC1CC1)[C@H](C)OC(=O)[C@H](C)NC(=O)c1nccc(OC)c1O] | Example 14A, Step 2 | Colorless Oil |

TABLE 1-continued

Compound Structure, Appearance, and Preparation Method

| *Cmpd. No. | Structure | Prepared According to Example: | Appearance |
|---|---|---|---|
| 319 | 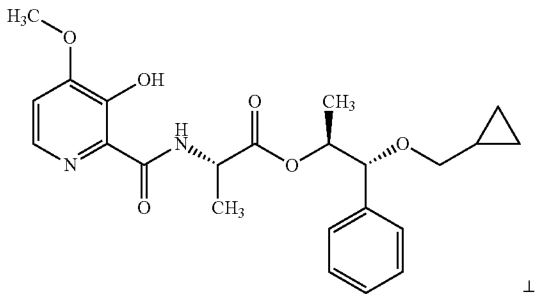 [SMILES: COc1ccnc(C(=O)N[C@@H](C)C(=O)O[C@@H](C)[C@H](OCC2CC2)c2ccccc2)c1O] | Example 14A, Step 2 | Colorless Semi Solid |
| 320 | 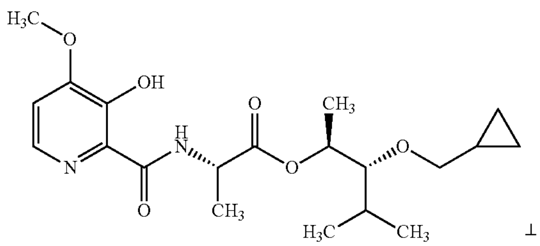 [SMILES: COc1ccnc(C(=O)N[C@@H](C)C(=O)O[C@@H](C)[C@H](OCC2CC2)C(C)C)c1O] | Example 14A, Step 2 | Colorless Oil |
| 321 | 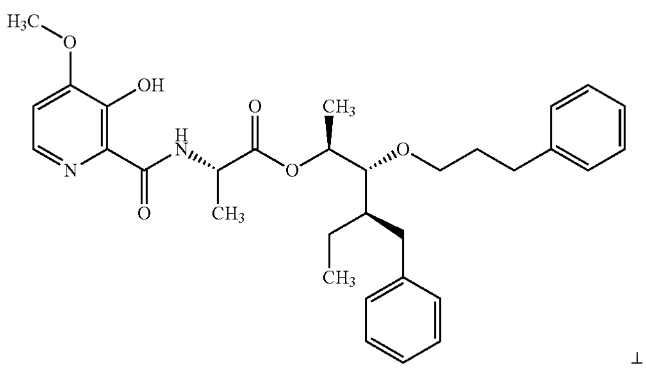 [SMILES: CC[C@H](Cc1ccccc1)[C@@H](OCCCc1ccccc1)[C@H](C)OC(=O)[C@H](C)NC(=O)c1nccc(OC)c1O] | Example 14B, Step 2 | Colorless Oil |
| 322 | 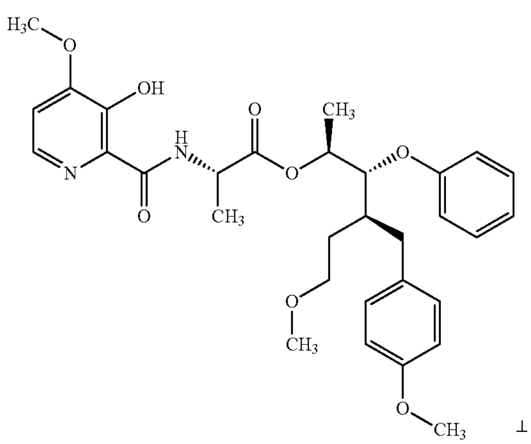 [SMILES: COCC[C@H](Cc1ccc(OC)cc1)[C@@H](Oc1ccccc1)[C@H](C)OC(=O)[C@H](C)NC(=O)c1nccc(OC)c1O] | Example 14A, Step 2 | Sticky Oil |

TABLE 1-continued

Compound Structure, Appearance, and Preparation Method

| *Cmpd. No. | Structure | Prepared According to Example: | Appearance |
|---|---|---|---|
| 323 | 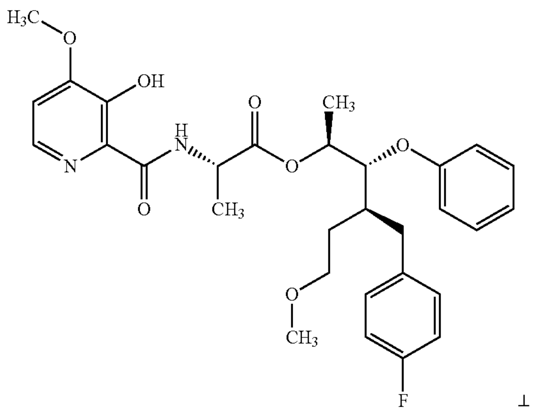 [SMILES: COCC[C@H](Cc1ccc(F)cc1)[C@@H](Oc1ccccc1)[C@H](C)OC(=O)[C@H](C)NC(=O)c1nccc(OC)c1O] | Example 14A, Step 2 | Sticky Oil |
| 324 | 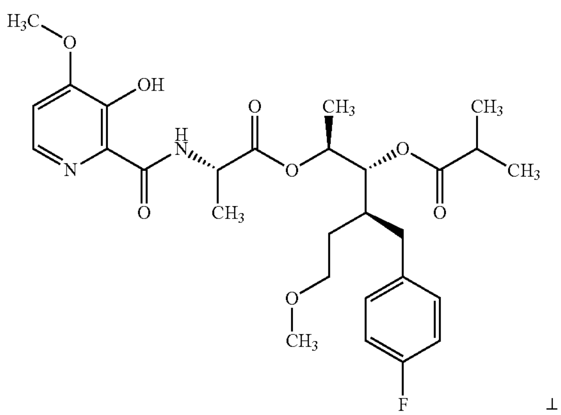 [SMILES: COCC[C@H](Cc1ccc(F)cc1)[C@@H](OC(=O)C(C)C)[C@H](C)OC(=O)[C@H](C)NC(=O)c1nccc(OC)c1O] | Example 14A, Step 2 | Sticky Oil |
| 325 | 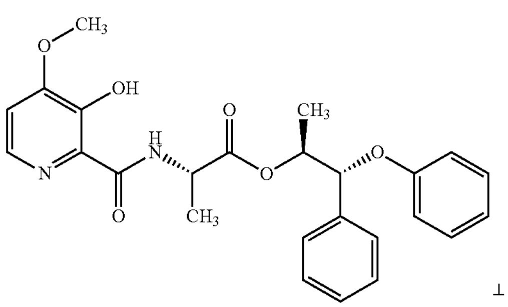 [SMILES: COc1ccnc(C(=O)N[C@@H](C)C(=O)O[C@@H](C)[C@H](Oc2ccccc2)c2ccccc2)c1O] | Example 14A, Step 2 | White Solid |
| 326 | 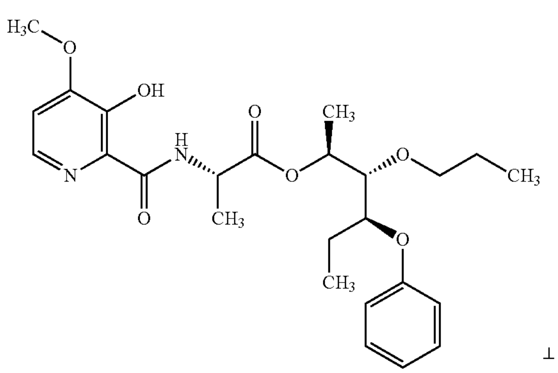 [SMILES: CCCO[C@@H]([C@H](C)OC(=O)[C@H](C)NC(=O)c1nccc(OC)c1O)[C@H](CC)Oc1ccccc1] | Example 14A, Steps 1, 2 | Light Yellow Oil |

TABLE 1-continued

Compound Structure, Appearance, and Preparation Method

| *Cmpd. No. | Structure | Prepared According to Example: | Appearance |
|---|---|---|---|
| 327 | 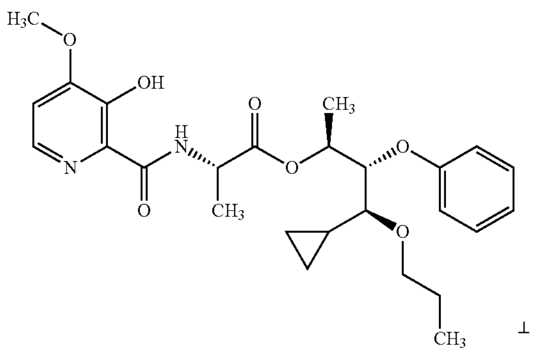 [SMILES: CCCO[C@@H](C1CC1)[C@@H](Oc1ccccc1)[C@H](C)OC(=O)[C@H](C)NC(=O)c1nccc(OC)c1O] | Example 14A, Step 2 | Colorless Oil |
| 328 | 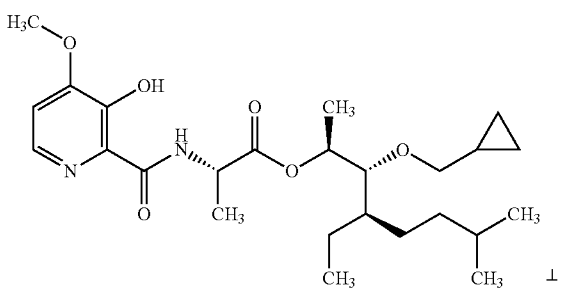 [SMILES: CC[C@H](CCC(C)C)[C@@H](OCC1CC1)[C@H](C)OC(=O)[C@H](C)NC(=O)c1nccc(OC)c1O] | Example 14A, Step 2 | Colorless Oil |
| 329 | 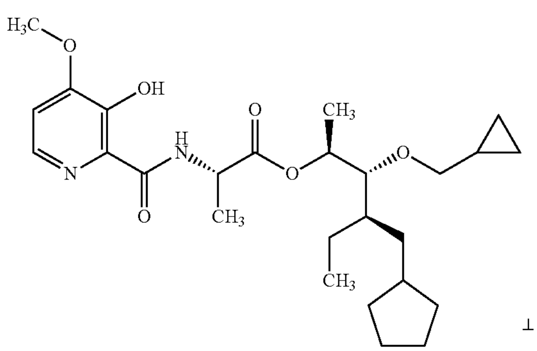 [SMILES: CC[C@H](CC1CCCC1)[C@@H](OCC1CC1)[C@H](C)OC(=O)[C@H](C)NC(=O)c1nccc(OC)c1O] | Example 14A, Step 2 | Colorless Oil |
| 330 | 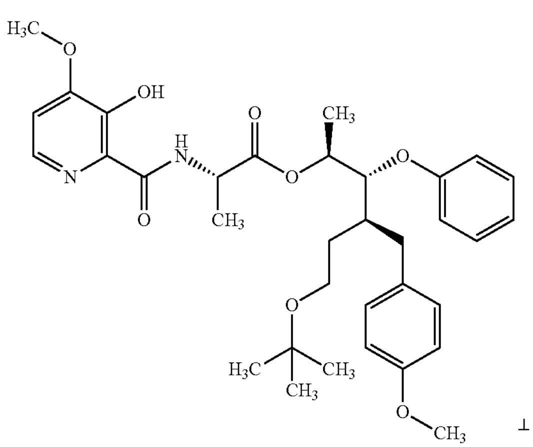 [SMILES: COc1ccc(C[C@@H](CCOC(C)(C)C)[C@@H](Oc2ccccc2)[C@H](C)OC(=O)[C@H](C)NC(=O)c2nccc(OC)c2O)cc1] | Example 14A, Step 2 | White Solid |

TABLE 1-continued

Compound Structure, Appearance, and Preparation Method

| *Cmpd. No. | Structure | Prepared According to Example: | Appearance |
|---|---|---|---|
| 331 | 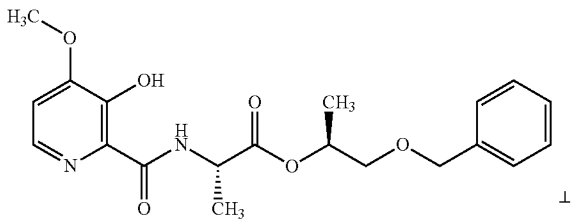 [SMILES: COc1ccnc(C(=O)N[C@@H](C)C(=O)O[C@@H](C)COCc2ccccc2)c1O] | Example 14A, Steps 1, 2 | Colorless Oil |
| 332 | 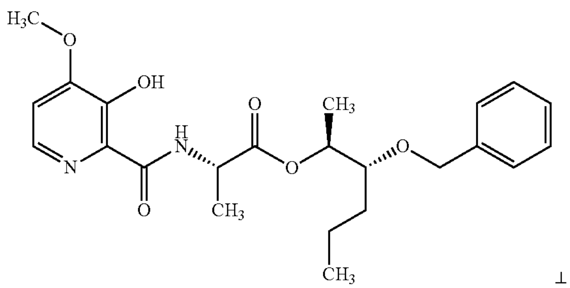 [SMILES: CCC[C@@H](OCc1ccccc1)[C@H](C)OC(=O)[C@H](C)NC(=O)c1nccc(OC)c1O] | Example 14A, Step 2 | Clear, Colorless Oil |
| 333 | 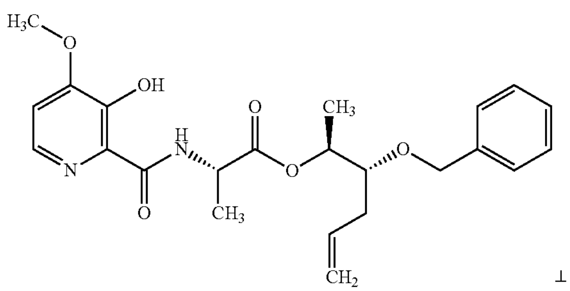 [SMILES: C=CC[C@@H](OCc1ccccc1)[C@H](C)OC(=O)[C@H](C)NC(=O)c1nccc(OC)c1O] | Example 14B, Step 2 | Clear, Colorless Oil |
| 334 | 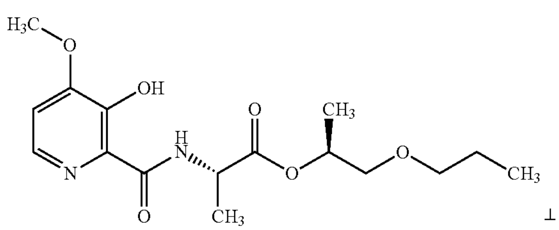 [SMILES: CCCOC[C@H](C)OC(=O)[C@H](C)NC(=O)c1nccc(OC)c1O] | Example 14A, Step 2 | Colorless Oil |
| 335 | 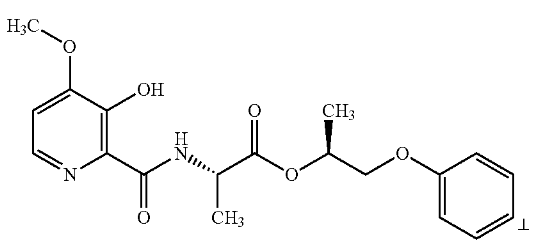 [SMILES: COc1ccnc(C(=O)N[C@@H](C)C(=O)O[C@@H](C)COc2ccccc2)c1O] | Example 14A, Step 2 | Oil |
| 336 | 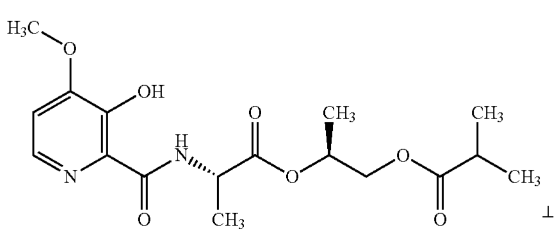 [SMILES: COc1ccnc(C(=O)N[C@@H](C)C(=O)O[C@@H](C)COC(=O)C(C)C)c1O] | Example 14A, Step 2 | Colorless Oil |

TABLE 1-continued

Compound Structure, Appearance, and Preparation Method

| *Cmpd. No. | Structure | Prepared According to Example: | Appearance |
|---|---|---|---|
| 337 | 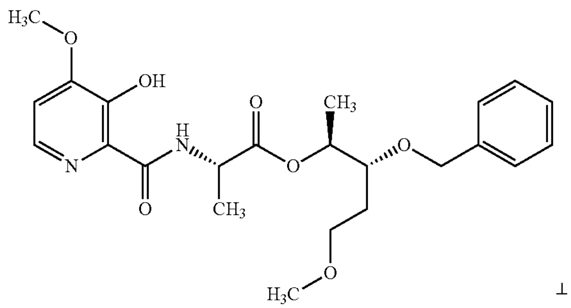 [SMILES: COCC[C@@H](OCc1ccccc1)[C@H](C)OC(=O)[C@H](C)NC(=O)c1nccc(OC)c1O] | Example 14A, Step 2 | Clear, Colorless Oil |
| 338 | 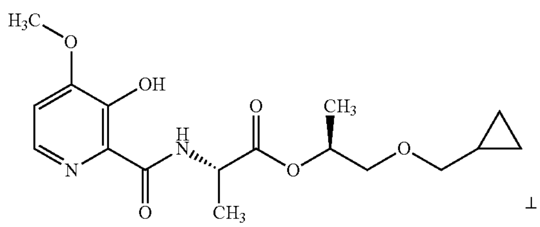 [SMILES: COc1ccnc(C(=O)N[C@@H](C)C(=O)O[C@@H](C)COCC2CC2)c1O] | Example 14A, Step 2 | Colorless Oil |
| 339 | 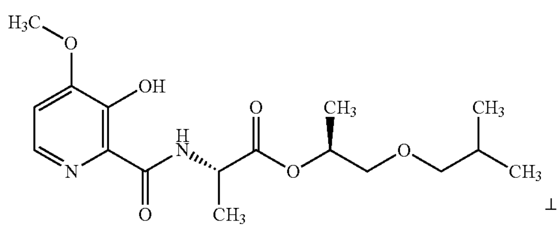 [SMILES: COc1ccnc(C(=O)N[C@@H](C)C(=O)O[C@@H](C)COCC(C)C)c1O] | Example 14A, Step 2 | Colorless Oil |
| 340 | 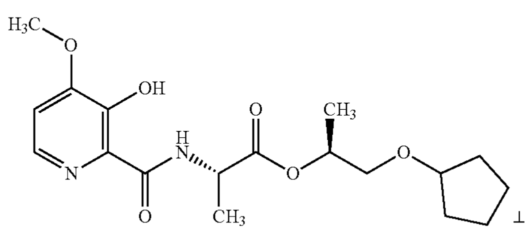 [SMILES: COc1ccnc(C(=O)N[C@@H](C)C(=O)O[C@@H](C)COC2CCCC2)c1O] | Example 14A, Step 2 | Colorless Oil |
| 341 | 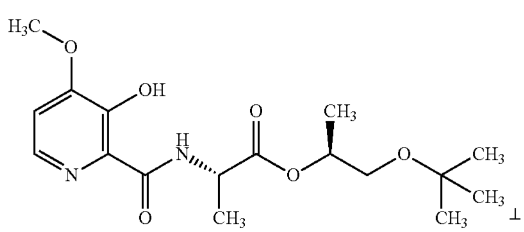 [SMILES: COc1ccnc(C(=O)N[C@@H](C)C(=O)O[C@@H](C)COC(C)(C)C)c1O] | Example 14A, Step 2 | Colorless Oil |
| 342 | 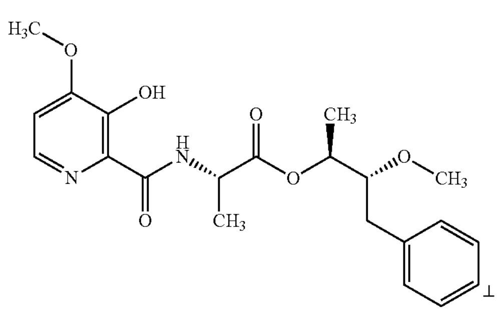 [SMILES: COc1ccnc(C(=O)N[C@@H](C)C(=O)O[C@@H](C)[C@@H](Cc2ccccc2)OC)c1O] | Example 14A, Step 2 | Colorless Oil |

TABLE 1-continued

Compound Structure, Appearance, and Preparation Method

| *Cmpd. No. | Structure | Prepared According to Example: | Appearance |
|---|---|---|---|
| 343 | 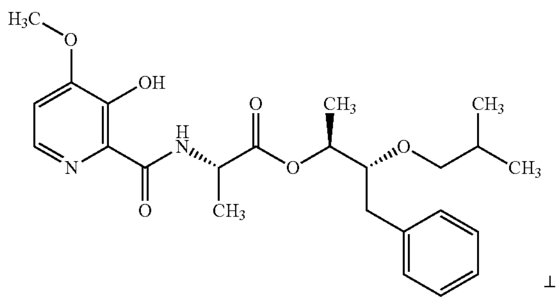 [SMILES: COc1ccnc(C(=O)N[C@@H](C)C(=O)O[C@@H](C)[C@@H](Cc2ccccc2)OCC(C)C)c1O] | Example 14A, Step 2 | Colorless Oil |
| 344 | 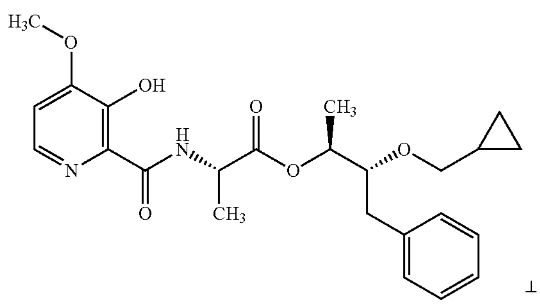 [SMILES: COc1ccnc(C(=O)N[C@@H](C)C(=O)O[C@@H](C)[C@@H](Cc2ccccc2)OCC2CC2)c1O] | Example 14A, Step 2 | Colorless Oil |
| 345 | 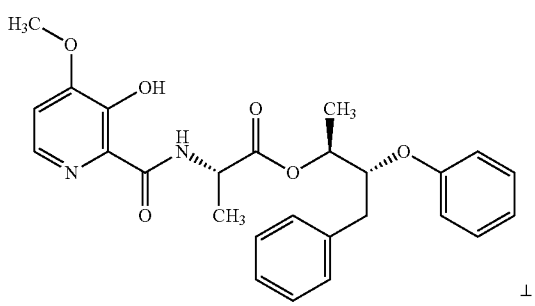 [SMILES: COc1ccnc(C(=O)N[C@@H](C)C(=O)O[C@@H](C)[C@@H](Cc2ccccc2)Oc2ccccc2)c1O] | Example 14A, Step 2 | Semi-Solid |
| 346 | 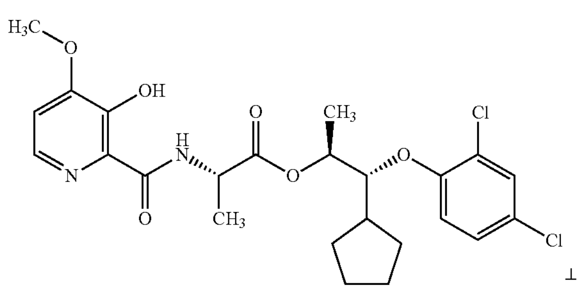 | Example 14A, Step 2 | White Powder |
| 347 | 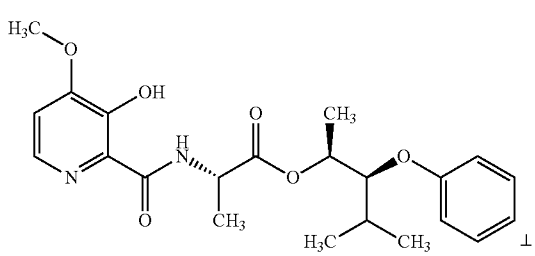 [SMILES: COc1ccnc(C(=O)N[C@@H](C)C(=O)O[C@@H](C)[C@@H](Oc2ccccc2)C(C)C)c1O] | Example 14A, Step 2 | White Solid |

TABLE 1-continued

Compound Structure, Appearance, and Preparation Method

| *Cmpd. No. | Structure | Prepared According to Example: | Appearance |
|---|---|---|---|
| 348 | (structure) | Example 14A, Step 2 | Sticky Wax |
| 349 | (structure) | Example 14A, Step 2 | Sticky Wax |
| 350 | (structure) | Example 14A, Step 2 | White Foam |
| 351 | (structure) | Example 14A, Step 2 | Sticky Wax |
| 352 | (structure) | Example 14A, Step 2 | White Foam |

TABLE 1-continued

Compound Structure, Appearance, and Preparation Method

| *Cmpd. No. | Structure | Prepared According to Example: | Appearance |
|---|---|---|---|
| 353 | 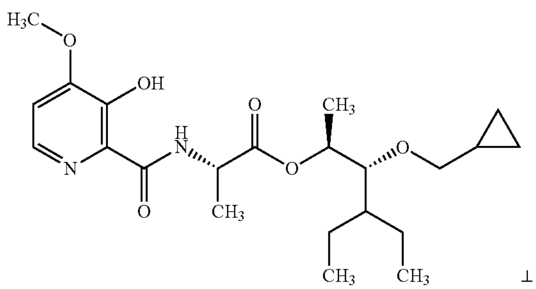 [SMILES: CCC(CC)[C@@H](OCC1CC1)[C@H](C)OC(=O)[C@H](C)NC(=O)c1nccc(OC)c1O] | Example 14A, Step 2 | Colorless Oil |
| 354 | 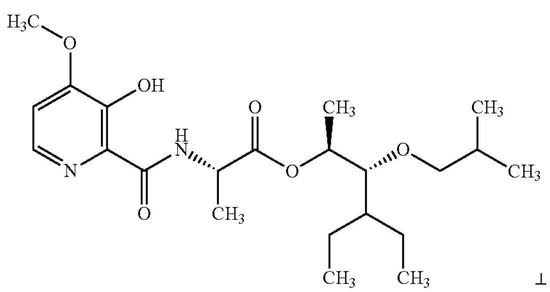 [SMILES: CCC(CC)[C@@H](OCC(C)C)[C@H](C)OC(=O)[C@H](C)NC(=O)c1nccc(OC)c1O] | Example 14A, Step 2 | Colorless Oil |
| 355 | 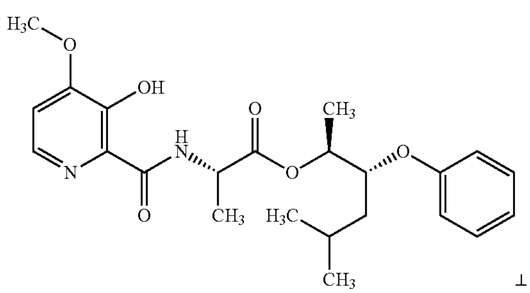 [SMILES: COc1ccnc(C(=O)N[C@@H](C)C(=O)O[C@@H](C)[C@@H](CC(C)C)Oc2ccccc2)c1O] | Example 14A, Step 2 | Sticky Oil |
| 356 | 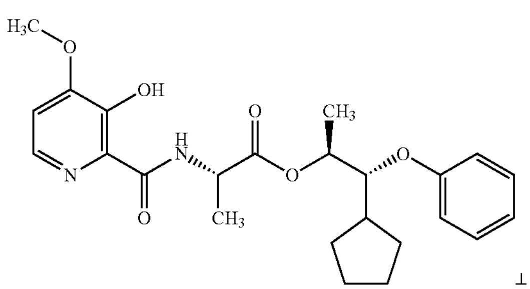 [SMILES: COc1ccnc(C(=O)N[C@@H](C)C(=O)O[C@@H](C)[C@H](Oc2ccccc2)C2CCCC2)c1O] | Example 14A, Step 2 | Sticky Oil |
| 357 | 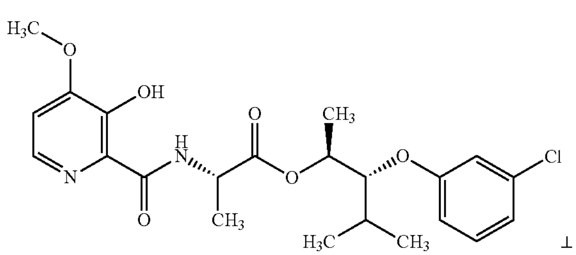 [SMILES: COc1ccnc(C(=O)N[C@@H](C)C(=O)O[C@@H](C)[C@H](Oc2cccc(Cl)c2)C(C)C)c1O] | Example 14A, Step 2 | Colorless Oil |

TABLE 1-continued

Compound Structure, Appearance, and Preparation Method

| *Cmpd. No. | Structure | Prepared According to Example: | Appearance |
|---|---|---|---|
| 358 | 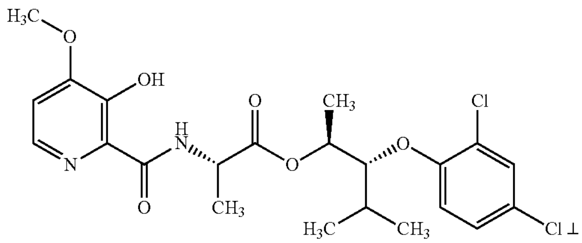 [SMILES: COc1ccnc(C(=O)N[C@@H](C)C(=O)O[C@@H](C)[C@H](Oc2ccc(Cl)cc2Cl)C(C)C)c1O] | Example 14A, Step 2 | White Solid |
| 359 | 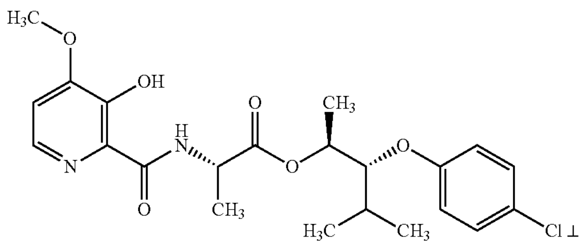 [SMILES: COc1ccnc(C(=O)N[C@@H](C)C(=O)O[C@@H](C)[C@H](Oc2ccc(Cl)cc2)C(C)C)c1O] | Example 14A, Step 2 | Sticky Oil |
| 360 | 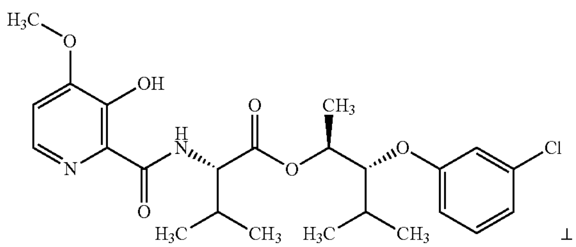 [SMILES: COc1ccnc(C(=O)N[C@H](C(=O)O[C@@H](C)[C@H](Oc2cccc(Cl)c2)C(C)C)C(C)C)c1O] | Example 14A, Step 2 | Colorless Oil |
| 361 | 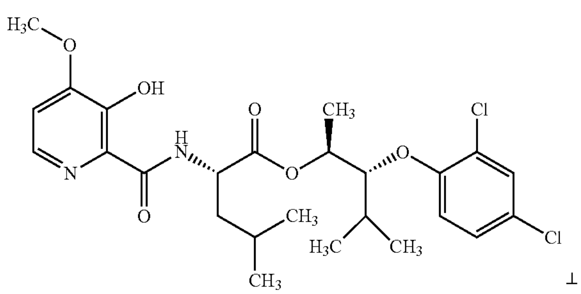 [SMILES: COc1ccnc(C(=O)N[C@@H](CC(C)C)C(=O)O[C@@H](C)[C@H](Oc2ccc(Cl)cc2Cl)C(C)C)c1O] | Example 14A, Step 2 | White Solid |
| 362 | 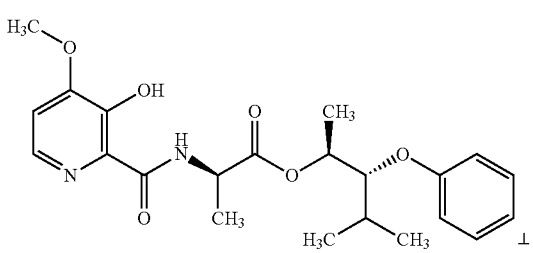 [SMILES: COc1ccnc(C(=O)N[C@H](C)C(=O)O[C@@H](C)[C@H](Oc2ccccc2)C(C)C)c1O] | Example 14A, Step 2 | Sticky Wax |
| 363 | 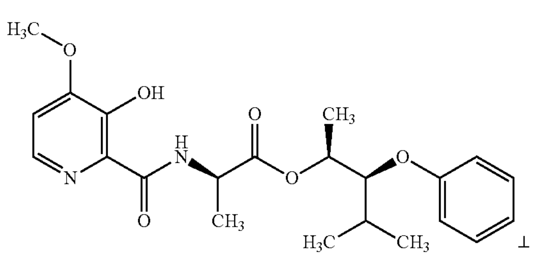 [SMILES: COc1ccnc(C(=O)N[C@H](C)C(=O)O[C@@H](C)[C@@H](Oc2ccccc2)C(C)C)c1O] | Example 14A, Step 2 | Sticky Wax |

TABLE 1-continued

Compound Structure, Appearance, and Preparation Method

| *Cmpd. No. | Structure | Prepared According to Example: | Appearance |
|---|---|---|---|
| 364 | 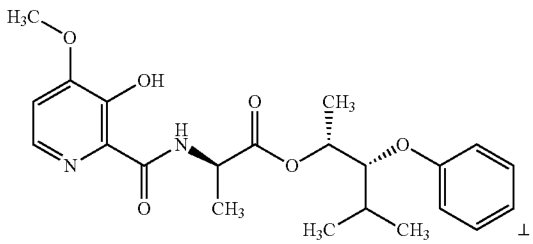 [SMILES: COc1ccnc(C(=O)N[C@H](C)C(=O)O[C@H](C)[C@H](Oc2ccccc2)C(C)C)c1O] | Example 14A, Step 2 | White Solid |
| 365 | 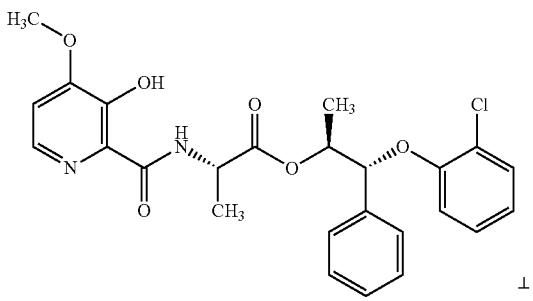 [SMILES: COc1ccnc(C(=O)N[C@@H](C)C(=O)O[C@@H](C)[C@H](Oc2ccccc2Cl)c2ccccc2)c1O] | Example 14A, Step 2 | White Powder |
| 366 | 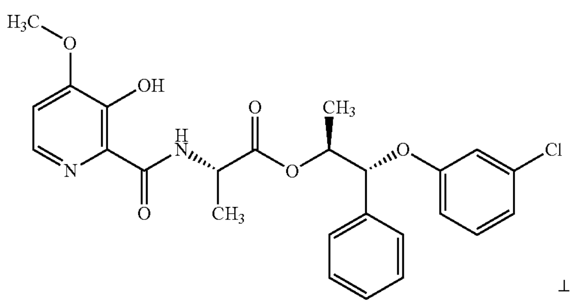 [SMILES: COc1ccnc(C(=O)N[C@@H](C)C(=O)O[C@@H](C)[C@H](Oc2cccc(Cl)c2)c2ccccc2)c1O] | Example 14A, Step 2 | White Powder |
| 367 | 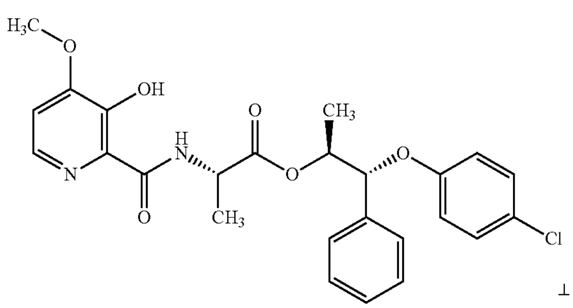 [SMILES: COc1ccnc(C(=O)N[C@@H](C)C(=O)O[C@@H](C)[C@H](Oc2ccc(Cl)cc2)c2ccccc2)c1O] | Example 14A, Step 2 | White Powder |
| 368 | 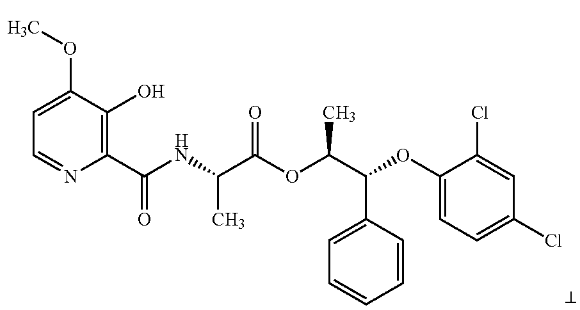 [SMILES: COc1ccnc(C(=O)N[C@@H](C)C(=O)O[C@@H](C)[C@H](Oc2ccc(Cl)cc2Cl)c2ccccc2)c1O] | Example 14A, Step 2 | White Powder |

TABLE 1-continued

Compound Structure, Appearance, and Preparation Method

| *Cmpd. No. | Structure | Prepared According to Example: | Appearance |
|---|---|---|---|
| 369 | 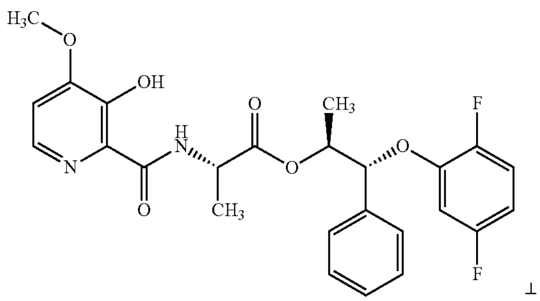 [SMILES: COc1ccnc(C(=O)N[C@@H](C)C(=O)O[C@@H](C)[C@H](Oc2cc(F)ccc2F)c2ccccc2)c1O] | Example 14A, Step 2 | Hygroscopic White Powder |
| 370 | 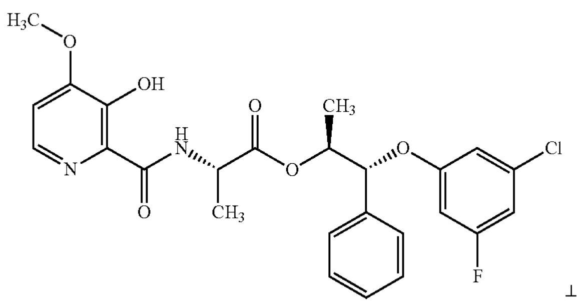 [SMILES: COc1ccnc(C(=O)N[C@@H](C)C(=O)O[C@@H](C)[C@H](Oc2cc(F)cc(Cl)c2)c2ccccc2)c1O] | Example 14A, Step 2 | Hygroscopic White Powder |
| 371 | 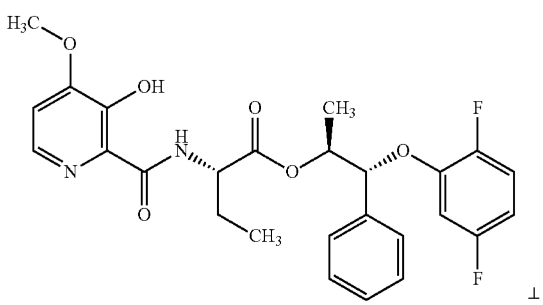 [SMILES: CC[C@H](NC(=O)c1nccc(OC)c1O)C(=O)O[C@@H](C)[C@H](Oc1cc(F)ccc1F)c1ccccc1] | Example 14A, Step 2 | Hygroscopic White Powder |
| 372 | 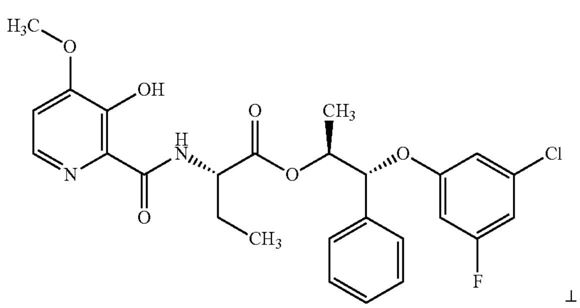 [SMILES: CC[C@H](NC(=O)c1nccc(OC)c1O)C(=O)O[C@@H](C)[C@H](Oc1cc(F)cc(Cl)c1)c1ccccc1] | Example 14A, Step 2 | Hygroscopic White Powder |
| 373 | 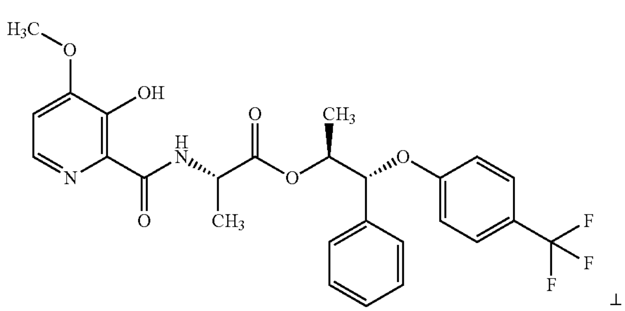 [SMILES: COc1ccnc(C(=O)N[C@@H](C)C(=O)O[C@@H](C)[C@H](Oc2ccc(C(F)(F)F)cc2)c2ccccc2)c1O] | Example 14A, Step 2 | White Powder |

TABLE 1-continued

Compound Structure, Appearance, and Preparation Method

| *Cmpd. No. | Structure | Prepared According to Example: | Appearance |
|---|---|---|---|
| 374 | 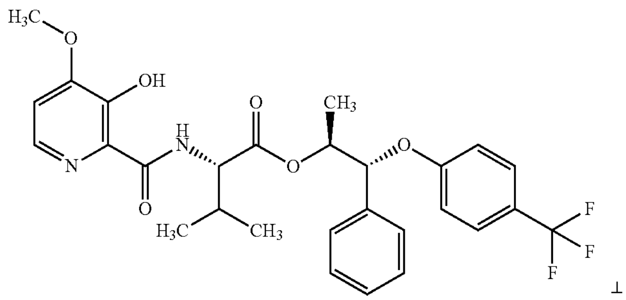 [SMILES: COc1ccnc(C(=O)N[C@H](C(=O)O[C@@H](C)[C@H](Oc2ccc(C(F)(F)F)cc2)c2ccccc2)C(C)C)c1O] | Example 14A, Step 2 | White Powder |
| 375 | 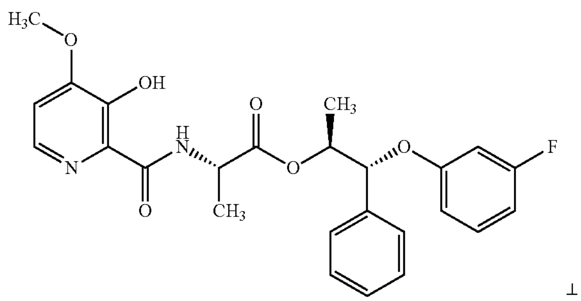 [SMILES: COc1ccnc(C(=O)N[C@@H](C)C(=O)O[C@@H](C)[C@H](Oc2cccc(F)c2)c2ccccc2)c1O] | Example 14A, Step 2 | Hygroscopic White Powder |
| 376 | 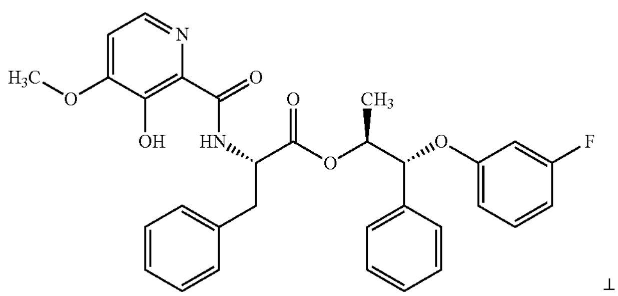 [SMILES: COc1ccnc(C(=O)N[C@@H](Cc2ccccc2)C(=O)O[C@@H](C)[C@H](Oc2cccc(F)c2)c2ccccc2)c1O] | Example 14A, Step 2 | White Powder |
| 377 | 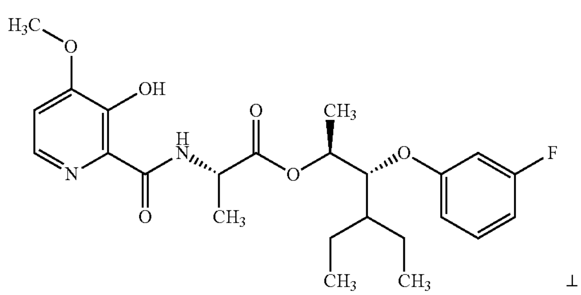 [SMILES: CCC(CC)[C@@H](Oc1cccc(F)c1)[C@H](C)OC(=O)[C@H](C)NC(=O)c1nccc(OC)c1O] | Example 14A, Step 2 | Colorless Oil |
| 378 | 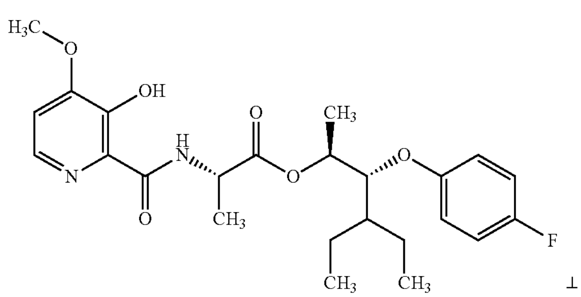 [SMILES: CCC(CC)[C@@H](Oc1ccc(F)cc1)[C@H](C)OC(=O)[C@H](C)NC(=O)c1nccc(OC)c1O] | Example 14A, Step 2 | Colorless Oil |

TABLE 1-continued

Compound Structure, Appearance, and Preparation Method

| *Cmpd. No. | Structure | Prepared According to Example: | Appearance |
|---|---|---|---|
| 379 | 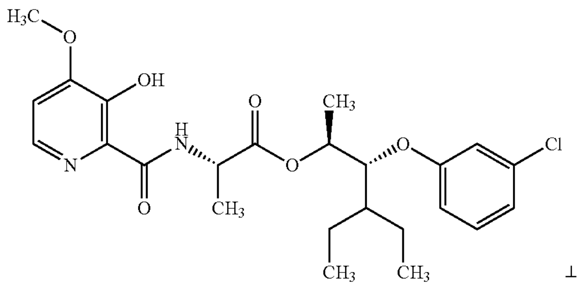 [SMILES: CCC(CC)[C@@H](Oc1cccc(Cl)c1)[C@H](C)OC(=O)[C@H](C)NC(=O)c1nccc(OC)c1O] | Example 14A, Step 2 | Colorless Oil |
| 380 | 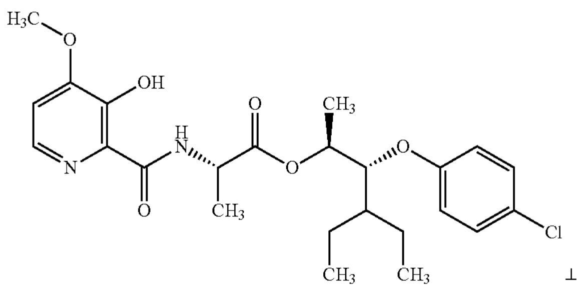 [SMILES: CCC(CC)[C@@H](Oc1ccc(Cl)cc1)[C@H](C)OC(=O)[C@H](C)NC(=O)c1nccc(OC)c1O] | Example 14A, Step 2 | Colorless Oil |
| 381 | 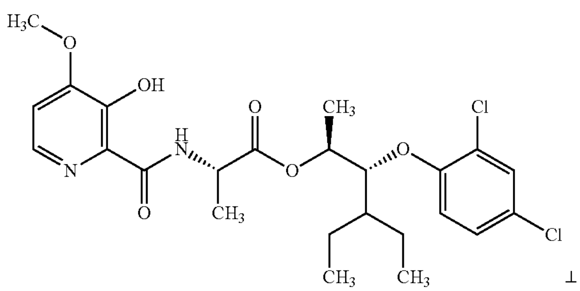 [SMILES: CCC(CC)[C@@H](Oc1ccc(Cl)cc1Cl)[C@H](C)OC(=O)[C@H](C)NC(=O)c1nccc(OC)c1O] | Example 14A, Step 2 | Colorless Oil |
| 382 | 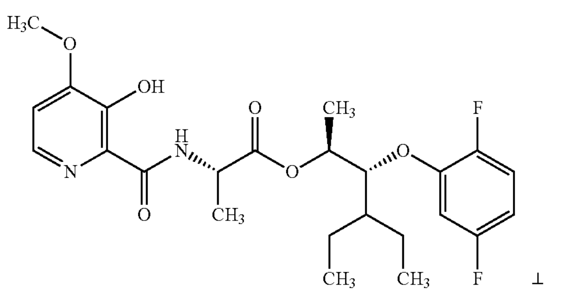 [SMILES: CCC(CC)[C@@H](Oc1cc(F)ccc1F)[C@H](C)OC(=O)[C@H](C)NC(=O)c1nccc(OC)c1O] | Example 14A, Step 2 | Colorless Oil |
| 383 | 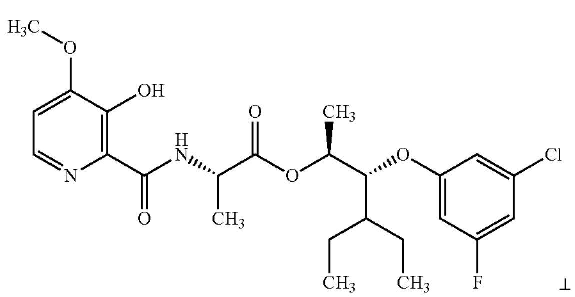 [SMILES: CCC(CC)[C@@H](Oc1cc(F)cc(Cl)c1)[C@H](C)OC(=O)[C@H](C)NC(=O)c1nccc(OC)c1O] | Example 14A, Step 2 | Colorless Oil |

TABLE 1-continued
Compound Structure, Appearance, and Preparation Method
| *Cmpd. No. | Structure | Prepared According to Example: | Appearance |
|---|---|---|---|
| 384 | 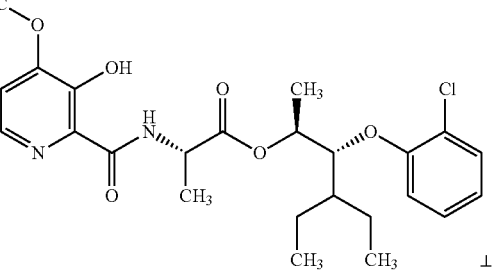 | Example 14A, Step 2 | Colorless Oil |
| 385 | 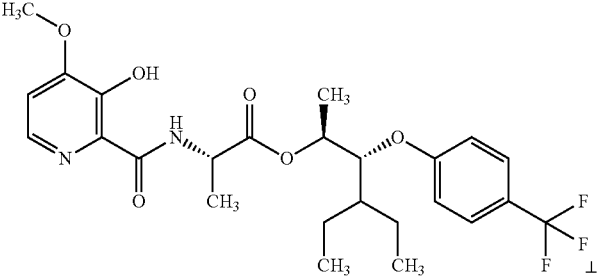 [SMILES: CCC(CC)[C@@H](Oc1ccc(C(F)(F)F)cc1)[C@H](C)OC(=O)[C@H](C)NC(=O)c1nccc(OC)c1O] | Example 14A, Step 2 | Colorless Oil |
| 386 | 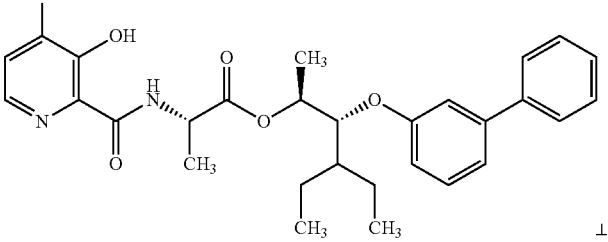 | Example 14A, Step 2 | Colorless Oil |
| 387 | 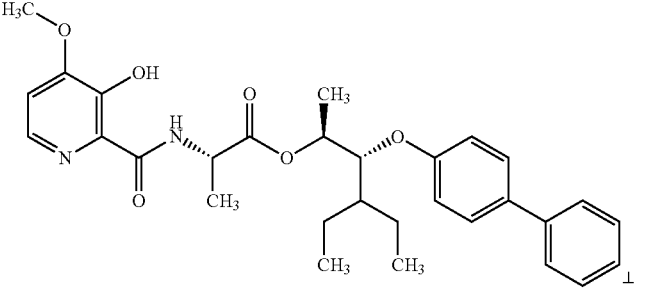 [SMILES: CCC(CC)[C@@H](Oc1ccc(-c2ccccc2)cc1)[C@H](C)OC(=O)[C@H](C)NC(=O)c1nccc(OC)c1O] | Example 14A, Step 2 | Colorless Oil |
| 388 | 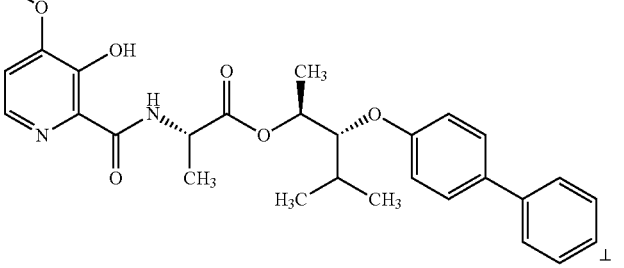 | Example 14A, Step 2 | White Solid |

TABLE 1-continued

Compound Structure, Appearance, and Preparation Method

| *Cmpd. No. | Structure | Prepared According to Example: | Appearance |
|---|---|---|---|
| 389 | 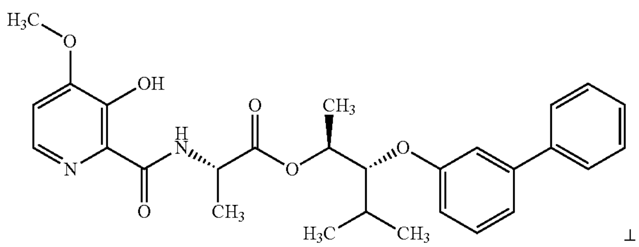 [SMILES: COc1ccnc(C(=O)N[C@@H](C)C(=O)O[C@@H](C)[C@H](Oc2cccc(-c3ccccc3)c2)C(C)C)c1O] | Example 14A, Step 2 | White Solid |
| 390 | 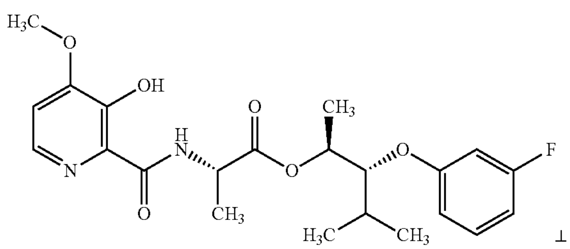 [SMILES: COc1ccnc(C(=O)N[C@@H](C)C(=O)O[C@@H](C)[C@H](Oc2cccc(F)c2)C(C)C)c1O] | Example 14A, Step 2 | Colorless Oil |
| 391 | 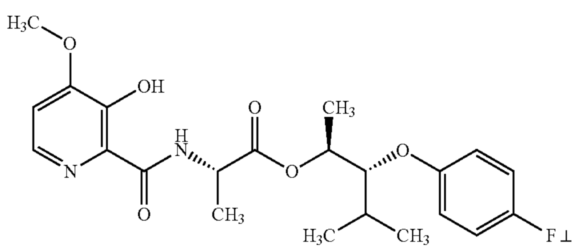 [SMILES: COc1ccnc(C(=O)N[C@@H](C)C(=O)O[C@@H](C)[C@H](Oc2ccc(F)cc2)C(C)C)c1O] | Example 14A, Step 2 | Colorless Oil |
| 392 | 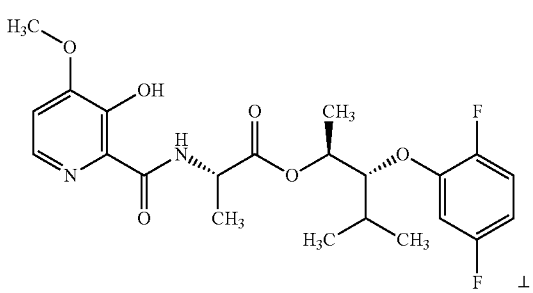 [SMILES: COc1ccnc(C(=O)N[C@@H](C)C(=O)O[C@@H](C)[C@H](Oc2cc(F)ccc2F)C(C)C)c1O] | Example 14A, Step 2 | Colorless Oil |
| 393 | 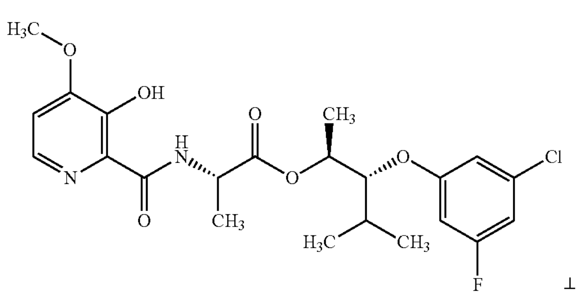 [SMILES: COc1ccnc(C(=O)N[C@@H](C)C(=O)O[C@@H](C)[C@H](Oc2cc(F)cc(Cl)c2)C(C)C)c1O] | Example 14A, Step 2 | Colorless Oil |

TABLE 1-continued

Compound Structure, Appearance, and Preparation Method

| *Cmpd. No. | Structure | Prepared According to Example: | Appearance |
|---|---|---|---|
| 394 | 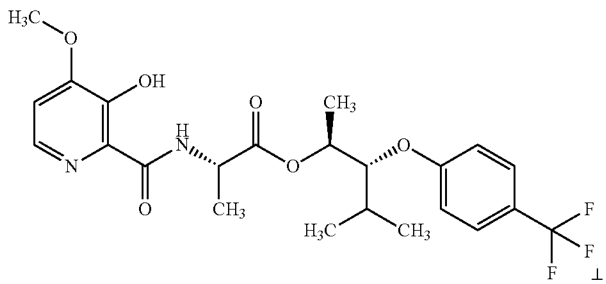 [SMILES: COc1ccnc(C(=O)N[C@@H](C)C(=O)O[C@@H](C)[C@H](Oc2ccc(C(F)(F)F)cc2)C(C)C)c1O] | Example 14A, Step 2 | Sticky Solid |
| 395 | 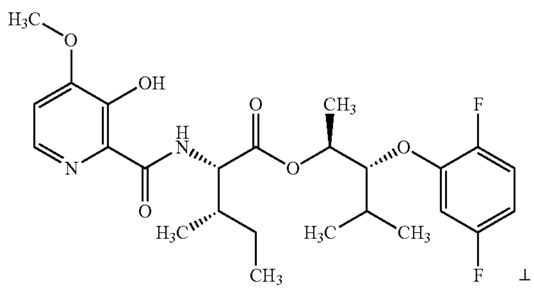 [SMILES: CC[C@H](C)[C@H](NC(=O)c1nccc(OC)c1O)C(=O)O[C@@H](C)[C@H](Oc1cc(F)ccc1F)C(C)C] | Example 14A, Step 2 | Colorless Oil |
| 396 | 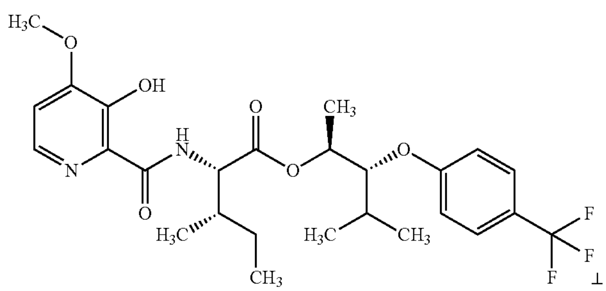 [SMILES: CC[C@H](C)[C@H](NC(=O)c1nccc(OC)c1O)C(=O)O[C@@H](C)[C@H](Oc1ccc(C(F)(F)F)cc1)C(C)C] | Example 14A, Step 2 | Colorless Oil |
| 397 | 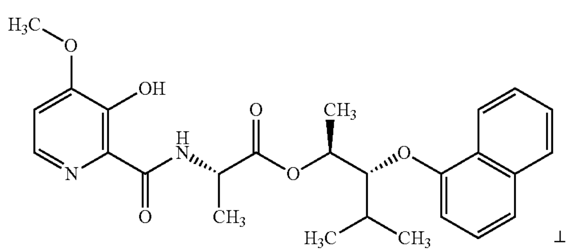 [SMILES: COc1ccnc(C(=O)N[C@@H](C)C(=O)O[C@@H](C)[C@H](Oc2cccc3ccccc23)C(C)C)c1O] | Example 14A, Step 2 | White Solid |
| 398 | 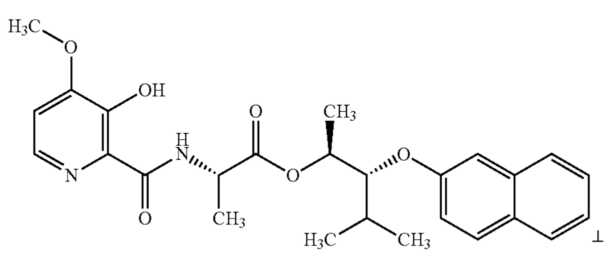 [SMILES: COc1ccnc(C(=O)N[C@@H](C)C(=O)O[C@@H](C)[C@H](Oc2ccc3ccccc3c2)C(C)C)c1O] | Example 14A, Step 2 | White Solid |

TABLE 1-continued

Compound Structure, Appearance, and Preparation Method

| *Cmpd. No. | Structure | Prepared According to Example: | Appearance |
|---|---|---|---|
| 399 | 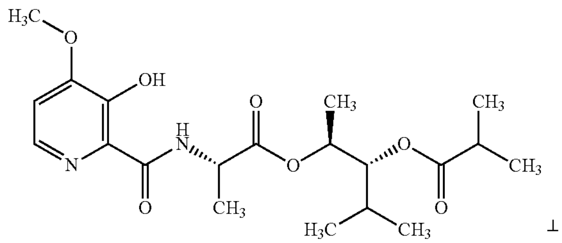 [SMILES: COc1ccnc(C(=O)N[C@@H](C)C(=O)O[C@@H](C)[C@H](OC(=O)C(C)C)C(C)C)c1O] | Example 14A, Step 2 | Colorless Oil |
| 400 | 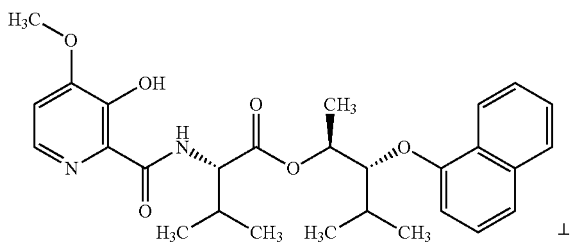 [SMILES: COc1ccnc(C(=O)N[C@H](C(=O)O[C@@H](C)[C@H](Oc2cccc3ccccc23)C(C)C)C(C)C)c1O] | Example 14A, Step 2 | White Solid |
| 401 | 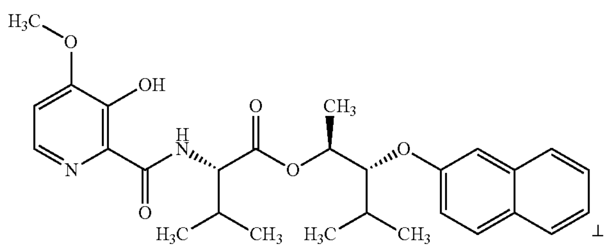 [SMILES: COc1ccnc(C(=O)N[C@H](C(=O)O[C@@H](C)[C@H](Oc2ccc3ccccc3c2)C(C)C)C(C)C)c1O] | Example 14A, Step 2 | Oil |
| 402 | 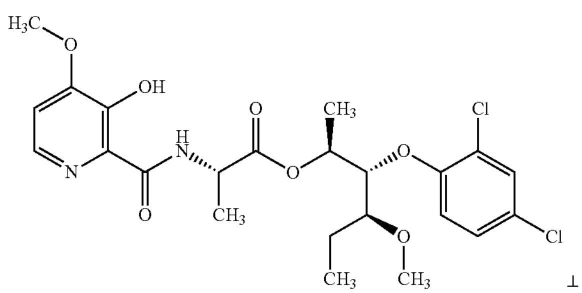 [SMILES: CC[C@H](OC)[C@@H](Oc1ccc(Cl)cc1Cl)[C@H](C)OC(=O)[C@H](C)NC(=O)c1nccc(OC)c1O] | Example 14A, Steps 1, 2 | Colorless Oil |
| 403 | 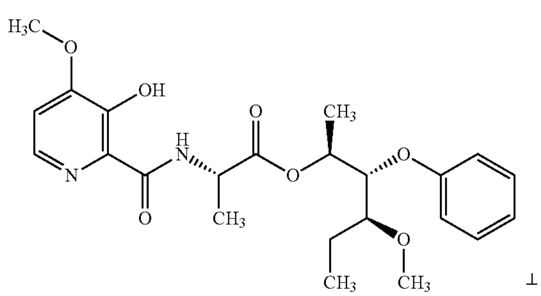 [SMILES: CC[C@H](OC)[C@@H](Oc1ccccc1)[C@H](C)OC(=O)[C@H](C)NC(=O)c1nccc(OC)c1O] | Example 15 | Colorless Oil |

TABLE 1-continued

Compound Structure, Appearance, and Preparation Method

| *Cmpd. No. | Structure | Prepared According to Example: | Appearance |
|---|---|---|---|
| 404 | 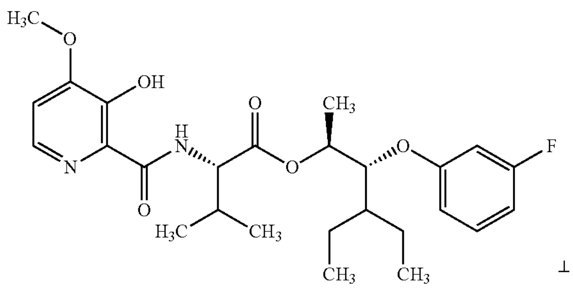 | Example 14A, Step 2 | Colorless Oil |
| 405 | 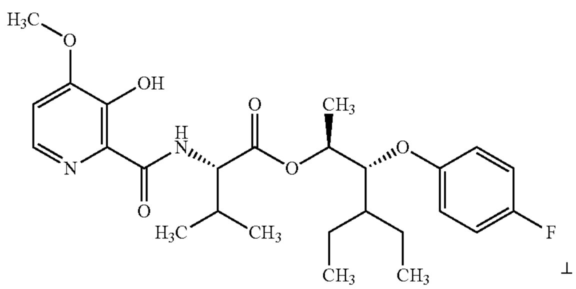 [SMILES: CCC(CC)[C@@H](Oc1ccc(F)cc1)[C@H](C)OC(=O)[C@@H](NC(=O)c1nccc(OC)c1O)C(C)C] | Example 14A, Step 2 | Colorless Oil |
| 406 | 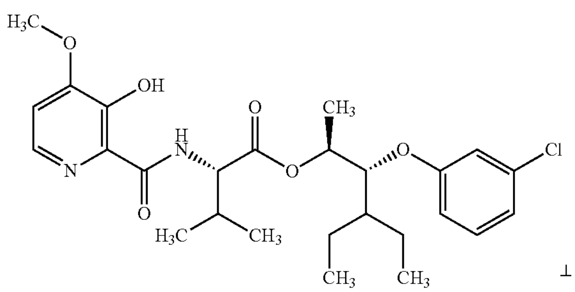 [SMILES: CCC(CC)[C@@H](Oc1cccc(Cl)c1)[C@H](C)OC(=O)[C@@H](NC(=O)c1nccc(OC)c1O)C(C)C] | Example 14A, Step 2 | Colorless Oil |
| 407 | 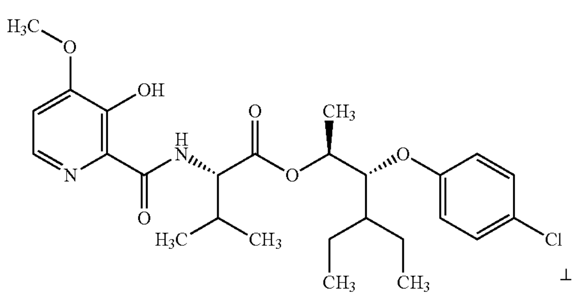 | Example 14A, Step 2 | Colorless Oil |
| 408 | 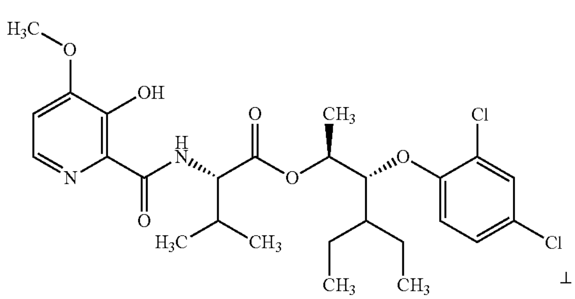 | Example 14A, Step 2 | Colorless Oil |

TABLE 1-continued

Compound Structure, Appearance, and Preparation Method

| *Cmpd. No. | Structure | Prepared According to Example: | Appearance |
|---|---|---|---|
| 409 | 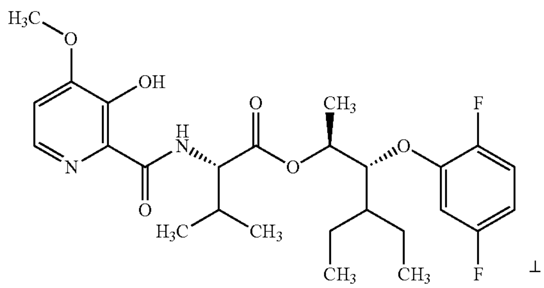 [SMILES: CCC(CC)[C@@H](Oc1cc(F)ccc1F)[C@H](C)OC(=O)[C@@H](NC(=O)c1nccc(OC)c1O)C(C)C] | Example 14A, Step 2 | Colorless Oil |
| 410 | 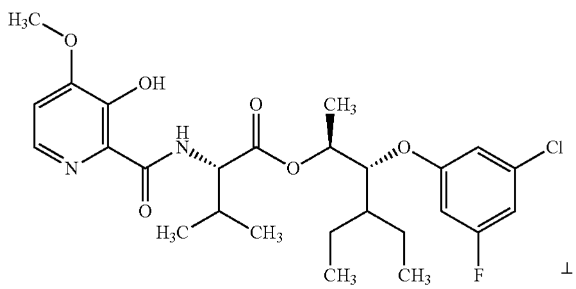 [SMILES: CCC(CC)[C@@H](Oc1cc(F)cc(Cl)c1)[C@H](C)OC(=O)[C@@H](NC(=O)c1nccc(OC)c1O)C(C)C] | Example 14A, Step 2 | Colorless Oil |
| 411 | 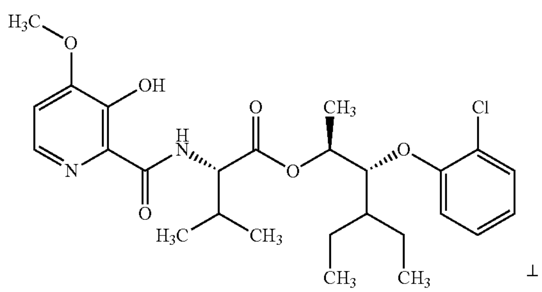 | Example 14A, Step 2 | Colorless Oil |
| 412 | 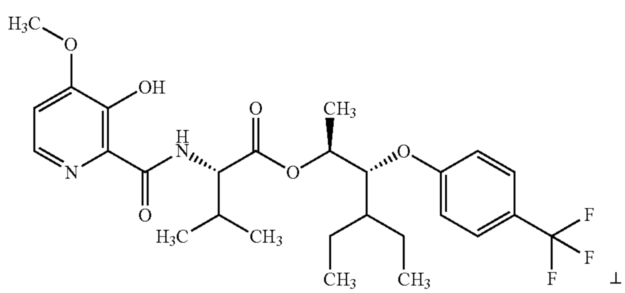 [SMILES: CCC(CC)[C@@H](Oc1ccc(C(F)(F)F)cc1)[C@H](C)OC(=O)[C@@H](NC(=O)c1nccc(OC)c1O)C(C)C] | Example 14A, Step 2 | Colorless Oil |
| 413 | 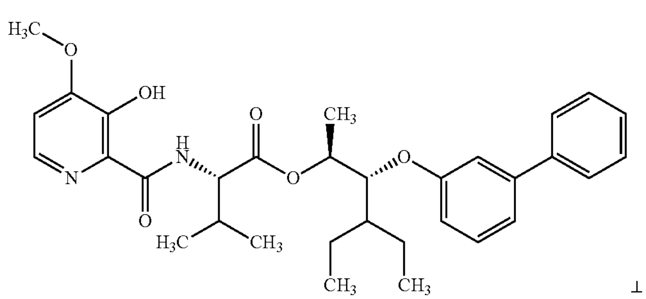 [SMILES: CCC(CC)[C@@H](Oc1cccc(-c2ccccc2)c1)[C@H](C)OC(=O)[C@@H](NC(=O)c1nccc(OC)c1O)C(C)C] | Example 14A, Step 2 | Colorless Oil |

TABLE 1-continued

Compound Structure, Appearance, and Preparation Method

| *Cmpd. No. | Structure | Prepared According to Example: | Appearance |
|---|---|---|---|
| 414 | 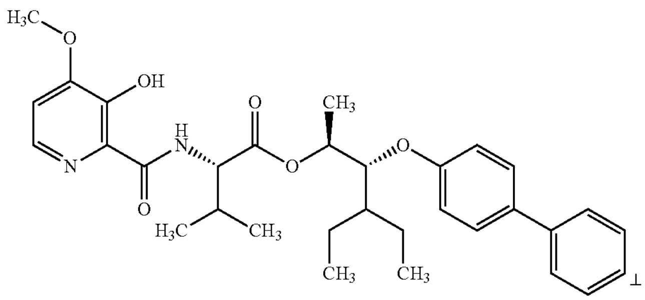 [SMILES: CCC(CC)[C@@H](Oc1ccc(-c2ccccc2)cc1)[C@H](C)OC(=O)[C@@H](NC(=O)c1nccc(OC)c1O)C(C)C] | Example 14A, Step 2 | Colorless Oil |
| 415 | 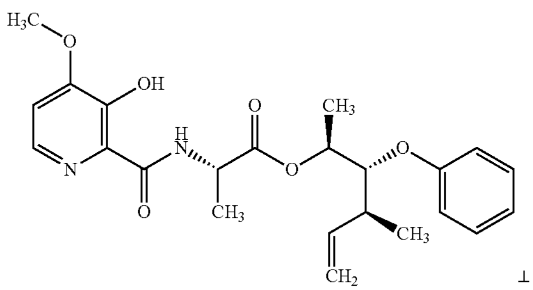 [SMILES: C=C[C@H](C)[C@@H](Oc1ccccc1)[C@H](C)OC(=O)[C@H](C)NC(=O)c1nccc(OC)c1O] | Example 14A, Step 2 | Clear Oil |
| 416 | 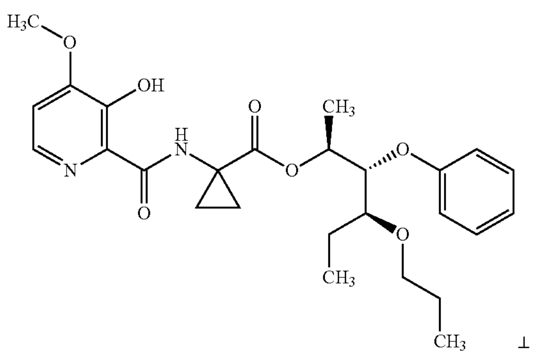 [SMILES: CCCO[C@@H](CC)[C@@H](Oc1ccccc1)[C@H](C)OC(=O)C1(NC(=O)c2nccc(OC)c2O)CC1] | Example 3; Example 4B; Example 8C; Example 12A Example 14A, Steps 1, 2 | Colorless Oil |
| 417 | 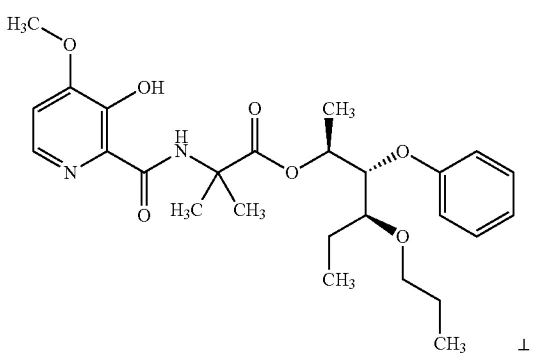 [SMILES: CCCO[C@@H](CC)[C@@H](Oc1ccccc1)[C@H](C)OC(=O)C(C)(C)NC(=O)c1nccc(OC)c1O] | Example 14A, Step 2 | Colorless Oil |
| 418 | 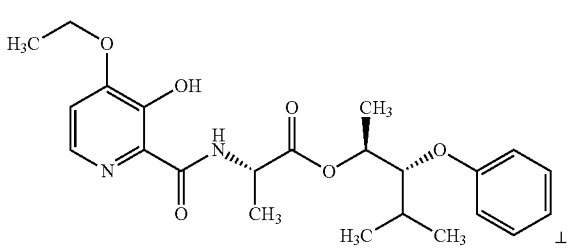 [SMILES: CCOc1ccnc(C(=O)N[C@@H](C)C(=O)O[C@@H](C)[C@H](Oc2ccccc2)C(C)C)c1O] | Example 14A, Step 2 | Colorless Glass |

TABLE 1-continued

Compound Structure, Appearance, and Preparation Method

| *Cmpd. No. | Structure | Prepared According to Example: | Appearance |
|---|---|---|---|
| 419 | 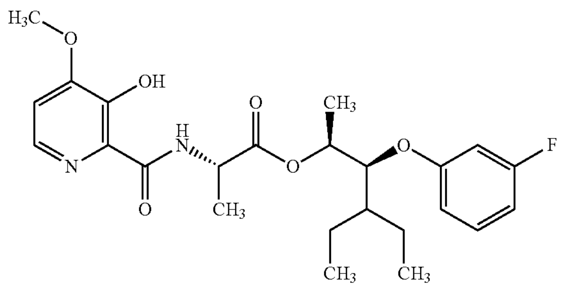 | Example 14A, Step 2 | Colorless Oil |
| 420 | 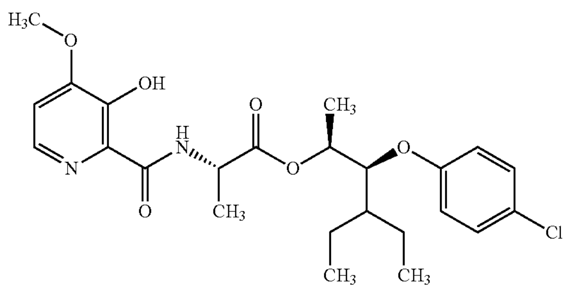 | Example 14A, Step 2 | Colorless Oil |
| 421 | 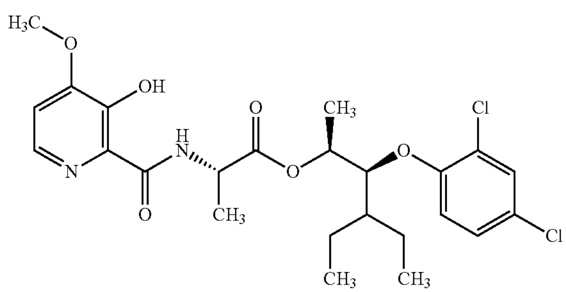 | Example 14A, Step 2 | Colorless Oil |
| 422 | 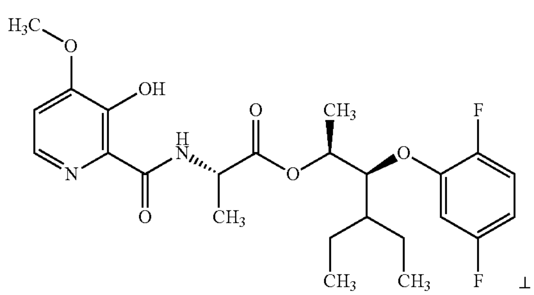 [SMILES: CCC(CC)[C@H](Oc1cc(F)ccc1F)[C@H](C)OC(=O)[C@H](C)NC(=O)c1nccc(OC)c1O] | Example 14A, Step 2 | Colorless Oil |
| 423 | 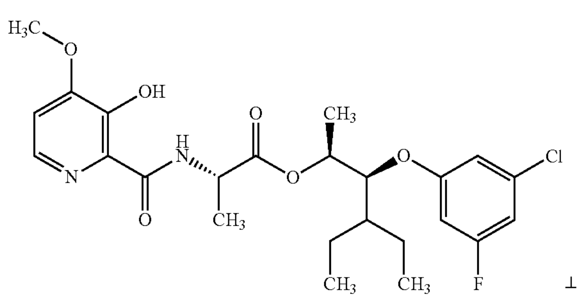 [SMILES: CCC(CC)[C@H](Oc1cc(F)cc(Cl)c1)[C@H](C)OC(=O)[C@H](C)NC(=O)c1nccc(OC)c1O] | Example 14A, Step 2 | Colorless Oil |

TABLE 1-continued

Compound Structure, Appearance, and Preparation Method

| *Cmpd. No. | Structure | Prepared According to Example: | Appearance |
|---|---|---|---|
| 424 | 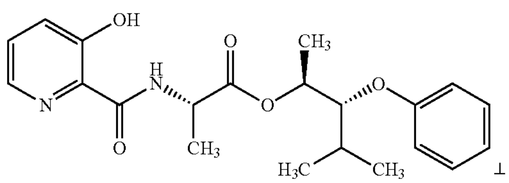 [SMILES: CC(C)[C@@H](Oc1ccccc1)[C@H](C)OC(=O)[C@H](C)NC(=O)c1ncccc1O] | Example 14A, Step 2 | Colorless Glass |
| 425 | 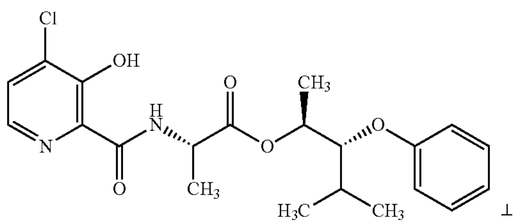 [SMILES: CC(C)[C@@H](Oc1ccccc1)[C@H](C)OC(=O)[C@H](C)NC(=O)c1nccc(Cl)c1O] | Example 14A, Step 2 | Clear Oil |
| 426 | 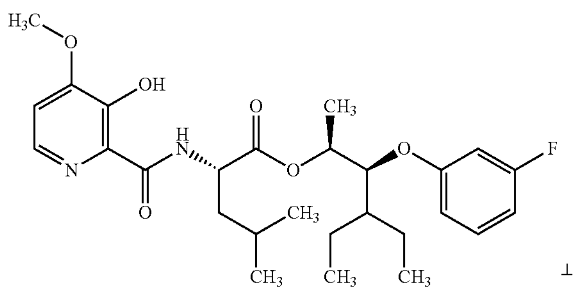 [SMILES: CCC(CC)[C@H](Oc1cccc(F)c1)[C@H](C)OC(=O)[C@H](CC(C)C)NC(=O)c1nccc(OC)c1O] | Example 14A, Step 2 | Colorless Oil |
| 427 | 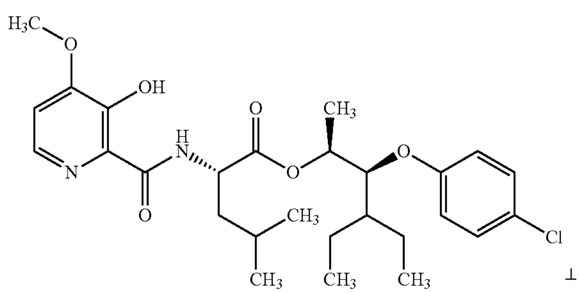 | Example 14A, Step 2 | Colorless Oil |
| 428 | 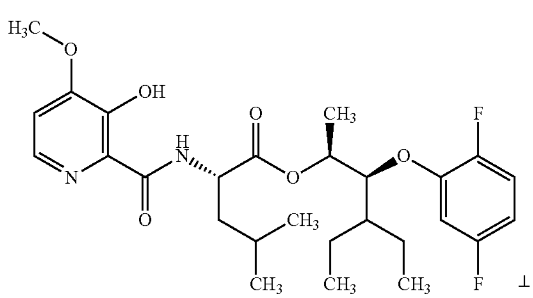 [SMILES: CCC(CC)[C@H](Oc1cc(F)ccc1F)[C@H](C)OC(=O)[C@H](CC(C)C)NC(=O)c1nccc(OC)c1O] | Example 14A, Step 2 | White Foam |

TABLE 1-continued

Compound Structure, Appearance, and Preparation Method

| *Cmpd. No. | Structure | Prepared According to Example: | Appearance |
|---|---|---|---|
| 429 | 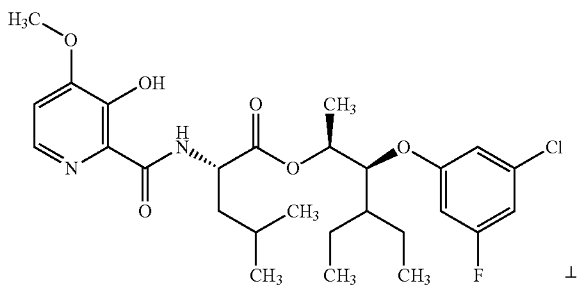 [SMILES: CCC(CC)[C@H](Oc1cc(F)cc(Cl)c1)[C@H](C)OC(=O)[C@H](CC(C)C)NC(=O)c1nccc(OC)c1O] | Example 14A, Step 2 | Colorless Oil |
| 430 | 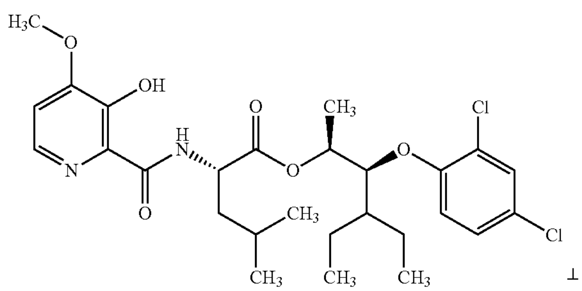 [SMILES: CCC(CC)[C@H](Oc1ccc(Cl)cc1Cl)[C@H](C)OC(=O)[C@H](CC(C)C)NC(=O)c1nccc(OC)c1O] | Example 14A, Step 2 | Colorless Oil |
| 431 | 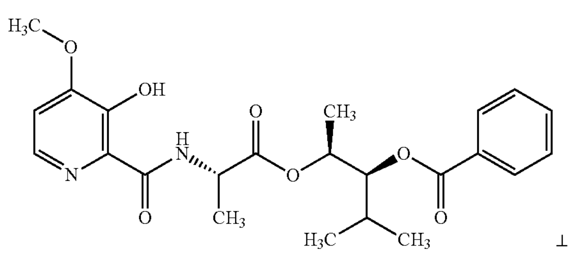 [SMILES: COc1ccnc(C(=O)N[C@@H](C)C(=O)O[C@@H](C)[C@@H](OC(=O)c2ccccc2)C(C)C)c1O] | Example 14A, Step 2 | White Solid |
| 432 | 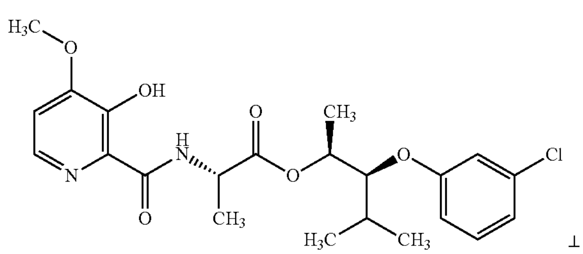 [SMILES: COc1ccnc(C(=O)N[C@@H](C)C(=O)O[C@@H](C)[C@@H](Oc2cccc(Cl)c2)C(C)C)c1O] | Example 14A, Step 2 | White Solid |
| 433 | 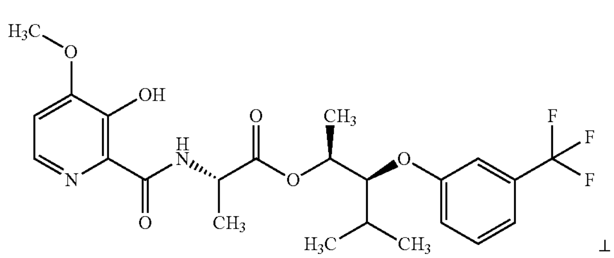 [SMILES: COc1ccnc(C(=O)N[C@@H](C)C(=O)O[C@@H](C)[C@@H](Oc2cccc(C(F)(F)F)c2)C(C)C)c1O] | Example 14A, Step 2 | White Solid |

TABLE 1-continued

Compound Structure, Appearance, and Preparation Method

| *Cmpd. No. | Structure | Prepared According to Example: | Appearance |
|---|---|---|---|
| 434 | 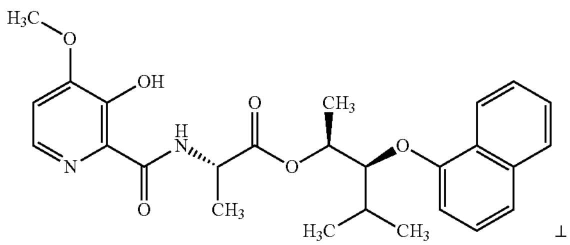 [SMILES: COc1ccnc(C(=O)N[C@@H](C)C(=O)O[C@@H](C)[C@@H](Oc2cccc3ccccc23)C(C)C)c1O] | Example 14A, Step 2 | White Solid |
| 435 | 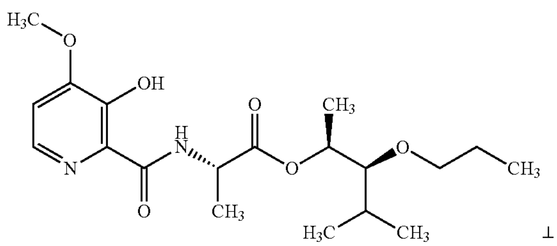 [SMILES: CCCO[C@@H](C(C)C)[C@H](C)OC(=O)[C@H](C)NC(=O)c1nccc(OC)c1O] | Example 14A, Step 2 | White Solid |
| 436 | 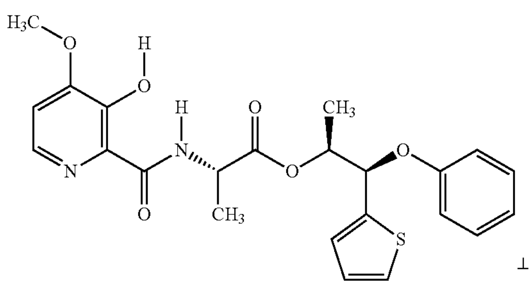 [SMILES: COc1ccnc(C(=O)N[C@@H](C)C(=O)O[C@@H](C)[C@@H](Oc2ccccc2)c2cccs2)c1O] | Example 14A, Steps 1, 2 | Colorless Oil |
| 437 | 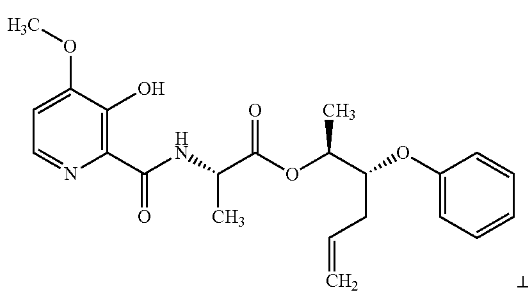 [SMILES: C=CC[C@@H](Oc1ccccc1)[C@H](C)OC(=O)[C@H](C)NC(=O)c1nccc(OC)c1O] | Example 14B, Step 2 | Clear, Colorless Oil |
| 438 | 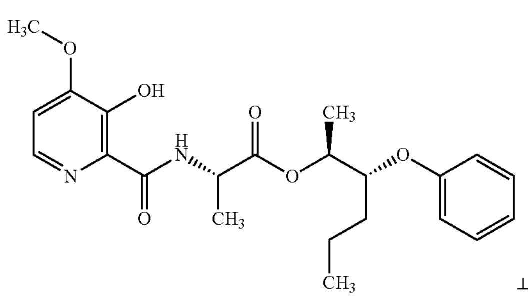 [SMILES: CCC[C@@H](Oc1ccccc1)[C@H](C)OC(=O)[C@H](C)NC(=O)c1nccc(OC)c1O] | Example 14A, Step 2 | Clear, Colorless Oil |

TABLE 1-continued

Compound Structure, Appearance, and Preparation Method

| *Cmpd. No. | Structure | Prepared According to Example: | Appearance |
|---|---|---|---|
| 439 | 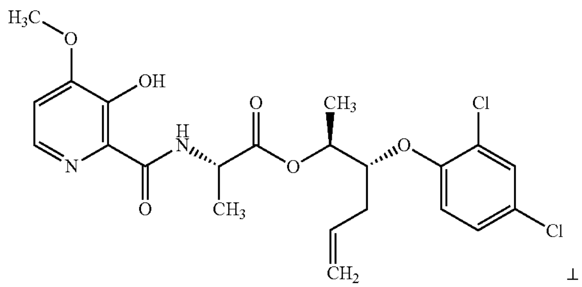 [SMILES: C=CC[C@@H](Oc1ccc(Cl)cc1Cl)[C@H](C)OC(=O)[C@H](C)NC(=O)c1nccc(OC)c1O] | Example 14B, Step 2 | Clear, Colorless Oil |
| 440 | 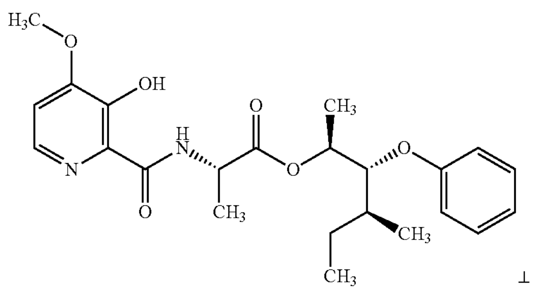 | Example 8B | Thick Clear Oil |
| 441 | 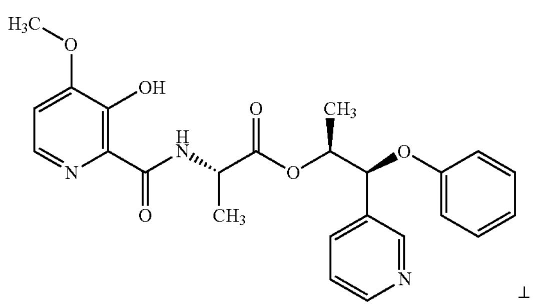 [SMILES: COc1ccnc(C(=O)N[C@@H](C)C(=O)O[C@@H](C)[C@@H](Oc2ccccc2)c2cccnc2)c1O] | Example 14A, Steps 1, 2 | Colorless Oil |
| 442 | 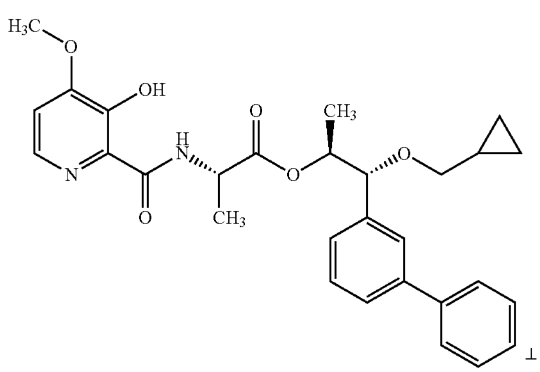 [SMILES: COc1ccnc(C(=O)N[C@@H](C)C(=O)O[C@@H](C)[C@H](OCC2CC2)c2cccc(-c3ccccc3)c2)c1O] | Example 14A, Step 2 | Colorless Oil |

TABLE 1-continued
Compound Structure, Appearance, and Preparation Method
| *Cmpd. No. | Structure | Prepared According to Example: | Appearance |
|---|---|---|---|
| 443 | 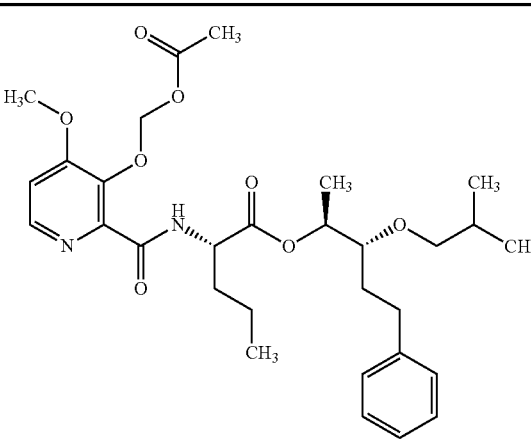 | Example 16B | Colorless Oil |
| 444 | 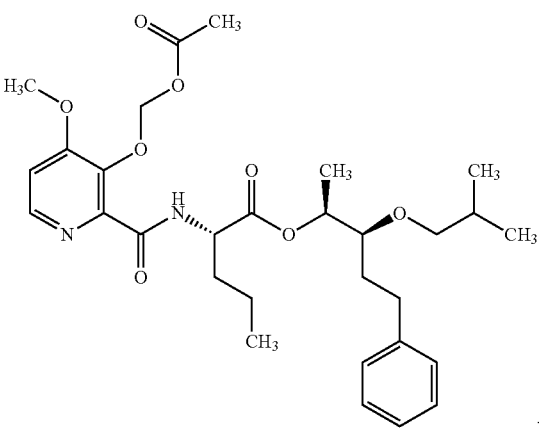 | Example 16B | Colorless Oil |
| 445 | 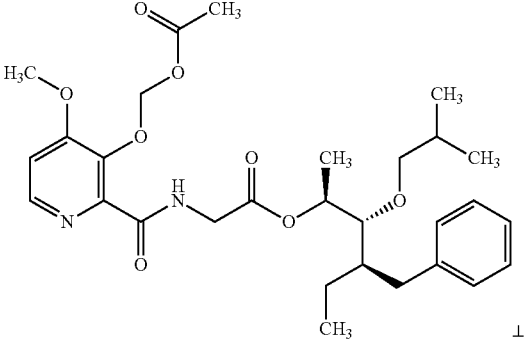 [SMILES: CC[C@H](Cc1ccccc1)[C@@H](OCC(C)C)[C@H](C)OC(=O)CNC(=O)c1nccc(OC)c1OCOC(C)=O] | Example 16B | Colorless Oil |

TABLE 1-continued
Compound Structure, Appearance, and Preparation Method
| *Cmpd. No. | Structure | Prepared According to Example: | Appearance |
|---|---|---|---|
| 446 | 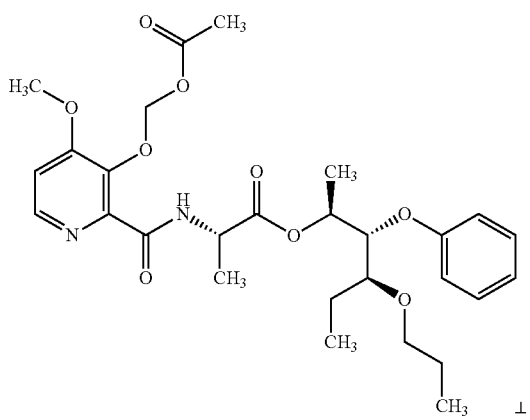 [SMILES: CCCO[C@@H](CC)[C@@H](Oc1ccccc1)[C@H](C)OC(=O)[C@H](C)NC(=O)c1nccc(OC)c1OCOC(C)=O] | Example 16B | Colorless Oil |
| 447 | 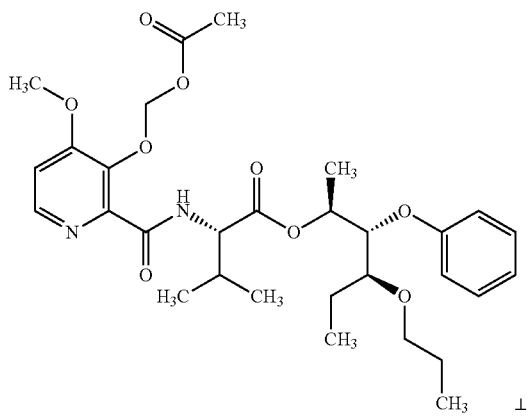 [SMILES: CCCO[C@@H](CC)[C@@H](Oc1ccccc1)[C@H](C)OC(=O)[C@@H](NC(=O)c1nccc(OC)c1OCOC(C)=O)C(C)C] | Example 16B | Colorless Oil |
| 448 | 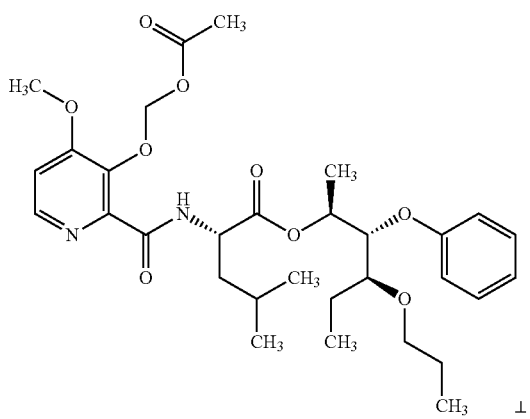 [SMILES: CCCO[C@@H](CC)[C@@H](Oc1ccccc1)[C@H](C)OC(=O)[C@H](CC(C)C)NC(=O)c1nccc(OC)c1OCOC(C)=O] | Example 16B | Colorless Oil |

TABLE 1-continued

Compound Structure, Appearance, and Preparation Method

| *Cmpd. No. | Structure | Prepared According to Example: | Appearance |
|---|---|---|---|
| 449 | 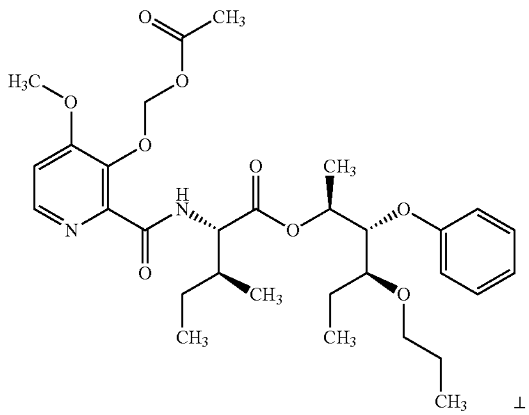 [SMILES: CCCO[C@@H](CC)[C@@H](Oc1ccccc1)[C@H](C)OC(=O)[C@@H](NC(=O)c1nccc(OC)c1OCOC(C)=O)[C@@H](C)CC] | Example 16B | Colorless Oil |
| 450 | 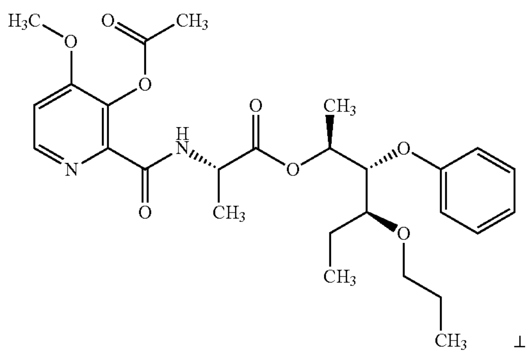 [SMILES: CCCO[C@@H](CC)[C@@H](Oc1ccccc1)[C@H](C)OC(=O)[C@H](C)NC(=O)c1nccc(OC)c1OC(C)=O] | Example 16A | Pale Yellow Oil |
| 451 | 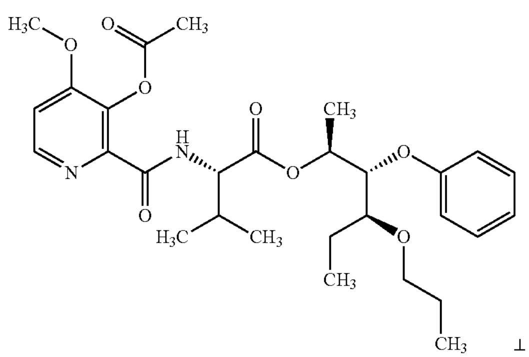 [SMILES: CCCO[C@@H](CC)[C@@H](Oc1ccccc1)[C@H](C)OC(=O)[C@@H](NC(=O)c1nccc(OC)c1OC(C)=O)C(C)C] | Example 16A | Pale Yellow Oil |
| 452 | 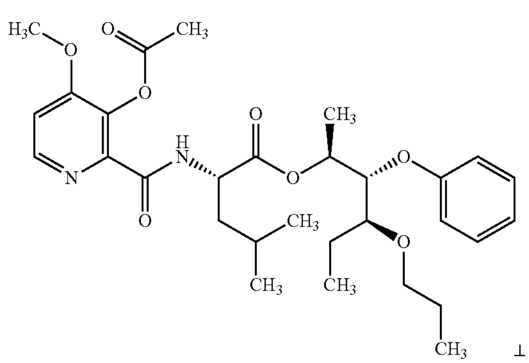 [SMILES: CCCO[C@@H](CC)[C@@H](Oc1ccccc1)[C@H](C)OC(=O)[C@H](CC(C)C)NC(=O)c1nccc(OC)c1OC(C)=O] | Example 16A | Pale Yellow Oil |

TABLE 1-continued
Compound Structure, Appearance, and Preparation Method
| *Cmpd. No. | Structure | Prepared According to Example: | Appearance |
|---|---|---|---|
| 453 | 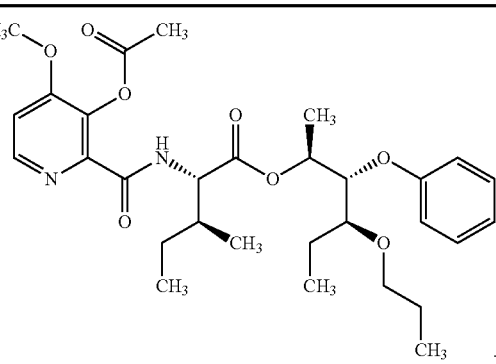 | Example 16A | Pale Yellow Oil |
| 454 | 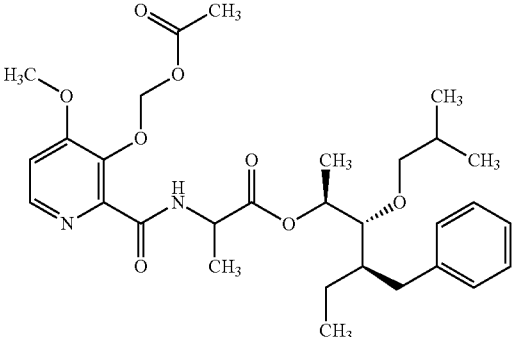 | Example 16B | Light Yellow Oil |
| 455 | 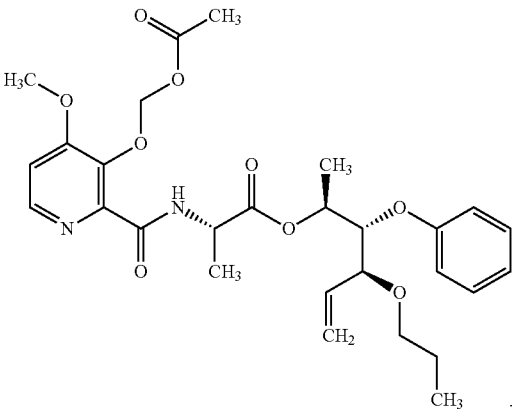 | Example 16B | Pale Yellow Oil |
| 456 | 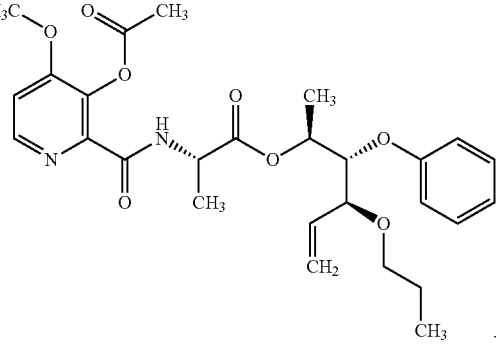 | Example 16A | Pale Yellow Oil |

TABLE 1-continued
Compound Structure, Appearance, and Preparation Method
| *Cmpd. No. | Structure | Prepared According to Example: | Appearance |
|---|---|---|---|
| 457 | 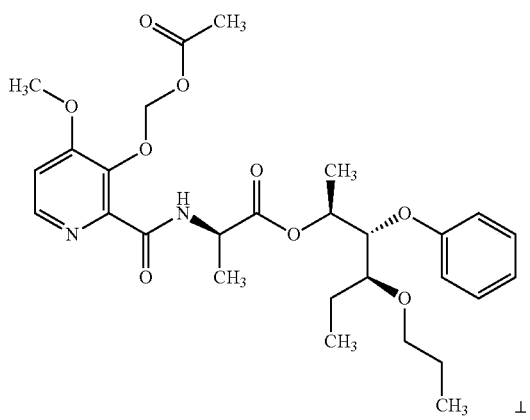 [SMILES: CCCO[C@@H](CC)[C@@H](Oc1ccccc1)[C@H](C)OC(=O)[C@@H](C)NC(=O)c1nccc(OC)c1OCOC(C)=O] | Example 16B | Colorless Oil |
| 458 | 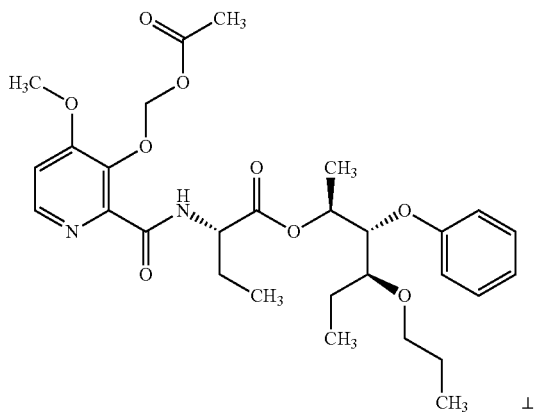 [SMILES: CCCO[C@@H](CC)[C@@H](Oc1ccccc1)[C@H](C)OC(=O)[C@H](CC)NC(=O)c1nccc(OC)c1OCOC(C)=O] | Example 16B | Colorless Oil |
| 459 | 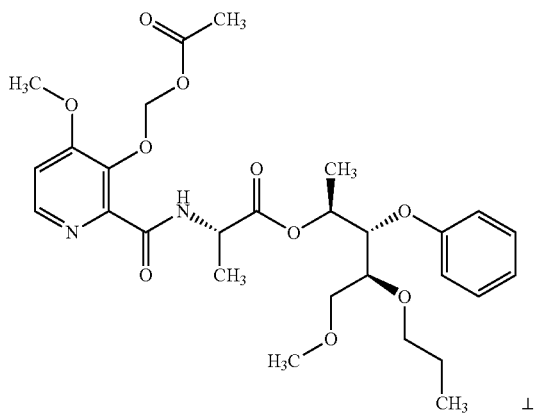 [SMILES: CCCO[C@@H](COC)[C@@H](Oc1ccccc1)[C@H](C)OC(=O)[C@H](C)NC(=O)c1nccc(OC)c1OCOC(C)=O] | Example 16B | Colorless Oil |

TABLE 1-continued

Compound Structure, Appearance, and Preparation Method

| *Cmpd. No. | Structure | Prepared According to Example: | Appearance |
|---|---|---|---|
| 460 | 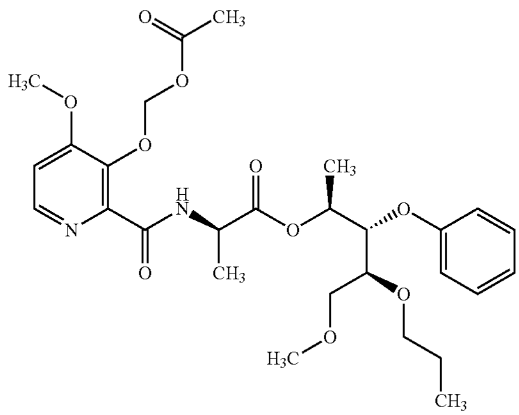 | Example 16B | Colorless Oil |
| 461 | 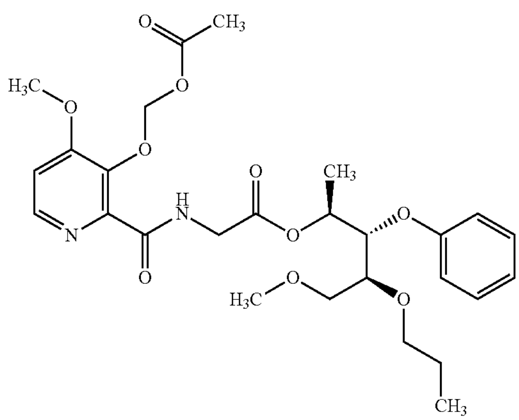 | Example 16B | Colorless Oil |
| 462 | 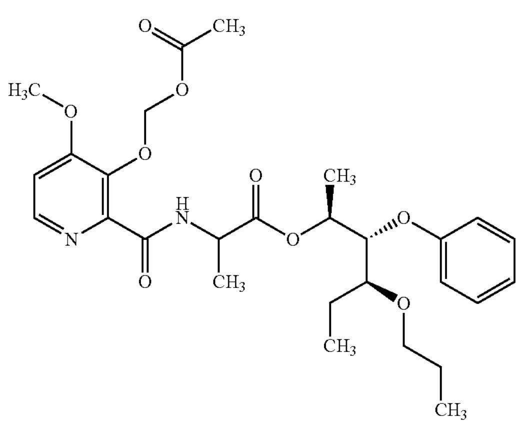 | Example 16B | Colorless Oil |

TABLE 1-continued

Compound Structure, Appearance, and Preparation Method

| *Cmpd. No. | Structure | Prepared According to Example: | Appearance |
|---|---|---|---|
| 463 | 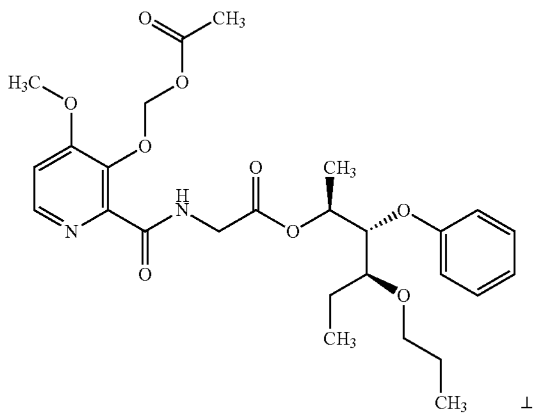 [SMILES: CCCO[C@@H](CC)[C@@H](Oc1ccccc1)[C@H](C)OC(=O)CNC(=O)c1nccc(OC)c1OCOC(C)=O] | Example 16B | Colorless Oil |
| 464 | 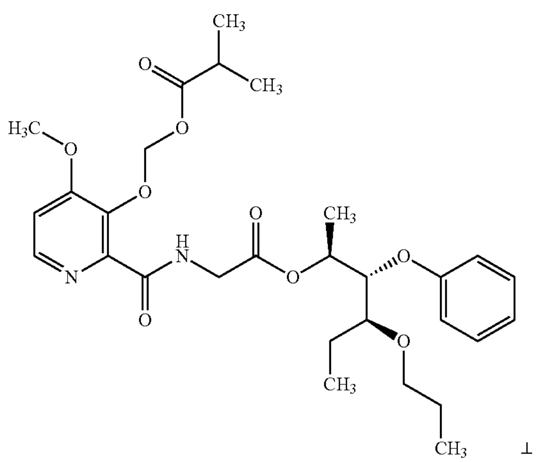 [SMILES: CCCO[C@@H](CC)[C@@H](Oc1ccccc1)[C@H](C)OC(=O)CNC(=O)c1nccc(OC)c1OCOC(=O)C(C)C] | Example 16C | Colorless Oil |
| 465 | 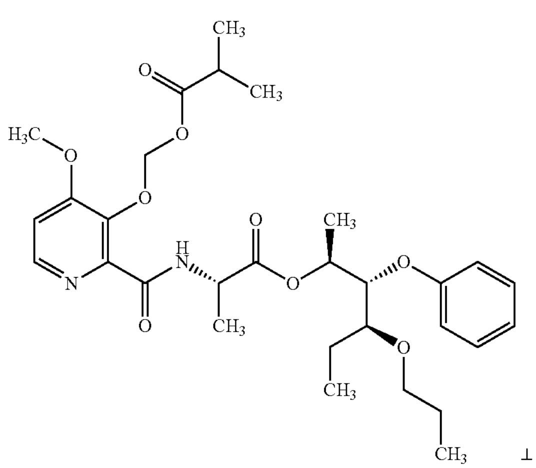 [SMILES: CCCO[C@@H](CC)[C@@H](Oc1ccccc1)[C@H](C)OC(=O)[C@H](C)NC(=O)c1nccc(OC)c1OCOC(=O)C(C)C] | Example 16C | Colorless Oil |

TABLE 1-continued
Compound Structure, Appearance, and Preparation Method
| *Cmpd. No. | Structure | Prepared According to Example: | Appearance |
|---|---|---|---|
| 466 | 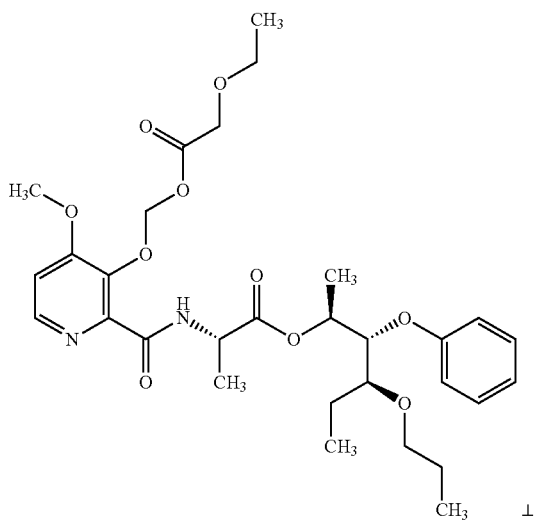 [SMILES: CCCO[C@@H](CC)[C@@H](Oc1ccccc1)[C@H](C)OC(=O)[C@H](C)NC(=O)c1nccc(OC)c1OCOC(=O)COCC] | Example 16C | Pale Yellow Oil |
| 467 | 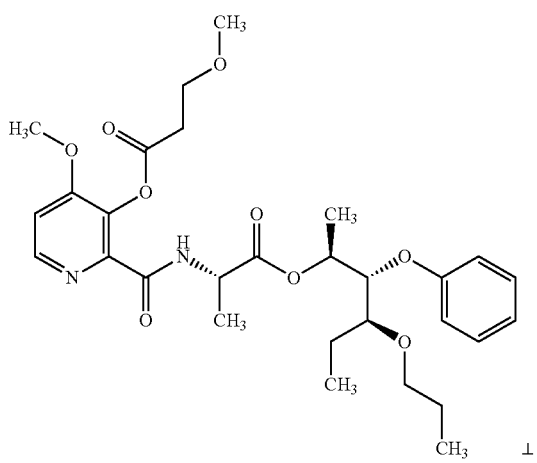 [SMILES: CCCO[C@@H](CC)[C@@H](Oc1ccccc1)[C@H](C)OC(=O)[C@H](C)NC(=O)c1nccc(OC)c1OC(=O)CCOC] | Example 16A | Pale Yellow Oil |
| 468 | 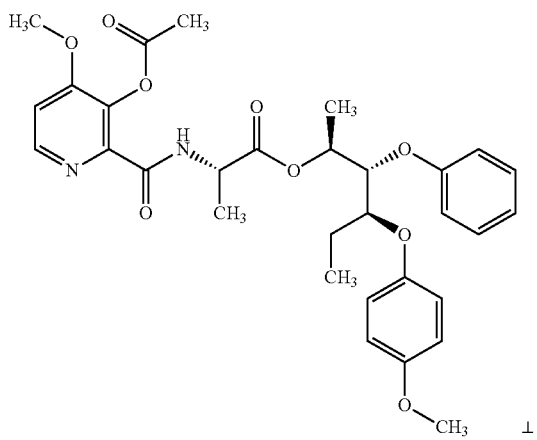 [SMILES: CC[C@H](Oc1ccc(OC)cc1)[C@@H](Oc1ccccc1)[C@H](C)OC(=O)[C@H](C)NC(=O)c1nccc(OC)c1OC(C)=O] | Example 16A | Hard White Foam |

TABLE 1-continued

Compound Structure, Appearance, and Preparation Method

| *Cmpd. No. | Structure | Prepared According to Example: | Appearance |
|---|---|---|---|
| 469 | 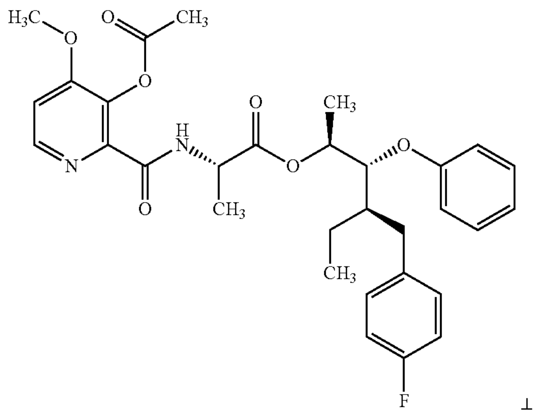 [SMILES: CC[C@H](Cc1ccc(F)cc1)[C@@H](Oc1ccccc1)[C@H](C)OC(=O)[C@H](C)NC(=O)c1nccc(OC)c1OC(C)=O] | Example 16A | Hard White Foam |
| 470 | 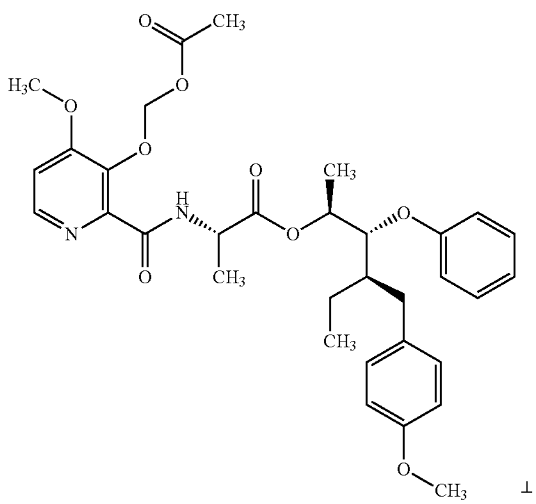 [SMILES: CC[C@H](Cc1ccc(OC)cc1)[C@@H](Oc1ccccc1)[C@H](C)OC(=O)[C@H](C)NC(=O)c1nccc(OC)c1OCOC(C)=O] | Example 16B | Sticky Yellow Solid |
| 471 | 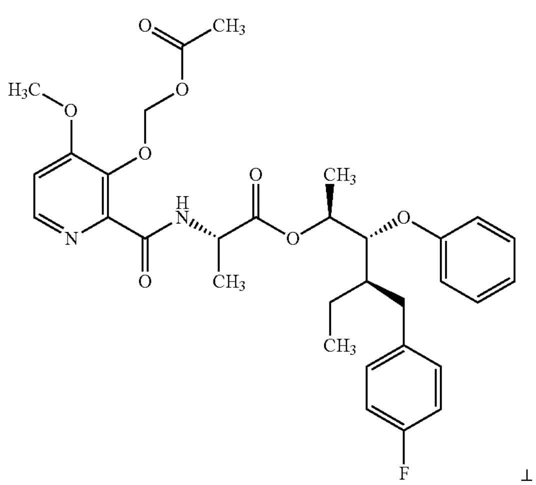 [SMILES: CC[C@H](Cc1ccc(F)cc1)[C@@H](Oc1ccccc1)[C@H](C)OC(=O)[C@H](C)NC(=O)c1nccc(OC)c1OCOC(C)=O] | Example 16B | Yellow Oil |

TABLE 1-continued

Compound Structure, Appearance, and Preparation Method

| *Cmpd. No. | Structure | Prepared According to Example: | Appearance |
|---|---|---|---|
| 472 | 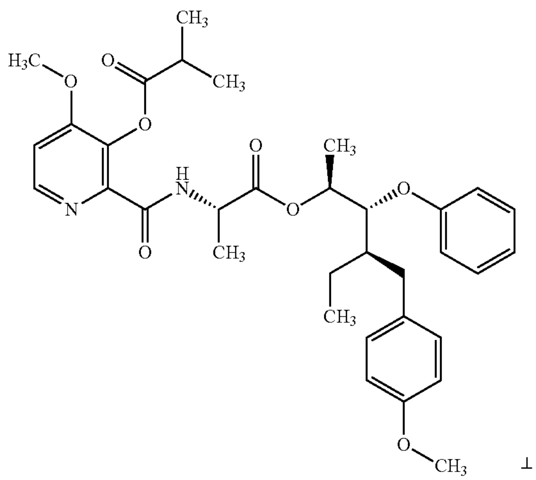 [SMILES: CC[C@H](Cc1ccc(OC)cc1)[C@@H](Oc1ccccc1)[C@H](C)OC(=O)[C@H](C)NC(=O)c1nccc(OC)c1OC(=O)C(C)C] | Example 16A | White Solid |
| 473 | 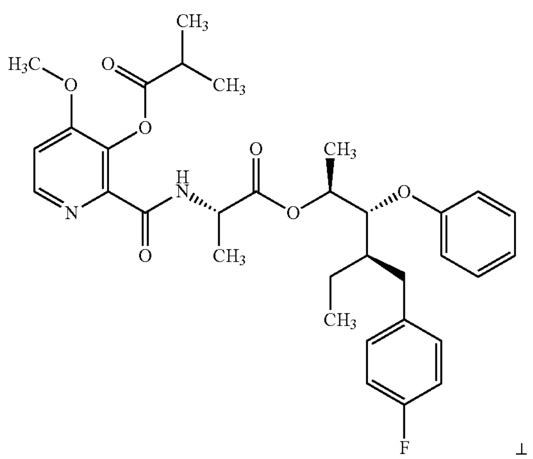 [SMILES: CC[C@H](Cc1ccc(F)cc1)[C@@H](Oc1ccccc1)[C@H](C)OC(=O)[C@H](C)NC(=O)c1nccc(OC)c1OC(=O)C(C)C] | Example 16A | White Solid |
| 474 | 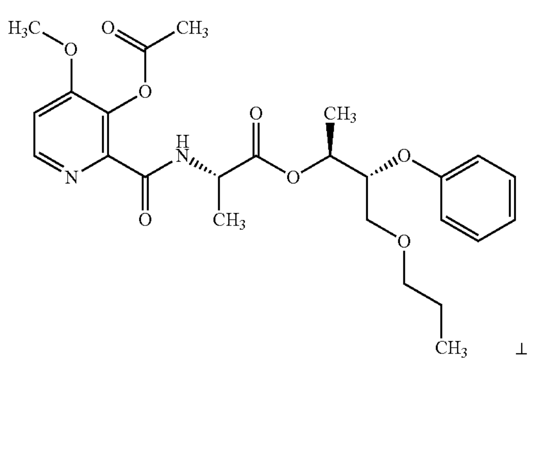 [SMILES: CCCOC[C@@H](Oc1ccccc1)[C@H](C)OC(=O)[C@H](C)NC(=O)c1nccc(OC)c1OC(C)=O] | Example 16A | Slightly Yellow Oil |

TABLE 1-continued

Compound Structure, Appearance, and Preparation Method

| *Cmpd. No. | Structure | Prepared According to Example: | Appearance |
|---|---|---|---|
| 475 | 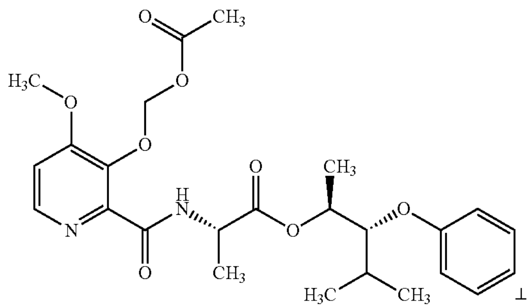 [SMILES: COc1ccnc(C(=O)N[C@@H](C)C(=O)O[C@@H](C)[C@H](Oc2ccccc2)C(C)C)c1OCOC(C)=O] | Example 16B | Light Yellow Semi Solid |
| 476 | 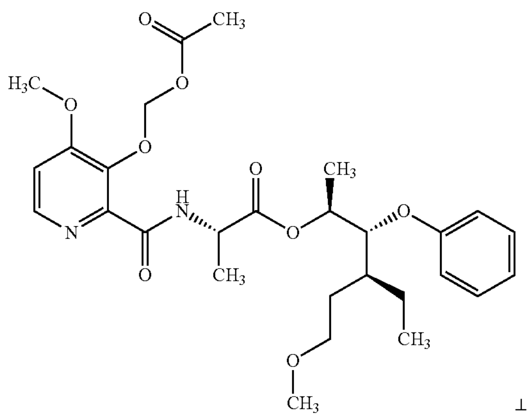 [SMILES: CC[C@@H](CCOC)[C@@H](Oc1ccccc1)[C@H](C)OC(=O)[C@H](C)NC(=O)c1nccc(OC)c1OCOC(C)=O] | Example 16B | Colorless Oil |
| 477 | 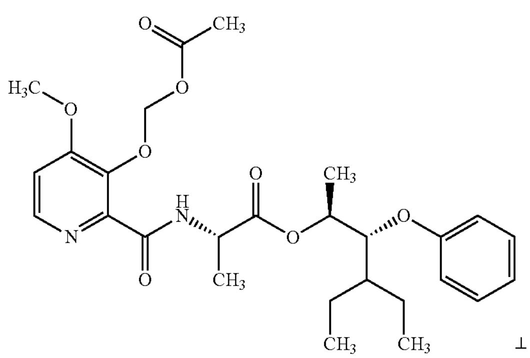 [SMILES: CCC(CC)[C@@H](Oc1ccccc1)[C@H](C)OC(=O)[C@H](C)NC(=O)c1nccc(OC)c1OCOC(C)=O] | Example 16B | Yellow Oil |
| 478 | 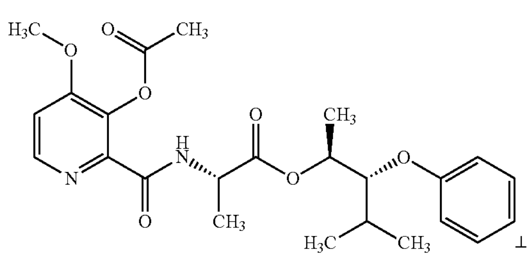 [SMILES: COc1ccnc(C(=O)N[C@@H](C)C(=O)O[C@@H](C)[C@H](Oc2ccccc2)C(C)C)c1OC(C)=O] | Example 16A | White Solid |

TABLE 1-continued

Compound Structure, Appearance, and Preparation Method

| *Cmpd. No. | Structure | Prepared According to Example: | Appearance |
|---|---|---|---|
| 479 | 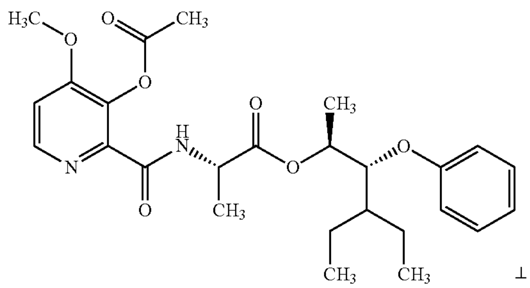 [SMILES: CCC(CC)[C@@H](Oc1ccccc1)[C@H](C)OC(=O)[C@H](C)NC(=O)c1nccc(OC)c1OC(C)=O] | Example 16A | Yellow Oil |
| 480 | 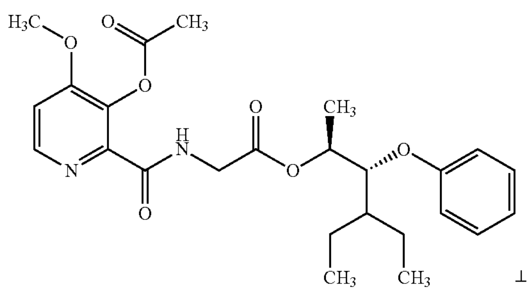 [SMILES: CCC(CC)[C@@H](Oc1ccccc1)[C@H](C)OC(=O)CNC(=O)c1nccc(OC)c1OC(C)=O] | Example 16A | Colorless Oil |
| 481 | 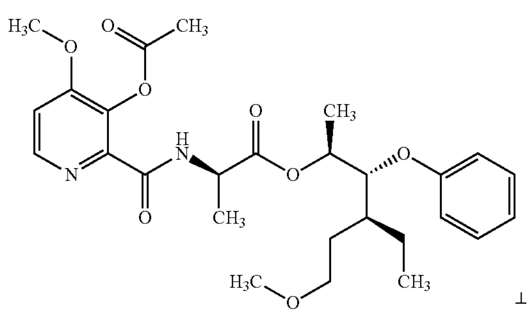 [SMILES: CC[C@@H](CCOC)[C@@H](Oc1ccccc1)[C@H](C)OC(=O)[C@@H](C)NC(=O)c1nccc(OC)c1OC(C)=O] | Example 16A | Yellow Oil |
| 482 | 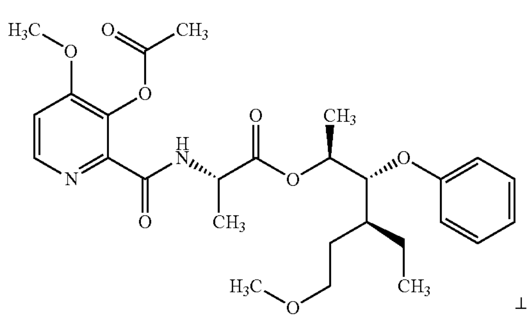 [SMILES: CC[C@@H](CCOC)[C@@H](Oc1ccccc1)[C@H](C)OC(=O)[C@H](C)NC(=O)c1nccc(OC)c1OC(C)=O] | Example 16A | Colorless Oil |

TABLE 1-continued

Compound Structure, Appearance, and Preparation Method

| *Cmpd. No. | Structure | Prepared According to Example: | Appearance |
|---|---|---|---|
| 483 | 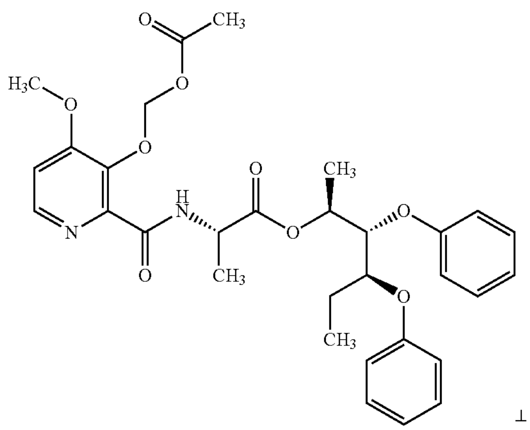 [SMILES: CC[C@H](Oc1ccccc1)[C@@H](Oc1ccccc1)[C@H](C)OC(=O)[C@H](C)NC(=O)c1nccc(OC)c1OCOC(C)=O] | Example 16B | White Foam |
| 484 | 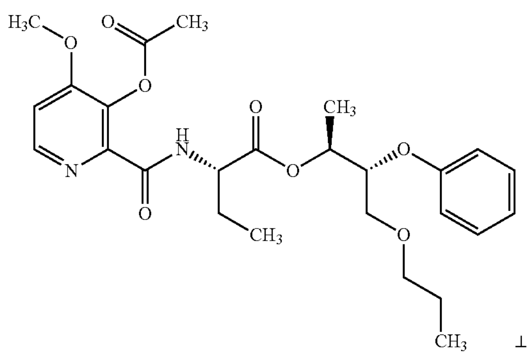 [SMILES: CCCOC[C@@H](Oc1ccccc1)[C@H](C)OC(=O)[C@H](CC)NC(=O)c1nccc(OC)c1OC(C)=O] | Example 16A | Colorless Oil |
| 485 | 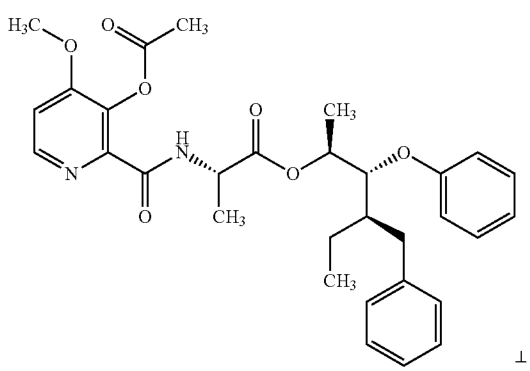 [SMILES: CC[C@H](Cc1ccccc1)[C@@H](Oc1ccccc1)[C@H](C)OC(=O)[C@H](C)NC(=O)c1nccc(OC)c1OC(C)=O] | Example 16A | Off White Foam |
| 486 | 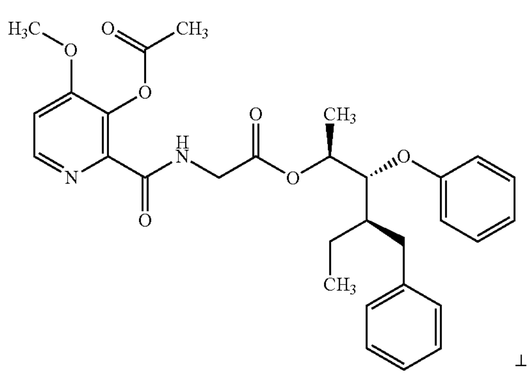 [SMILES: CC[C@H](Cc1ccccc1)[C@@H](Oc1ccccc1)[C@H](C)OC(=O)CNC(=O)c1nccc(OC)c1OC(C)=O] | Example 16A | Orange Oil |

TABLE 1-continued
Compound Structure, Appearance, and Preparation Method
| *Cmpd. No. | Structure | Prepared According to Example: | Appearance |
|---|---|---|---|
| 487 | 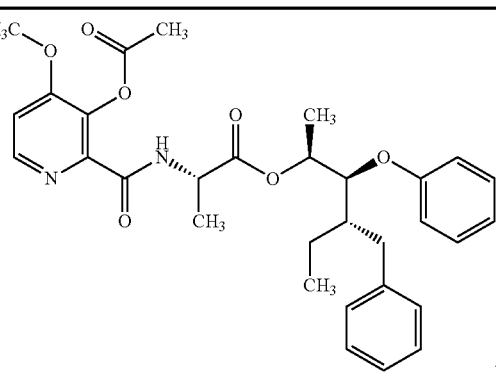 | Example 16A | Off White Foam |
| 488 | 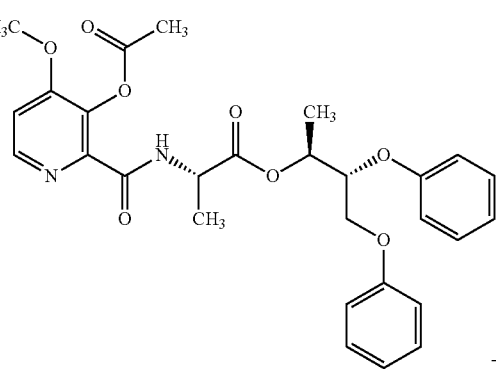 | Example 16A | Hygroscopic White Powder |
| 489 | 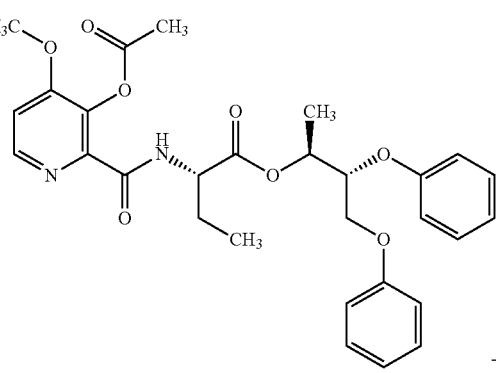 | Example 16A | Hygroscopic White Powder |
| 490 | 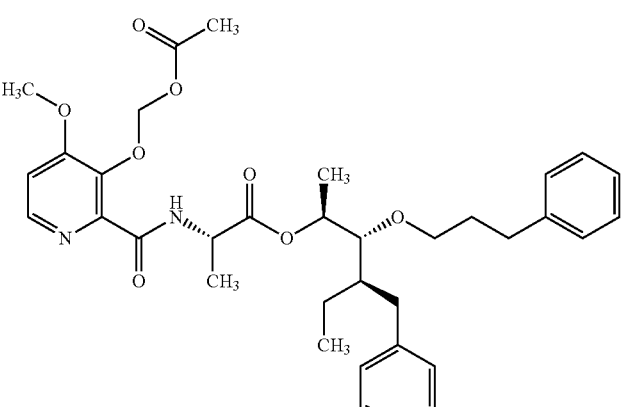 | Example 16B | Light Yellow Oil |

TABLE 1-continued

Compound Structure, Appearance, and Preparation Method

| *Cmpd. No. | Structure | Prepared According to Example: | Appearance |
|---|---|---|---|
| 491 | 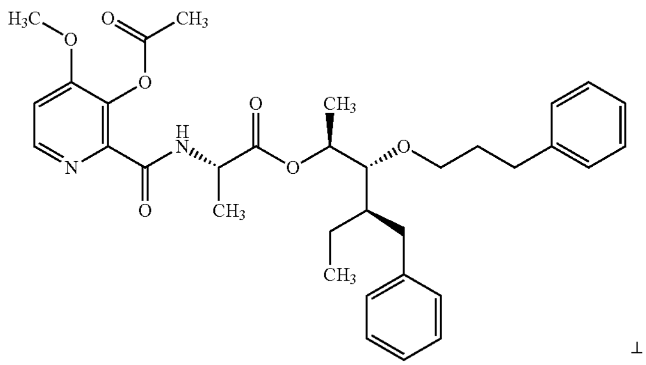 [SMILES: CC[C@H](Cc1ccccc1)[C@@H](OCCCc1ccccc1)[C@H](C)OC(=O)[C@H](C)NC(=O)c1nccc(OC)c1OC(C)=O] | Example 16A | Light Yellow Oil |
| 492 | 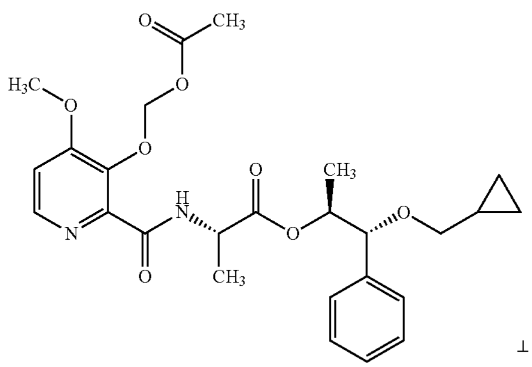 [SMILES: COc1ccnc(C(=O)N[C@@H](C)C(=O)O[C@@H](C)[C@H](OCC2CC2)c2ccccc2)c1OCOC(C)=O] | Example 16B | Light Yellow Semi Solid |
| 493 | 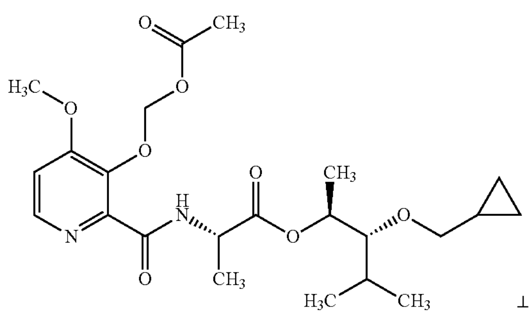 [SMILES: COc1ccnc(C(=O)N[C@@H](C)C(=O)O[C@@H](C)[C@H](OCC2CC2)C(C)C)c1OCOC(C)=O] | Example 16B | Colorless Semi Solid |
| 494 | 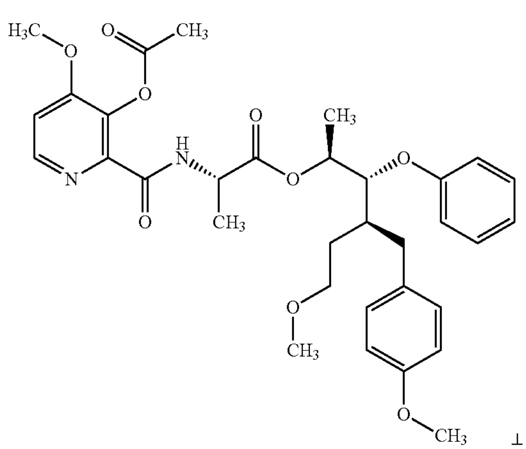 [SMILES: COCC[C@H](Cc1ccc(OC)cc1)[C@@H](Oc1ccccc1)[C@H](C)OC(=O)[C@H](C)NC(=O)c1nccc(OC)c1OC(C)=O] | Example 16A | White Solid |

TABLE 1-continued
Compound Structure, Appearance, and Preparation Method
| *Cmpd. No. | Structure | Prepared According to Example: | Appearance |
|---|---|---|---|
| 495 | 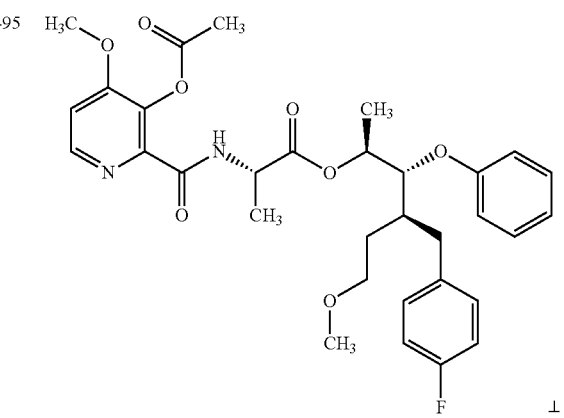 | Example 16A | White Solid |
| 496 | 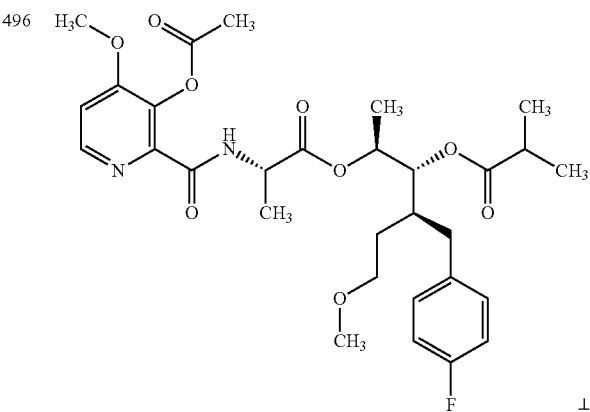 | Example 16A | Colorless Oil |
| 497 | 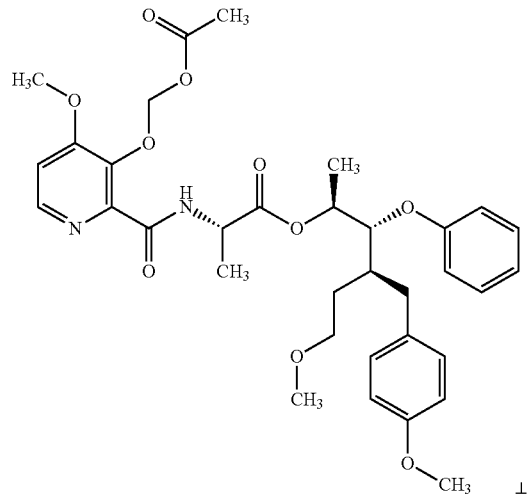 [SMILES: COCC[C@H](Cc1ccc(OC)cc1)[C@@H](Oc1ccccc1)[C@H](C)OC(=O)[C@H](C)NC(=O)c1nccc(OC)c1OCOC(C)=O] | Example 16B | Yellow Oil |

TABLE 1-continued

Compound Structure, Appearance, and Preparation Method

| *Cmpd. No. | Structure | Prepared According to Example: | Appearance |
|---|---|---|---|
| 498 | 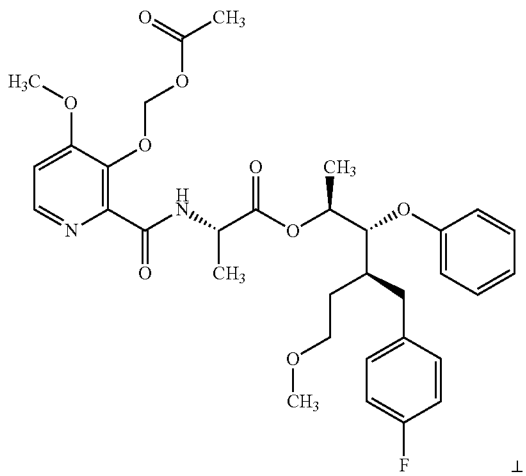 [SMILES: COCC[C@H](Cc1ccc(F)cc1)[C@@H](Oc1ccccc1)[C@H](C)OC(=O)[C@H](C)NC(=O)c1nccc(OC)c1OCOC(C)=O] | Example 16B | Yellow Oil |
| 499 | 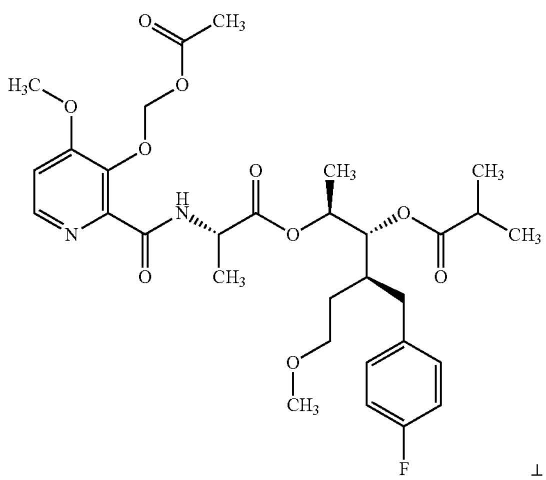 [SMILES: COCC[C@H](Cc1ccc(F)cc1)[C@@H](OC(=O)C(C)C)[C@H](C)OC(=O)[C@H](C)NC(=O)c1nccc(OC)c1OCOC(C)=O] | Example 16B | Yellow Oil |
| 500 | 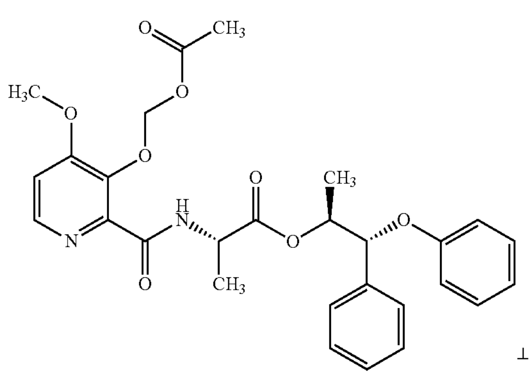 [SMILES: COc1ccnc(C(=O)N[C@@H](C)C(=O)O[C@@H](C)[C@H](Oc2ccccc2)c2ccccc2)c1OCOC(C)=O] | Example 16B | Yellow Solid |

TABLE 1-continued

Compound Structure, Appearance, and Preparation Method

| *Cmpd. No. | Structure | Prepared According to Example: | Appearance |
|---|---|---|---|
| 501 | 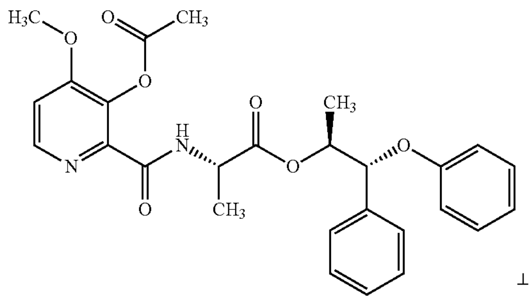 [SMILES: COc1ccnc(C(=O)N[C@@H](C)C(=O)O[C@@H](C)[C@H](Oc2ccccc2)c2ccccc2)c1OC(C)=O] | Example 16A | White Solid |
| 502 | 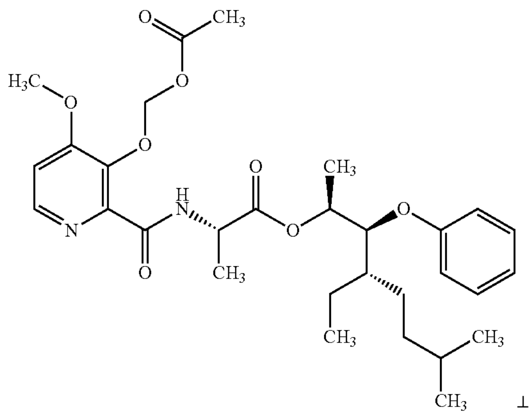 [SMILES: CC[C@@H](CCC(C)C)[C@H](Oc1ccccc1)[C@H](C)OC(=O)[C@H](C)NC(=O)c1nccc(OC)c1OCOC(C)=O] | Example 16B | Colorless Oil |
| 503 | 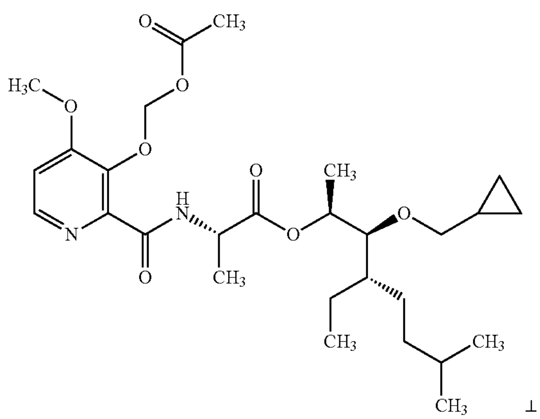 [SMILES: CC[C@@H](CCC(C)C)[C@H](OCC1CC1)[C@H](C)OC(=O)[C@H](C)NC(=O)c1nccc(OC)c1OCOC(C)=O] | Example 16B | Colorless Oil |
| 504 | 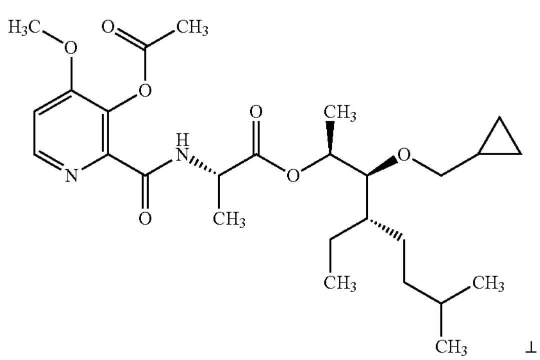 [SMILES: CC[C@@H](CCC(C)C)[C@H](OCC1CC1)[C@H](C)OC(=O)[C@H](C)NC(=O)c1nccc(OC)c1OC(C)=O] | Example 16A | Pale Yellow Oil |

TABLE 1-continued

Compound Structure, Appearance, and Preparation Method

| *Cmpd. No. | Structure | Prepared According to Example: | Appearance |
|---|---|---|---|
| 505 | 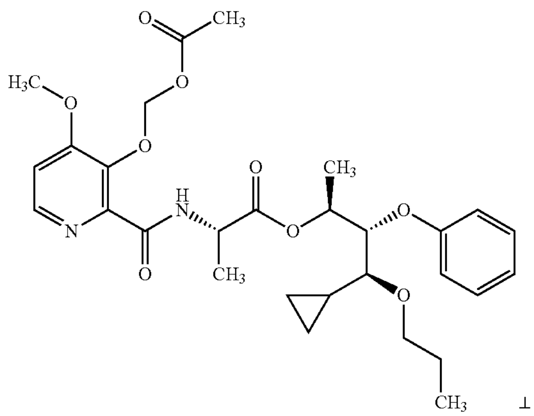 [SMILES: CCCO[C@@H](C1CC1)[C@@H](Oc1ccccc1)[C@H](C)OC(=O)[C@H](C)NC(=O)c1nccc(OC)c1OCOC(C)=O] | Example 16B | Colorless Oil |
| 506 | 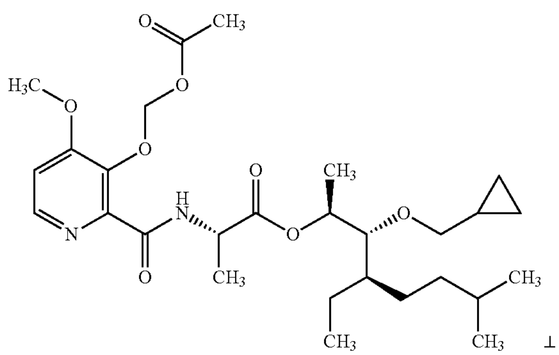 [SMILES: CC[C@H](CCC(C)C)[C@@H](OCC1CC1)[C@H](C)OC(=O)[C@H](C)NC(=O)c1nccc(OC)c1OCOC(C)=O] | Example 16B | Colorless Oil |
| 507 | 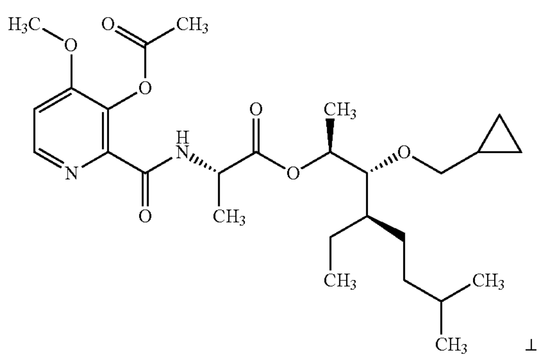 [SMILES: CC[C@H](CCC(C)C)[C@@H](OCC1CC1)[C@H](C)OC(=O)[C@H](C)NC(=O)c1nccc(OC)c1OC(C)=O] | Example 16A | Colorless Oil |
| 508 | 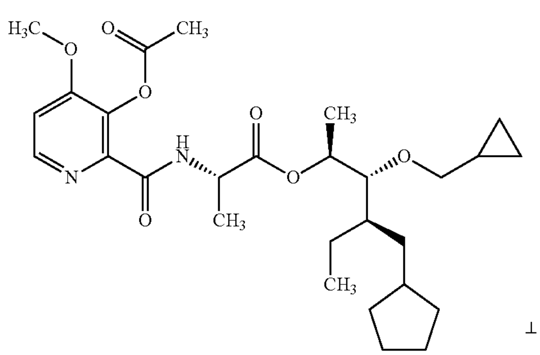 [SMILES: CC[C@H](CC1CCCC1)[C@@H](OCC1CC1)[C@H](C)OC(=O)[C@H](C)NC(=O)c1nccc(OC)c1OC(C)=O] | Example 16A | Pale Yellow Sticky Oil |

TABLE 1-continued
Compound Structure, Appearance, and Preparation Method
| *Cmpd. No. | Structure | Prepared According to Example: | Appearance |
|---|---|---|---|
| 509 | 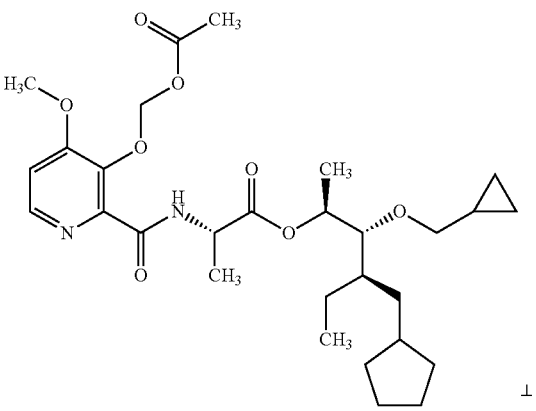 [SMILES: CC[C@H](CC1CCCC1)[C@@H](OCC1CC1)[C@H](C)OC(=O)[C@H](C)NC(=O)c1nccc(OC)c1OCOC(C)=O] | Example 16B | Colorless Oil |
| 510 | 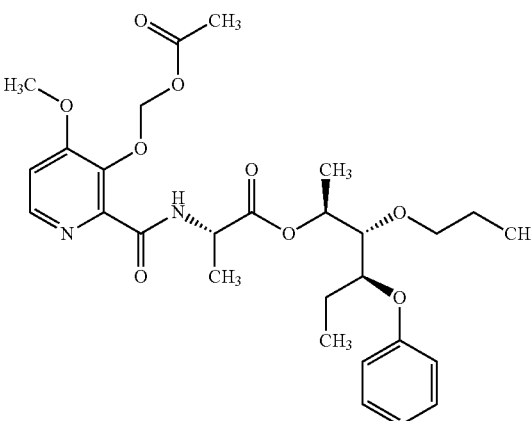 | Example 16B | Light Yellow Oil |
| 511 | 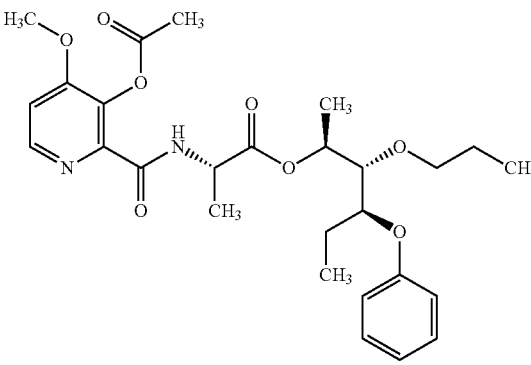 | Example 16A | Light Yellow Oil |

TABLE 1-continued
Compound Structure, Appearance, and Preparation Method
| *Cmpd. No. | Structure | Prepared According to Example: | Appearance |
|---|---|---|---|
| 512 | 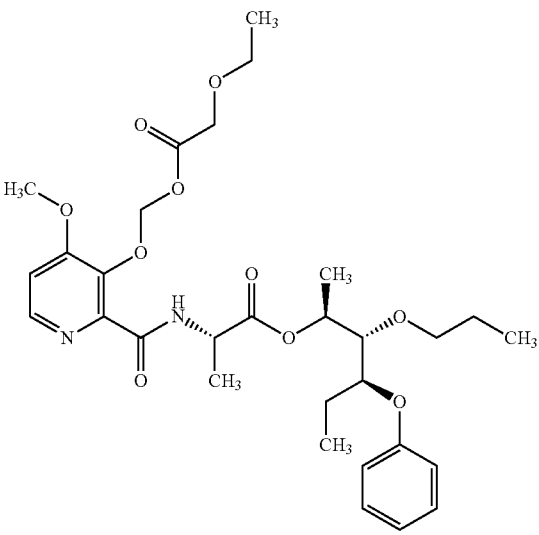 | Example 16C | Colorless Oil |
| 513 | 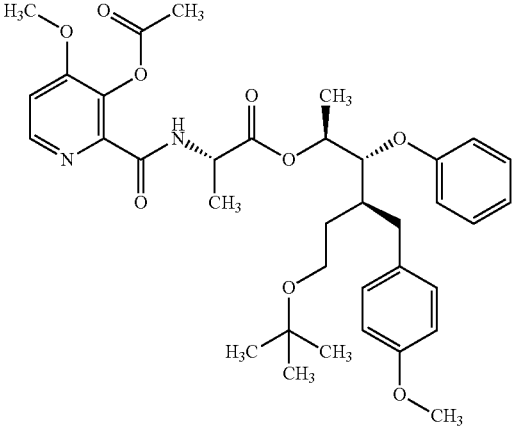 | Example 16A | White Solid |
| 514 | 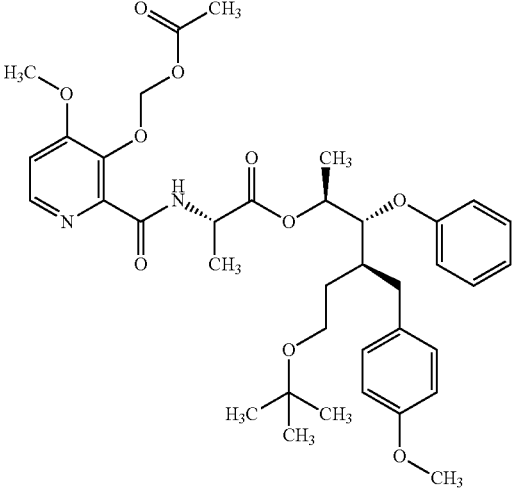 | Example 16B | Yellow Oil |

TABLE 1-continued

Compound Structure, Appearance, and Preparation Method

| *Cmpd. No. | Structure | Prepared According to Example: | Appearance |
|---|---|---|---|
| 515 | 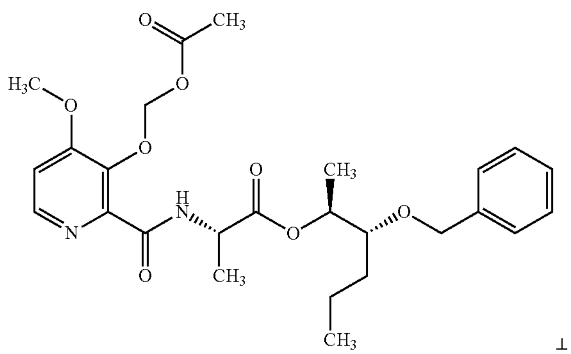 [SMILES: CCC[C@@H](OCc1ccccc1)[C@H](C)OC(=O)[C@H](C)NC(=O)c1nccc(OC)c1OCOC(C)=O] | Example 16B | Clear, Colorless Oil |
| 516 | 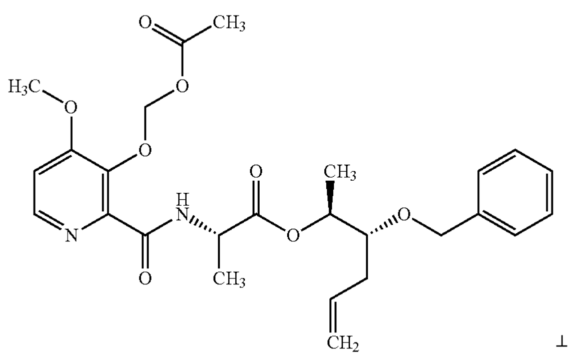 [SMILES: C=CC[C@@H](OCc1ccccc1)[C@H](C)OC(=O)[C@H](C)NC(=O)c1nccc(OC)c1OCOC(C)=O] | Example 16B | Clear, Colorless Oil |
| 517 | 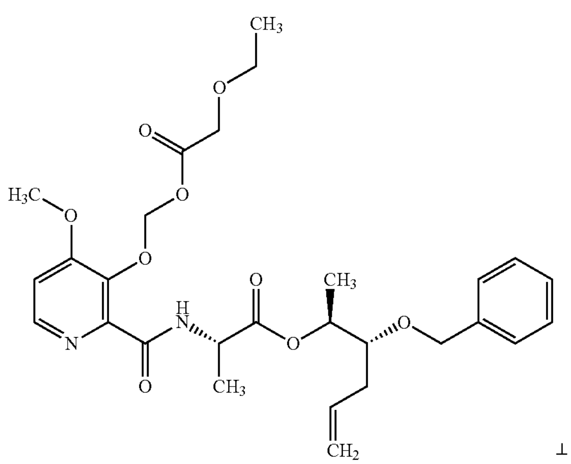 [SMILES: C=CC[C@@H](OCc1ccccc1)[C@H](C)OC(=O)[C@H](C)NC(=O)c1nccc(OC)c1OCOC(=O)COCC] | Example 16C | Clear, Colorless Oil |
| 518 | 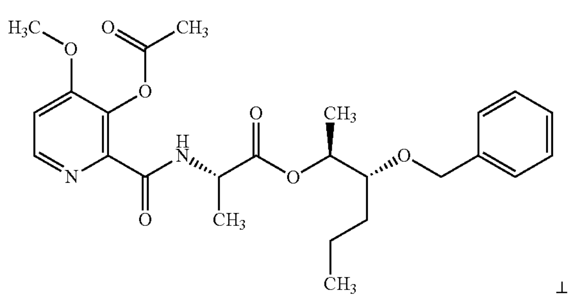 [SMILES: CCC[C@@H](OCc1ccccc1)[C@H](C)OC(=O)[C@H](C)NC(=O)c1nccc(OC)c1OC(C)=O] | Example 16A | Yellow Oil |

TABLE 1-continued

Compound Structure, Appearance, and Preparation Method

| *Cmpd. No. | Structure | Prepared According to Example: | Appearance |
|---|---|---|---|
| 519 | 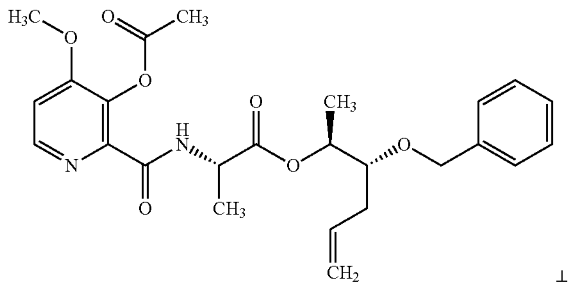 [SMILES: C=CC[C@@H](OCc1ccccc1)[C@H](C)OC(=O)[C@H](C)NC(=O)c1nccc(OC)c1OC(C)=O] | Example 16A | Yellow Oil |
| 520 | 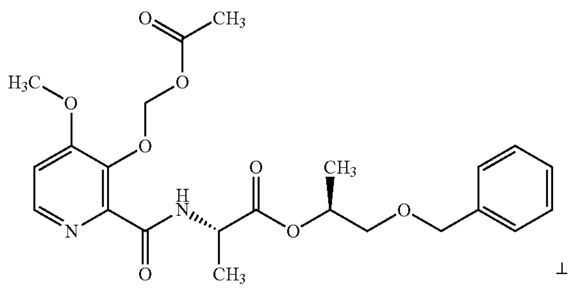 [SMILES: COc1ccnc(C(=O)N[C@@H](C)C(=O)O[C@@H](C)COCc2ccccc2)c1OCOC(C)=O] | Example 16B | Light Yellow Oil |
| 521 | 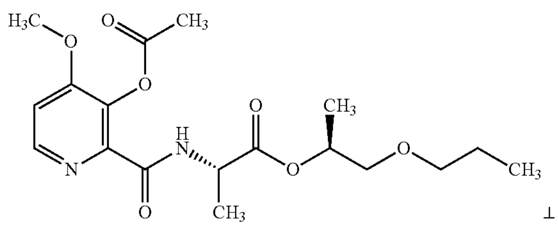 [SMILES: CCCOC[C@H](C)OC(=O)[C@H](C)NC(=O)c1nccc(OC)c1OC(C)=O] | Example 16A | Colorless Oil |
| 522 | 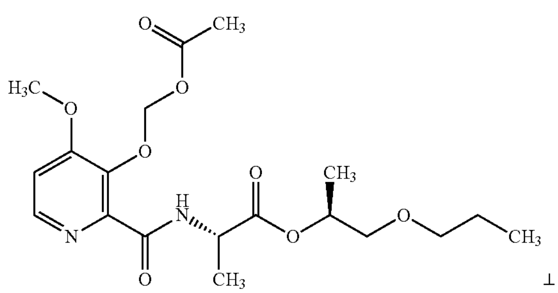 [SMILES: CCCOC[C@H](C)OC(=O)[C@H](C)NC(=O)c1nccc(OC)c1OCOC(C)=O] | Example 16B | Yellow Oil |
| 523 | 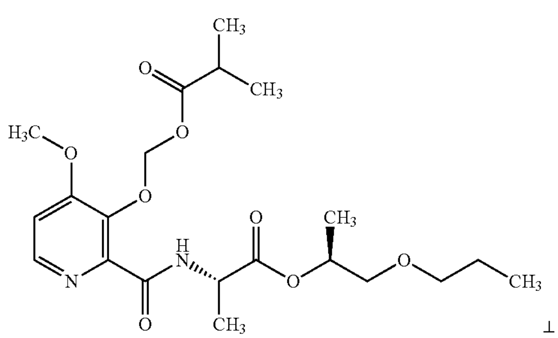 [SMILES: CCCOC[C@H](C)OC(=O)[C@H](C)NC(=O)c1nccc(OC)c1OCOC(=O)C(C)C] | Example 16C | Colorless Oil |

TABLE 1-continued

Compound Structure, Appearance, and Preparation Method

| *Cmpd. No. | Structure | Prepared According to Example: | Appearance |
|---|---|---|---|
| 524 | 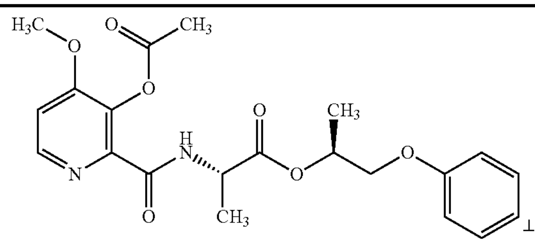 | Example 16A | Sticky Oil |
| 525 | 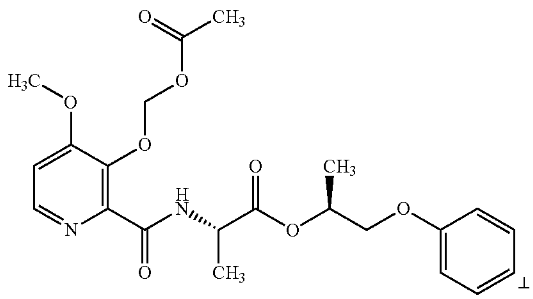 [SMILES: COc1ccnc(C(=O)N[C@@H](C)C(=O)O[C@@H](C)COc2ccccc2)c1OCOC(C)=O] | Example 16B | Yellow Oil |
| 526 | 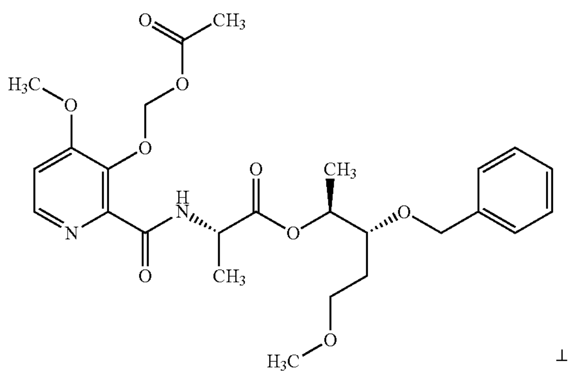 [SMILES: COCC[C@@H](OCc1ccccc1)[C@H](C)OC(=O)[C@H](C)NC(=O)c1nccc(OC)c1OCOC(C)=O] | Example 16B | Pale Yellow Oil |
| 527 | 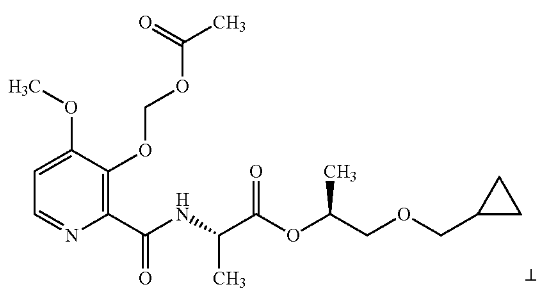 [SMILES: COc1ccnc(C(=O)N[C@@H](C)C(=O)O[C@@H](C)COCC2CC2)c1OCOC(C)=O] | Example 16B | Yellow Oil |
| 528 | 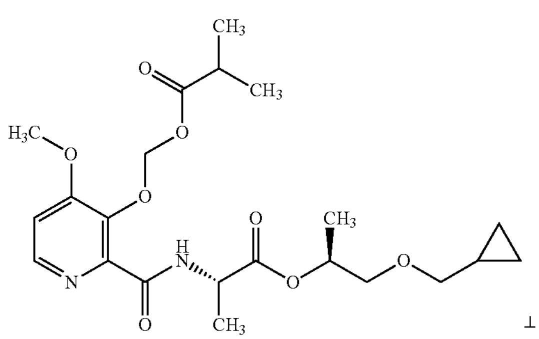 [SMILES: COc1ccnc(C(=O)N[C@@H](C)C(=O)O[C@@H](C)COCC2CC2)c1OCOC(=O)C(C)C] | Example 16C | Colorless Oil |

TABLE 1-continued

Compound Structure, Appearance, and Preparation Method

| *Cmpd. No. | Structure | Prepared According to Example: | Appearance |
|---|---|---|---|
| 529 | 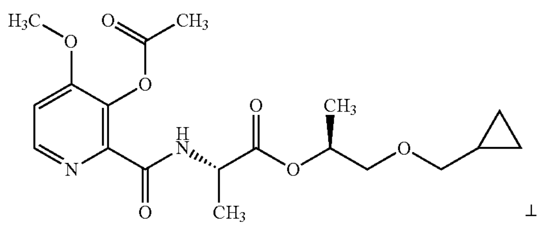 [SMILES: COc1ccnc(C(=O)N[C@@H](C)C(=O)O[C@@H](C)COCC2CC2)c1OC(C)=O] | Example 16A | Colorless Oil |
| 530 | 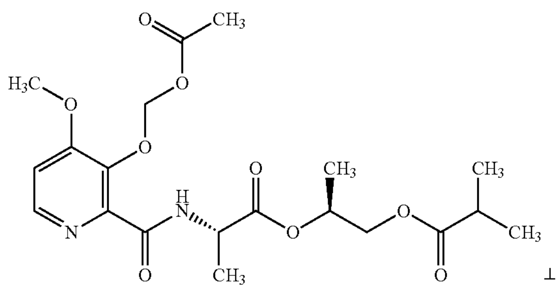 [SMILES: COc1ccnc(C(=O)N[C@@H](C)C(=O)O[C@@H](C)COC(=O)C(C)C)c1OCOC(C)=O] | Example 16B | Yellow Oil |
| 531 | 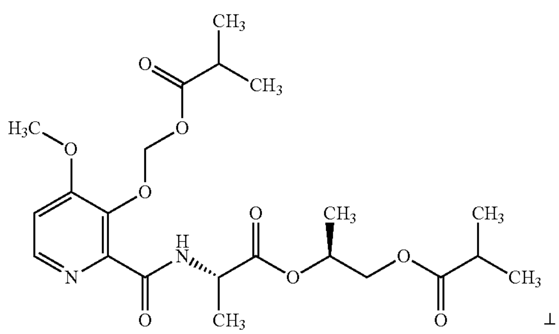 [SMILES: COc1ccnc(C(=O)N[C@@H](C)C(=O)O[C@@H](C)COC(=O)C(C)C)c1OCOC(=O)C(C)C] | Example 16C | Colorless Oil |
| 532 | 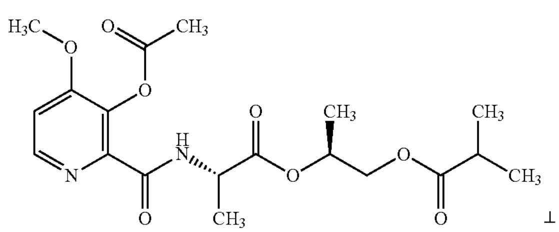 [SMILES: COc1ccnc(C(=O)N[C@@H](C)C(=O)O[C@@H](C)COC(=O)C(C)C)c1OC(C)=O] | Example 16A | Colorless Oil |
| 533 | 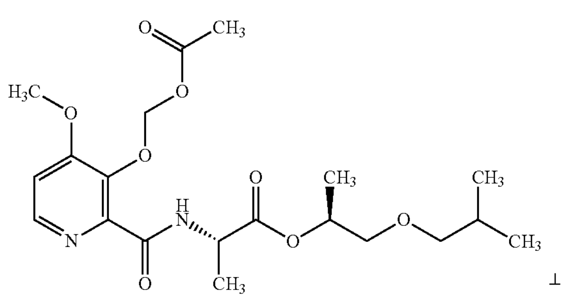 [SMILES: COc1ccnc(C(=O)N[C@@H](C)C(=O)O[C@@H](C)COCC(C)C)c1OCOC(C)=O] | Example 16B | Yellow Oil |

TABLE 1-continued

Compound Structure, Appearance, and Preparation Method

| *Cmpd. No. | Structure | Prepared According to Example: | Appearance |
|---|---|---|---|
| 534 | 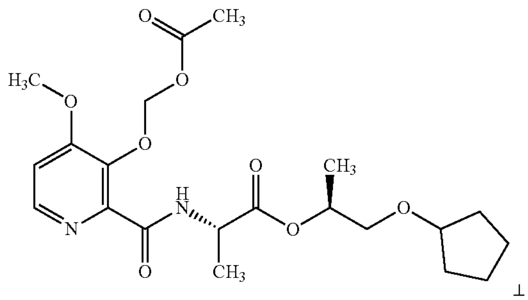 [SMILES: COc1ccnc(C(=O)N[C@@H](C)C(=O)O[C@@H](C)COC2CCCC2)c1OCOC(C)=O] | Example 16B | Yellow Oil |
| 535 | 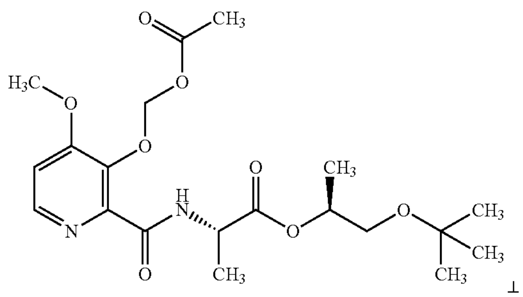 [SMILES: COc1ccnc(C(=O)N[C@@H](C)C(=O)O[C@@H](C)COC(C)(C)C)c1OCOC(C)=O] | Example 16B | Yellow Oil |
| 536 | 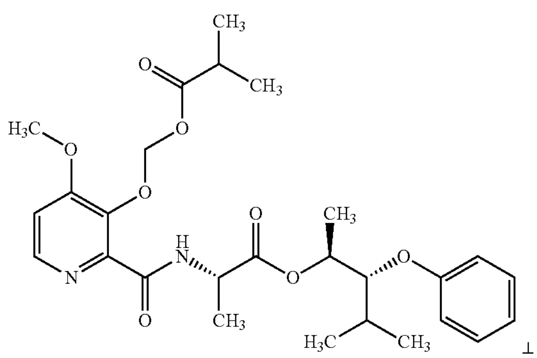 [SMILES: COc1ccnc(C(=O)N[C@@H](C)C(=O)O[C@@H](C)[C@H](Oc2ccccc2)C(C)C)c1OCOC(=O)C(C)C] | Example 16C | Light Yellow Oil |
| 537 | 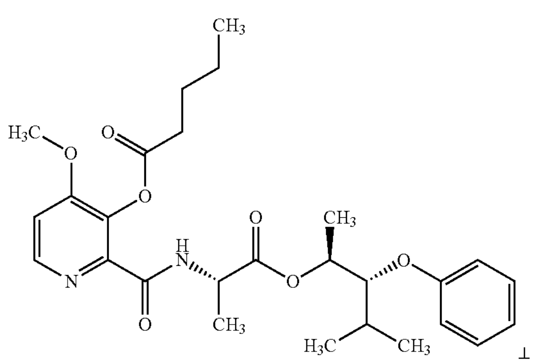 [SMILES: CCCCC(=O)Oc1c(OC)ccnc1C(=O)N[C@@H](C)C(=O)O[C@@H](C)[C@H](Oc1ccccc1)C(C)C] | Example 16A | Light Yellow Oil |

| *Cmpd. No. | Structure | Prepared According to Example: | Appearance |
|---|---|---|---|
| 538 | 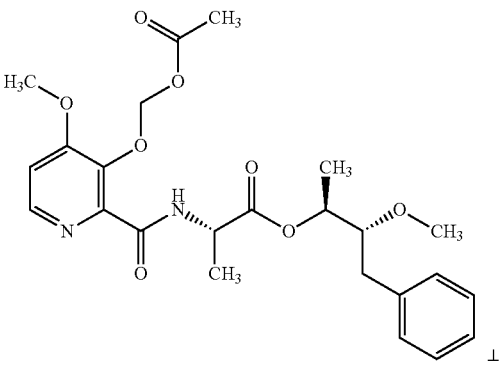 [SMILES: COc1ccnc(C(=O)N[C@@H](C)C(=O)O[C@@H](C)[C@@H](Cc2ccccc2)OC)c1OCOC(C)=O] | Example 16B | Colorless Oil |
| 539 | 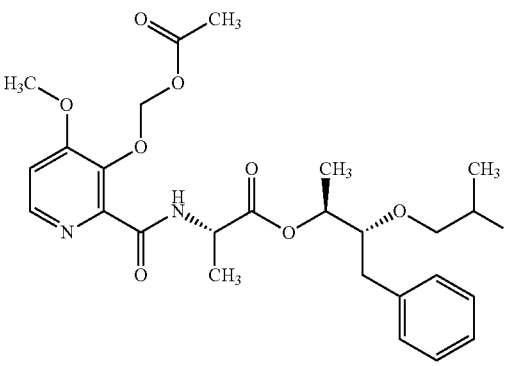 | Example 16B | Colorless Oil |
| 540 | 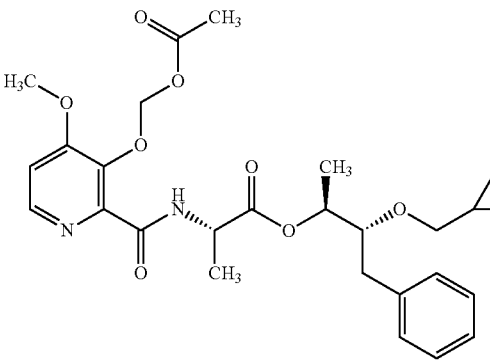 | Example 16B | Colorless Oil |
| 541 | 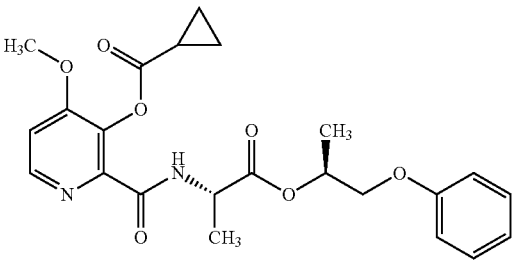 | Example 16A | Sticky Oil |

TABLE 1-continued

Compound Structure, Appearance, and Preparation Method

| *Cmpd. No. | Structure | Prepared According to Example: | Appearance |
|---|---|---|---|
| 542 | 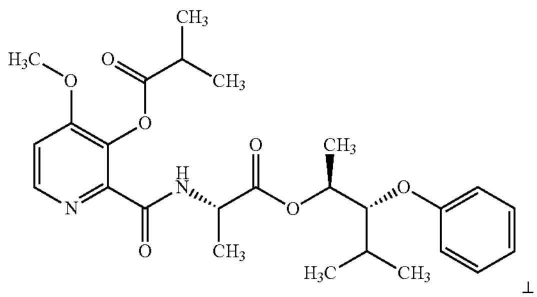 [SMILES: COc1ccnc(C(=O)N[C@@H](C)C(=O)O[C@@H](C)[C@H](Oc2ccccc2)C(C)C)c1OC(=O)C(C)C] | Example 16A | Light Yellow Oil |
| 543 | 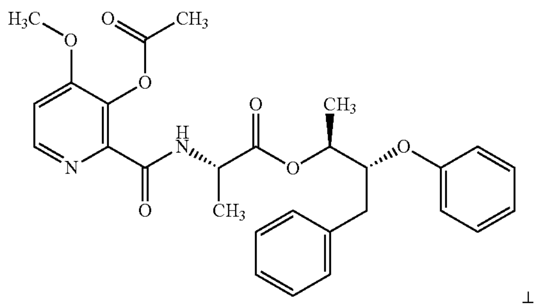 [SMILES: COc1ccnc(C(=O)N[C@@H](C)C(=O)O[C@@H](C)[C@@H](Cc2ccccc2)Oc2ccccc2)c1OC(C)=O] | Example 16A | Sticky Solid |
| 544 | 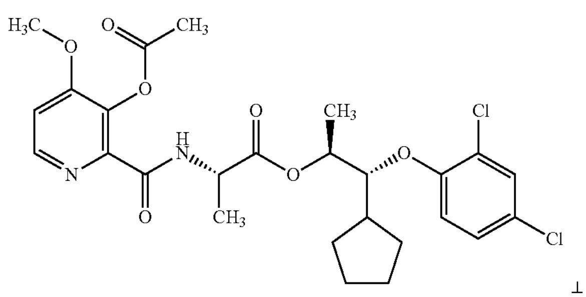 [SMILES: COc1ccnc(C(=O)N[C@@H](C)C(=O)O[C@@H](C)[C@H](Oc2ccc(Cl)cc2Cl)C2CCCC2)c1OC(C)=O] | Example 16A | Sticky Solid |
| 545 | 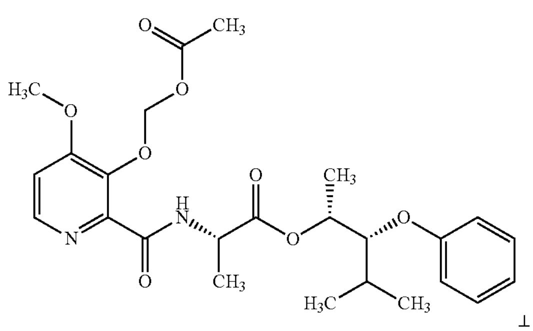 [SMILES: COc1ccnc(C(=O)N[C@@H](C)C(=O)O[C@H](C)[C@H](Oc2ccccc2)C(C)C)c1OCOC(C)=O] | Example 16B | Sticky Wax |

TABLE 1-continued
Compound Structure, Appearance, and Preparation Method
| *Cmpd. No. | Structure | Prepared According to Example: | Appearance |
|---|---|---|---|
| 546 | 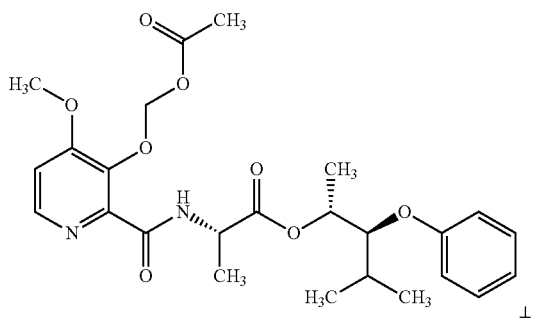 [SMILES: COc1ccnc(C(=O)N[C@@H](C)C(=O)O[C@H](C)[C@@H](Oc2ccccc2)C(C)C)c1OCOC(C)=O] | Example 16B | Sticky Wax |
| 547 | 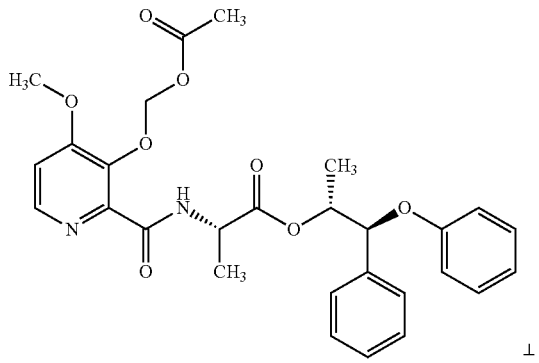 [SMILES: COc1ccnc(C(=O)N[C@@H](C)C(=O)O[C@H](C)[C@@H](Oc2ccccc2)c2ccccc2)c1OCOC(C)=O] | Example 16B | White Foam |
| 548 | 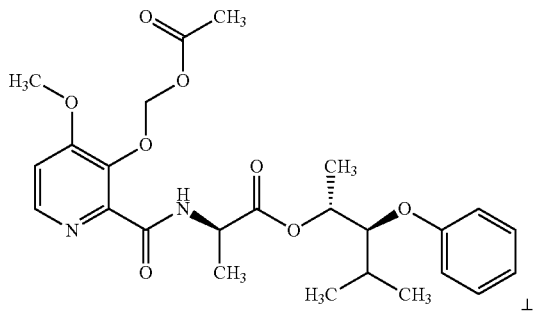 [SMILES: COc1ccnc(C(=O)N[C@H](C)C(=O)O[C@H](C)[C@@H](Oc2ccccc2)C(C)C)c1OCOC(C)=O] | Example 16B | Sticky Wax |
| 549 | 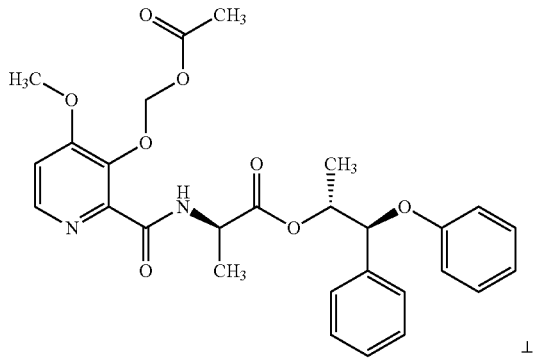 [SMILES: COc1ccnc(C(=O)N[C@H](C)C(=O)O[C@H](C)[C@@H](Oc2ccccc2)c2ccccc2)c1OCOC(C)=O] | Example 16B | White Foam |

TABLE 1-continued

Compound Structure, Appearance, and Preparation Method

| *Cmpd. No. | Structure | Prepared According to Example: | Appearance |
|---|---|---|---|
| 550 | 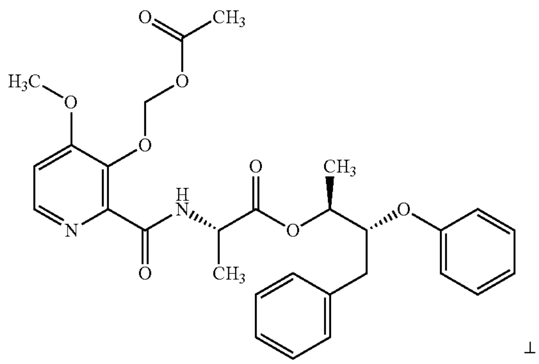 [SMILES: COc1ccnc(C(=O)N[C@@H](C)C(=O)O[C@@H](C)[C@@H](Cc2ccccc2)Oc2ccccc2)c1OCOC(C)=O] | Example 16B | Viscous Oil |
| 551 | 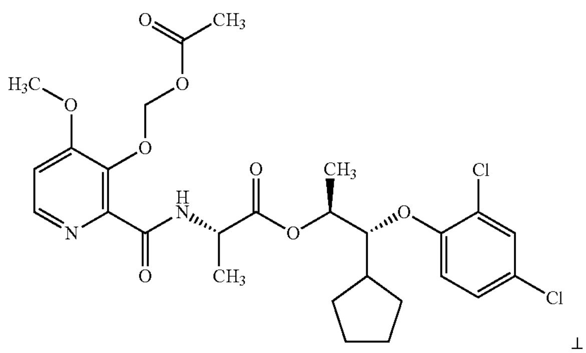 [SMILES: COc1ccnc(C(=O)N[C@@H](C)C(=O)O[C@@H](C)[C@H](Oc2ccc(Cl)cc2Cl)C2CCCC2)c1OCOC(C)=O] | Example 16B | Sticky Oil |
| 552 | 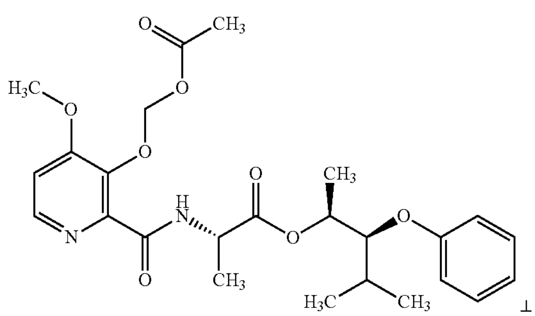 [SMILES: COc1ccnc(C(=O)N[C@@H](C)C(=O)O[C@@H](C)[C@@H](Oc2ccccc2)C(C)C)c1OCOC(C)=O] | Example 16B | Yellow Oil |
| 553 | 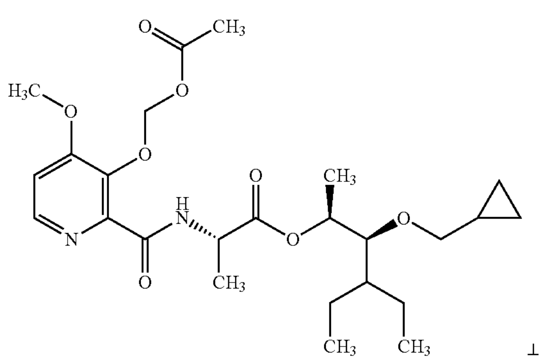 [SMILES: CCC(CC)[C@H](OCC1CC1)[C@H](C)OC(=O)[C@H](C)NC(=O)c1nccc(OC)c1OCOC(C)=O] | Example 16B | Colorless Oil |

TABLE 1-continued

Compound Structure, Appearance, and Preparation Method

| *Cmpd. No. | Structure | Prepared According to Example: | Appearance |
|---|---|---|---|
| 554 | 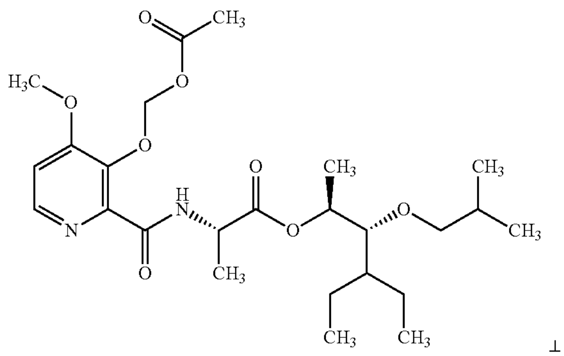 [SMILES: CCC(CC)[C@@H](OCC(C)C)[C@H](C)OC(=O)[C@H](C)NC(=O)c1nccc(OC)c1OCOC(C)=O] | Example 16B | Colorless Oil |
| 555 | 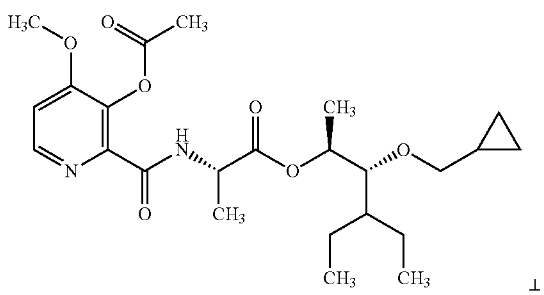 [SMILES: CCC(CC)[C@@H](OCC1CC1)[C@H](C)OC(=O)[C@H](C)NC(=O)c1nccc(OC)c1OC(C)=O] | Example 16A | Colorless Oil |
| 556 | 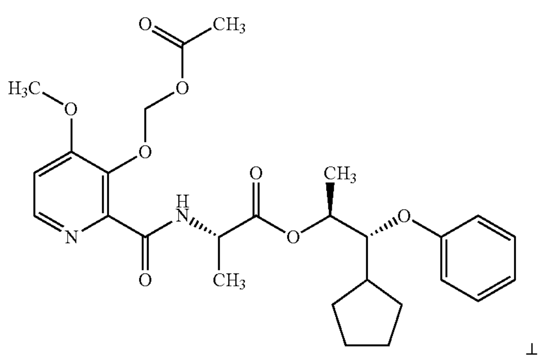 [SMILES: COc1ccnc(C(=O)N[C@@H](C)C(=O)O[C@@H](C)[C@H](Oc2ccccc2)C2CCCC2)c1OCOC(C)=O] | Example 16B | Sticky Oil |
| 557 | 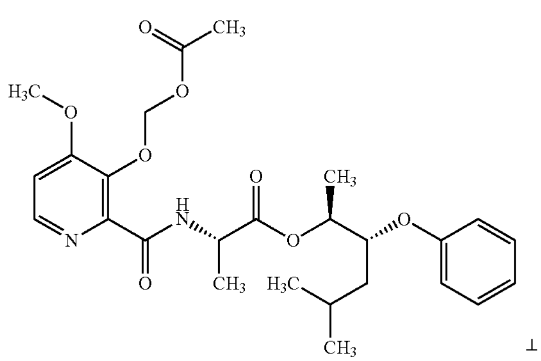 [SMILES: COc1ccnc(C(=O)N[C@@H](C)C(=O)O[C@@H](C)[C@@H](CC(C)C)Oc2ccccc2)c1OCOC(C)=O] | Example 16B | Sticky Oil |

TABLE 1-continued

Compound Structure, Appearance, and Preparation Method

| *Cmpd. No. | Structure | Prepared According to Example: | Appearance |
|---|---|---|---|
| 558 | 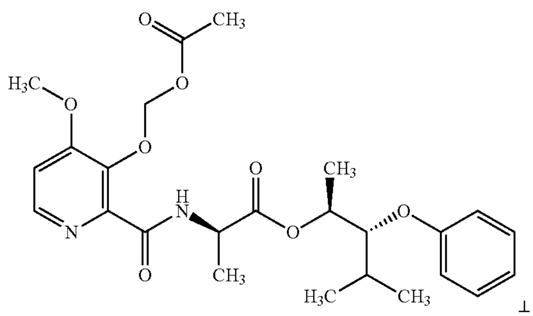 [SMILES: COc1ccnc(C(=O)N[C@H](C)C(=O)O[C@@H](C)[C@H](Oc2ccccc2)C(C)C)c1OCOC(C)=O] | Example 16B | Sticky Wax |
| 559 | 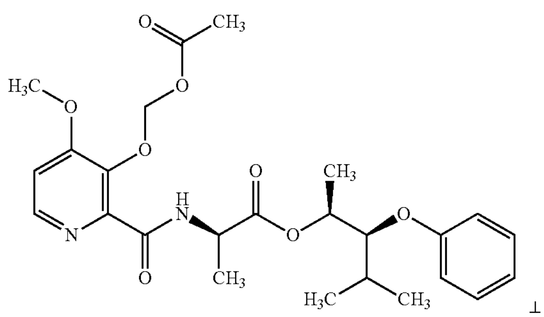 [SMILES: COc1ccnc(C(=O)N[C@H](C)C(=O)O[C@@H](C)[C@@H](Oc2ccccc2)C(C)C)c1OCOC(C)=O] | Example 16B | Sticky Wax |
| 560 | 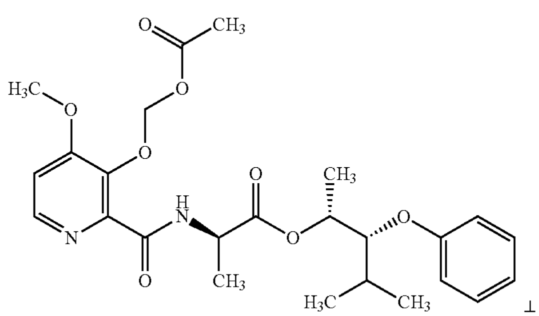 [SMILES: COc1ccnc(C(=O)N[C@H](C)C(=O)O[C@H](C)[C@H](Oc2ccccc2)C(C)C)c1OCOC(C)=O] | Example 16B | Sticky Wax |
| 561 | 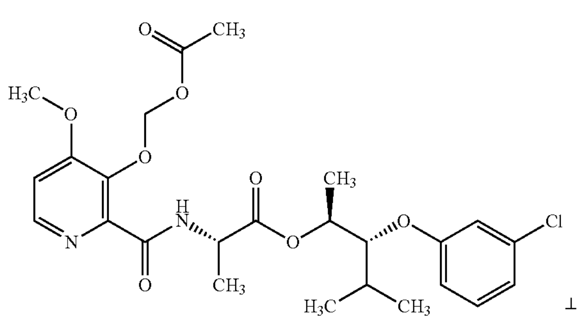 [SMILES: COc1ccnc(C(=O)N[C@@H](C)C(=O)O[C@@H](C)[C@H](Oc2cccc(Cl)c2)C(C)C)c1OCOC(C)=O] | Example 16B | Colorless Oil |

TABLE 1-continued

Compound Structure, Appearance, and Preparation Method

| *Cmpd. No. | Structure | Prepared According to Example: | Appearance |
|---|---|---|---|
| 562 | 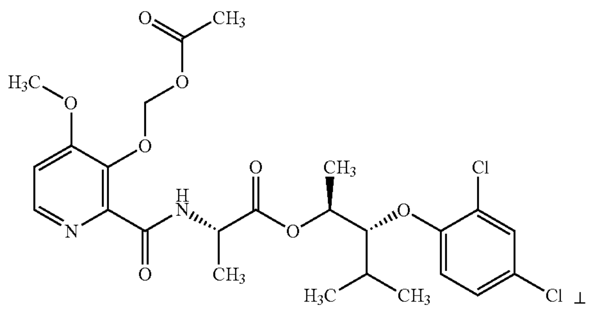 [SMILES: COc1ccnc(C(=O)N[C@@H](C)C(=O)O[C@@H](C)[C@H](Oc2ccc(Cl)cc2Cl)C(C)C)c1OCOC(C)=O] | Example 16B | Colorless Oil |
| 563 | 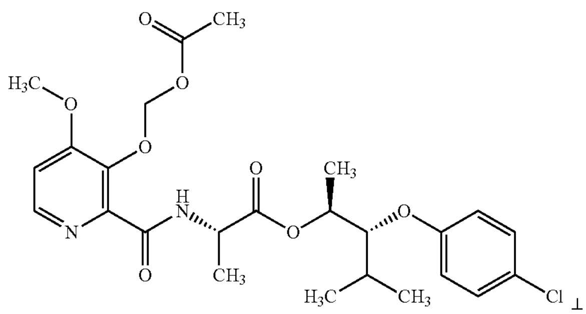 [SMILES: COc1ccnc(C(=O)N[C@@H](C)C(=O)O[C@@H](C)[C@H](Oc2ccc(Cl)cc2)C(C)C)c1OCOC(C)=O] | Example 16B | Colorless Oil |
| 564 | 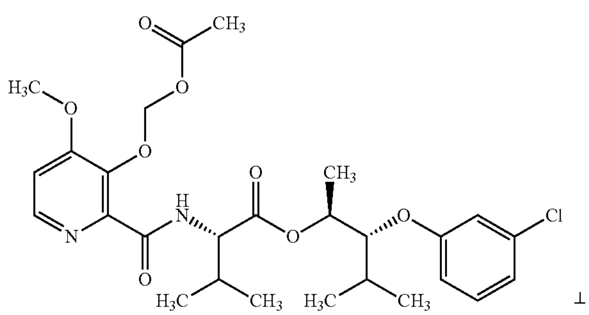 [SMILES: COc1ccnc(C(=O)N[C@H](C(=O)O[C@@H](C)[C@H](Oc2cccc(Cl)c2)C(C)C)C(C)C)c1OCOC(C)=O] | Example 16B | Colorless Oil |
| 565 | 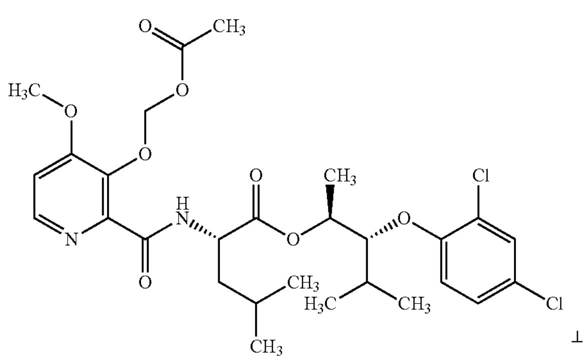 [SMILES: COc1ccnc(C(=O)N[C@@H](CC(C)C)C(=O)O[C@@H](C)[C@H](Oc2ccc(Cl)cc2Cl)C(C)C)c1OCOC(C)=O] | Example 16B | Colorless Oil |

TABLE 1-continued

Compound Structure, Appearance, and Preparation Method

| *Cmpd. No. | Structure | Prepared According to Example: | Appearance |
|---|---|---|---|
| 566 | 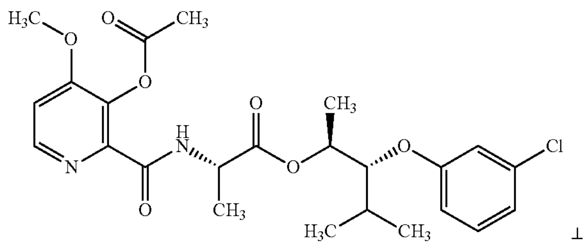 [SMILES: COc1ccnc(C(=O)N[C@@H](C)C(=O)O[C@@H](C)[C@H](Oc2cccc(Cl)c2)C(C)C)c1OC(C)=O] | Example 16A | Colorless Oil |
| 567 | 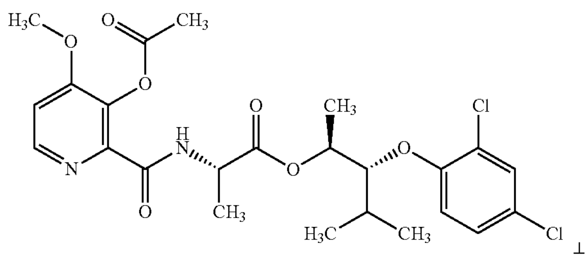 [SMILES: COc1ccnc(C(=O)N[C@@H](C)C(=O)O[C@@H](C)[C@H](Oc2ccc(Cl)cc2Cl)C(C)C)c1OC(C)=O] | Example 16A | Colorless Oil |
| 568 | 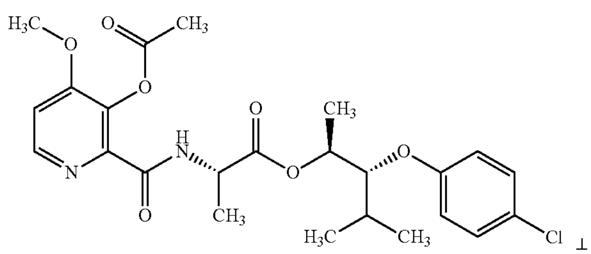 [SMILES: COc1ccnc(C(=O)N[C@@H](C)C(=O)O[C@@H](C)[C@H](Oc2ccc(Cl)cc2)C(C)C)c1OC(C)=O] | Example 16A | White Solid |
| 569 | 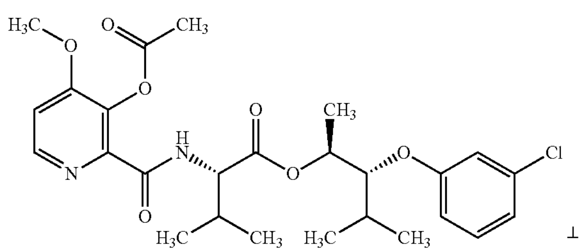 [SMILES: COc1ccnc(C(=O)N[C@H](C(=O)O[C@@H](C)[C@H](Oc2cccc(Cl)c2)C(C)C)C(C)C)c1OC(C)=O] | Example 16A | Colorless Oil |
| 570 | 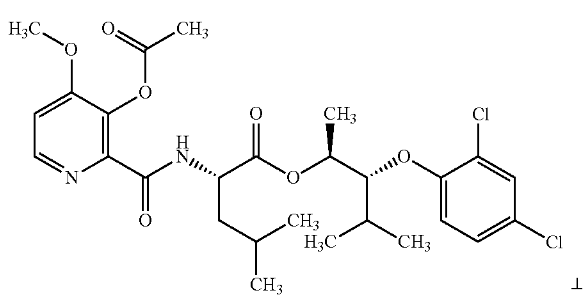 [SMILES: COc1ccnc(C(=O)N[C@@H](CC(C)C)C(=O)O[C@@H](C)[C@H](Oc2ccc(Cl)cc2Cl)C(C)C)c1OC(C)=O] | Example 16A | White Solid |

TABLE 1-continued

Compound Structure, Appearance, and Preparation Method

| *Cmpd. No. | Structure | Prepared According to Example: | Appearance |
|---|---|---|---|
| 571 | 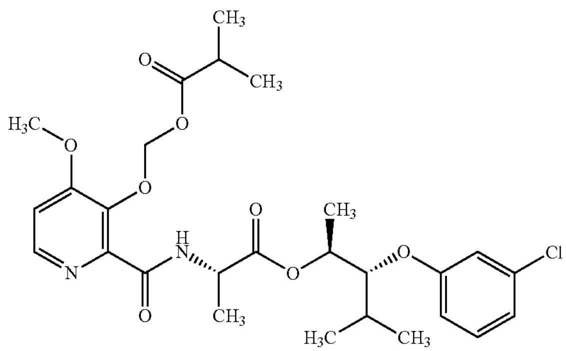 | Example 16C | Colorless Oil |
| 572 | 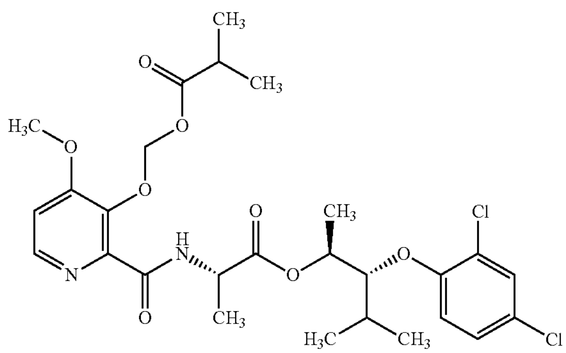 | Example 16C | Colorless Oil |
| 573 | 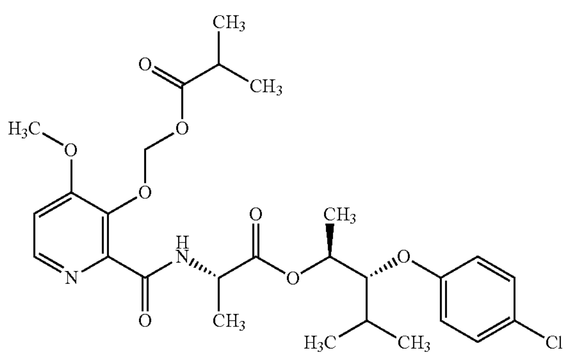 | Example 16C | Colorless Oil |
| 574 | 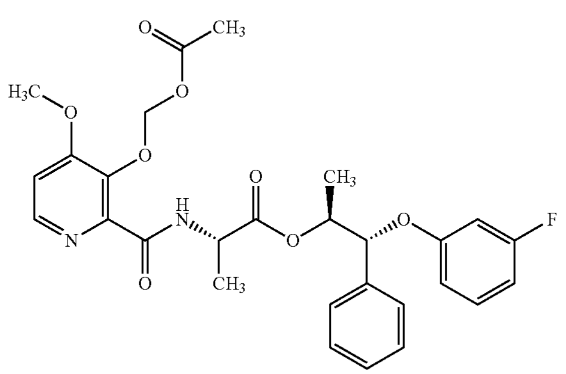 | Example 16B | White Powder |

TABLE 1-continued

Compound Structure, Appearance, and Preparation Method

| *Cmpd. No. | Structure | Prepared According to Example: | Appearance |
|---|---|---|---|
| 575 | 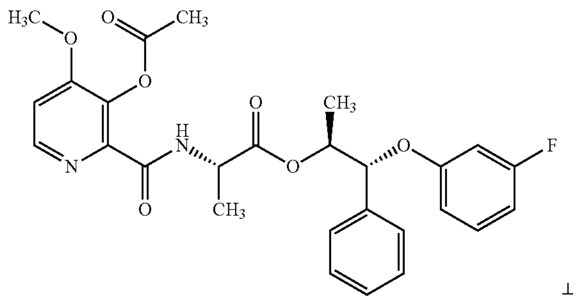 [SMILES: COc1ccnc(C(=O)N[C@@H](C)C(=O)O[C@@H](C)[C@H](Oc2cccc(F)c2)c2ccccc2)c1OC(C)=O] | Example 16A | White Powder |
| 576 | 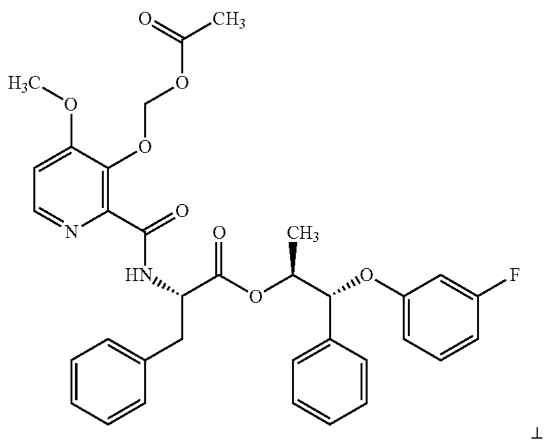 [SMILES: COc1ccnc(C(=O)N[C@@H](Cc2ccccc2)C(=O)O[C@@H](C)[C@H](Oc2cccc(F)c2)c2ccccc2)c1OCOC(C)=O] | Example 16B | White Powder |
| 577 | 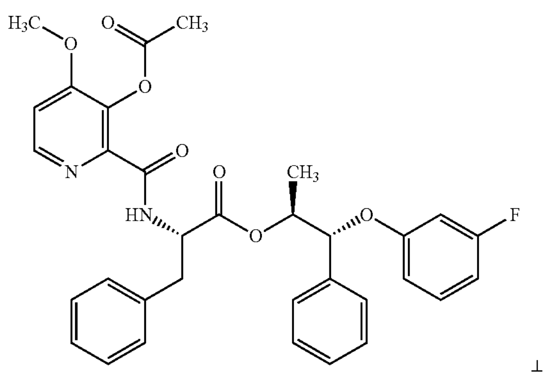 [SMILES: COc1ccnc(C(=O)N[C@@H](Cc2ccccc2)C(=O)O[C@@H](C)[C@H](Oc2cccc(F)c2)c2ccccc2)c1OC(C)=O] | Example 16A | White Powder |
| 578 | 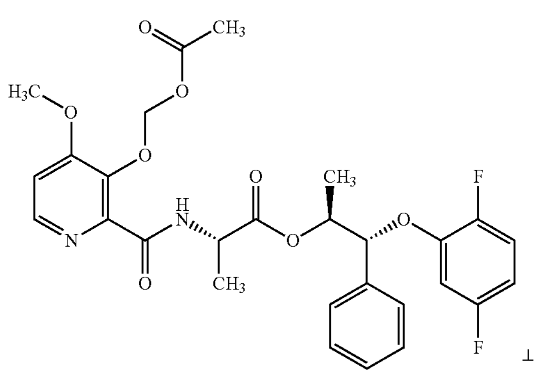 [SMILES: COc1ccnc(C(=O)N[C@@H](C)C(=O)O[C@@H](C)[C@H](Oc2cc(F)ccc2F)c2ccccc2)c1OCOC(C)=O] | Example 16B | White Powder |

TABLE 1-continued

Compound Structure, Appearance, and Preparation Method

| *Cmpd. No. | Structure | Prepared According to Example: | Appearance |
|---|---|---|---|
| 579 | 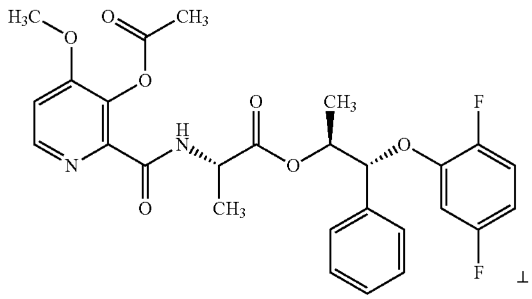 [SMILES: COc1ccnc(C(=O)N[C@@H](C)C(=O)O[C@@H](C)[C@H](Oc2cc(F)ccc2F)c2ccccc2)c1OC(C)=O] | Example 16A | White Powder |
| 580 | 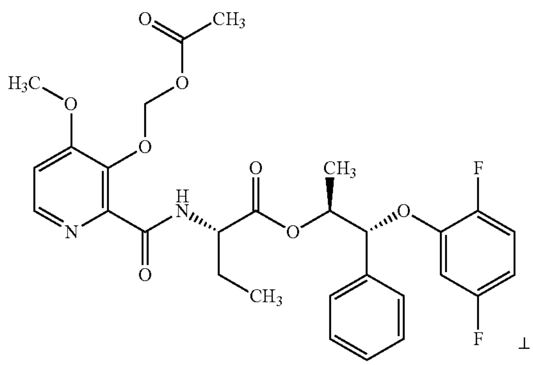 [SMILES: CC[C@H](NC(=O)c1nccc(OC)c1OCOC(C)=O)C(=O)O[C@@H](C)[C@H](Oc1cc(F)ccc1F)c1ccccc1] | Example 16B | Hygroscopic Solid |
| 581 | 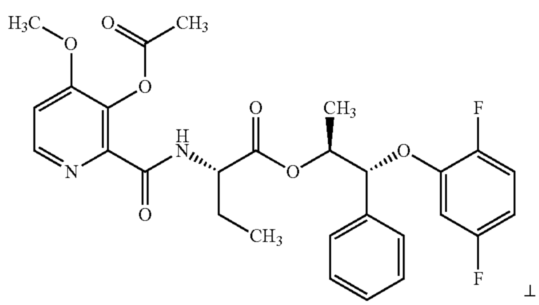 [SMILES: CC[C@H](NC(=O)c1nccc(OC)c1OC(C)=O)C(=O)O[C@@H](C)[C@H](Oc1cc(F)ccc1F)c1ccccc1] | Example 16A | White Powder |
| 582 | 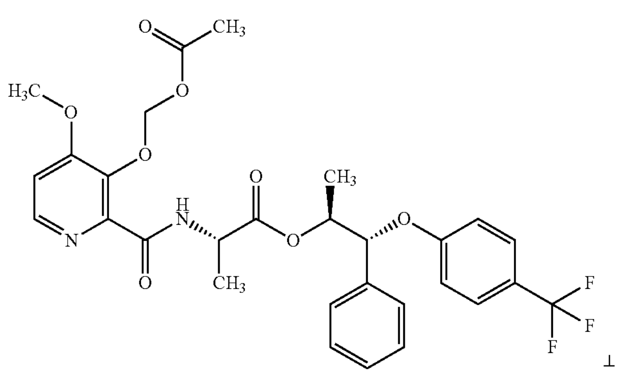 [SMILES: COc1ccnc(C(=O)N[C@@H](C)C(=O)O[C@@H](C)[C@H](Oc2ccc(C(F)(F)F)cc2)c2ccccc2)c1OCOC(C)=O] | Example 16B | White Powder |

TABLE 1-continued

Compound Structure, Appearance, and Preparation Method

| *Cmpd. No. | Structure | Prepared According to Example: | Appearance |
|---|---|---|---|
| 583 | 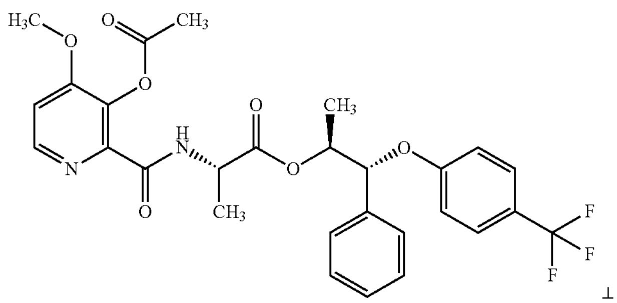 [SMILES: COc1ccnc(C(=O)N[C@@H](C)C(=O)O[C@@H](C)[C@H](Oc2ccc(C(F)(F)F)cc2)c2ccccc2)c1OC(C)=O] | Example 16A | White Powder |
| 584 | 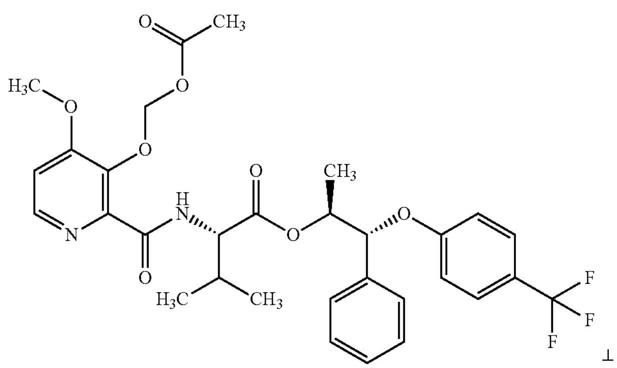 [SMILES: COc1ccnc(C(=O)N[C@H](C(=O)O[C@@H](C)[C@H](Oc2ccc(C(F)(F)F)cc2)c2ccccc2)C(C)C)c1OCOC(C)=O] | Example 16B | Hygroscopic Powder |
| 585 | 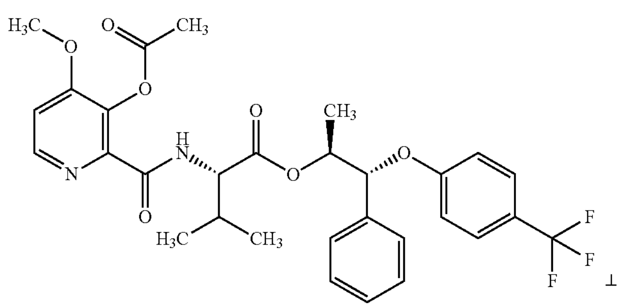 [SMILES: COc1ccnc(C(=O)N[C@H](C(=O)O[C@@H](C)[C@H](Oc2ccc(C(F)(F)F)cc2)c2ccccc2)C(C)C)c1OC(C)=O] | Example 16A | White Powder |
| 586 | 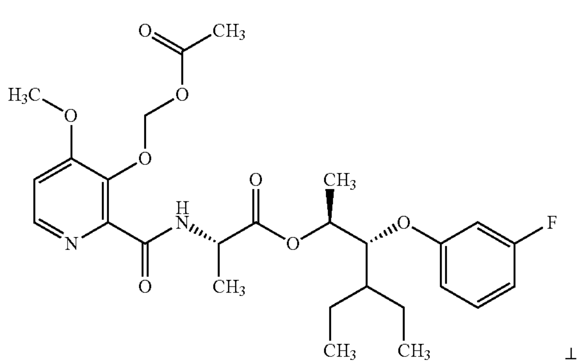 [SMILES: CCC(CC)[C@@H](Oc1cccc(F)c1)[C@H](C)OC(=O)[C@H](C)NC(=O)c1nccc(OC)c1OCOC(C)=O] | Example 16B | Colorless Oil |

TABLE 1-continued

Compound Structure, Appearance, and Preparation Method

| *Cmpd. No. | Structure | Prepared According to Example: | Appearance |
|---|---|---|---|
| 587 | 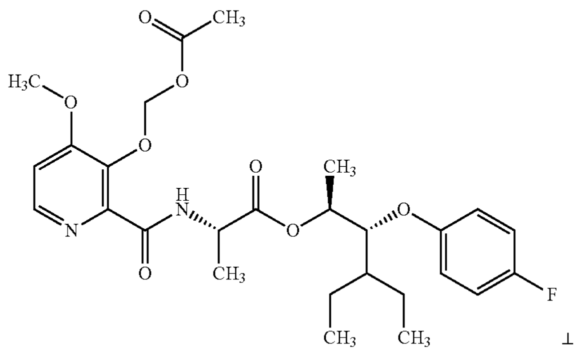 | Example 16B | Colorless Oil |
| 588 | 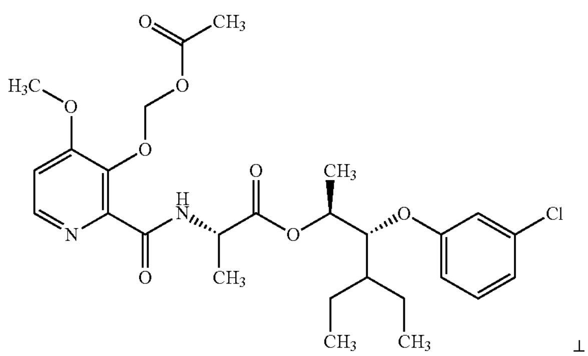 [SMILES: CCC(CC)[C@@H](Oc1cccc(Cl)c1)[C@H](C)OC(=O)[C@H](C)NC(=O)c1nccc(OC)c1OCOC(C)=O] | Example 16B | Colorless Oil |
| 589 | 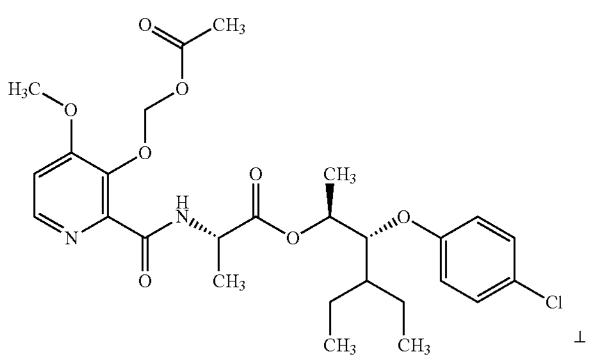 [SMILES: CCC(CC)[C@@H](Oc1ccc(Cl)cc1)[C@H](C)OC(=O)[C@H](C)NC(=O)c1nccc(OC)c1OCOC(C)=O] | Example 16B | Colorless Oil |
| 590 | 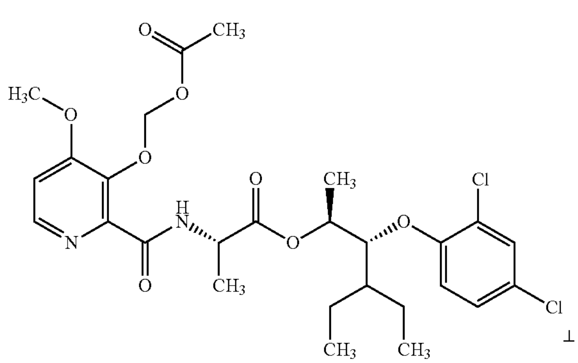 [SMILES: CCC(CC)[C@@H](Oc1ccc(Cl)cc1Cl)[C@H](C)OC(=O)[C@H](C)NC(=O)c1nccc(OC)c1OCOC(C)=O] | Example 16B | Colorless Oil |

TABLE 1-continued

Compound Structure, Appearance, and Preparation Method

| *Cmpd. No. | Structure | Prepared According to Example: | Appearance |
|---|---|---|---|
| 591 | 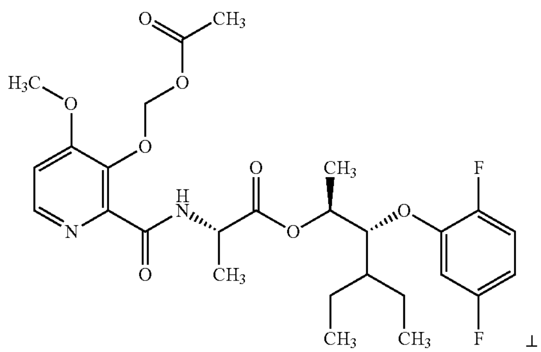 [SMILES: CCC(CC)[C@@H](Oc1cc(F)ccc1F)[C@H](C)OC(=O)[C@H](C)NC(=O)c1nccc(OC)c1OCOC(C)=O] | Example 16B | Colorless Oil |
| 592 | 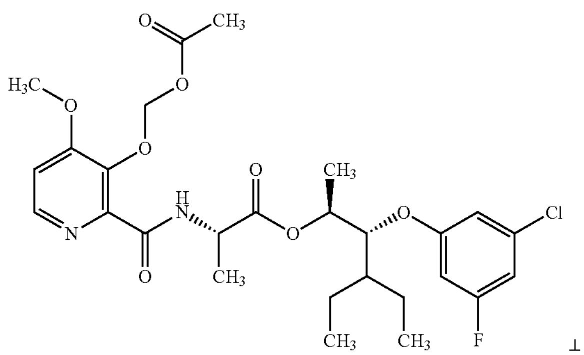 [SMILES: CCC(CC)[C@@H](Oc1cc(F)cc(Cl)c1)[C@H](C)OC(=O)[C@H](C)NC(=O)c1nccc(OC)c1OCOC(C)=O] | Example 16B | Colorless Oil |
| 593 | 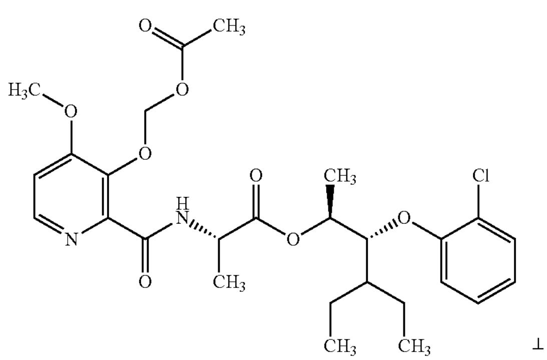 [SMILES: CCC(CC)[C@@H](Oc1ccccc1Cl)[C@H](C)OC(=O)[C@H](C)NC(=O)c1nccc(OC)c1OCOC(C)=O] | Example 16B | Colorless Oil |
| 594 | 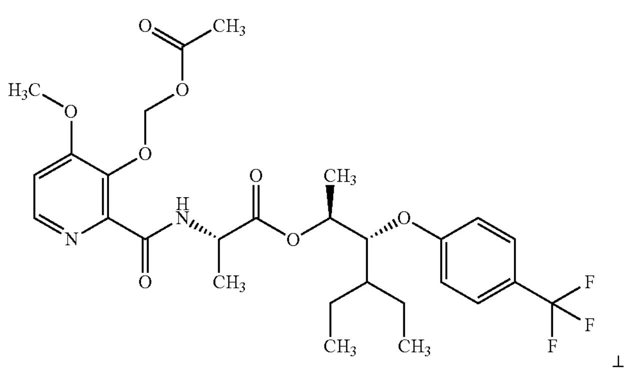 [SMILES: CCC(CC)[C@@H](Oc1ccc(C(F)(F)F)cc1)[C@H](C)OC(=O)[C@H](C)NC(=O)c1nccc(OC)c1OCOC(C)=O] | Example 16B | Colorless Oil |

TABLE 1-continued

Compound Structure, Appearance, and Preparation Method

| *Cmpd. No. | Structure | Prepared According to Example: | Appearance |
|---|---|---|---|
| 595 | 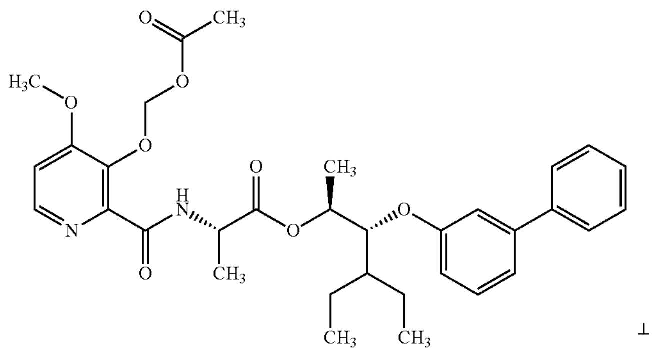 [SMILES: CCC(CC)[C@@H](Oc1cccc(-c2ccccc2)c1)[C@H](C)OC(=O)[C@H](C)NC(=O)c1nccc(OC)c1OCOC(C)=O] | Example 16B | Colorless Oil |
| 596 | 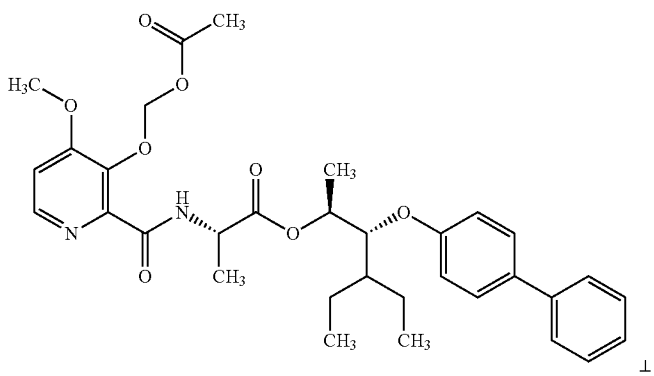 [SMILES: CCC(CC)[C@@H](Oc1ccc(-c2ccccc2)cc1)[C@H](C)OC(=O)[C@H](C)NC(=O)c1nccc(OC)c1OCOC(C)=O] | Example 16B | Colorless Oil |
| 597 | 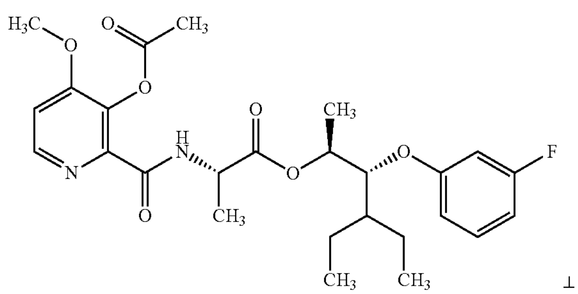 [SMILES: CCC(CC)[C@@H](Oc1cccc(F)c1)[C@H](C)OC(=O)[C@H](C)NC(=O)c1nccc(OC)c1OC(C)=O] | Example 16A | Tacky Oil |
| 598 | 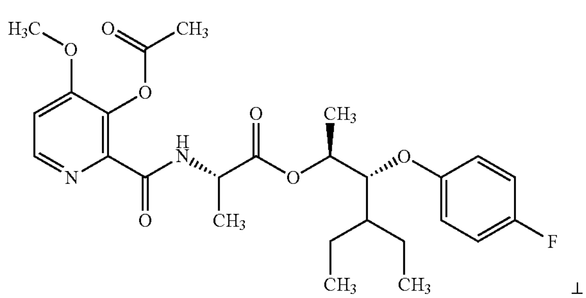 [SMILES: CCC(CC)[C@@H](Oc1ccc(F)cc1)[C@H](C)OC(=O)[C@H](C)NC(=O)c1nccc(OC)c1OC(C)=O] | Example 16A | Tacky Oil |

TABLE 1-continued

Compound Structure, Appearance, and Preparation Method

| *Cmpd. No. | Structure | Prepared According to Example: | Appearance |
|---|---|---|---|
| 599 | 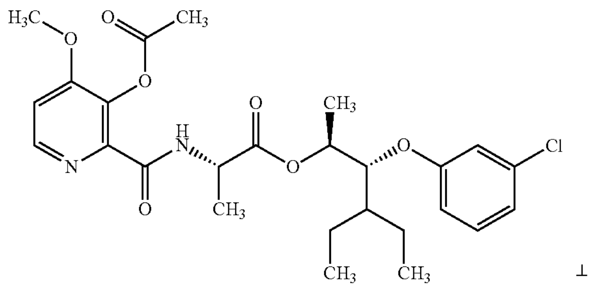 [SMILES: CCC(CC)[C@@H](Oc1cccc(Cl)c1)[C@H](C)OC(=O)[C@H](C)NC(=O)c1nccc(OC)c1OC(C)=O] | Example 16A | Tacky Oil |
| 600 | 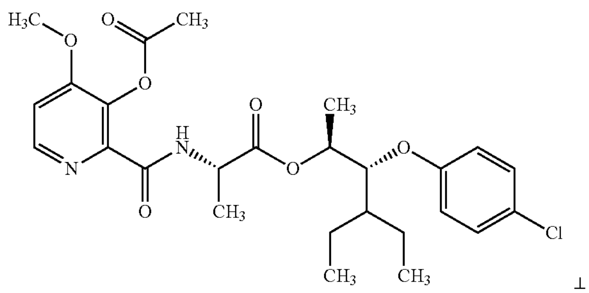 | Example 16A | White Foam |
| 601 | 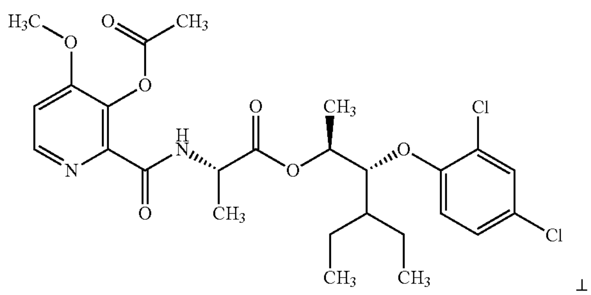 [SMILES: CCC(CC)[C@@H](Oc1ccc(Cl)cc1Cl)[C@H](C)OC(=O)[C@H](C)NC(=O)c1nccc(OC)c1OC(C)=O] | Example 16A | White Foam |
| 602 | 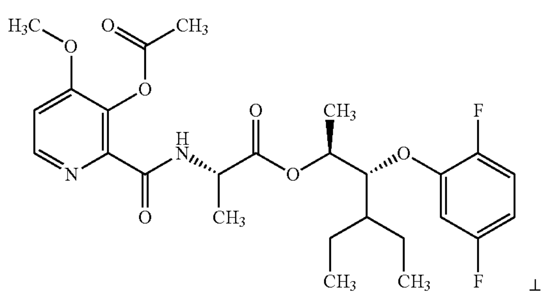 [SMILES: CCC(CC)[C@@H](Oc1cc(F)ccc1F)[C@H](C)OC(=O)[C@H](C)NC(=O)c1nccc(OC)c1OC(C)=O] | Example 16A | Tacky Oil |
| 603 | 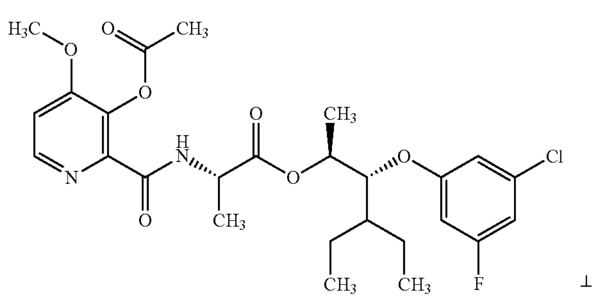 [SMILES: CCC(CC)[C@@H](Oc1cc(F)cc(Cl)c1)[C@H](C)OC(=O)[C@H](C)NC(=O)c1nccc(OC)c1OC(C)=O] | Example 16A | Tacky Oil |

TABLE 1-continued
Compound Structure, Appearance, and Preparation Method
| *Cmpd. No. | Structure | Prepared According to Example: | Appearance |
|---|---|---|---|
| 604 | 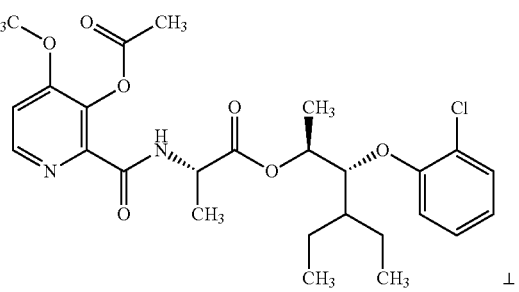 | Example 16A | Tacky Oil |
| 605 | 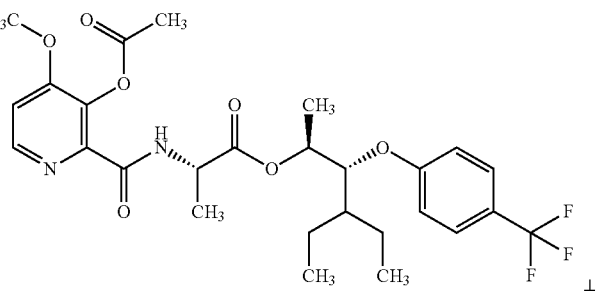 | Example 16A | White Foam |
| 606 | 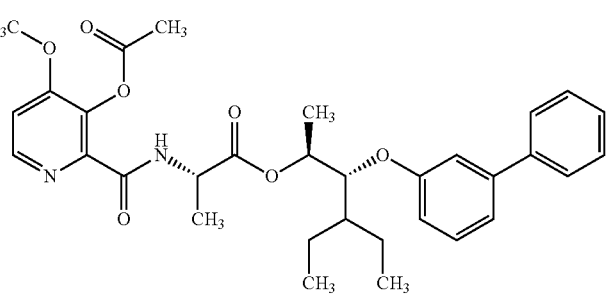 | Example 16A | Tacky Oil |
| 607 | 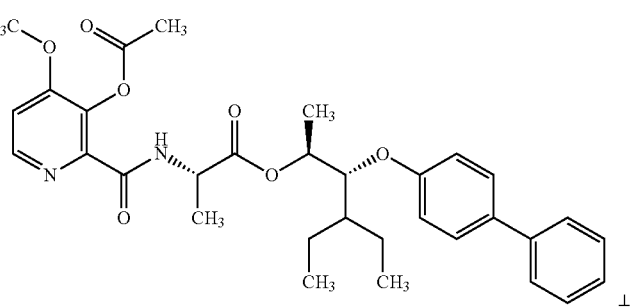 | Example 16A | Tacky Oil |

TABLE 1-continued

Compound Structure, Appearance, and Preparation Method

| *Cmpd. No. | Structure | Prepared According to Example: | Appearance |
|---|---|---|---|
| 608 | 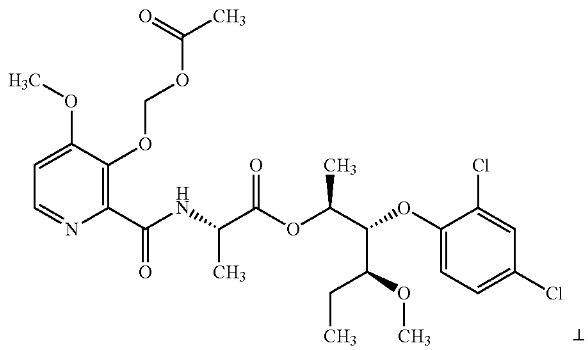 [SMILES: CC[C@H](OC)[C@@H](Oc1ccc(Cl)cc1Cl)[C@H](C)OC(=O)[C@H](C)NC(=O)c1nccc(OC)c1OCOC(C)=O] | Example 16B | Colorless Oil |
| 609 | 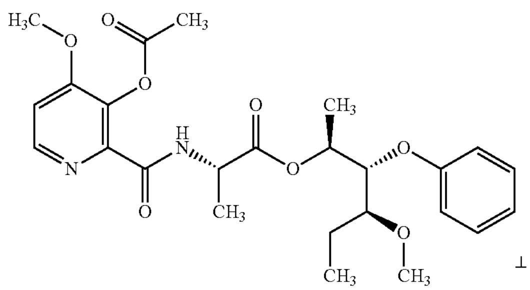 [SMILES: CC[C@H](OC)[C@@H](Oc1ccccc1)[C@H](C)OC(=O)[C@H](C)NC(=O)c1nccc(OC)c1OC(C)=O] | Example 16A | Colorless Oil |
| 610 | 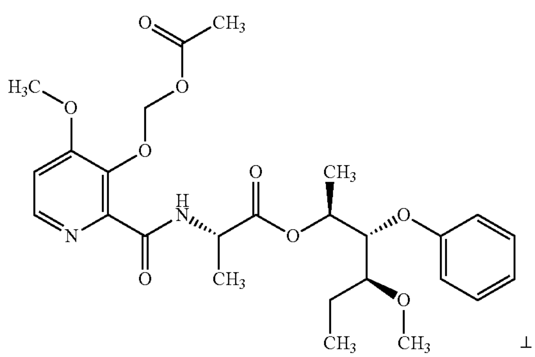 [SMILES: CC[C@H](OC)[C@@H](Oc1ccccc1)[C@H](C)OC(=O)[C@H](C)NC(=O)c1nccc(OC)c1OCOC(C)=O] | Example 16B | Colorless Oil |
| 611 | 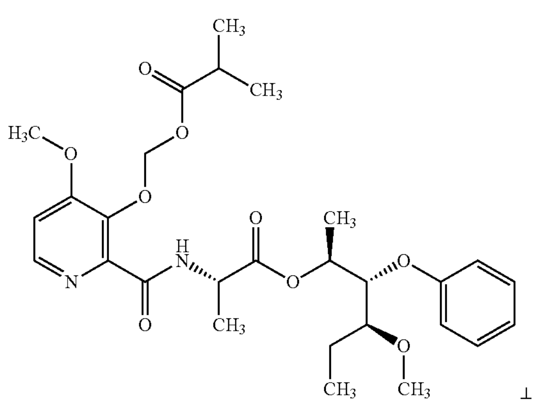 [SMILES: CC[C@H](OC)[C@@H](Oc1ccccc1)[C@H](C)OC(=O)[C@H](C)NC(=O)c1nccc(OC)c1OCOC(=O)C(C)C] | Example 16C | Colorless Oil |

TABLE 1-continued

Compound Structure, Appearance, and Preparation Method

| *Cmpd. No. | Structure | Prepared According to Example: | Appearance |
|---|---|---|---|
| 612 | 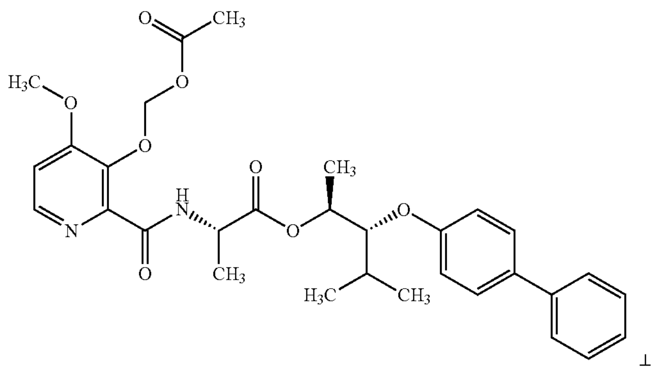 [SMILES: COc1ccnc(C(=O)N[C@@H](C)C(=O)O[C@@H](C)[C@H](Oc2ccc(-c3ccccc3)cc2)C(C)C)c1OCOC(C)=O] | Example 16B | White Solid |
| 613 | 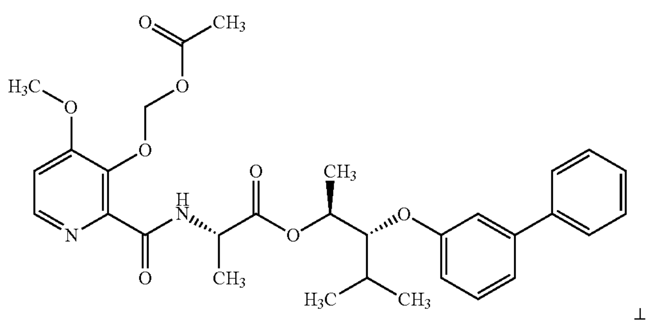 [SMILES: COc1ccnc(C(=O)N[C@@H](C)C(=O)O[C@@H](C)[C@H](Oc2cccc(-c3ccccc3)c2)C(C)C)c1OCOC(C)=O] | Example 16B | Sticky Solid |
| 614 | 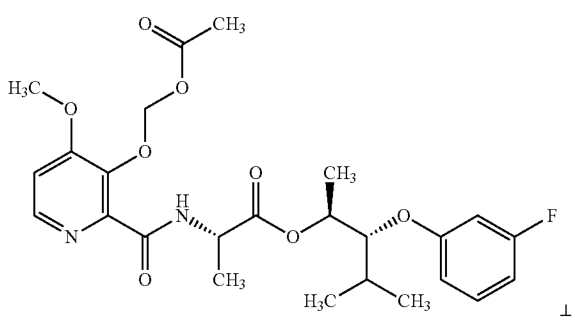 [SMILES: COc1ccnc(C(=O)N[C@@H](C)C(=O)O[C@@H](C)[C@H](Oc2cccc(F)c2)C(C)C)c1OCOC(C)=O] | Example 16B | Yellow Oil |
| 615 | 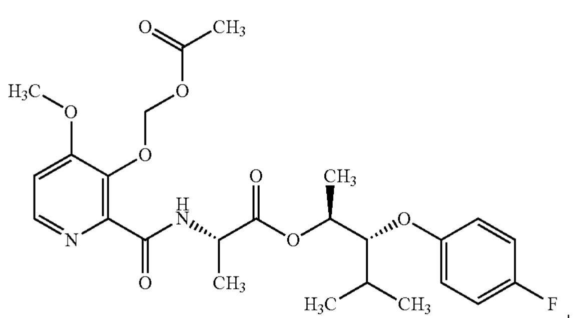 | Example 16B | Yellow Oil |

TABLE 1-continued

Compound Structure, Appearance, and Preparation Method

| *Cmpd. No. | Structure | Prepared According to Example: | Appearance |
|---|---|---|---|
| 616 | 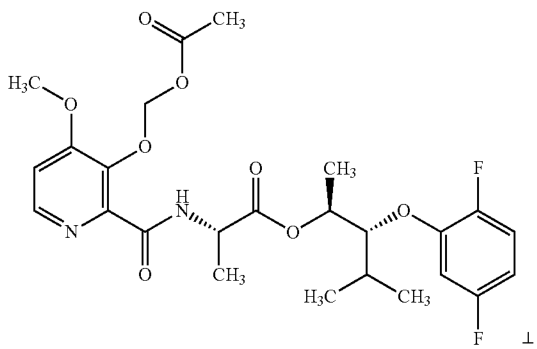 [SMILES: COc1ccnc(C(=O)N[C@@H](C)C(=O)O[C@@H](C)[C@H](Oc2cc(F)ccc2F)C(C)C)c1OCOC(C)=O] | Example 16B | Yellow Oil |
| 617 | 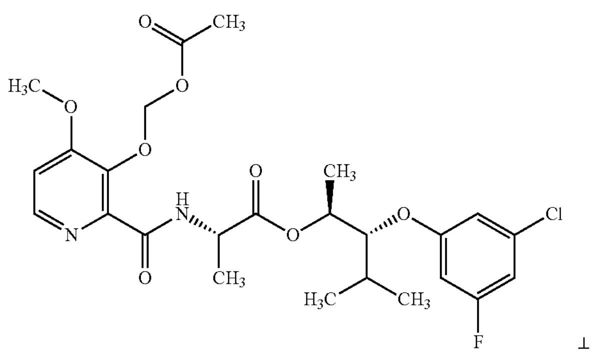 [SMILES: COc1ccnc(C(=O)N[C@@H](C)C(=O)O[C@@H](C)[C@H](Oc2cc(F)cc(Cl)c2)C(C)C)c1OCOC(C)=O] | Example 16B | Yellow Oil |
| 618 | 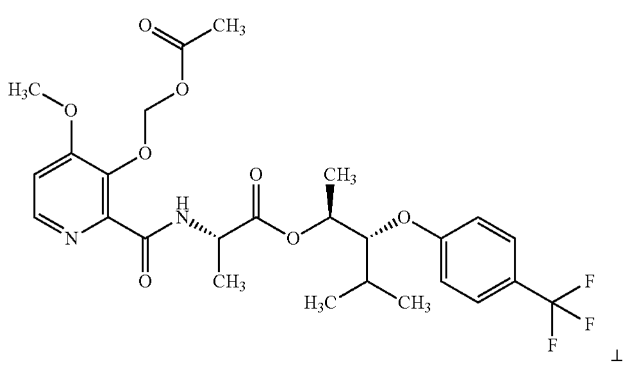 [SMILES: COc1ccnc(C(=O)N[C@@H](C)C(=O)O[C@@H](C)[C@H](Oc2ccc(C(F)(F)F)cc2)C(C)C)c1OCOC(C)=O] | Example 16B | Yellow Oil |
| 619 | 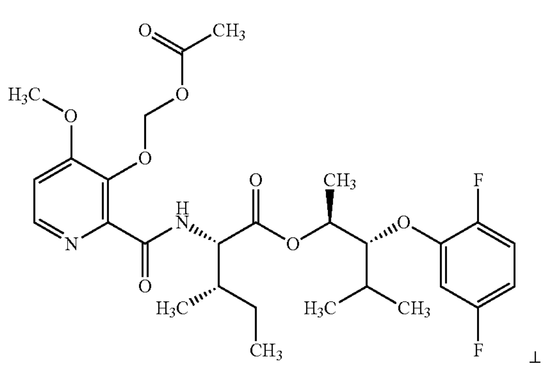 [SMILES: CC[C@H](C)[C@H](NC(=O)c1nccc(OC)c1OCOC(C)=O)C(=O)O[C@@H](C)[C@H](Oc1cc(F)ccc1F)C(C)C] | Example 16B | Colorless Oil |

TABLE 1-continued

Compound Structure, Appearance, and Preparation Method

| *Cmpd. No. | Structure | Prepared According to Example: | Appearance |
|---|---|---|---|
| 620 | 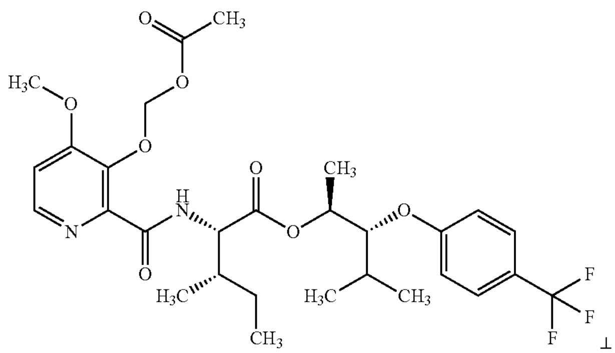 [SMILES: CC[C@H](C)[C@H](NC(=O)c1nccc(OC)c1OCOC(C)=O)C(=O)O[C@@H](C)[C@H](Oc1ccc(C(F)(F)F)cc1)C(C)C] | Example 16B | Colorless Oil |
| 621 | 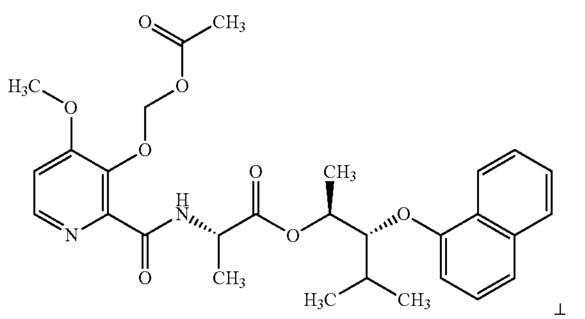 [SMILES: COc1ccnc(C(=O)N[C@@H](C)C(=O)O[C@@H](C)[C@H](Oc2cccc3ccccc23)C(C)C)c1OCOC(C)=O] | Example 16B | White Solid |
| 622 | 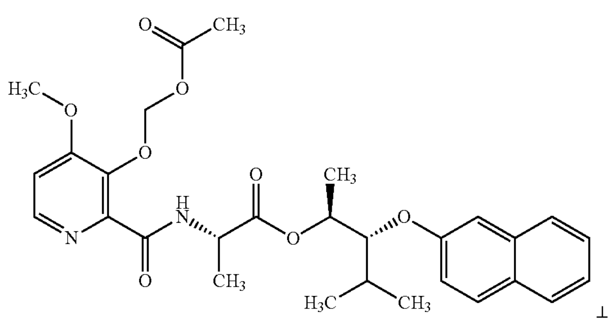 [SMILES: COc1ccnc(C(=O)N[C@@H](C)C(=O)O[C@@H](C)[C@H](Oc2ccc3ccccc3c2)C(C)C)c1OCOC(C)=O] | Example 16B | Yellow Solid |
| 623 | 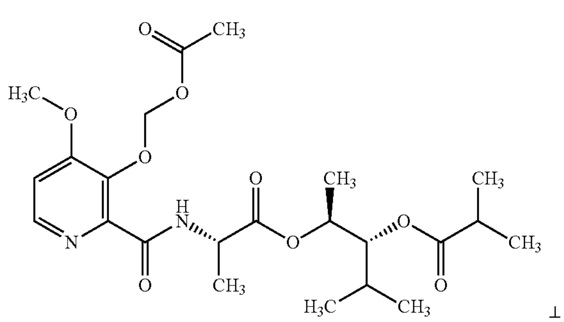 [SMILES: COc1ccnc(C(=O)N[C@@H](C)C(=O)O[C@@H](C)[C@H](OC(=O)C(C)C)C(C)C)c1OCOC(C)=O] | Example 16B | Yellow Oil |

TABLE 1-continued

Compound Structure, Appearance, and Preparation Method

| *Cmpd. No. | Structure | Prepared According to Example: | Appearance |
|---|---|---|---|
| 624 | 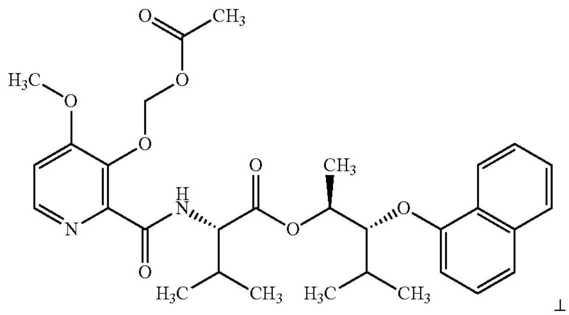 [SMILES: COc1ccnc(C(=O)N[C@H](C(=O)O[C@@H](C)[C@H](Oc2cccc3ccccc23)C(C)C)C(C)C)c1OCOC(C)=O] | Example 16B | Sticky Solid |
| 625 | 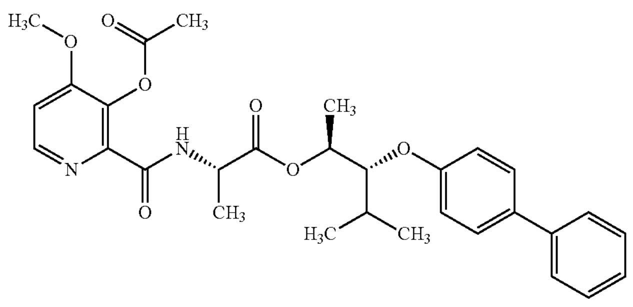 | Example 16A | White Solid |
| 626 | 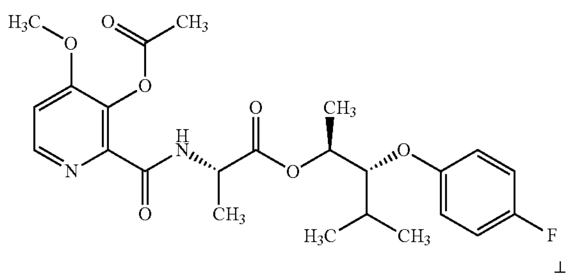 [SMILES: COc1ccnc(C(=O)N[C@@H](C)C(=O)O[C@@H](C)[C@H](Oc2ccc(F)cc2)C(C)C)c1OC(C)=O] | Example 16A | White Solid |
| 627 | 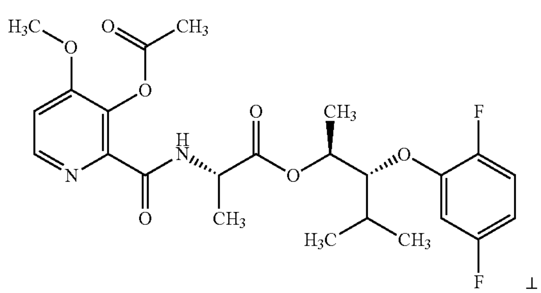 [SMILES: COc1ccnc(C(=O)N[C@@H](C)C(=O)O[C@@H](C)[C@H](Oc2cc(F)ccc2F)C(C)C)c1OC(C)=O] | Example 16A | White Solid |
| 628 | 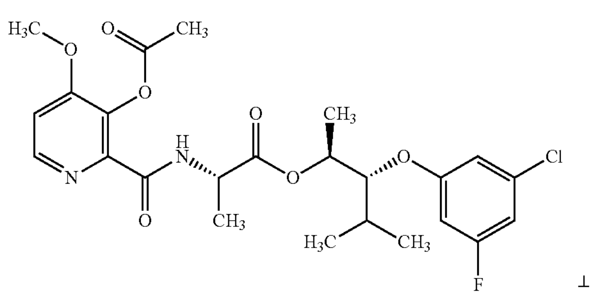 [SMILES: COc1ccnc(C(=O)N[C@@H](C)C(=O)O[C@@H](C)[C@H](Oc2cc(F)cc(Cl)c2)C(C)C)c1OC(C)=O] | Example 16A | White Solid |

TABLE 1-continued

Compound Structure, Appearance, and Preparation Method

| *Cmpd. No. | Structure | Prepared According to Example: | Appearance |
|---|---|---|---|
| 629 | 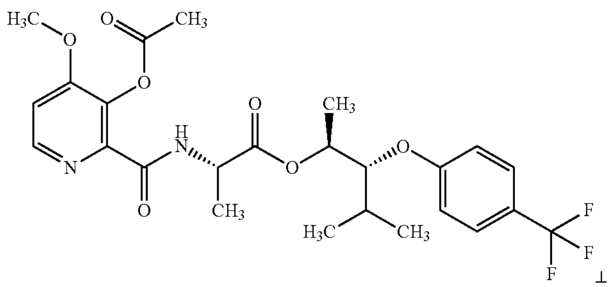 [SMILES: COc1ccnc(C(=O)N[C@@H](C)C(=O)O[C@@H](C)[C@H](Oc2ccc(C(F)(F)F)cc2)C(C)C)c1OC(C)=O] | Example 16A | White Solid |
| 630 | 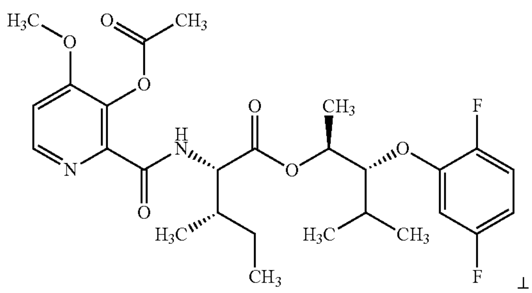 [SMILES: CC[C@H](C)[C@H](NC(=O)c1nccc(OC)c1OC(C)=O)C(=O)O[C@@H](C)[C@H](Oc1cc(F)ccc1F)C(C)C] | Example 16A | Colorless Oil |
| 631 | 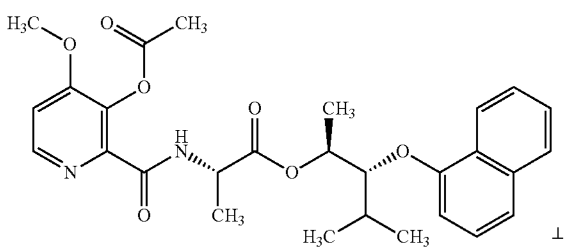 [SMILES: COc1ccnc(C(=O)N[C@@H](C)C(=O)O[C@@H](C)[C@H](Oc2cccc3ccccc23)C(C)C)c1OC(C)=O] | Example 16A | White Solid |
| 632 | 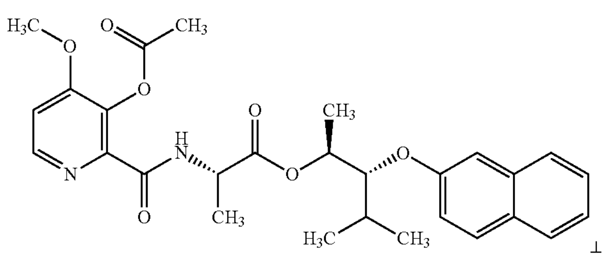 [SMILES: COc1ccnc(C(=O)N[C@@H](C)C(=O)O[C@@H](C)[C@H](Oc2ccc3ccccc3c2)C(C)C)c1OC(C)=O] | Example 16A | White Solid |
| 633 | 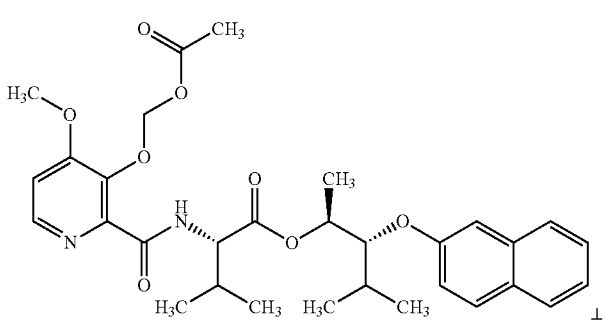 [SMILES: COc1ccnc(C(=O)N[C@H](C(=O)O[C@@H](C)[C@H](Oc2ccc3ccccc3c2)C(C)C)C(C)C)c1OCOC(C)=O] | Example 16B | Colorless Oil |

TABLE 1-continued
Compound Structure, Appearance, and Preparation Method
| *Cmpd. No. | Structure | Prepared According to Example: | Appearance |
|---|---|---|---|
| 634 | 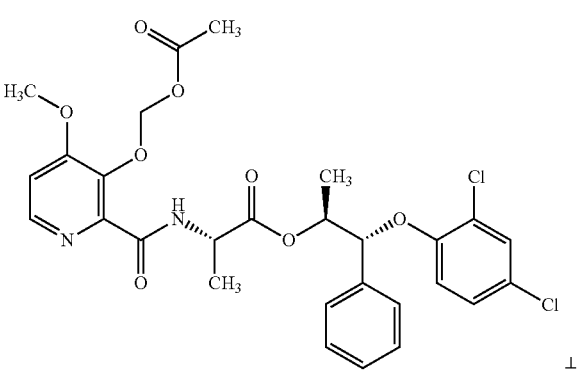 [SMILES: COc1ccnc(C(=O)N[C@@H](C)C(=O)O[C@@H](C)[C@H](Oc2ccc(Cl)cc2Cl)c2ccccc2)c1OCOC(C)=O] | Example 16B | White Powder |
| 635 | 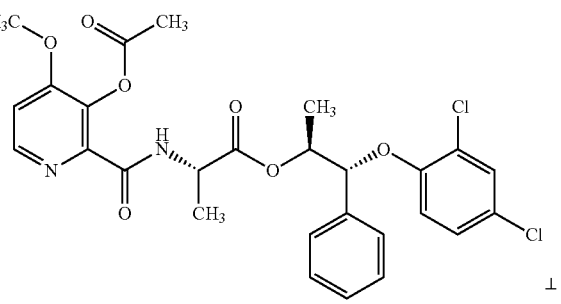 | Example 16A | White Powder |
| 636 | 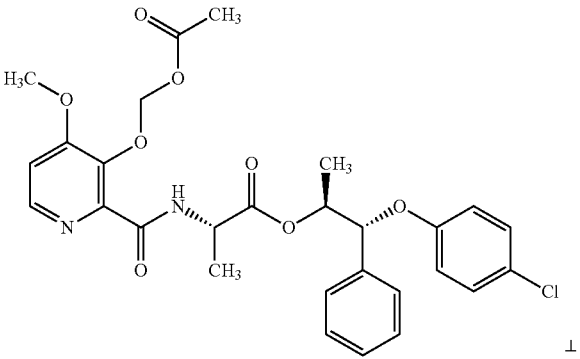 [SMILES: COc1ccnc(C(=O)N[C@@H](C)C(=O)O[C@@H](C)[C@H](Oc2ccc(Cl)cc2)c2ccccc2)c1OCOC(C)=O] | Example 16B | White Powder |
| 637 | 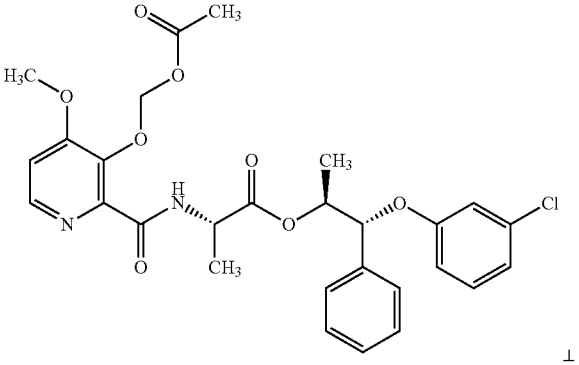 [SMILES: COc1ccnc(C(=O)N[C@@H](C)C(=O)O[C@@H](C)[C@H](Oc2cccc(Cl)c2)c2ccccc2)c1OCOC(C)=O] | Example 16B | Sticky Oil |

TABLE 1-continued
Compound Structure, Appearance, and Preparation Method
| *Cmpd. No. | Structure | Prepared According to Example: | Appearance |
|---|---|---|---|
| 638 | 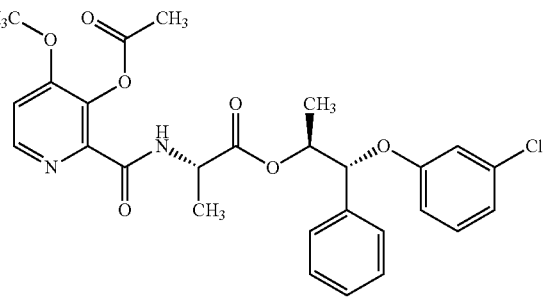 | Example 16A | White Powder |
| 639 | 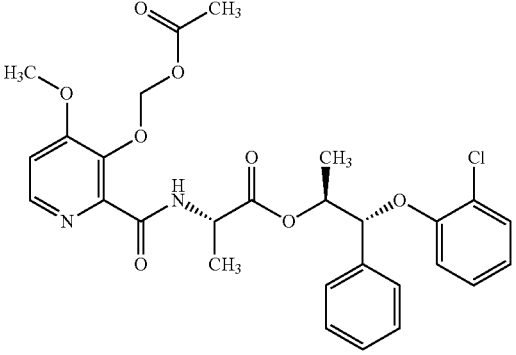 | Example 16B | White Powder |
| 640 | 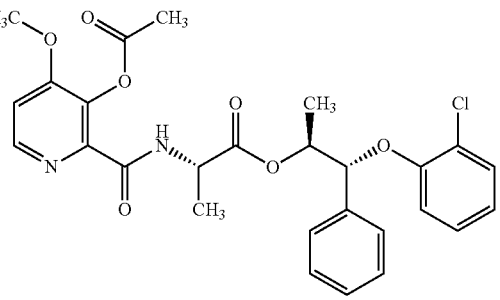 | Example 16A | White Powder |
| 641 | 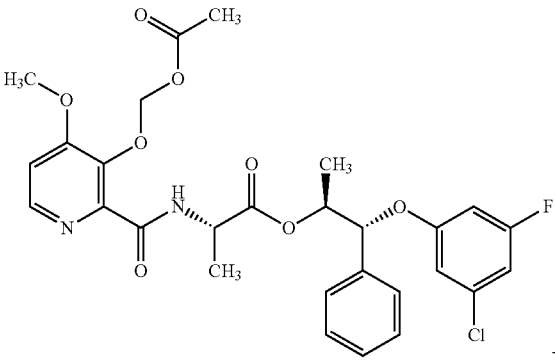 | Example 16B | Semi Solid |

TABLE 1-continued
Compound Structure, Appearance, and Preparation Method
| *Cmpd. No. | Structure | Prepared According to Example: | Appearance |
|---|---|---|---|
| 642 | 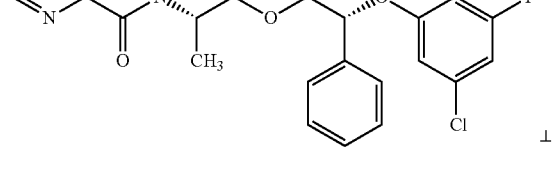 | Example 16A | White Powder |
| 643 | 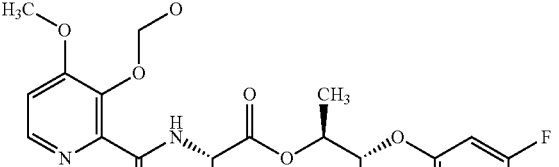 | Example 16B | Sticky White Solid |
| 644 | 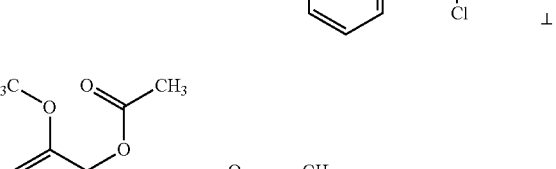 | Example 16A | White Powder |
| 645 | 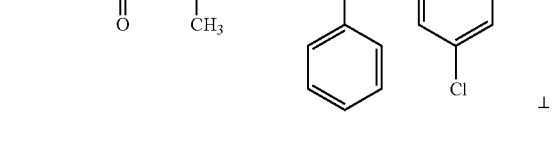 | Example 16B | Colorless Oil |

TABLE 1-continued

Compound Structure, Appearance, and Preparation Method

| *Cmpd. No. | Structure | Prepared According to Example: | Appearance |
|---|---|---|---|
| 646 | 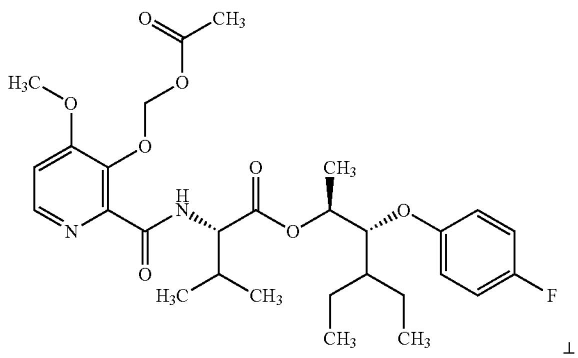 [SMILES: CCC(CC)[C@@H](Oc1ccc(F)cc1)[C@H](C)OC(=O)[C@@H](NC(=O)c1nccc(OC)c1OCOC(C)=O)C(C)C] | Example 16B | Colorless Oil |
| 647 | 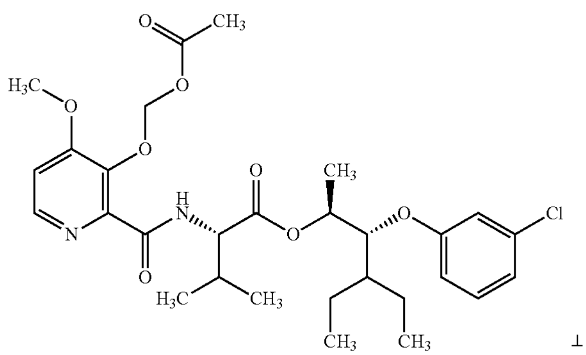 [SMILES: CCC(CC)[C@@H](Oc1cccc(Cl)c1)[C@H](C)OC(=O)[C@@H](NC(=O)c1nccc(OC)c1OCOC(C)=O)C(C)C] | Example 16B | Colorless Oil |
| 648 | 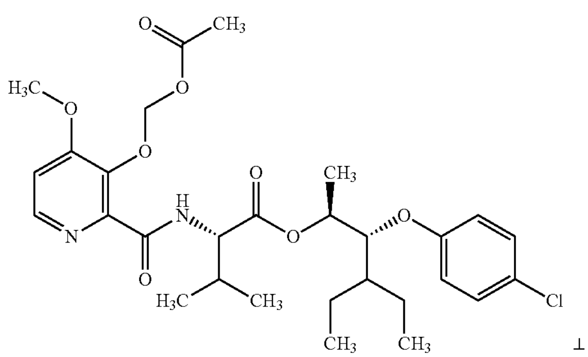 [SMILES: CCC(CC)[C@@H](Oc1ccc(Cl)cc1)[C@H](C)OC(=O)[C@@H](NC(=O)c1nccc(OC)c1OCOC(C)=O)C(C)C] | Example 16B | Colorless Oil |
| 649 | 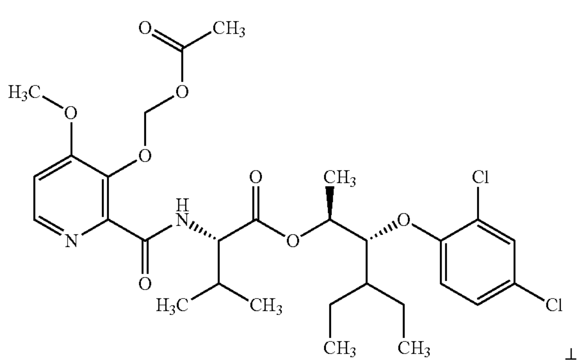 [SMILES: CCC(CC)[C@@H](Oc1ccc(Cl)cc1Cl)[C@H](C)OC(=O)[C@@H](NC(=O)c1nccc(OC)c1OCOC(C)=O)C(C)C] | Example 16B | Colorless Oil |

TABLE 1-continued
Compound Structure, Appearance, and Preparation Method
| *Cmpd. No. | Structure | Prepared According to Example: | Appearance |
|---|---|---|---|
| 650 | 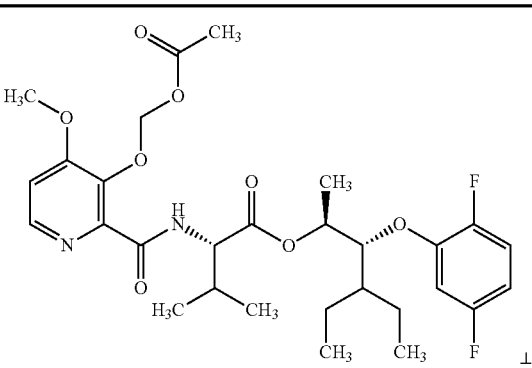 | Example 16B | Colorless Oil |
| 651 | 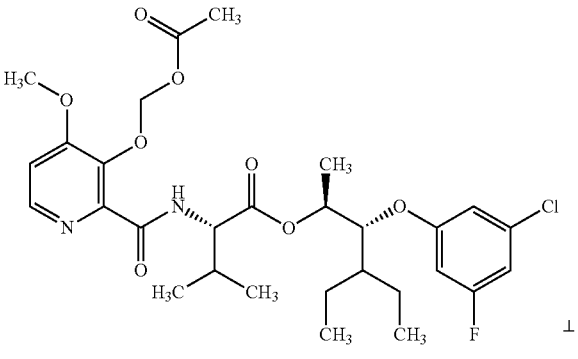 [SMILES: CCC(CC)[C@@H](Oc1cc(F)cc(Cl)c1)[C@H](C)OC(=O)[C@@H](NC(=O)c1nccc(OC)c1OCOC(C)=O)C(C)C] | Example 16B | Colorless Oil |
| 652 | 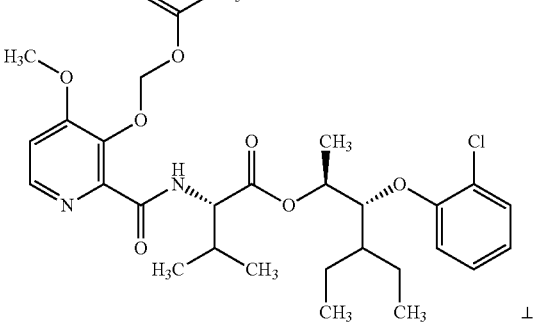 | Example 16B | Colorless Oil |
| 653 | 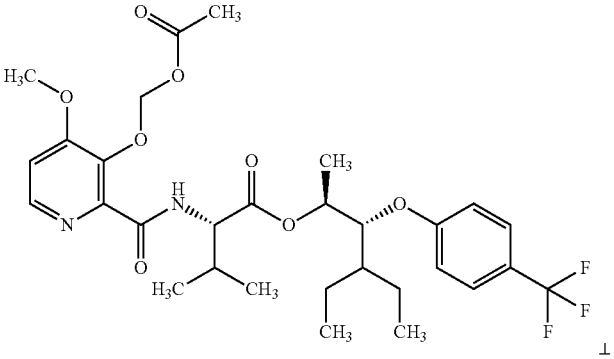 [SMILES: CCC(CC)[C@@H](Oc1ccc(C(F)(F)F)cc1)[C@H](C)OC(=O)[C@@H](NC(=O)c1nccc(OC)c1OCOC(C)=O)C(C)C] | Example 16B | Colorless Oil |

TABLE 1-continued

Compound Structure, Appearance, and Preparation Method

| *Cmpd. No. | Structure | Prepared According to Example: | Appearance |
|---|---|---|---|
| 654 | 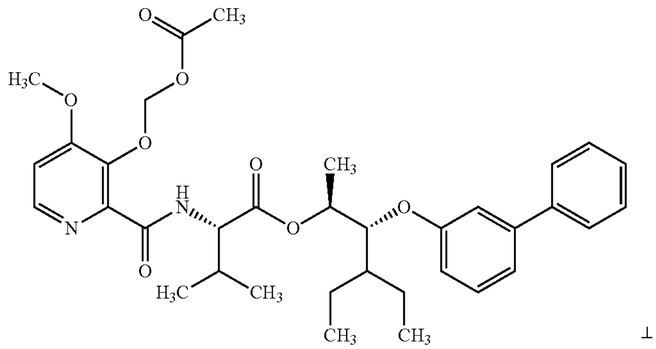 [SMILES: CCC(CC)[C@@H](Oc1cccc(-c2ccccc2)c1)[C@H](C)OC(=O)[C@@H](NC(=O)c1nccc(OC)c1OCOC(C)=O)C(C)C] | Example 16B | Colorless Oil |
| 655 | 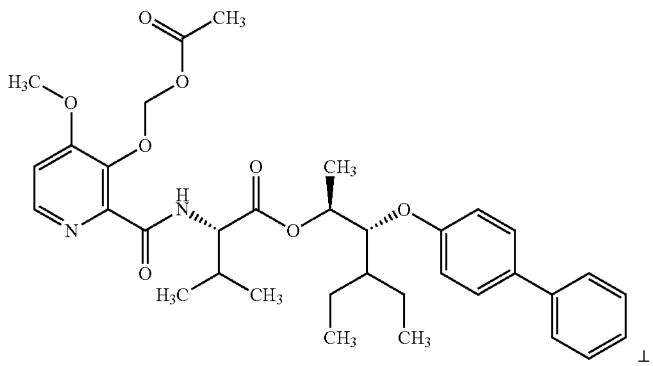 [SMILES: CCC(CC)[C@@H](Oc1ccc(-c2ccccc2)cc1)[C@H](C)OC(=O)[C@@H](NC(=O)c1nccc(OC)c1OCOC(C)=O)C(C)C] | Example 16B | Colorless Oil |
| 656 | 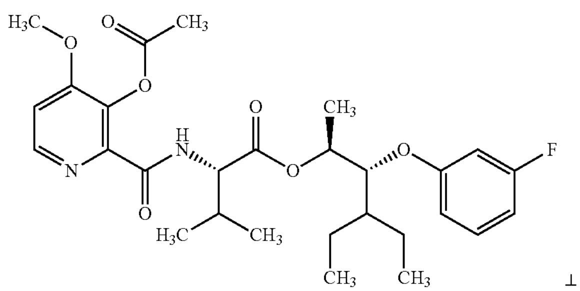 [SMILES: CCC(CC)[C@@H](Oc1cccc(F)c1)[C@H](C)OC(=O)[C@@H](NC(=O)c1nccc(OC)c1OC(C)=O)C(C)C] | Example 16A | Colorless Oil |
| 657 | 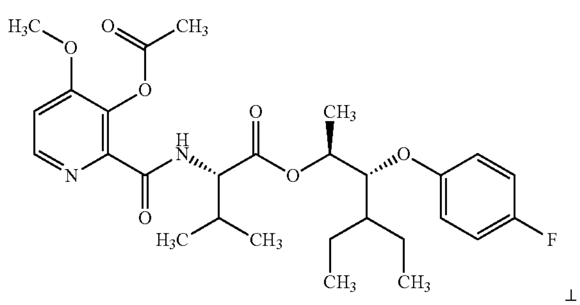 [SMILES: CCC(CC)[C@@H](Oc1ccc(F)cc1)[C@H](C)OC(=O)[C@@H](NC(=O)c1nccc(OC)c1OC(C)=O)C(C)C] | Example 16A | Colorless Oil |

TABLE 1-continued

Compound Structure, Appearance, and Preparation Method

| *Cmpd. No. | Structure | Prepared According to Example: | Appearance |
|---|---|---|---|
| 658 | 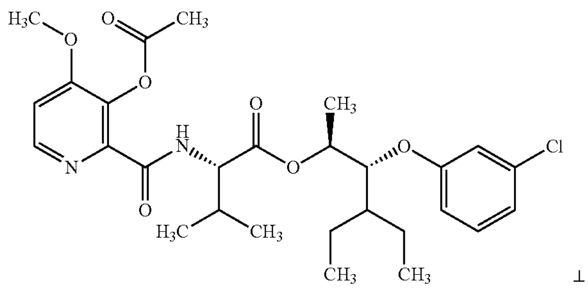 [SMILES: CCC(CC)[C@@H](Oc1cccc(Cl)c1)[C@H](C)OC(=O)[C@@H](NC(=O)c1nccc(OC)c1OC(C)=O)C(C)C] | Example 16A | Colorless Oil |
| 659 | 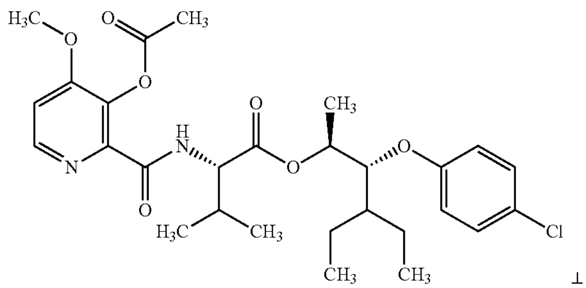 [SMILES: CCC(CC)[C@@H](Oc1ccc(Cl)cc1)[C@H](C)OC(=O)[C@@H](NC(=O)c1nccc(OC)c1OC(C)=O)C(C)C] | Example 16A | Colorless Oil |
| 660 | 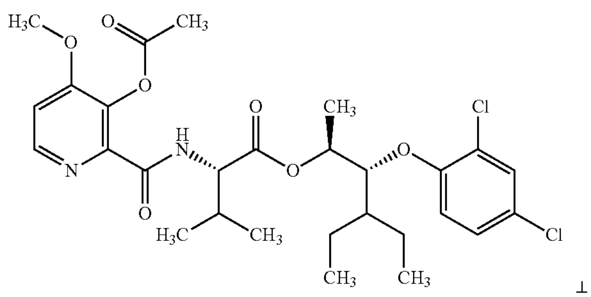 [SMILES: CCC(CC)[C@@H](Oc1ccc(Cl)cc1Cl)[C@H](C)OC(=O)[C@@H](NC(=O)c1nccc(OC)c1OC(C)=O)C(C)C] | Example 16A | Colorless Oil |
| 661 | 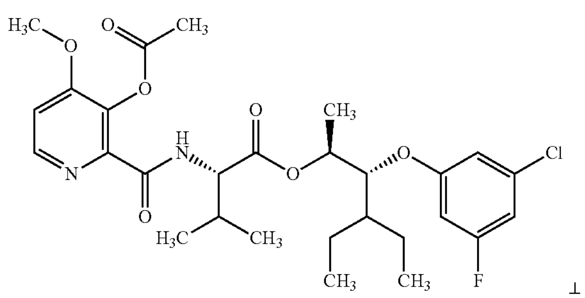 [SMILES: CCC(CC)[C@@H](Oc1cc(F)cc(Cl)c1)[C@H](C)OC(=O)[C@@H](NC(=O)c1nccc(OC)c1OC(C)=O)C(C)C] | Example 16A | Colorless Oil |
| 662 | 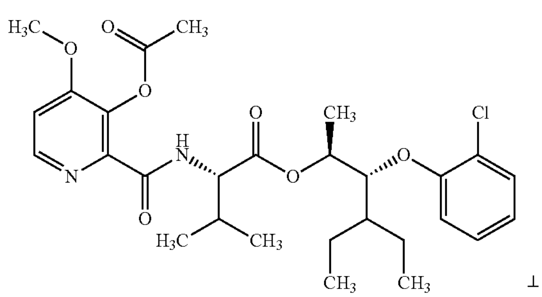 [SMILES: CCC(CC)[C@@H](Oc1ccccc1Cl)[C@H](C)OC(=O)[C@@H](NC(=O)c1nccc(OC)c1OC(C)=O)C(C)C] | Example 16A | Colorless Oil |

TABLE 1-continued

Compound Structure, Appearance, and Preparation Method

| *Cmpd. No. | Structure | Prepared According to Example: | Appearance |
|---|---|---|---|
| 663 | 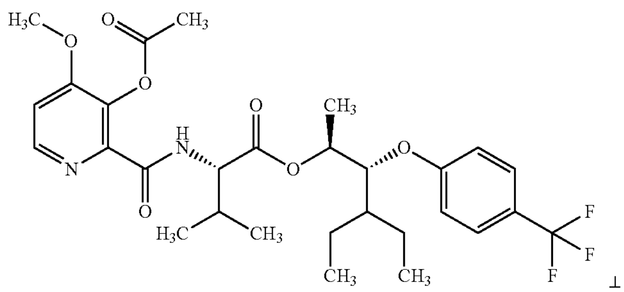 [SMILES: CCC(CC)[C@@H](Oc1ccc(C(F)(F)F)cc1)[C@H](C)OC(=O)[C@@H](NC(=O)c1nccc(OC)c1OC(C)=O)C(C)C] | Example 16A | Colorless Oil |
| 664 | 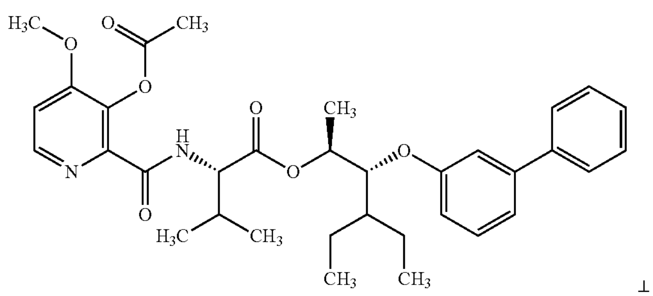 [SMILES: CCC(CC)[C@@H](Oc1cccc(-c2ccccc2)c1)[C@H](C)OC(=O)[C@@H](NC(=O)c1nccc(OC)c1OC(C)=O)C(C)C] | Example 16A | Tacky Oil |
| 665 | 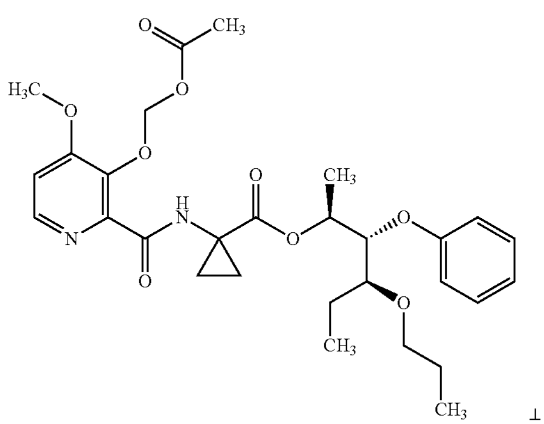 [SMILES: CCCO[C@@H](CC)[C@@H](Oc1ccccc1)[C@H](C)OC(=O)C1(NC(=O)c2nccc(OC)c2OCOC(C)=O)CC1] | Example 16B | Colorless Oil |
| 666 | 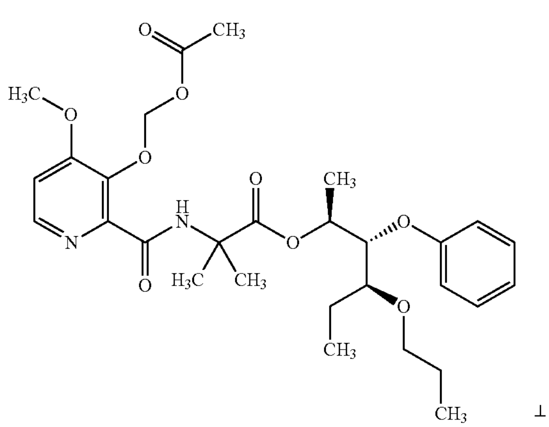 [SMILES: CCCO[C@@H](CC)[C@@H](Oc1ccccc1)[C@H](C)OC(=O)C(C)(C)NC(=O)c1nccc(OC)c1OCOC(C)=O] | Example 16B | Colorless Oil |

TABLE 1-continued

Compound Structure, Appearance, and Preparation Method

| *Cmpd. No. | Structure | Prepared According to Example: | Appearance |
|---|---|---|---|
| 667 | 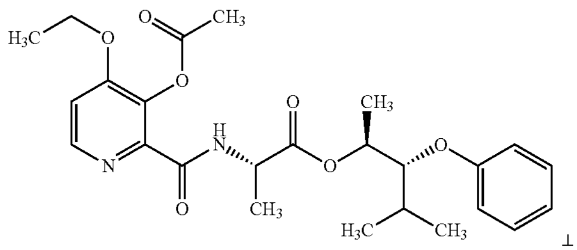 [SMILES: CCOc1ccnc(C(=O)N[C@@H](C)C(=O)O[C@@H](C)[C@H](Oc2ccccc2)C(C)C)c1OC(C)=O] | Example 16A | Light Yellow Oil |
| 668 | 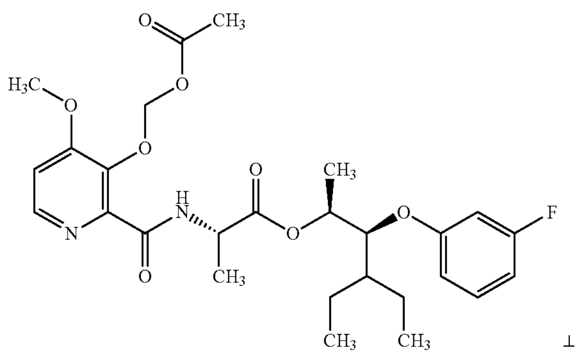 [SMILES: CCC(CC)[C@H](Oc1cccc(F)c1)[C@H](C)OC(=O)[C@H](C)NC(=O)c1nccc(OC)c1OCOC(C)=O] | Example 16B | Colorless Oil |
| 669 | 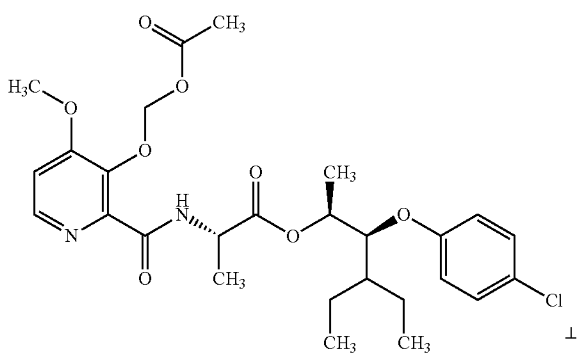 [SMILES: CCC(CC)[C@H](Oc1ccc(Cl)cc1)[C@H](C)OC(=O)[C@H](C)NC(=O)c1nccc(OC)c1OCOC(C)=O] | Example 16B | Colorless Oil |
| 670 | 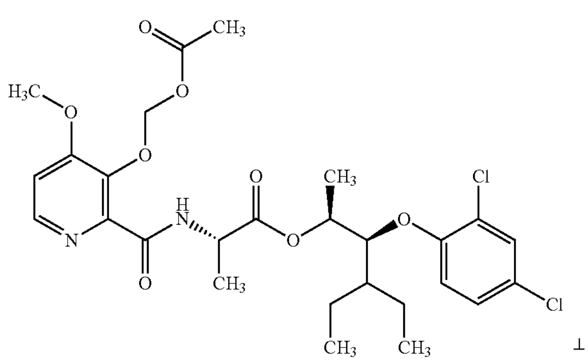 [SMILES: CCC(CC)[C@H](Oc1ccc(Cl)cc1Cl)[C@H](C)OC(=O)[C@H](C)NC(=O)c1nccc(OC)c1OCOC(C)=O] | Example 16B | Colorless Oil |

TABLE 1-continued

Compound Structure, Appearance, and Preparation Method

| *Cmpd. No. | Structure | Prepared According to Example: | Appearance |
|---|---|---|---|
| 671 | 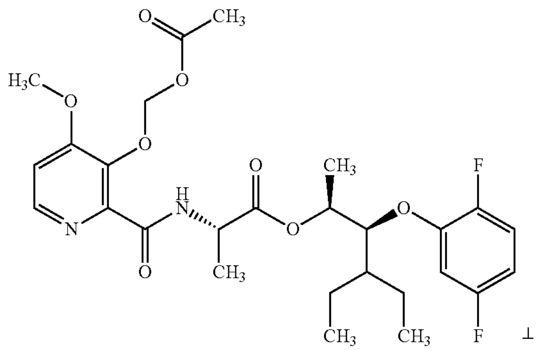 [SMILES: CCC(CC)[C@H](Oc1cc(F)ccc1F)[C@H](C)OC(=O)[C@H](C)NC(=O)c1nccc(OC)c1OCOC(C)=O] | Example 16B | Colorless Oil |
| 672 | 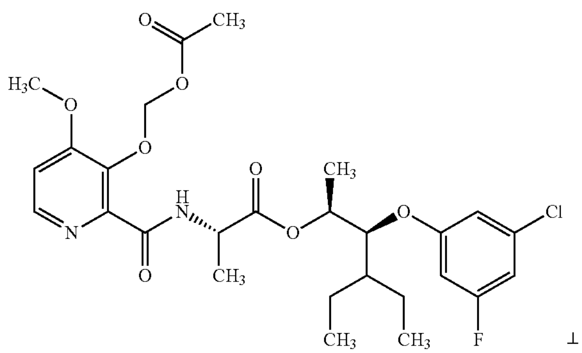 [SMILES: CCC(CC)[C@H](Oc1cc(F)cc(Cl)c1)[C@H](C)OC(=O)[C@H](C)NC(=O)c1nccc(OC)c1OCOC(C)=O] | Example 16B | Colorless Oil |
| 673 | 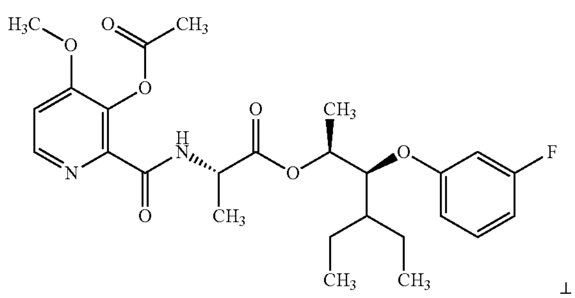 [SMILES: CCC(CC)[C@H](Oc1cccc(F)c1)[C@H](C)OC(=O)[C@H](C)NC(=O)c1nccc(OC)c1OC(C)=O] | Example 16A | Colorless Oil |
| 674 | 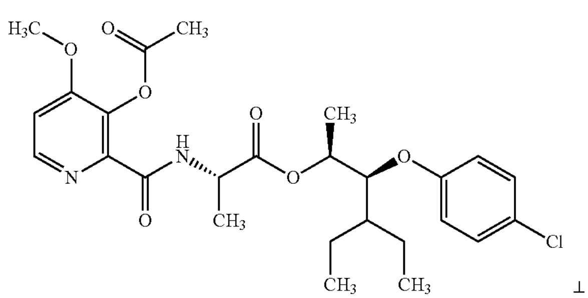 [SMILES: CCC(CC)[C@H](Oc1ccc(Cl)cc1)[C@H](C)OC(=O)[C@H](C)NC(=O)c1nccc(OC)c1OC(C)=O] | Example 16A | Colorless Oil |

TABLE 1-continued

Compound Structure, Appearance, and Preparation Method

| *Cmpd. No. | Structure | Prepared According to Example: | Appearance |
|---|---|---|---|
| 675 | 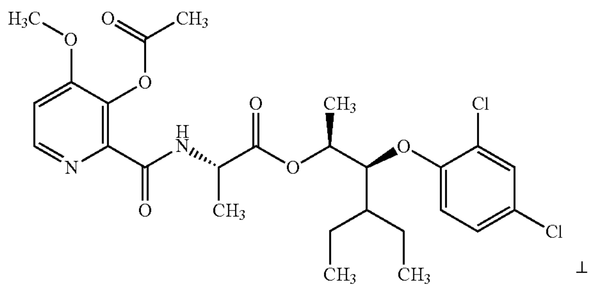 [SMILES: CCC(CC)[C@H](Oc1ccc(Cl)cc1Cl)[C@H](C)OC(=O)[C@H](C)NC(=O)c1nccc(OC)c1OC(C)=O] | Example 16A | Colorless Oil |
| 676 | 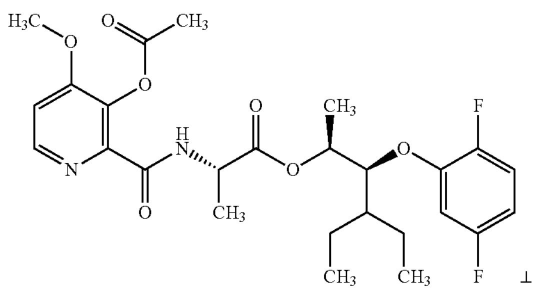 [SMILES: CCC(CC)[C@H](Oc1cc(F)ccc1F)[C@H](C)OC(=O)[C@H](C)NC(=O)c1nccc(OC)c1OC(C)=O] | Example 16A | Colorless Oil |
| 677 | 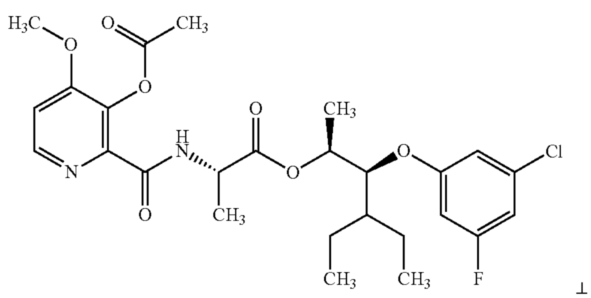 [SMILES: CCC(CC)[C@H](Oc1cc(F)cc(Cl)c1)[C@H](C)OC(=O)[C@H](C)NC(=O)c1nccc(OC)c1OC(C)=O] | Example 16A | Colorless Oil |
| 678 | 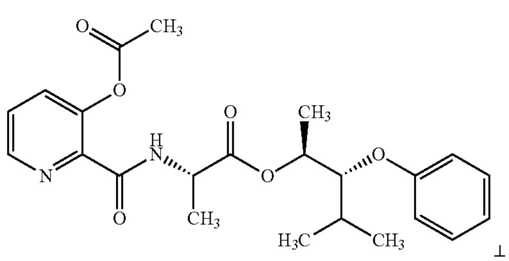 [SMILES: CC(=O)Oc1cccnc1C(=O)N[C@@H](C)C(=O)O[C@@H](C)[C@H](Oc1ccccc1)C(C)C] | Example 16A | Light Yellow Oil |
| 679 | 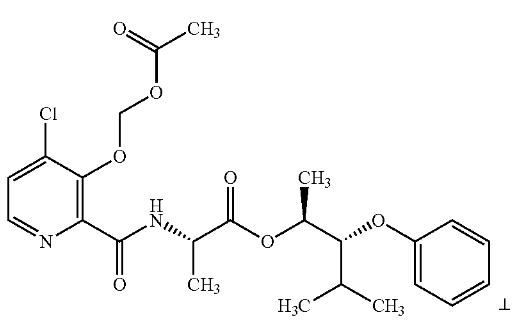 [SMILES: CC(=O)OCOc1c(Cl)ccnc1C(=O)N[C@@H](C)C(=O)O[C@@H](C)[C@H](Oc1ccccc1)C(C)C] | Example 16B | Clear Oil |

TABLE 1-continued
Compound Structure, Appearance, and Preparation Method
| *Cmpd. No. | Structure | Prepared According to Example: | Appearance |
|---|---|---|---|
| 680 | 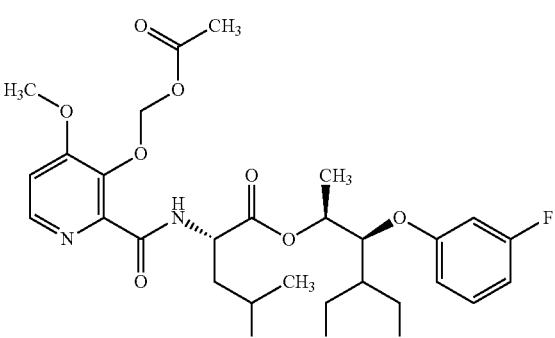 | Example 16B | Colorless Oil |
| 681 | 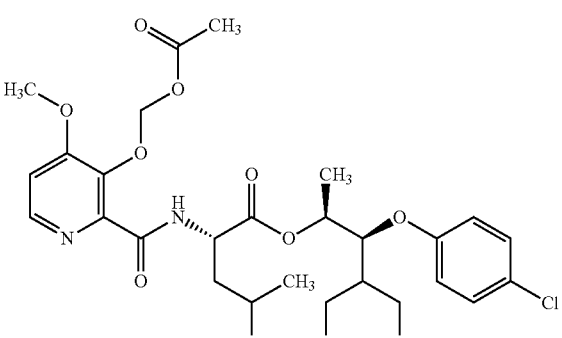 | Example 16B | White Foam |
| 682 | 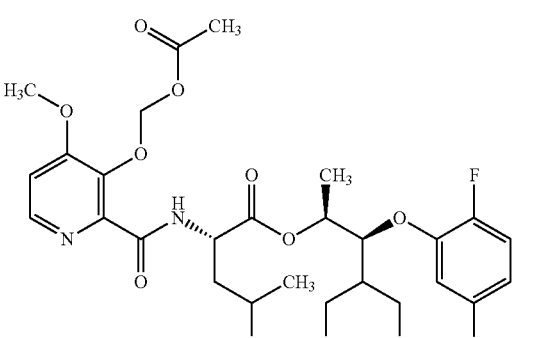 | Example 16B | Colorless Oil |
| 683 | 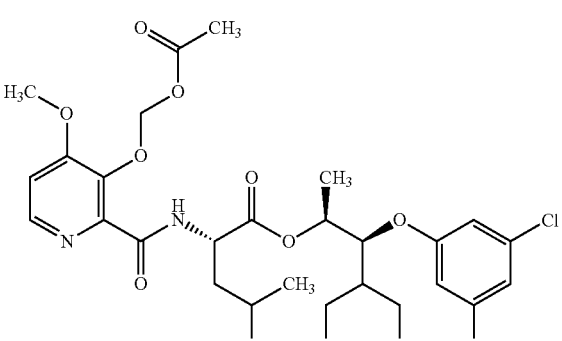 | Example 16B | Colorless Oil |

TABLE 1-continued
Compound Structure, Appearance, and Preparation Method
| *Cmpd. No. | Structure | Prepared According to Example: | Appearance |
|---|---|---|---|
| 684 | 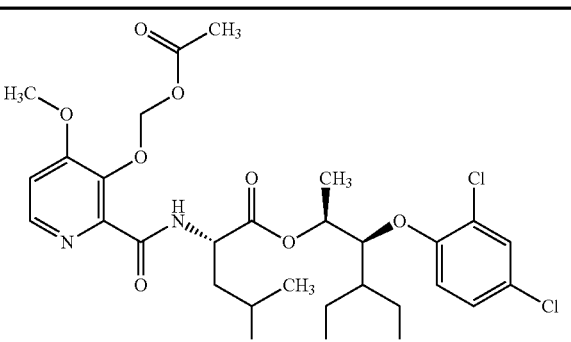 | Example 16B | Colorless Oil |
| 685 | 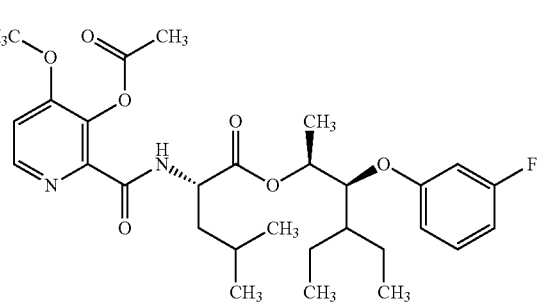 | Example 16A | Colorless Oil |
| 686 | 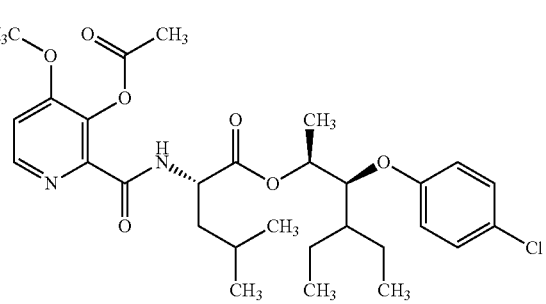 | Example 16A | Colorless Oil |
| 687 | 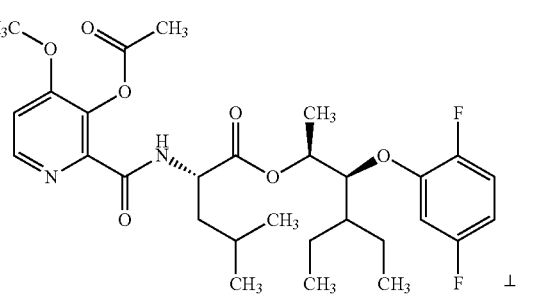 | Example 16A | Colorless Oil |
| 688 | 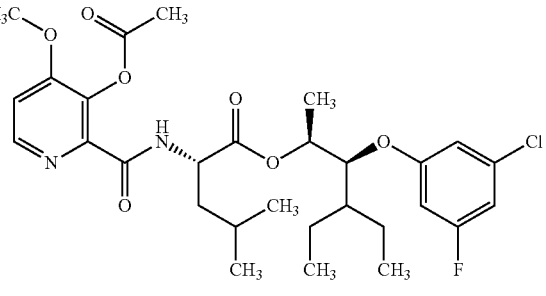 | Example 16A | Colorless Oil |

TABLE 1-continued

Compound Structure, Appearance, and Preparation Method

| *Cmpd. No. | Structure | Prepared According to Example: | Appearance |
|---|---|---|---|
| 689 | 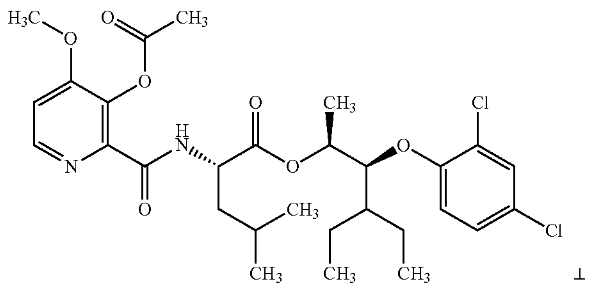 [SMILES: CCC(CC)[C@H](Oc1ccc(Cl)cc1)[C@H](C)OC(=O)[C@H](CC(C)C)NC(=O)c1nccc(OC)c1OC(C)=O] | Example 16A | Colorless Oil |
| 690 | 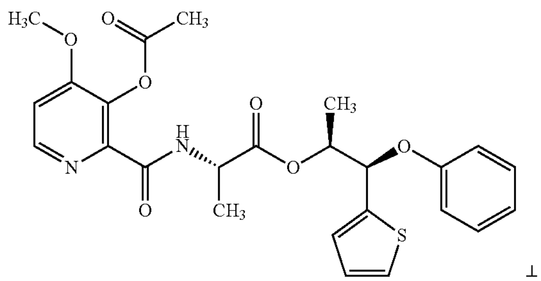 [SMILES: COc1ccnc(C(=O)N[C@@H](C)C(=O)O[C@@H](C)[C@@H](Oc2ccccc2)c2cccs2)c1OC(C)=O] | Example 16A | Colorless Oil |
| 691 | 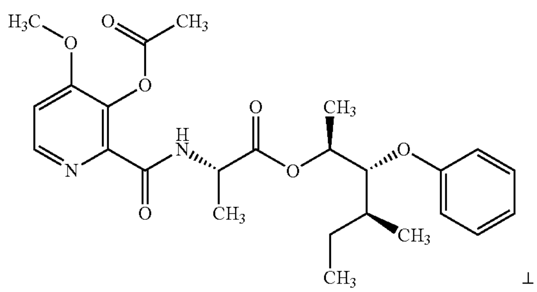 [SMILES: CC[C@H](C)[C@@H](Oc1ccccc1)[C@H](C)OC(=O)[C@H](C)NC(=O)c1nccc(OC)c1OC(C)=O] | Example 16A | Waxy Solid |
| 692 | 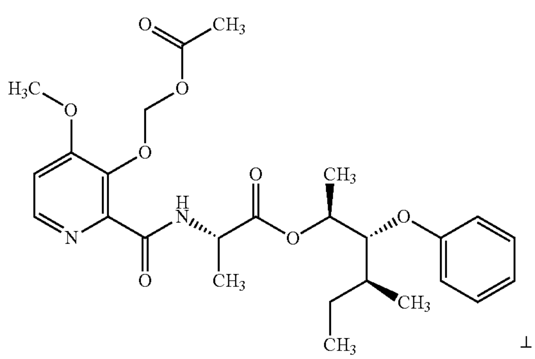 | Example 16B | Clear Yellow Oil |
| 693 | 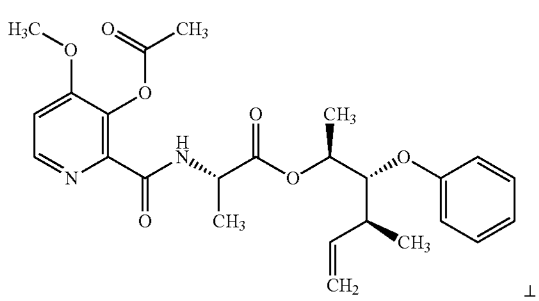 [SMILES: C=C[C@H](C)[C@@H](Oc1ccccc1)[C@H](C)OC(=O)[C@H](C)NC(=O)c1nccc(OC)c1OC(C)=O] | Example 16A | White Solid |

TABLE 1-continued

Compound Structure, Appearance, and Preparation Method

| *Cmpd. No. | Structure | Prepared According to Example: | Appearance |
|---|---|---|---|
| 694 | 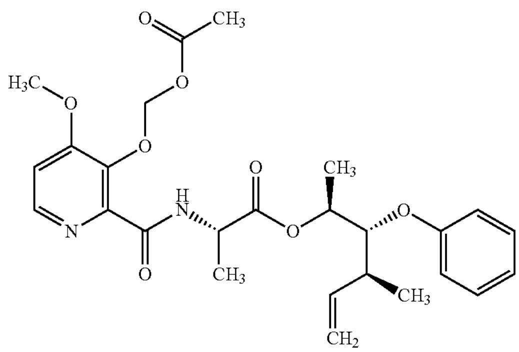 | Example 16B | Yellow Oil |
| 695 | 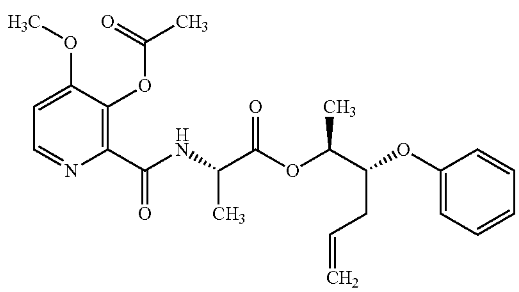 | Example 16A | Yellow Oil |
| 696 | 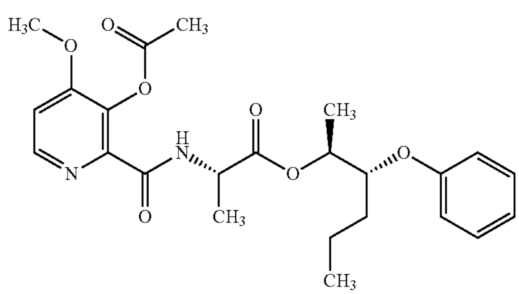 | Example 16A | Yellow Oil |
| 697 | 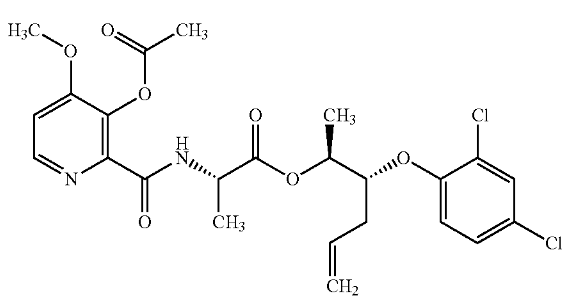 | Example 16A | Yellow Oil |

TABLE 1-continued

Compound Structure, Appearance, and Preparation Method

| *Cmpd. No. | Structure | Prepared According to Example: | Appearance |
|---|---|---|---|
| 698 | 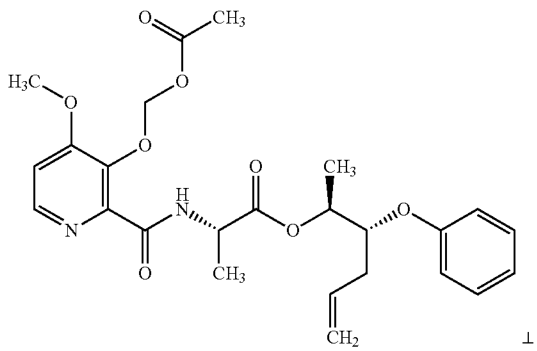 [SMILES: C=CC[C@@H](Oc1ccccc1)[C@H](C)OC(=O)[C@H](C)NC(=O)c1nccc(OC)c1OCOC(C)=O] | Example 16B | Clear, Colorless Oil |
| 699 | 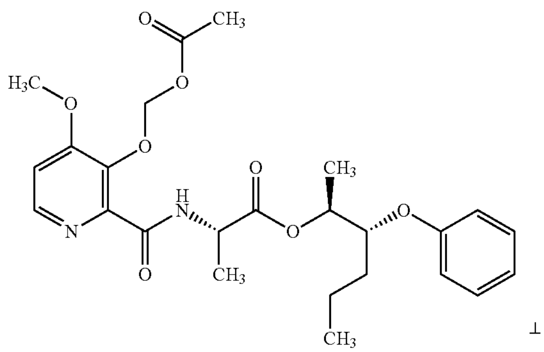 [SMILES: CCC[C@@H](Oc1ccccc1)[C@H](C)OC(=O)[C@H](C)NC(=O)c1nccc(OC)c1OCOC(C)=O] | Example 16B | Clear, Colorless Oil |
| 700 | 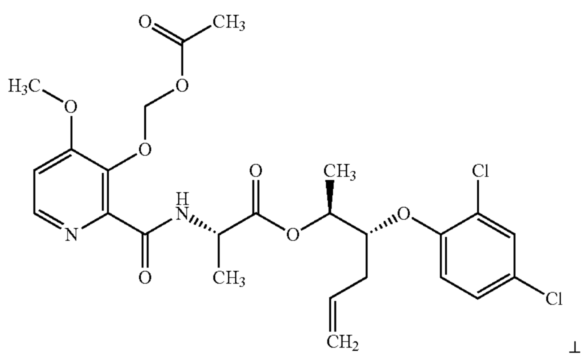 [SMILES: C=CC[C@@H](Oc1ccc(Cl)cc1Cl)[C@H](C)OC(=O)[C@H](C)NC(=O)c1nccc(OC)c1OCOC(C)=O] | Example 16B | Clear, Colorless Oil |
| 701 | 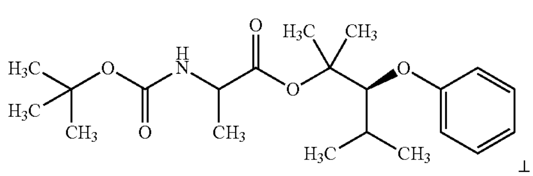 [SMILES: CC(NC(=O)OC(C)(C)C)C(=O)OC(C)(C)[C@@H](Oc1ccccc1)C(C)C] | Example 9, Steps 1-3; Example 11 Steps 1, 2; Example 12B | Colorless Oil |
| 702 | 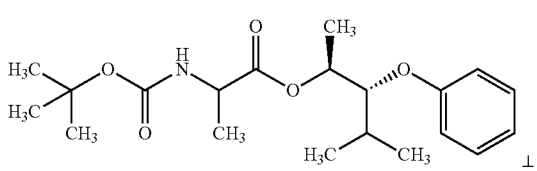 [SMILES: CC(NC(=O)OC(C)(C)C)C(=O)O[C@@H](C)[C@H](Oc1ccccc1)C(C)C] | Example 1A; Example 4B; Example 8C; Example 12A | Colorless Oil |

TABLE 1-continued

Compound Structure, Appearance, and Preparation Method

| *Cmpd. No. | Structure | Prepared According to Example: | Appearance |
|---|---|---|---|
| 703 | 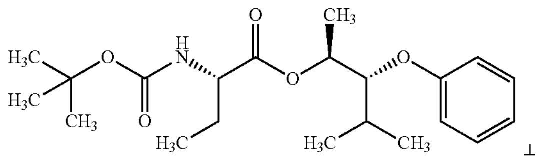 [SMILES: CC[C@H](NC(=O)OC(C)(C)C)C(=O)O[C@@H](C)[C@H](Oc1ccccc1)C(C)C] | Example 1A; Example 4B; Example 8C; Example 12A | Colorless Oil |
| 704 | 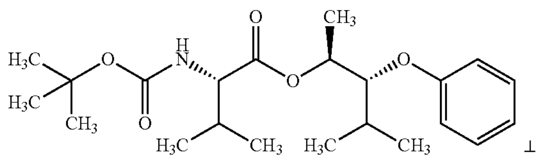 | Example 1A; Example 4B; Example 8C; Example 12A | Colorless Oil |
| 705 | 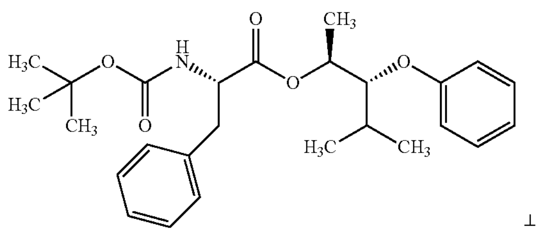 [SMILES: CC(C)[C@@H](Oc1ccccc1)[C@H](C)OC(=O)[C@H](Cc1ccccc1)NC(=O)OC(C)(C)C] | Example 1A; Example 4B; Example 8C; Example 12A | Colorless Oil |
| 706 | 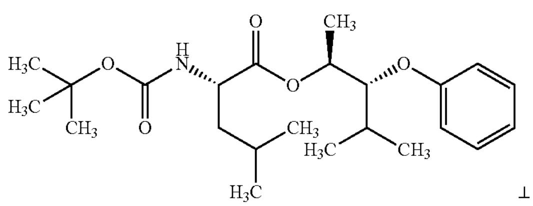 [SMILES: CC(C)C[C@H](NC(=O)OC(C)(C)C)C(=O)O[C@@H](C)[C@H](Oc1ccccc1)C(C)C] | Example 1A; Example 4B; Example 8C; Example 12A | Colorless Oil |
| 707 | 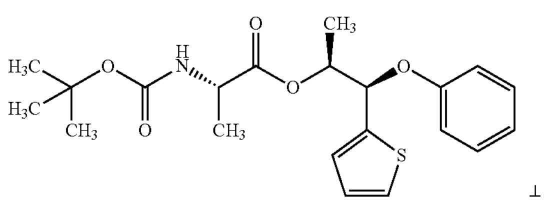 [SMILES: C[C@H](NC(=O)OC(C)(C)C)C(=O)O[C@@H](C)[C@@H](Oc1ccccc1)c1cccs1] | Example 1E; Example 4B; Example 8D; Example 12A | Colorless Oil |
| 708 | 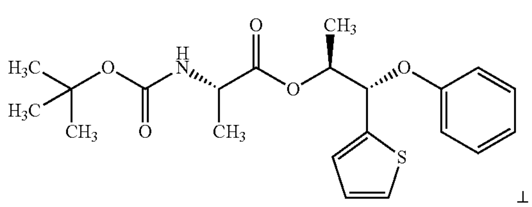 [SMILES: C[C@H](NC(=O)OC(C)(C)C)C(=O)O[C@@H](C)[C@H](Oc1ccccc1)c1cccs1] | Example 1E; Example 4B; Example 8D; Example 12A | Colorless Oil |
| 709 | 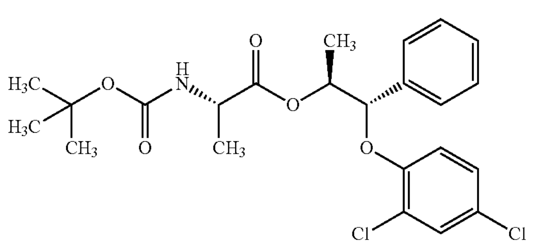 | Example 1B, Steps 1, 2; Example 4C; Example 8A; Example 12A | Colorless Oil |

TABLE 1-continued

Compound Structure, Appearance, and Preparation Method

| *Cmpd. No. | Structure | Prepared According to Example: | Appearance |
|---|---|---|---|
| 710 | 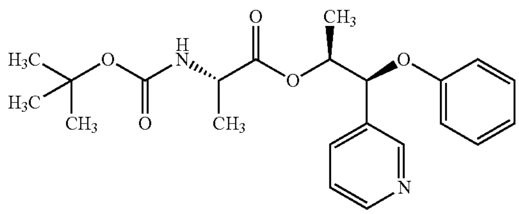 | Example 1E; Example 4B; Example 8D; Example 12A | Colorless Oil |
| 711 | 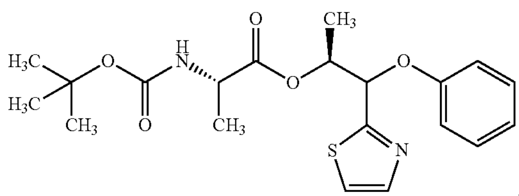 | Example 1E; Example 4B; Example 8D; Example 12A | Colorless Oil |
| 712 | 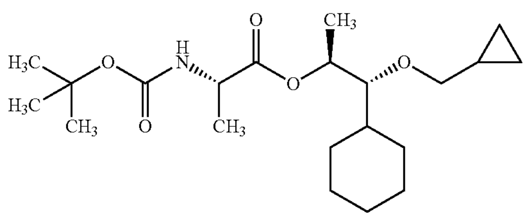 | Example 1A; Example 4D; Example 8A; Example 12A | Colorless Oil |
| 713 | 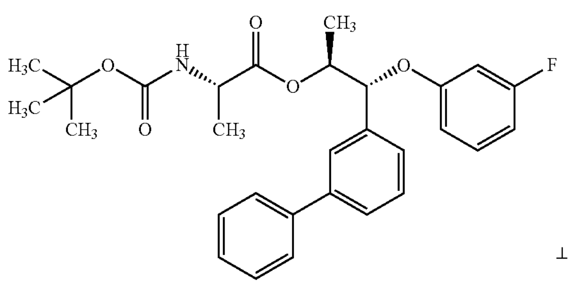 [SMILES: C[C@H](NC(=O)OC(C)(C)C)C(=O)O[C@@H](C)[C@H](Oc1cccc(F)c1)c1cccc(-c2ccccc2)c1] | Example 1A; Example 4C; Example 8A; Example 12A | Colorless Oil |
| 714 | 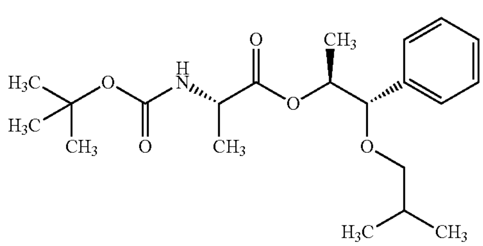 | Example 1B, Steps 1, 2; Example 4F; Example 8B; Example 12A | Colorless Oil |
| 715 | 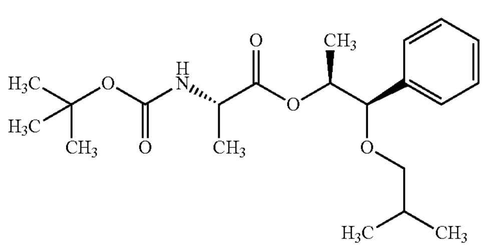 | Example 1B, Steps 1, 2; Example 4F; Example 8B; Example 12A | Colorelss Oil |

TABLE 1-continued

Compound Structure, Appearance, and Preparation Method

| *Cmpd. No. | Structure | Prepared According to Example: | Appearance |
|---|---|---|---|
| 716 | 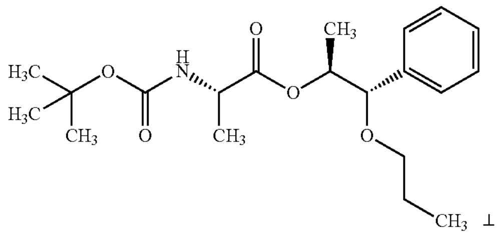 [SMILES: CCCO[C@@H](c1ccccc1)[C@H](C)OC(=O)[C@H](C)NC(=O)OC(C)(C)C] | Example 1B, Steps 1, 2; Example 4F; Example 8C; Example 12A | Colorless Oil |
| 717 | 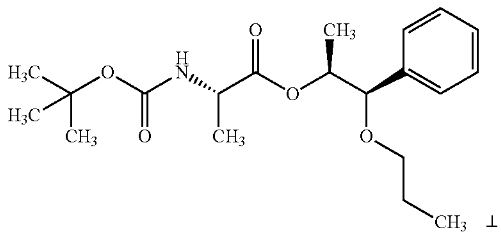 [SMILES: CCCO[C@H](c1ccccc1)[C@H](C)OC(=O)[C@H](C)NC(=O)OC(C)(C)C] | Example 1B, Steps 1, 2; Example 4F; Example 8C; Example 12A | Colorless Oil |
| 718 | 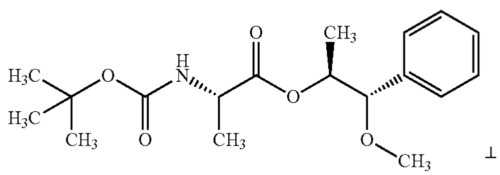 [SMILES: CO[C@@H](c1ccccc1)[C@H](C)OC(=O)[C@H](C)NC(=O)OC(C)(C)C] | Example 1B, Steps 1, 2; Example 4D; Example 8D; Example 12A | Colorless Oil |
| 719 | 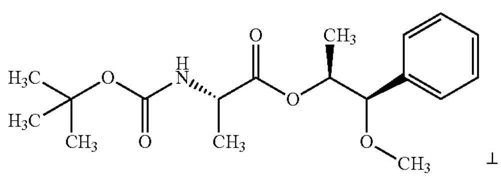 [SMILES: CO[C@H](c1ccccc1)[C@H](C)OC(=O)[C@H](C)NC(=O)OC(C)(C)C] | Example 1B, Steps 1, 2; Example 4D; Example 8D; Example 12A | Colorless Oil |
| 720 | 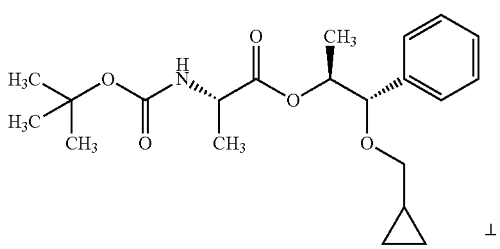 [SMILES: C[C@H](NC(=O)OC(C)(C)C)C(=O)O[C@@H](C)[C@@H](OCC1CC1)c1ccccc1] | Example 1B, Steps 1, 2; Example 4D; Example 8D; Example 12A | Colorless Oil |
| 721 | 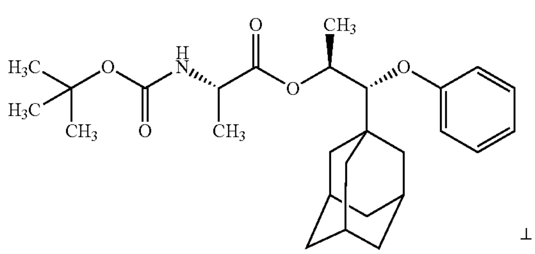 [SMILES: C[C@H](NC(=O)OC(C)(C)C)C(=O)O[C@@H](C)[C@H](Oc1ccccc1)C12CC3CC(CC(C3)C1)C2] | Example 1A; Example 4B; Example 8A; Example 12A | Clear Oil |

TABLE 1-continued

Compound Structure, Appearance, and Preparation Method

| *Cmpd. No. | Structure | Prepared According to Example: | Appearance |
|---|---|---|---|
| 722 | 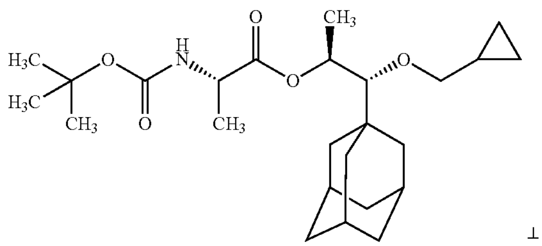 [SMILES: C[C@H](NC(=O)OC(C)(C)C)C(=O)O[C@@H](C)[C@H](OCC1CC1)C12CC3CC(CC(C3)C1)C2] | Example 1A; Example 4D; Example 8A; Example 12A | Clear Oil |
| 723 | 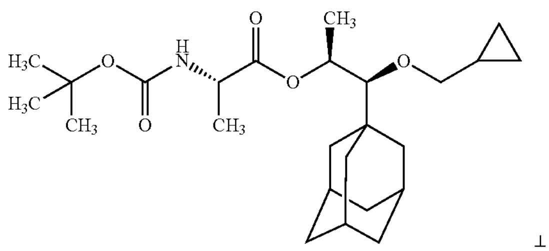 [SMILES: C[C@H](NC(=O)OC(C)(C)C)C(=O)O[C@@H](C)[C@@H](OCC1CC1)C12CC3CC(CC(C3)C1)C2] | Example 1A; Example 4D; Example 8A; Example 12A | Clear Oil |
| 724 | 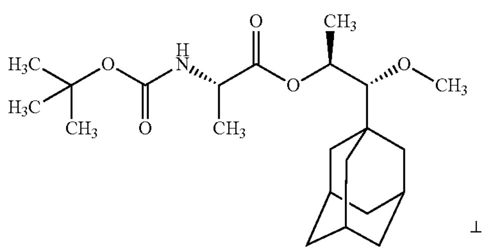 [SMILES: CO[C@@H]([C@H](C)OC(=O)[C@H](C)NC(=O)OC(C)(C)C)C12CC3CC(CC(C3)C1)C2] | Example 1A; Example 4G; Example 8A; Example 12A | Clear Oil |
| 725 | 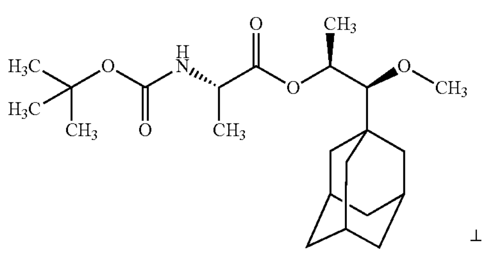 [SMILES: CO[C@H]([C@H](C)OC(=O)[C@H](C)NC(=O)OC(C)(C)C)C12CC3CC(CC(C3)C1)C2] | Example 1A; Example 4G; Example 8A; Example 12A | Clear Oil |
| 726 | 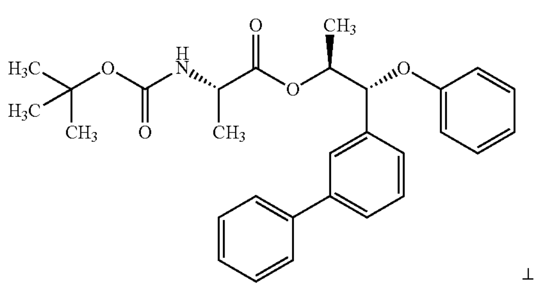 [SMILES: C[C@H](NC(=O)OC(C)(C)C)C(=O)O[C@@H](C)[C@H](Oc1ccccc1)c1cccc(-c2ccccc2)c1] | Example 1A; Example 4B; Example 8A; Example 12A | Colorless Oil |
| 727 | 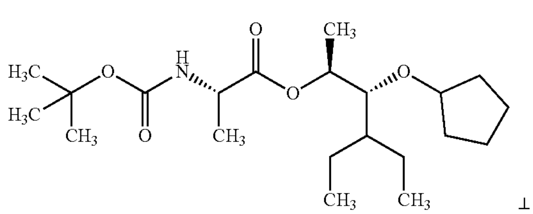 [SMILES: CCC(CC)[C@@H](OC1CCCC1)[C@H](C)OC(=O)[C@H](C)NC(=O)OC(C)(C)C] | Example 1A; Example 4H; Example 8C; Example 12A | Colorless Oil |

TABLE 1-continued

Compound Structure, Appearance, and Preparation Method

| *Cmpd. No. | Structure | Prepared According to Example: | Appearance |
|---|---|---|---|
| 728 | 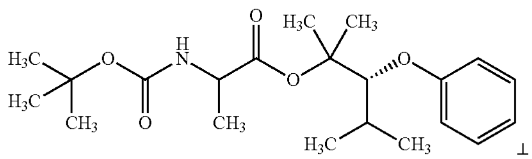 [SMILES: CC(NC(=O)OC(C)(C)C)C(=O)OC(C)(C)[C@H](Oc1ccccc1)C(C)C] | Example 9, Steps 1-3; Example 11, Steps 1, 2; Example 12B | Colorless Oil |
| 729 | 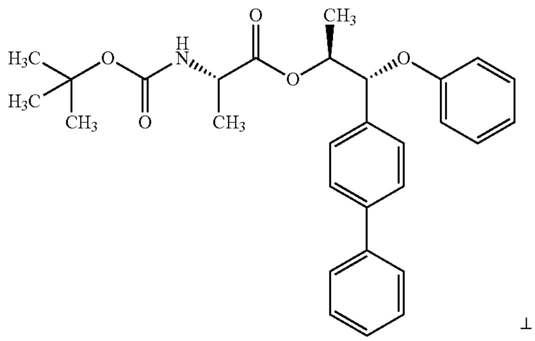 [SMILES: C[C@H](NC(=O)OC(C)(C)C)C(=O)O[C@@H](C)[C@H](Oc1ccccc1)c1ccc(-c2ccccc2)cc1] | Example 1A; Example 4B; Example 8A; Example 12A | Colorless Oil |
| 730 | 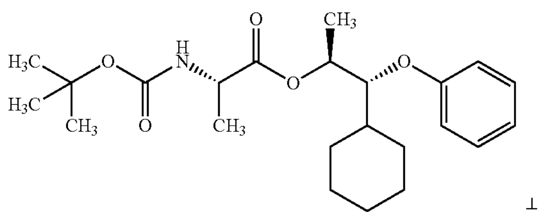 [SMILES: C[C@H](NC(=O)OC(C)(C)C)C(=O)O[C@@H](C)[C@H](Oc1ccccc1)C1CCCCC1] | Example 1A; Example 4B; Example 8A; Example 12A | Colorless Oil |
| 731 | 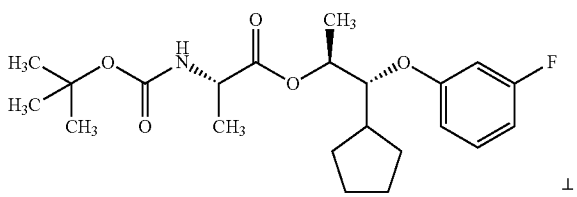 [SMILES: C[C@H](NC(=O)OC(C)(C)C)C(=O)O[C@@H](C)[C@H](Oc1cccc(F)c1)C1CCCC1] | Example 1A; Example 4C; Example 8A; Example 12A | Colorless Oil |
| 732 | 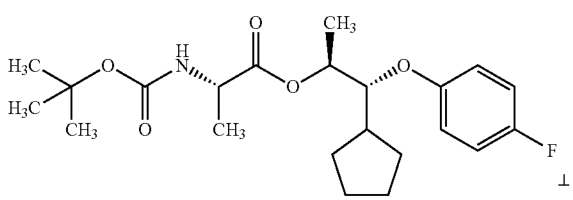 [SMILES: C[C@H](NC(=O)OC(C)(C)C)C(=O)O[C@@H](C)[C@H](Oc1ccc(F)cc1)C1CCCC1] | Example 1A; Example 4C; Example 8A; Example 12A | Colorless Oil |
| 733 | 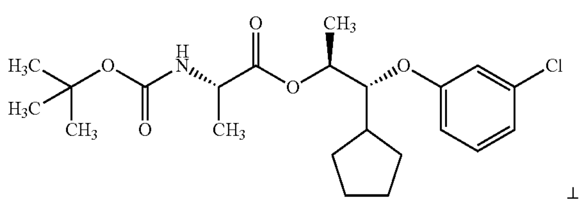 [SMILES: C[C@H](NC(=O)OC(C)(C)C)C(=O)O[C@@H](C)[C@H](Oc1cccc(Cl)c1)C1CCCC1] | Example 1A; Example 4C; Example 8A; Example 12A | Colorless Oil |
| 734 | 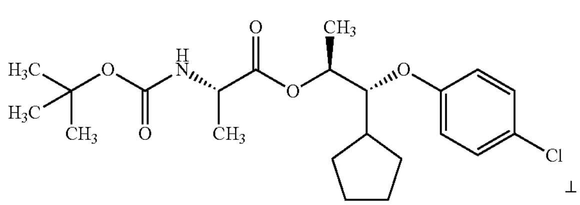 [SMILES: C[C@H](NC(=O)OC(C)(C)C)C(=O)O[C@@H](C)[C@H](Oc1ccc(Cl)cc1)C1CCCC1] | Example 1A; Example 4C; Example 8A; Example 12A | Colorless Oil |

TABLE 1-continued

Compound Structure, Appearance, and Preparation Method

| *Cmpd. No. | Structure | Prepared According to Example: | Appearance |
|---|---|---|---|
| 735 | 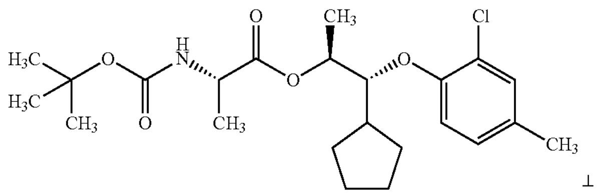 [SMILES: Cc1ccc(O[C@H](C2CCCC2)[C@H](C)OC(=O)[C@H](C)NC(=O)OC(C)(C)C)c(Cl)c1] | Example 1A; Example 4C; Example 8A; Example 12A | Colorless Oil |
| 736 | 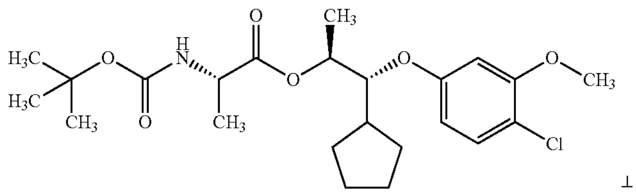 [SMILES: COc1cc(O[C@H](C2CCCC2)[C@H](C)OC(=O)[C@H](C)NC(=O)OC(C)(C)C)ccc1Cl] | Example 1A; Example 4C; Example 8A; Example 12A | Colorless Oil |
| 737 | 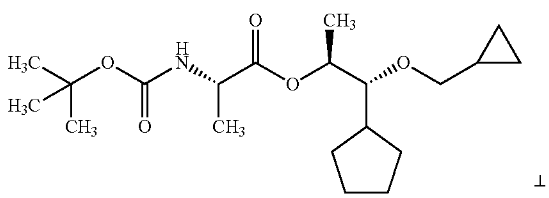 [SMILES: C[C@H](NC(=O)OC(C)(C)C)C(=O)O[C@@H](C)[C@H](OCC1CC1)C1CCCC1] | Example 1A; Example 4D; Example 8A; Example 12A | Colorless Oil |
| 738 | 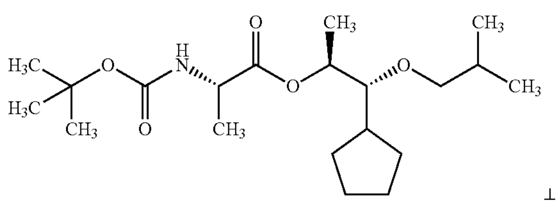 [SMILES: CC(C)CO[C@H](C1CCCC1)[C@H](C)OC(=O)[C@H](C)NC(=O)OC(C)(C)C] | Example 1A; Example 4F; Example 8C; Example 12A | Colorless Oil |
| 739 | 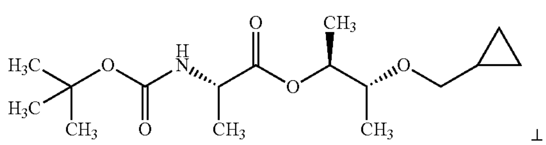 [SMILES: C[C@H](NC(=O)OC(C)(C)C)C(=O)O[C@@H](C)[C@@H](C)OCC1CC1] | Example 1A; Example 4D; Example 8C; Example 12A | Yellow Oil |
| 740 | 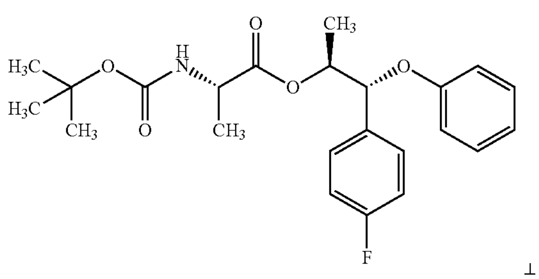 [SMILES: C[C@H](NC(=O)OC(C)(C)C)C(=O)O[C@@H](C)[C@H](Oc1ccccc1)c1ccc(F)cc1] | Example 1A; Example 4B; Example 8D; Example 12A | Colorless Oil |
| 741 | 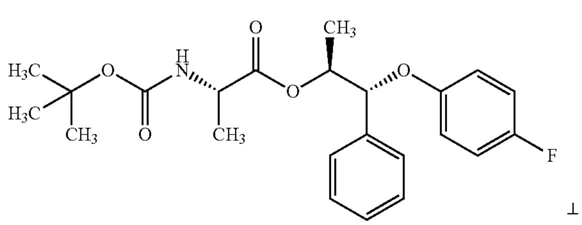 [SMILES: C[C@H](NC(=O)OC(C)(C)C)C(=O)O[C@@H](C)[C@H](Oc1ccc(F)cc1)c1ccccc1] | Example 1A; Example 4B; Example 8A; Example 12A | Colorless Oil |

TABLE 1-continued

Compound Structure, Appearance, and Preparation Method

| *Cmpd. No. | Structure | Prepared According to Example: | Appearance |
|---|---|---|---|
| 742 | 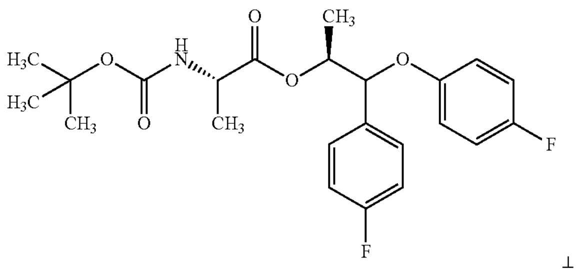 [SMILES: C[C@H](NC(=O)OC(C)(C)C)C(=O)O[C@@H](C)C(Oc1ccc(F)cc1)c1ccc(F)cc1] | Example 1B, Steps 1, 2; Example 4B; Example 8A; Example 12A | Colorless Oil |
| 743 | 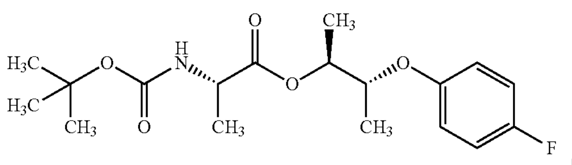 | Example 1A; Example 4C; Example 8A; Example 12A | Colorless Oil |
| 744 | 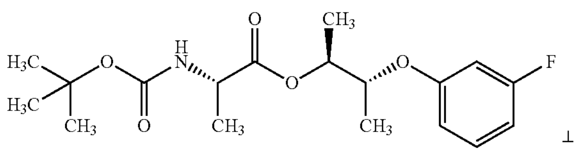 [SMILES: C[C@H](NC(=O)OC(C)(C)C)C(=O)O[C@@H](C)[C@@H](C)Oc1cccc(F)c1] | Example 1A; Example 4C; Example 8A; Example 12A | Colorless Oil |
| 745 | 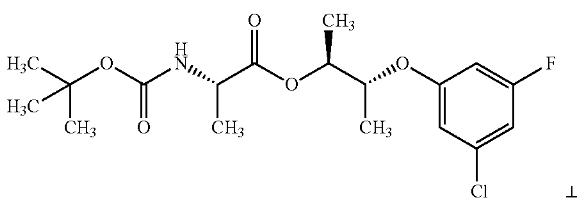 [SMILES: C[C@H](NC(=O)OC(C)(C)C)C(=O)O[C@@H](C)[C@@H](C)Oc1cc(F)cc(Cl)c1] | Example 1A; Example 4C; Example 8A; Example 12A | Colorless Oil |
| 746 | 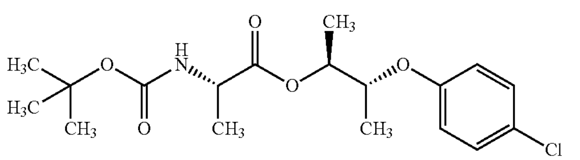 | Example 1A; Example 4C; Example 8A; Example 12A | Colorless Oil |
| 747 | 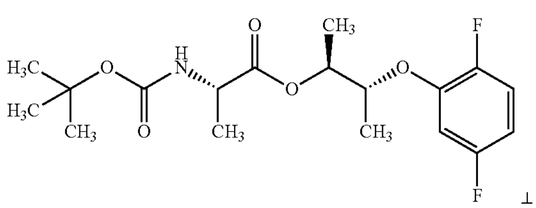 [SMILES: C[C@H](NC(=O)OC(C)(C)C)C(=O)O[C@@H](C)[C@@H](C)Oc1cc(F)ccc1F] | Example 1A; Example 4C; Example 8A; Example 12A | Colorless Oil |
| 748 | 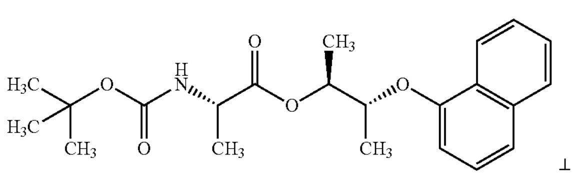 [SMILES: C[C@H](NC(=O)OC(C)(C)C)C(=O)O[C@@H](C)[C@@H](C)Oc1cccc2ccccc12] | Example 1A; Example 4C; Example 8A; Example 12A | Colorless Oil |

TABLE 1-continued

Compound Structure, Appearance, and Preparation Method

| *Cmpd. No. | Structure | Prepared According to Example: | Appearance |
|---|---|---|---|
| 749 | 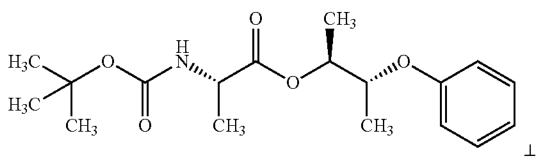 [SMILES: C[C@H](NC(=O)OC(C)(C)C)C(=O)O[C@@H](C)[C@@H](C)Oc1ccccc1] | Example 1A; Example 4C; Example 8F; Example 12A | Yellow Oil |
| 750 | 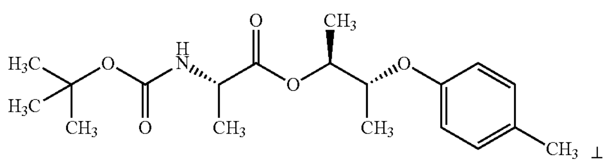 [SMILES: Cc1ccc(O[C@H](C)[C@H](C)OC(=O)[C@H](C)NC(=O)OC(C)(C)C)cc1] | Example 1A; Example 4C; Example 8F; Example 12A | Yellow Oil |
| 751 | 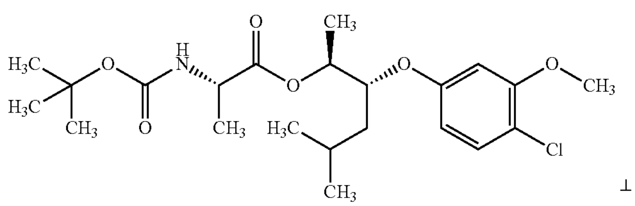 [SMILES: COc1cc(O[C@H](CC(C)C)[C@H](C)OC(=O)[C@H](C)NC(=O)OC(C)(C)C)ccc1Cl] | Example 1A; Example 4C; Example 8A; Example 12A | Brown Oil |
| 752 | 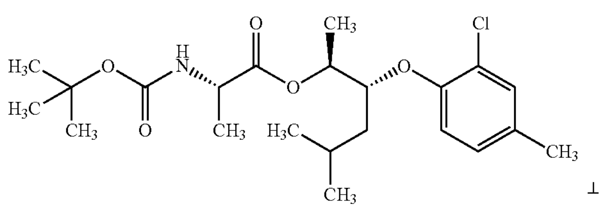 [SMILES: Cc1ccc(O[C@H](CC(C)C)[C@H](C)OC(=O)[C@H](C)NC(=O)OC(C)(C)C)c(Cl)c1] | Example 1A; Example 4C; Example 8A; Example 12A | Colorless Oil |
| 753 | 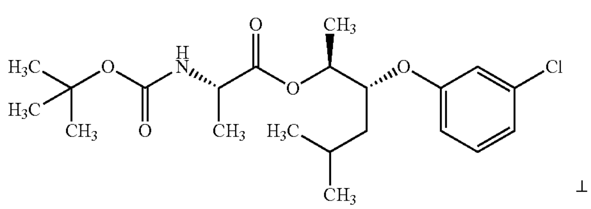 [SMILES: CC(C)C[C@@H](Oc1cccc(Cl)c1)[C@H](C)OC(=O)[C@H](C)NC(=O)OC(C)(C)C] | Example 1A; Example 4C; Example 8A; Example 12A | Colorless Oil |
| 754 | 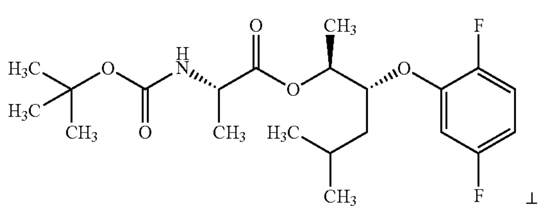 [SMILES: CC(C)C[C@@H](Oc1cc(F)ccc1F)[C@H](C)OC(=O)[C@H](C)NC(=O)OC(C)(C)C] | Example 1A; Example 4C; Example 8A; Example 12A | Colorless Oil |
| 755 | 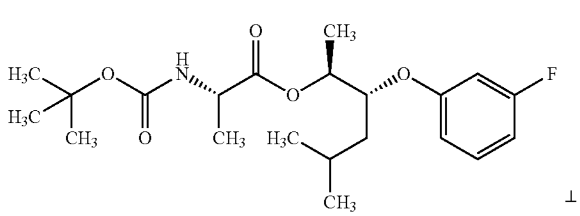 [SMILES: CC(C)C[C@@H](Oc1cccc(F)c1)[C@H](C)OC(=O)[C@H](C)NC(=O)OC(C)(C)C] | Example 1A; Example 4C; Example 8A; Example 12A | Colorless Oil |

TABLE 1-continued

Compound Structure, Appearance, and Preparation Method

| *Cmpd. No. | Structure | Prepared According to Example: | Appearance |
|---|---|---|---|
| 756 | 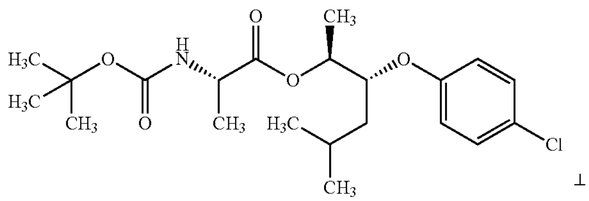 [SMILES: CC(C)C[C@@H](Oc1ccc(Cl)cc1)[C@H](C)OC(=O)[C@H](C)NC(=O)OC(C)(C)C] | Example 1A; Example 4C; Example 8A; Example 12A | Colorless Oil |
| 757 | 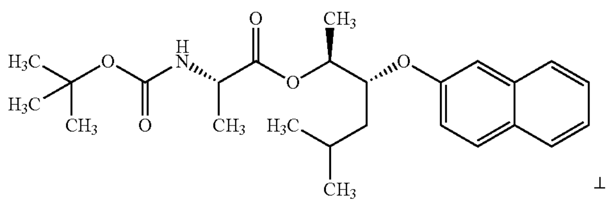 [SMILES: CC(C)C[C@@H](Oc1ccc2ccccc2c1)[C@H](C)OC(=O)[C@H](C)NC(=O)OC(C)(C)C] | Example 1A; Example 4C; Example 8A; Example 12A | Yellow Oil |
| 758 | 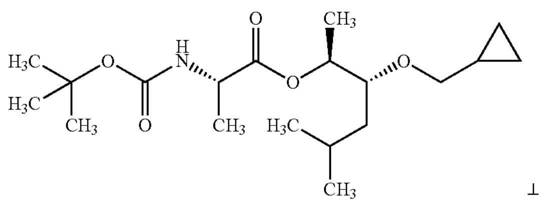 [SMILES: CC(C)C[C@@H](OCC1CC1)[C@H](C)OC(=O)[C@H](C)NC(=O)OC(C)(C)C] | Example 1A; Example 4D; Example 8A; Example 12A | Colorless Oil |
| 759 | 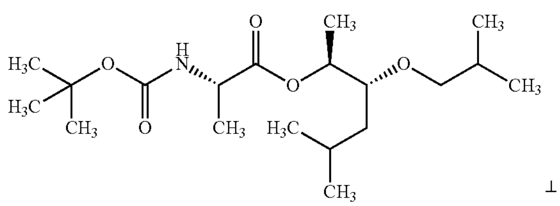 [SMILES: CC(C)CO[C@H](CC(C)C)[C@H](C)OC(=O)[C@H](C)NC(=O)OC(C)(C)C] | Example 1A; Example 4F; Example 8C; Example 12A | Colorless Oil |
| 760 | 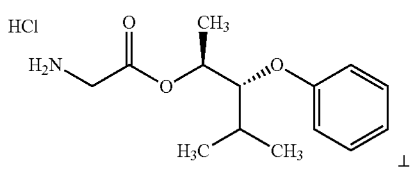 [SMILES: Cl ; CC(C)[C@@H](Oc1ccccc1)[C@H](C)OC(=O)CN] | Example 14A, Step 1 | Colorless Oil |
| 761 | 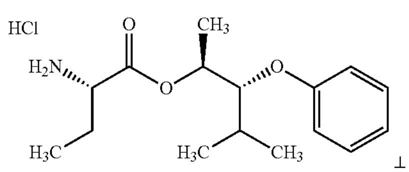 [SMILES: Cl ; CC[C@H](N)C(=O)O[C@@H](C)[C@H](Oc1ccccc1)C(C)C] | Example 14A, Step 1 | Colorless Oil |
| 762 | 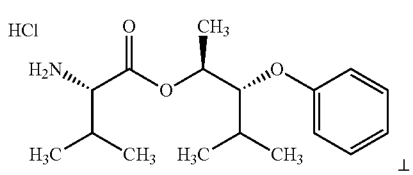 [SMILES: Cl ; CC(C)[C@H](N)C(=O)O[C@@H](C)[C@H](Oc1ccccc1)C(C)C] | Example 14A, Step 1 | Colorless Oil |

TABLE 1-continued
Compound Structure, Appearance, and Preparation Method
| *Cmpd. No. | Structure | Prepared According to Example: | Appearance |
|---|---|---|---|
| 763 | 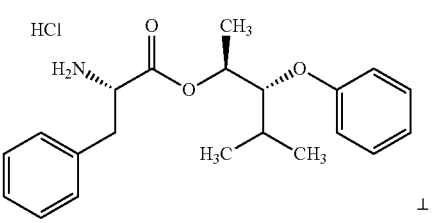 [SMILES: CC(C)[C@@H](Oc1ccccc1)[C@H](C)OC(=O)[C@@H](N)Cc1ccccc1 ; Cl] | Example 14A, Step 1 | Colorless Oil |
| 764 | 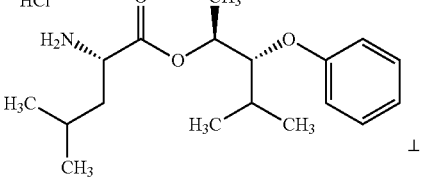 | Example 14A, Step 1 | Colorless Oil |
| 765 | 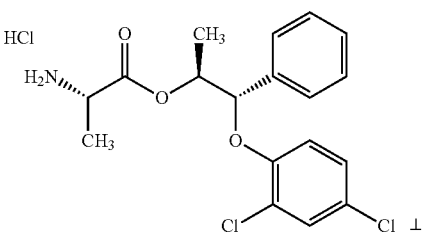 [SMILES: Cl ; C[C@H](N)C(=O)O[C@@H](C)[C@@H](Oc1ccc(Cl)cc1Cl)c1ccccc1] | Example 14A, Step 1 | Colorless Oil |
| 766 | 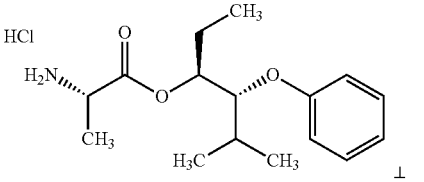 [SMILES: Cl ; CC[C@H](OC(=O)[C@H](C)N)[C@H](Oc1ccccc1)C(C)C] | Example 14A, Step 1 | White Solid |
| 767 | 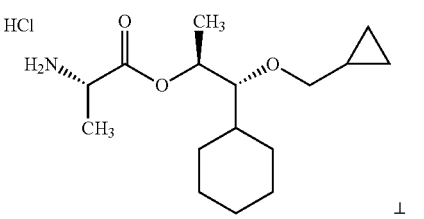 [SMILES: Cl ; C[C@H](N)C(=O)O[C@@H](C)[C@H](OCC1CC1)C1CCCCC1] | Example 14A, Step 1 | Cloudy Colorless Oil |
| 768 | 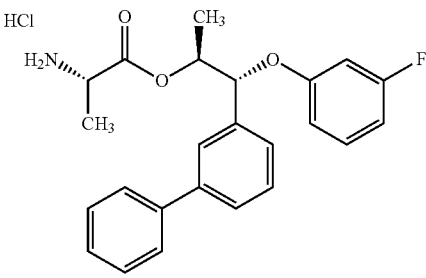 | Example 14A, Step 1 | Colorless Oil |

TABLE 1-continued
Compound Structure, Appearance, and Preparation Method
| *Cmpd. No. | Structure | Prepared According to Example: | Appearance |
|---|---|---|---|
| 769 | 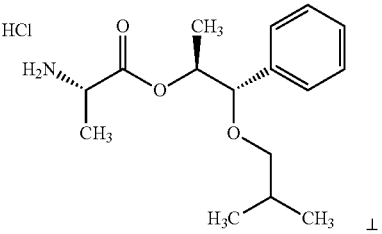 [SMILES: Cl ; CC(C)CO[C@@H](c1ccccc1)[C@H](C)OC(=O)[C@H](C)N] | Example 14A, Step 1 | Colorless Oil |
| 770 | 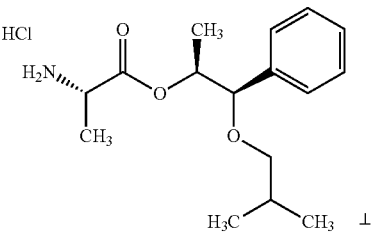 [SMILES: Cl ; CC(C)CO[C@H](c1ccccc1)[C@H](C)OC(=O)[C@H](C)N] | Example 14A, Step 1 | Colorless Oil |
| 771 | 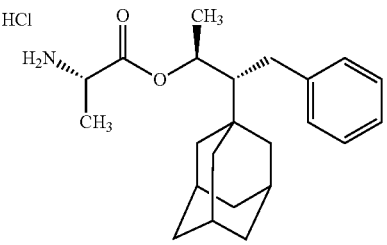 | Example 14A, Step 1 | White Solid |
| 772 | 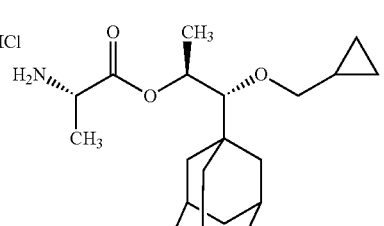 | Example 14A, Step 1 | White Solid |
| 773 | 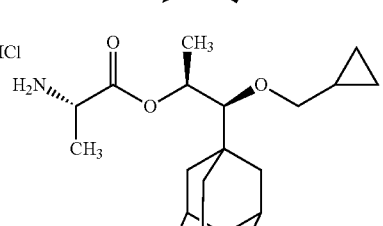 | Example 14A, Step 1 | White Solid |
| 774 | 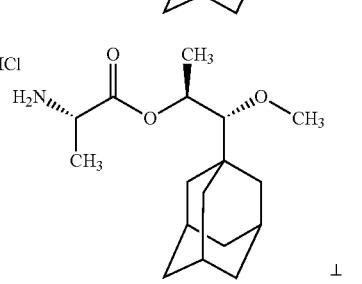 | Example 14A, Step 1 | White Solid |

TABLE 1-continued

Compound Structure, Appearance, and Preparation Method

| *Cmpd. No. | Structure | Prepared According to Example: | Appearance |
|---|---|---|---|
| 775 | 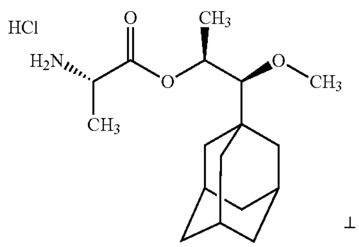 [SMILES: Cl ; CO[C@H]([C@H](C)OC(=O)[C@H](C)N)C12CC3CC(CC(C3)C1)C2] | Example 14A, Step 1 | White Solid |
| 776 | 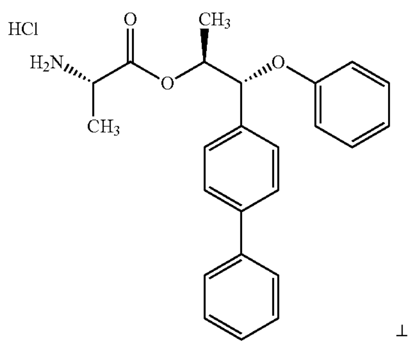 [SMILES: Cl ; C[C@H](N)C(=O)O[C@@H](C)[C@H](Oc1ccccc1)c1ccc(-c2ccccc2)cc1] | Example 14A, Step 1 | Beige Solid |
| 777 | 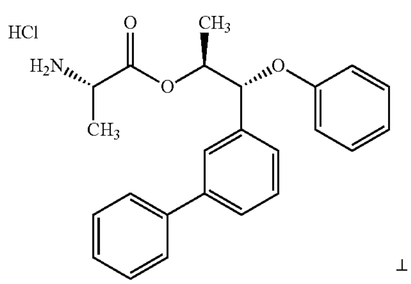 [SMILES: Cl ; C[C@H](N)C(=O)O[C@@H](C)[C@H](Oc1ccccc1)c1cccc(-c2ccccc2)c1] | Example 14A, Step 1 | Colorless Oil |
| 778 | 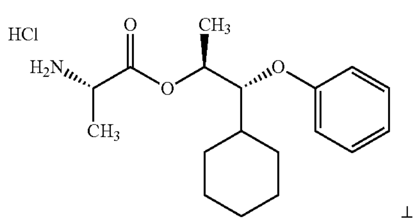 [SMILES: Cl ; C[C@H](N)C(=O)O[C@@H](C)[C@H](Oc1ccccc1)C1CCCCC1] | Example 14A, Step 1 | Beige Solid |
| 779 | 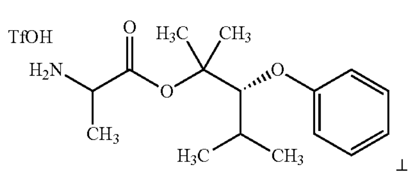 [SMILES: "TfOH" ; CC(N)C(=O)OC(C)(C)[C@H](Oc1ccccc1)C(C)C] | Example 14D, Step 1 | Oil |
| 780 | 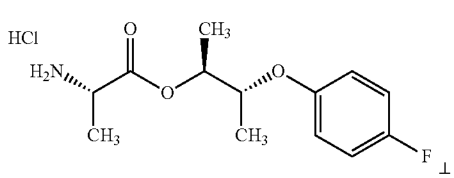 [SMILES: Cl ; C[C@H](N)C(=O)O[C@@H](C)[C@@H](C)Oc1ccc(F)cc1] | Example 14A, Step 1 | Yellow Oil |

TABLE 1-continued
Compound Structure, Appearance, and Preparation Method
| *Cmpd. No. | Structure | Prepared According to Example: | Appearance |
|---|---|---|---|
| 781 | 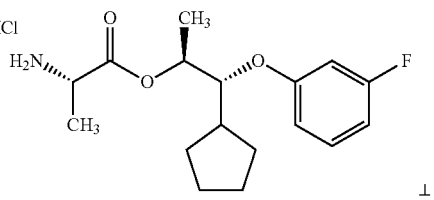 | Example 14A, Step 1 | Colorless Oil |
| 782 | 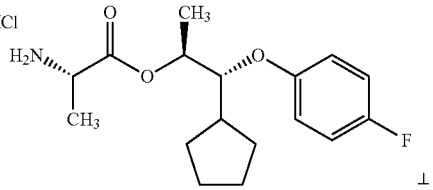 | Example 14A, Step 1 | Colorless Oil |
| 783 | 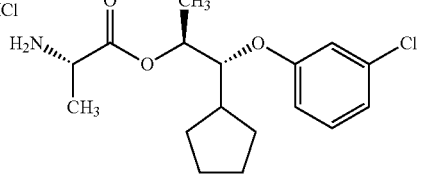 | Example 14A, Step 1 | Colorless Oil |
| 784 | 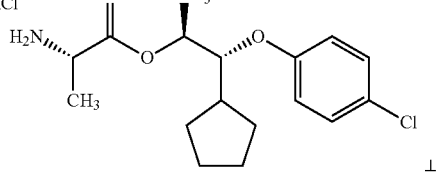 | Example 14A, Step 1 | Colorless Oil |
| 785 | 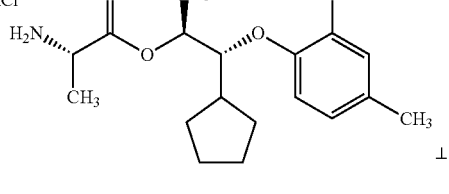 | Example 14A, Step 1 | Colorless Oil |
| 786 | 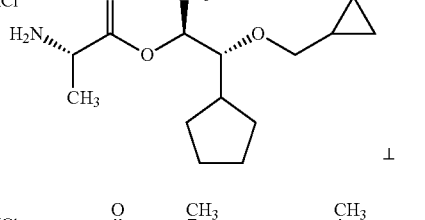 | Example 14A, Step 1 | Colorless Oil |
| 787 | 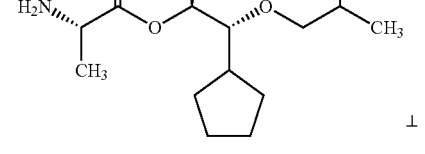 | Example 14A, Step 1 | Colorless Oil |

TABLE 1-continued
Compound Structure, Appearance, and Preparation Method
| *Cmpd. No. | Structure | Prepared According to Example: | Appearance |
|---|---|---|---|
| 788 | 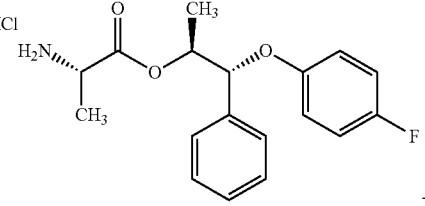 | Example 14A, Step 1 | Colorless Oil |
| 789 | 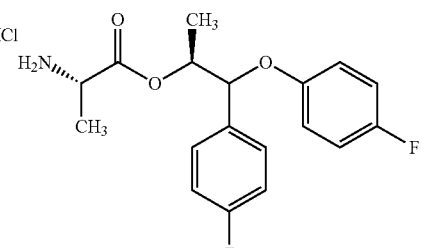 | Example 14A, Step 1 | Colorless Oil |
| 790 | 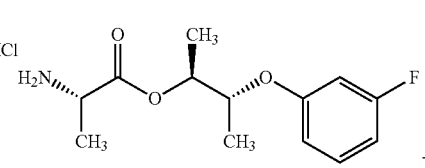 | Example 14A, Step 1 | Yellow Oil |
| 791 | 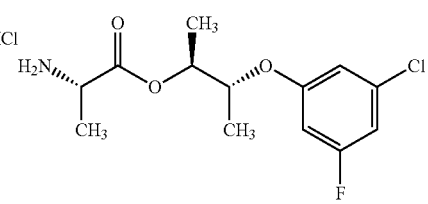 | Example 14A, Step 1 | Yellow Oil |
| 792 | 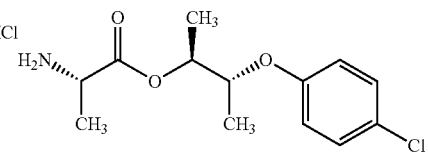 | Example 14A, Step 1 | Yellow Oil |
| 793 | 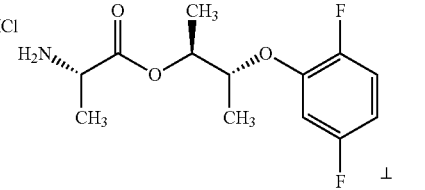 | Example 14A, Step 1 | Yellow Oil |
| 794 | 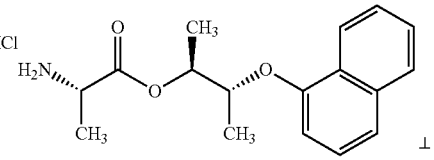 | Example 14A, Step 1 | Yellow Oil |

TABLE 1-continued

Compound Structure, Appearance, and Preparation Method

| *Cmpd. No. | Structure | Prepared According to Example: | Appearance |
|---|---|---|---|
| 795 | 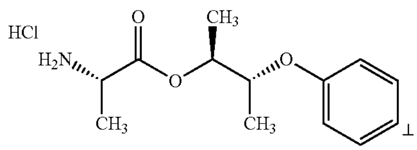 [SMILES: Cl ; C[C@H](N)C(=O)O[C@@H](C)[C@@H](C)Oc1ccccc1] | Example 14A, Step 1 | Yellow Oil |
| 796 | 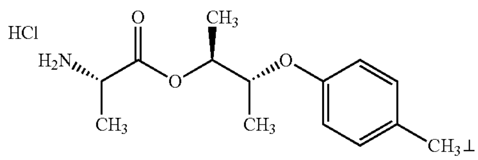 [SMILES: Cl ; Cc1ccc(O[C@H](C)[C@H](C)OC(=O)[C@H](C)N)cc1] | Example 14A, Step 1 | Yellow Oil |
| 797 | 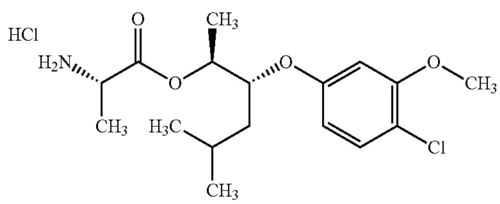 [SMILES: Cl ; COc1cc(O[C@H](CC(C)C)[C@H](C)OC(=O)[C@H](C)N)ccc1Cl] | Example 14A, Step 1 | Yellow Oil |
| 798 | 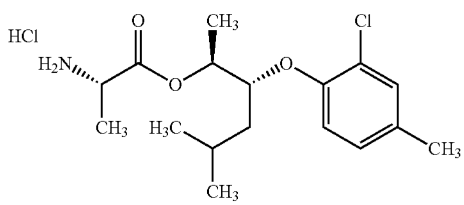 [SMILES: Cl ; Cc1ccc(O[C@H](CC(C)C)[C@H](C)OC(=O)[C@H](C)N)c(Cl)c1] | Example 14A, Step 1 | Yellow Oil |
| 799 | 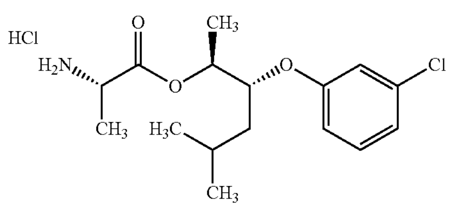 [SMILES: Cl ; CC(C)C[C@@H](Oc1cccc(Cl)c1)[C@H](C)OC(=O)[C@H](C)N] | Example 14A, Step 1 | Yellow Oil |
| 800 | 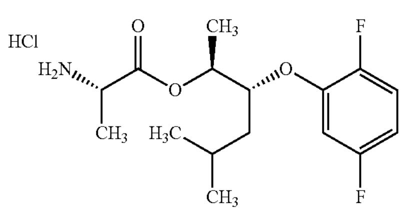 [SMILES: Cl ; CC(C)C[C@@H](Oc1cc(F)ccc1F)[C@H](C)OC(=O)[C@H](C)N] | Example 14A, Step 1 | Yellow Oil |
| 801 | 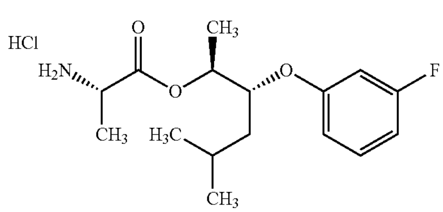 [SMILES: Cl ; CC(C)C[C@@H](Oc1cccc(F)c1)[C@H](C)OC(=O)[C@H](C)N] | Example 14A, Step 1 | Yellow Oil |

TABLE 1-continued

Compound Structure, Appearance, and Preparation Method

| *Cmpd. No. | Structure | Prepared According to Example: | Appearance |
|---|---|---|---|
| 802 | HCl salt of alanine ester with 4-chlorophenoxy group | Example 14A, Step 1 | Yellow Oil |
| 803 | HCl salt of alanine ester with 2-naphthyloxy group | Example 14A, Step 1 | Yellow Oil |
| 804 | HCl salt of alanine ester with cyclopropylmethoxy group | Example 14A, Step 1 | Yellow Oil |
| 805 | HCl salt of alanine ester with isobutoxy group | Example 14A, Step 1 | Yellow Oil |
| 806 | HCl salt of alanine ester with cyclopropylmethoxy group | Example 14A, Step 1 | Yellow Oil |
| 807 | HCl salt of alanine ester with propoxy group | Example 14A, Step 1 | Yellow Oil |
| 808 | 4-methoxy-3-hydroxypyridine-2-carboxamide alanine ester with phenoxy-thiazolyl group | Example 14A, Steps 1, 2 | Colorless Foam/Oil |

TABLE 1-continued

Compound Structure, Appearance, and Preparation Method

| *Cmpd. No. | Structure | Prepared According to Example: | Appearance |
|---|---|---|---|
| 809 | 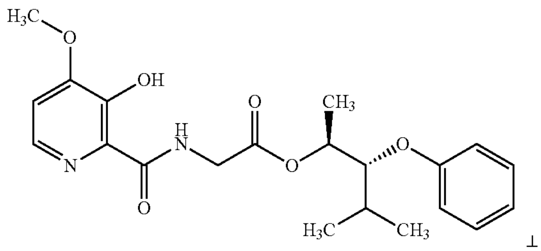 [SMILES: COc1ccnc(C(=O)NCC(=O)O[C@@H](C)[C@H](Oc2ccccc2)C(C)C)c1O] | Example 14A, Step 2 | Colorless Oil |
| 810 | 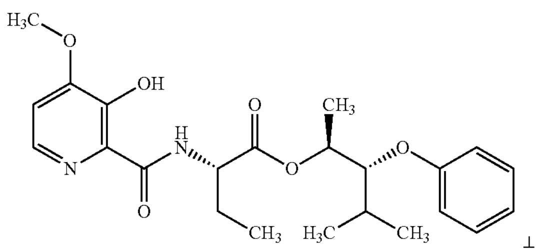 [SMILES: CC[C@H](NC(=O)c1nccc(OC)c1O)C(=O)O[C@@H](C)[C@H](Oc1ccccc1)C(C)C] | Example 14A, Step 2 | Colorless Oil |
| 811 | 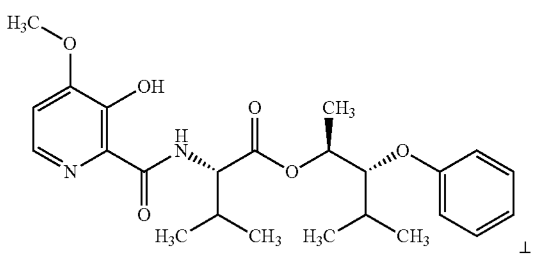 [SMILES: COc1ccnc(C(=O)N[C@H](C(=O)O[C@@H](C)[C@H](Oc2ccccc2)C(C)C)C(C)C)c1O] | Example 14A, Step 2 | Colorless Oil |
| 812 | 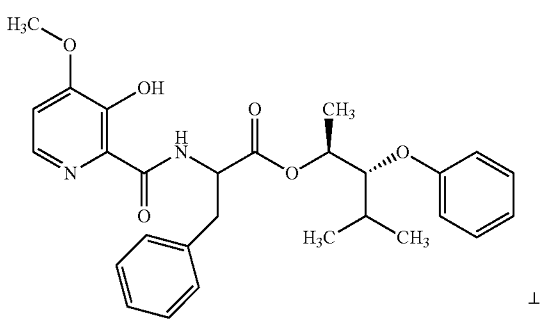 [SMILES: COc1ccnc(C(=O)NC(Cc2ccccc2)C(=O)O[C@@H](C)[C@H](Oc2ccccc2)C(C)C)c1O] | Example 14A, Step 2 | Colorless Oil |
| 813 | 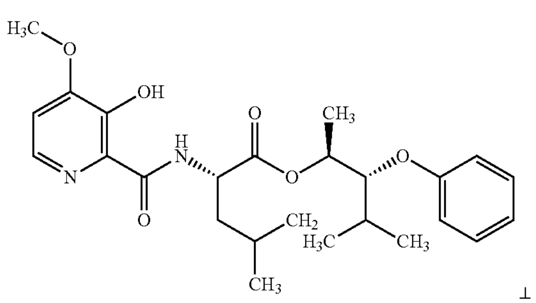 [SMILES: COc1ccnc(C(=O)N[C@@H](CC(C)C)C(=O)O[C@@H](C)[C@H](Oc2ccccc2)C(C)C)c1O] | Example 14A, Step 2 | Colorless Oil |

TABLE 1-continued

Compound Structure, Appearance, and Preparation Method

| *Cmpd. No. | Structure | Prepared According to Example: | Appearance |
|---|---|---|---|
| 814 | 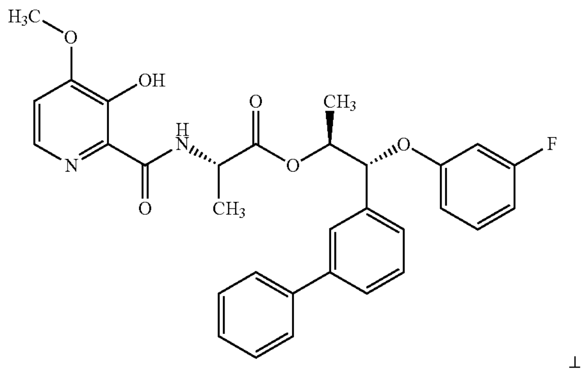 [SMILES: COc1ccnc(C(=O)N[C@@H](C)C(=O)O[C@@H](C)[C@H](Oc2cccc(F)c2)c2cccc(-c3ccccc3)c2)c1O] | Example 14A, Step 2 | Foamy White Solid |
| 815 | 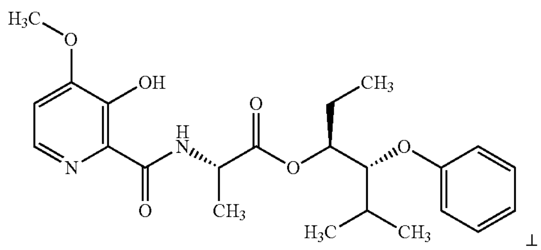 [SMILES: CC[C@H](OC(=O)[C@H](C)NC(=O)c1nccc(OC)c1O)[C@H](Oc1ccccc1)C(C)C] | Example 14A, Step 2 | Thick Oil |
| 816 | 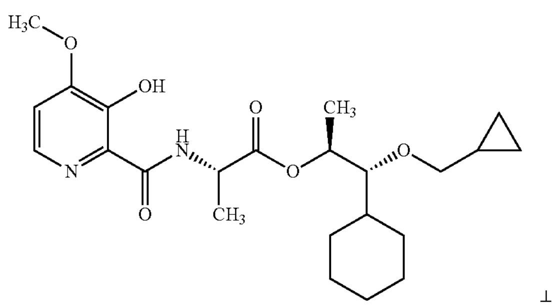 [SMILES: COc1ccnc(C(=O)N[C@@H](C)C(=O)O[C@@H](C)[C@H](OCC2CC2)C2CCCCC2)c1O] | Example 14A, Step 2 | Colorless Oil |
| 817 | 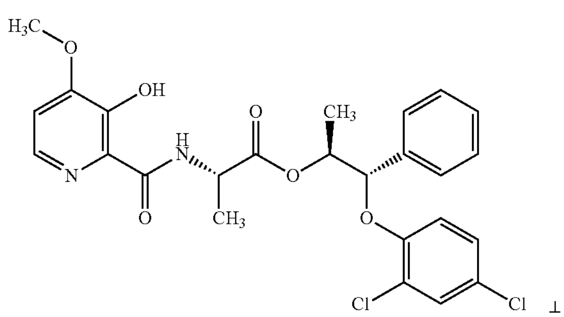 [SMILES: COc1ccnc(C(=O)N[C@@H](C)C(=O)O[C@@H](C)[C@@H](Oc2ccc(Cl)cc2Cl)c2ccccc2)c1O] | Example 14A, Step 2 | White Foam |

TABLE 1-continued

Compound Structure, Appearance, and Preparation Method

| *Cmpd. No. | Structure | Prepared According to Example: | Appearance |
|---|---|---|---|
| 818 | 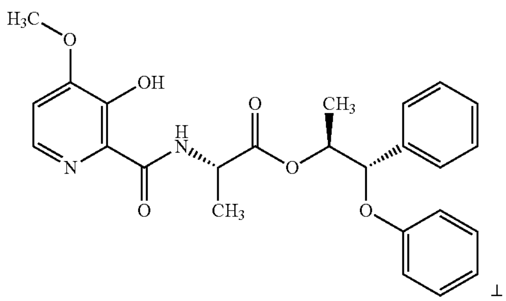 [SMILES: COc1ccnc(C(=O)N[C@@H](C)C(=O)O[C@@H](C)[C@@H](Oc2ccccc2)c2ccccc2)c1O] | Example 15 | Colorless Oil |
| 819 | 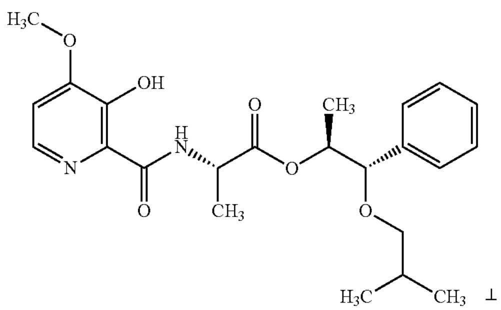 [SMILES: COc1ccnc(C(=O)N[C@@H](C)C(=O)O[C@@H](C)[C@@H](OCC(C)C)c2ccccc2)c1O] | Example 14A, Step 2 | Colorless Oil |
| 820 | 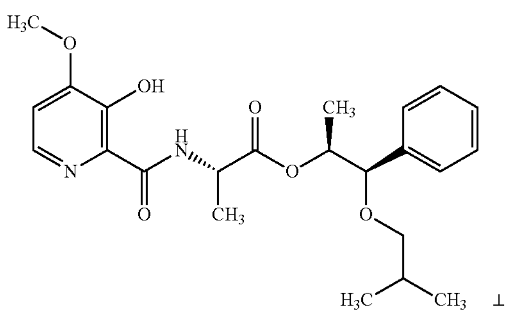 [SMILES: COc1ccnc(C(=O)N[C@@H](C)C(=O)O[C@@H](C)[C@H](OCC(C)C)c2ccccc2)c1O] | Example 14A, Step 2 | Colorless Oil |
| 821 | 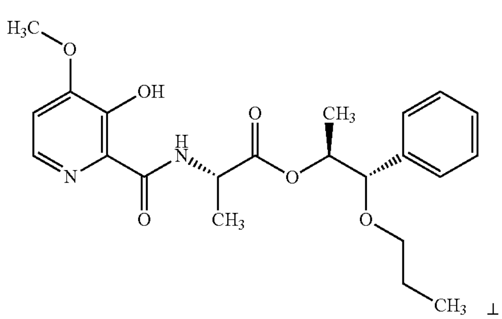 [SMILES: CCCO[C@@H](c1ccccc1)[C@H](C)OC(=O)[C@H](C)NC(=O)c1nccc(OC)c1O] | Example 14A, Steps 1, 2 | Colorless Oil |

TABLE 1-continued

Compound Structure, Appearance, and Preparation Method

| *Cmpd. No. | Structure | Prepared According to Example: | Appearance |
|---|---|---|---|
| 822 | 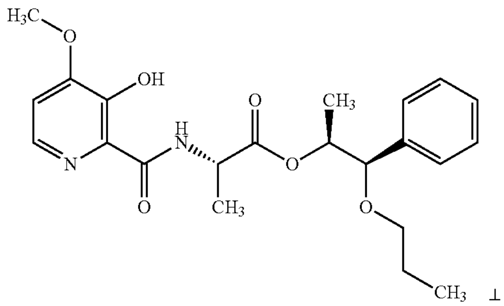 [SMILES: CCCO[C@H](c1ccccc1)[C@H](C)OC(=O)[C@H](C)NC(=O)c1nccc(OC)c1O] | Example 14A, Steps 1, 2 | Colorless Oil |
| 823 | 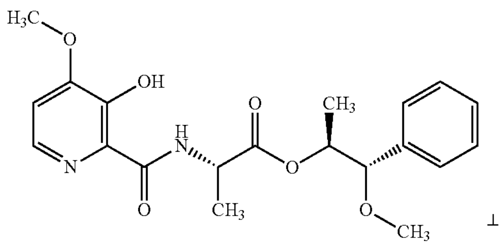 [SMILES: COc1ccnc(C(=O)N[C@@H](C)C(=O)O[C@@H](C)[C@@H](OC)c2ccccc2)c1O] | Example 14A, Steps 1, 2 | Colorless Oil |
| 824 | 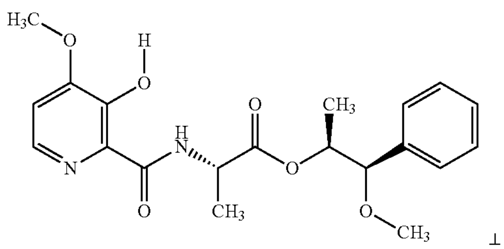 [SMILES: COc1ccnc(C(=O)N[C@@H](C)C(=O)O[C@@H](C)[C@H](OC)c2ccccc2)c1O] | Example 14A, Steps 1, 2 | Colorless Oil |
| 825 | 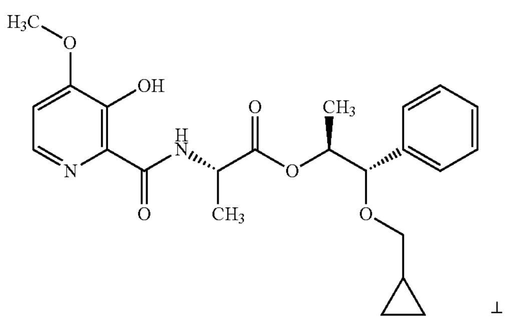 [SMILES: COc1ccnc(C(=O)N[C@@H](C)C(=O)O[C@@H](C)[C@@H](OCC2CC2)c2ccccc2)c1O] | Example 14A, Steps 1, 2 | Colorless Oil |
| 826 | 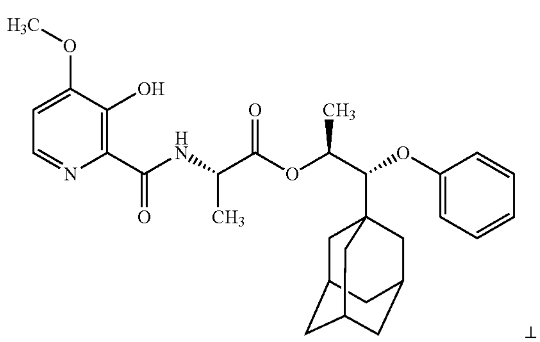 [SMILES: COc1ccnc(C(=O)N[C@@H](C)C(=O)O[C@@H](C)[C@H](Oc2ccccc2)C23CC4CC(CC(C4)C2)C3)c1O] | Example 14A, Step 2 | White Foam |

TABLE 1-continued

Compound Structure, Appearance, and Preparation Method

| *Cmpd. No. | Structure | Prepared According to Example: | Appearance |
|---|---|---|---|
| 827 | 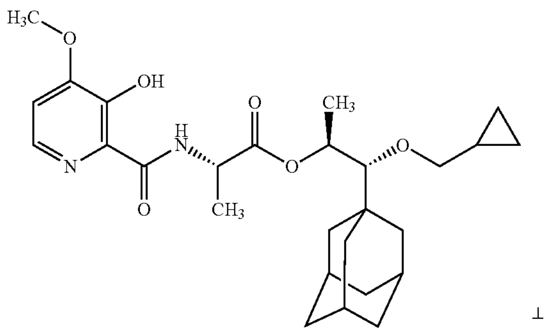 [SMILES: COc1ccnc(C(=O)N[C@@H](C)C(=O)O[C@@H](C)[C@H](OCC2CC2)C23CC4CC(CC(C4)C2)C3)c1O] | Example 14A, Step 2 | White Foam |
| 828 | 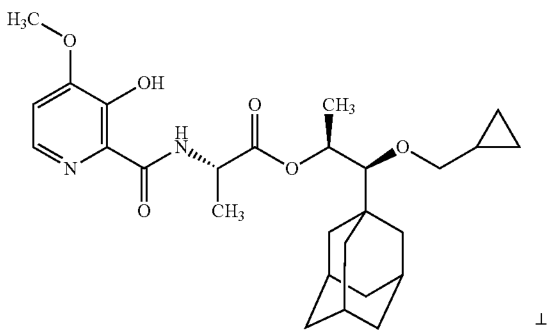 [SMILES: COc1ccnc(C(=O)N[C@@H](C)C(=O)O[C@@H](C)[C@@H](OCC2CC2)C23CC4CC(CC(C4)C2)C3)c1O] | Example 14A, Step 2 | White Foam |
| 829 | 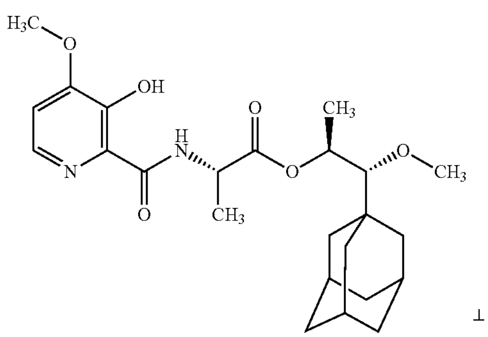 [SMILES: COc1ccnc(C(=O)N[C@@H](C)C(=O)O[C@@H](C)[C@H](OC)C23CC4CC(CC(C4)C2)C3)c1O] | Example 14A, Step 2 | White Foam |
| 830 | 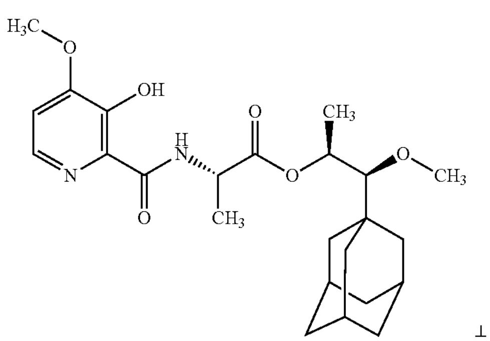 [SMILES: COc1ccnc(C(=O)N[C@@H](C)C(=O)O[C@@H](C)[C@@H](OC)C23CC4CC(CC(C4)C2)C3)c1O] | Example 14A, Step 2 | White Foam |

TABLE 1-continued

Compound Structure, Appearance, and Preparation Method

| *Cmpd. No. | Structure | Prepared According to Example: | Appearance |
|---|---|---|---|
| 831 | 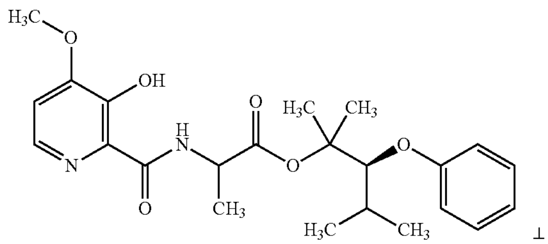 [SMILES: COc1ccnc(C(=O)NC(C)C(=O)OC(C)(C)[C@@H](Oc2ccccc2)C(C)C)c1O] | Example 14D, Step 2 | Oil |
| 832 | 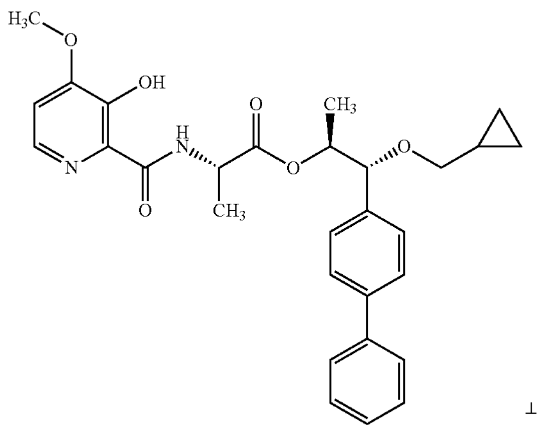 [SMILES: COc1ccnc(C(=O)N[C@@H](C)C(=O)O[C@@H](C)[C@H](OCC2CC2)c2ccc(-c3ccccc3)cc2)c1O] | Example 14A, Step 2 | Beige Solid |
| 833 | 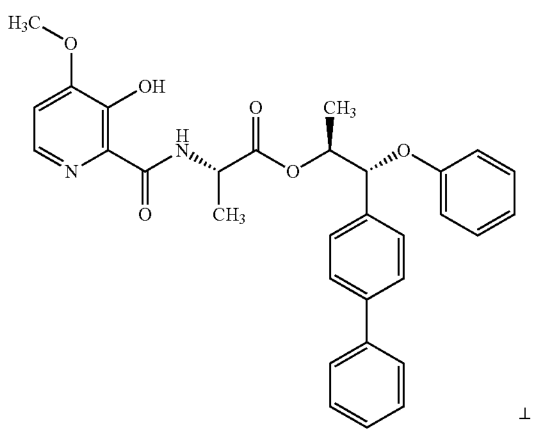 [SMILES: COc1ccnc(C(=O)N[C@@H](C)C(=O)O[C@@H](C)[C@H](Oc2ccccc2)c2ccc(-c3ccccc3)cc2)c1O] | Example 14A, Step 2 | Colorless Oil |
| 834 | 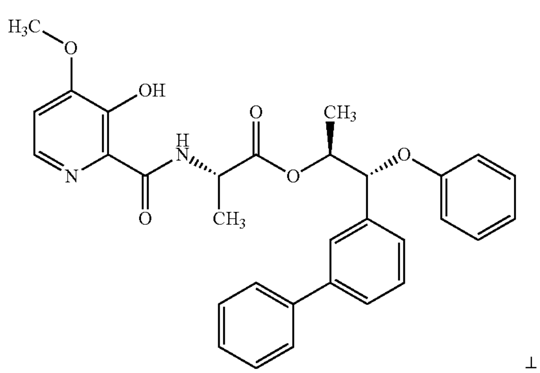 [SMILES: COc1ccnc(C(=O)N[C@@H](C)C(=O)O[C@@H](C)[C@H](Oc2ccccc2)c2cccc(-c3ccccc3)c2)c1O] | Example 14A, Step 2 | Colorless Oil |

TABLE 1-continued
Compound Structure, Appearance, and Preparation Method
| *Cmpd. No. | Structure | Prepared According to Example: | Appearance |
|---|---|---|---|
| 835 | 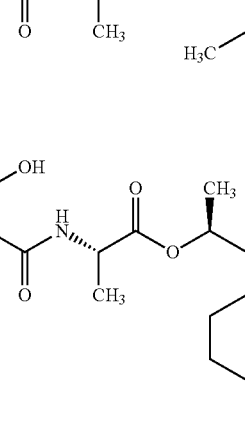 | Example 14D, Step 2 | Colorless Oil |
| 836 | 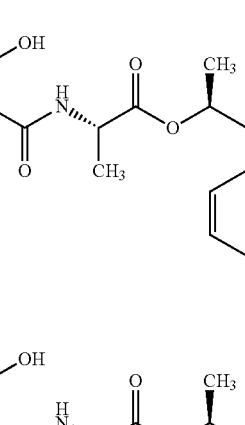 | Example 14A, Step 2 | Foamy White Solid |
| 837 | 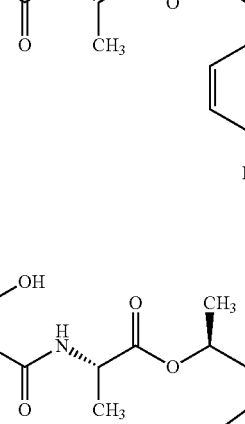 | Example 14A, Step 2 | Colorless Oil |
| 838 | 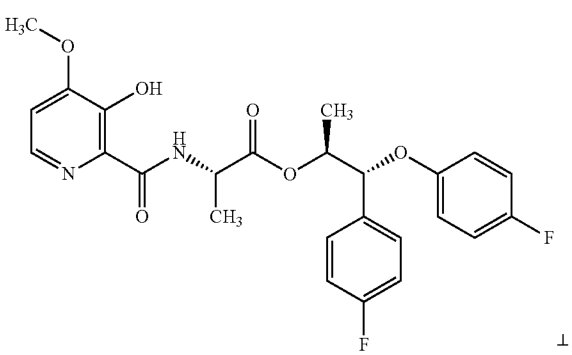 [SMILES: COc1ccnc(C(=O)N[C@@H](C)C(=O)O[C@@H](C)[C@H](Oc2ccc(F)cc2)c2ccc(F)cc2)c1O] | Example 14A, Step 2 | Colorless Oil |
| 839 | 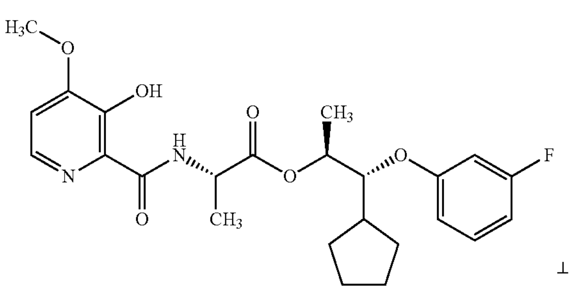 [SMILES: COc1ccnc(C(=O)N[C@@H](C)C(=O)O[C@@H](C)[C@H](Oc2cccc(F)c2)C2CCCC2)c1O] | Example 14A, Step 2 | Colorless Oil |

TABLE 1-continued

Compound Structure, Appearance, and Preparation Method

| *Cmpd. No. | Structure | Prepared According to Example: | Appearance |
|---|---|---|---|
| 840 | 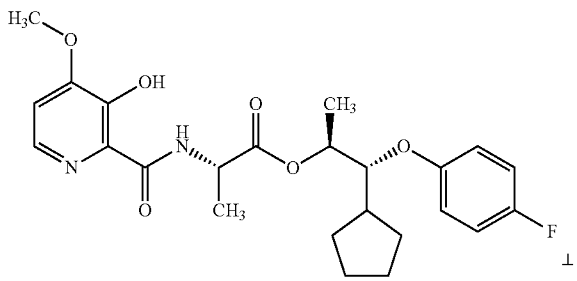 [SMILES: COc1ccnc(C(=O)N[C@@H](C)C(=O)O[C@@H](C)[C@H](Oc2ccc(F)cc2)C2CCCC2)c1O] | Example 14A, Step 2 | Colorless Oil |
| 841 | 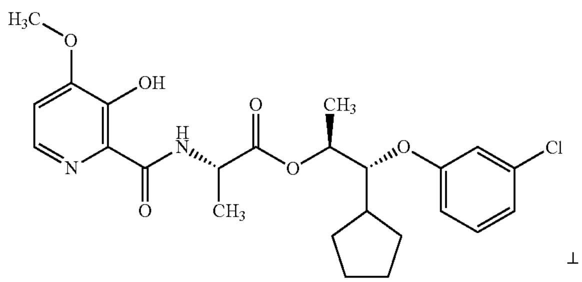 [SMILES: COc1ccnc(C(=O)N[C@@H](C)C(=O)O[C@@H](C)[C@H](Oc2cccc(Cl)c2)C2CCCC2)c1O] | Example 14A, Step 2 | Colorless Oil |
| 842 | 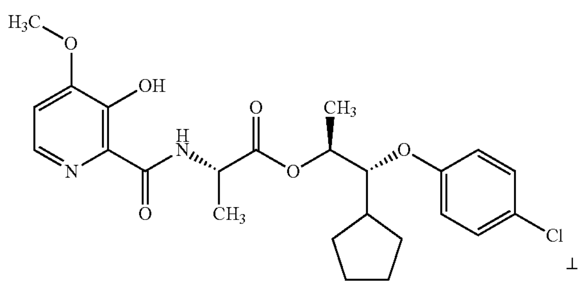 [SMILES: COc1ccnc(C(=O)N[C@@H](C)C(=O)O[C@@H](C)[C@H](Oc2ccc(Cl)cc2)C2CCCC2)c1O] | Example 14A, Step 2 | Colorless Oil |
| 843 | 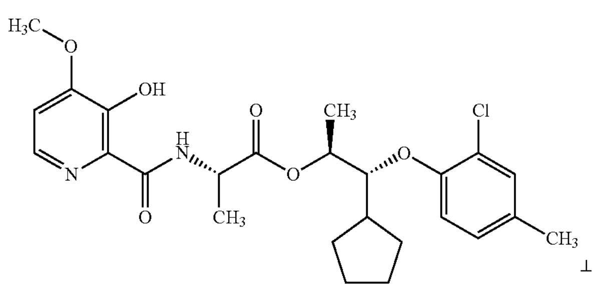 [SMILES: COc1ccnc(C(=O)N[C@@H](C)C(=O)O[C@@H](C)[C@H](Oc2ccc(C)cc2Cl)C2CCCC2)c1O] | Example 14A, Step 2 | Colorless Oil |
| 844 | 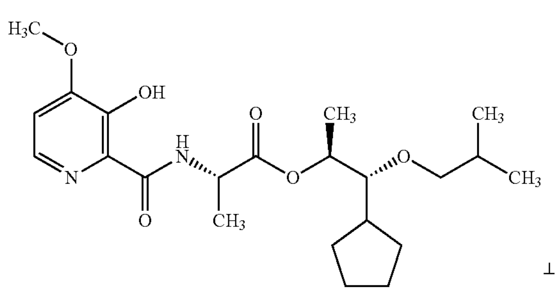 [SMILES: COc1ccnc(C(=O)N[C@@H](C)C(=O)O[C@@H](C)[C@H](OCC(C)C)C2CCCC2)c1O] | Example 14A, Step 2 | Colorless Oil |

TABLE 1-continued

Compound Structure, Appearance, and Preparation Method

| *Cmpd. No. | Structure | Prepared According to Example: | Appearance |
|---|---|---|---|
| 845 | 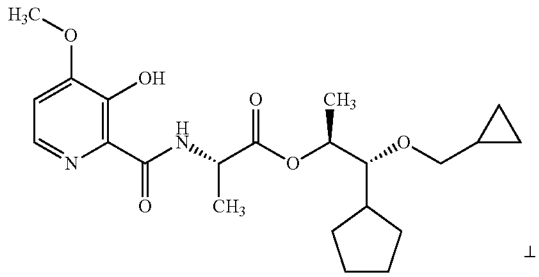 [SMILES: COc1ccnc(C(=O)N[C@@H](C)C(=O)O[C@@H](C)[C@H](OCC2CC2)C2CCCC2)c1O] | Example 14A, Step 2 | Colorless Oil |
| 846 | 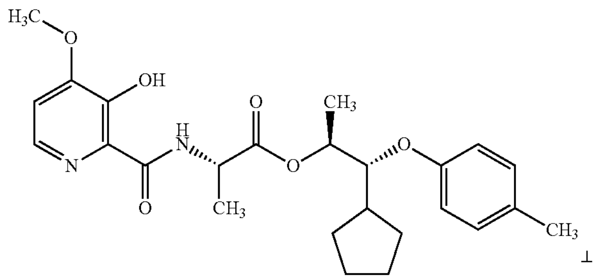 [SMILES: COc1ccnc(C(=O)N[C@@H](C)C(=O)O[C@@H](C)[C@H](Oc2ccc(C)cc2)C2CCCC2)c1O] | Example 15 | White Foam |
| 847 | 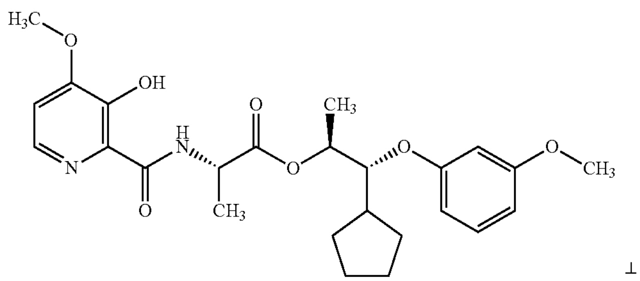 [SMILES: COc1cccc(O[C@H](C2CCCC2)[C@H](C)OC(=O)[C@H](C)NC(=O)c2nccc(OC)c2O)c1] | Example 15 | Colorless Oil |
| 848 | 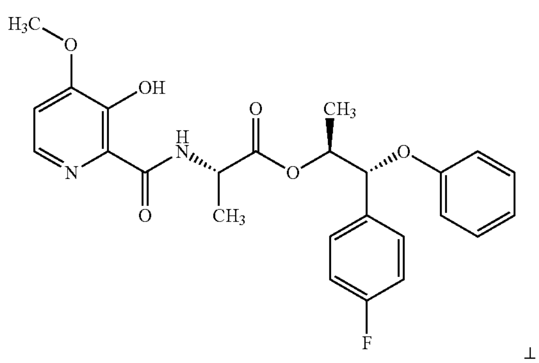 [SMILES: COc1ccnc(C(=O)N[C@@H](C)C(=O)O[C@@H](C)[C@H](Oc2ccccc2)c2ccc(F)cc2)c1O] | Example 14A, Step 2 | Colorless Oil |
| 849 | 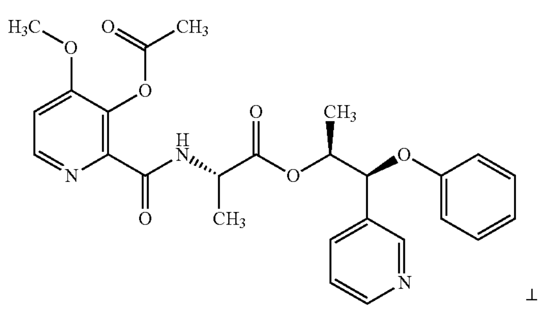 [SMILES: COc1ccnc(C(=O)N[C@@H](C)C(=O)O[C@@H](C)[C@@H](Oc2ccccc2)c2cccnc2)c1OC(C)=O] | Example 16A | Colorless Oil |

TABLE 1-continued

Compound Structure, Appearance, and Preparation Method

| *Cmpd. No. | Structure | Prepared According to Example: | Appearance |
|---|---|---|---|
| 850 | 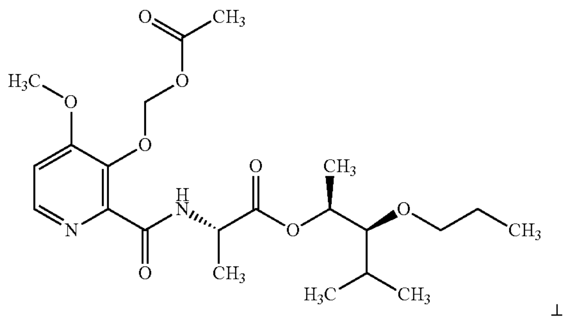 [SMILES: CCCO[C@@H](C(C)C)[C@H](C)OC(=O)[C@H](C)NC(=O)c1nccc(OC)c1OCOC(C)=O] | Example 16B | Yellow Oil |
| 851 | 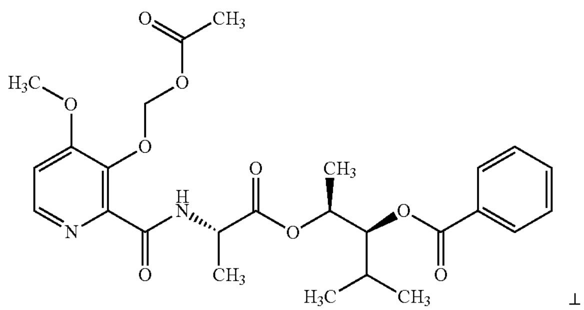 [SMILES: COc1ccnc(C(=O)N[C@@H](C)C(=O)O[C@@H](C)[C@@H](OC(=O)c2ccccc2)C(C)C)c1OCOC(C)=O] | Example 16B | Yellow Oil |
| 852 | 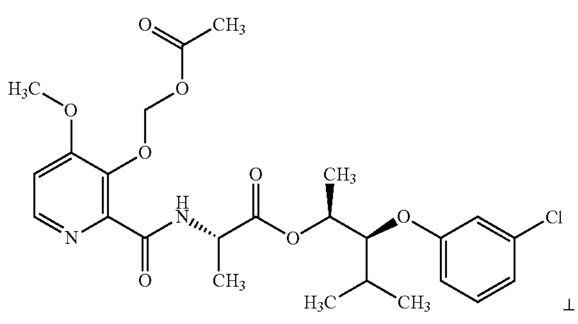 | Example 16B | Yellow Oil |
| 853 | 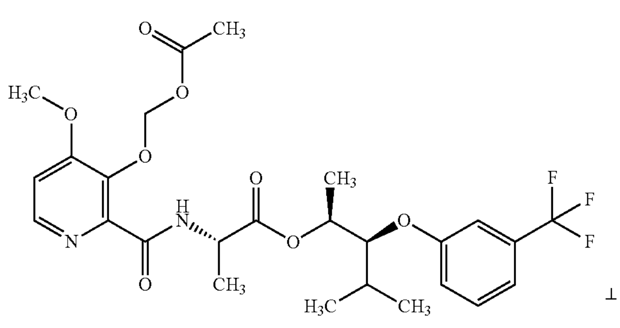 [SMILES: COc1ccnc(C(=O)N[C@@H](C)C(=O)O[C@@H](C)[C@@H](Oc2cccc(C(F)(F)F)c2)C(C)C)c1OCOC(C)=O] | Example 16B | Yellow Oil |

TABLE 1-continued
Compound Structure, Appearance, and Preparation Method
| *Cmpd. No. | Structure | Prepared According to Example: | Appearance |
|---|---|---|---|
| 854 | 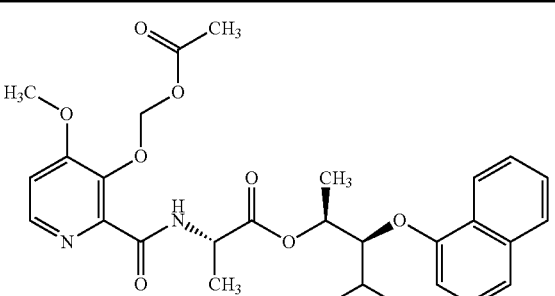 | Example 16B | Yellow Solid |
| 855 | 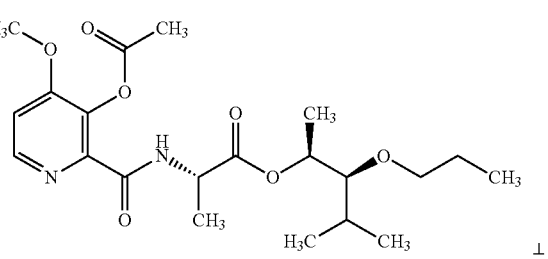 | Example 16A | Oil |
| 856 | 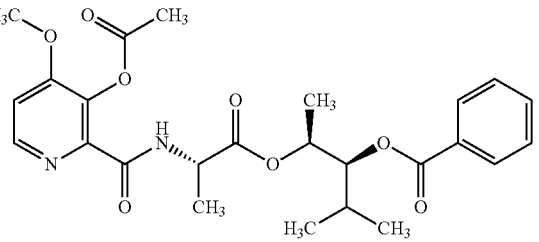 | Example 16A | White Solid |
| 857 | 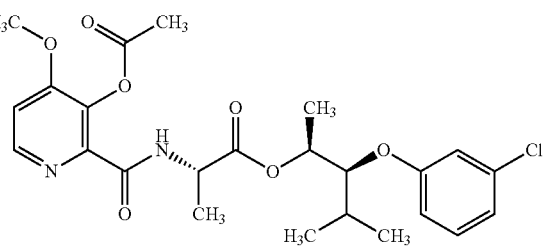 | Example 16A | White Solid |
| 858 | 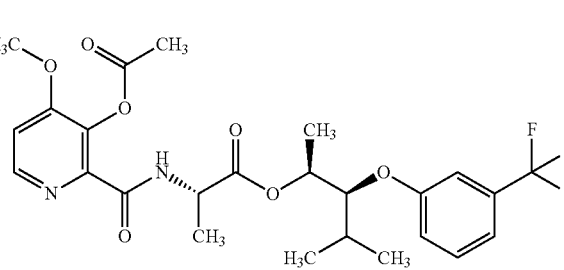 | Example 16A | White Solid |

TABLE 1-continued

Compound Structure, Appearance, and Preparation Method

| *Cmpd. No. | Structure | Prepared According to Example: | Appearance |
|---|---|---|---|
| 859 | 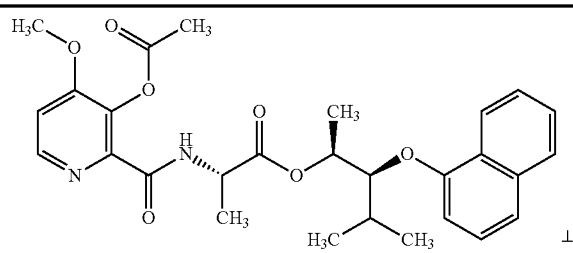 | Example 16A | White Solid |
| 860 | 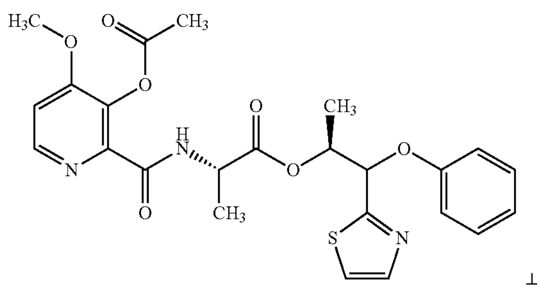 [SMILES: COc1ccnc(C(=O)N[C@@H](C)C(=O)O[C@@H](C)C(Oc2ccccc2)c2nccs2)c1OC(C)=O] | Example 16A | Colorless Foam/Oil |
| 861 | 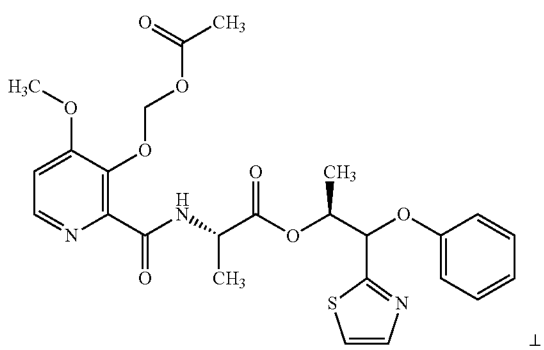 [SMILES: COc1ccnc(C(=O)N[C@@H](C)C(=O)O[C@@H](C)C(Oc2ccccc2)c2nccs2)c1OCOC(C)=O] | Example 16B | Colorless Foam/Oil |
| 862 | 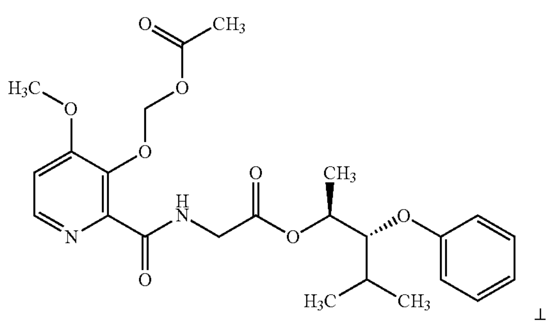 [SMILES: COc1ccnc(C(=O)NCC(=O)O[C@@H](C)[C@H](Oc2ccccc2)C(C)C)c1OCOC(C)=O] | Example 16B | Tacky Oil |
| 863 | 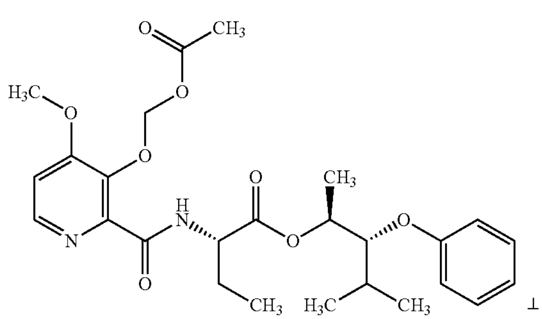 [SMILES: CC[C@H](NC(=O)c1nccc(OC)c1OCOC(C)=O)C(=O)O[C@@H](C)[C@H](Oc1ccccc1)C(C)C] | Example 16B | Colorless Oil |

TABLE 1-continued

Compound Structure, Appearance, and Preparation Method

| *Cmpd. No. | Structure | Prepared According to Example: | Appearance |
|---|---|---|---|
| 864 | 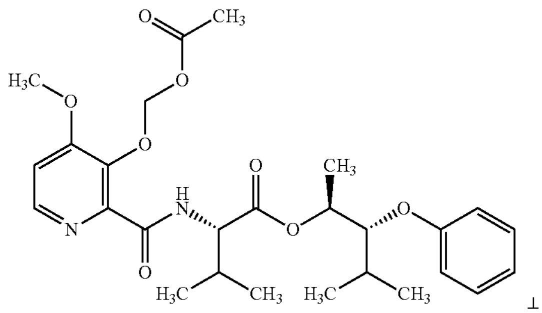 [SMILES: COc1ccnc(C(=O)N[C@H](C(=O)O[C@@H](C)[C@H](Oc2ccccc2)C(C)C)C(C)C)c1OCOC(C)=O] | Example 16B | Colorless Oil |
| 865 | 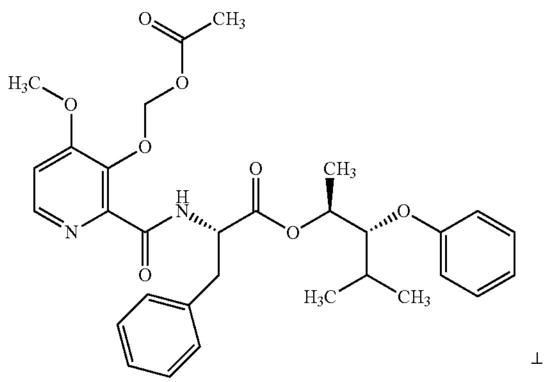 [SMILES: COc1ccnc(C(=O)N[C@@H](Cc2ccccc2)C(=O)O[C@@H](C)[C@H](Oc2ccccc2)C(C)C)c1OCOC(C)=O] | Example 16B | Colorless Oil |
| 866 | 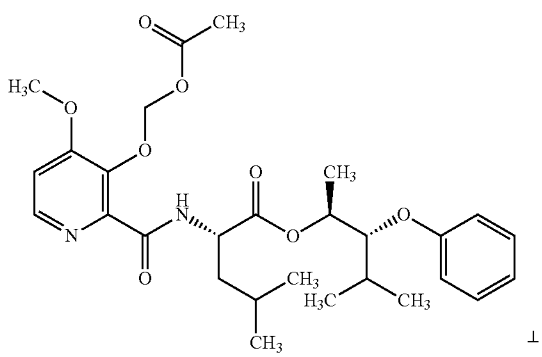 [SMILES: COc1ccnc(C(=O)N[C@@H](CC(C)C)C(=O)O[C@@H](C)[C@H](Oc2ccccc2)C(C)C)c1OCOC(C)=O] | Example 16B | Colorless Oil |
| 867 | 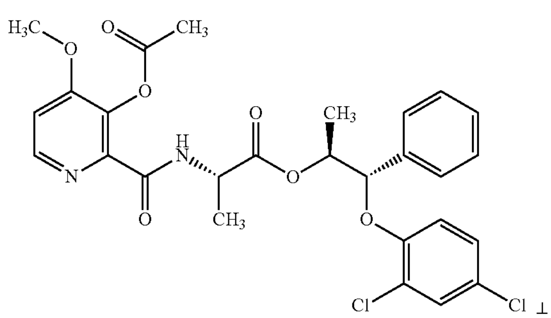 [SMILES: COc1ccnc(C(=O)N[C@@H](C)C(=O)O[C@@H](C)[C@@H](Oc2ccc(Cl)cc2Cl)c2ccccc2)c1OC(C)=O] | Example 16A | Colorless Oil |

TABLE 1-continued

Compound Structure, Appearance, and Preparation Method

| *Cmpd. No. | Structure | Prepared According to Example: | Appearance |
|---|---|---|---|
| 868 | 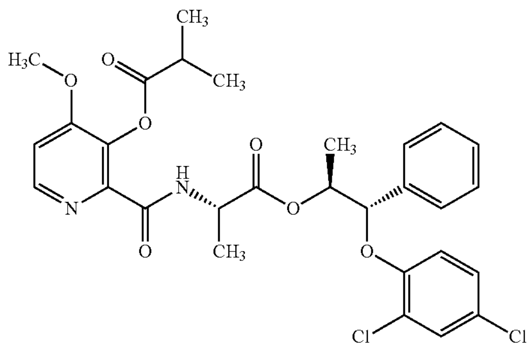 | Example 16A | Colorless Oil |
| 869 | 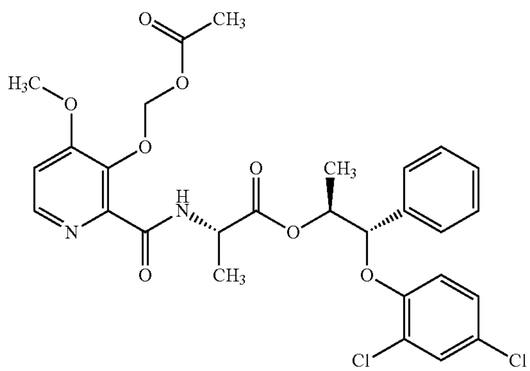 | Example 16B | Colorless Oil |
| 870 | 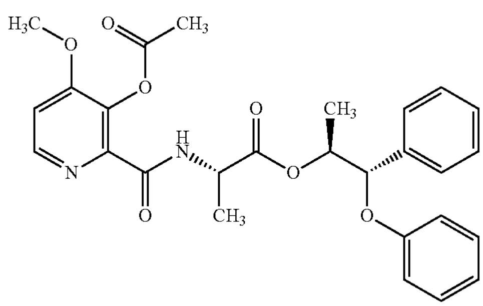 | Example 16A | Colorless Oil |
| 871 | 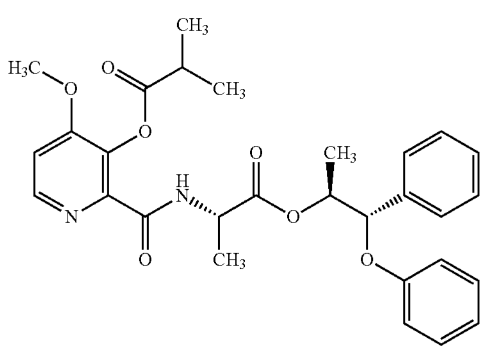 | Example 16A | Colorless Oil |

TABLE 1-continued

Compound Structure, Appearance, and Preparation Method

| *Cmpd. No. | Structure | Prepared According to Example: | Appearance |
|---|---|---|---|
| 872 | 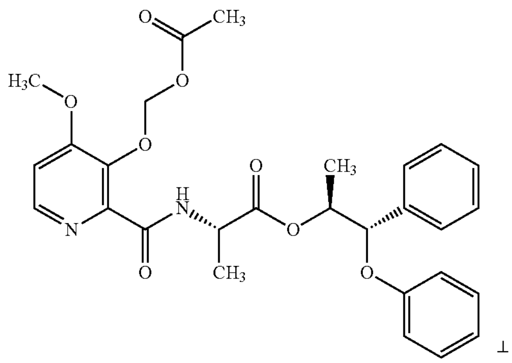 [SMILES: COc1ccnc(C(=O)N[C@@H](C)C(=O)O[C@@H](C)[C@@H](Oc2ccccc2)c2ccccc2)c1OCOC(C)=O] | Example 16B | Colorless Oil |
| 873 | 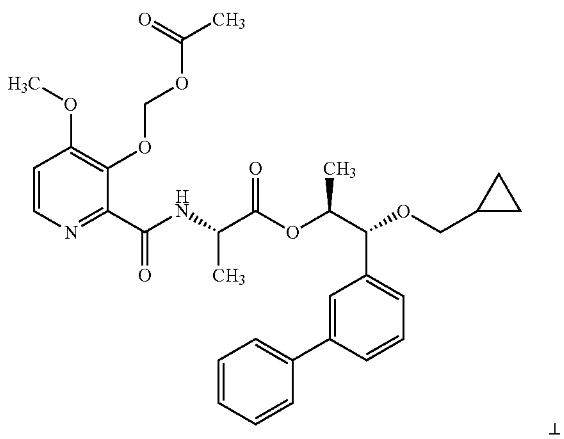 [SMILES: COc1ccnc(C(=O)N[C@@H](C)C(=O)O[C@@H](C)[C@H](OCC2CC2)c2cccc(-c3ccccc3)c2)c1OCOC(C)=O] | Example 16B | Colorless Oil |
| 874 | 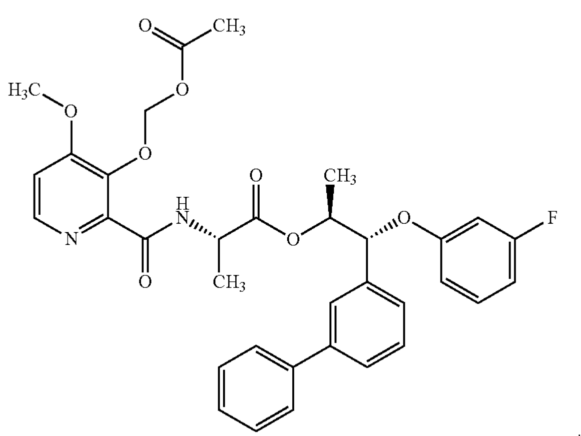 | Example 16B | Colorless Oil |

TABLE 1-continued

Compound Structure, Appearance, and Preparation Method

| *Cmpd. No. | Structure | Prepared According to Example: | Appearance |
|---|---|---|---|
| 875 | (structure) | Example 16A | Colorless Oil |
| 876 | (structure) | Example 16A | Off White Foam |
| 877 | (structure) | Example 16B | Amber Colored Oil |
| 878 | (structure) | Example 16A | Colorless Oil |

TABLE 1-continued

Compound Structure, Appearance, and Preparation Method

| *Cmpd. No. | Structure | Prepared According to Example: | Appearance |
|---|---|---|---|
| 879 | 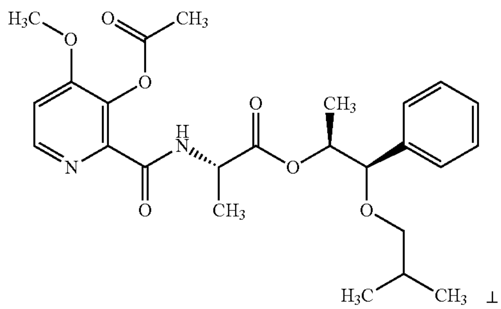 [SMILES: COc1ccnc(C(=O)N[C@@H](C)C(=O)O[C@@H](C)[C@H](OCC(C)C)c2ccccc2)c1OC(C)=O] | Example 16A | Colorless Oil |
| 880 | 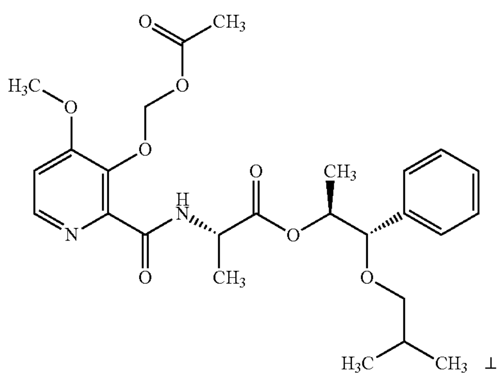 [SMILES: COc1ccnc(C(=O)N[C@@H](C)C(=O)O[C@@H](C)[C@@H](OCC(C)C)c2ccccc2)c1OCOC(C)=O] | Example 16B | Colorless Oil |
| 881 | 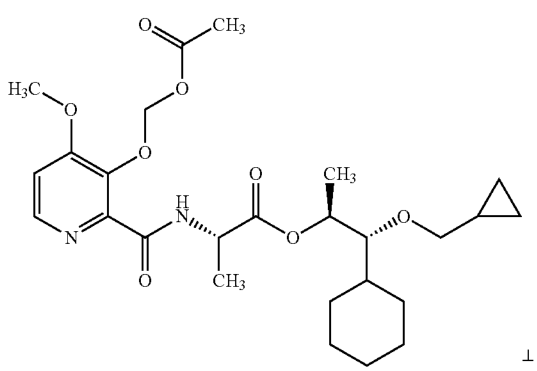 [SMILES: COc1ccnc(C(=O)N[C@@H](C)C(=O)O[C@@H](C)[C@H](OCC2CC2)C2CCCCC2)c1OCOC(C)=O] | Example 16B | Colorless Oil |
| 882 | 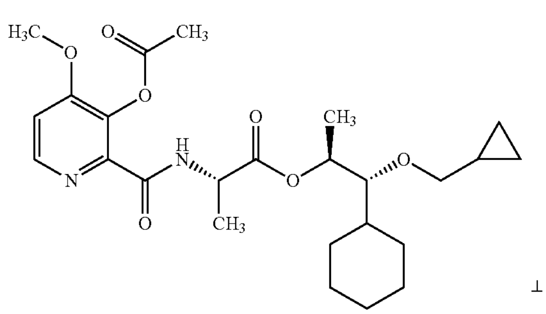 [SMILES: COc1ccnc(C(=O)N[C@@H](C)C(=O)O[C@@H](C)[C@H](OCC2CC2)C2CCCCC2)c1OC(C)=O] | Example 16A | Colorless Oil |

TABLE 1-continued

Compound Structure, Appearance, and Preparation Method

| *Cmpd. No. | Structure | Prepared According to Example: | Appearance |
|---|---|---|---|
| 883 | 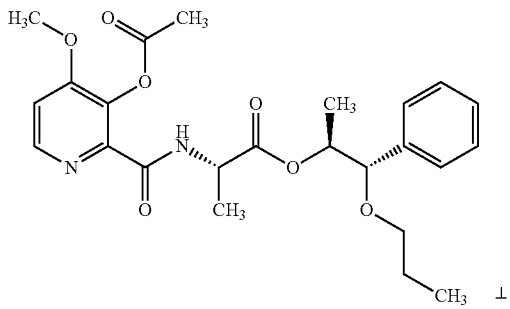 [SMILES: CCCO[C@@H](c1ccccc1)[C@H](C)OC(=O)[C@H](C)NC(=O)c1nccc(OC)c1OC(C)=O] | Example 16A | Colorless Oil |
| 884 | 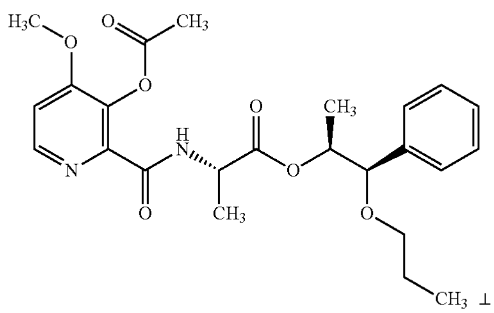 [SMILES: CCCO[C@H](c1ccccc1)[C@H](C)OC(=O)[C@H](C)NC(=O)c1nccc(OC)c1OC(C)=O] | Example 16A | Colorless Oil |
| 885 | 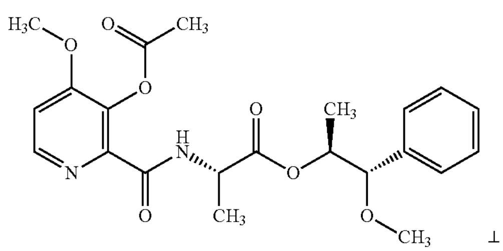 [SMILES: COc1ccnc(C(=O)N[C@@H](C)C(=O)O[C@@H](C)[C@@H](OC)c2ccccc2)c1OC(C)=O] | Example 16A | Colorless Oil |
| 886 | 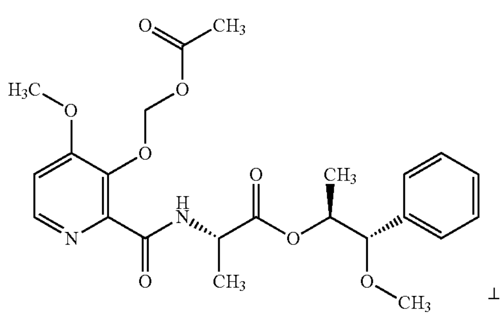 [SMILES: COc1ccnc(C(=O)N[C@@H](C)C(=O)O[C@@H](C)[C@@H](OC)c2ccccc2)c1OCOC(C)=O] | Example 16B | Colorless Oil |
| 887 | 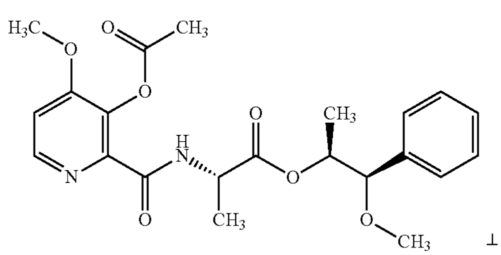 [SMILES: COc1ccnc(C(=O)N[C@@H](C)C(=O)O[C@@H](C)[C@H](OC)c2ccccc2)c1OC(C)=O] | Example 16A | Colorless Oil |

… TABLE 1-continued

Compound Structure, Appearance, and Preparation Method

| *Cmpd. No. | Structure | Prepared According to Example: | Appearance |
|---|---|---|---|
| 888 | 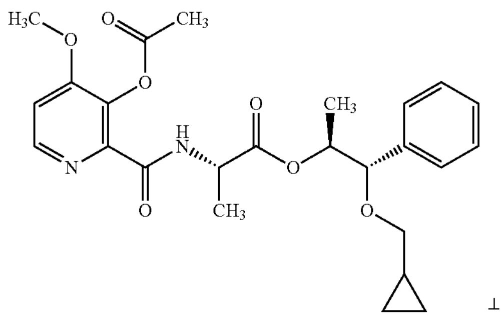 [SMILES: COc1ccnc(C(=O)N[C@@H](C)C(=O)O[C@@H](C)[C@@H](OCC2CC2)c2ccccc2)c1OC(C)=O] | Example 16A | Colorless Oil |
| 889 | 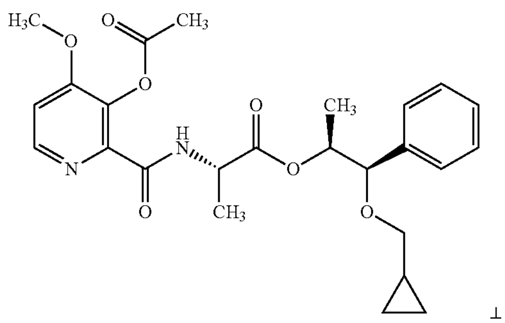 [SMILES: COc1ccnc(C(=O)N[C@@H](C)C(=O)O[C@@H](C)[C@H](OCC2CC2)c2ccccc2)c1OC(C)=O] | Example 16A | Colorless Oil |
| 890 | 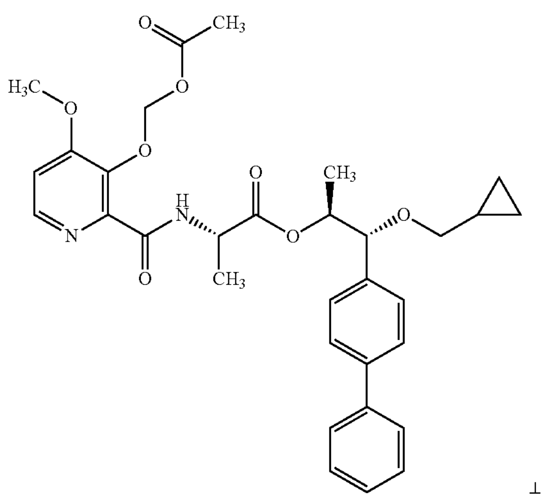 [SMILES: COc1ccnc(C(=O)N[C@@H](C)C(=O)O[C@@H](C)[C@H](OCC2CC2)c2ccc(-c3ccccc3)cc2)c1OCOC(C)=O] | Example 16B | Colorless Oil |
| 891 | 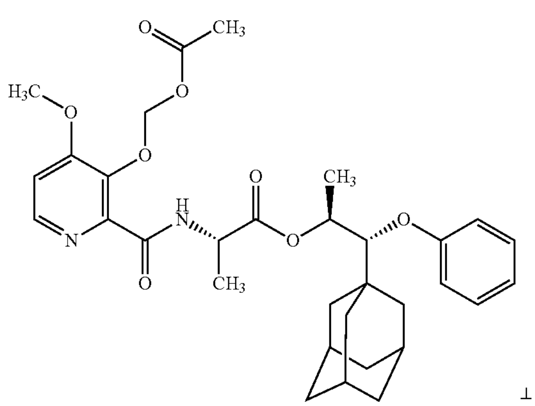 [SMILES: COc1ccnc(C(=O)N[C@@H](C)C(=O)O[C@@H](C)[C@H](Oc2ccccc2)C23CC4CC(CC(C4)C2)C3)c1OCOC(C)=O] | Example 16B | White Foam |

TABLE 1-continued
Compound Structure, Appearance, and Preparation Method
| *Cmpd. No. | Structure | Prepared According to Example: | Appearance |
|---|---|---|---|
| 892 | 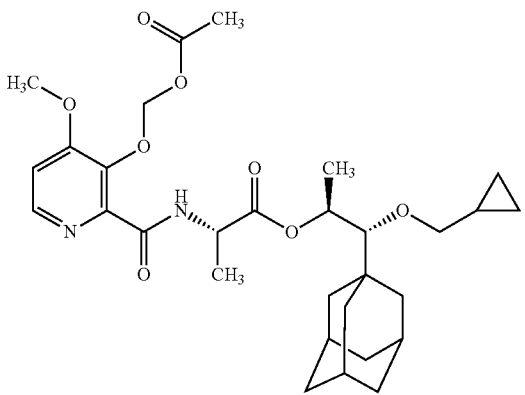 | Example 16B | Sticky Wax |
| 893 | 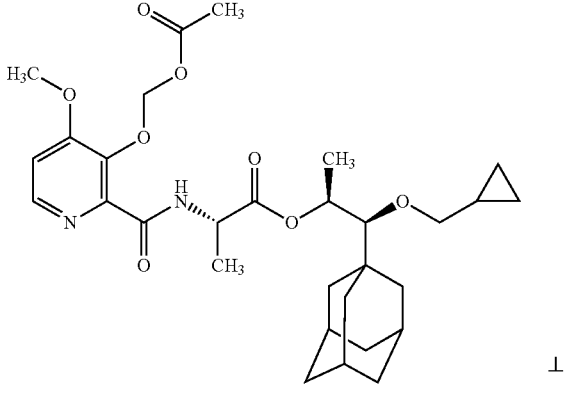 [SMILES: COc1ccnc(C(=O)N[C@@H](C)C(=O)O[C@@H](C)[C@@H](OCC2CC2)C23CC4CC(CC(C4)C2)C3)c1OCOC(C)=O] | Example 16B | Sticky Wax |
| 894 | 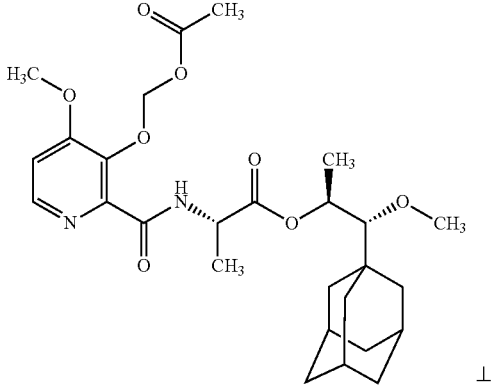 [SMILES: COc1ccnc(C(=O)N[C@@H](C)C(=O)O[C@@H](C)[C@H](OC)C23CC4CC(CC(C4)C2)C3)c1OCOC(C)=O] | Example 16B | Sticky Wax |

TABLE 1-continued
Compound Structure, Appearance, and Preparation Method
| *Cmpd. No. | Structure | Prepared According to Example: | Appearance |
|---|---|---|---|
| 895 | 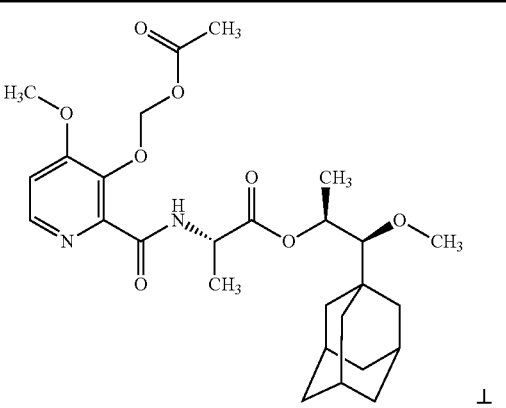 | Example 16B | Sticky Wax |
| 896 | 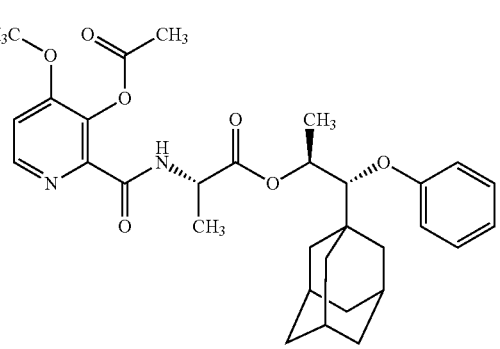 | Example 16A | Pale Yellow Wax |
| 897 | 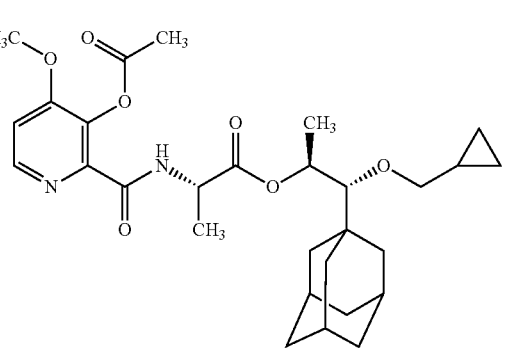 | Example 16A | Pale Yellow Wax |
| 898 | 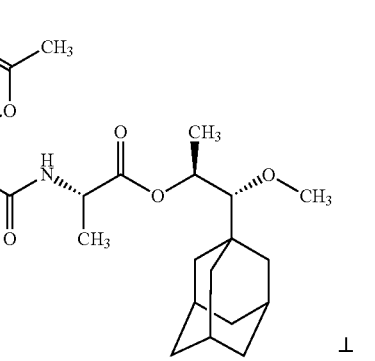 | Example 16A | Pale Yellow Wax |

TABLE 1-continued

Compound Structure, Appearance, and Preparation Method

| *Cmpd. No. | Structure | Prepared According to Example: | Appearance |
|---|---|---|---|
| 899 | 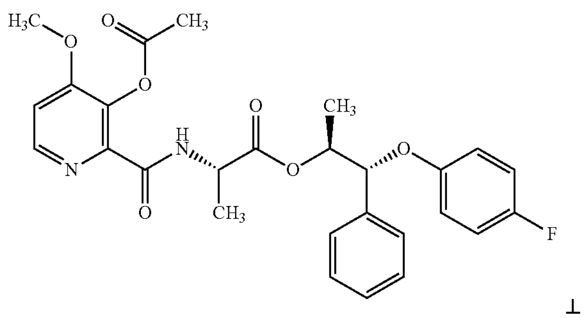 [SMILES: COc1ccnc(C(=O)N[C@@H](C)C(=O)O[C@@H](C)[C@H](Oc2ccc(F)cc2)c2ccccc2)c1OC(C)=O] | Example 16A | Colorless Oil |
| 900 | 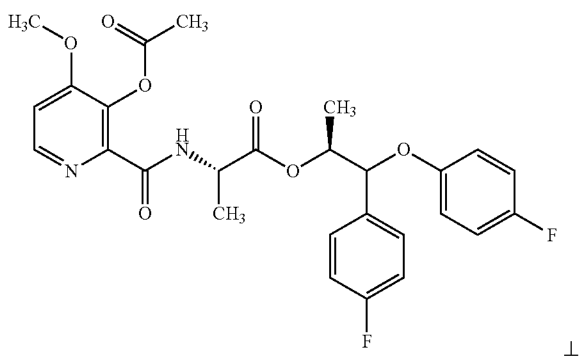 [SMILES: COc1ccnc(C(=O)N[C@@H](C)C(=O)O[C@@H](C)C(Oc2ccc(F)cc2)c2ccc(F)cc2)c1OC(C)=O] | Example 16A | Colorless Oil |
| 901 | 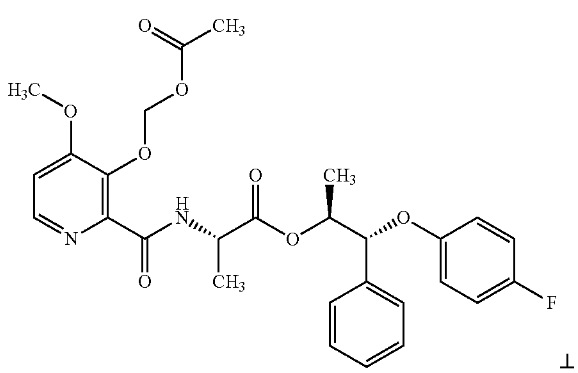 [SMILES: COc1ccnc(C(=O)N[C@@H](C)C(=O)O[C@@H](C)[C@H](Oc2ccc(F)cc2)c2ccccc2)c1OCOC(C)=O] | Example 16B | Colorless Oil |
| 902 | 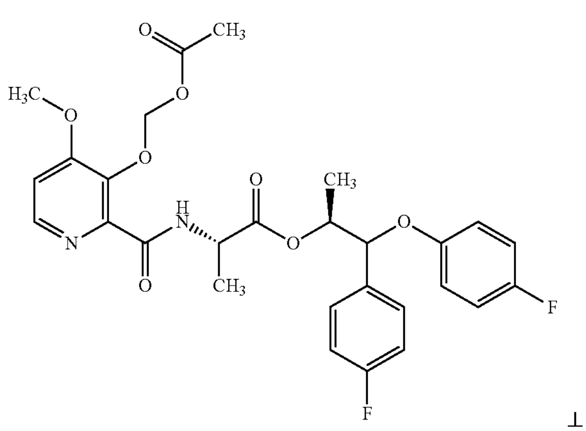 [SMILES: COc1ccnc(C(=O)N[C@@H](C)C(=O)O[C@@H](C)C(Oc2ccc(F)cc2)c2ccc(F)cc2)c1OCOC(C)=O] | Example 16B | Colorless Oil |

TABLE 1-continued
Compound Structure, Appearance, and Preparation Method
| *Cmpd. No. | Structure | Prepared According to Example: | Appearance |
|---|---|---|---|
| 903 | 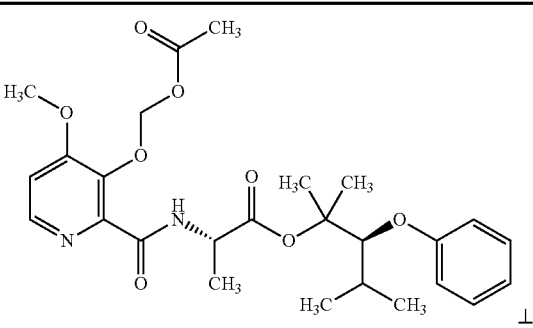 | Example 16B | Yellow Oil |
| 904 | 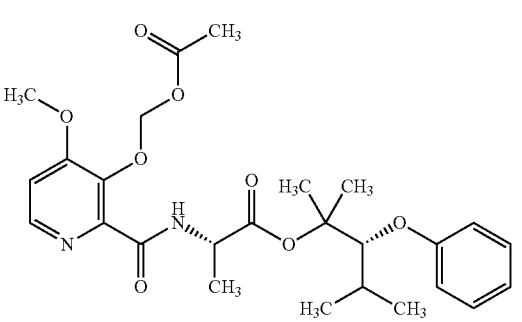 | Example 16B | Yellow Oil |
| 905 | 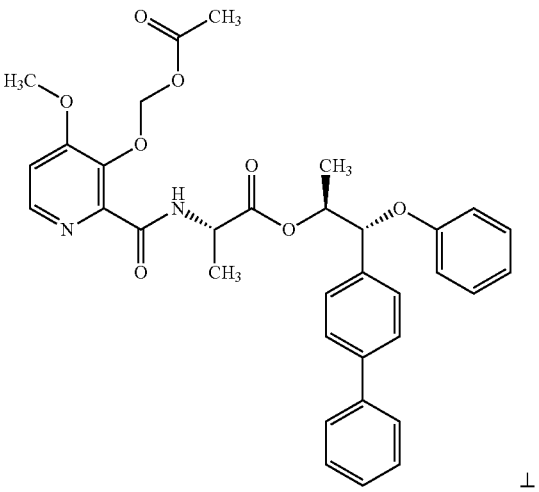 [SMILES: COc1ccnc(C(=O)N[C@@H](C)C(=O)O[C@@H](C)[C@H](Oc2ccccc2)c2ccc(-c3ccccc3)cc2)c1OCOC(C)=O] | Example 16B | Colorless Oil |

TABLE 1-continued
Compound Structure, Appearance, and Preparation Method
| *Cmpd. No. | Structure | Prepared According to Example: | Appearance |
|---|---|---|---|
| 906 | 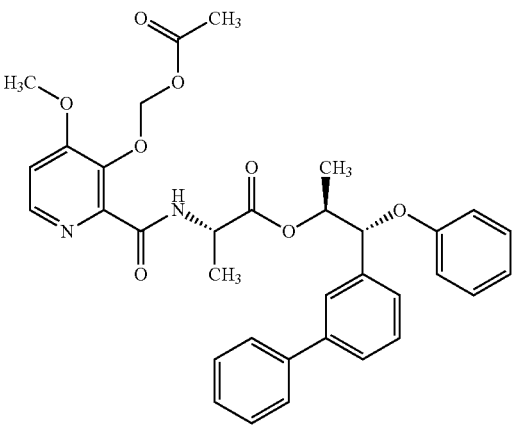 | Example 16B | Colorless Oil |
| 907 | 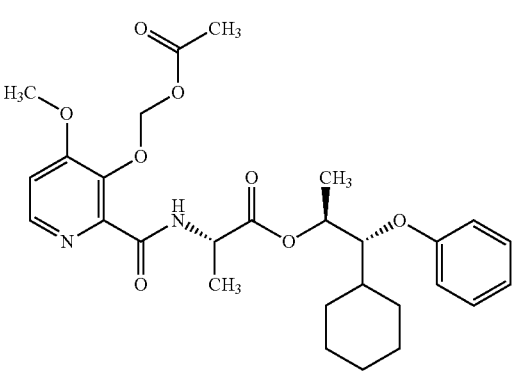 | Example 16B | Light Yellow Oil |
| 908 | 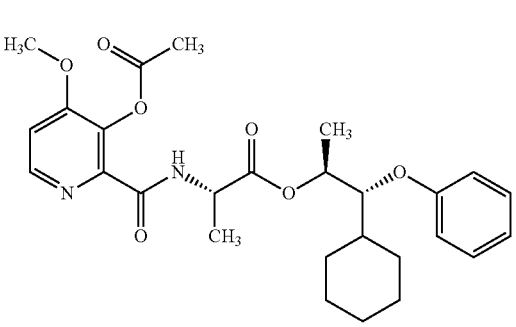 | Example 16A | Yellow Oil |
| 909 | 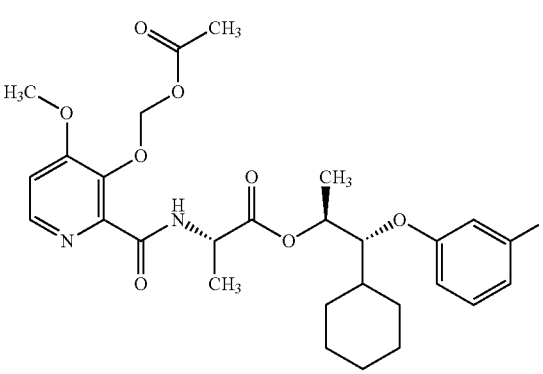 | Example 16B | Colorless Oil |

TABLE 1-continued

Compound Structure, Appearance, and Preparation Method

| *Cmpd. No. | Structure | Prepared According to Example: | Appearance |
|---|---|---|---|
| 910 | 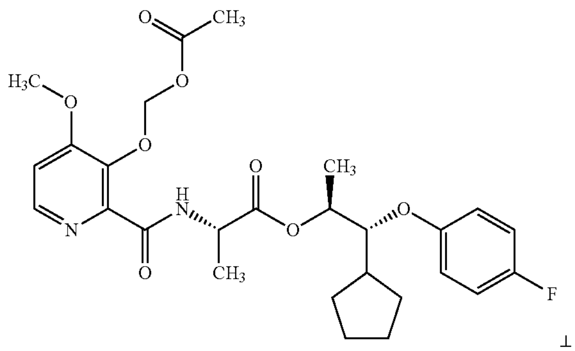 [SMILES: COc1ccnc(C(=O)N[C@@H](C)C(=O)O[C@@H](C)[C@H](Oc2ccc(F)cc2)C2CCCC2)c1OCOC(C)=O] | Example 16B | Colorless Oil |
| 911 | 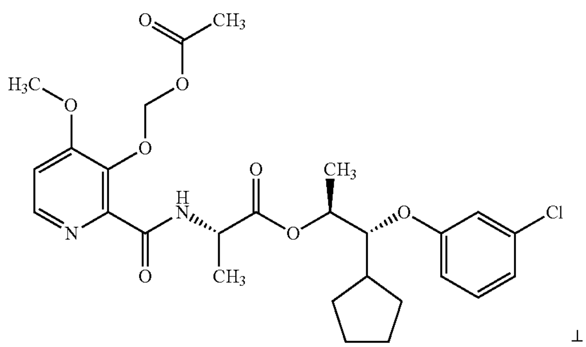 [SMILES: COc1ccnc(C(=O)N[C@@H](C)C(=O)O[C@@H](C)[C@H](Oc2cccc(Cl)c2)C2CCCC2)c1OCOC(C)=O] | Example 16B | Colorless Oil |
| 912 | 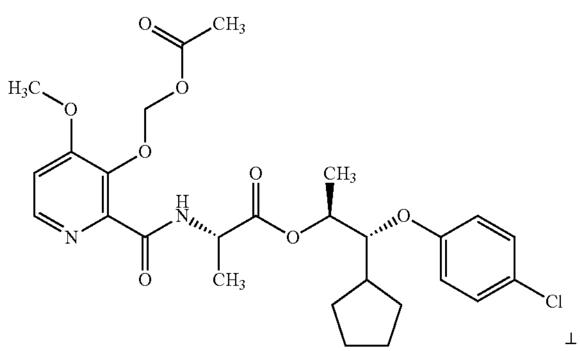 [SMILES: COc1ccnc(C(=O)N[C@@H](C)C(=O)O[C@@H](C)[C@H](Oc2ccc(Cl)cc2)C2CCCC2)c1OCOC(C)=O] | Example 16B | Colorless Oil |
| 913 | 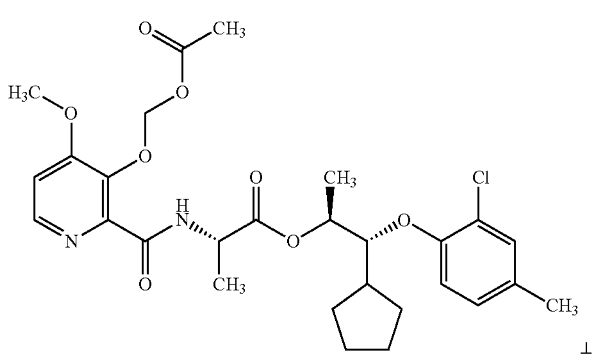 [SMILES: COc1ccnc(C(=O)N[C@@H](C)C(=O)O[C@@H](C)[C@H](Oc2ccc(C)cc2Cl)C2CCCC2)c1OCOC(C)=O] | Example 16B | Colorless Oil |

TABLE 1-continued

Compound Structure, Appearance, and Preparation Method

| *Cmpd. No. | Structure | Prepared According to Example: | Appearance |
|---|---|---|---|
| 914 | 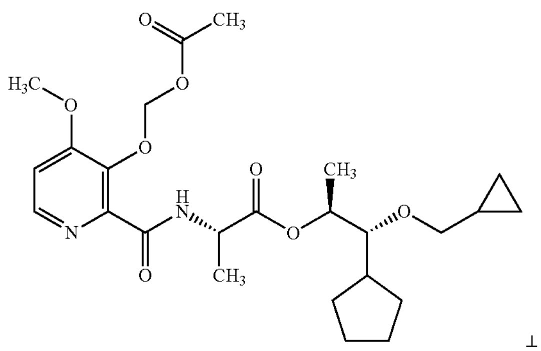 [SMILES: COc1ccnc(C(=O)N[C@@H](C)C(=O)O[C@@H](C)[C@H](OCC2CC2)C2CCCC2)c1OCOC(C)=O] | Example 16B | Colorless Oil |
| 915 | 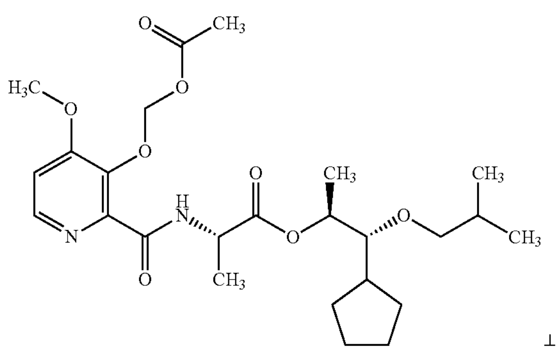 [SMILES: COc1ccnc(C(=O)N[C@@H](C)C(=O)O[C@@H](C)[C@H](OCC(C)C)C2CCCC2)c1OCOC(C)=O] | Example 16B | Colorless Oil |
| 916 | 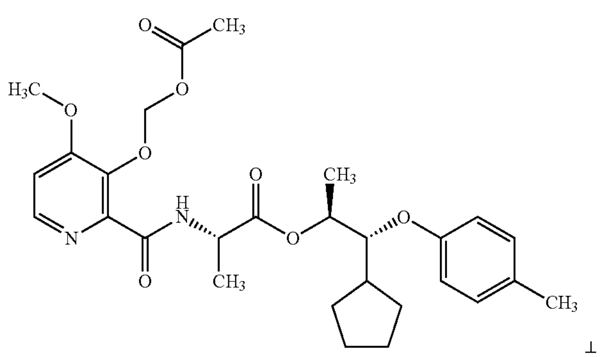 [SMILES: COc1ccnc(C(=O)N[C@@H](C)C(=O)O[C@@H](C)[C@H](Oc2ccc(C)cc2)C2CCCC2)c1OCOC(C)=O] | Example 16B | Colorless Oil |
| 917 | 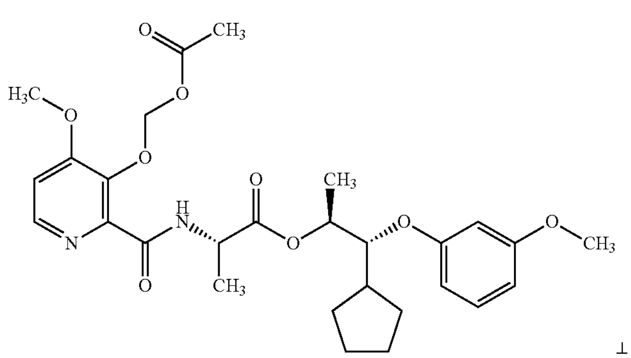 [SMILES: COc1cccc(O[C@H](C2CCCC2)[C@H](C)OC(=O)[C@H](C)NC(=O)c2nccc(OC)c2OCOC(C)=O)c1] | Example 16B | Colorless Oil |

TABLE 1-continued

Compound Structure, Appearance, and Preparation Method

| *Cmpd. No. | Structure | Prepared According to Example: | Appearance |
|---|---|---|---|
| 918 | 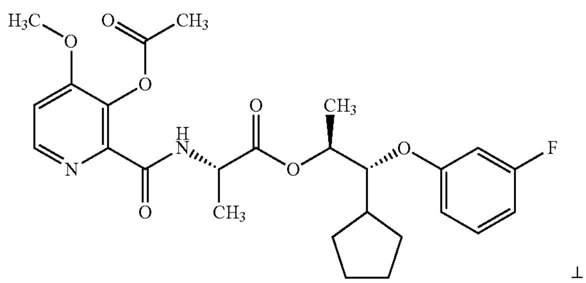 [SMILES: COc1ccnc(C(=O)N[C@@H](C)C(=O)O[C@@H](C)[C@H](Oc2cccc(F)c2)C2CCCC2)c1OC(C)=O] | Example 16A | Colorless Oil |
| 919 | 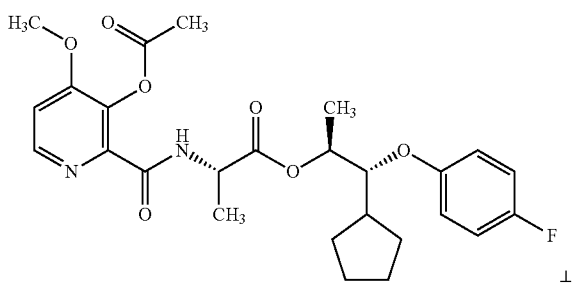 [SMILES: COc1ccnc(C(=O)N[C@@H](C)C(=O)O[C@@H](C)[C@H](Oc2ccc(F)cc2)C2CCCC2)c1OC(C)=O] | Example 16A | Colorless Oil |
| 920 | 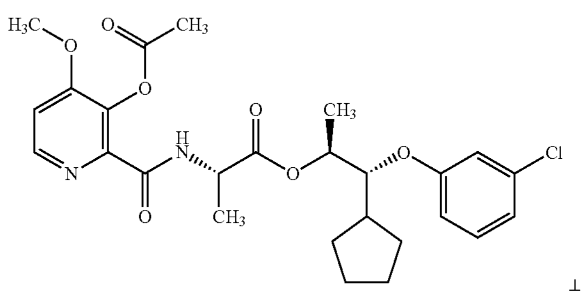 [SMILES: COc1ccnc(C(=O)N[C@@H](C)C(=O)O[C@@H](C)[C@H](Oc2cccc(Cl)c2)C2CCCC2)c1OC(C)=O] | Example 16A | Colorless Oil |
| 921 | 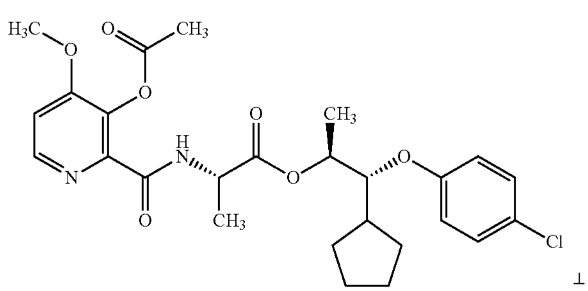 [SMILES: COc1ccnc(C(=O)N[C@@H](C)C(=O)O[C@@H](C)[C@H](Oc2ccc(Cl)cc2)C2CCCC2)c1OC(C)=O] | Example 16A | Colorless Oil |
| 922 | 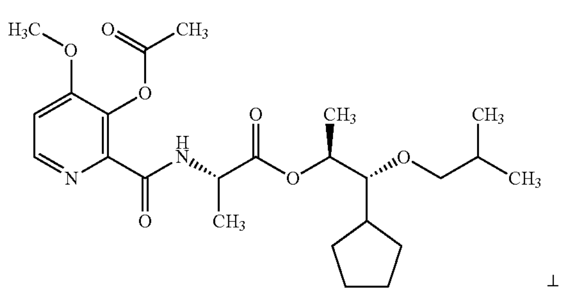 [SMILES: COc1ccnc(C(=O)N[C@@H](C)C(=O)O[C@@H](C)[C@H](OCC(C)C)C2CCCC2)c1OC(C)=O] | Example 16A | Colorless Oil |

TABLE 1-continued

Compound Structure, Appearance, and Preparation Method

| *Cmpd. No. | Structure | Prepared According to Example: | Appearance |
|---|---|---|---|
| 923 | 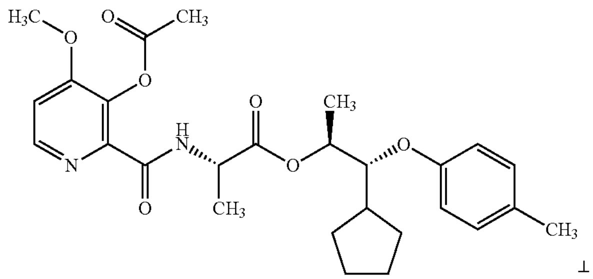 [SMILES: COc1ccnc(C(=O)N[C@@H](C)C(=O)O[C@@H](C)[C@H](Oc2ccc(C)cc2)C2CCCC2)c1OC(C)=O] | Example 16A | Colorless Oil |
| 924 | 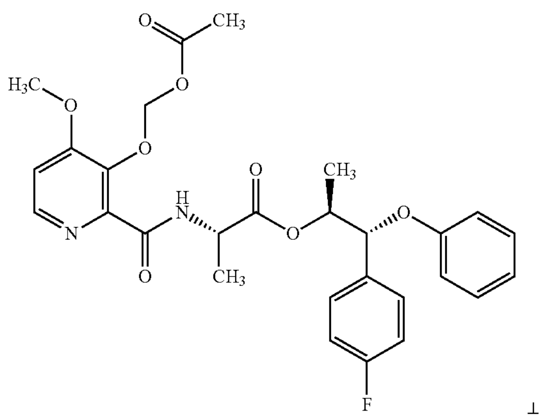 [SMILES: COc1ccnc(C(=O)N[C@@H](C)C(=O)O[C@@H](C)[C@H](Oc2ccccc2)c2ccc(F)cc2)c1OCOC(C)=O] | Example 16B | Colorless Oil |
| 925 | 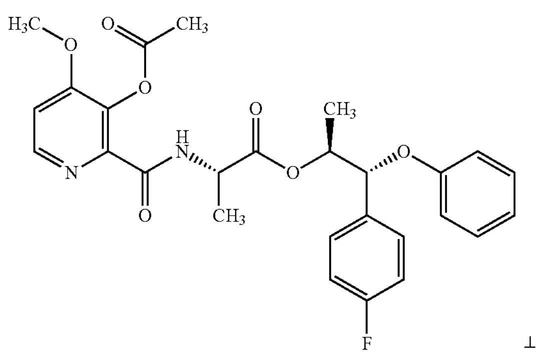 [SMILES: COc1ccnc(C(=O)N[C@@H](C)C(=O)O[C@@H](C)[C@H](Oc2ccccc2)c2ccc(F)cc2)c1OC(C)=O] | Example 16A | Light Yellow Oil |
| 926 | 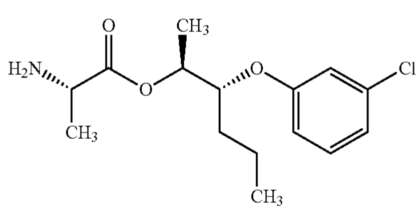 [SMILES: CCC[C@@H](Oc1cccc(Cl)c1)[C@H](C)OC(=O)[C@H](C)N] | Example 14A, Step 1. | Tacky Oil |
| 927 | 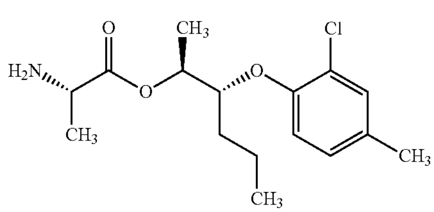 [SMILES: CCC[C@@H](Oc1ccc(C)cc1Cl)[C@H](C)OC(=O)[C@H](C)N] | Example 14A, Step 1. | Tacky Oil |

TABLE 1-continued

Compound Structure, Appearance, and Preparation Method

| *Cmpd. No. | Structure | Prepared According to Example: | Appearance |
|---|---|---|---|
| 928 | 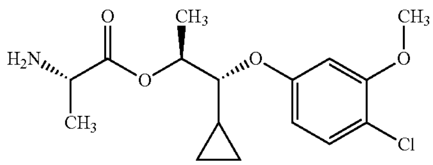 [SMILES: COc1cc(O[C@H](C2CC2)[C@H](C)OC(=O)[C@H](C)N)ccc1Cl] | Example 14A, Step 1. | Tacky Oil |
| 929 | 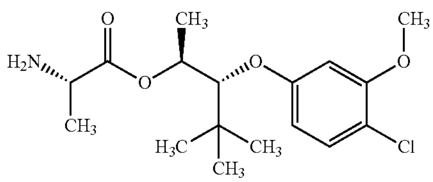 [SMILES: COc1cc(O[C@@H]([C@H](C)OC(=O)[C@H](C)N)C(C)(C)C)ccc1Cl] | Example 14A, Step 1. | Tacky Oil |
| 930 | 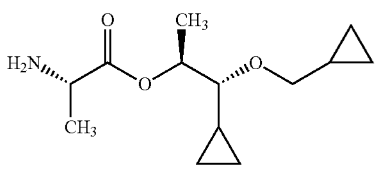 [SMILES: C[C@H](N)C(=O)O[C@@H](C)[C@H](OCC1CC1)C1CC1] | Example 14A, Step 1. | Tacky Oil |
| 931 | 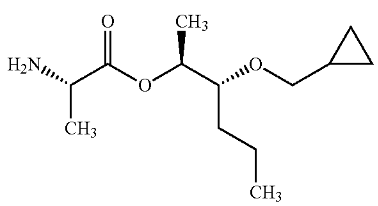 [SMILES: CCC[C@@H](OCC1CC1)[C@H](C)OC(=O)[C@H](C)N] | Example 14A, Step 1. | Tacky Oil |
| 932 | 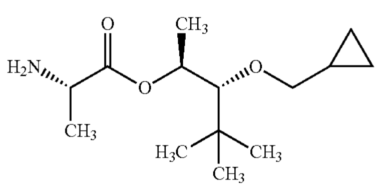 [SMILES: C[C@H](N)C(=O)O[C@@H](C)[C@H](OCC1CC1)C(C)(C)C] | Example 14A, Step 1. | Tacky Oil |
| 933 | 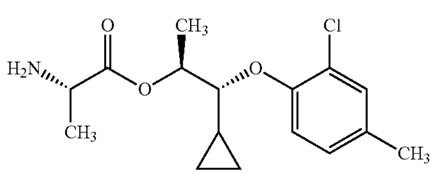 [SMILES: Cc1ccc(O[C@H](C2CC2)[C@H](C)OC(=O)[C@H](C)N)c(Cl)c1] | Example 14A, Step 1. | Tacky Oil |
| 934 | 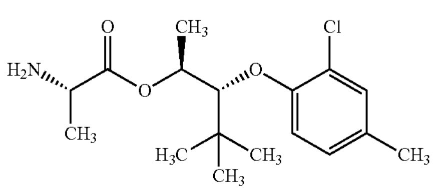 [SMILES: Cc1ccc(O[C@@H]([C@H](C)OC(=O)[C@H](C)N)C(C)(C)C)c(Cl)c1] | Example 14A, Step 1. | Tacky Oil |
| 935 | 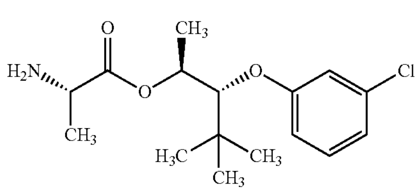 [SMILES: C[C@H](N)C(=O)O[C@@H](C)[C@H](Oc1cccc(Cl)c1)C(C)(C)C] | Example 14A, Step 1. | Tacky Oil |

TABLE 1-continued

Compound Structure, Appearance, and Preparation Method

| *Cmpd. No. | Structure | Prepared According to Example: | Appearance |
|---|---|---|---|
| 936 | 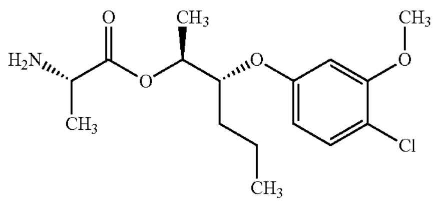 [SMILES: CCC[C@@H](Oc1ccc(Cl)c(OC)c1)[C@H](C)OC(=O)[C@H](C)N] | Example 14A, Step 1. | Tacky Oil |
| 937 | 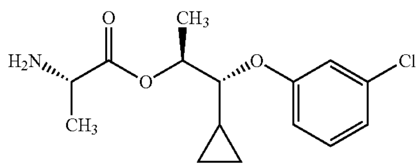 [SMILES: C[C@H](N)C(=O)O[C@@H](C)[C@H](Oc1cccc(Cl)c1)C1CC1] | Example 14A, Step 1. | Tacky Oil |
| 938 | 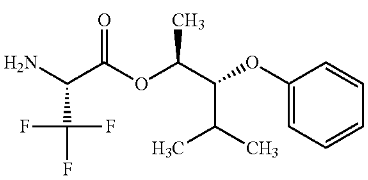 [SMILES: CC(C)[C@@H](Oc1ccccc1)[C@H](C)OC(=O)[C@@H](N)C(F)(F)F] | Example 14A, Step 1. | Yellow Sticky Wax |
| 939 | 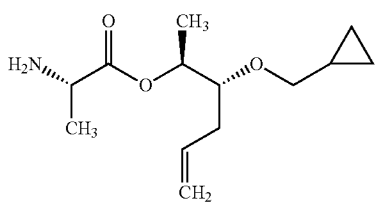 [SMILES: C=CC[C@@H](OCC1CC1)[C@H](C)OC(=O)[C@H](C)N] | Example 14B, Step 1. | Pale Yellow Oil |
| 940 | 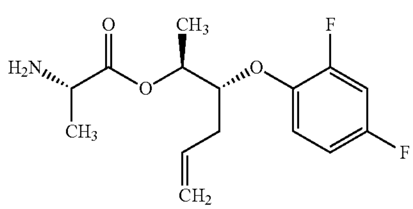 [SMILES: C=CC[C@@H](Oc1ccc(F)cc1F)[C@H](C)OC(=O)[C@H](C)N] | Example 14B, Step 1. | Pale Yellow Oil |
| 941 | 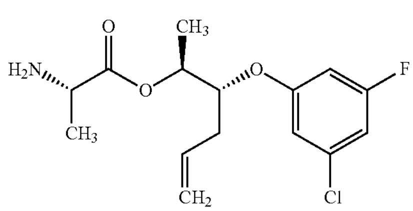 [SMILES: C=CC[C@@H](Oc1cc(F)cc(Cl)c1)[C@H](C)OC(=O)[C@H](C)N] | Example 14B, Step 1. | Pale Yellow Oil |
| 942 | 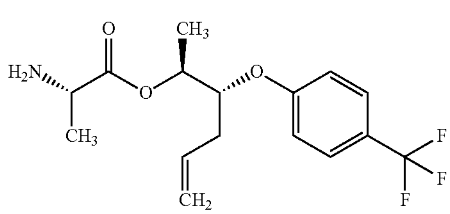 [SMILES: C=CC[C@@H](Oc1ccc(C(F)(F)F)cc1)[C@H](C)OC(=O)[C@H](C)N] | Example 14B, Step 1. | Pale Yellow Oil |

TABLE 1-continued

Compound Structure, Appearance, and Preparation Method

| *Cmpd. No. | Structure | Prepared According to Example: | Appearance |
|---|---|---|---|
| 943 | 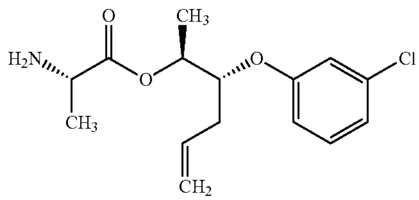 [SMILES: C=CC[C@@H](Oc1cccc(Cl)c1)[C@H](C)OC(=O)[C@H](C)N] | Example 14B, Step 1. | Pale Yellow Oil |
| 944 | 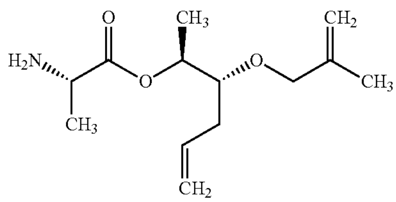 [SMILES: C=CC[C@@H](OCC(=C)C)[C@H](C)OC(=O)[C@H](C)N] | Example 14B, Step 1. | Orange Oil |
| 945 | 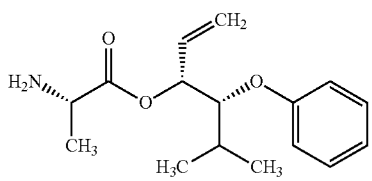 [SMILES: C=C[C@@H](OC(=O)[C@H](C)N)[C@H](Oc1ccccc1)C(C)C] | Example 14A, Step 1 | White Solid |
| 946 | 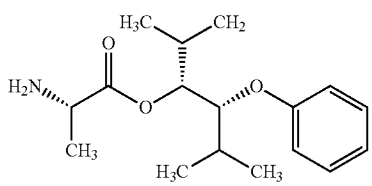 [SMILES: CC(C)[C@@H](OC(=O)[C@H](C)N)[C@H](Oc1ccccc1)C(C)C] | Example 14A, Step 1 | Colorless Oil |
| 947 | 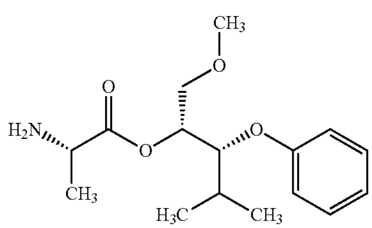 | Example 14A, Step 1 | White Solid |
| 948 | 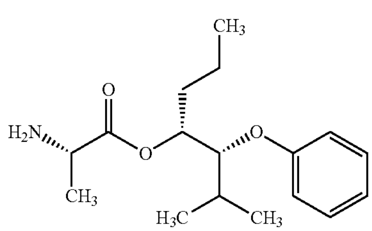 [SMILES: COC[C@@H](OC(=O)[C@H](C)N)[C@H](Oc1ccccc1)C(C)C] | Example 14A, Step 1 | Colorless Oil |
| 949 | 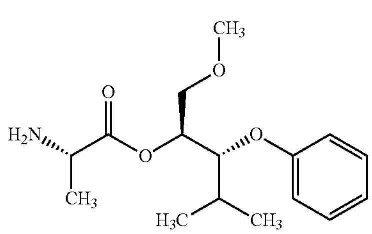 | Example 14A, Step 1 | White Solid |

TABLE 1-continued

Compound Structure, Appearance, and Preparation Method

| *Cmpd. No. | Structure | Prepared According to Example: | Appearance |
|---|---|---|---|
| 950 | 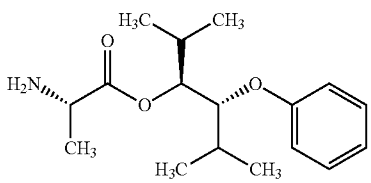 [SMILES: CC(C)[C@@H](Oc1ccccc1)[C@@H](OC(=O)[C@H](C)N)C(C)C] | Example 14A, Step 1 | White Solid |
| 951 | 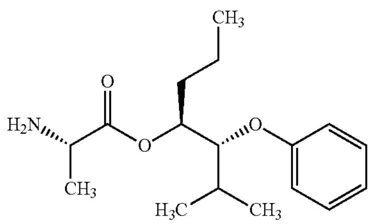 [SMILES: CCC[C@H](OC(=O)[C@H](C)N)[C@H](Oc1ccccc1)C(C)C] | Example 14A, Step 1 | White Solid |
| 952 | 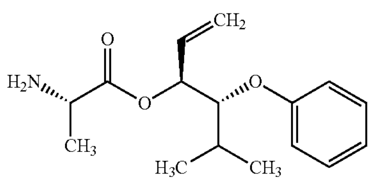 [SMILES: C=C[C@H](OC(=O)[C@H](C)N)[C@H](Oc1ccccc1)C(C)C] | Example 14A, Step 1 | White Solid |
| 953 | 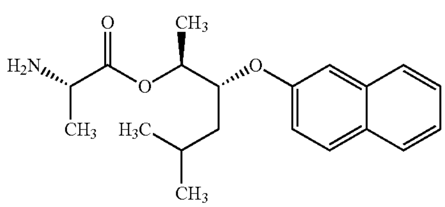 [SMILES: CC(C)C[C@@H](Oc1ccc2ccccc2c1)[C@H](C)OC(=O)[C@H](C)N] | Example 14A, Step 1 | Yellow Oil |
| 954 | 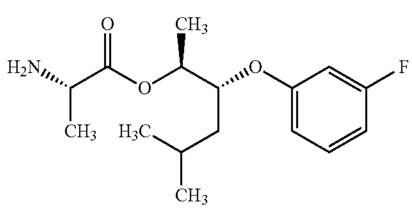 [SMILES: CC(C)C[C@@H](Oc1cccc(F)c1)[C@H](C)OC(=O)[C@H](C)N] | Example 14A, Step 1 | Yellow Oil |
| 955 | 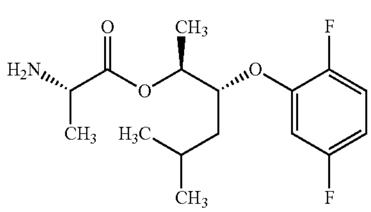 [SMILES: CC(C)C[C@@H](Oc1cc(F)ccc1F)[C@H](C)OC(=O)[C@H](C)N] | Example 14A, Step 1 | Yellow Oil |
| 956 | 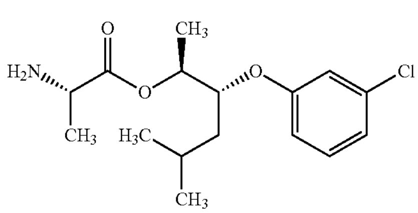 [SMILES: CC(C)C[C@@H](Oc1cccc(Cl)c1)[C@H](C)OC(=O)[C@H](C)N] | Example 14A, Step 1 | Yellow Oil |

TABLE 1-continued

Compound Structure, Appearance, and Preparation Method

| *Cmpd. No. | Structure | Prepared According to Example: | Appearance |
|---|---|---|---|
| 957 | 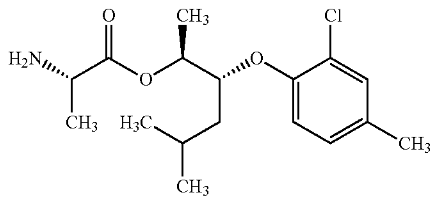 [SMILES: Cc1ccc(O[C@H](CC(C)C)[C@H](C)OC(=O)[C@H](C)N)c(Cl)c1] | Example 14A, Step 1 | Yellow Oil |
| 958 | 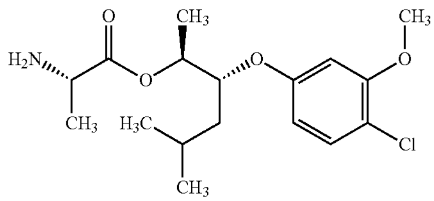 [SMILES: COc1cc(O[C@H](CC(C)C)[C@H](C)OC(=O)[C@H](C)N)ccc1Cl] | Example 14A, Step 1 | Yellow Oil |
| 959 | 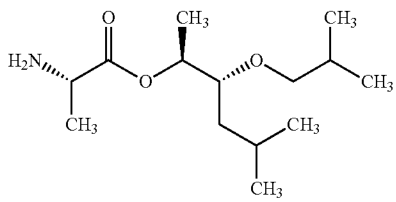 [SMILES: CC(C)CO[C@H](CC(C)C)[C@H](C)OC(=O)[C@H](C)N] | Example 14A, Step 1 | Yellow Oil |
| 960 | 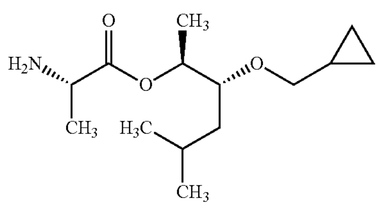 [SMILES: CC(C)C[C@@H](OCC1CC1)[C@H](C)OC(=O)[C@H](C)N] | Example 14A, Step 1 | Yellow Oil |
| 961 | 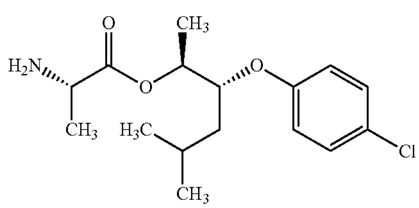 [SMILES: CC(C)C[C@@H](Oc1ccc(Cl)cc1)[C@H](C)OC(=O)[C@H](C)N] | Example 14A, Step 1 | Yellow Oil |
| 962 | 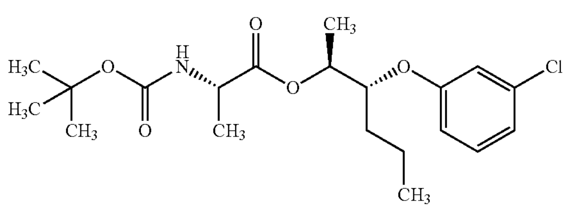 [SMILES: CCC[C@@H](Oc1cccc(Cl)c1)[C@H](C)OC(=O)[C@H](C)NC(=O)OC(C)(C)C] | Example 1A; Example 4C; Example 8A; Example 12A. | Pale Yellow Oil |
| 963 | 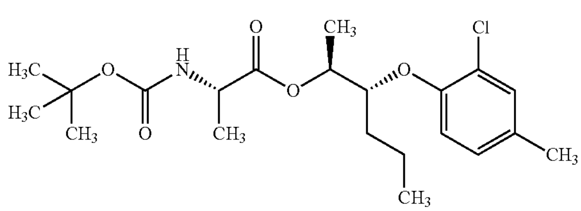 [SMILES: CCC[C@@H](Oc1ccc(C)cc1Cl)[C@H](C)OC(=O)[C@H](C)NC(=O)OC(C)(C)C] | Example 1A; Example 4C; Example 8A; Example 12A. | Pale Yellow Oil |

TABLE 1-continued

Compound Structure, Appearance, and Preparation Method

| *Cmpd. No. | Structure | Prepared According to Example: | Appearance |
|---|---|---|---|
| 964 | 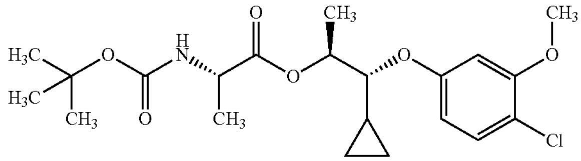 [SMILES: COc1cc(O[C@H](C2CC2)[C@H](C)OC(=O)[C@H](C)NC(=O)OC(C)(C)C)ccc1Cl] | Example 1A; Example 4C; Example 8A; Example 12A. | Pale Yellow Oil |
| 965 | 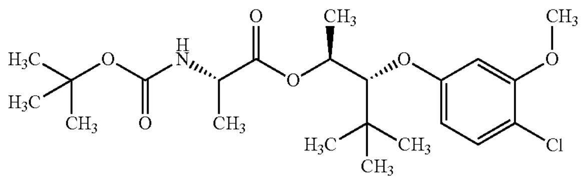 [SMILES: COc1cc(O[C@@H]([C@H](C)OC(=O)[C@H](C)NC(=O)OC(C)(C)C)C(C)(C)C)ccc1Cl] | Example 1A; Example 4C; Example 8A; Example 12A. | Pale Yellow Oil |
| 966 | 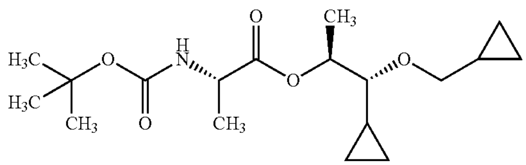 [SMILES: C[C@H](NC(=O)OC(C)(C)C)C(=O)O[C@@H](C)[C@H](OCC1CC1)C1CC1] | Example 1A; Example 4D; Example 8C; Example 12A | Colorless Oil |
| 967 | 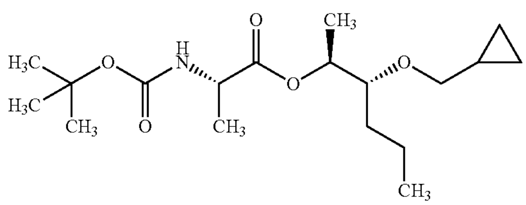 [SMILES: CCC[C@@H](OCC1CC1)[C@H](C)OC(=O)[C@H](C)NC(=O)OC(C)(C)C] | Example 1A; Example 4D; Example 8C; Example 12A | Colorless Oil |
| 968 | 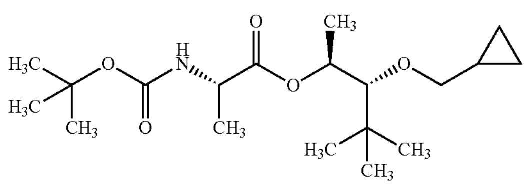 [SMILES: C[C@H](NC(=O)OC(C)(C)C)C(=O)O[C@@H](C)[C@H](OCC1CC1)C(C)(C)C] | Example 1A; Example 4D; Example 8C; Example 12A | Colorless Oil |
| 969 | 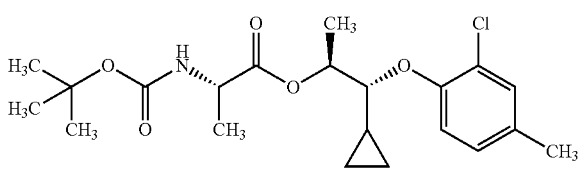 [SMILES: Cc1ccc(O[C@H](C2CC2)[C@H](C)OC(=O)[C@H](C)NC(=O)OC(C)(C)C)c(Cl)c1] | Example 1A; Example 4C; Example 8A; Example 12A. | Pale Yellow Oil |
| 970 | 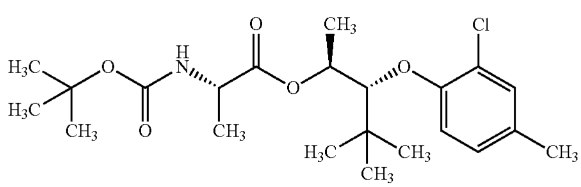 [SMILES: Cc1ccc(O[C@@H]([C@H](C)OC(=O)[C@H](C)NC(=O)OC(C)(C)C)C(C)(C)C)c(Cl)c1] | Example 1A; Example 4C; Example 8A; Example 12A. | Pale Yellow Oil |
| 971 | 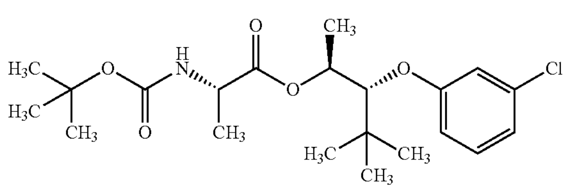 [SMILES: C[C@H](NC(=O)OC(C)(C)C)C(=O)O[C@@H](C)[C@H](Oc1cccc(Cl)c1)C(C)(C)C] | Example 1A; Example 4C; Example 8A; Example 12A. | Pale Yellow Oil |

TABLE 1-continued

Compound Structure, Appearance, and Preparation Method

| *Cmpd. No. | Structure | Prepared According to Example: | Appearance |
|---|---|---|---|
| 972 | 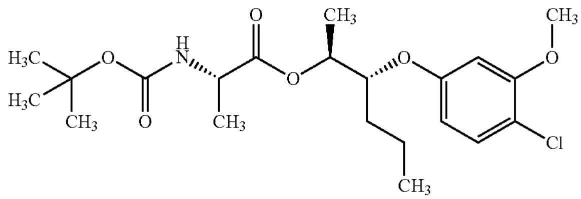 [SMILES: CCC[C@@H](Oc1ccc(Cl)c(OC)c1)[C@H](C)OC(=O)[C@H](C)NC(=O)OC(C)(C)C] | Example 1A; Example 4C; Example 8A; Example 12A. | Pale Yellow Oil |
| 973 | 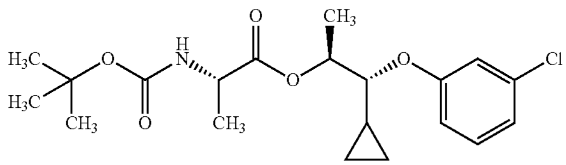 [SMILES: C[C@H](NC(=O)OC(C)(C)C)C(=O)O[C@@H](C)[C@H](Oc1cccc(Cl)c1)C1CC1] | Example 1A; Example 4C; Example 8A; Example 12A. | Pale Yellow Oil |
| 974 | 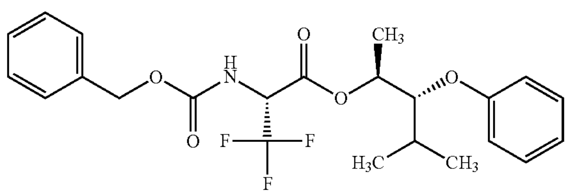 [SMILES: CC(C)[C@@H](Oc1ccccc1)[C@H](C)OC(=O)[C@@H](NC(=O)OCc1ccccc1)C(F)(F)F] | Example 1A; Example 4B; Example 8A; Example 12A | White Semi-Solid |
| 975 | 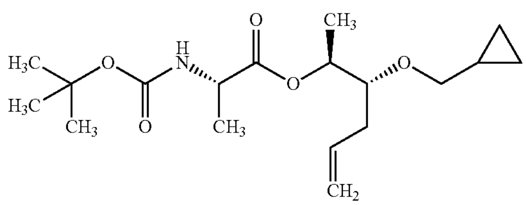 [SMILES: C=CC[C@@H](OCC1CC1)[C@H](C)OC(=O)[C@H](C)NC(=O)OC(C)(C)C] | Example 1B, Step 1; Example 1C, Step 2; Example 4D; Example 8D; Example 12A. | Clear, Colorless Oil |
| 976 | 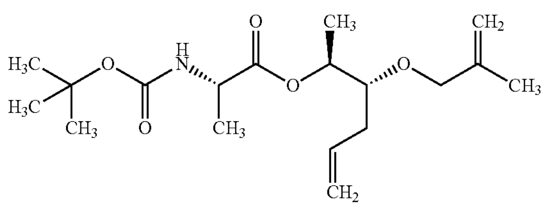 [SMILES: C=CC[C@@H](OCC(=C)C)[C@H](C)OC(=O)[C@H](C)NC(=O)OC(C)(C)C] | Example 1B, Step 1; Example 1C, Step 2; Example 4D; Example 8D; Example 12A. | Clear, Colorless Oil |
| 977 | 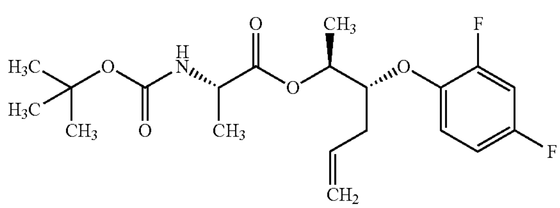 [SMILES: C=CC[C@@H](Oc1ccc(F)cc1F)[C@H](C)OC(=O)[C@H](C)NC(=O)OC(C)(C)C] | Example 1B, Step 1; Example 1C, Step 2; Example 4C; Example 8D; Example 12A. | Clear, Colorless Oil |
| 978 | 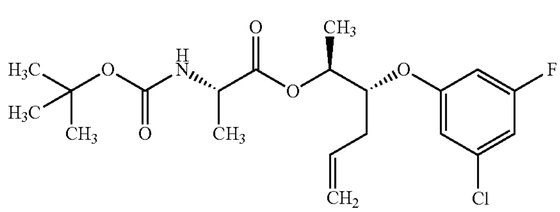 [SMILES: C=CC[C@@H](Oc1cc(F)cc(Cl)c1)[C@H](C)OC(=O)[C@H](C)NC(=O)OC(C)(C)C] | Example 1B, Step 1; Example 1C, Step 2; Example 4C; Example 8D; Example 12A. | Clear, Colorless Oil |

TABLE 1-continued

Compound Structure, Appearance, and Preparation Method

| *Cmpd. No. | Structure | Prepared According to Example: | Appearance |
|---|---|---|---|
| 979 | 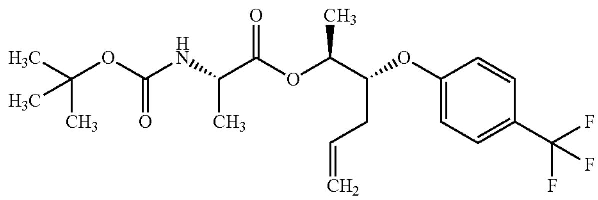 [SMILES: C=CC[C@@H](Oc1ccc(C(F)(F)F)cc1)[C@H](C)OC(=O)[C@H](C)NC(=O)OC(C)(C)C] | Example 1B, Step 1; Example 1C, Step 2; Example 4C; Example 8D; Example 12A. | Yellow Oil |
| 980 | 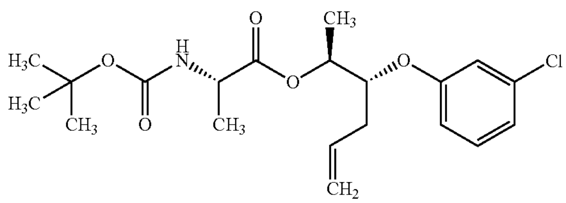 [SMILES: C=CC[C@@H](Oc1cccc(Cl)c1)[C@H](C)OC(=O)[C@H](C)NC(=O)OC(C)(C)C] | Example 1B, Step 1; Example 1C, Step 2; Example 4C; Example 8D; Example 12A. | Clear, Colorless Oil |
| 981 | 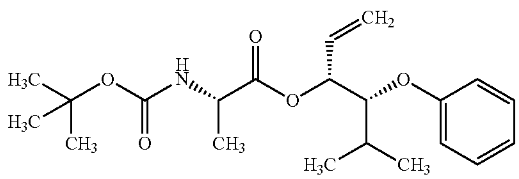 [SMILES: C=C[C@@H](OC(=O)[C@H](C)NC(=O)OC(C)(C)C)[C@H](Oc1ccccc1)C(C)C] | Example 9, Step 1; Example 9, Step 2; Example 9, Step 3; Example 10, Step 1; Example 10, Step 3b; Example 12A. | Colorless Oil |
| 982 | 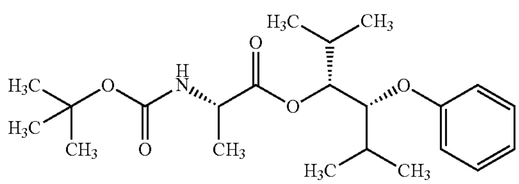 [SMILES: CC(C)[C@@H](OC(=O)[C@H](C)NC(=O)OC(C)(C)C)[C@H](Oc1ccccc1)C(C)C] | Example 9, Step 1; Example 9, Step 2; Example 9, Step 3; Example 10, Step 1; Example 10, Step 3b; Example 12A. | Colorless Oil |
| 983 | 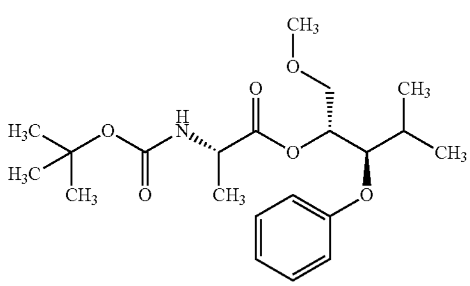 [SMILES: COC[C@@H](OC(=O)[C@H](C)NC(=O)OC(C)(C)C)[C@H](Oc1ccccc1)C(C)C] | Example 12A. | Colorless Oil |
| 984 | 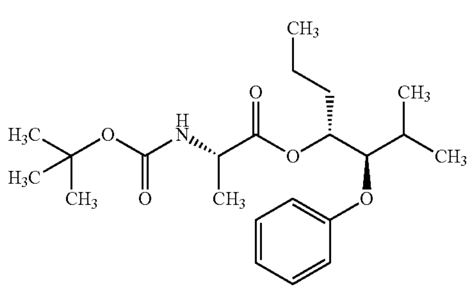 [SMILES: CCC[C@@H](OC(=O)[C@H](C)NC(=O)OC(C)(C)C)[C@H](Oc1ccccc1)C(C)C] | Example 9, Step 1; Example 9, Step 2; Example 9, Step 3; Example 10, Step 1; Example 10, Step 3b; Example 12A. | Colorless Oil |

TABLE 1-continued

Compound Structure, Appearance, and Preparation Method

| *Cmpd. No. | Structure | Prepared According to Example: | Appearance |
|---|---|---|---|
| 985 | 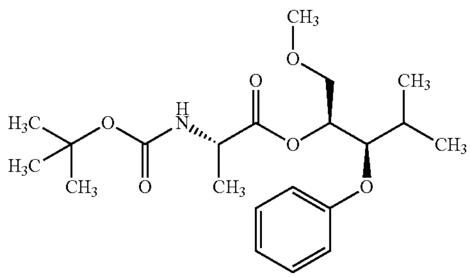 [SMILES: COC[C@H](OC(=O)[C@H](C)NC(=O)OC(C)(C)C)[C@H](Oc1ccccc1)C(C)C] | Example 12A. | Colorless Oil |
| 986 | 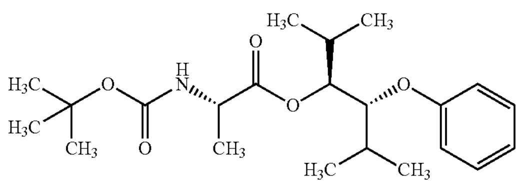 [SMILES: CC(C)[C@@H](Oc1ccccc1)[C@@H](OC(=O)[C@H](C)NC(=O)OC(C)(C)C)C(C)C] | Example 9, Step 1; Example 9, Step 2; Example 9, Step 3; Example 10, Step 1; Example 10, Step 3b; Example 12A. | White Solid |
| 987 | 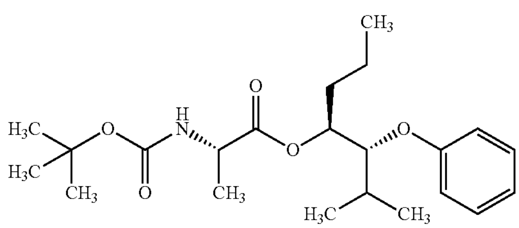 [SMILES: CCC[C@H](OC(=O)[C@H](C)NC(=O)OC(C)(C)C)[C@H](Oc1ccccc1)C(C)C] | Example 9, Step 1; Example 9, Step 2; Example 9, Step 3; Example 10, Step 1; Example 10, Step 3b; Example 12A. | Colorless Oil |
| 988 | 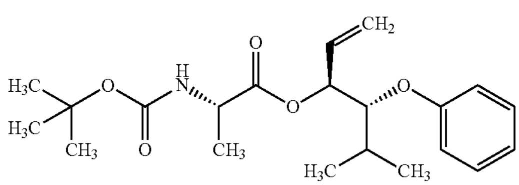 [SMILES: C=C[C@H](OC(=O)[C@H](C)NC(=O)OC(C)(C)C)[C@H](Oc1ccccc1)C(C)C] | Example 9, Step 1; Example 9, Step 2; Example 9, Step 3; Example 10, Step 1; Example 10, Step 3b; Example 12A. | Colorless Oil |
| 989 | 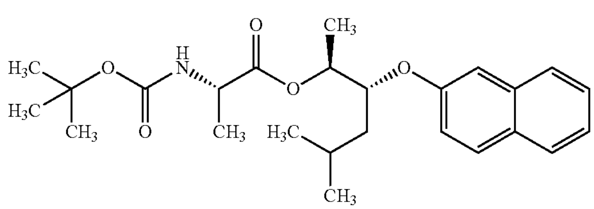 [SMILES: CC(C)C[C@@H](Oc1ccc2ccccc2c1)[C@H](C)OC(=O)[C@H](C)NC(=O)OC(C)(C)C] | Example 1A; Example 4C; Example 8A; Example 12A. | Yellow Oil |
| 990 | 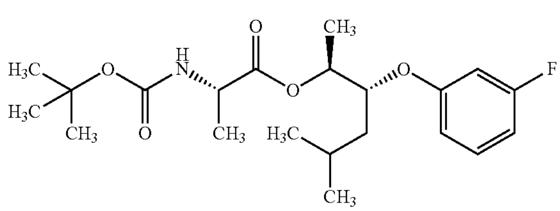 [SMILES: CC(C)C[C@@H](Oc1cccc(F)c1)[C@H](C)OC(=O)[C@H](C)NC(=O)OC(C)(C)C] | Example 1A; Example 4C; Example 8A; Example 12A. | Colorless Oil |

TABLE 1-continued

Compound Structure, Appearance, and Preparation Method

| *Cmpd. No. | Structure | Prepared According to Example: | Appearance |
|---|---|---|---|
| 991 | 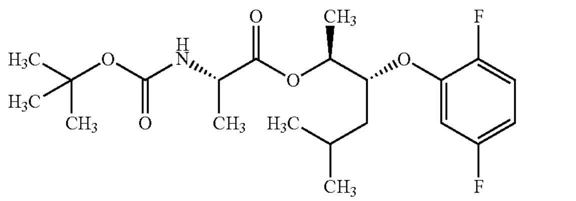 [SMILES: CC(C)C[C@@H](Oc1cc(F)ccc1F)[C@H](C)OC(=O)[C@H](C)NC(=O)OC(C)(C)C] | Example 1A; Example 4C; Example 8A; Example 12A. | Colorless Oil |
| 992 | 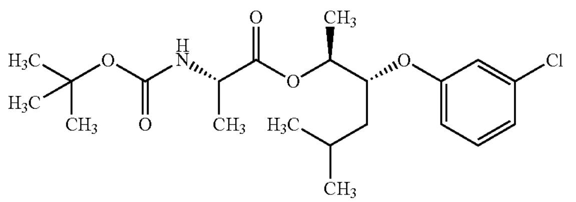 [SMILES: CC(C)C[C@@H](Oc1cccc(Cl)c1)[C@H](C)OC(=O)[C@H](C)NC(=O)OC(C)(C)C] | Example 1A; Example 4C; Example 8A; Example 12A. | Colorless Oil |
| 993 | 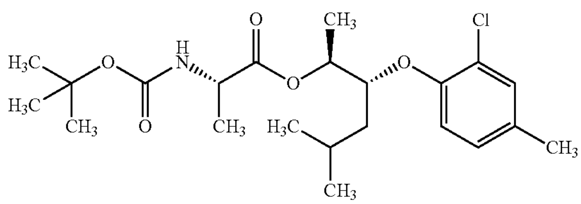 [SMILES: Cc1ccc(O[C@H](CC(C)C)[C@H](C)OC(=O)[C@H](C)NC(=O)OC(C)(C)C)c(Cl)c1] | Example 1A; Example 4C; Example 8A; Example 12A. | Colorless Oil |
| 994 | 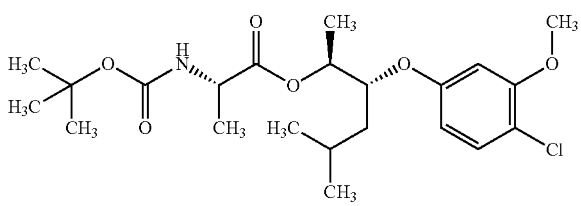 [SMILES: COc1cc(O[C@H](CC(C)C)[C@H](C)OC(=O)[C@H](C)NC(=O)OC(C)(C)C)ccc1Cl] | Example 1A; Example 4C; Example 8A; Example 12A. | Brown Oil |
| 995 | 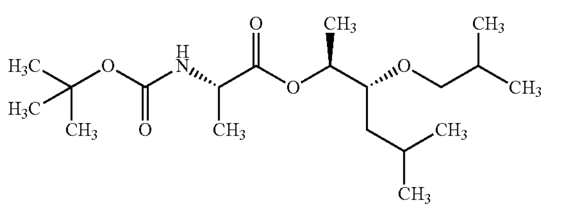 [SMILES: CC(C)CO[C@H](CC(C)C)[C@H](C)OC(=O)[C@H](C)NC(=O)OC(C)(C)C] | Example 1A; Example 4F; Example 8C; Example 12A | Colorless Oil |
| 996 | 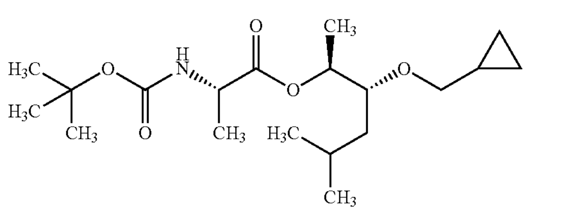 [SMILES: CC(C)C[C@@H](OCC1CC1)[C@H](C)OC(=O)[C@H](C)NC(=O)OC(C)(C)C] | Example 1A; Example 4D; Example 12A | Colorless Oil |
| 997 | 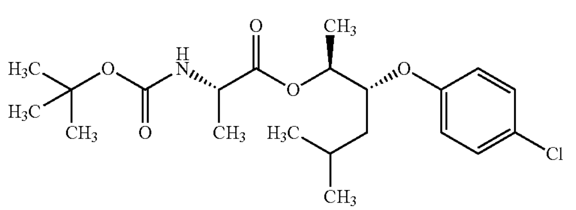 [SMILES: CC(C)C[C@@H](Oc1ccc(Cl)cc1)[C@H](C)OC(=O)[C@H](C)NC(=O)OC(C)(C)C] | Example 1A; Example 4C; Example 8A; Example 12A. | Colorless Oil |

TABLE 1-continued
Compound Structure, Appearance, and Preparation Method
| *Cmpd. No. | Structure | Prepared According to Example: | Appearance |
|---|---|---|---|
| 998 | 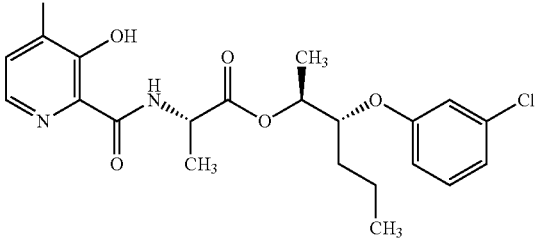 | Example 14A, Step 2. | Tacky Colorless Oil |
| 999 | 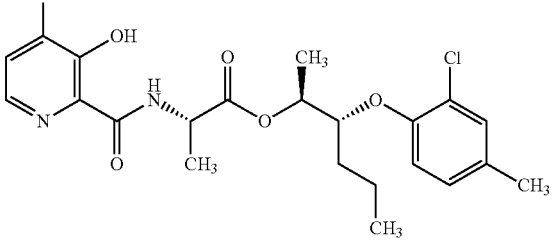 | Example 14A, Step 2. | Tacky Colorless Oil |
| 1000 | 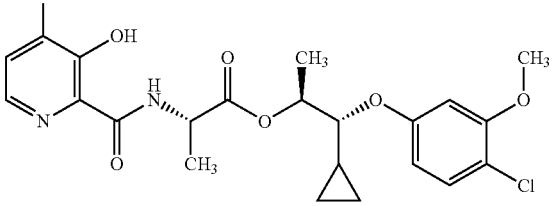 | Example 14A, Step 2. | Tacky Colorless Oil |
| 1001 | 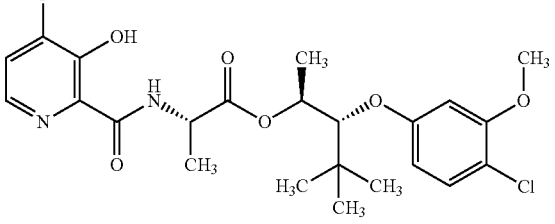 | Example 14A, Step 2. | Pale Yellow Wax |
| 1002 | 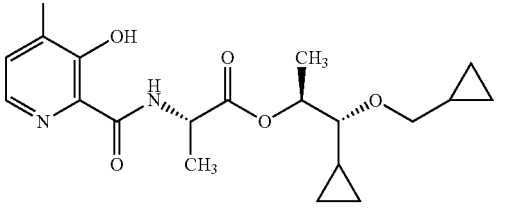 | Example 14A, Step 2. | Colorless Oil |

TABLE 1-continued

Compound Structure, Appearance, and Preparation Method

| *Cmpd. No. | Structure | Prepared According to Example: | Appearance |
|---|---|---|---|
| 1003 | 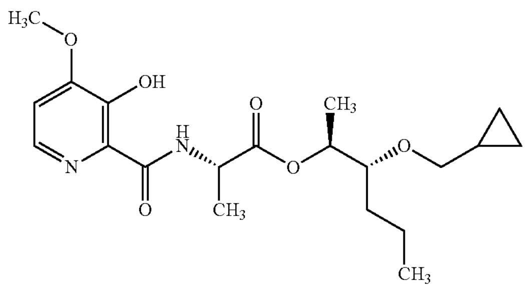 [SMILES: CCC[C@@H](OCC1CC1)[C@H](C)OC(=O)[C@H](C)NC(=O)c1nccc(OC)c1O] | Example 14A, Step 2. | Colorless Oil |
| 1004 | 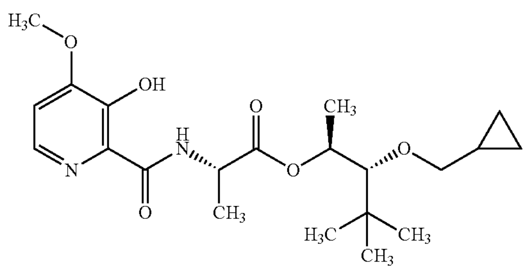 [SMILES: COc1ccnc(C(=O)N[C@@H](C)C(=O)O[C@@H](C)[C@H](OCC2CC2)C(C)(C)C)c1O] | Example 14A, Step 2. | Colorless Oil |
| 1005 | 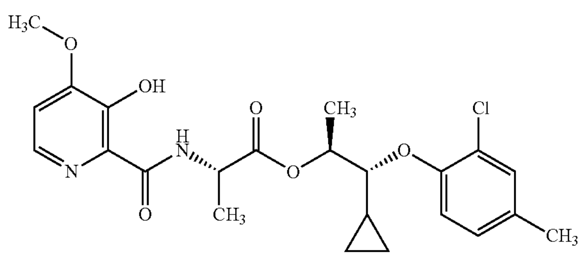 [SMILES: COc1ccnc(C(=O)N[C@@H](C)C(=O)O[C@@H](C)[C@H](Oc2ccc(C)cc2Cl)C2CC2)c1O] | Example 14A, Step 2. | Tacky Colorless Oil |
| 1006 | 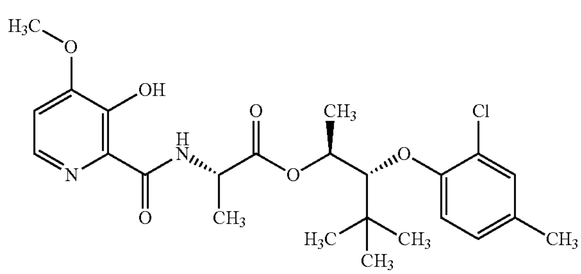 [SMILES: COc1ccnc(C(=O)N[C@@H](C)C(=O)O[C@@H](C)[C@H](Oc2ccc(C)cc2Cl)C(C)(C)C)c1O] | Example 14A, Step 2. | White Foam |
| 1007 | 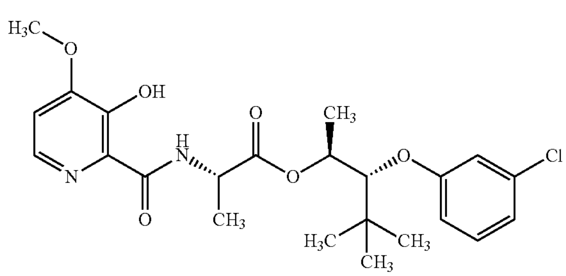 [SMILES: COc1ccnc(C(=O)N[C@@H](C)C(=O)O[C@@H](C)[C@H](Oc2cccc(Cl)c2)C(C)(C)C)c1O] | Example 14A, Step 2. | Tacky Colorless Oil |

TABLE 1-continued
Compound Structure, Appearance, and Preparation Method
| *Cmpd. No. | Structure | Prepared According to Example: | Appearance |
|---|---|---|---|
| 1008 | 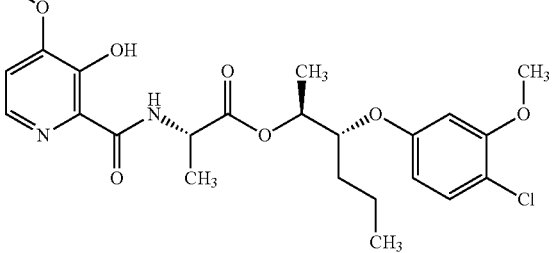 | Example 14A, Step 2. | Tacky Yellow Oil |
| 1009 | 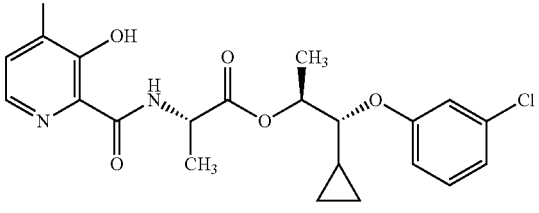 | Example 14A, Step 2. | Tacky Colorless Oil |
| 1010 | 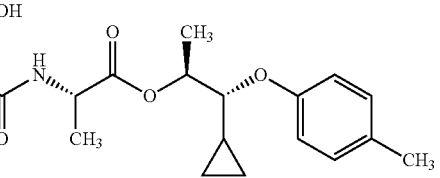 | Example 14A, Step 2. | Tacky Oil |
| 1011 | 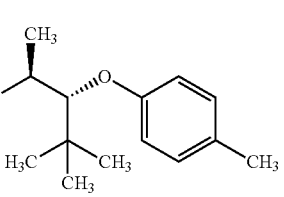 | Example 14A, Step 2. | Tacky Oil |
| 1012 | 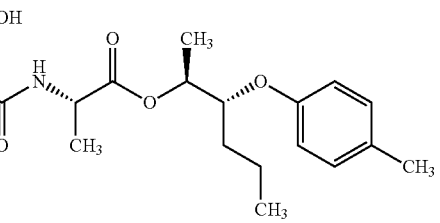 | Example 14A, Step 2. | Tacky Oil |

TABLE 1-continued
Compound Structure, Appearance, and Preparation Method
| *Cmpd. No. | Structure | Prepared According to Example: | Appearance |
|---|---|---|---|
| 1013 | 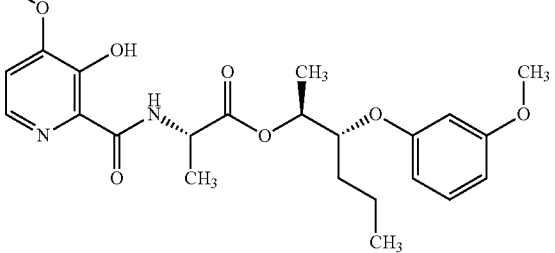 | Example 14A, Step 2. | Tacky Oil |
| 1014 | 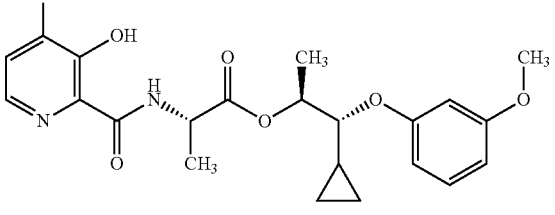 | Example 14A, Step 2. | Tacky Oil |
| 1015 | 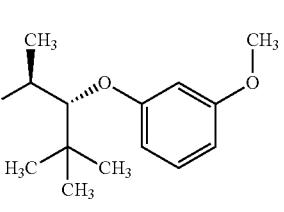 | Example 14A, Step 2. | Tacky Oil |
| 1016 | 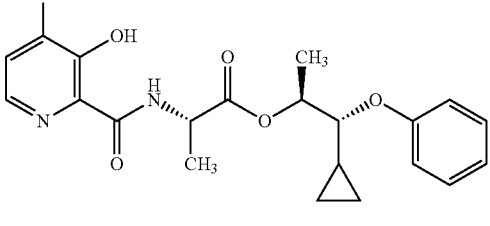 | Example 14A, Step 2. | Tacky Oil |
| 1017 | 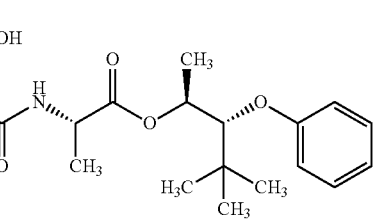 | Example 14A, Step 2. | Tacky Oil |

TABLE 1-continued

Compound Structure, Appearance, and Preparation Method

| *Cmpd. No. | Structure | Prepared According to Example: | Appearance |
|---|---|---|---|
| 1018 | 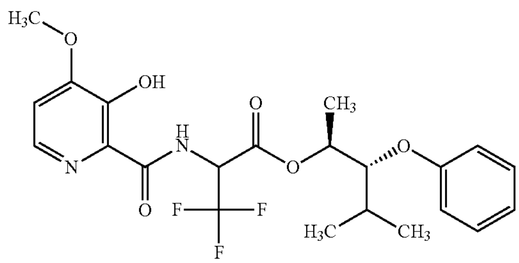 [SMILES: COc1ccnc(C(=O)NC(C(=O)O[C@@H](C)[C@H](Oc2ccccc2)C(C)C)C(F)(F)F)c1O] | Example 14C, Step 2 | Sticky Wax |
| 1019 | 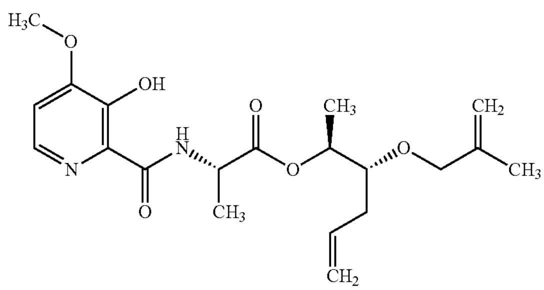 [SMILES: C=CC[C@@H](OCC(=C)C)[C@H](C)OC(=O)[C@H](C)NC(=O)c1nccc(OC)c1O] | Example 14B, Step 2. | Pale Yellow Oil |
| 1020 | 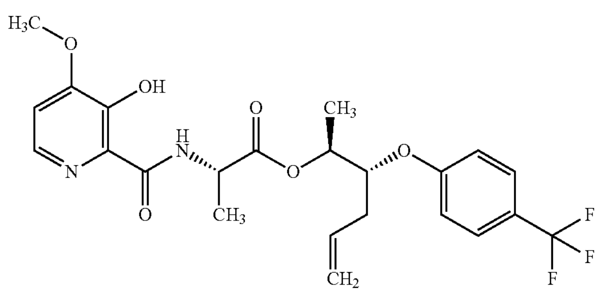 [SMILES: C=CC[C@@H](Oc1ccc(C(F)(F)F)cc1)[C@H](C)OC(=O)[C@H](C)NC(=O)c1nccc(OC)c1O] | Example 14B, Step 2. | Pale Yellow Oil |
| 1021 | 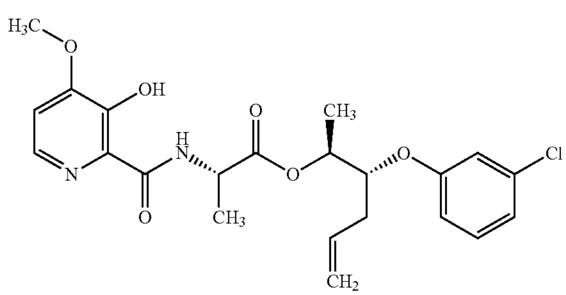 [SMILES: C=CC[C@@H](Oc1cccc(Cl)c1)[C@H](C)OC(=O)[C@H](C)NC(=O)c1nccc(OC)c1O] | Example 14B, Step 2. | Pale Yellow Oil |
| 1022 | 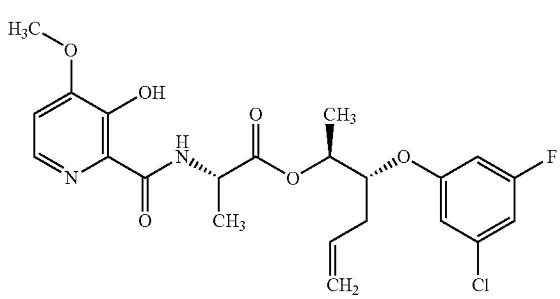 [SMILES: C=CC[C@@H](Oc1cc(F)cc(Cl)c1)[C@H](C)OC(=O)[C@H](C)NC(=O)c1nccc(OC)c1O] | Example 14B, Step 2. | Pale Yellow Oil |

TABLE 1-continued

Compound Structure, Appearance, and Preparation Method

| *Cmpd. No. | Structure | Prepared According to Example: | Appearance |
|---|---|---|---|
| 1023 | 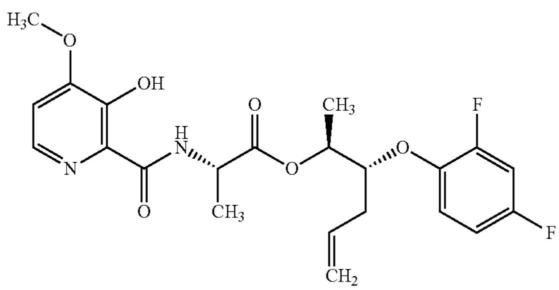 [SMILES: C=CC[C@@H](Oc1ccc(F)cc1F)[C@H](C)OC(=O)[C@H](C)NC(=O)c1nccc(OC)c1O] | Example 14B, Step 2. | Pale Yellow Oil |
| 1024 | 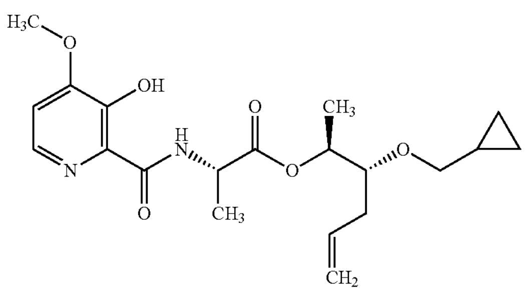 [SMILES: C=CC[C@@H](OCC1CC1)[C@H](C)OC(=O)[C@H](C)NC(=O)c1nccc(OC)c1O] | Example 14B, Step 2. | Clear, Colorless Oil |
| 1025 | 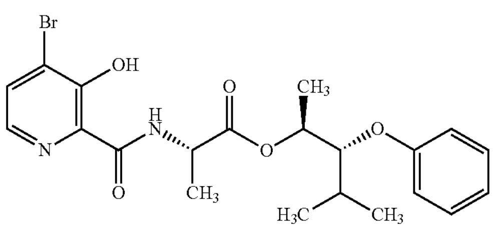 [SMILES: CC(C)[C@@H](Oc1ccccc1)[C@H](C)OC(=O)[C@H](C)NC(=O)c1nccc(Br)c1O] | Example 14A, Step 2. | Clear, Colorless Oil |
| 1026 | 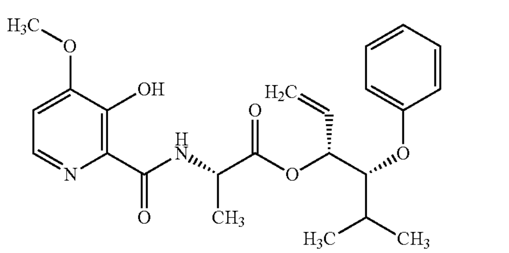 [SMILES: C=C[C@@H](OC(=O)[C@H](C)NC(=O)c1nccc(OC)c1O)[C@H](Oc1ccccc1)C(C)C] | Example 14A, Step 2. | Colorless Oil |
| 1027 | 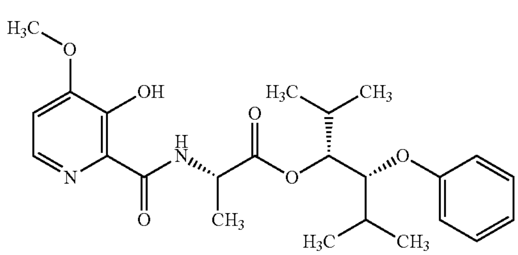 [SMILES: COc1ccnc(C(=O)N[C@@H](C)C(=O)O[C@H](C(C)C)[C@H](Oc2ccccc2)C(C)C)c1O] | Example 14A, Step 2. | Colorless Oil |

TABLE 1-continued

Compound Structure, Appearance, and Preparation Method

| *Cmpd. No. | Structure | Prepared According to Example: | Appearance |
|---|---|---|---|
| 1028 | 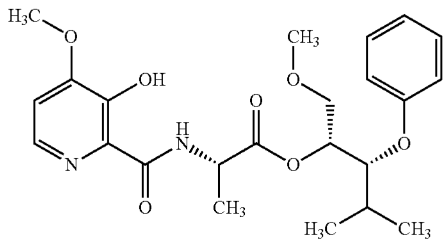 [SMILES: COC[C@@H](OC(=O)[C@H](C)NC(=O)c1nccc(OC)c1O)[C@H](Oc1ccccc1)C(C)C] | Example 14A, Step 2. | Colorless Oil |
| 1029 | 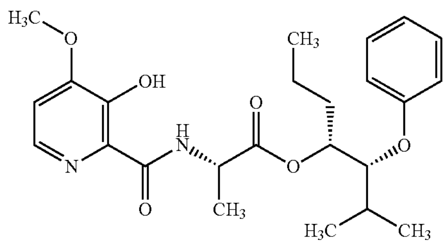 [SMILES: CCC[C@@H](OC(=O)[C@H](C)NC(=O)c1nccc(OC)c1O)[C@H](Oc1ccccc1)C(C)C] | Example 14A, Step 2. | Colorless Oil |
| 1030 | 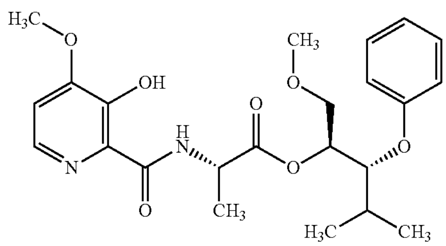 [SMILES: COC[C@H](OC(=O)[C@H](C)NC(=O)c1nccc(OC)c1O)[C@H](Oc1ccccc1)C(C)C] | Example 14A, Step 2. | Colorless Oil |
| 1031 | 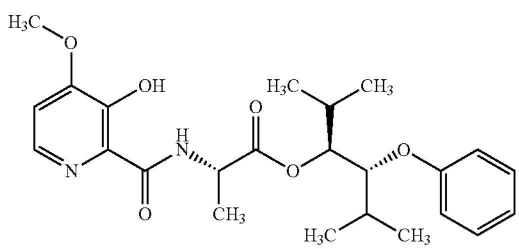 [SMILES: COc1ccnc(C(=O)N[C@@H](C)C(=O)O[C@@H](C(C)C)[C@H](Oc2ccccc2)C(C)C)c1O] | Example 14A, Step 2. | Colorless Oil |
| 1032 | 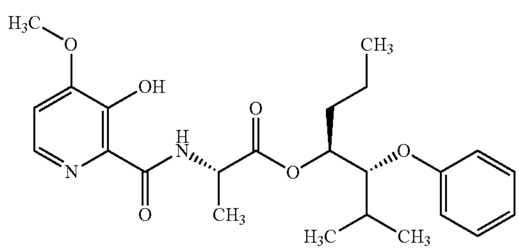 [SMILES: CCC[C@H](OC(=O)[C@H](C)NC(=O)c1nccc(OC)c1O)[C@H](Oc1ccccc1)C(C)C] | Example 14A, Step 2. | Colorless Oil |
| 1033 | 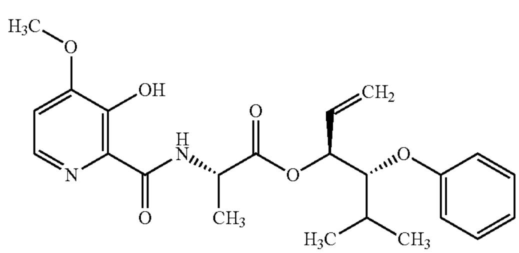 [SMILES: C=C[C@H](OC(=O)[C@H](C)NC(=O)c1nccc(OC)c1O)[C@H](Oc1ccccc1)C(C)C] | Example 14A, Step 2. | Colorless Oil |

TABLE 1-continued

Compound Structure, Appearance, and Preparation Method

| *Cmpd. No. | Structure | Prepared According to Example: | Appearance |
|---|---|---|---|
| 1034 | 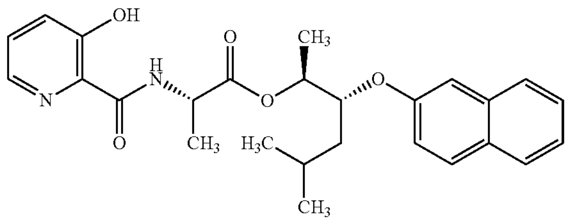 [SMILES: CC(C)C[C@@H](Oc1ccc2ccccc2c1)[C@H](C)OC(=O)[C@H](C)NC(=O)c1ncccc1O] | Example 14A, Step 2. | Colorless Oil |
| 1035 | 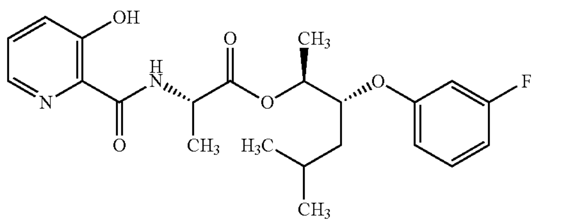 [SMILES: CC(C)C[C@@H](Oc1cccc(F)c1)[C@H](C)OC(=O)[C@H](C)NC(=O)c1ncccc1O] | Example 14A, Step 2. | Colorless Oil |
| 1036 | 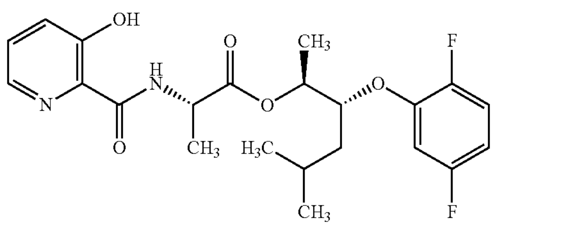 [SMILES: CC(C)C[C@@H](Oc1cc(F)ccc1F)[C@H](C)OC(=O)[C@H](C)NC(=O)c1ncccc1O] | Example 14A, Step 2. | Colorless Oil |
| 1037 | 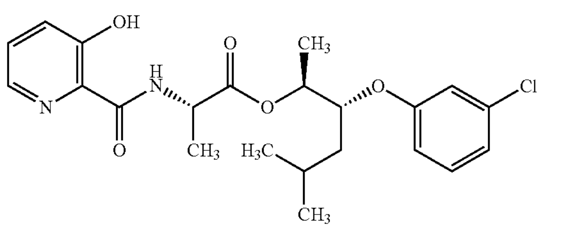 [SMILES: CC(C)C[C@@H](Oc1cccc(Cl)c1)[C@H](C)OC(=O)[C@H](C)NC(=O)c1ncccc1O] | Example 14A, Step 2. | Colorless Oil |
| 1038 | 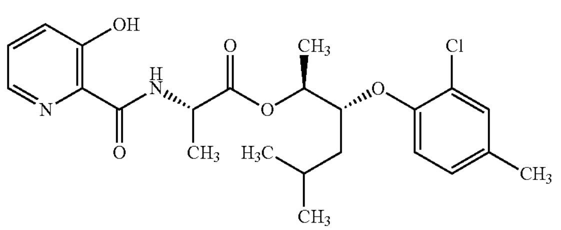 [SMILES: Cc1ccc(O[C@H](CC(C)C)[C@H](C)OC(=O)[C@H](C)NC(=O)c2ncccc2O)c(Cl)c1] | Example 14A, Step 2. | Colorless Oil |
| 1039 | 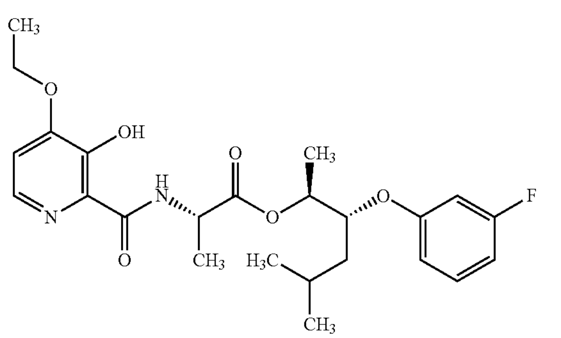 [SMILES: CCOc1ccnc(C(=O)N[C@@H](C)C(=O)O[C@@H](C)[C@@H](CC(C)C)Oc2cccc(F)c2)c1O] | Example 14A, Step 2. | Yellow Oil |

TABLE 1-continued

Compound Structure, Appearance, and Preparation Method

| *Cmpd. No. | Structure | Prepared According to Example: | Appearance |
|---|---|---|---|
| 1040 | 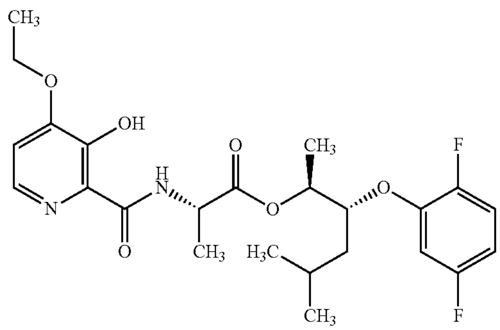 [SMILES: CCOc1ccnc(C(=O)N[C@@H](C)C(=O)O[C@@H](C)[C@@H](CC(C)C)Oc2cc(F)ccc2F)c1O] | Example 14A, Step 2. | Colorless Oil |
| 1041 | 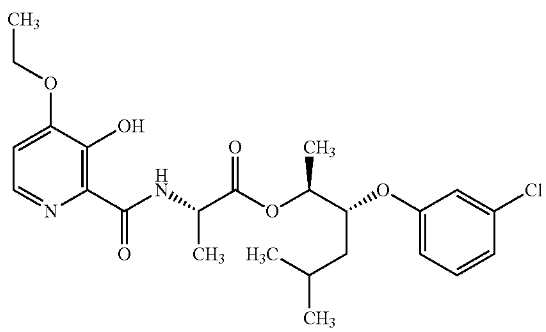 [SMILES: CCOc1ccnc(C(=O)N[C@@H](C)C(=O)O[C@@H](C)[C@@H](CC(C)C)Oc2cccc(Cl)c2)c1O] | Example 14A, Step 2. | Colorless Oil |
| 1042 | 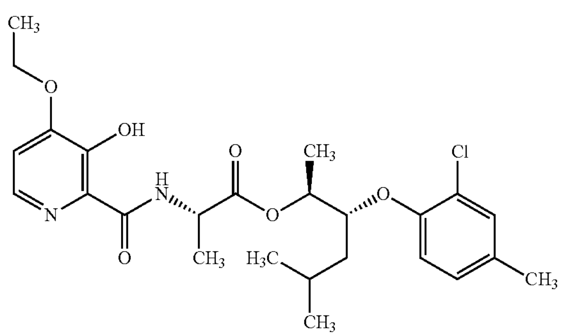 [SMILES: CCOc1ccnc(C(=O)N[C@@H](C)C(=O)O[C@@H](C)[C@@H](CC(C)C)Oc2ccc(C)cc2Cl)c1O] | Example 14A, Step 2. | Colorless Oil |
| 1043 | 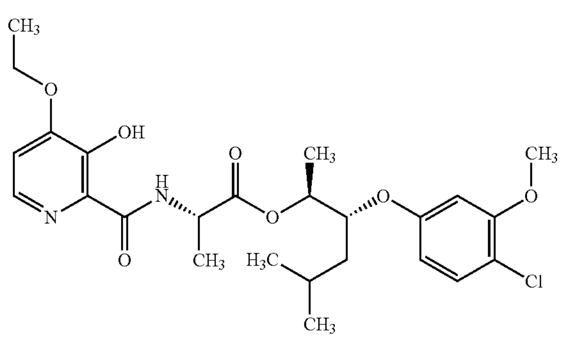 [SMILES: CCOc1ccnc(C(=O)N[C@@H](C)C(=O)O[C@@H](C)[C@@H](CC(C)C)Oc2ccc(Cl)c(OC)c2)c1O] | Example 14A, Step 2. | Colorless Oil |

TABLE 1-continued

Compound Structure, Appearance, and Preparation Method

| *Cmpd. No. | Structure | Prepared According to Example: | Appearance |
|---|---|---|---|
| 1044 | 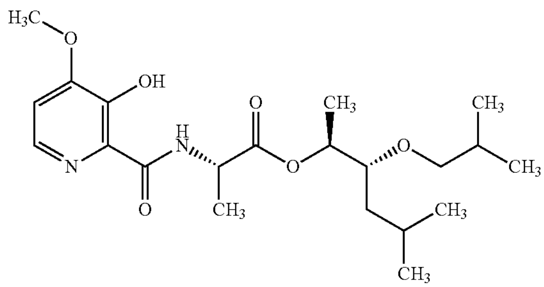 [SMILES: COc1ccnc(C(=O)N[C@@H](C)C(=O)O[C@@H](C)[C@@H](CC(C)C)OCC(C)C)c1O] | Example 14A, Step 2. | Colorless Oil |
| 1045 | 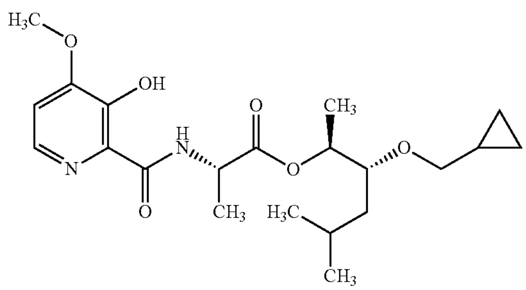 [SMILES: COc1ccnc(C(=O)N[C@@H](C)C(=O)O[C@@H](C)[C@@H](CC(C)C)OCC2CC2)c1O] | Example 14A, Step 2. | Colorless Oil |
| 1046 | 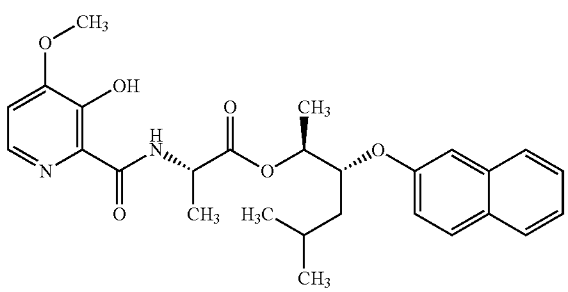 [SMILES: COc1ccnc(C(=O)N[C@@H](C)C(=O)O[C@@H](C)[C@@H](CC(C)C)Oc2ccc3ccccc3c2)c1O] | Example 14A, Step 2. | Colorless Oil |
| 1047 | 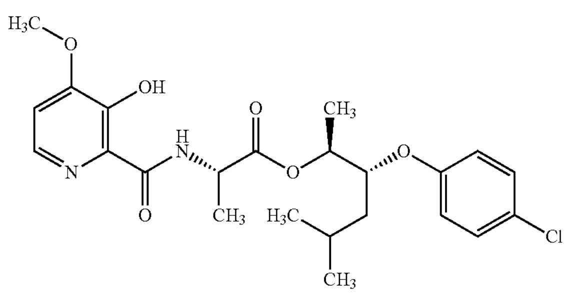 [SMILES: COc1ccnc(C(=O)N[C@@H](C)C(=O)O[C@@H](C)[C@@H](CC(C)C)Oc2ccc(Cl)cc2)c1O] | Example 14A, Step 2. | Yellow Oil |
| 1048 | 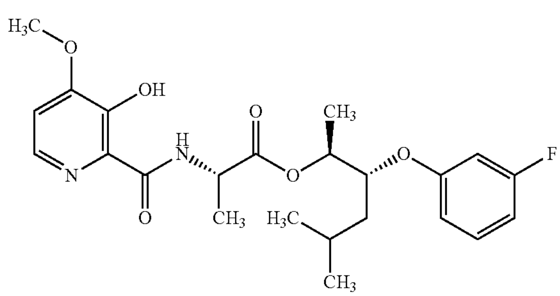 [SMILES: COc1ccnc(C(=O)N[C@@H](C)C(=O)O[C@@H](C)[C@@H](CC(C)C)Oc2cccc(F)c2)c1O] | Example 14A, Step 2. | Colorless Oil |

TABLE 1-continued

Compound Structure, Appearance, and Preparation Method

| *Cmpd. No. | Structure | Prepared According to Example: | Appearance |
|---|---|---|---|
| 1049 | 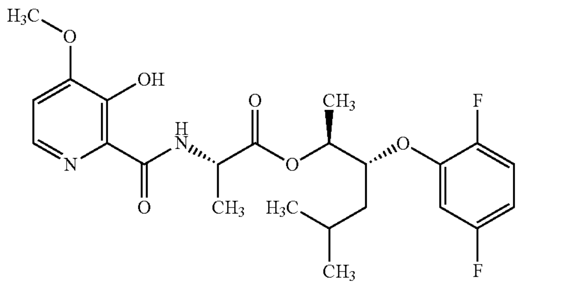 [SMILES: COc1ccnc(C(=O)N[C@@H](C)C(=O)O[C@@H](C)[C@@H](CC(C)C)Oc2cc(F)ccc2F)c1O] | Example 14A, Step 2. | Colorless Oil |
| 1050 | 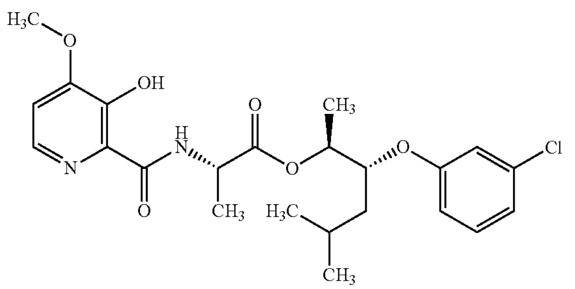 [SMILES: COc1ccnc(C(=O)N[C@@H](C)C(=O)O[C@@H](C)[C@@H](CC(C)C)Oc2cccc(Cl)c2)c1O] | Example 14A, Step 2. | Colorless Oil |
| 1051 | 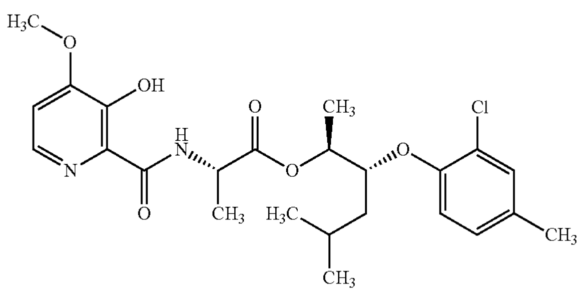 [SMILES: COc1ccnc(C(=O)N[C@@H](C)C(=O)O[C@@H](C)[C@@H](CC(C)C)Oc2ccc(C)cc2Cl)c1O] | Example 14A, Step 2. | Colorless Oil |
| 1052 | 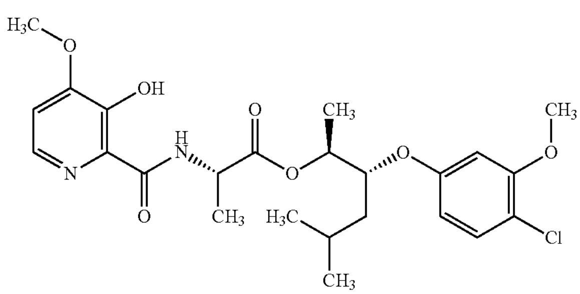 [SMILES: COc1cc(O[C@H](CC(C)C)[C@H](C)OC(=O)[C@H](C)NC(=O)c2nccc(OC)c2O)ccc1Cl] | Example 14A, Step 2. | Yellow Oil |
| 1053 | 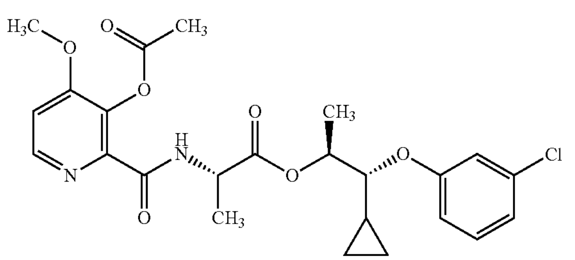 [SMILES: COc1ccnc(C(=O)N[C@@H](C)C(=O)O[C@@H](C)[C@H](Oc2cccc(Cl)c2)C2CC2)c1OC(C)=O] | Example 16A. | Colorless Oil |

TABLE 1-continued

Compound Structure, Appearance, and Preparation Method

| *Cmpd. No. | Structure | Prepared According to Example: | Appearance |
|---|---|---|---|
| 1054 | 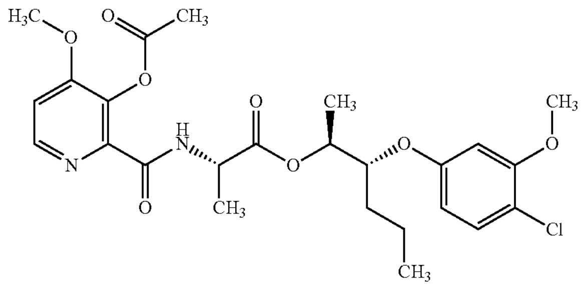 [SMILES: CCC[C@@H](Oc1ccc(Cl)c(OC)c1)[C@H](C)OC(=O)[C@H](C)NC(=O)c1nccc(OC)c1OC(C)=O] | Example 16A. | Colorless Oil |
| 1055 | 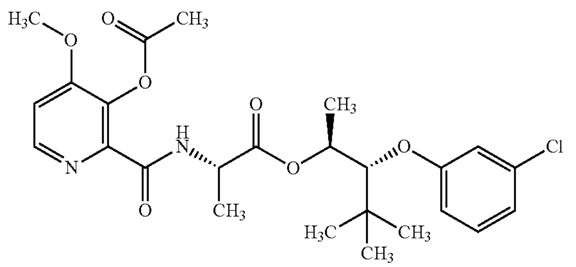 [SMILES: COc1ccnc(C(=O)N[C@@H](C)C(=O)O[C@@H](C)[C@H](Oc2cccc(Cl)c2)C(C)(C)C)c1OC(C)=O] | Example 16A. | Colorless Oil |
| 1056 | 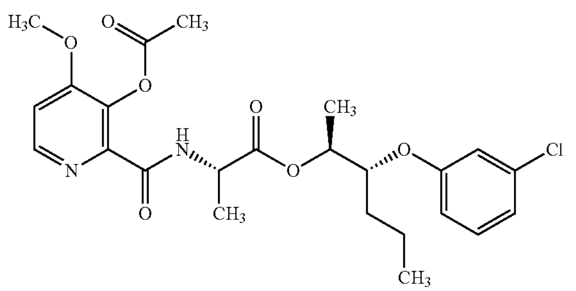 [SMILES: CCC[C@@H](Oc1cccc(Cl)c1)[C@H](C)OC(=O)[C@H](C)NC(=O)c1nccc(OC)c1OC(C)=O] | Example 16A. | Colorless Oil |
| 1057 | 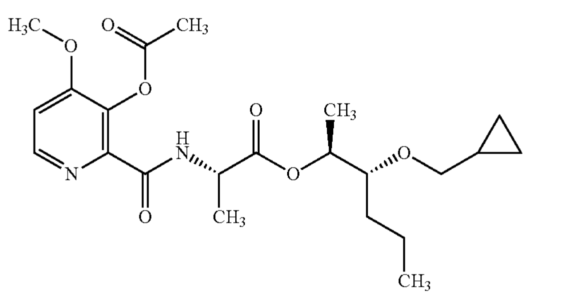 [SMILES: CCC[C@@H](OCC1CC1)[C@H](C)OC(=O)[C@H](C)NC(=O)c1nccc(OC)c1OC(C)=O] | Example 16A. | Colorless Oil |
| 1058 | 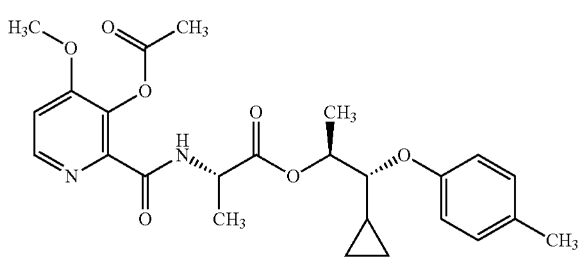 [SMILES: COc1ccnc(C(=O)N[C@@H](C)C(=O)O[C@@H](C)[C@H](Oc2ccc(C)cc2)C2CC2)c1OC(C)=O] | Example 16A. | Colorless Oil |

TABLE 1-continued

Compound Structure, Appearance, and Preparation Method

| *Cmpd. No. | Structure | Prepared According to Example: | Appearance |
|---|---|---|---|
| 1059 | 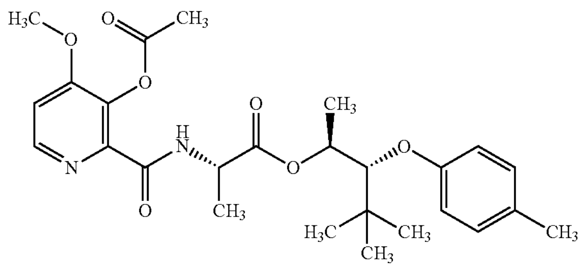 [SMILES: COc1ccnc(C(=O)N[C@@H](C)C(=O)O[C@@H](C)[C@H](Oc2ccc(C)cc2)C(C)(C)C)c1OC(C)=O] | Example 16A. | Colorless Oil |
| 1060 | 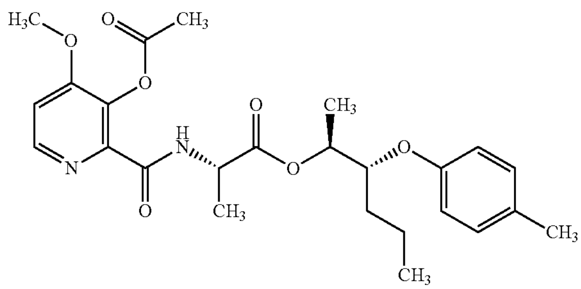 [SMILES: CCC[C@@H](Oc1ccc(C)cc1)[C@H](C)OC(=O)[C@H](C)NC(=O)c1nccc(OC)c1OC(C)=O] | Example 16A. | Colorless Oil |
| 1061 | 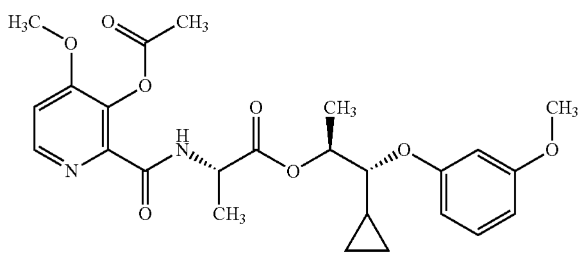 [SMILES: COc1cccc(O[C@H](C2CC2)[C@H](C)OC(=O)[C@H](C)NC(=O)c2nccc(OC)c2OC(C)=O)c1] | Example 16A. | Colorless Oil |
| 1062 | 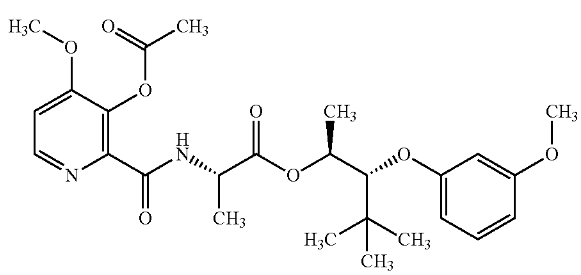 [SMILES: COc1cccc(O[C@@H]([C@H](C)OC(=O)[C@H](C)NC(=O)c2nccc(OC)c2OC(C)=O)C(C)(C)C)c1] | Example 16A. | Colorless Oil |
| 1063 | 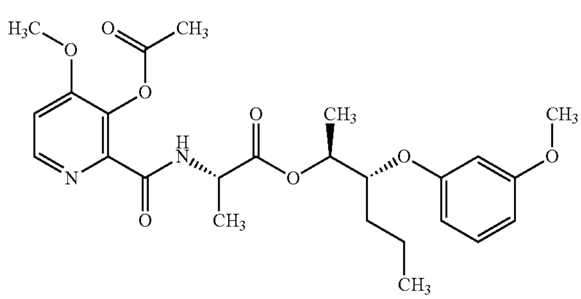 [SMILES: CCC[C@@H](Oc1cccc(OC)c1)[C@H](C)OC(=O)[C@H](C)NC(=O)c1nccc(OC)c1OC(C)=O] | Example 16A. | Colorless Oil |

//

TABLE 1-continued

Compound Structure, Appearance, and Preparation Method

| *Cmpd. No. | Structure | Prepared According to Example: | Appearance |
|---|---|---|---|
| 1064 | 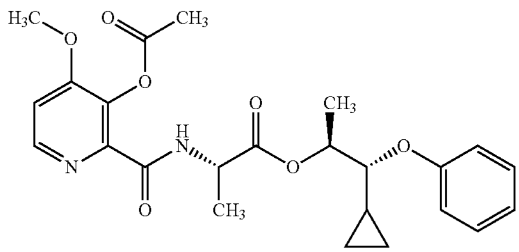 [SMILES: COc1ccnc(C(=O)N[C@@H](C)C(=O)O[C@@H](C)[C@H](Oc2ccccc2)C2CC2)c1OC(C)=O] | Example 16A. | Colorless Oil |
| 1065 | 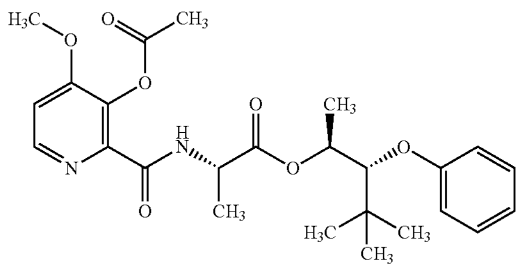 [SMILES: COc1ccnc(C(=O)N[C@@H](C)C(=O)O[C@@H](C)[C@H](Oc2ccccc2)C(C)(C)C)c1OC(C)=O] | Example 16A. | Colorless Oil |
| 1066 | 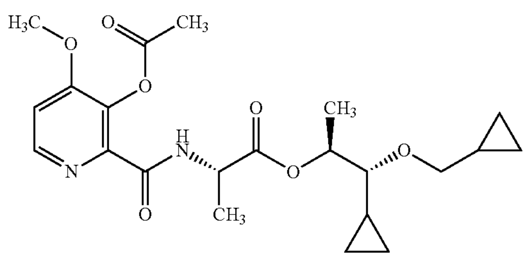 [SMILES: COc1ccnc(C(=O)N[C@@H](C)C(=O)O[C@@H](C)[C@H](OCC2CC2)C2CC2)c1OC(C)=O] | Example 16A. | Colorless Oil |
| 1067 | 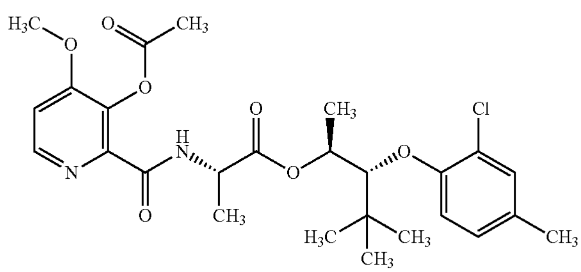 [SMILES: COc1ccnc(C(=O)N[C@@H](C)C(=O)O[C@@H](C)[C@H](Oc2ccc(C)cc2Cl)C(C)(C)C)c1OC(C)=O] | Example 16A. | Colorless Oil |
| 1068 | 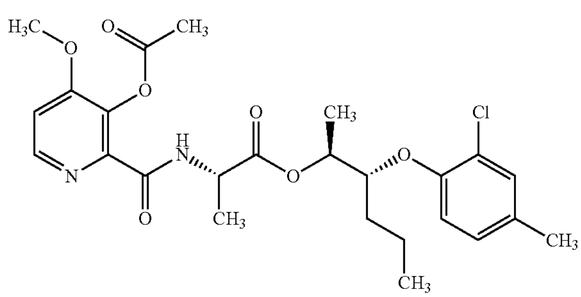 [SMILES: CCC[C@@H](Oc1ccc(C)cc1Cl)[C@H](C)OC(=O)[C@H](C)NC(=O)c1nccc(OC)c1OC(C)=O] | Example 16A. | Colorless Oil |

TABLE 1-continued

Compound Structure, Appearance, and Preparation Method

| *Cmpd. No. | Structure | Prepared According to Example: | Appearance |
|---|---|---|---|
| 1069 | 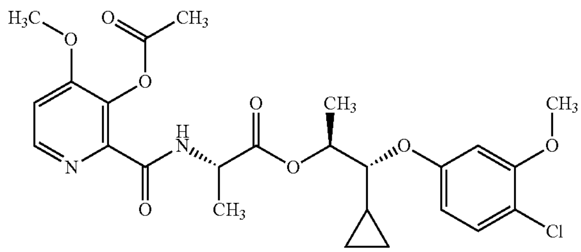 [SMILES: COc1cc(O[C@H](C2CC2)[C@H](C)OC(=O)[C@H](C)NC(=O)c2nccc(OC)c2OC(C)=O)ccc1Cl] | Example 16A. | Colorless Oil |
| 1070 | 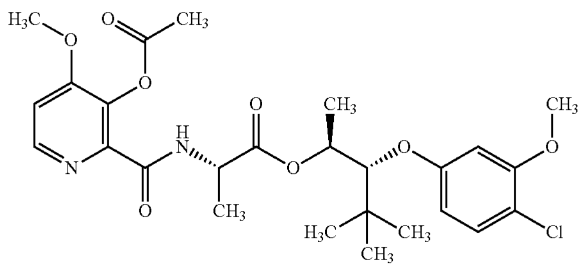 [SMILES: COc1cc(O[C@@H]([C@H](C)OC(=O)[C@H](C)NC(=O)c2nccc(OC)c2OC(C)=O)C(C)(C)C)ccc1Cl] | Example 16A. | Colorless Oil |
| 1071 | 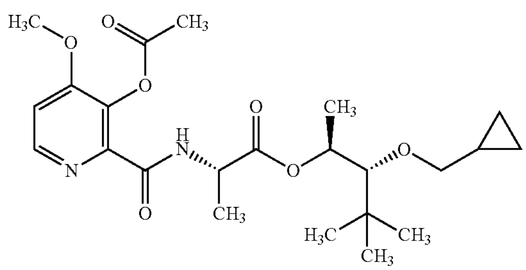 [SMILES: COc1ccnc(C(=O)N[C@@H](C)C(=O)O[C@@H](C)[C@H](OCC2CC2)C(C)(C)C)c1OC(C)=O] | Example 16A. | Colorless Oil |
| 1072 | 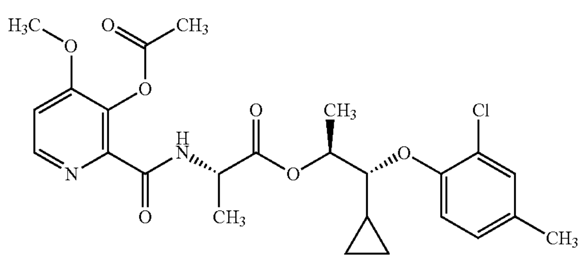 [SMILES: COc1ccnc(C(=O)N[C@@H](C)C(=O)O[C@@H](C)[C@H](Oc2ccc(C)cc2Cl)C2CC2)c1OC(C)=O] | Example 16A. | Colorless Oil |
| 1073 | 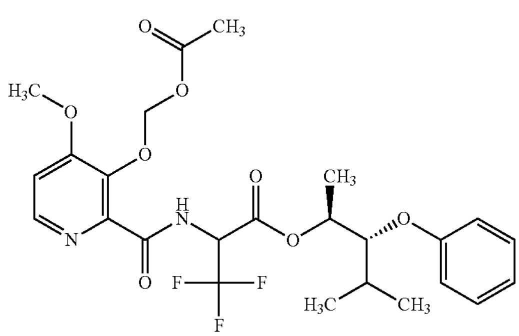 [SMILES: COc1ccnc(C(=O)NC(C(=O)O[C@@H](C)[C@H](Oc2ccccc2)C(C)C)C(F)(F)F)c1OCOC(C)=O] | Example 16B | Sticky Wax |

TABLE 1-continued

Compound Structure, Appearance, and Preparation Method

| *Cmpd. No. | Structure | Prepared According to Example: | Appearance |
|---|---|---|---|
| 1074 | 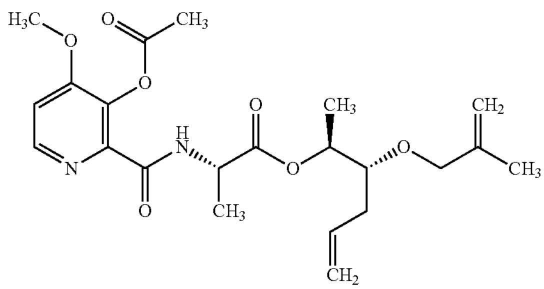 [SMILES: C=CC[C@@H](OCC(=C)C)[C@H](C)OC(=O)[C@H](C)NC(=O)c1nccc(OC)c1OC(C)=O] | Example 16A. | Clear, Colorless Oil |
| 1075 | 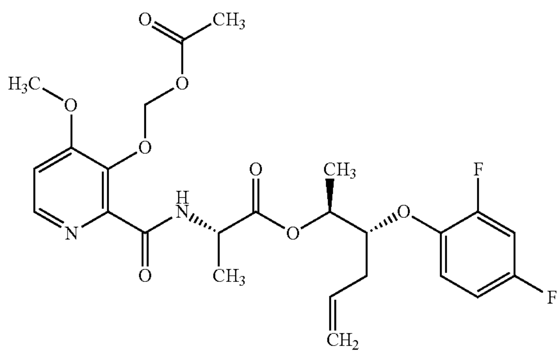 [SMILES: C=CC[C@@H](Oc1ccc(F)cc1F)[C@H](C)OC(=O)[C@H](C)NC(=O)c1nccc(OC)c1OCOC(C)=O] | Example 16B. | Clear, Colorless Oil |
| 1076 | 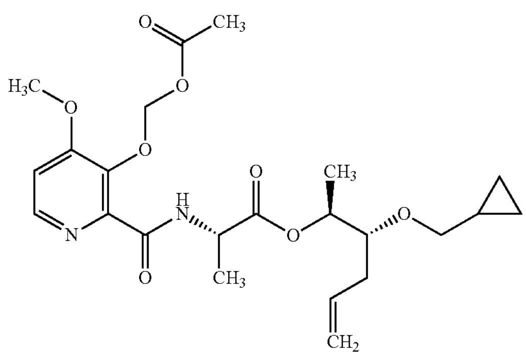 [SMILES: C=CC[C@@H](OCC1CC1)[C@H](C)OC(=O)[C@H](C)NC(=O)c1nccc(OC)c1OCOC(C)=O] | Example 16B. | Clear, Colorless Oil |
| 1077 | 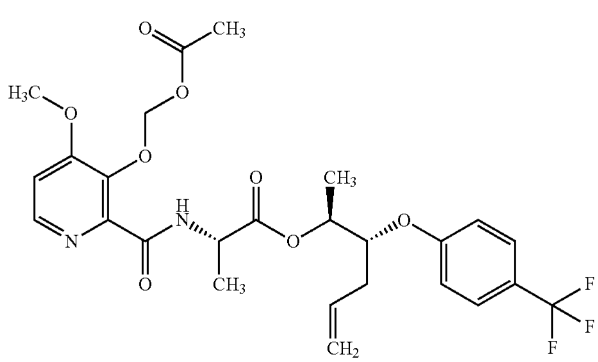 [SMILES: C=CC[C@@H](Oc1ccc(C(F)(F)F)cc1)[C@H](C)OC(=O)[C@H](C)NC(=O)c1nccc(OC)c1OCOC(C)=O] | Example 16B. | Clear, Colorless Oil |

TABLE 1-continued

Compound Structure, Appearance, and Preparation Method

| *Cmpd. No. | Structure | Prepared According to Example: | Appearance |
|---|---|---|---|
| 1078 | 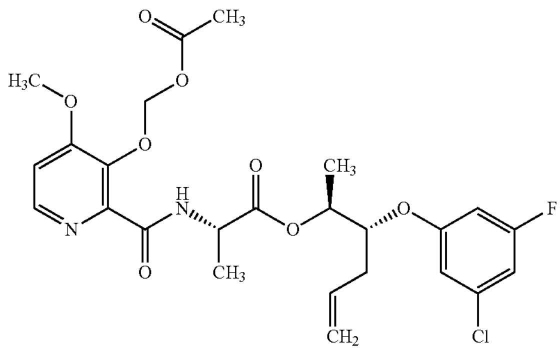 [SMILES: C=CC[C@@H](Oc1cc(F)cc(Cl)c1)[C@H](C)OC(=O)[C@H](C)NC(=O)c1nccc(OC)c1OCOC(C)=O] | Example 16B. | Clear, Colorless Oil |
| 1079 | 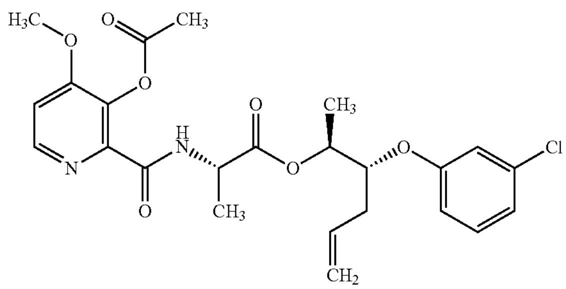 [SMILES: C=CC[C@@H](Oc1cccc(Cl)c1)[C@H](C)OC(=O)[C@H](C)NC(=O)c1nccc(OC)c1OC(C)=O] | Example 16A. | Clear, Colorless Oil |
| 1080 | 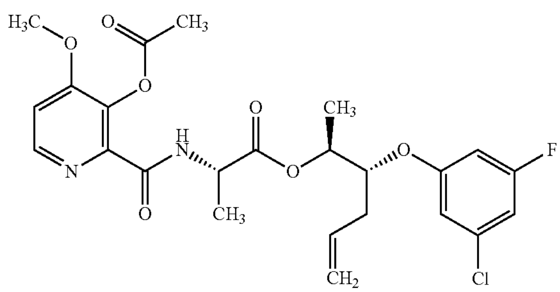 [SMILES: C=CC[C@@H](Oc1cc(F)cc(Cl)c1)[C@H](C)OC(=O)[C@H](C)NC(=O)c1nccc(OC)c1OC(C)=O] | Example 16A. | Clear, Colorless Oil |
| 1081 | 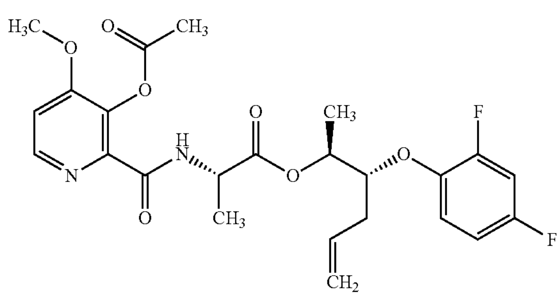 [SMILES: C=CC[C@@H](Oc1ccc(F)cc1F)[C@H](C)OC(=O)[C@H](C)NC(=O)c1nccc(OC)c1OC(C)=O] | Example 16A. | Clear, Colorless Oil |

TABLE 1-continued

Compound Structure, Appearance, and Preparation Method

| *Cmpd. No. | Structure | Prepared According to Example: | Appearance |
|---|---|---|---|
| 1082 | 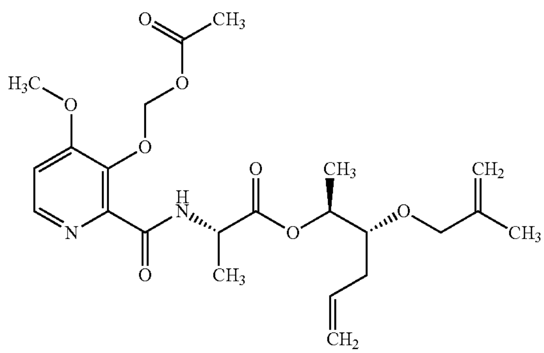 [SMILES: C=CC[C@@H](OCC(=C)C)[C@H](C)OC(=O)[C@H](C)NC(=O)c1nccc(OC)c1OCOC(C)=O] | Example 16B. | Clear, Colorless Oil |
| 1083 | 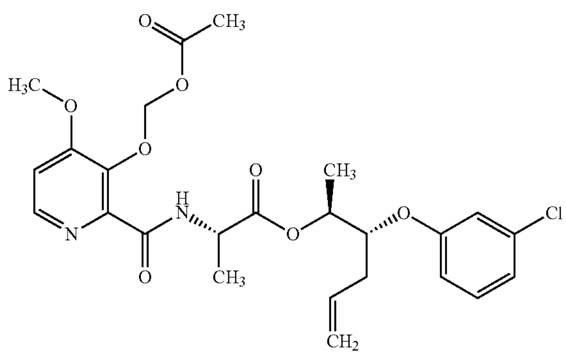 [SMILES: C=CC[C@@H](Oc1cccc(Cl)c1)[C@H](C)OC(=O)[C@H](C)NC(=O)c1nccc(OC)c1OCOC(C)=O] | Example 16B. | Clear, Colorless Oil |
| 1084 | 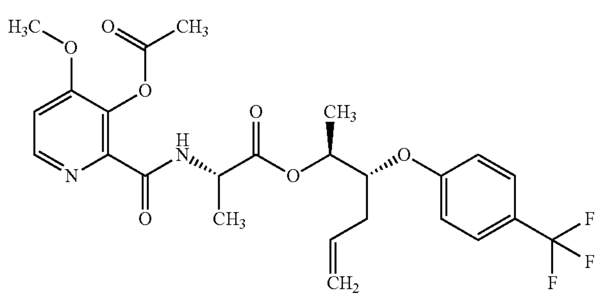 [SMILES: C=CC[C@@H](Oc1ccc(C(F)(F)F)cc1)[C@H](C)OC(=O)[C@H](C)NC(=O)c1nccc(OC)c1OC(C)=O] | Example 16A. | Clear, Colorless Oil |
| 1085 | 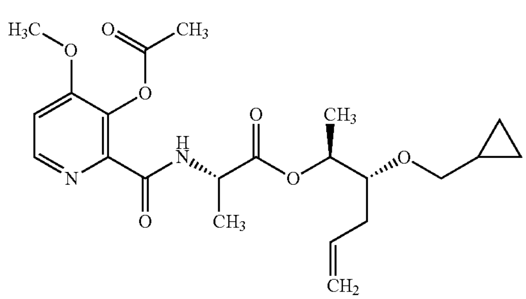 [SMILES: C=CC[C@@H](OCC1CC1)[C@H](C)OC(=O)[C@H](C)NC(=O)c1nccc(OC)c1OC(C)=O] | Example 16A. | Clear, Colorless Oil |

TABLE 1-continued

Compound Structure, Appearance, and Preparation Method

| *Cmpd. No. | Structure | Prepared According to Example: | Appearance |
|---|---|---|---|
| 1086 | 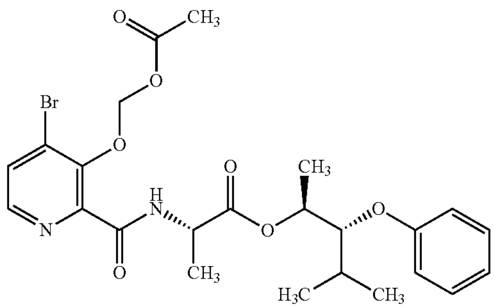 [SMILES: CC(=O)OCOc1c(Br)ccnc1C(=O)N[C@@H](C)C(=O)O[C@@H](C)[C@H](Oc1ccccc1)C(C)C] | Example 16B. | Clear, Colorless Oil |
| 1087 | 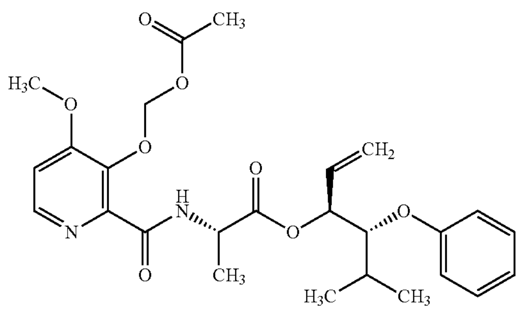 [SMILES: C=C[C@H](OC(=O)[C@H](C)NC(=O)c1nccc(OC)c1OCOC(C)=O)[C@H](Oc1ccccc1)C(C)C] | Example 16B. | Yellow Oil |
| 1088 | 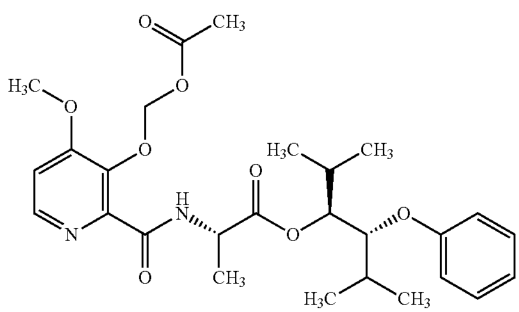 [SMILES: COc1ccnc(C(=O)N[C@@H](C)C(=O)O[C@@H](C(C)C)[C@H](Oc2ccccc2)C(C)C)c1OCOC(C)=O] | Example 16B. | Yellow Oil |
| 1089 | 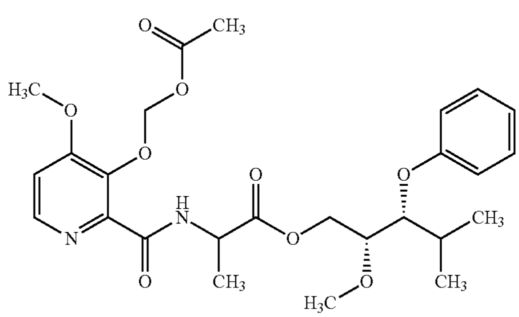 [SMILES: COc1ccnc(C(=O)NC(C)C(=O)OC[C@@H](OC)[C@H](Oc2ccccc2)C(C)C)c1OCOC(C)=O] | Example 16B. | Yellow Oil |

TABLE 1-continued

Compound Structure, Appearance, and Preparation Method

| *Cmpd. No. | Structure | Prepared According to Example: | Appearance |
|---|---|---|---|
| 1090 | 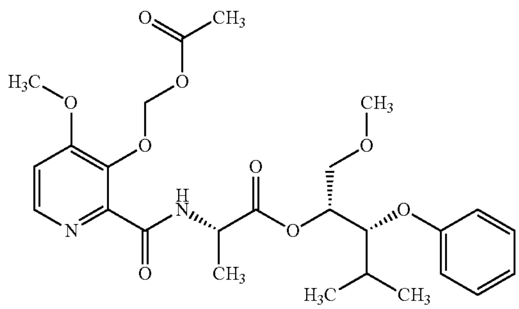 [SMILES: COC[C@@H](OC(=O)[C@H](C)NC(=O)c1nccc(OC)c1OCOC(C)=O)[C@H](Oc1ccccc1)C(C)C] | Example 16B. | Yellow Oil |
| 1091 | 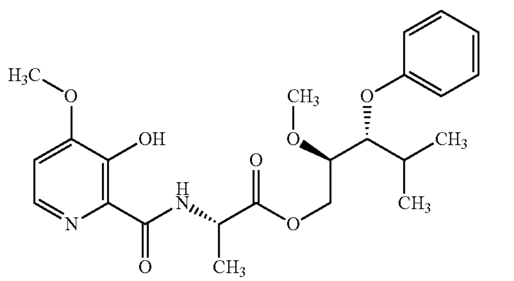 [SMILES: COc1ccnc(C(=O)N[C@@H](C)C(=O)OC[C@@H](OC)[C@H](Oc2ccccc2)C(C)C)c1O] | Example 16B. | Colorless Oil |
| 1092 | 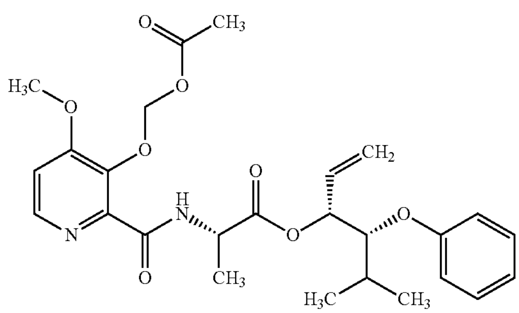 [SMILES: C=C[C@@H](OC(=O)[C@H](C)NC(=O)c1nccc(OC)c1OCOC(C)=O)[C@H](Oc1ccccc1)C(C)C] | Example 16B. | Yellow Oil |
| 1093 | 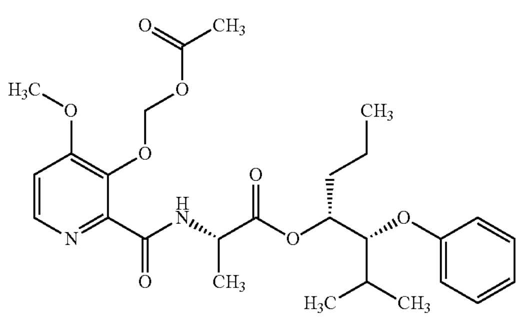 [SMILES: CCC[C@@H](OC(=O)[C@H](C)NC(=O)c1nccc(OC)c1OCOC(C)=O)[C@H](Oc1ccccc1)C(C)C] | Example 16B. | Yellow Oil |
| 1094 | 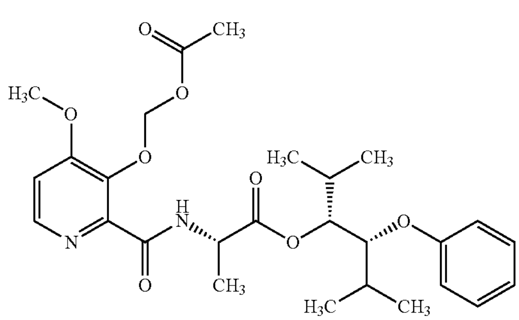 [SMILES: COc1ccnc(C(=O)N[C@@H](C)C(=O)O[C@H](C(C)C)[C@H](Oc2ccccc2)C(C)C)c1OCOC(C)=O] | Example 16B. | Yellow Oil |

TABLE 1-continued

Compound Structure, Appearance, and Preparation Method

| *Cmpd. No. | Structure | Prepared According to Example: | Appearance |
|---|---|---|---|
| 1095 | 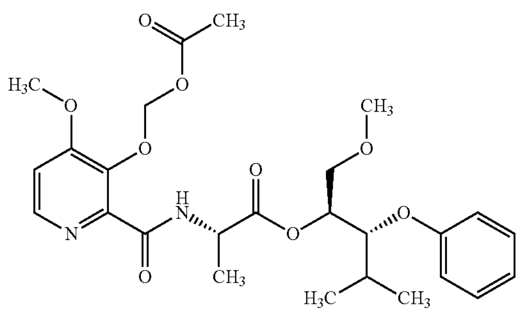 [SMILES: COC[C@H](OC(=O)[C@H](C)NC(=O)c1nccc(OC)c1OCOC(C)=O)[C@H](Oc1ccccc1)C(C)C] | Example 16B. | Yellow Oil |
| 1096 | 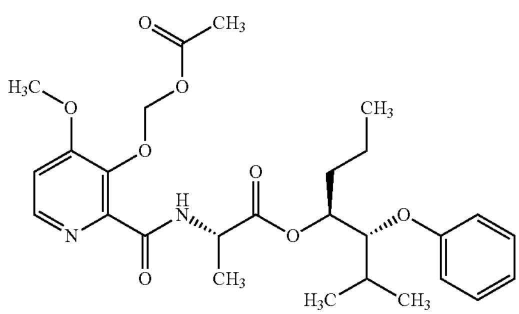 [SMILES: CCC[C@H](OC(=O)[C@H](C)NC(=O)c1nccc(OC)c1OCOC(C)=O)[C@H](Oc1ccccc1)C(C)C] | Example 16B. | Yellow Oil |
| 1097 | 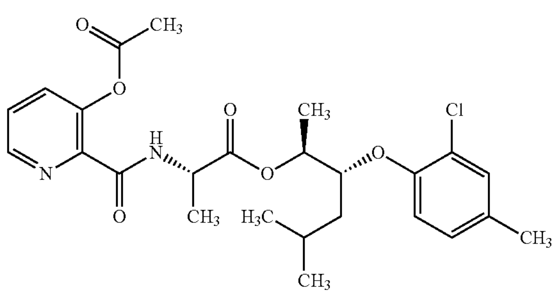 [SMILES: CC(=O)Oc1cccnc1C(=O)N[C@@H](C)C(=O)O[C@@H](C)[C@@H](CC(C)C)Oc1ccc(C)cc1Cl] | Example 16A. | Oil |
| 1098 | 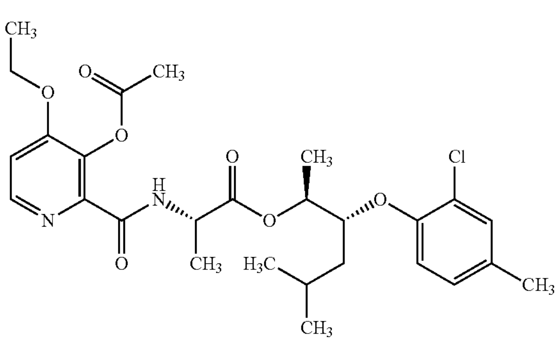 [SMILES: CCOc1ccnc(C(=O)N[C@@H](C)C(=O)O[C@@H](C)[C@@H](CC(C)C)Oc2ccc(C)cc2Cl)c1OC(C)=O] | Example 16A. | Oil |

TABLE 1-continued

Compound Structure, Appearance, and Preparation Method

| *Cmpd. No. | Structure | Prepared According to Example: | Appearance |
|---|---|---|---|
| 1099 | 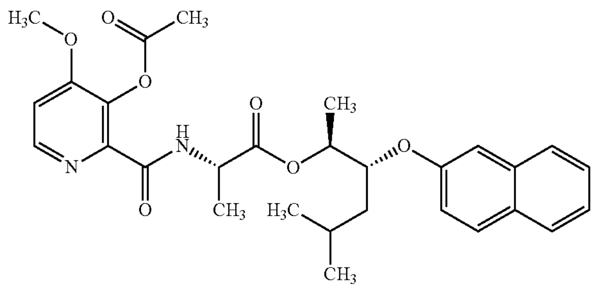 [SMILES: COc1ccnc(C(=O)N[C@@H](C)C(=O)O[C@@H](C)[C@@H](CC(C)C)Oc2ccc3ccccc3c2)c1OC(C)=O] | Example 16A. | Oil |
| 1100 | 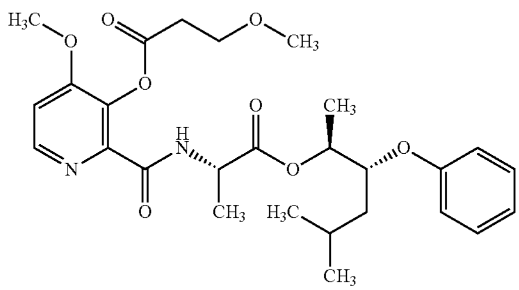 [SMILES: COCCC(=O)Oc1c(OC)ccnc1C(=O)N[C@@H](C)C(=O)O[C@@H](C)[C@@H](CC(C)C)Oc1ccccc1] | Example 16A. | Oil |
| 1101 | 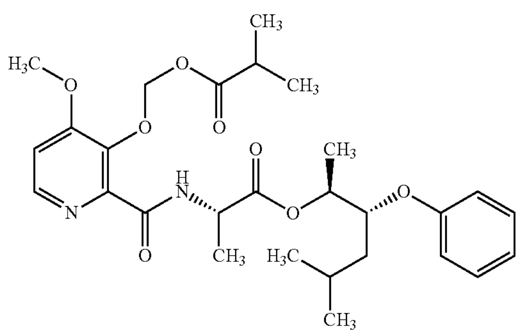 [SMILES: COc1ccnc(C(=O)N[C@@H](C)C(=O)O[C@@H](C)[C@@H](CC(C)C)Oc2ccccc2)c1OCOC(=O)C(C)C] | Example 16C. | Oil |
| 1102 | 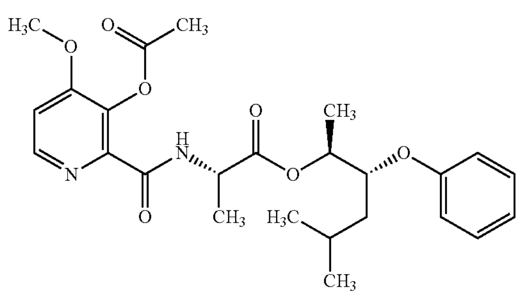 [SMILES: COc1ccnc(C(=O)N[C@@H](C)C(=O)O[C@@H](C)[C@@H](CC(C)C)Oc2ccccc2)c1OC(C)=O] | Example 16A. | Oil |
| 1103 | 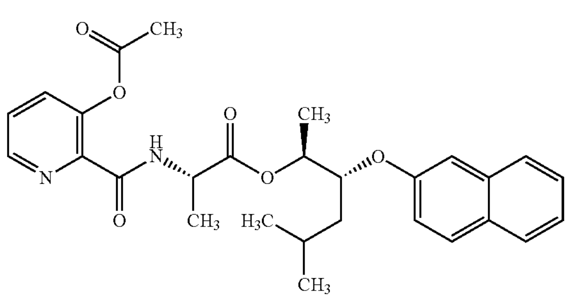 [SMILES: CC(=O)Oc1cccnc1C(=O)N[C@@H](C)C(=O)O[C@@H](C)[C@@H](CC(C)C)Oc1ccc2ccccc2c1] | Example 16A. | Oil |

TABLE 1-continued

Compound Structure, Appearance, and Preparation Method

| *Cmpd. No. | Structure | Prepared According to Example: | Appearance |
|---|---|---|---|
| 1104 | 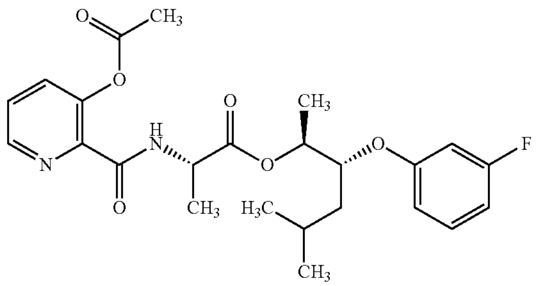 [SMILES: CC(=O)Oc1cccnc1C(=O)N[C@@H](C)C(=O)O[C@@H](C)[C@@H](CC(C)C)Oc1cccc(F)c1] | Example 16A. | Oil |
| 1105 | 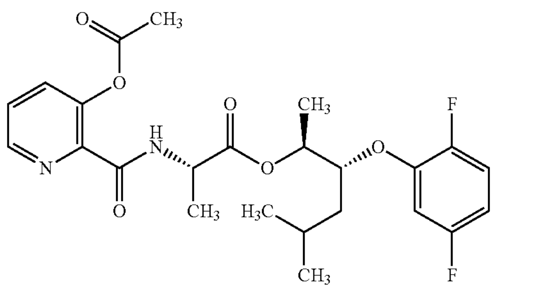 [SMILES: CC(=O)Oc1cccnc1C(=O)N[C@@H](C)C(=O)O[C@@H](C)[C@@H](CC(C)C)Oc1cc(F)ccc1F] | Example 16A. | Oil |
| 1106 | 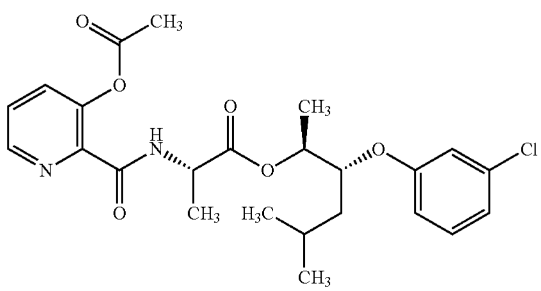 [SMILES: CC(=O)Oc1cccnc1C(=O)N[C@@H](C)C(=O)O[C@@H](C)[C@@H](CC(C)C)Oc1cccc(Cl)c1] | Example 16A. | Oil |
| 1107 | 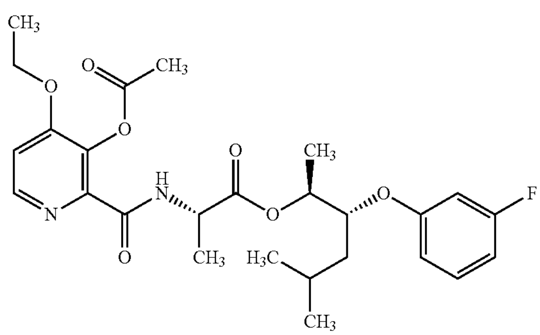 [SMILES: CCOc1ccnc(C(=O)N[C@@H](C)C(=O)O[C@@H](C)[C@@H](CC(C)C)Oc2cccc(F)c2)c1OC(C)=O] | Example 16A. | Oil |
| 1108 | 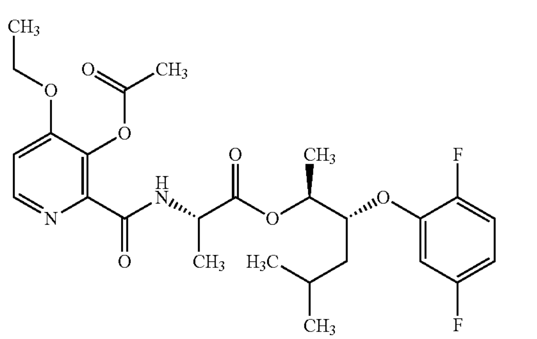 [SMILES: CCOc1ccnc(C(=O)N[C@@H](C)C(=O)O[C@@H](C)[C@@H](CC(C)C)Oc2cc(F)ccc2F)c1OC(C)=O] | Example 16A. | Oil |

TABLE 1-continued

Compound Structure, Appearance, and Preparation Method

| *Cmpd. No. | Structure | Prepared According to Example: | Appearance |
|---|---|---|---|
| 1109 | 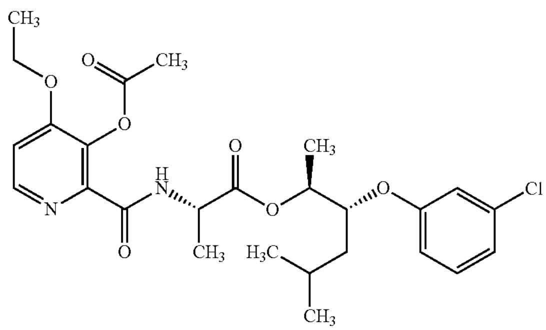 [SMILES: CCOc1ccnc(C(=O)N[C@@H](C)C(=O)O[C@@H](C)[C@@H](CC(C)C)Oc2cccc(Cl)c2)c1OC(C)=O] | Example 16A. | Oil |
| 1110 | 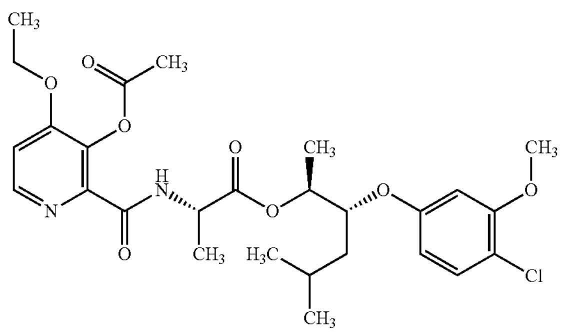 [SMILES: CCOc1ccnc(C(=O)N[C@@H](C)C(=O)O[C@@H](C)[C@@H](CC(C)C)Oc2ccc(Cl)c(OC)c2)c1OC(C)=O] | Example 16A. | Oil |
| 1111 | 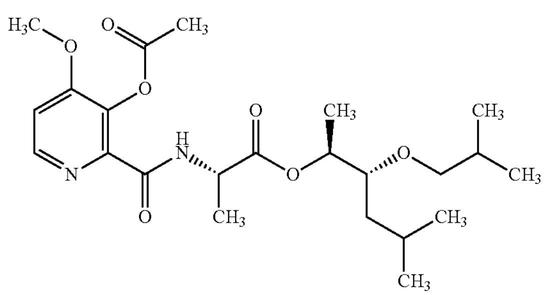 [SMILES: COc1ccnc(C(=O)N[C@@H](C)C(=O)O[C@@H](C)[C@@H](CC(C)C)OCC(C)C)c1OC(C)=O] | Example 16A. | Oil |
| 1112 | 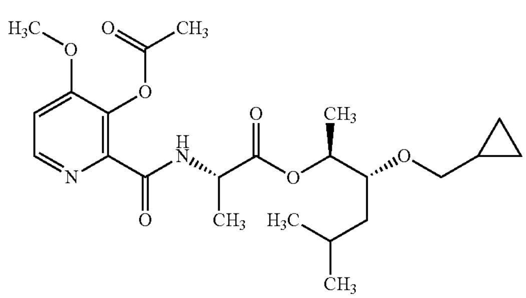 [SMILES: COc1ccnc(C(=O)N[C@@H](C)C(=O)O[C@@H](C)[C@@H](CC(C)C)OCC2CC2)c1OC(C)=O] | Example 16A. | Oil |

TABLE 1-continued

Compound Structure, Appearance, and Preparation Method

| *Cmpd. No. | Structure | Prepared According to Example: | Appearance |
|---|---|---|---|
| 1113 | 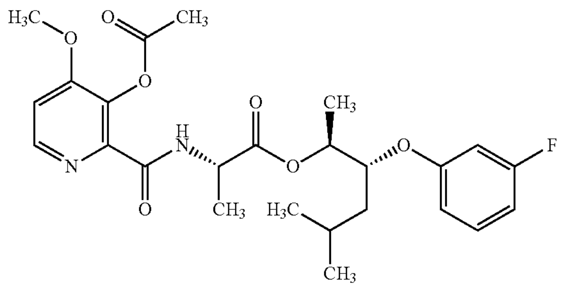 [SMILES: COc1ccnc(C(=O)N[C@@H](C)C(=O)O[C@@H](C)[C@@H](CC(C)C)Oc2cccc(F)c2)c1OC(C)=O] | Example 16A. | Oil |
| 1114 | 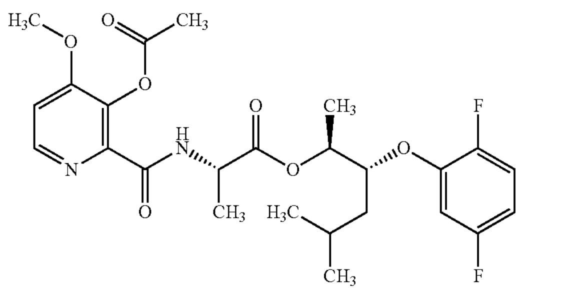 [SMILES: COc1ccnc(C(=O)N[C@@H](C)C(=O)O[C@@H](C)[C@@H](CC(C)C)Oc2cc(F)ccc2F)c1OC(C)=O] | Example 16A. | Oil |
| 1115 | 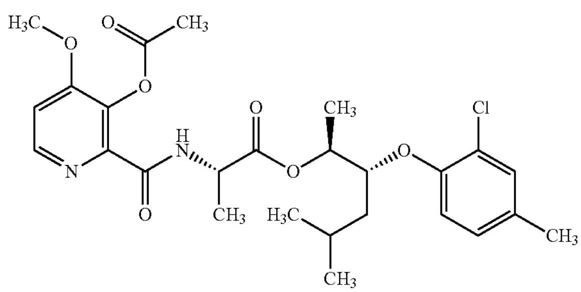 [SMILES: COc1ccnc(C(=O)N[C@@H](C)C(=O)O[C@@H](C)[C@@H](CC(C)C)Oc2ccc(C)cc2Cl)c1OC(C)=O] | Example 16A. | Oil |
| 1116 | 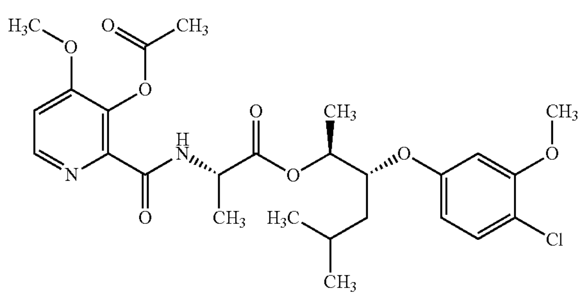 [SMILES: COc1cc(O[C@H](CC(C)C)[C@H](C)OC(=O)[C@H](C)NC(=O)c2nccc(OC)c2OC(C)=O)ccc1Cl] | Example 16A. | Oil |

*Cmpd. No. — Compound Number

LENGTHY TABLES

The patent contains a lengthy table section. A copy of the table is available in electronic form from the USPTO web site (http://seqdata.uspto.gov/?pageRequest=docDetail&DocID=US10433555B2). An electronic copy of the table will also be available from the USPTO upon request and payment of the fee set forth in 37 CFR 1.19(b)(3).

What is claimed is:

1. A compound of Formula I

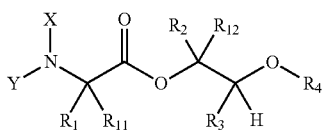

I wherein
X is hydrogen;
Y is Q;
Q is

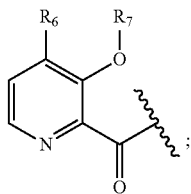

$R_1$ and $R_{11}$ are independently chosen from hydrogen or alkyl, optionally substituted with 0, 1 or multiple $R_8$; alternatively, $R_1$ and $R_{11}$ may be taken together to form a 3-6 membered saturated or partially saturated carbocycle or heterocycle, optionally substituted with 0, 1 or multiple $R_8$;

$R_2$ and $R_{12}$ are independently chosen from hydrogen, alkyl, aryl, or alkenyl, each optionally substituted with 0, 1 or multiple $R_8$;

$R_3$ is chosen from hydrogen, $C_2$-$C_6$ alkyl, aryl, or alkenyl, each optionally substituted with 0, 1 or multiple $R_8$;

$R_4$ is chosen from alkyl, aryl, or acyl, each optionally substituted with 0, 1 or multiple $R_8$;

$R_6$ is chosen from hydrogen, alkoxy, or halo, each optionally substituted with 0, 1, or multiple $R_8$;

$R_7$ is chosen from hydrogen, —C(O)$R_9$, or —CH$_2$OC(O)$R_9$;

$R_8$ is chosen from hydrogen, alkyl, aryl, acyl, halo, alkenyl, alkoxy, or heterocyclyl, each optionally substituted with 0, 1, or multiple $R_{10}$;

$R_9$ is chosen from alkyl, alkoxy, or aryl, each optionally substituted with 0, 1, or multiple $R_8$; and $R_{10}$ is chosen from hydrogen, alkyl, aryl, acyl, halo, alkenyl, alkoxy, or heterocyclyl.

2. The compound according to claim 1, wherein $R_6$ is alkoxy.

3. The compound according to claim 2, wherein $R_7$ is hydrogen.

4. The compound according to claim 2, wherein $R_1$ and $R_{11}$ are independently chosen from hydrogen or alkyl.

5. The compound according to claim 4, wherein $R_2$ and $R_{12}$ are independently chosen from hydrogen or alkyl.

6. The compound according to claim 1, wherein $R_3$ is chosen from $C_2$-$C_6$ alkyl, aryl, or alkenyl, each optionally substituted with 0, 1 or multiple $R_8$.

7. The compound according to claim 6, wherein $R_4$ is chosen from alkyl or aryl, each optionally substituted with 0, 1 or multiple $R_8$.

8. The compound according to claim 1, wherein $R_1$ and $R_{11}$ are independently chosen from hydrogen or alkyl, $R_2$ and $R_{12}$ are independently chosen from hydrogen or alkyl, $R_3$ is chosen from $C_2$-$C_6$ alkyl, aryl, or alkenyl, each optionally substituted with 0, 1 or multiple $R_8$, and $R_4$ is chosen from alkyl or aryl, each optionally substituted with 0, 1 or multiple $R_8$.

9. The compound according to claim 8, wherein $R_7$ is —C(O)$R_9$.

10. The compound according to claim 9, wherein $R_9$ is alkyl, optionally substituted with 0, 1 or multiple $R_8$.

11. The compound according to claim 1, wherein $R_1$ and $R_{11}$ are independently chosen from hydrogen or alkyl, $R_2$ and $R_{12}$ are independently chosen from hydrogen or alkyl, $R_3$ is $C_2$-$C_6$ alkyl, optionally substituted with 0, 1 or multiple $R_8$, and $R_4$ is chosen from alkyl or aryl, each optionally substituted with 0, 1 or multiple $R_8$.

12. The compound according to claim 11, wherein $R_9$ is chosen from —$CH_3$, —$CH_2OCH_2CH_3$, —$CH_2CH_2OCH_3$, —$CH(CH_3)_2$, —$CH_2CH_2CH_2CH_3$, or -cyclopropyl.

* * * * *